US006960570B2

(12) United States Patent
Wang et al.

(10) Patent No.: US 6,960,570 B2
(45) Date of Patent: Nov. 1, 2005

(54) COMPOSITIONS AND METHODS FOR THE THERAPY AND DIAGNOSIS OF LUNG CANCER

(75) Inventors: Tongtong Wang, Medina, WA (US); Robert A. Henderson, Edmonds, WA (US); Teresa M. Foy, Federal Way, WA (US)

(73) Assignee: Corixa Corporation, Seattle, WA (US)

( * ) Notice: Subject to any disclaimer, the term of this patent is extended or adjusted under 35 U.S.C. 154(b) by 412 days.

(21) Appl. No.: 10/007,700

(22) Filed: Nov. 30, 2001

(65) Prior Publication Data

US 2003/0064947 A1 Apr. 3, 2003

Related U.S. Application Data

(63) Continuation-in-part of application No. 09/897,778, filed on Jun. 28, 2001, which is a continuation-in-part of application No. 09/850,716, filed on May 7, 2001, which is a continuation-in-part of application No. 09/735,705, filed on Dec. 12, 2000, which is a continuation-in-part of application No. 09/685,696, filed on Oct. 9, 2000, which is a continuation-in-part of application No. 09/662,786, filed on Sep. 15, 2000, which is a continuation-in-part of application No. 09/643,597, filed on Aug. 21, 2000, which is a continuation-in-part of application No. 09/630,940, filed on Aug. 2, 2000, which is a continuation-in-part of application No. 09/606,421, filed on Jun. 28, 2000, which is a continuation-in-part of application No. 09/542,615, filed on Apr. 4, 2000, which is a continuation-in-part of application No. 09/510,376, filed on Feb. 22, 2000, which is a continuation-in-part of application No. 09/480,884, filed on Jan. 10, 2000, which is a continuation-in-part of application No. 09/476,496, filed on Dec. 30, 1999, which is a continuation-in-part of application No. 09/466,396, filed on Dec. 17, 1999, which is a continuation-in-part of application No. 09/285,479, filed on Apr. 2, 1999, which is a continuation-in-part of application No. 09/221,107, filed on Dec. 22, 1998, which is a continuation-in-part of application No. 09/123,912, filed on Jul. 27, 1998, now Pat. No. 6,312,695, which is a continuation-in-part of application No. 09/040,802, filed on Mar. 18, 1998.

(51) Int. Cl.[7] ........................ A01N 43/04; C07H 21/04; C12N 15/63; C12N 15/09

(52) U.S. Cl. ........................ 514/44; 536/23.5; 435/69.3; 435/455

(58) Field of Search ........................ 514/44; 536/23.5, 536/23.1; 435/69.3, 455; 424/93.2, 93.21

(56) References Cited

U.S. PATENT DOCUMENTS

| | | | | |
|---|---|---|---|---|
| 5,589,579 | A | 12/1996 | Torczynski et al. | 536/23.1 |
| 5,705,159 | A | 1/1998 | Irie et al. | 424/185.1 |
| 5,783,422 | A | 7/1998 | Suminami et al. | 435/69.3 |
| 6,200,764 | B1 | 3/2001 | Carney | 435/7.23 |
| 6,297,364 | B1 | 10/2001 | Chen et al. | 536/23.1 |

FOREIGN PATENT DOCUMENTS

| | | | |
|---|---|---|---|
| EP | 679716 A1 | 11/1995 |
| EP | 0695760 A1 | 2/1996 |
| EP | 1033401 A2 | 9/2000 |
| EP | 1130094 A2 | 9/2001 |
| WO | WO 91/18926 | 12/1991 |
| WO | WO 94/06929 | 3/1994 |
| WO | WO 95/21862 | 8/1995 |
| WO | WO 96/02552 | 2/1996 |
| WO | WO 96/28473 | 9/1996 |
| WO | WO 96/30389 | 10/1996 |
| WO | WO 97/07244 | 2/1997 |
| WO | WO 98/35985 | 8/1998 |
| WO | WO 98/46788 | 10/1998 |
| WO | WO 99/38973 | 8/1999 |
| WO | WO 99/46594 | 9/1999 |
| WO | WO 99/47674 | 9/1999 |
| WO | WO 99/54738 | 10/1999 |
| WO | WO 00/61612 | 10/2000 |
| WO | WO 01/47944 | 7/2001 |
| WO | WO 01/55322 | 8/2001 |
| WO | WO 01/57272 | 8/2001 |
| WO | WO 01/57275 | 8/2001 |
| WO | WO 01/57276 | 8/2001 |
| WO | WO 01/57277 | 8/2001 |
| WO | WO 01/75067 | 10/2001 |

OTHER PUBLICATIONS

Chen, Shen–Lin et al., "Isolation and characterization of a novel gene expressed in multiple cancers," *Oncogene 12*: 741–751, 1996.

Güre, A.O. et al., "Human Lung Cancer Antigens Recognized by Autologous Antibodies: Definition of a Novel cDNA Derived from the Tumor Suppressor," *Cancer Research 58*: 1034–1041, Mar. 1, 1998.

GenBank Database, Accession No. AAB82295, Oct. 30, 1997.

GenBank Database, Accession No. AAB97457, Jan. 22, 1998.

GenBank Database, Accession No. AAC18597, Jun. 3, 1998.

GenBank Database, Accession No. AAC18598, Jun. 3, 1998.

GenBank Database, Accession No. AAC35208, May 13, 1997.

GenBank Database, Accession No. AAC41285, May 13, 1998.

GenBank Database, Accession No. AAC65900, Oct. 10, 2003.

(Continued)

*Primary Examiner*—Shin-Lin Chen
(74) *Attorney, Agent, or Firm*—Seed IP Law Group PLLC

(57) ABSTRACT

Compositions and methods for the therapy and diagnosis of cancer, particularly lung cancer, are disclosed. Illustrative compositions comprise one or more lung tumor polypeptides, immunogenic portions thereof, polynucleotides that encode such polypeptides, antigen presenting cell that expresses such polypeptides, and T cells that are specific for cells expressing such polypeptides. The disclosed compositions are useful, for example, in the diagnosis, prevention and/or treatment of diseases, particularly lung cancer.

7 Claims, No Drawings

OTHER PUBLICATIONS

GenBank Database, Accession No. AAD09223, Jan. 26, 1999.
GenBank Database, Accession No. AAD09827, Jan. 26, 1999.
GenBank Database, Accession No. AAD09828, Jan. 26, 1999.
GenBank Database, Accession No. AAF37203, Mar. 2, 2000.
GenBank Database, Accession No. AC005082, Sep. 8, 1999.
GenBank Database, Accession No. AC021876, Jan. 21, 2000.
GenBank Database, Accession No. AC079780, Feb. 21, 2002.
GenBank Database, Accession No. AC092447, Jul. 4, 2001.
GenBank Database, Accession No. AF117108, Jan. 26, 1999.
GenBank Database, Accession No. AF198254, Mar. 2, 2000.
GenBank Database, Accession No. AL023775, Nov. 23, 1999.
GenBank Database, Accession No. BAB19755, Dec. 20, 2000.
GenBank Database, Accession No. BAB27779, Feb. 8, 2001.
GenBank Database, Accession No. BAB27848, Feb. 8, 2001.
GenBank Database, Accession No. BC019258, Dec. 19, 2001.
GenBank Database, Accession No. O00425, Jul. 1, 1997.
GenBank Database, Accession No. NM_006547, Nov. 1, 2000.
GenBank Database, Accession No. NP_034081, Jan. 25, 2000.
GenBank Database, Accession No. NP_006537, Aug. 10, 1999.
GenBank Database, Accession No. NP_006538, Nov. 1, 2000.
GenBank Database, Accession No. NP_006539, Aug. 10, 1999.
GenBank Database, Accession No. NP_571566, Feb. 20, 2002.
GenBank Database, Accession No. NP_076159, Feb. 19, 2001.
GenBank Database, Accession No. U76705, Jan. 26, 1999.
GenBank Database, Accession No. U97188, May 20, 1997.
GenBank Database, Accession No. XM_004780, Nov. 16, 2000.
GenBank Database, Accession No. XP_004780, Nov. 16, 2000.
Geneseq Database (Thomson Derwent), Accession AAL28189, Jan. 24, 2002.
Geneseq Database (Thomson Derwent), Accession AAM93826, Nov. 6, 2001.
Geneseq Database (Thomson Derwent), Accession AAT26750, Oct. 23, 1996.
Geneseq Database (Thomson Derwent), Accession AAU16161, Nov. 7, 2001.
Geneseq Database (Thomson Derwent), Accession AAU16163, Nov. 7, 2001.
Geneseq Database (Thomson Derwent), Accession AAU16164, Nov. 7, 2001.
Geneseq Database (Thomson Derwent), Accession AAU16166, Nov. 7, 2001.
Geneseq Database (Thomson Derwent), Accession AAU16579, Nov. 7, 2001.
Geneseq Database (Thomson Derwent), Accession AAU16583, Nov. 7, 2001.
Ackermann, R. "Monoclonal antibodies," *Human Cell 1*(1):46–53, 1988 (Abstract Only; PubMed ID:3154013).
Arceci, R.J., "The potential for antitumor vaccination in acute myelogenous leukemia," *J. Mol. Med. 76*: 80–93, 1998.
Bergers and Coussens, "Extrinsic regulators of epithelial tumor progression: metalloproteinases," *Current Opinion in Genetics & Developments 10*: 120–127, 200.
Bodey, B. et al., "Failure of Cancer Vaccines: The Significant Limitations of this Approach to Immunotherapy," *Anticancer Research 20*: 2665–2676, 2000.
Boon, T., "Toward a Genetic Analysis of Tumor Rejection Antigens," *Advances in Cancer Research 58*: 177–210, 1992.
Eck and Wilson, "Gene–Based Therapy," in *Goodman & Gilman's The Pharmacological Basis of Therapeutics*, 9$^{th}$ Edition, McGraw–Hill, New York, 1996, pp. 77–101.
Ezzell, C., "Cancer 'Vaccines': An Idea Whose Time Has Come?" *The Journal of NIH Research 7*: 46–49, Jan. 1995.
Greenspan and Cooper, "Complementarity, specificity and the nature of epitopes and paratopes in multivalent interactions," *Immunology Today 16*(5): 226–230, 1995.
Gura, T., "System for Identifying New Drugs Are Often Faulty," *Science 278*: 1041–1042, Nov. 7, 1997.
Kaye, F.J. et al. "A single amino acid substitution results in a retinoblastoma protein defective in phosphorylation and oncoprotein binding," *Proc. Natl. Acad. Sci. USA 87*: 6922–6926, Sep. 1990.
Lee, K–H. et al., "Increased Vaccine–Specific T Cell Frequency After Peptide–Based Vaccination Correlates with Increased Susceptibility to In Vitro Stimulation But Does Not Lead to Tumor Regression," *The Journal of Immunology 163*: 6292–6300, 1999.
Müeller–Pillasch, F. et al., "Cloning of a gene highly overexpressed in cancer coding for a novel KH–domain containing protein," *Oncogene 14*: 2729–2733, 1997.
Nielsen, J. et al., "A Family of Insulin–Like Growth Factor II mRNA–Binding Proteins Represses Translation in Late Development," *Molecular and Cellular Biology 19*(2): 1262–1270, Feb. 1999.
Radoja and Frey, "Cancer–induced Defective Cytotoxic T Lymphocyte Effector Function: Another Mechanism How Antigenic Tumors Escape Immune–mediated Killing," *Molecular Medicine 6*(6): 465–479, Jun. 2000.
Rudinger, J., "Characteristics of the amino acids as components of a peptide hormone sequence," in *Peptide Hormones*, Parsons, J.A. (ed.), University Park Press, Baltimore MD, Jun. 1976, pp. 1–7.
Sjölander, A. et al., "Kinetics, localization and cytokine profile of T cell responses to immune stimulating complexes (iscoms) containing human influenza virus envelope glycoproteins," *Vaccine 15*(9): 1030–1038, 1997.
Skolnick and Fetrow, "From genes to protein structure and function: novel applications of computational approaches in the genomic era," *Trends in Biotechnology 18*: 34–39, Jan. 2000.
Spitler, L.E., "Cancer Vaccines: The Interferon Analogy," *Cancer Biotherapy 10*(1): 1–3, 1995.
Stern, P.S., "Predicting antigenic sites on proteins," *Trends in Biotechnology 9*: 163–169, May 1991.

Timmerman and Levy, "Dendritic Cell Vaccines for Cancer Immunotherapy," *Annu. Rev. Med. 50*: 507–529, 1999.
Wong, C.P. et al., "TCR Vaccines Against T Cell Lymphoma: QS–21 and IL–12 Adjuvants Induce a Protective CD8$^+$ T Cell Response," *The Journal of Immunology 162*: 2251–2258, 1999.
Zaks and Rosenberg, "Immunization with Peptide Epitope (p369–377) from HER–2/neu Leads to Peptide–specific Cytotoxic T Lymphocytes That Fail to Recognize HER–2/neu+ Tumors," *Cancer Research 58*: 4902–4908, Nov. 1, 1998.
Geneseq Accession No. AAC66035, Feb. 21, 2001.
Geneseq Accession No. AAZ36150, Dec. 7, 1999.
Jolly, D., "Viral vector systems for gene therapy," *Cancer Gene Therapy 1*(1):51–64, 1994.
GenBank Accession No. AF043977, Jun. 23, 1999.
GenBank Accession No. U85946, Jul. 30, 1999.
Geneseq Accession No. AAZ24653, Dec. 7, 1999.
Gruber et al., "Molecular cloning and transmembrane structure of hCLCA2 from human lung, trachea, and mammary gland," *Am. J. Physiol. 276*(Cell Physiol 45):C1261–C1270, 1999.
Guo et al., "Identification and characterization of homologues of the Exocyst component Sec10p," *FEBS Letters 404*(2–3):135–139, 1997.
Baldi et al., "Differential expression of Rb2/p130 and p107 in normal human tissues and in primary lung cancer," *Clinical Cancer Research 3*(10):1691–1697, Oct. 1997.
Brass et al., "Translation initiation factor eIF–4gamma is encoded by an amplified gene and induces an immune response in squamous cell lung carcinoma," *Human Molecular Genetics, 6*(1):33–39, 1997.
Database EMBL Nucleotide and Protein Sequence, Accession No. AI468638, Mar. 17, 1999.
Database EMBLest17 Accession No. AA340797:EST46165 Fetal kidney II *Homo sapiens* cDNA 3' end, Apr. 18, 1997.
Database EMBLest17 Accession No. W2264:Human retina cDNATsp–509I–cleaved sublibrary *Homo sapiens* cDNA not directional, May 9, 1996.
Davidson et al., "Lung tumours immunoreactive for parathyroid hormone related peptide: analysis of serum calcium levels and tumour type," *Journal of Pathology 178*:398–401, Jan. 1996.
Finch et al., "Identification of a cloned sequence activated during multi–stage carcinogenesis in mouse skin," *Carcinogenesis, 12*(8):1519–1522, Aug. 1991.
Gerhold and Caskey, "It's the genes! EST access to human genome content," *BioEssays 18*(12):973–981, 1996.
Hara et al., "Characterization of cell phenotype by a novel cDNA library subtraction system: expression of CD8α in a mast cell–derived interleukin–4–dependent cell line," *Blood 84*(1):189–199, Jul. 1, 1994.
Henderson et al., "Identification of lung tumor antigens for cancer immunotherapy: immunological and molecular approaches," *Immunological Investigation 29*(2):87–91, May 2000.
Hogan et al., "The peptide recognized by HLA–A68.2–restricted, squamous cell carcinoma of the lung–specific cytotoxic T lymphocytes is derived from a mutated elongation factor 2 gene," *Cancer Research 58*(22):5144–5150, Nov. 15, 1998.
Hu et al., "A small proline–rich protein, spr1: specific marker for squamous lung carcinoma," *Lung Cancer 20*:25–30, 1998.
Lelievre et al., "Structural properties of chimeric peptides containing a T–cell epitope linked to a fusion peptide and their importance for in vivo induction of cytotoxic T–cell responses," *European Journal of Biochemistry 249*(3):895–904, 1997.
Marshall and Hodgson, "DNA chips: an array of possibilities," *Nature Biotechnology 16*:27–31, Jan. 1998.
Pastor et al., "Diagnostic value of SCC, CEA and CYFRA 21.1 in lung cancer: a Bayesian analysis," *Eur. Respir J. 10*(3):603–609, Mar. 1997.
Rammensee et al., "MHC ligands and peptide motifs: first listing," *Immunogenetics 41*:178–228, 1995.
Ramsay, G., "DNA chips: state–of–the–art," *Nature Biotechnology 16*:40–44, Jan. 1998.
Ruppert et al., "Prominent role of secondary anchor residues in peptide binding to HLA–A2.1 molecules," *Cell 74*:929–937, Sep. 10, 1993.
Russell and Barton, "Structural features can be unconserved in proteins with similar folds," *J. Mol. Biol. 244*:332–350, 1994.
Sherman et al., "Selecting T cell receptors with high affinity for self–MHC by decreasing the contribution of CD8," *Science 258*:815–818, Oct. 30, 1992.
Skeiky et al., "Cloning, expression and immunological evaluation of two putative secreted serine protease antigens of Mycobacterium tuberculosis," *Infection and Immunity 67*(8):3998–4007, Aug. 1999.
Theobald et al., "Targeting p53 as a general tumor antigen," *Proc. Natl. Acad. Sci. USA 92*:11993–11997, Dec. 1995.
Visseren et al., "Identification of HLA–A *0201–restricted CTL epitopes encoded by the tumor–specific MAGE–2 gene product," *International Journal of Cancer 73*(1):125–130, 1997.
Wang et al., "Identification of genes differentially over–expressed in lung squamous cell carcinoma using combination of cDNA subtraction and microarray analysis," *Oncogene 19*(12):1519–1528, Mar. 16, 2000.
Wells and Peitsch, "The chemokine information source: identification and characterization of novel chemokines using the WorldWideWeb and expressed sequence tag databases," *Journal of Leukocyte Biology 61*:545–550, May 1997.
Yee et al., "Isolation of tyrosinase–specific CD8$^+$ and CD4$^+$ T cell clones from the peripheral blood of melanoma patients following in vitro stimulation with recombinant vaccinia virus," *The Journal of Immunology 157*:4079–4086, 1996.

COMPOSITIONS AND METHODS FOR THE THERAPY AND DIAGNOSIS OF LUNG CANCER

CROSS REFERENCE TO RELATED APPLICATIONS

This application is a continuation-in-part of U.S. patent application Ser. No. 09/897,778 filed Jun. 28, 2001 now abandoned; which is a continuation-in-part of U.S. patent application Ser. No. 09/850,716 filed May 7, 2001 now abandoned; which is a continuation-in-part of U.S. patent application Ser. No. 09/735,705 filed Dec. 12, 2000; which is a continuation-in-part of U.S. patent application Ser. No. 09/685,696 filed Oct. 9, 2000; which is a continuation-in-part of U.S. patent application Ser. No. 09/662,786 filed Sep. 15, 2000; which is a continuation-in-part of U.S. patent application Ser. No. 09/643,597 filed Aug. 21, 2000; which is a continuation-in-part of U.S. patent application Ser. No. 09/630,940 filed Aug. 2, 2000; which is a continuation-in-part of U.S. patent application Ser. No. 09/606,421 filed Jun. 28, 2000; which is a continuation-in-part of U.S. patent application Ser. No. 09/542,615 filed Apr. 4, 2000; which is a continuation-in-part of U.S. patent application No. Ser. No. 09/510,376 filed Feb. 22, 2000; which is a continuation-in-part of U.S. patent application Ser. No. 09/480,884 filed Jan. 10, 2000; which is a continuation-in-part of U.S. patent application Ser. No. 09/476,496 filed Dec. 30, 1999; which is a continuation-in-part of U.S. patent application Ser. No. 09/466,396 filed Dec. 17, 1999; which is a continuation-in-part of U.S. patent application Ser. No. 09/285,479 filed Apr. 2, 1999; which is a continuation-in-part of U.S. patent application Ser. No. 09/221,107 filed Dec. 22, 1998; which is a continuation-in-part of U.S. patent application Ser. No. 09/123,912 filed Jul. 27, 1998 now U.S. Pat. No. 6,312,695; which is a continuation-in-part of U.S. patent application Ser. No. 09/040,802 filed Mar. 18, 1998 now abandoned and all incorporated by reference herein.

TECHNICAL FIELD OF THE INVENTION

The present invention relates generally to therapy and diagnosis of cancer, such as lung cancer. The invention is more specifically related to polypeptides, comprising at least a portion of a lung tumor protein, and to polynucleotides encoding such polypeptides. Such polypeptides and polynucleotides are useful in pharmaceutical compositions, e.g., vaccines, and other compositions for the diagnosis and treatment of lung cancer.

BACKGROUND OF THE INVENTION

1. Field of the Invention

Cancer is a significant health problem throughout the world. Although advances have been made in detection and therapy of cancer, no vaccine or other universally successful method for prevention and/or treatment is currently available. Current therapies, which are generally based on a combination of chemotherapy or surgery and radiation, continue to prove inadequate in many patients.

2. Description of Related Art

Lung cancer is the primary cause of cancer death among both men and women in the U.S., with an estimated 172,000 new cases being reported in 1994. The five-year survival rate among all lung cancer patients, regardless of the stage of disease at diagnosis, is only 13%. This contrasts with a five-year survival rate of 46% among cases detected while the disease is still localized. However, only 16% of lung cancers are discovered before the disease has spread.

In spite of considerable research into therapies for these and other cancers, lung cancer remains difficult to diagnose and treat effectively. Accordingly, there is a need in the art for improved methods for detecting and treating such cancers. The present invention fulfills these needs and further provides other related advantages.

SUMMARY OF THE INVENTION

In one aspect, the present invention provides polynucleotide compositions comprising a sequence selected from the group consisting of:

(a) sequences provided in SEQ ID NO:1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168, 171, 179, 182, 184–186, 188–191, 193, 194, 198–207, 209, 210, 213, 214, 217, 220–224, 253–337, 345, 347, 349, 358, 362, 364, 365, 368, 370–375, 420, 424, 428, 431, 434, 442, 447, 450 and 467;

(b) complements of the sequences provided in SEQ ID NO:1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168, 171, 179, 182, 184–186, 188–191, 193, 194, 198–207, 209, 210, 213, 214, 217, 220–224, 253–337, 345, 347, 349, 358, 362, 364, 365, 368, 370–375, 420, 424, 428, 431, 434, 442, 447, 450 and 467;

(c) sequences consisting of at least 10, 15, 20, 25, 30, 35, 40, 45, 50, 75 and 100 contiguous residues of a sequence provided in SEQ ID NO:1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168, 171, 179, 182, 184–186, 188–191, 193, 194, 198–207, 209, 210, 213, 214, 217, 220–224, 253–337, 345, 347, 349, 358, 362, 364, 365, 368, 370–375, 420, 424, 428, 431, 434, 442, 447, 450 and 467;

(d) sequences that hybridize to a sequence provided in SEQ ID NO:1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168, 171, 179, 182, 184–186, 188–191, 193, 194, 198–207, 209, 210, 213, 214, 217, 220–224, 253–337, 345, 347, 349, 358, 362, 364, 365, 368, 370–375, 420, 424, 428, 431, 434, 442, 447, 450 and 467, under moderate or highly stringent conditions;

(e) sequences having at least 75%, 80%, 85%, 90%, 95%, 96%, 97%, 98% or 99% identity to a sequence of SEQ ID NO:1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168, 171, 179, 182, 184–186, 188–191, 193, 194, 198–207, 209, 210, 213, 214, 217, 220–224, 253–337, 345, 347, 349, 358, 362, 364, 365, 368, 370–375, 420, 424, 428, 431, 434, 442, 447, 450 and 467; and (f) degenerate variants of a sequence provided in SEQ ID NO:1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168, 171, 179, 182, 184–186, 188–191, 193, 194, 198–207, 209, 210, 213, 214, 217, 220–224, 253–337, 345, 347, 349, 358, 362, 364, 365, 368, 370–375, 420, 424, 428, 431, 434, 442, 447, 450 and 467.

In one preferred embodiment, the polynucleotide compositions of the invention are expressed in at least about 20%, more preferably in at least about 30%, and most preferably in at least about 50% of lung tumors samples tested, at a level that is at least about 2-fold, preferably at least about 5-fold, and most preferably at least about 10-fold higher than that for normal tissues.

The present invention, in another aspect, provides polypeptide compositions comprising an amino acid sequence that is encoded by a polynucleotide sequence described above.

The present invention further provides polypeptide compositions comprising an amino acid sequence selected from the group consisting of sequences recited in SEQ ID NO:152, 155, 156, 165, 166, 169, 170, 172, 174, 176, 226–252, 338–344, 346, 350, 357, 361, 363, 365, 367, 369, 376–382, 387–419, 423, 427, 430, 433, 441, 443, 446, 449, 451–466 and 468–469.

In certain preferred embodiments, the polypeptides and/or polynucleotides of the present invention are immunogenic, i.e., they are capable of eliciting an immune response, particularly a humoral and/or cellular immune response, as further described herein.

The present invention further provides fragments, variants and/or derivatives of the disclosed polypeptide and/or polynucleotide sequences, wherein the fragments, variants and/or derivatives preferably have a level of immunogenic activity of at least about 50%, preferably at least about 70% and more preferably at least about 90% of the level of immunogenic activity of a polypeptide sequence set forth in SEQ ID NO:152, 155, 156, 165, 166, 169, 170, 172, 174, 176, 226–252, 338–344, 346, 350, 357, 361, 363, 365, 367, 369, 376–382, 387–419, 423, 427, 430, 433, 441, 443, 446, 449 and 451–466, or a polypeptide sequence encoded by a polynucleotide sequence set forth in SEQ ID NO:1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168, 171, 179, 182, 184–186, 188–191, 193, 194, 198–207, 209, 210, 213, 214, 217, 220–224, 253–337, 345, 347, 349, 358, 362, 364, 365, 368, 370–375, 420, 424, 428, 431, 434, 442, 447, 450 and 467.

The present invention further provides polynucleotides that encode a polypeptide described above, expression vectors comprising such polynucleotides and host cells transformed or transfected with such expression vectors.

Within other aspects, the present invention provides pharmaceutical compositions comprising a polypeptide or polynucleotide as described above and a physiologically acceptable carrier.

Within a related aspect of the present invention, the pharmaceutical compositions, e.g., vaccine compositions, are provided for prophylactic or therapeutic applications. Such compositions generally comprise an immunogenic polypeptide or polynucleotide of the invention and an immunostimulant, such as an adjuvant.

The present invention further provides pharmaceutical compositions that comprise: (a) an antibody or antigen-binding fragment thereof that specifically binds to a polypeptide of the present invention, or a fragment thereof; and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Illustrative antigen presenting cells include dendritic cells, macrophages, monocytes, fibroblasts and B cells.

Within related aspects, pharmaceutical compositions are provided that comprise: (a) an antigen presenting cell that expresses a polypeptide as described above and (b) an immunostimulant.

The present invention further provides, in other aspects, fusion proteins that comprise at least one polypeptide as described above, as well as polynucleotides encoding such fusion proteins, typically in the form of pharmaceutical compositions, e.g., vaccine compositions, comprising a physiologically acceptable carrier and/or an immunostimulant. The fusions proteins may comprise multiple immunogenic polypeptides or portions/variants thereof, as described herein, and may further comprise one or more polypeptide segments for facilitating the expression, purification and/or immunogenicity of the polypeptide(s).

Within further aspects, the present invention provides methods for stimulating an immune response in a patient, preferably a T cell response in a human patient, comprising administering a pharmaceutical composition described herein. The patient may be afflicted with lung cancer, in which case the methods provide treatment for the disease, or patient considered at risk for such a disease may be treated prophylactically.

Within further aspects, the present invention provides methods for inhibiting the development of a cancer in a patient, comprising administering to a patient a pharmaceutical composition as recited above. The patient may be afflicted with lung cancer, in which case the methods provide treatment for the disease, or patient considered at risk for such a disease may be treated prophylactically.

The present invention further provides, within other aspects, methods for removing tumor cells from a biological sample, comprising contacting a biological sample with T cells that specifically react with a polypeptide of the present invention, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a polypeptide of the present invention, comprising contacting T cells with one or more of: (i) a polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Isolated T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating $CD4^+$ and/or $CD8^+$ T cells isolated from a patient with one or more of: (i) a polypeptide comprising at least an immunogenic portion of polypeptide disclosed herein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer, preferably a lung cancer, in a patient comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a polypeptide of the present invention; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a polypeptide of the present invention; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description. All references disclosed herein are hereby incorporated by reference in their entirety as if each was incorporated individually.

Sequence Identifiers

SEQ ID NO:1 is the determined cDNA sequence for LST-S1-2

SEQ ID NO:2 is the determined cDNA sequence for LST-S1-28

SEQ ID NO:3 is the determined cDNA sequence for LST-S1-90

SEQ ID NO:4 is the determined cDNA sequence for LST-S1-144

SEQ ID NO:5 is the determined cDNA sequence for LST-S1-133

SEQ ID NO:6 is the determined cDNA sequence for LST-S1-169

SEQ ID NO:7 is the determined cDNA sequence for LST-S2-6

SEQ ID NO:8 is the determined cDNA sequence for LST-S2-11

SEQ ID NO:9 is the determined cDNA sequence for LST-S2-17

SEQ ID NO:10 is the determined cDNA sequence for LST-S2-25

SEQ ID NO:11 is the determined cDNA sequence for LST-S2-39

SEQ ID NO:12 is a first determined cDNA sequence for LST-S2-43

SEQ ID NO:13 is a second determined cDNA sequence for LST-S2-43

SEQ ID NO:14 is the determined cDNA sequence for LST-S2-65

SEQ ID NO:15 is the determined cDNA sequence for LST-S2-68

SEQ ID NO:16 is the determined cDNA sequence for LST-S2-72

SEQ ID NO:17 is the determined cDNA sequence for LST-S2-74

SEQ ID NO:18 is the determined cDNA sequence for LST-S2-103

SEQ ID NO:19 is the determined cDNA sequence for LST-S2-N1-1F

SEQ ID NO:20 is the determined cDNA sequence for LST-S2-N1-2A

SEQ ID NO:21 is the determined cDNA sequence for LST-S2-N1-4H

SEQ ID NO:22 is the determined cDNA sequence for LST-S2-N1-5A

SEQ ID NO:23 is the determined cDNA sequence for LST-S2-N1-6B

SEQ ID NO:24 is the determined cDNA sequence for LST-S2-N1-7B

SEQ ID NO:25 is the determined cDNA sequence for LST-S2-N1-7H

SEQ ID NO:26 is the determined cDNA sequence for LST-S2-N1-8A

SEQ ID NO:27 is the determined cDNA sequence for LST-S2-N1-8D

SEQ ID NO:28 is the determined cDNA sequence for LST-S2-N1-9A

SEQ ID NO:29 is the determined cDNA sequence for LST-S2-N1-9E

SEQ ID NO:30 is the determined cDNA sequence for LST-S2-N1-10A

SEQ ID NO:31 is the determined cDNA sequence for LST-S2-N1-10G

SEQ ID NO:32 is the determined cDNA sequence for LST-S2-N1-11A

SEQ ID NO:33 is the determined cDNA sequence for LST-S2-N1-12C

SEQ ID NO:34 is the determined cDNA sequence for LST-S2-N1-12E

SEQ ID NO:35 is the determined cDNA sequence for LST-S2-B1-3D

SEQ ID NO:36 is the determined cDNA sequence for LST-S2-B1-6C

SEQ ID NO:37 is the determined cDNA sequence for LST-S2-B1-5D

SEQ ID NO:38 is the determined cDNA sequence for LST-S2-B1-5F

SEQ ID NO:39 is the determined cDNA sequence for LST-S2-B1-6G

SEQ ID NO:40 is the determined cDNA sequence for LST-S2-B1-8A

SEQ ID NO:41 is the determined cDNA sequence for LST-S2-B1-8D

SEQ ID NO:42 is the determined cDNA sequence for LST-S2-B1-10A

SEQ ID NO:43 is the determined cDNA sequence for LST-S2-B1-9B

SEQ ID NO:44 is the determined cDNA sequence for LST-S2-B1-9F

SEQ ID NO:45 is the determined cDNA sequence for LST-S2-B1-12D

SEQ ID NO:46 is the determined cDNA sequence for LST-S2-I2-2B

SEQ ID NO:47 is the determined cDNA sequence for LST-S2-I2-5F

SEQ ID NO:48 is the determined cDNA sequence for LST-S2-I2-6B

SEQ ID NO:49 is the determined cDNA sequence for LST-S2-I2-7F

SEQ ID NO:50 is the determined cDNA sequence for LST-S2-I2-8G

SEQ ID NO:51 is the determined cDNA sequence for LST-S2-I2-9E

SEQ ID NO:52 is the determined cDNA sequence for LST-S2-I2-12B

SEQ ID NO:53 is the determined cDNA sequence for LST-S2-H2-2C

SEQ ID NO:54 is the determined cDNA sequence for LST-S2-H2-1G

SEQ ID NO:55 is the determined cDNA sequence for LST-S2-H2-4G

SEQ ID NO:56 is the determined cDNA sequence for LST-S2-H2-3H

SEQ ID NO:57 is the determined cDNA sequence for LST-S2-H2-5G

SEQ ID NO:58 is the determined cDNA sequence for LST-S2-H2-9B

SEQ ID NO:59 is the determined cDNA sequence for LST-S2-H2-10H

SEQ ID NO:60 is the determined cDNA sequence for LST-S2-H2-12D

SEQ ID NO: 61 is the determined cDNA sequence for LST-S3-2

SEQ ID NO: 62 is the determined cDNA sequence for LST-S3-4

SEQ ID NO: 63 is the determined cDNA sequence for LST-S3-7

SEQ ID NO: 64 is the determined cDNA sequence for LST-S3-8

SEQ ID NO: 65 is the determined cDNA sequence for LST-S3-12

SEQ ID NO: 66 is the determined cDNA sequence for LST-S3-13

SEQ ID NO: 67 is the determined cDNA sequence for LST-S3-14

SEQ ID NO: 68 is the determined cDNA sequence for LST-S3-16

SEQ ID NO: 69 is the determined cDNA sequence for LST-S3-21

SEQ ID NO: 70 is the determined cDNA sequence for LST-S3-22

SEQ ID NO: 71 is the determined cDNA sequence for LST-S1-7

SEQ ID NO: 72 is the determined cDNA sequence for LST-S1-A-1E

SEQ ID NO: 73 is the determined cDNA sequence for LST-S1-A-1G

SEQ ID NO: 74 is the determined cDNA sequence for LST-S1-A-3E

SEQ ID NO: 75 is the determined cDNA sequence for LST-S1-A-4E

SEQ ID NO: 76 is the determined cDNA sequence for LST-S1-A-6D

SEQ ID NO: 77 is the determined cDNA sequence for LST-S1-A-8D

SEQ ID NO: 78 is the determined cDNA sequence for LST-S1-A-10A

SEQ ID NO: 79 is the determined cDNA sequence for LST-S1-A-10C

SEQ ID NO: 80 is the determined cDNA sequence for LST-S1-A-9D

SEQ ID NO: 81 is the determined cDNA sequence for LST-S1-A-10D

SEQ ID NO: 82 is the determined cDNA sequence for LST-S1-A-9H

SEQ ID NO: 83 is the determined cDNA sequence for LST-S1-A-11D

SEQ ID NO: 84 is the determined cDNA sequence for LST-S1-A-12D

SEQ ID NO: 85 is the determined cDNA sequence for LST-S1-A-11E

SEQ ID NO: 86 is the determined cDNA sequence for LST-S1-A-12E

SEQ ID NO: 87 is the determined cDNA sequence for L513S (T3).

SEQ ID NO: 88 is the determined cDNA sequence for L513S contig 1.

SEQ ID NO: 89 is a first determined cDNA sequence for L514S.

SEQ ID NO: 90 is a second determined cDNA sequence for L514S.

SEQ ID NO: 91 is a first determined cDNA sequence for L516S.

SEQ ID NO: 92 is a second determined cDNA sequence for L516S.

SEQ ID NO: 93 is the determined cDNA sequence for L517S.

SEQ ID NO: 94 is the extended cDNA sequence for LST-S1-169 (also known as L519S).

SEQ ID NO: 95 is a first determined cDNA sequence for L520S.

SEQ ID NO: 96 is a second determined cDNA sequence for L520S.

SEQ ID NO: 97 is a first determined cDNA sequence for L521S.

SEQ ID NO: 98 is a second determined cDNA sequence for L521S.

SEQ ID NO: 99 is the determined cDNA sequence for L522S.

SEQ ID NO: 100 is the determined cDNA sequence for L523S.

SEQ ID NO: 101 is the determined cDNA sequence for L524S.

SEQ ID NO: 102 is the determined cDNA sequence for L525S

SEQ ID NO: 103 is the determined cDNA sequence for L526S.

SEQ ID NO: 104 is the determined cDNA sequence for L5275S.

SEQ ID NO: 105 is the determined cDNA sequence for L528S.

SEQ ID NO: 106 is the determined cDNA sequence for L529S.

SEQ ID NO: 107 is a first determined cDNA sequence for L530S.

SEQ ID NO: 108 is a second determined cDNA sequence for L530S.

SEQ ID NO: 109 is the determined full-length cDNA sequence for L531S short form

SEQ ID NO: 110 is the amino acid sequence encoded by SEQ ID NO: 109.

SEQ ID NO: 111 is the determined full-length cDNA sequence for L531S long form

SEQ ID NO: 112 is the amino acid sequence encoded by SEQ ID NO: 111.

SEQ ID NO: 113 is the determined full-length cDNA sequence for L520S.

SEQ ID NO: 114 is the amino acid sequence encoded by SEQ ID NO: 113.

SEQ ID NO: 115 is the determined cDNA sequence for contig 1.

SEQ ID NO: 116 is the determined cDNA sequence for contig 3.

SEQ ID NO: 117 is the determined cDNA sequence for contig 4.

SEQ ID NO: 118 is the determined cDNA sequence for contig 5.

SEQ ID NO: 119 is the determined cDNA sequence for contig 7.

SEQ ID NO: 120 is the determined cDNA sequence for contig 8.

SEQ ID NO: 121 is the determined cDNA sequence for contig 9.

SEQ ID NO: 122 is the determined cDNA sequence for contig 10.

SEQ ID NO: 123 is the determined cDNA sequence for contig 12.

SEQ ID NO: 124 is the determined cDNA sequence for contig 11.

SEQ ID NO: 125 is the determined cDNA sequence for contig 13 (also known as L761P).

SEQ ID NO: 126 is the determined cDNA sequence for contig 15.

SEQ ID NO: 127 is the determined cDNA sequence for contig 16.

SEQ ID NO: 128 is the determined cDNA sequence for contig 17.

SEQ ID NO: 129 is the determined cDNA sequence for contig 19.

SEQ ID NO: 130 is the determined cDNA sequence for contig 20.

SEQ ID NO: 131 is the determined cDNA sequence for contig 22.

SEQ ID NO: 132 is the determined cDNA sequence for contig 24.

SEQ ID NO: 133 is the determined cDNA sequence for contig 29.

SEQ ID NO: 134 is the determined cDNA sequence for contig 31.

SEQ ID NO: 135 is the determined cDNA sequence for contig 33.

SEQ ID NO: 136 is the determined cDNA sequence for contig 38.

SEQ ID NO: 137 is the determined cDNA sequence for contig 39.

SEQ ID NO: 138 is the determined cDNA sequence for contig 41.

SEQ ID NO: 139 is the determined cDNA sequence for contig 43.

SEQ ID NO: 140 is the determined cDNA sequence for contig 44.

SEQ ID NO: 141 is the determined cDNA sequence for contig 45.

SEQ ID NO: 142 is the determined cDNA sequence for contig 47.

SEQ ID NO: 143 is the determined cDNA sequence for contig 48.

SEQ ID NO: 144 is the determined cDNA sequence for contig 49.

SEQ ID NO: 145 is the determined cDNA sequence for contig 50.

SEQ ID NO: 146 is the determined cDNA sequence for contig 53.

SEQ ID NO: 147 is the determined cDNA sequence for contig 54.

SEQ ID NO: 148 is the determined cDNA sequence for contig 56.

SEQ ID NO: 149 is the determined cDNA sequence for contig 57.

SEQ ID NO: 150 is the determined cDNA sequence for contig 58.

SEQ ID NO: 151 is the full-length cDNA sequence for L530S.

SEQ ID NO: 152 is the amino acid sequence encoded by SEQ ID NO: 151

SEQ ID NO: 153 is the full-length cDNA sequence of a first variant of L514S

SEQ ID NO: 154 is the full-length cDNA sequence of a second variant of L514S

SEQ ID NO: 155 is the amino acid sequence encoded by SEQ ID NO: 153.

SEQ ID NO: 156 is the amino acid sequence encoded by SEQ ID NO: 154.

SEQ ID NO: 157 is the determined cDNA sequence for contig 59.

SEQ ID NO: 158 is the full-length cDNA sequence for L763P (also referred to as contig 22).

SEQ ID NO: 159 is the amino acid sequence encoded by SEQ ID NO: 158.

SEQ ID NO: 160 is the full-length cDNA sequence for L762P (also referred to as contig 17).

SEQ ID NO: 161 is the amino acid sequence encoded by SEQ ID NO: 160.

SEQ ID NO: 162 is the determined cDNA sequence for L515S.

SEQ ID NO: 163 is the full-length cDNA sequence of a first variant of L524S.

SEQ ID NO: 164 is the full-length cDNA sequence of a second variant of L524S.

SEQ ID NO: 165 is the amino acid sequence encoded by SEQ ID NO: 163.

SEQ ID NO: 166 is the amino acid sequence encoded by SEQ ID NO: 164.

SEQ ID NO: 167 is the full-length cDNA sequence of a first variant of L762P.

SEQ ID NO: 168 is the full-length cDNA sequence of a second variant of L762P.

SEQ ID NO: 169 is the amino acid sequence encoded by SEQ ID NO: 167.

SEQ ID NO: 170 is the amino acid sequence encoded by SEQ ID NO: 168.

SEQ ID NO: 171 is the full-length cDNA sequence for L773P (also referred to as contig 56).

SEQ ID NO: 172 is the amino acid sequence encoded by SEQ ID NO: 171.

SEQ ID NO: 173 is an extended cDNA sequence for L519S.

SEQ ID NO: 174 is the amino acid sequence encoded by SEQ ID NO: 174.

SEQ ID NO: 175 is the full-length cDNA sequence for L523S.

SEQ ID NO: 176 is the amino acid sequence encoded by SEQ ID NO: 175.

SEQ ID NO: 177 is the determined cDNA sequence for LST-sub5-7A.

SEQ ID NO: 178 is the determined cDNA sequence for LST-sub5-8G.

SEQ ID NO: 179 is the determined cDNA sequence for LST-sub5-8H.

SEQ ID NO: 180 is the determined cDNA sequence for LST-sub5-10B.

SEQ ID NO: 181 is the determined cDNA sequence for LST-sub5-10H.

SEQ ID NO: 182 is the determined cDNA sequence for LST-sub5-12B.

SEQ ID NO: 183 is the determined cDNA sequence for LST-sub5-11C.

SEQ ID NO: 184 is the determined cDNA sequence for LST-sub6-1c.

SEQ ID NO: 185 is the determined cDNA sequence for LST-sub6-2f.

SEQ ID NO: 186 is the determined cDNA sequence for LST-sub6-2G.

SEQ ID NO: 187 is the determined cDNA sequence for LST-sub6-4d.

SEQ ID NO: 188 is the determined cDNA sequence for LST-sub6-4e.

SEQ ID NO: 189 is the determined cDNA sequence for LST-sub6-4f.

SEQ ID NO: 190 is the determined cDNA sequence for LST-sub6-3h.

SEQ ID NO: 191 is the determined cDNA sequence for LST-sub6-5d.

SEQ ID NO: 192 is the determined cDNA sequence for LST-sub6-5h.

SEQ ID NO: 193 is the determined cDNA sequence for LST-sub6-6h.

SEQ ID NO: 194 is the determined cDNA sequence for LST-sub6-7a.

SEQ ID NO: 195 is the determined cDNA sequence for LST-sub6-8a.

SEQ ID NO: 196 is the determined cDNA sequence for LST-sub6-7d.

SEQ ID NO: 197 is the determined cDNA sequence for LST-sub6-7e.

SEQ ID NO: 198 is the determined cDNA sequence for LST-sub6-8e.

SEQ ID NO: 199 is the determined cDNA sequence for LST-sub6-7g.

SEQ ID NO: 200 is the determined cDNA sequence for LST-sub6-9f.

SEQ ID NO: 201 is the determined cDNA sequence for LST-sub6-9h.

SEQ ID NO: 202 is the determined cDNA sequence for LST-sub6-11b.

SEQ ID NO: 203 is the determined cDNA sequence for LST-sub6-11c.

SEQ ID NO: 204 is the determined cDNA sequence for LST-sub6-12c.

SEQ ID NO: 205 is the determined cDNA sequence for LST-sub6-12e.

SEQ ID NO: 206 is the determined cDNA sequence for LST-sub6-12f.

SEQ ID NO: 207 is the determined cDNA sequence for LST-sub6-11g.

SEQ ID NO: 208 is the determined cDNA sequence for LST-sub6-12g.

SEQ ID NO: 209 is the determined cDNA sequence for LST-sub6-12h.

SEQ ID NO: 210 is the determined cDNA sequence for LST-sub6-II-1a.

SEQ ID NO: 211 is the determined cDNA sequence for LST-sub6-II-2b.

SEQ ID NO: 212 is the determined cDNA sequence for LST-sub6-II-2g.

SEQ ID NO: 213 is the determined cDNA sequence for LST-sub6-II-1h.

SEQ ID NO: 214 is the determined cDNA sequence for LST-sub6-II-4a.

SEQ ID NO: 215 is the determined cDNA sequence for LST-sub6-II-4b.

SEQ ID NO: 216 is the determined cDNA sequence for LST-sub6-II-3e.

SEQ ID NO: 217 is the determined cDNA sequence for LST-sub6-II-4f

SEQ ID NO: 218 is the determined cDNA sequence for LST-sub6-II-4g.

SEQ ID NO: 219 is the determined cDNA sequence for LST-sub6-II-4h.

SEQ ID NO: 220 is the determined cDNA sequence for LST-sub6-II-5c.

SEQ ID NO: 221 is the determined cDNA sequence for LST-sub6-II-5e.

SEQ ID NO: 222 is the determined cDNA sequence for LST-sub6-II-6f.

SEQ ID NO: 223 is the determined cDNA sequence for LST-sub6-II-5g.

SEQ ID NO: 224 is the determined cDNA sequence for LST-sub6-II-6g.

SEQ ID NO: 225 is the amino acid sequence for L528S.

SEQ ID NO: 226–251 are synthetic peptides derived from L762P.

SEQ ID NO: 252 is the expressed amino acid sequence of L514S.

SEQ ID NO: 253 is the DNA sequence corresponding to SEQ ID NO: 252.

SEQ ID NO: 254 is the DNA sequence of a L762P expression construct.

SEQ ID NO: 255 is the determined cDNA sequence for clone 23785.

SEQ ID NO: 256 is the determined cDNA sequence for clone 23786.

SEQ ID NO: 257 is the determined cDNA sequence for clone 23788.

SEQ ID NO: 258 is the determined cDNA sequence for clone 23790.

SEQ ID NO: 259 is the determined cDNA sequence for clone 23793.

SEQ ID NO: 260 is the determined cDNA sequence for clone 23794.

SEQ ID NO: 261 is the determined cDNA sequence for clone 23795.

SEQ ID NO: 262 is the determined cDNA sequence for clone 23796.

SEQ ID NO: 263 is the determined cDNA sequence for clone 23797.

SEQ ID NO: 264 is the determined cDNA sequence for clone 23798.

SEQ ID NO: 265 is the determined cDNA sequence for clone 23799.

SEQ ID NO: 266 is the determined cDNA sequence for clone 23800.

SEQ ID NO: 267 is the determined cDNA sequence for clone 23802.

SEQ ID NO: 268 is the determined cDNA sequence for clone 23803.

SEQ ID NO: 269 is the determined cDNA sequence for clone 23804.

SEQ ID NO: 270 is the determined cDNA sequence for clone 23805.

SEQ ID NO: 271 is the determined cDNA sequence for clone 23806.

SEQ ID NO: 272 is the determined cDNA sequence for clone 23807.

SEQ ID NO: 273 is the determined cDNA sequence for clone 23808.

SEQ ID NO: 274 is the determined cDNA sequence for clone 23809.

SEQ ID NO: 275 is the determined cDNA sequence for clone 23810.

SEQ ID NO: 276 is the determined cDNA sequence for clone 23811.

SEQ ID NO: 277 is the determined cDNA sequence for clone 23812.

SEQ ID NO: 278 is the determined cDNA sequence for clone 23813.

SEQ ID NO: 279 is the determined cDNA sequence for clone 23815.

SEQ ID NO: 280 is the determined cDNA sequence for clone 25298.

SEQ ID NO: 281 is the determined cDNA sequence for clone 25299.

SEQ ID NO: 282 is the determined cDNA sequence for clone 25300.

SEQ ID NO: 283 is the determined cDNA sequence for clone 25301

SEQ ID NO: 284 is the determined cDNA sequence for clone 25304

SEQ ID NO: 285 is the determined cDNA sequence for clone 25309.

SEQ ID NO: 286 is the determined cDNA sequence for clone 25312.

SEQ ID NO: 287 is the determined cDNA sequence for clone 25317.

SEQ ID NO:288 is the determined cDNA sequence for clone 25321.

SEQ ID NO:289 is the determined cDNA sequence for clone 25323.

SEQ ID NO:290 is the determined cDNA sequence for clone 25327.

SEQ ID NO:291 is the determined cDNA sequence for clone 25328.

SEQ ID NO:292 is the determined cDNA sequence for clone 25332.

SEQ ID NO:293 is the determined cDNA sequence for clone 25333.

SEQ ID NO:294 is the determined cDNA sequence for clone 25336.

SEQ ID NO:295 is the determined cDNA sequence for clone 25340.

SEQ ID NO:296 is the determined cDNA sequence for clone 25342.

SEQ ID NO:297 is the determined cDNA sequence for clone 25356.

SEQ ID NO:298 is the determined cDNA sequence for clone 25357.

SEQ ID NO:299 is the determined cDNA sequence for clone 25361.

SEQ ID NO:300 is the determined cDNA sequence for clone 25363.

SEQ ID NO:301 is the determined cDNA sequence for clone 25397.

SEQ ID NO:302 is the determined cDNA sequence for clone 25402.

SEQ ID NO:303 is the determined cDNA sequence for clone 25403.

SEQ ID NO:304 is the determined cDNA sequence for clone 25405.

SEQ ID NO:305 is the determined cDNA sequence for clone 25407.

SEQ ID NO:306 is the determined cDNA sequence for clone 25409.

SEQ ID NO:307 is the determined cDNA sequence for clone 25396.

SEQ ID NO:308 is the determined cDNA sequence for clone 25414.

SEQ ID NO:309 is the determined cDNA sequence for clone 25410.

SEQ ID NO:310 is the determined cDNA sequence for clone 25406.

SEQ ID NO:311 is the determined cDNA sequence for clone 25306.

SEQ ID NO:312 is the determined cDNA sequence for clone 25362.

SEQ ID NO:313 is the determined cDNA sequence for clone 25360.

SEQ ID NO:314 is the determined cDNA sequence for clone 25398.

SEQ ID NO:315 is the determined cDNA sequence for clone 25355.

SEQ ID NO:316 is the determined cDNA sequence for clone 25351.

SEQ ID NO:317 is the determined cDNA sequence for clone 25331.

SEQ ID NO:318 is the determined cDNA sequence for clone 25338.

SEQ ID NO:319 is the determined cDNA sequence for clone 25335.

SEQ ID NO:320 is the determined cDNA sequence for clone 25329.

SEQ ID NO:321 is the determined cDNA sequence for clone 25324

SEQ ID NO:322 is the determined cDNA sequence for clone 25322.

SEQ ID NO:323 is the determined cDNA sequence for clone 25319.

SEQ ID NO:324 is the determined cDNA sequence for clone 25316.

SEQ ID NO:325 is the determined cDNA sequence for clone 25311.

SEQ ID NO:326 is the determined cDNA sequence for clone 25310.

SEQ ID NO:327 is the determined cDNA sequence for clone 25302.

SEQ ID NO:328 is the determined cDNA sequence for clone 25315.

SEQ ID NO:329 is the determined cDNA sequence for clone 25308.

SEQ ID NO:330 is the determined cDNA sequence for clone 25303.

SEQ ID NO:331–337 are the cDNA sequences of isoforms of the p53 tumor suppressor homologue, p63 (also referred to as L530S).

SEQ ID NO:338–344 are the amino acid sequences encoded by SEQ ID NO:331–337, respectively SEQ ID NO:345 is a second cDNA sequence for the antigen L763P.

SEQ ID NO:346 is the amino acid sequence encoded by the sequence of SEQ ID NO: 345.

SEQ ID NO:347 is a determined full-length cDNA sequence for L523S.

SEQ ID NO:348 is the amino acid sequence encoded by SEQ ID NO: 347.

SEQ ID NO:349 is the cDNA sequence encoding the N-terminal portion of L773P.

SEQ ID NO:350 is the amino acid sequence of the N-terminal portion of L773P.

SEQ ID NO:351 is the DNA sequence for a fusion of Ra12 and the N-terminal portion of L763P.

SEQ ID NO:352 is the amino acid sequence of the fusion of Ra12 and the N-terminal portion of L763P.

SEQ ID NO:353 is the DNA sequence for a fusion of Ra12 and the C-terminal portion of L763P.

SEQ ID NO:354 is the amino acid sequence of the fusion of Ra12 and the C-terminal portion of L763P.

SEQ ID NO:355 is a primer.

SEQ ID NO:356 is a primer.

SEQ ID NO:357 is the protein sequence of expressed recombinant L762P.

SEQ ID NO:358 is the DNA sequence of expressed recombinant L762P.

SEQ ID NO:359 is a primer.

SEQ ID NO:360 is a primer.

SEQ ID NO:361 is the protein sequence of expressed recombinant L773P A.

SEQ ID NO:362 is the DNA sequence of expressed recombinant L773P A.

SEQ ID NO:363 is an epitope derived from clone L773P polypeptide.

SEQ ID NO:364 is a polynucleotide encoding the polypeptide of SEQ ID NO:363.

SEQ ID NO:365 is an epitope derived from clone L773P polypeptide.

SEQ ID NO:366 is a polynucleotide encoding the polypeptide of SEQ ID NO:365.

SEQ ID NO:367 is an epitope consisting of amino acids 571–590 of SEQ ID NO:161, clone L762P.

SEQ ID NO:368 is the full-length DNA sequence for contig 13 (SEQ ID NO:125), also referred to as L761P.

SEQ ID NO:369 is the protein sequence encoded by the DNA sequence of SEQ ID NO:368.

SEQ ID NO:370 is an L762P DNA sequence from nucleotides 2071–2130.

SEQ ID NO:371 is an L762P DNA sequence from nucleotides 1441–1500.

SEQ ID NO:372 is an L762P DNA sequence from nucleotides 1936–1955.

SEQ ID NO:373 is an L762P DNA sequence from nucleotides 2620–2679.

SEQ ID NO:374 is an L762P DNA sequence from nucleotides 1801–1860.

SEQ ID NO:375 is an L762P DNA sequence from nucleotides 1531–1591.

SEQ ID NO:376 is the amino acid sequence of the L762P peptide encoded by SEQ ID NO:373.

SEQ ID NO:377 is the amino acid sequence of the L762P peptide encoded by SEQ ID NO:370.

SEQ ID NO:378 is the amino acid sequence of the L762P peptide encoded by SEQ ID NO:372.

SEQ ID NO:379 is the amino acid sequence of the L762P peptide encoded by SEQ ID NO:374.

SEQ ID NO:380 is the amino acid sequence of the L762P peptide encoded by SEQ ID NO:371.

SEQ ID NO:381 is the amino acid sequence of the L762P peptide encoded by SEQ ID NO:375.

SEQ ID NO:382 is the amino acid sequence of an epitope of L762P.

SEQ ID NO:383–386 are PCR primers.

SEQ ID NO:387–395 are the amino acid sequences of L773P peptides.

SEQ ID NO:396–419 are the amino acid sequences of L523S peptides.

SEQ ID NO:420 is the determined cDNA sequence for clone #19014.

SEQ ID NO:421 is the forward primer PDM-278 for the L514S-13160 coding region.

SEQ ID NO:422 is the reverse primer PDM-278 for the L514S-13160 coding region.

SEQ ID NO:423 is the amino acid sequence for the expressed recombinant L514S.

SEQ ID NO:424 is the DNA coding sequence for the recombinant L514S.

SEQ ID NO:425 is the forward primer PDM-414 for the L523S coding region.

SEQ ID NO:426 is the reverse primer PDM-414 for the L523S coding region.

SEQ ID NO:427 is the amino acid sequence for the expressed recombinant L523S.

SEQ ID NO:428 is the DNA coding sequence for the recombinant L523S.

SEQ ID NO:429 is the reverse primer PDM-279 for the L762PA coding region.

SEQ ID NO:430 is the amino acid sequence for the expressed recombinant L762PA.

SEQ ID NO:431 is the DNA coding sequence for the recombinant L762PA.

SEQ ID NO:432 is the reverse primer PDM-300 for the L773P coding region.

SEQ ID NO:433 is the amino acid sequence of the expressed recombinant L773P.

SEQ ID NO:434 is the DNA coding sequence for the recombinant L773P.

SEQ ID NO:435 is the forward primer for TCR Valpha8.

SEQ ID NO:436 is the reverse primer for TCR Valpha8.

SEQ ID NO:437 is the forward primer for TCR Vbeta8.

SEQ ID NO:438 is the reverse primer for TCR Vbeta8.

SEQ ID NO:439 is the TCR Valpha DNA sequence of the TCR clone specific for the lung antigen L762P.

SEQ ID NO:440 is the TCR Vbeta DNA sequence of the TCR clone specific for the lung antigen L762P.

SEQ ID NO:441 is the amino acid sequence of L763 peptide #2684.

SEQ ID NO:442 is the predicted full-length cDNA for the cloned partial sequence of clone L529S (SEQ ID NO:106).

SEQ ID NO:443 is the deduced amino acid sequence encoded by SEQ ID NO:442.

SEQ ID NO:444 is the forward primer PDM-734 for the coding region of clone L523S.

SEQ ID NO:445 is the reverse primer PDM-735 for the coding region of clone L523S.

SEQ ID NO:446 is the amino acid sequence for the expressed recombinant L523S.

SEQ ID NO:447 is the DNA coding sequence for the recombinant L523S.

SEQ ID NO:448 is another forward primer PDM-733 for the coding region of clone L523S.

SEQ ID NO:449 is the amino acid sequence for a second expressed recombinant L523S.

SEQ ID NO:450 is the DNA coding sequence for a second recombinant L523S.

SEQ ID NO:451 corresponds to amino acids 86–110, an epitope of L514S-specific in the generation of antibodies.

SEQ ID NO:452 corresponds to amino acids 21–45, an epitope of L514S-specific in the generation of antibodies.

SEQ ID NO:453 corresponds to amino acids 121–135, an epitope of L514S-specific in the generation of antibodies.

SEQ ID NO:454 corresponds to amino acids 440–460, an epitope of L523S-specific in the generation of antibodies.

SEQ ID NO:455 corresponds to amino acids 156–175, an epitope of L523S-specific in the generation of antibodies.

SEQ ID NO:456 corresponds to amino acids 326–345, an epitope of L523S-specific in the generation of antibodies.

SEQ ID NO:457 corresponds to amino acids 40–59, an epitope of L523S-specific in the generation of antibodies.

SEQ ID NO:458 corresponds to amino acids 80–99, an epitope of L523S-specific in the generation of antibodies.

SEQ ID NO:459 corresponds to amino acids 160–179, an epitope of L523S-specific in the generation of antibodies.

SEQ ID NO:460 corresponds to amino acids 180–199, an epitope of L523S-specific in the generation of antibodies.

SEQ ID NO:461 corresponds to amino acids 320–339, an epitope of L523S-specific in the generation of antibodies.

SEQ ID NO:462 corresponds to amino acids 340–359, an epitope of L523S-specific in the generation of antibodies.

SEQ ID NO:463 corresponds to amino acids 370–389, an epitope of L523S-specific in the generation of antibodies.

SEQ ID NO:464 corresponds to amino acids 380–399, an epitope of L523S-specific in the generation of antibodies.

SEQ ID NO:465 corresponds to amino acids 37–55, an epitope of L523S-recognized by the L523S-specific CTL line 6B1.

SEQ ID NO:466 corresponds to amino acids 41–51, the mapped antigenic epitope of L523S-recognized by the L523S-specific CTL line 6B1.

SEQ ID NO:467 corresponds to the DNA sequence which encodes SEQ ID NO:466.

SEQ ID NO:468 corresponds to the amino acids of peptide 16, 17 of hL523S.

SEQ ID NO:469 corresponds to the amino acids of peptide 16, 17 of mL523S

DETAILED DESCRIPTION OF THE INVENTION

The present invention is directed generally to compositions and their use in the therapy and diagnosis of cancer, particularly lung cancer. As described further below, illustrative compositions of the present invention include, but are not restricted to, polypeptides, particularly immunogenic polypeptides, polynucleotides encoding such polypeptides, antibodies and other binding agents, antigen presenting cells (APCs) and immune system cells (e.g., T cells).

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

All publications, patents and patent applications cited herein, whether supra or infra, are hereby incorporated by reference in their entirety.

As used in this specification and the appended claims, the singular forms “a,” “an” and “the” include plural references unless the content clearly dictates otherwise.

Polypeptide Compositions

As used herein, the term “polypeptide” “is used in its conventional meaning, i.e., as a sequence of amino acids. The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising epitopes, i.e., antigenic determinants substantially responsible for the immunogenic properties of a polypeptide and being capable of evoking an immune response.

Particularly illustrative polypeptides of the present invention comprise those encoded by a polynucleotide sequence set forth in any one of SEQ ID NO:1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168, 171, 179, 182, 184–186, 188–191, 193, 194, 198–207, 209, 210, 213, 214, 217, 220–224, 253–337, 345, 347, 349, 358, 362, 364, 365, 368, 370–375, 420, 424, 428, 431, 434, 442, 447, 450 and 467, or a sequence that hybridizes under moderately stringent conditions, or, alternatively, under highly stringent conditions, to a polynucleotide sequence set forth in any one of SEQ ID NO:1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168, 171, 179, 182, 184–186, 188–191, 193, 194, 198–207, 209, 210, 213, 214, 217, 220–224, 253–337, 345, 347, 349, 358, 362, 364, 365, 368, 370–375, 420, 424, 428, 431, 434, 442, 447, 450 and 467. Certain illustrative polypeptides of the invention comprise amino acid sequences as set forth in any one of SEQ ID NO:152, 155, 156, 165, 166, 169, 170, 172, 174, 176, 226–252, 338–344, 346, 350, 357, 361, 363, 365, 367, 369, 376–382, 387–419, 423, 427, 430, 433, 441, 443, 446, 449, 451–466 and 468–469.

The polypeptides of the present invention are sometimes herein referred to as lung tumor proteins or lung tumor polypeptides, as an indication that their identification has been based at least in part upon their increased levels of expression in lung tumor samples. Thus, a “lung tumor polypeptide” or “lung tumor protein,” refers generally to a polypeptide sequence of the present invention, or a polynucleotide sequence encoding such a polypeptide, that is expressed in a substantial proportion of lung tumor samples, for example preferably greater than about 20%, more preferably greater than about 30%, and most preferably greater than about 50% or more of lung tumor samples tested, at a level that is at least two fold, and preferably at least five fold, greater than the level of expression in normal tissues, as determined using a representative assay provided herein. A lung tumor polypeptide sequence of the invention, based upon its increased level of expression in tumor cells, has particular utility both as a diagnostic marker as well as a therapeutic target, as further described below.

In certain preferred embodiments, the polypeptides of the invention are immunogenic, i.e., they react detectably within an immunoassay (such as an ELISA or T-cell stimulation assay) with antisera and/or T-cells from a patient with lung cancer. Screening for immunogenic activity can be performed using techniques well known to the skilled artisan. For example, such screens can be performed using methods such as those described in Harlow and Lane, *Antibodies: A Laboratory Manual*, Cold Spring Harbor Laboratory, 1988. In one illustrative example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As would be recognized by the skilled artisan, immunogenic portions of the polypeptides disclosed herein are also encompassed by the present invention. An "immunogenic portion," as used herein, is a fragment of an immunogenic polypeptide of the invention that itself is immunologically reactive (i.e., specifically binds) with the B-cells and/or T-cell surface antigen receptors that recognize the polypeptide. Immunogenic portions may generally be identified using well known techniques, such as those summarized in Paul, *Fundamental Immunology,* 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well-known techniques.

In one preferred embodiment, an immunogenic portion of a polypeptide of the present invention is a portion that reacts with antisera and/or T-cells at a level that is not substantially less than the reactivity of the full-length polypeptide (e.g., in an ELISA and/or T-cell reactivity assay). Preferably, the level of immunogenic activity of the immunogenic portion is at least about 50%, preferably at least about 70% and most preferably greater than about 90% of the immunogenicity for the full-length polypeptide. In some instances, preferred immunogenic portions will be identified that have a level of immunogenic activity greater than that of the corresponding full-length polypeptide, e.g., having greater than about 100% or 150% or more immunogenic activity.

In certain other embodiments, illustrative immunogenic portions may include peptides in which an N-terminal leader sequence and/or transmembrane domain have been deleted. Other illustrative immunogenic portions will contain a small N- and/or C-terminal deletion (e.g., 1–30 amino acids, preferably 5–15 amino acids), relative to the mature protein.

In another embodiment, a polypeptide composition of the invention may also comprise one or more polypeptides that are immunologically reactive with T cells and/or antibodies generated against a polypeptide of the invention, particularly a polypeptide having an amino acid sequence disclosed herein, or to an immunogenic fragment or variant thereof.

In another embodiment of the invention, polypeptides are provided that comprise one or more polypeptides that are capable of eliciting T cells and/or antibodies that are immunologically reactive with one or more polypeptides described herein, or one or more polypeptides encoded by contiguous nucleic acid sequences contained in the polynucleotide sequences disclosed herein, or immunogenic fragments or variants thereof, or to one or more nucleic acid sequences which hybridize to one or more of these sequences under conditions of moderate to high stringency.

The present invention, in another aspect, provides polypeptide fragments comprising at least about 5, 10, 15, 20, 25, 50, or 100 contiguous amino acids, or more, including all intermediate lengths, of a polypeptide compositions set forth herein, such as those set forth in SEQ ID NO:152, 155, 156, 165, 166, 169, 170, 172, 174, 176, 226–252, 338–344, 346, 350, 357, 361, 363, 365, 367, 369, 376–382 and 387–419, 441, 443, 446, 449, 451–466 and 468–469, or those encoded by a polynucleotide sequence set forth in a sequence of SEQ ID NO:1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168, 171, 179, 182, 184–186, 188–191, 193, 194, 198–207, 209, 210, 213, 214, 217, 220–224, 253–337, 345, 347, 349, 358, 362, 364, 365, 368, 370–375, 420, 424, 428, 431, 434, 442, 447, 450 and 467.

In another aspect, the present invention provides variants of the polypeptide compositions described herein. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequences set forth herein.

In one preferred embodiment, the polypeptide fragments and variants provide by the present invention are immunologically reactive with an antibody and/or T-cell that reacts with a full-length polypeptide specifically set for the herein.

In another preferred embodiment, the polypeptide fragments and variants provided by the present invention exhibit a level of immunogenic activity of at least about 50%, preferably at least about 70%, and most preferably at least about 90% or more of that exhibited by a full-length polypeptide sequence specifically set forth herein.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating their immunogenic activity as described herein and/or using any of a number of techniques well known in the art.

For example, certain illustrative variants of the polypeptides of the invention include those in which one or more portions, such as an N-terminal leader sequence or transmembrane domain, have been removed. Other illustrative variants include variants in which a small portion (e.g., 1–30 amino acids, preferably 5–15 amino acids) has been removed from the N- and/or C-terminal of the mature protein.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics, e.g., with immunogenic characteristics. When it is desired to alter the amino acid sequence of a polypeptide to create an equivalent, or even an improved, immunogenic variant or portion of a polypeptide of the invention, one skilled in the art will typically change one or more of the codons of the encoding DNA sequence according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their biological utility or activity.

TABLE 1

| Amino Acids | | Codons |
|---|---|---|
| Alanine | Ala | A GCA GCC GCG GCU |
| Cysteine | Cys | C UGC UGU |
| Aspartic acid | Asp | D GAC GAU |
| Glutamic acid | Glu | E GAA GAG |
| Phenylalanine | Phe | F UUC UUU |
| Glycine | Gly | G GGA GGC GGG GGU |
| Histidine | His | H CAC CAU |
| Isoleucine | Ile | I AUA AUC AUU |
| Lysine | Lys | K AAA AAG |
| Leucine | Leu | L UUA UUG CUA CUC CUG CUU |
| Methionine | Met | M AUG |
| Asparagine | Asn | N AAC AAU |
| Proline | Pro | P CCA CCC CCG CCU |
| Glutamine | Gln | Q CAA CAG |
| Arginine | Arg | R AGA AGG CGA CGC CGG CGU |
| Serine | Ser | S AGC AGU UCA UCC UCG UCU |
| Threonine | Thr | T ACA ACC ACG ACU |
| Valine | Val | V GUA GUC GUG GUU |
| Tryptophan | Trp | W UGG |
| Tyrosine | Tyr | Y UAC UAU |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain non-conservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726–730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389–3402 and Altschul et al. (1990) *J. Mol. Biol.* 215:403–410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one preferred approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

Within other illustrative embodiments, a polypeptide may be a fusion polypeptide that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the polypeptide or to enable the polypeptide to be targeted to desired intracellular compartments. Still further fusion partners include affinity tags, which facilitate purification of the polypeptide.

Fusion polypeptides may generally be prepared using standard techniques, including chemical conjugation. Preferably, a fusion polypeptide is expressed as a recombinant polypeptide, allowing the production of increased levels, relative to a non-fused polypeptide, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

The fusion polypeptide can comprise a polypeptide as described herein together with an unrelated immunogenic protein, such as an immunogenic protein capable of eliciting a recall response. Examples of such proteins include tetanus, tuberculosis and hepatitis proteins (see, for example, Stoute et al. *New Engl. J. Med.,* 336:86–91, 1997).

In one preferred embodiment, the immunological fusion partner is derived from a *Mycobacterium* sp., such as a *Mycobacterium* tuberculosis-derived Ra12 fragment. Ra12 compositions and methods for their use in enhancing the expression and/or immunogenicity of heterologous polynucleotide/polypeptide sequences is described in U.S. Patent Application 60/158,585, the disclosure of which is incorporated herein by reference in its entirety. Briefly, Ra12 refers to a polynucleotide region that is a subsequence of a *Mycobacterium tuberculosis* MTB32A nucleic acid. MTB32A is a serine protease of 32 KD molecular weight encoded by a gene in virulent and avirulent strains of *M. tuberculosis*. The nucleotide sequence and amino acid sequence of MTB32A have been described (for example, U.S. Patent Application 60/158,585; see also, Skeiky et al, *Infection and Immun.* (1999) 67:3998–4007, incorporated herein by reference). C-terminal fragments of the MTB32A coding sequence express at high levels and remain as a soluble polypeptides throughout the purification process. Moreover, Ra12 may enhance the immunogenicity of heterologous immunogenic polypeptides with which it is fused. One preferred Ra12 fusion polypeptide comprises a 14 KD C-terminal fragment corresponding to amino acid residues 192 to 323 of MTB32A.

Other preferred Ra12 polynucleotides generally comprise at least about 15 consecutive nucleotides, at least about 30 nucleotides, at least about 60 nucleotides, at least about 100 nucleotides, at least about 200 nucleotides, or at least about 300 nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants preferably exhibit at least about 70% identity, more preferably at least about 80% identity and most preferably at least about 90% identity to a polynucleotide sequence that encodes a native Ra12 polypeptide or a portion thereof.

Within other preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion polypeptide. A repeat portion is found in the C-terminal region starting at residue 178. A particularly preferred repeat portion incorporates residues 188–305.

Yet another illustrative embodiment involves fusion polypeptides, and the polynucleotides encoding them, wherein the fusion partner comprises a targeting signal capable of directing a polypeptide to the endosomal/lysosomal compartment, as described in U.S. Pat. No. 5,633,234. An immunogenic polypeptide of the invention, when fused with this targeting signal, will associate more efficiently with MHC class II molecules and thereby provide enhanced in vivo stimulation of $CD4^+$ T-cells specific for the polypeptide.

Polypeptides of the invention are prepared using any of a variety of well known synthetic and/or recombinant techniques, the latter of which are further described below. Polypeptides, portions and other variants generally less than about 150 amino acids can be generated by synthetic means, using techniques well known to those of ordinary skill in the art. In one illustrative example, such polypeptides are synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division (Foster City, Calif.), and may be operated according to the manufacturer's instructions.

In general, polypeptide compositions (including fusion polypeptides) of the invention are isolated. An "isolated" polypeptide is one that is removed from its original environment. For example, a naturally-occurring protein or polypeptide is isolated if it is separated from some or all of the coexisting materials in the natural system. Preferably, such polypeptides are also purified, e.g., are at least about 90% pure, more preferably at least about 95% pure and most preferably at least about 99% pure.

Polynucleotide Compositions

The present invention, in other aspects, provides polynucleotide compositions. The terms "DNA" and "polynucleotide" are used essentially interchangeably herein to refer to a DNA molecule that has been isolated free of total genomic DNA of a particular species. "Isolated," as used herein, means that a polynucleotide is substantially away from other coding sequences, and that the DNA molecule does not contain large portions of unrelated coding DNA, such as large chromosomal fragments or other functional genes or polypeptide coding regions. Of course, this refers to the DNA molecule as originally isolated, and does not exclude genes or coding regions later added to the segment by the hand of man.

As will be understood by those skilled in the art, the polynucleotide compositions of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be also recognized by the skilled artisan, polynucleotides of the invention may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a polypeptide/protein of the invention or a portion thereof) or may comprise a sequence that encodes a variant or derivative, preferably and immunogenic variant or derivative, of such a sequence.

Therefore, according to another aspect of the present invention, polynucleotide compositions are provided that comprise some or all of a polynucleotide sequence set forth in any one of SEQ ID NO:1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168, 171, 179, 182, 184–186, 188–191, 193, 194, 198–207, 209, 210, 213, 214, 217, 220–224, 253–337, 345, 347, 349, 358, 362, 364, 365, 368, 370–375, 420, 424, 428, 431, 434, 442, 447, 450 and 467, complements of a polynucleotide sequence set forth in any one of SEQ ID NO:1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168, 171, 179, 182, 184–186, 188–191, 193, 194, 198–207, 209, 210, 213, 214, 217, 220–224, 253–337, 345, 347, 349, 358, 362, 364, 365, 368, 370–375, 420, 424, 428, 431, 434, 442, 447, 450 and 467, and degenerate variants of a polynucleotide sequence set forth in any one of SEQ ID NO:1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168, 171, 179, 182, 184–186, 188–191, 193, 194, 198–207, 209, 210, 213, 214, 217, 220–224, 253–337, 345, 347, 349, 358, 362, 364, 365, 368, 370–375, 420, 424, 428, 431, 434, 442, 447, 450 and 467. In certain preferred embodiments, the polynucleotide sequences set forth herein encode immunogenic polypeptides, as described above.

In other related embodiments, the present invention provides polynucleotide variants having substantial identity to the sequences disclosed herein in SEQ ID NO:1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168, 171, 179, 182, 184–186, 188–191, 193, 194, 198–207, 209, 210, 213, 214, 217, 220–224, 253–337, 345, 347, 349, 358, 362, 364, 365, 368, 370–375, 420, 424, 428, 431, 434, 442, 447, 450 and 467, for example those comprising at least 70% sequence identity, preferably at least 75%, 80%, 85%, 90%, 95%, 96%, 97%, 98%, or 99% or higher, sequence identity compared to a polynucleotide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the immunogenicity of the polypeptide encoded by the variant polynucleotide is not substantially diminished relative to a polypeptide encoded by a polynucleotide sequence specifically set forth herein). The term "variants" should also be understood to encompasses homologous genes of xenogenic origin.

In additional embodiments, the present invention provides polynucleotide fragments comprising various lengths of contiguous stretches of sequence identical to or complementary to one or more of the sequences disclosed herein. For example, polynucleotides are provided by this invention that comprise at least about 10, 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200–500; 500–1,000, and the like.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.–60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60–65° C. or 65–70° C.

In certain preferred embodiments, the polynucleotides described above, e.g., polynucleotide variants, fragments and hybridizing sequences, encode polypeptides that are immunologically cross-reactive with a polypeptide sequence specifically set forth herein. In other preferred embodiments, such polynucleotides encode polypeptides that have a level of immunogenic activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726–730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389–3402 and Altschul et al. (1990) *J. Mol. Biol.* 215:403–410, respectively. BLAST and BLAST 2.0 can be used, for example with the parameters described herein, to determine percent sequence identity for the polynucleotides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Therefore, in another embodiment of the invention, a mutagenesis approach, such as site-specific mutagenesis, is employed for the preparation of immunogenic variants and/or derivatives of the polypeptides described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter one or more properties of the encoded polypeptide, such as the immunogenicity of a polypeptide vaccine. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants of the present invention, recursive sequence recombination, as described in U.S. Pat. No. 5,837,458, may be employed. In this approach, iterative cycles of recombination and screening or selection are performed to "evolve" individual polynucleotide variants of the invention having, for example, enhanced immunogenic activity.

In other embodiments of the present invention, the polynucleotide sequences provided herein can be advantageously used as probes or primers for nucleic acid hybridization. As such, it is contemplated that nucleic acid segments that comprise a sequence region of at least about 15 nucleotide long contiguous sequence that has the same sequence as, or is complementary to, a 15 nucleotide long contiguous sequence disclosed herein will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to a sequence of interest will enable them to be of use in detecting the presence of complementary sequences in a given sample. However, other uses are also envisioned, such as the use of the sequence information for the preparation of mutant species primers, or primers for use in preparing other genetic constructions.

Polynucleotide molecules having sequence regions consisting of contiguous nucleotide stretches of 10–14, 15–20, 30, 50, or even of 100–200 nucleotides or so (including intermediate lengths as well), identical or complementary to a polynucleotide sequence disclosed herein, are particularly contemplated as hybridization probes for use in, e.g., Southern and Northern blotting. This would allow a gene product, or fragment thereof, to be analyzed, both in diverse cell types and also in various bacterial cells. The total size of fragment, as well as the size of the complementary stretch (es), will ultimately depend on the intended use or application of the particular nucleic acid segment. Smaller fragments will generally find use in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15–25 nucleotides in length allows the formation of a duplex molecule that is both stable and selective. Molecules having contiguous complementary sequences over stretches greater than 15 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the sequences set forth herein, or to any continuous portion of the sequences, from about 15–25 nucleotides in length up to and including the full length sequence, that one wishes to utilize as a probe or primer. The choice of probe and primer sequences may be governed by various factors. For example, one may wish to employ primers from towards the termini of the total sequence.

Small polynucleotide segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

The nucleotide sequences of the invention may be used for their ability to selectively form duplex molecules with complementary stretches of the entire gene or gene fragments of interest. Depending on the application envisioned, one will typically desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by a salt concentration of from about 0.02 M to about 0.15 M salt at temperatures of from about 50° C. to about 70° C. Such selective conditions tolerate little, if any, mismatch between the probe and the template or target strand, and would be particularly suitable for isolating related sequences.

Of course, for some applications, for example, where one desires to prepare mutants employing a mutant primer strand hybridized to an underlying template, less stringent (reduced stringency) hybridization conditions will typically be needed in order to allow formation of the heteroduplex. In these circumstances, one may desire to employ salt conditions such as those of from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

According to another embodiment of the present invention, polynucleotide compositions comprising antisense oligonucleotides are provided. Antisense oligonucleotides have been demonstrated to be effective and targeted inhibitors of protein synthesis, and, consequently, provide a therapeutic approach by which a disease can be treated by inhibiting the synthesis of proteins that contribute to the disease. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (U.S. Pat. No. 5,739,119 and U.S. Pat. No. 5,759,829). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., Science. 1988 Jun. 10; 240(4858):1544–6; Vasanthakumar and Ahmed, Cancer Commun. 1989;1(4):225–32; Peris et al., Brain Res Mol Brain Res. 1998 Jun. 15; 57(2):310–20; U.S. Pat. No. 5,801,154; U.S. Pat. No. 5,789,573; U.S. Pat. No. 5,718,709 and U.S. Pat. No. 5,610,288). Antisense constructs have also been described that inhibit and can be used to treat a variety of abnormal cellular proliferations, e.g. cancer (U.S. Pat. No. 5,747,470; U.S. Pat. No. 5,591,317 and U.S. Pat. No. 5,783,683).

Therefore, in certain embodiments, the present invention provides oligonucleotide sequences that comprise all, or a portion of, any sequence that is capable of specifically binding to polynucleotide sequence described herein, or a complement thereof. In one embodiment, the antisense oligonucleotides comprise DNA or derivatives thereof. In another embodiment, the oligonucleotides comprise RNA or derivatives thereof. In a third embodiment, the oligonucleotides are modified DNAs comprising a phosphorothioated modified backbone. In a fourth embodiment, the oligonucleotide sequences comprise peptide nucleic acids or derivatives thereof. In each case, preferred compositions comprise a sequence region that is complementary, and more preferably substantially-complementary, and even more preferably, completely complementary to one or more portions of polynucleotides disclosed herein. Selection of antisense compositions specific for a given gene sequence is based upon analysis of the chosen target sequence and determination of secondary structure, $T_m$, binding energy, and relative stability. Antisense compositions may be selected based upon their relative inability to form dimers, hairpins, or other secondary structures that would reduce or prohibit specific binding to the target mRNA in a host cell. Highly preferred target regions of the mRNA, are those which are at or near the AUG translation initiation codon, and those sequences which are substantially complementary to 5' regions of the mRNA. These secondary structure analyses and target site selection considerations can be performed, for example, using v.4 of the OLIGO primer analysis software and/or the BLASTN 2.0.5 algorithm software (Altschul et al., Nucleic Acids Res. 1997, 25(17):3389–402).

The use of an antisense delivery method employing a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., Nucleic Acids Res. 1997 Jul. 15; 25(14):2730–6). It has been demonstrated that several molecules of the MPG peptide coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane.

According to another embodiment of the invention, the polynucleotide compositions described herein are used in the design and preparation of ribozyme molecules for inhibiting expression of the tumor polypeptides and proteins of the present invention in tumor cells. Ribozymes are RNA-protein complexes that cleave nucleic acids in a site-specific fashion. Ribozymes have specific catalytic domains that possess endonuclease activity (Kim and Cech, Proc Natl Acad Sci USA. 1987 December; 84(24):8788–92; Forster and Symons, Cell. 1987 Apr. 24; 49(2):211–20). For example, a large number of ribozymes accelerate phosphoester transfer reactions with a high degree of specificity, often cleaving only one of several phosphoesters in an oligonucleotide substrate (Cech et al., Cell. 1981 December; 27(3 Pt 2):487–96; Michel and Westhof, J Mol Biol. 1990 Dec. 5; 216(3):585–610; Reinhold-Hurek and Shub, Nature. 1992 May 14; 357(6374):173–6). This specificity has been attributed to the requirement that the substrate bind via specific base-pairing interactions to the internal guide sequence ("IGS") of the ribozyme prior to chemical reaction.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., Proc Natl Acad Sci USA. 1992 Aug. 15; 89(16):7305–9). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif. Examples of hammerhead motifs are described by Rossi et al. Nucleic Acids Res. 1992 Sep. 11; 20(17):4559–65. Examples of hairpin motifs are described by Hampel et al. (Eur. Pat. Appl. Publ. No. EP 0360257), Hampel and Tritz, Biochemistry 1989 Jun. 13; 28(12):4929–33; Hampel et al., Nucleic Acids Res. 1990 Jan. 25; 18(2):299–304 and U.S. Pat. No. 5,631,359. An example of the hepatitis δ virus motif is described by Perrotta and Been, Biochemistry. 1992 Dec. 1; 31(47):11843–52; an example of the RNaseP motif is described by Guerrier-Takada et al., Cell. 1983 December; 35(3 Pt 2):849–57; Neurospora VS RNA ribozyme motif is described by Collins (Saville and Collins, Cell. 1990 May 18; 61(4):685–96; Saville and Collins, Proc Natl Acad Sci USA. 1991 Oct. 1; 88(19):8826–30; Collins and Olive, Biochemistry. 1993 Mar. 23; 32(11):2795–9); and an example of the Group I intron is described in (U.S. Pat. No. 4,987,071). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

Ribozymes may be designed as described in Int. Pat. Appl. Publ. No. WO 93/23569 and Int. Pat. Appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stint. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. Appl. Publ. No. WO 94/02595 and Int. Pat. Appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells. Ribozymes expressed from such promoters have been shown to function in mammalian cells. Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

In another embodiment of the invention, peptide nucleic acids (PNAs) compositions are provided. PNA is a DNA mimic in which the nucleobases are attached to a pseudopeptide backbone (Good and Nielsen, Antisense Nucleic Acid Drug Dev. 1997 7(4) 431–37). PNA is able to be utilized in a number methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (*Trends Biotechnol* 1997 June; 15(6):224–9). As such, in certain embodiments, one may prepare PNA sequences that are complementary to one or more portions of the ACE mRNA sequence, and such PNA compositions may be used to regulate, alter, decrease, or reduce the translation of ACE-specific mRNA, and thereby alter the level of ACE activity in a host cell to which such PNA compositions have been administered.

PNAs have 2-aminoethyl-glycine linkages replacing the normal phosphodiester backbone of DNA (Nielsen et al., *Science* 1991 Dec. 6; 254(5037):1497–500; Hanvey et al., Science. 1992 Nov. 27; 258(5087):1481–5; Hyrup and Nielsen, Bioorg Med Chem. 1996 January; 4(1):5–23). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc or Fmoc protocols for solid-phase peptide synthesis, although other methods, including a modified Merrifield method, have been used.

PNA monomers or ready-made oligomers are commercially available from PerSeptive Biosystems (Framingham, Mass.). PNA syntheses by either Boc or Fmoc protocols are straightforward using manual or automated protocols (Norton et al., Bioorg Med Chem. 1995 April; 3(4):437–45). The manual protocol lends itself to the production of chemically modified PNAs or the simultaneous synthesis of families of closely related PNAs.

As with peptide synthesis. the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography, providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (for example, Norton et al., Bioorg Med Chem. 1995 April; 3(4):437–45; Petersen et al., J Pept Sci. 1995 May–June; 1(3):175–83; Orum et al., Biotechniques. 1995 September; 19(3):472–80; Footer et al., Biochemistry. 1996 Aug. 20; 35(33):10673–9; Griffith et al., Nucleic Acids Res. 1995 Aug. 11; 23(15):3003–8; Pardridge et al., Proc Natl Acad Sci USA. 1995 Jun. 6; 92(12):5592–6; Boffa et al., Proc Natl Acad Sci USA. 1995 Mar. 14; 92(6):1901–5; Gambacorti-Passerini et al., Blood. 1996 Aug. 15; 88(4):1411–7; Armitage et al., Proc Natl Acad Sci USA. 1997 Nov. 11; 94(23):12320–5; Seeger et al., Biotechniques. 1997 September; 23(3):512–7). U.S. Pat. No. 5,700,922 discusses PNA-DNA-PNA chimeric molecules and their uses in diagnostics, modulating protein in organisms, and treatment of conditions susceptible to therapeutics.

Methods of characterizing the antisense binding properties of PNAs are discussed in Rose (Anal Chem. 1993 Dec. 15; 65(24):3545–9) and Jensen et al. (Biochemistry. 1997 Apr. 22; 36(16):5072–7). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs that have been described and will be apparent to the skilled artisan include use in DNA strand invasion, antisense inhibition, mutational analysis, enhancers of transcription, nucleic acid purification, isolation of transcriptionally active genes, blocking of transcription factor binding, genome cleavage, biosensors, in situ hybridization, and the like.

Polynucleotide Identification, Characterization and Expression

Polynucleotides compositions of the present invention may be identified, prepared and/or manipulated using any of a variety of well established techniques (see generally, Sambrook et al., *Molecular Cloning: A Laboratory Manual*, Cold Spring Harbor Laboratories, Cold Spring Harbor, N.Y., 1989, and other like references). For example, a polynucleotide may be identified, as described in more detail below, by screening a microarray of cDNAs for tumor-associated expression (i.e., expression that is at least two fold greater in a tumor than in normal tissue, as determined using a representative assay provided herein). Such screens may be performed, for example, using the microarray technology of Affymetrix, Inc. (Santa Clara, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997). Alternatively, polynucleotides may be amplified from cDNA prepared from cells expressing the proteins described herein, such as tumor cells.

Many template dependent processes are available to amplify a target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Any of a number of other template dependent processes, many of which are variations of the PCR™ amplification technique, are readily known and available in the art. Illustratively, some such methods include the ligase chain reaction (referred to as LCR), described, for example, in Eur. Pat. Appl. Publ. No. 320,308 and U.S. Pat. No. 4,883,750; Qbeta Replicase, described in PCT Intl. Pat. Appl. Publ. No. PCT/US87/00880; Strand Displacement Amplification (SDA) and Repair Chain Reaction (RCR). Still other amplification methods are described in Great Britain Pat. Appl. No. 2 202 328, and in PCT Intl. Pat. Appl. Publ. No. PCT/US89/01025. Other nucleic acid amplification procedures include transcription-based amplification systems (TAS) (PCT Intl. Pat. Appl. Publ. No. WO 88/10315), including nucleic acid sequence based amplification (NASBA) and 3SR. Eur. Pat. Appl. Publ. No. 329,822 describes a nucleic acid amplification process involving cyclically synthesizing single-stranded RNA ("ssRNA"), ssDNA, and double-stranded DNA (dsDNA). PCT Intl. Pat. Appl. Publ. No. WO 89/06700 describes a nucleic acid sequence amplification scheme based on the hybridization of a promoter/primer sequence to a target single-stranded DNA ("ssDNA") followed by transcription of many RNA copies of the sequence. Other amplification methods such as "RACE" (Frohman, 1990), and "one-sided PCR" (Ohara, 1989) are also well-known to those of skill in the art.

An amplified portion of a polynucleotide of the present invention may be used to isolate a full length gene from a suitable library (e.g., a tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full length cDNA molecule can be generated by ligating suitable fragments, using well known techniques.

Alternatively, amplification techniques, such as those described above, can be useful for obtaining a full length coding sequence from a partial cDNA sequence. One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al. (1980) *Nucl. Acids Res. Symp. Ser.* 215–223. Horn, T. et al. (1980) *Nucl. Acids Res. Symp. Ser.* 225–232). Alternatively, the protein itself may be produced using chemical methods to synthesize the amino acid sequence of a polypeptide, or a portion thereof. For example, peptide synthesis can be performed using various solid-phase techniques (Roberge, J. Y. et al. (1995) *Science* 269:202–204) and automated synthesis may be achieved, for example, using the ABI 43 1A Peptide Synthesizer (Perkin Elmer, Palo Alto, Calif.).

A newly synthesized peptide may be substantially purified by preparative high performance liquid chromatography (e.g, Creighton, T. (1983) Proteins, Structures and Molecular Principles, WH Freeman and Co., New York, N.Y.) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters. may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, any of a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of .beta.-galactosidase so that a hybrid protein is produced; pIN vectors (Van Heeke, G. and S. M. Schuster (1989) *J. Biol. Chem.* 264:5503–5509); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) *Methods Enzymol.* 153:516–544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) *EMBO J.*

6:307–311. Alternatively, plant promoters such as the small subunit of RUBISCO or heat shock promoters may be used (Coruzzi, G. et al. (1984) *EMBO J.* 3:1671–1680; Broglie, R. et al. (1984) *Science* 224:838–843; and Winter, J. et al. (1991) *Results Probl. Cell Differ.* 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191–196).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia* larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* larvae in which the polypeptide of interest may be expressed (Engelhard, E. K. et al. (1994) *Proc. Natl. Acad. Sci.* 91 :3224–3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing which cleaves a "prepro" form of the protein may also be used to facilitate correct insertion, folding and/or function. Different host cells such as CHO, COS, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) *Cell* 11:223–32) and adenine phosphoribosyltransferase (Lowy, I. et al. (1990) *Cell* 22:817–23) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567–70); npt, which confers resistance to the aminoglycosides, neomycin and G-418 (Colbere-Garapin, F. et al (1981) *J. Mol. Biol.* 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) *Proc. Natl. Acad. Sci.* 85:8047–51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121–131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence may be identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (PIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; *J. Exp. Med.* 158:1211–1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, *Prot. Exp. Purif.* 3:263–281) while the enterokinase cleavage site provides a means for purifying the desired polypeptide from the fusion protein. A discussion of vectors which contain fusion proteins is provided in Kroll, D. J. et al. (1993; *DNA Cell Biol.* 12:441–453).

In addition to recombinant production methods, polypeptides of the invention, and fragments thereof, may be produced by direct peptide synthesis using solid-phase techniques (Merrifield J. (1963) *J. Am. Chem. Soc.* 85:2149–2154). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

Antibody Compositions, Fragments thereof and other Binding Agents

According to another aspect, the present invention further provides binding agents, such as antibodies and antigen-binding fragments thereof, that exhibit immunological binding to a tumor polypeptide disclosed herein, or to a portion, variant or derivative thereof. An antibody, or antigen-binding fragment thereof, is said to "specifically bind," "immunogically bind," and/or is "immunologically reactive" to a polypeptide of the invention if it reacts at a detectable level (within, for example, an ELISA assay) with the polypeptide, and does not react detectably with unrelated polypeptides under similar conditions.

Immunological binding, as used in this context, generally refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) Annual Rev. Biochem. 59:439–473.

An "antigen-binding site," or "binding portion" of an antibody refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

Binding agents may be further capable of differentiating between patients with and without a cancer, such as lung cancer, using the representative assays provided herein. For example, antibodies or other binding agents that bind to a tumor protein will preferably generate a signal indicating the presence of a cancer in at least about 20% of patients with the disease, more preferably at least about 30% of patients. Alternatively, or in addition, the antibody will generate a negative signal indicating the absence of the disease in at least about 90% of individuals without the cancer. To determine whether a binding agent satisfies this requirement, biological samples (e.g., blood, sera, sputum, urine and/or tumor biopsies) from patients with and without a cancer (as determined using standard clinical tests) may be assayed as described herein for the presence of polypeptides that bind to the binding agent. Preferably, a statistically significant number of samples with and without the disease will be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts. in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "$F(ab')_2$" fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) Proc. Nat. Acad. Sci. USA 69:2659–2662; Hochman et al. (1976) Biochem 15:2706–2710; and Ehrlich et al. (1980) Biochem 19:4091–4096.

A single chain Fv ("sFv") polypeptide is a covalently linked $V_H$::$V_L$ heterodimer which is expressed from a gene fusion including $V_H$- and $V_L$-encoding genes linked by a peptide-encoding linker. Huston et al. (1988) Proc. Nat. Acad. Sci. USA 85(16):5879–5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRS and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

A number of "humanized" antibody molecules comprising an antigen-binding site derived from a non-human immunoglobulin have been described, including chimeric antibodies having rodent V regions and their associated CDRs fused to human constant domains (Winter et al. (1991) Nature 349:293–299; Lobuglio et al. (1989) Proc. Nat. Acad. Sci. USA 86:4220–4224; Shaw et al. (1987) J Immunol. 138:4534–4538; and Brown et al. (1987) Cancer Res. 47:3577–3583), rodent CDRs grafted into a human supporting FR prior to fusion with an appropriate human antibody constant domain (Riechmann et al. (1988) Nature 332:323–327; Verhoeyen et al. (1988) Science 239:1534–1536; and Jones et al. (1986) Nature 321:522–525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site which retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al. (1990) Ann. Rev. Biochem. 59:439–473. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

The process of veneering makes use of the available sequence data for human antibody variable domains compiled by Kabat et al., in Sequences of Proteins of Immunological Interest, 4th ed., (U.S. Dept. of Health and Human Services, U.S. Government Printing Office, 1987), updates to the Kabat database, and other accessible U.S. and foreign databases (both nucleic acid and protein). Solvent accessibilities of V region amino acids can be deduced from the known three-dimensional structure for human and murine antibody fragments. There are two general steps in veneering a murine antigen-binding site. Initially, the FRs of the variable domains of an antibody molecule of interest are compared with corresponding FR sequences of human variable domains obtained from the above-identified sources. The most homologous human V regions are then compared residue by residue to corresponding murine amino acids. The residues in the murine FR which differ from the human counterpart are replaced by the residues present in the human moiety using recombinant techniques well known in the art. Residue switching is only carried out with moieties which are at least partially exposed (solvent accessible), and care is exercised in the replacement of amino acid residues which may have a significant effect on the tertiary structure of V region domains, such as proline, glycine and charged amino acids.

In this manner, the resultant "veneered" murine antigen-binding sites are thus designed to retain the murine CDR residues, the residues substantially adjacent to the CDRs, the residues identified as buried or mostly buried (solvent inaccessible), the residues believed to participate in non-covalent (e.g., electrostatic and hydrophobic) contacts between heavy and light chain domains, and the residues from conserved structural regions of the FRs which are believed to influence the "canonical" tertiary structures of the CDR loops. These design criteria are then used to prepare recombinant nucleotide sequences which combine the CDRs of both the heavy and light chain of a murine antigen-binding site into human-appearing FRs that can be used to transfect mammalian cells for the expression of recombinant human antibodies which exhibit the antigen specificity of the murine antibody molecule.

In another embodiment of the invention, monoclonal antibodies of the present invention may be coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

T Cell Compositions

The present invention, in another aspect, provides T cells specific for a tumor polypeptide disclosed herein, or for a variant or derivative thereof. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a polypeptide, polynucleotide encoding a polypeptide and/or an antigen presenting cell (APC) that expresses such a polypeptide. Such stimulation is performed under conditions and for a time sufficient to permit the generation of T cells that are specific for the polypeptide of interest. Preferably, a tumor polypeptide or polynucleotide of the invention is present within a delivery vehicle, such as a microsphere, to facilitate the generation of specific T cells.

T cells are considered to be specific for a polypeptide of the present invention if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a tumor polypeptide (100 ng/ml–100 $\mu$g/ml, preferably 200 ng/ml–25 $\mu$g/ml) for 3–7 days will typically result in at least a two fold increase in proliferation of the T cells. Contact as described above for 2–3 hours should result in activation of the T cells, as measured using standard cytokine assays in which a two fold increase in the level of cytokine release (e.g., TNF or IFN-$\gamma$) is indicative of T cell activation (see Coligan et al., Current Protocols in Immunology, vol. 1, Wiley Interscience (Greene 1998)). T cells that have been activated in response to a tumor polypeptide, polynucleotide or polypeptide-expressing APC may be $CD4^+$ and/or $CD8^+$. Tumor polypeptide-specific T cells may be expanded using standard techniques. Within preferred embodiments, the T cells are derived from a patient, a related donor or an unrelated donor, and are administered to the patient following stimulation and expansion.

For therapeutic purposes, $CD4^+$ or $CD8^+$ T cells that proliferate in response to a tumor polypeptide, polynucleotide or APC can be expanded in number either in vitro or in vivo. Proliferation of such T cells in vitro may be accomplished in a variety of ways. For example, the T cells can be re-exposed to a tumor polypeptide, or a short peptide corresponding to an immunogenic portion of such a polypeptide, with or without the addition of T cell growth factors, such as interleukin-2, and/or stimulator cells that synthesize a tumor polypeptide. Alternatively, one or more T cells that proliferate in the presence of the tumor polypeptide can be expanded in number by cloning. Methods for cloning cells are well known in the art, and include limiting dilution.

T Cell Receptor Compositions

The T cell receptor (TCR) consists of 2 different, highly variable polypeptide chains, termed the T-cell receptor $\alpha$ and $\beta$ chains, that are linked by a disulfide bond (Janeway, Travers, Walport. *Immunobiology*. Fourth Ed., 148–159. Elsevier Science Ltd/Garland Publishing. 1999). The $\alpha/\beta$ heterodimer complexes with the invariant CD3 chains at the cell membrane. This complex recognizes specific antigenic peptides bound to MHC molecules. The enormous diversity of TCR specificities is generated much like immunoglobulin diversity, through somatic gene rearrangement. The $\beta$ chain genes contain over 50 variable (V), 2 diversity (D), over 10 joining (J) segments, and 2 constant region segments (C). The $\alpha$ chain genes contain over 70 V segments, and over 60 J segments but no D segments, as well as one C segment.

During T cell development in the thymus, the D to J gene rearrangement of the β chain occurs, followed by the V gene segment rearrangement to the DJ. This functional $VDJ_β$ exon is transcribed and spliced to join to a $C_β$. For the a chain, a $V_α$ gene segment rearranges to a $J_α$ gene segment to create the functional exon that is then transcribed and spliced to the $C_α$. Diversity is further increased during the recombination process by the random addition of P and N-nucleotides between the V, D, and J segments of the β chain and between the V and J segments in the α chain (Janeway, Travers, Walport. *Immunobiology*. Fourth Ed., 98 and 150. Elsevier Science Ltd/Garland Publishing. 1999).

The present invention, in another aspect, provides TCRs specific for a polypeptide disclosed herein, or for a variant or derivative thereof. In accordance with the present invention, polynucleotide and amino acid sequences are provided for the V-J or V-D-J junctional regions or parts thereof for the alpha and beta chains of the T-cell receptor which recognize tumor polypeptides described herein. In general, this aspect of the invention relates to T-cell receptors which recognize or bind tumor polypeptides presented in the context of MHC. In a preferred embodiment the tumor antigens recognized by the T-cell receptors comprise a polypeptide of the present invention. For example, cDNA encoding a TCR specific for a tumor peptide can be isolated from T cells specific for a tumor polypeptide using standard molecular biological and recombinant DNA techniques.

This invention further includes the T-cell receptors or analogs thereof having substantially the same function or activity as the T-cell receptors of this invention which recognize or bind tumor polypeptides. Such receptors include, but are not limited to, a fragment of the receptor, or a substitution, addition or deletion mutant of a T-cell receptor provided herein. This invention also encompasses polypeptides or peptides that are substantially homologous to the T-cell receptors provided herein or that retain substantially the same activity. The term "analog" includes any protein or polypeptide having an amino acid residue sequence substantially identical to the T-cell receptors provided herein in which one or more residues, preferably no more than 5 residues, more preferably no more than 25 residues have been conservatively substituted with a functionally similar residue and which displays the functional aspects of the T-cell receptor as described herein.

The present invention further provides for suitable mammalian host cells, for example, non-specific T cells, that are transfected with a polynucleotide encoding TCRs specific for a polypeptide described herein, thereby rendering the host cell specific for the polypeptide. The α and β chains of the TCR may be contained on separate expression vectors or alternatively, on a single expression vector that also contains an internal ribosome entry site (IRES) for cap-independent translation of the gene downstream of the IRES. Said host cells expressing TCRs specific for the polypeptide may be used, for example, for adoptive immunotherapy of lung cancer as discussed further below.

In further aspects of the present invention, cloned TCRs specific for a polypeptide recited herein may be used in a kit for the diagnosis of lung cancer. For example, the nucleic acid sequence or portions thereof, of tumor-specific TCRs can be used as probes or primers for the detection of expression of the rearranged genes encoding the specific TCR in a biological sample. Therefore, the present invention further provides for an assay for detecting messenger RNA or DNA encoding the TCR specific for a polypeptide.

Pharmaceutical Compositions

In additional embodiments, the present invention concerns formulation of one or more of the polynucleotide, polypeptide, T-cell and/or antibody compositions disclosed herein in pharmaceutically-acceptable carriers for administration to a cell or an animal, either alone, or in combination with one or more other modalities of therapy.

It will be understood that, if desired, a composition as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Therefore, in another aspect of the present invention, pharmaceutical compositions are provided comprising one or more of the polynucleotide, polypeptide, antibody, and/or T-cell compositions described herein in combination with a physiologically acceptable carrier. In certain preferred embodiments, the pharmaceutical compositions of the invention comprise immunogenic polynucleotide and/or polypeptide compositions of the invention for use in prophylactic and theraputic vaccine applications. Vaccine preparation is generally described in, for example, M. F. Powell and M. J. Newman, eds., "Vaccine Design (the subunit and adjuvant approach)," Plenum Press (NY, 1995). Generally, such compositions will comprise one or more polynucleotide and/or polypeptide compositions of the present invention in combination with one or more immunostimulants.

It will be apparent that any of the pharmaceutical compositions described herein can contain pharmaceutically acceptable salts of the polynucleotides and polypeptides of the invention. Such salts can be prepared, for example, from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

In another embodiment, illustrative immunogenic compositions, e.g., vaccine compositions, of the present invention comprise DNA encoding one or more of the polypeptides as described above, such that the polypeptide is generated in situ. As noted above, the polynucleotide may be administered within any of a variety of delivery systems known to those of ordinary skill in the art. Indeed, numerous gene delivery techniques are well known in the art, such as those described by Rolland, *Crit. Rev. Therap. Drug Carrier Systems* 15:143–198, 1998, and references cited therein. Appropriate polynucleotide expression systems will, of course, contain the necessary regulatory DNA regulatory sequences for expression in a patient (such as a suitable promoter and terminating signal). Alternatively, bacterial delivery systems may involve the administration of a bacterium (such as *Bacillus-Calmette-Guerrin*) that expresses an immunogenic portion of the polypeptide on its cell surface or secretes such an epitope.

Therefore, in certain embodiments, polynucleotides encoding immunogenic polypeptides described herein are introduced into suitable mammalian host cells for expression using any of a number of known viral-based systems. In one illustrative embodiment, retroviruses provide a convenient and effective platform for gene delivery systems. A selected nucleotide sequence encoding a polypeptide of the present invention can be inserted into a vector and packaged in retroviral particles using techniques known in the art. The recombinant virus can then be isolated and delivered to a subject. A number of illustrative retroviral systems have been described (e.g., U.S. Pat. No. 5,219,740; Miller and Rosman (1989) BioTechniques 7:980–990; Miller, A. D. (1990) Human Gene Therapy 1:5–14; Scarpa et al. (1991) Virology 180:849–852; Burns et al. (1993) Proc. Natl. Acad. Sci. USA 90:8033–8037; and Boris-Lawrie and Temin (1993) Cur. Opin. Genet. Develop. 3:102–109.

In addition, a number of illustrative adenovirus-based systems have also been described. Unlike retroviruses which integrate into the host genome, adenoviruses persist extrachromosomally thus minimizing the risks associated with insertional mutagenesis (Haj-Ahmad and Graham (1986) J. Virol. 57:267–274; Bett et al. (1993) J. Virol. 67:5911–5921; Mittereder et al. (1994) Human Gene Therapy 5:717–729; Seth et al. (1994) J. Virol. 68:933–940; Barr et al. (1994) Gene Therapy 1:51–58; Berkner, K. L. (1988) BioTechniques 6:616–629; and Rich et al. (1993) Human Gene Therapy 4:461–476).

Various adeno-associated virus (AAV) vector systems have also been developed for polynucleotide delivery. AAV vectors can be readily constructed using techniques well known in the art. See, e.g., U.S. Pat. Nos. 5,173,414 and 5,139,941; International Publication Nos. WO 92/01070 and WO 93/03769; Lebkowski et al. (1988) Molec. Cell. Biol. 8:3988–3996; Vincent et al. (1990) Vaccines 90 (Cold Spring Harbor Laboratory Press); Carter, B. J. (1992) Current Opinion in Biotechnology 3:533–539; Muzyczka, N. (1992) Current Topics in Microbiol. and Immunol. 158:97–129; Kotin, R. M. (1994) Human Gene Therapy 5:793–801; Shelling and Smith (1994) Gene Therapy 1:165–169; and Zhou et al. (1994) J. Exp. Med. 179:1867–1875.

Additional viral vectors useful for delivering the polynucleotides encoding polypeptides of the present invention by gene transfer include those derived from the pox family of viruses, such as vaccinia virus and avian poxvirus. By way of example, vaccinia virus recombinants expressing the novel molecules can be constructed as follows. The DNA encoding a polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the polypeptide of interest into the viral genome. The resulting TK.sup.(−) recombinant can be selected by culturing the cells in the presence of 5-bromodeoxyuridine and picking viral plaques resistant thereto.

A vaccinia-based infection/transfection system can be conveniently used to provide for inducible, transient expression or coexpression of one or more polypeptides described herein in host cells of an organism. In this particular system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide or polynucleotides of interest, driven by a T7 promoter. The polymerase expressed in the cytoplasm from the vaccinia virus recombinant transcribes the transfected DNA into RNA which is then translated into polypeptide by the host translational machinery. The method provides for high level, transient, cytoplasmic production of large quantities of RNA and its translation products. See, e.g., Elroy-Stein and Moss, Proc. Natl. Acad. Sci. USA (1990) 87:6743–6747; Fuerst et al. Proc. Natl. Acad. Sci. USA (1986) 83:8122–8126.

Alternatively, avipoxviruses, such as the fowlpox and canarypox viruses, can also be used to deliver the coding sequences of interest. Recombinant avipox viruses, expressing immunogens from mammalian pathogens, are known to confer protective immunity when administered to non-avian species. The use of an Avipox vector is particularly desirable in human and other mammalian species since members of the Avipox genus can only productively replicate in susceptible avian species and therefore are not infective in mammalian cells. Methods for producing recombinant Avipoxviruses are known in the art and employ genetic recombination, as described above with respect to the production of vaccinia viruses. See, e.g., WO 91/12882; WO 89/03429; and WO 92/03545.

Any of a number of alphavirus vectors can also be used for delivery of polynucleotide compositions of the present invention, such as those vectors described in U.S. Pat. Nos. 5,843,723; 6,015,686; 6,008,035 and 6,015,694. Certain vectors based on Venezuelan Equine Encephalitis (VEE) can also be used, illustrative examples of which can be found in U.S. Pat. Nos. 5,505,947 and 5,643,576.

Moreover, molecular conjugate vectors, such as the adenovirus chimeric vectors described in Michael et al. J. Biol. Chem. (1993) 268:6866–6869 and Wagner et al. Proc. Natl. Acad. Sci. USA (1992) 89:6099–6103, can also be used for gene delivery under the invention.

Additional illustrative information on these and other known viral-based delivery systems can be found, for example, in Fisher-Hoch et al., *Proc. Natl. Acad. Sci. USA* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *Proc. Natl. Acad. Sci. USA* 91:215–219, 1994; Kass-Eisler et al., *Proc. Natl. Acad. Sci. USA* 90:11498–11502, 1993; Guzman et al., *Circulation* 88:2838–2848, 1993; and Guzman et al., *Cir. Res.* 73:1202–1207, 1993.

In certain embodiments, a polynucleotide may be integrated into the genome of a target cell. This integration may be in the specific location and orientation via homologous recombination (gene replacement) or it may be integrated in a random, non-specific location (gene augmentation). In yet further embodiments, the polynucleotide may be stably maintained in the cell as a separate, episomal segment of DNA. Such polynucleotide segments or "episomes" encode sequences sufficient to permit maintenance and replication independent of or in synchronization with the host cell cycle. The manner in which the expression construct is delivered to a cell and where in the cell the polynucleotide remains is dependent on the type of expression construct employed.

In another embodiment of the invention, a polynucleotide is administered/delivered as "naked" DNA, for example as described in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

In still another embodiment, a composition of the present invention can be delivered via a particle bombardment approach, many of which have been described. In one illustrative example, gas-driven particle acceleration can be achieved with devices such as those manufactured by Powderject Pharmaceuticals PLC (Oxford, UK) and Powderject Vaccines Inc. (Madison, Wis.), some examples of which are described in U.S. Pat. Nos. 5,846,796; 6,010,478; 5,865,796; 5,584,807; and EP Patent No. 0500 799. This approach offers a needle-free delivery approach wherein a dry powder formulation of microscopic particles, such as polynucleotide or polypeptide particles, are accelerated to high speed within a helium gas jet generated by a hand held device, propelling the particles into a target tissue of interest.

In a related embodiment, other devices and methods that may be useful for gas-driven needle-less injection of compositions of the present invention include those provided by Bioject, Inc. (Portland, Oreg.), some examples of which are described in U.S. Pat. Nos. 4,790,824; 5,064,413; 5,312,335; 5,383,851; 5,399,163; 5,520,639 and 5,993,412.

According to another embodiment, the pharmaceutical compositions described herein will comprise one or more immunostimulants in addition to the immunogenic polynucleotide, polypeptide, antibody, T-cell and/or APC compositions of this invention. An immunostimulant refers to essentially any substance that enhances or potentiates an immune response (antibody and/or cell-mediated) to an exogenous antigen. One preferred type of immunostimulant comprises an adjuvant. Many adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

Within certain embodiments of the invention, the adjuvant composition is preferably one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g, IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145–173, 1989.

Certain preferred adjuvants for eliciting a predominantly Th1-type response include, for example, a combination of monophosphoryl lipid A, preferably 3-de-O-acylated monophosphoryl lipid A, together with an aluminum salt. MPL® adjuvants are available from Corixa Corporation (Seattle, Wash.; see, for example, U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Another preferred adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other preferred formulations include more than one saponin in the adjuvant combinations of the present invention, for example combinations of at least two of the following group comprising QS21, QS7, Quil A, β-escin, or digitonin.

Alternatively the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM. The saponins may also be formulated with excipients such as Carbopol$^R$ to increase viscosity, or may be formulated in a dry powder form with a powder excipient such as lactose.

In one preferred embodiment, the adjuvant system includes the combination of a monophosphoryl lipid A and a saponin derivative, such as the combination of QS21 and 3D-MPL® adjuvant, as described in WO 94/00153, or a less reactogenic composition where the QS21 is quenched with cholesterol, as described in WO 96/33739. Other preferred formulations comprise an oil-in-water emulsion and tocopherol. Another particularly preferred adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 is disclosed in WO 00/09159. Preferably the formulation additionally comprises an oil in water emulsion and tocopherol.

Additional illustrative adjuvants for use in the pharmaceutical compositions of the invention include Montanide ISA 720 (Seppic, France), SAF (Chiron, California, United States), ISCOMS (CSL), MF-59 (Chiron), the SBAS series of adjuvants (e.g., SBAS-2 or SBAS-4, available from SmithKline Beecham, Rixensart, Belgium), Detox (Enhanzyn®) (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

Other preferred adjuvants include adjuvant molecules of the general formula $$HO(CH_2CH_2O)_n\text{-}A\text{-}R, \qquad (I)$$

wherein, n is 1–50, A is a bond or —C(O)—, R is $C_{1-50}$ alkyl or Phenyl $C_{1-50}$ alkyl.

One embodiment of the present invention consists of a vaccine formulation comprising a polyoxyethylene ether of general formula (I), wherein n is between 1 and 50, preferably 4–24, most preferably 9; the R component is $C_{1-50}$, preferably $C_4$–$C_{20}$ alkyl and most preferably $C_{12}$ alkyl, and A is a bond. The concentration of the polyoxyethylene ethers should be in the range 0.1–20%, preferably from 0.1–10%, and most preferably in the range 0.1–1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index ($12^{th}$ edition: entry 7717). These adjuvant molecules are described in WO 99/52549.

The polyoxyethylene ether according to the general formula (I) above may, if desired, be combined with another adjuvant. For example, a preferred adjuvant combination is preferably with CpG as described in the pending UK patent application GB 9820956.2.

According to another embodiment of this invention, an immunogenic composition described herein is delivered to a host via antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245–251, 1998) and have been shown to be effective as a physiological adjuvant for eliciting prophylactic or therapeutic antitumor immunity (see Timmerman and Levy, *Ann. Rev. Med.* 50:507–529, 1999). In general, dendritic cells may be identified based on their typical shape (stellate in situ, with marked cytoplasmic processes (dendrites) visible in vitro), their ability to take up, process and present antigens with high efficiency and their ability to activate naive T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g, CD54 and CD11) and costimulatory molecules (e.g., CD40, CD80, CD86 and 4-1BB).

APCs may generally be transfected with a polynucleotide of the invention (or portion or other variant thereof) such that the encoded polypeptide, or an immunogenic portion thereof, is expressed on the cell surface. Such transfection may take place ex vivo, and a pharmaceutical composition comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

While any suitable carrier known to those of ordinary skill in the art may be employed in the pharmaceutical compositions of this invention, the type of carrier will typically vary depending on the mode of administration. Compositions of the present invention may be formulated for any appropriate manner of administration, including for example, topical, oral, nasal, mucosal, intravenous, intracranial, intraperitoneal, subcutaneous and intramuscular administration.

Carriers for use within such pharmaceutical compositions are biocompatible, and may also be biodegradable. In certain embodiments, the formulation preferably provides a relatively constant level of active component release. In other embodiments, however, a more rapid rate of release immediately upon administration may be desired. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

In another illustrative embodiment, biodegradable microspheres (e.g., polylactate polyglycolate) are employed as carriers for the compositions of this invention. Suitable biodegradable microspheres are disclosed, for example, in U.S. Pat. Nos. 4,897,268; 5,075,109; 5,928,647; 5,811,128; 5,820,883, 5,853,763; 5,814,344, 5,407,609 and 5,942,252. Modified hepatitis B core protein carrier systems. such as described in WO/99 40934, and references cited therein, will also be useful for many applications. Another illustrative carrier/delivery system employs a carrier comprising particulate-protein complexes, such as those described in U.S. Pat. No. 5,928,647, which are capable of inducing a class I-restricted cytotoxic T lymphocyte responses in a host.

The pharmaceutical compositions of the invention will often further comprise one or more buffers (e.g. neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (see, for example, Mathiowitz et al., Nature 1997 Mar. 27; 386(6623):410–4; Hwang et al., Crit Rev Ther Drug Carrier Syst 1998; 15(3):243–84; U.S. Pat. No. 5,641,515; U.S. Pat. No. 5,580,579 and U.S. Pat. No. 5,792,451). Tablets, troches, pills, capsules and the like may also contain any of a variety of additional components, for example, a binder, such as gum tragacanth, acacia. cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Of course, any material used in preparing any dosage unit form should be pharmaceutically pure and substantially non-toxic in the amounts employed. In addition, the active compounds may be incorporated into sustained-release preparation and formulations.

Typically, these formulations will contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

In certain circumstances it will be desirable to deliver the pharmaceutical compositions disclosed herein parenterally, intravenously, intramuscularly, or even intraperitoneally. Such approaches are well known to the skilled artisan, some of which are further described, for example, in U.S. Pat. No. 5,543,158; U.S. Pat. No. 5,641,515 and U.S. Pat. No. 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g, glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described, e.g., in U.S. Pat. No. 5,756,353 and U.S. Pat. No. 5,804,212. Likewise, the delivery of drugs using intranasal microparticle resins (Takenaga et al., J Controlled Release 1998 Mar. 2; 52(1–2):81–7) and lysophosphatidyl-glycerol compounds (U.S. Pat. No. 5,725,871) are also well-known in the pharmaceutical arts. Likewise, illustrative transmucosal drug delivery in the form of a polytetrafluoroetheylene support matrix is described in U.S. Pat. No. 5,780,045.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol 1998 July; 16(7):307–21; Takakura, Nippon Rinsho 1998 March; 56(3):691–5; Chandran et al., Indian J Exp Biol. 1997 August; 35(8):801–9; Margalit, Crit Rev Ther Drug Carrier Syst. 1995; 12(2–3):233–61; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally difficult to transfect by other procedures, including T cell suspensions, primary hepatocyte cultures and PC 12 cells (Renneisen et al., J Biol Chem. 1990 Sep. 25;265(27):16337–42; Muller et al., DNA Cell Biol. 1990 April; 9(3):221–9). In addition, liposomes are free of the DNA length constraints that are typical of viral-based delivery systems. Liposomes have been used effectively to introduce genes, various drugs, radiotherapeutic agents, enzymes, viruses, transcription factors, allosteric effectors and the like, into a variety of cultured cell lines and animals. Furthermore, he use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev Ind Pharm. 1998 December; 24(12):1113–28). To avoid side effects due to intracellular polymeric overloading, such ultrafine particles (sized around 0.1 $\mu$m) may be designed using polymers able to be degraded in vivo. Such particles can be made as described, for example, by Couvreur et al., Crit Rev Ther Drug Carrier Syst. 1988; 5(1):1–20; zur Muhlen et al., Eur J Pharm Biopharm. 1998 March; 45(2):149–55; Zambaux et al. J Controlled Release. 1998 Jan. 2; 50(1–3):31–40; and U.S. Pat. No. 5,145,684.

Cancer Therapeutic Methods

Immunologic approaches to cancer therapy are based on the recognition that cancer cells can often evade the body's defenses against aberrant or foreign cells and molecules, and that these defenses might be therapeutically stimulated to regain the lost ground, e.g. pgs. 623–648 in Klein, Immunology (Wiley-Interscience, New York, 1982). Numerous recent observations that various immune effectors can directly or indirectly inhibit growth of tumors has led to renewed interest in this approach to cancer therapy, e.g. Jager, et al., Oncology 2001; 60(1):1–7; Renner, et al., Ann Hematol 2000 December; 79(12):651–9.

Four-basic cell types whose function has been associated with antitumor cell immunity and the elimination of tumor cells from the body are: i) B-lymphocytes which secrete immunoglobulins into the blood plasma for identifying and labeling the nonself invader cells; ii) monocytes which secrete the complement proteins that are responsible for lysing and processing the immunoglobulin-coated target invader cells; iii) natural killer lymphocytes having two mechanisms for the destruction of tumor cells, antibody-dependent cellular cytotoxicity and natural killing; and iv) T-lymphocytes possessing antigen-specific receptors and having the capacity to recognize a tumor cell carrying complementary marker molecules (Schreiber, H., 1989, in Fundamental Immunology (ed). W. E. Paul, pp. 923–955).

Cancer immunotherapy generally focuses on inducing humoral immune responses, cellular immune responses, or both. Moreover, it is well established that induction of $CD4^+$ T helper cells is necessary in order to secondarily induce either antibodies or cytotoxic $CD8^+$ T cells. Polypeptide antigens that are selective or ideally specific for cancer cells, particularly lung cancer cells, offer a powerful approach for inducing immune responses against lung cancer, and are an important aspect of the present invention.

Therefore, in further aspects of the present invention, the pharmaceutical compositions described herein may be used for the treatment of cancer, particularly for the immunotherapy of lung cancer. Within such methods, the pharmaceutical compositions described herein are administered to a patient, typically a warm-blooded animal, preferably a human. A patient may or may not be afflicted with cancer. Accordingly, the above pharmaceutical compositions may be used to prevent the development of a cancer or to treat a patient afflicted with a cancer. Pharmaceutical compositions and vaccines may be administered either prior to or following surgical removal of primary tumors and/or treatment such as administration of radiotherapy or conventional chemotherapeutic drugs. As discussed above, administration of the pharmaceutical compositions may be by any suitable method, including administration by intravenous, intraperitoneal, intramuscular, subcutaneous, intranasal, intradermal, anal, vaginal, topical and oral routes.

Within certain embodiments, immunotherapy may be active immunotherapy, in which treatment relies on the in vivo stimulation of the endogenous host immune system to react against tumors with the administration of immune response-modifying agents (such as polypeptides and polynucleotides as provided herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Monoclonal antibodies may be labeled with any of a variety of labels for desired selective usages in detection, diagnostic assays or therapeutic applications (as described in U.S. Pat. Nos. 6,090,365; 6,015,542; 5,843,398; 5,595,721; and 4,708,930, hereby incorporated by reference in their entirety as if each was incorporated individually). In each case, the binding of the labelled monoclonal antibody to the determinant site of the antigen will signal detection or delivery of a particular therapeutic agent to the antigenic determinant on the non-normal cell. A further object of this invention is to provide the specific monoclonal antibody suitably labelled for achieving such desired selective usages thereof.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions described herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 25 μg to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

Cancer Detection and Diagnostic Compositions, Methods and Kits

In general, a cancer may be detected in a patient based on the presence of one or more lung tumor proteins and/or polynucleotides encoding such proteins in a biological sample (for example, blood, sera, sputum urine and/or tumor biopsies) obtained from the patient. In other words, such proteins may be used as markers to indicate the presence or absence of a cancer such as lung cancer. In addition, such proteins may be useful for the detection of other cancers. The binding agents provided herein generally permit detection of the level of antigen that binds to the agent in the biological sample.

Polynucleotide primers and probes may be used to detect the level of mRNA encoding a tumor protein, which is also indicative of the presence or absence of a cancer. In general, a tumor sequence should be present at a level that is at least two-fold, preferably three-fold, and more preferably five-fold or higher in tumor tissue than in normal tissue of the same type from which the tumor arose. Expression levels of a particular tumor sequence in tissue types different from that in which the tumor arose are irrelevant in certain diagnostic embodiments since the presence of tumor cells can be confirmed by observation of predetermined differential expression levels, e.g., 2-fold, 5-fold, etc, in tumor tissue to expression levels in normal tissue of the same type.

Other differential expression patterns can be utilized advantageously for diagnostic purposes. For example, in one aspect of the invention, overexpression of a tumor sequence in tumor tissue and normal tissue of the same type, but not in other normal tissue types, e.g. PBMCs, can be exploited diagnostically. In this case, the presence of metastatic tumor cells, for example in a sample taken from the circulation or some other tissue site different from that in which the tumor arose, can be identified and/or confirmed by detecting expression of the tumor sequence in the sample, for example using RT-PCR analysis. In many instances, it will be desired to enrich for tumor cells in the sample of interest, e.g., PBMCs, using cell capture or other like techniques.

There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length lung tumor proteins and polypeptide portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 μg, and preferably about 100 ng to about 1 μg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with lung cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as lung cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use tumor polypeptides to detect antibodies that bind to such polypeptides in a biological sample. The detection of such tumor protein specific antibodies may correlate with the presence of a cancer.

A cancer may also, or alternatively, be detected based on the presence of T cells that specifically react with a tumor protein in a biological sample. Within certain methods, a biological sample comprising $CD4^+$ and/or $CD8^+$ T cells isolated from a patient is incubated with a tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with polypeptide (e.g., 5–25 $\mu$g/ml). It may be desirable to incubate another aliquot of a T cell sample in the absence of tumor polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a tumor protein in a biological sample. For example, at least two oligonucleotide primers may be employed in a polymerase chain reaction (PCR) based assay to amplify a portion of a tumor cDNA derived from a biological sample, wherein at least one of the oligonucleotide primers is specific for (i.e. hybridizes to) a polynucleotide encoding the tumor protein. The amplified cDNA is then separated and detected using techniques well known in the art, such as gel electrophoresis.

Similarly, oligonucleotide probes that specifically hybridize to a polynucleotide encoding a tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a tumor protein of the invention that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence as disclosed herein. Techniques for both PCR based assays and hybridization assays are well known in the art (see, for example, Mullis et al., *Cold Spring Harbor Symp. Quant. Biol.,* 51:263, 1987; Erlich ed., *PCR Technology*, Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another aspect of the present invention, cell capture technologies may be used in conjunction, with, for example, real-time PCR to provide a more sensitive tool for detection of metastatic cells expressing lung tumor antigens. Detection of lung cancer cells in biological samples, e.g., bone marrow samples, peripheral blood, and small needle aspiration samples is desirable for diagnosis and prognosis in lung cancer patients.

Immunomagnetic beads coated with specific monoclonal antibodies to surface cell markers, or tetrameric antibody complexes, may be used to first enrich or positively select cancer cells in a sample. Various commercially available kits may be used, including Dynabeads® Epithelial Enrich (Dynal Biotech, Oslo, Norway), StemSep™ (StemCell Technologies, Inc., Vancouver, BC), and RosetteSep (StemCell Technologies). A skilled artisan will recognize that other methodologies and kits may also be used to enrich or positively select desired cell populations. Dynabeads® Epithelial Enrich contains magnetic beads coated with mAbs specific for two glycoprotein membrane antigens expressed on normal and neoplastic epithelial tissues. The coated beads may be added to a sample and the sample then applied to a magnet, thereby capturing the cells bound to the beads. The unwanted cells are washed away and the magnetically isolated cells eluted from the beads and used in further analyses.

RosetteSep can be used to enrich cells directly from a blood sample and consists of a cocktail of tetrameric antibodies that targets a variety of unwanted cells and crosslinks them to glycophorin A on red blood cells (RBC) present in the sample, forming rosettes. When centrifuged over Ficoll, targeted cells pellet along with the free RBC. The combination of antibodies in the depletion cocktail determines which cells will be removed and consequently which cells will be recovered. Antibodies that are available include, but are not limited to: CD2, CD3, CD4, CD5, CD8, CD10, CD11b, CD14, CD15, CD16, CD19, CD20, CD24, CD25, CD29, CD33, CD34, CD36, CD38, CD41, CD45, CD45RA, CD45RO, CD56, CD66B, CD66e, HLA-DR, IgE, and TCRαβ.

Additionally, it is contemplated in the present invention that mAbs specific for lung tumor antigens can be generated and used in a similar manner. For example, mAbs that bind to tumor-specific cell surface antigens may be conjugated to magnetic beads, or formulated in a tetrameric antibody complex, and used to enrich or positively select metastatic lung tumor cells from a sample. Once a sample is enriched or positively selected, cells may be lysed and RENA isolated. RNA may then be subjected to RT-PCR analysis using lung tumor-specific primers in a real-time PCR assay as described herein. One skilled in the art will recognize that enriched or selected populations of cells may be analyzed by other methods (e.g. in situ hybridization or flow cytometry).

In another embodiment, the compositions described herein may be used as markers for the progression of cancer. In this embodiment, assays as described above for the diagnosis of a cancer may be performed over time, and the change in the level of reactive polypeptide(s) or polynucleotide(s) evaluated. For example, the assays may be performed every 24–72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

The present invention farther provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a tumor protein in a biological sample. Such kits generally comprise at least one oligonucleotide probe or primer, as described above, that hybridizes to a polynucleotide encoding a tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a tumor protein.

The following examples are offered by way of illustration and not by way of limitation.

EXAMPLES

Example 1

Isolation and Characterization of cDNA Sequences Encoding Lung Tumor Polypeptides This example illustrates the isolation of cDNA molecules encoding lung tumor-specific polypeptides from lung tumor cDNA libraries.

A. Insolation of cDNA Sequences from a Lung Squamous Cell Carcinoma Library

A human lung squamous cell carcinoma cDNA expression library was constructed from poly $A^+$ RNA from a pool of two patient tissues using a Superscript Plasmid System for cDNA Synthesis and Plasmid Cloning kit (BRL Life Technologies, Gaithersburg, Md.) following the manufacturer's protocol. Specifically, lung carcinoma tissues were homogenized with polytron (Kinematica, Switzerland) and total RNA was extracted using Trizol reagent (BRL Life Technologies) as directed by the manufacturer. The poly $A^+$ RNA was then purified using an oligo dT cellulose column as described in Sambrook et al., *Molecular Cloning: A Laboratory Manual*, Cold Spring Harbor Laboratories, Cold Spring Harbor, N.Y., 1989. First-strand cDNA was synthesized using the NotI/Oligo-dT18 primer. Double-stranded cDNA was synthesized, ligated with BstXI/EcoRI adaptors (Invitrogen, San Diego, Calif.) and digested with NotI. Following size fractionation with cDNA size fractionation columns (BRL Life Technologies), the cDNA was ligated into the BstXI/NotI site of pcDNA3.1 (Invitrogen) and transformed into ElectroMax *E. coli* DH10B cells (BRL Life Technologies) by electroporation.

Using the same procedure, a normal human lung cDNA expression library was prepared from a pool of four tissue specimens. The cDNA libraries were characterized by determining the number of independent colonies, the percentage of clones that carried insert, the average insert size and by sequence analysis. The lung squamous cell carcinoma library contained $2.7\times10^6$ independent colonies, with 100% of clones having an insert and the average insert size being 2100 base pairs. The normal lung cDNA library contained $1.4\times10^6$ independent colonies, with 90% of clones having inserts and the average insert size being 1800 base pairs. For both libraries, sequence analysis showed that the majority of clones had a full length cDNA sequence and were synthesized from mRNA cDNA library subtraction was performed using the above lung squamous cell carcinoma and normal lung cDNA libraries,. as described by Hara et al. (*Blood,* 84:189–199, 1994) with some modifications. Specifically, a lung squamous cell carcinoma-specific subtracted cDNA library was generated as follows. Normal tissue cDNA library (80 $\mu$g) was digested with BamHI and XhoI, followed by a filling-in reaction with DNA polymerase Klenow fragment. After phenol-chloroform extraction and ethanol precipitation, the DNA was dissolved in 133 $\mu$l of $H_2O$, heat-denatured and mixed with 133 $\mu$l (133 $\mu$g) of Photoprobe biotin (Vector Laboratories, Burlingame, Calif.). As recommended by the manufacturer, the resulting mixture was irradiated with a 270 W sunlamp on ice for 20 minutes. Additional Photoprobe biotin (67 $\mu$l) was added and the biotinylation reaction was repeated. After extraction with butanol five times, the DNA was ethanol-precipitated and dissolved in 23 $\mu$l $H_2O$ to form the driver DNA.

To form the tracer DNA, 10 $\mu$g lung squamous cell carcinoma cDNA library was digested with NotI and SpeI, phenol chloroform extracted and passed through Chroma spin-400 columns (Clontech, Palo Alto, Calif.). Typically, 5 $\mu$g of cDNA was recovered after the sizing column. Following ethanol precipitation, the tracer DNA was dissolved in 5 $\mu$l $H_2O$. Tracer DNA was mixed with 15 $\mu$l driver DNA and 20 $\mu$l of 2× hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68° C. water bath and incubated for 20 hours (long hybridization [LH]). The reaction mixture was then subjected to a streptavidin treatment followed by phenol/chloroform extraction. This process was repeated three more times. Subtracted DNA was precipitated, dissolved in 12 $\mu$l $H_2O$, mixed with 8 $\mu$l driver DNA and 20 $\mu$l of 2× hybridization buffer, and subjected to a hybridization at 68° C. for 2 hours (short hybridization [SH]). After removal of biotinylated double-stranded DNA, subtracted cDNA was ligated into NotI/SpeI site of chloramphenicol resistant pBCSK$^+$ (Stratagene, La Jolla, Calif.) and transformed into ElectroMax *E. coli* DH10B cells by electroporation to generate a lung squamous cell carcinoma specific subtracted cDNA library (herein after referred to as "lung subtraction I").

A second lung squamous cell carcinoma specific subtracted cDNA library (referred to as "lung subtraction II") was generated in a similar way to the lung subtraction library I, except that eight frequently recovered genes from lung subtraction I were included in the driver DNA, and 24,000 independent clones were recovered.

To analyze the subtracted cDNA libraries, plasmid DNA was prepared from 320 independent clones, randomly picked from the subtracted lung squamous cell carcinoma specific libraries. Representative cDNA clones were further characterized by DNA sequencing with a Perkin Elmer/Applied Biosystems Division Automated Sequencer Model 373A and/or Model 377 (Foster City, Calif.). The cDNA sequences for sixty isolated clones are provided in SEQ ID NO: 1–60. These sequences were compared to known sequences in the gene bank using the EMBL, and GenBank databases (release 96). No significant homologies were found to the sequences provided in SEQ ID NO: 2, 3, 19, 38 and 46. The sequences of SEQ ID NO: 1, 6–8, 10–13, 15, 17, 18, 20–27, 29, 30, 32, 34–37, 39–45, 47–49, 51, 52, 54, 55 and 57–59 were found to show some homology to previously identified expressed sequence tags (ESTs). The sequences of SEQ ID NO: 9, 28, 31 and 33 were found to show some homology to previously identified non-human gene sequences and the sequences of SEQ ID NO: 4, 5, 14, 50, 53, 56 and 60 were found to show some homology to gene sequences previously identified in humans.

The subtraction procedure described above was repeated using the above lung squamous cell carcinoma cDNA library as the tracer DNA, and the above normal lung tissue cDNA library and a cDNA library from normal liver and heart (constructed from a pool of one sample of each tissue as described above), plus twenty other cDNA clones that were frequently recovered in lung subtractions I and II, as the driver DNA (lung subtraction III). The normal liver and heart cDNA library contained $1.76 \times 10^6$ independent colonies, with 100% of clones having inserts and the average insert size being 1600 base pairs. Ten additional clones were isolated (SEQ ID NO: 61–70). Comparison of these cDNA sequences with those in the gene bank as described above, revealed no significant homologies to the sequences provided in SEQ ID NO: 62 and 67. The sequences of SEQ ID NO: 61, 63–66, 68 and 69 were found to show some homology to previously isolated ESTs and the sequence provided in SEQ ID NO: 70 was found to show some homology to a previously identified rat gene.

In further studies, the subtraction procedure described above was repeated using the above lung squamous cell carcinoma cDNA library as the tracer DNA, and a cDNA library from a pool of normal lung, kidney, colon, pancreas, brain, resting PBMC, heart, skin and esophagus as the driver DNA, with esophagus cDNAs making up one third of the driver material. Since esophagus is enriched in normal epithelial cells, including differentiated squamous cells, this procedure is likely to enrich genes that are tumor specific rather than tissues specific. The cDNA sequences of 48 clones determined in this subtraction are provided in SEQ ID NO: 177–224. The sequences of SEQ ID NO: 177, 178, 180, 181, 183, 187, 192, 195–197, 208, 211, 212, 215, 216, 218 and 219 showed some homology to previously identified genes. The sequences of SEQ ID NO: 179, 182, 184–186, 188–191, 193, 194, 198–207, 209 210, 213, 214, 217, 220 and 224 showed some homology to previously determined ESTs. The sequence of SEQ ID NO: 221–223 showed no homology to any previously determined sequence.

B. Isolation of cDNA Sequences from a Lung Adenocarcinoma Library

A human lung adenocarcinoma cDNA expression library was constructed as described above. The library contained $3.2 \times 10^6$ independent colonies, with 100% of clones having an insert and the average insert size being 1500 base pairs. Library subtraction was performed as described above using the normal lung and normal liver and heart cDNA expression libraries described above as the driver DNA. Twenty-six hundred independent clones were recovered.

Initial cDNA sequence analysis from 100 independent clones revealed many ribosomal protein genes. The cDNA sequences for fifteen clones isolated in this subtraction are provided in SEQ ID NO: 71–86. Comparison of these sequences with those in the gene bank as described above revealed no significant homologies to the sequence provided in SEQ ID NO: 84. The sequences of SEQ ID NO: 71, 73, 74, 77, 78 and 80–82 were found to show some homology to previously isolated ESTs. and the sequences of SEQ ID NO: 72, 75, 76, 79, 83 and 85 were found to show some homology to previously identified human genes.

In further studies, a cDNA library (referred to as mets3616A) was constructed from a metastatic lung adepocarcinoma. The determined cDNA sequences of 25 clones sequenced at random from this library are provided in SEQ ID NO: 255–279. The mets3616A cDNA library was subtracted against a cDNA library prepared from a pool of normal lung, liver, pancreas, skin, kidney, brain and resting PBMC. To increase the specificity of the subtraction, the driver was spiked with genes that were determined to be most abundant in the mets3616A cDNA library, such as EF1-alpha, integrin-beta and anticoagulant protein PP4, as well as with cDNAs that were previously found to be differentially expressed in subtracted lung adenocarcinoma cDNA libraries. The determined cDNA sequences of 51 clones isolated from the subtracted library (referred to as mets3616A-S1) are provided in SEQ ID NO: 280–330.

Comparison of the sequences of SEQ ID NO: 255–330 with those in the public databases revealed no significant homologies to the sequences of SEQ ID NO: 255–258, 260, 262–264, 270, 272, 275, 276, 279, 281, 287, 291, 296, 300 and 310. The sequences of SEQ ID NO: 259, 261, 265–269, 271, 273, 274, 277, 278. 282–285, 288–290, 292, 294, 297–299, 301, 303–309, 313, 314, 316, 320–324 and 326–330 showed some homology to previously identified gene sequences, while the sequences of SEQ ID NO: 280, 286, 293, 302, 310, 312, 315, 317–319 and 325 showed some homology to previously isolated expressed sequence tags (ESTs).

Example 2

Determination of Tissue Specificity of Lung Tumor Polypeptides

Using gene specific primers, mRNA expression levels for seven representative lung tumor polypeptides described in Example 1 were examined in a variety of normal and tumor tissues using RT-PCR.

Briefly, total RNA was extracted from a variety of normal and tumor tissues using Trizol reagent as described above. First strand synthesis was carried out using 2 μg of total RNA with SuperScript II reverse transcriptase (BRL Life Technologies) at 42° C. for one hour. The cDNA was then amplified by PCR with gene-specific primers. To ensure the semi-quantitative nature of the RT-PCR, β-actin was used as an internal control for each of the tissues examined. 1 μl of 1:30 dilution of cDNA was employed to enable the linear range amplification of the β-actin template and was sensitive enough to reflect the differences in the initial copy numbers. Using these conditions, the β-actin levels were determined for each reverse transcription reaction from each tissue. DNA contamination was minimized by DNase treatment and by assuring a negative PCR result when using first strand cDNA that was prepared without adding reverse transcriptase.

mRNA Expression levels were examined in five different types of tumor tissue (lung squamous cell carcinoma from 3 patients, lung adenocarcinoma, colon tumor from 2 patients, breast tumor and prostate tumor), and thirteen different normal tissues (lung from 4 donors, prostate, brain, kidney, liver, ovary, skeletal muscle, skin, small intestine, stomach, myocardium, retina and testes). Using a 10-fold amount of cDNA, the antigen LST-S1-90 (SEQ ID NO: 3) was found to be expressed at high levels in lung squamous cell carcinoma and in breast tumor, and at low to undetectable levels in the other tissues examined.

The antigen LST-S2-68 (SEQ ID NO: 15) appears to be specific to lung and breast tumor, however, expression was also detected in normal kidney. Antigens LST-S1-169 (SEQ ID NO: 6) and LST-S1-133 (SEQ ID NO: 5) appear to be very abundant in lung tissues (both normal and tumor), with the expression of these two genes being decreased in most of the normal tissues tested. Both LST-S1-169 and LST-S1-133 were also expressed in breast and colon tumors. Antigens LST-S1-6 (SEQ ID NO: 7) and LST-S2-I2-5F (SEQ ID NO: 47) did not show tumor or tissue specific expression, with the expression of LST-S1-28 being rare and only detectable in a few tissues. The antigen LST-S3-7 (SEQ ID NO: 63) showed lung and breast tumor specific expression, with its message only being detected in normal testes when the PCR was performed for 30 cycles. Lower level expression was detected in some normal tissues when the cycle number was increased to 35. Antigen LST-S3-13 (SEQ ID NO: 66) was found to be expressed in 3 out of 4 lung tumors, one breast tumor and both colon tumor samples. Its expression in normal tissues was lower compared to tumors, and was only detected in 1 out of 4 normal lung tissues and in normal tissues from kidney, ovary and retina. Expression of antigens LST-S3-4 (SEQ ID NO: 62) and LST-S3-14 (SEQ ID NO: 67) was rare and did not show any tissue or tumor specificity. Consistent with Northern blot analyses, the RT-PCR results on antigen LAT-S1-A-10A (SEQ ID NO: 78) suggested that its expression is high in lung, colon, stomach and small intestine tissues, including lung and colon tumors, whereas its expression was low or undetectable in other tissues.

A total of 2002 cDNA fragments isolated in lung subtractions I, II and III, described above, were colony PCR amplified and their mRNA expression levels in lung tumor, normal lung, and various other normal and tumor tissues were determined using microarray technology (Synteni, Palo Alto, Calif.). Briefly, the PCR amplification products were dotted onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. This intensity correlates with the hybridization intensity. Seventeen non-redundant cDNA clones showed over-expression in lung squamous tumors, with expression in normal tissues tested (lung, skin, lymph node, colon, liver, pancreas, breast, heart, bone marrow, large intestine, kidney, stomach, brain, small intestine, bladder and salivary gland) being either undetectable, or 10-fold less compared to lung squamous tumors. The determined cDNA sequences for the clone L513S are provided in SEQ ID NO: 87 and 88; those for L514S are provided in SEQ ID NO: 89 and 90; those for L516S in SEQ ID NO: 91 and 92; that for L517S in SEQ ID NO: 93; that for L519S in SEQ ID NO: 94; those for L520S in SEQ ID NO: 95 and 96; those for L521S in SEQ ID NO: 97 and 98; that for L522S in SEQ ID NO: 99; that for L523S in SEQ ID NO: 100; that for L524S in SEQ ID NO: 101; that for L525S in SEQ ID NO: 102; that for L526S in SEQ ID NO: 103; that for L527S in SEQ ID NO: 104; that for L528S in SEQ ID NO: 105; that for L529S in SEQ ID NO: 106; and those for L530S in SEQ ID NO: 107 and 108. Additionally, the full-length cDNA sequence for L530S is provided in SEQ ID NO: 151, with the corresponding amino acid sequence being provided in SEQ ID NO: 152. L530S shows homology to a splice variant of a p53 tumor suppressor homologue, p63. The cDNA sequences of 7 known isoforms of p63 are provided in SEQ ID NO: 331–337, with the corresponding amino acid sequences being provided in SEQ ID NO: 338–344, respectively.

Due to polymorphisms, the clone L531S appears to have two forms. A first determined full-length cDNA sequence for L531S is provided in SEQ ID NO: 109, with the corresponding amino acid sequence being provided in SEQ ID NO: 110. A second determined full-length cDNA sequence for L531S is provided in SEQ ID NO: 111, with the corresponding amino acid sequence being provided in SEQ ID NO: 112. The sequence of SEQ ID NO: 111 is identical to that of SEQ ID NO: 109, except that it contains a 27 bp insertion. Similarly, L514S has two alternatively spliced forms; the first variant cDNA is listed as SEQ ID NO: 153, with the corresponding amino acid sequence being provided in SEQ ID NO: 155. The full-length cDNA for the second variant form of L514S is provided in SEQ ID NO: 154, with the corresponding amino acid sequence being provided in SEQ ID NO: 156.

Full length cloning for L524S (SEQ ID NO: 101) yielded two variants (SEQ ID NO: 163 and 164) with the corresponding amino acid sequences of SEQ ID NO: 165 and 166, respectively. Both variants have been shown to encode parathyroid hormone-related peptide.

Attempts to isolate the full-length cDNA for L519S, resulted in the isolation of the extended cDNA sequence provided in SEQ ID NO: 173, which contains a potential open reading frame. The amino acid sequence encoded by the sequence of SEQ ID NO: 173 is provided in SEQ ID NO: 174. Additionally, the full-length cDNA sequence for the clone of SEQ ID NO: 100 (known as L523S), a known gene, is provided in SEQ ID NO: 175, with the corresponding amino acid sequence being provided in SEQ ID NO: 176. In further studies, a full-length cDNA sequence for L523S was isolated from a L523S-positive tumor cDNA library by PCR amplification using gene specific primers designed from the sequence of SEQ ID NO: 175. The determined full-length cDNA sequence is provided in SEQ ID NO: 347. The amino acid sequence encoded by this sequence is provided in SEQ ID NO: 348. This protein sequence differs from the previously published protein sequence at two amino acid positions, namely at positions 158 and 410.

Comparison of the sequences of L514S and L531S (SEQ ID NO: 87 and 88, and 109, respectively) with those in the gene bank, as described above, revealed no significant homologies to known sequences. The sequences of L513S, L516S, L517S, L519S, L520S and L530S (SEQ ID NO: 87 and 88, 91 and 92, 93, 94, 95 and 96, 107 and 108, respectively) were found to show some homology to previously identified ESTs. The sequences of L521S, L522S, L523S, L524S, L525S, L526S, L527S, L528S and L529S (SEQ ID NO: 97 and 98, 99, 99, 101, 102, 103, 104, 105, and 106, respectively) were found to represent known genes. The determined full-length cDNA sequence for L520S is provided in SEQID NO: 113, with the corresponding amino acid sequence being provided in SEQ ID NO: 114. Subsequent microarray analysis showed L520S to be overexpressed in breast tumors in addition to lung squamous tumors.

Further analysis demonstrated that L529S (SEQ ID NO: 106 and 115), L525S (SEQ ID NO: 102 and 120) and L527S (SEQ ID NO: 104) are cytoskeletal components and potentially squamous cell specific proteins. L529S is connexin 26, a gap junction protein. It was found to be highly expressed in one lung squamous tumor, referred to as 9688T, and moderately over-expressed in two others. However, lower level expression of connexin 26 is also detectable in normal skin, colon, liver and stomach. The over-expression of connexin 26 in some breast tumors has been reported and a mutated form of L529S may result in over-expression in lung tumors. L525S is plakophilin 1, a desmosomal protein found in plaque-bearing adhering junctions of the skin. Expression levels for L525S mRNA was highly elevated in three out of four lung squamous tumors tested, and in normal skin. L527S has been identified as keratin 6 isoform, type II 58 Kd keratin and cytokeratin 13, and shows over-expression in squamous tumors and low expression in normal skin, breast and colon tissues. Keratin and keratin-related genes have been extensively documented as potential markers for lung cancer including CYFRA2.1 (Pastor, A., et al, *Eur. Respir. J.,* 10:603–609, 1997). L513S (SEQ ID NO: 87 and 88) shows moderate over-expression in several tumor tissues tested, and encodes a protein that was first isolated as a pemphigus vulgaris antigen.

L520S (SEQ ID NO: 95 and 96) and L521S (SEQ ID NO: 97 and 98) are highly expressed in lung squamous tumors, with L520S being up-regulated in normal salivary gland and L521S being over-expressed in normal skin. Both belong to a family of small proline rich proteins and represent markers for fully differentiated squamous cells. L521S has been described as a specific marker for lung squamous tumor (Hu, R., et al, *Lung Cancer,* 20:25–30, 1998). L515S (SEQ ID NO: 162) encodes IGF-β2 and L516S is an aldose reductase homologue. Both are moderately expressed in lung squamous tumors and in normal colon. Notably, L516S (SEQ ID NO: 91 and 92) is up-regulated in metastatic tumors but not primary lung adenocarcinoma, an indication of its potential role in metatasis and a potential prognostic marker. L522S (SEQ ID NO: 99) is moderately over-expressed in lung squamous tumors with minimum expression in normal tissues. L522S has been shown to belong to a class IV alcohol dehydrogenase, ADH7, and its expression profile suggests it is a squamous cell specific antigen. L523S (SEQ ID NO: 100) is moderately over-expressed in lung squamous tumor, human pancreatic cancer cell lines and pancreatic cancer tissues, suggesting this gene may be a shared antigen between pancreatic and lung squamous cell cancer.

L524S (SEQ ID NO: 101) is over-expressed in the majority of squamous tumors tested and is homologous with parathyroid hormone-related peptide (PTHrP), which is best known to cause humoral hypercalcaemia associated with malignant tumors such as leukemia, prostate and breast cancer. It is also believed that PTHrP is most commonly associated with squamous carcinoma of lung and rarely with lung adenocarcinoma (Davidson, L. A., et al, *J. Pathol.,* 178: 398–401, 1996). L528S (SEQ ID NO: 105) is highly over-expressed in two lung squamous tumors with moderate expression in two other squamous tumors, one lung adenocarcinoma and some normal tissues, including skin, lymph nodes, heart, stomach and lung. It encodes the NMB gene that is similar to the precursor of melanocyte specific gene Pmel17, which is reported to be preferentially expressed in low-metastatic potential melanoma cell lines. This suggests that L528S may be a shared antigen in both melanoma and lung squamous cell carcinoma. L526S (SEQ ID NO: 103) was overexpressed in all lung squamous cell tumor tissues tested and has been shown to share homology with a gene (ATM) in which a mutation causes ataxia telangiectasia, a genetic disorder in humans causing a predisposition to cancer, among other symptoms. ATM encodes a protein that activates a p53 mediated cell-cycle checkpoint through direct binding and phosphorylation of the p53 molecule. Approximately 40% of lung cancers are associated with p53 mutations, and it is speculated that over-expression of ATM is a result of compensation for loss of p53 function, but it is unknown whether over-expression is the cause of result of lung squamous cell carcinoma. Additionally, expression of L526S (ATM) is also detected in a metastatic but not lung adenocarcinoma, suggesting a role in metastasis.

Expression of L523S (SEQ ID NO: 175), was examined by real time RT-PCR as described above. In a first study using a panel of lung squamous tumors, L523S was found to be expressed in 4/7 lung squamous tumors, 2/3 head and neck squamous tumors and 2/2 lung adenocarcinomas, with low level expression being observed in skeletal muscle, soft palate and tonsil. In a second study using a lung adenocarcinoma panel, expression of L523S was observed in 4/9 primary adenocarcinomas, 2/2 lung pleural effusions, 1/1 metastatic lung adenocarcinomas and 2/2 lung squamous tumors, with little expression being observed in normal tissues.

Expression of L523S in lung tumors and various normal tissues was also examined by Northern blot analysis, using standard techniques. In a first study, L523S was found to be expressed in a number of lung adenocarcinomas and squamous cell carcinomas, as well as normal tonsil. No expression was observed in normal lung. In a second study using a normal tissue blot (referred to as HB-12) from Clontech, no expression was observed in brain, skeletal muscle, colon, thymus, spleen, kidney, liver, small intestine, lung or PBMC, although there was strong expression in placenta.

Example 3

Isolation and Characterization of Lung Tumor Polypeptides by PCR-Based Subtraction Eight hundred and fifty seven clones from a cDNA subtraction library, containing cDNA from a pool of two human lung squamous tumors subtracted against eight normal human tissue cDNAs including lung, PBMC, brain, heart, kidney, liver, pancreas, and skin, (Clontech, Palo Alto, Calif.) were derived and submitted to a first round of PCR amplification. This library was subjected to a second round of PCR amplification, following the manufacturer's protocol. The resulting cDNA fragments were subcloned into the P7-Adv vector (Clontech, Palo Alto, Calif.) and transformed into DH5α *E. coli* (Gibco, BRL). DNA was isolated from independent clones and sequenced using a Perkin Elmer/Applied Biosystems Division Automated Sequencer Model 373A.

One hundred and sixty two positive clones were sequenced. Comparison of the DNA sequences of these clones with those in the EMBL and GenBank databases, as described above, revealed no significant homologies to 13 of these clones, hereinafter referred to as Contigs 13, 16, 17, 19, 22, 24, 29, 47, 49, 56–59. The determined cDNA sequences for these clones are provided in SEQ ID NO: 125, 127–129, 131–133, 142, 144, 148–150, and 157, respectively. Contigs 1, 3–5, 7–10, 12, 11, 15, 20, 31, 33, 38, 39, 41, 43, 44, 45, 48, 50, 53, 54 (SEQ ID NO: 115–124, 126, 130, 134–141, 143, 145–147, respectively) were found to show some degree of homology to previously identified DNA sequences. Contig 57 (SEQ ID NO: 149) was found to represent the clone L519S (SEQ ID NO: 94) disclosed in U.S. patent application Ser. No. 09/123,912, filed Jul. 27, 1998. To the best of the inventors' knowledge, none of these sequences have been previously shown to be differentially over-expressed in lung tumors.

mRNA expression levels for representative clones in lung tumor tissues, normal lung tissues (n=4), resting PBMC, salivary gland, heart, stomach, lymph nodes, skeletal muscle, soft palate, small intestine, large intestine, bronchial, bladder, tonsil, kidney, esophagus, bone marrow, colon, adrenal gland, pancreas, and skin (all derived from human) were determined by RT-PCR as described above. Expression levels using microarray technology, as described above, were examined in one sample of each tissue type unless otherwise indicated.

Contig 3 (SEQ ID NO: 116) was found to be highly expressed in all head and neck squamous cell tumors tested (17/17), and expressed in the majority (8/12) of lung squamous tumors, (high expression in 7/12, moderate in 2/12, and low in 2/12), while showing negative expression for 2/4 normal lung tissues and low expression in the remaining two samples. Contig 3 showed moderate expression in skin and soft palate, and lowered expression levels in resting PBMC, large intestine, salivary gland, tonsil, pancreas, esophagus, and colon. Contig 11 (SEQ ID NO: 124) was found to be expressed in all head and neck squamous cell tumors tested (17/17), with high levels of expression being seen in 14/17 tumors, and moderately levels of expression being seen in 3/17 tumors. Additionally, high expression was seen in 3/12 lung squamous tumors and moderate expression in 4/12 lung squamous tumors. Contig 11 was negative for 3/4 normal lung samples, with the remaining sample having only low expression. Contig 11 showed low to moderate reactivity to salivary gland, soft palate, bladder, tonsil, skin, esophagus, and large intestine. Contig 13 (SEQ ID NO: 125) was found to be expressed in all head and neck squamous cell tumors tested (17/17), with high expression in 12/17, and moderate expression in 5/17. Contig 13 was expressed in 7/12 lung squamous tumors, with high expression in 4/12 and moderate expression in three samples. Analysis of normal lung samples showed negative expression for 2/4 and low to moderate expression in the remaining two samples. Contig 13 showed low to moderate reactivity to resting PBMC, salivary gland, bladder, pancreas, tonsil, skin, esophagus, and large intestine, as well as high expression in soft palate. Subsequent full-length cloning efforts revealed that contig 13 (also known as L761P) maps to the 3' untranslated region of the hSec10p gene. The full-length sequence for this gene is set forth in SEQ ID NO: 368, and encodes the protein set forth in SEQ ID NO: 369.

Contig 16 (SEQ ID NO: 127) was found to be moderately expressed in several head and neck squamous cell tumors (6/17) and one lung squamous tumor, while showing no expression in any normal lung samples tested. Contig 16 showed low reactivity to resting PBMC, large intestine, skin, salivary gland, and soft palate. Contig 17 (SEQ ID NO: 128) was shown to be expressed in all head and neck squamous cell tumors tested (17/17) (highly expressed in 5/17, and moderately expressed in 12/17). Determination of expression levels in lung squamous tumors showed one tumor sample with high expression and 3/12 with moderate levels. Contig 17 was negative for 2/4 normal lung samples, with the remaining samples having only low expression. Additionally, low level expression was found in esophagus and soft palate. Contig 19 (SEQ ID NO: 129) was found to be expressed in most head and neck squamous cell tumors tested (11/17); with two samples having high expression levels, 6/17 showing moderate expression, and low expression being found in 3/17. Testing in lung squamous tumors revealed only moderate expression in 3/12 samples. Expression levels in 2/4 of normal lung samples were negative, the two other samples having only low expression. Contig 19 showed low expression levels in esophagus, resting PBMC, salivary gland, bladder, soft palate and pancreas.

Contig 22 (SEQ ID NO: 131), was shown to be expressed in most head and neck squamous cell tumors tested (13/17) with high expression in four of these samples, moderate expression in 6/17, and low expression in 3/17. Expression levels in lung squamous tumors were found to be moderate to high for 3/12 tissues tested, with negative expression in two normal lung samples and low expression in two other samples (n=4). Contig 22 showed low expression in skin, salivary gland and soft palate. Similarly, Contig 24 (SEQ ID NO: 132) was found to be expressed in most head and neck squamous cell tumors tested (13/17) with high expression in three of these samples, moderate expression in 6/17, and low expression in 4/17. Expression levels in lung squamous tumors were found to be moderate to high for 3/12 tissues tested, with negative expression for three normal lung samples and low expression in one sample (n=4). Contig 24 showed low expression in skin, salivary gland and soft palate. Contig 29 (SEQ ID NO: 133) was expressed in nearly all head and neck squamous cell tumors tested (16/17): highly expressed in 4/17, moderately expressed in 11/17, with low expression in one sample. Also, it was moderately expressed in 3/12 lung squamous tumors, while being negative for 2/4 normal lung samples. Contig 29 showed low to moderate expression in large intestine, skin, salivary gland, pancreas, tonsil. heart and soft palate. Contig 47 (SEQ ID NO: 142) was expressed in most head and neck squamous cell tumors tested (12/17): moderate expression in 10/17, and low expression in two samples. In lung squamous tumors, it was highly expressed in one sample and moderately expressed in two others (n=13). Contig 47 was negative for 2/4 normal lung samples, with the remaining two samples having moderate expression. Also, Contig 47 showed moderate expression in large intestine, and pancreas, and low expression in skin, salivary gland, soft palate, stomach, bladder, resting PBMC, and tonsil.

Contig 48 (SEQ ID NO: 143) was expressed in all head and neck squamous cell tumors tested (17/17): highly expressed in 8/17 and moderately expressed in 7/17, with low expression in two samples. Expression levels in lung squamous tumors were high to moderate in three samples (n=13). Contig 48 was negative for one out of four normal lung samples, the remaining showing low or moderate expression. Contig 48 showed moderate expression in soft palate, large intestine, pancreas, and bladder, and low expression in esophagus, salivary gland, resting PBMC, and heart. Contig 49 (SEQ ID NO: 144) was expressed at low to moderate levels in 6/17 head and neck squamous cell tumors tested. Expression levels in lung squamous tumors were moderate in three samples (n=13). Contig 49 was negative for 2/4 normal lung samples, the remaining samples showing low expression. Moderate expression levels in skin, salivary gland, large intestine, pancreas, bladder and resting PBMC were shown, as well as low expression in soft palate, lymph nodes, and tonsil. Contig 56 (SEQ ID NO: 148) was expressed in low to moderate levels in 3/17 head and neck squamous cell tumors tested, and in lung squamous tumors, showing low to moderate levels in three out of thirteen samples. Notably, low expression levels were detected in one adenocarcinoma lung tumor sample (n=2). Contig 56 was negative for 3/4 normal lung samples, and showed moderate expression levels in only large intestine, and low expression in salivary gland, soft palate, pancreas, bladder, and resting PBMC. Contig 58, also known as L769P, (SEQ ID NO: 150) was expressed at moderate levels in 11/17 head and neck squamous cell tumors tested and low expression in one additional sample. Expression in lung squamous tumors showed low to moderate levels in three out of thirteen samples. Contig 58 was negative for 3/4 normal lung samples, with one sample having low expression. Moderate expression levels in skin, large intestine, and resting PBMC were demonstrated, as well as low expression in salivary gland, soft palate, pancreas, and bladder. Contig 59 (SEQ ID NO: 157) was expressed in some head, neck, and lung squamous tumors. Low level expression of Contig 59 was also detected in salivary gland and large intestine.

The full-length cDNA sequence for Contig 22, also referred to as L763P, is provided in SEQ ID NO: 158, with the corresponding amino acid sequence being provided in SEQ ID NO: 159. Real-time RT-PCR analysis of L763P revealed that it is highly expressed in 3/4 lung squamous tumors as well as 4/4 head and neck squamous tumors, with low level expression being observed in normal brain, skin, soft pallet and trachea. Subsequent database searches revealed that the sequence of SEQ ID NO: 158 contains a mutation, resulting in a frameshift in the corresponding protein sequence. A second cDNA sequence for L763P is provided in SEQ ID NO: 345, with the corresponding amino acid sequence being provided in SEQ ID NO: 346. The sequences of SEQ ID NO: 159 and 346 are identical with the exception of the C-terminal 33 amino acids of SEQ ID NO: 159.

The full-length cDNA sequence incorporating Contigs 17, 19, and 24, referred to as L762P, is provided in SEQ ID NO: 160, with the corresponding amino acid sequence being provided in SEQ ID NO: 161. Further analysis of L762P has determined it to be a type I membrane protein and two additional variants have been sequenced. Variant 1 (SEQ ID NO: 167, with the corresponding amino acid sequence in SEQ ID NO: 169) is an alternatively spliced form of SEQ ID NO: 160 resulting in deletion of 503 nucleotides, as well as deletion of a short segment of the expressed protein. Variant 2 (SEQ ID NO: 168, with the corresponding amino acid sequence in SEQ ID NO: 170) has a two nucleotide deletion at the 3' coding region in comparison to SEQ ID NO: 160, resulting in a secreted form of the expressed protein. Real-time RT-PCR analysis of L762P revealed that is over-expressed in 3/4 lung squamous tumors and 4/4 head & neck tumors, with low level expression being observed in normal skin, soft pallet and trachea.

An epitope of L762P was identified as having the sequence KPGHWTYTLNNTHHSLQALK (SEQ ID NO: 382), which corresponds to amino acids 571–590 of SEQ ID NO: 161.

The full-length cDNA sequence for contig 56 (SEQ ID NO: 148), also referred to as L773P, is provided in SEQ ID NO: 171, with the amino acid sequence in SEQ ID NO: 172. L773P was found to be identical to dihydroxyl dehydrogenase at the 3' portion of the gene, with divergent 5' sequence. As a result, the 69 N-terminal amino acids are unique. The cDNA sequence encoding the 69 N-terminal amino acids is provided in SEQ ID NO: 349, with the N-terminal amino acid sequence being provided in SEQ ID NO: 350. Real-time PCR revealed that L773P is highly expressed in lung squamous tumor and lung adenocarcinoma, with no detectable expression in normal tissues. Subsequent Northern blot analysis of L773P demonstrated that this transcript is differentially over-expressed in squamous tumors and detected at approximately 1.6 Kb in primary lung tumor tissue and approximately 1.3 Kb in primary head and neck tumor tissue.

Subsequent microarray analysis has shown Contig 58, also referred to as L769S (SEQ ID NO: 150), to be over-expressed in breast tumors in addition to lung squamous tumors.

Example 4

Isolation and Characterization of Lung Tumor Polypeptides by PCR-Based Subtraction Seven hundred and sixty clones from a cDNA subtraction library, containing cDNA from a pool of two human lung primary adenocarcinomas subtracted against a pool of nine normal human tissue cDNAs including skin, colon, lung, esophagus, brain, kidney, spleen, pancreas and liver, (Clontech, Palo Alto, Calif.) were derived and submitted to a first round of PCR amplification. This library (referred to as ALT-1) was subjected to a second round of PCR amplification, following the manufacturer's protocol. The expression levels of these 760 cDNA clones in lung tumor, normal lung, and various other normal and tumor tissues, were examined using microarray technology (Incyte, Palo Alto, Calif.). Briefly, the PCR amplification products were dotted onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. This intensity correlates with the hybridization intensity. A total of 118 clones, of which 55 were unique, were found to be over-expressed in lung tumor tissue, with expression in normal tissues tested (lung, skin, lymph node, colon, liver, pancreas, breast, heart, bone marrow, large intestine, kidney, stomach, brain, small intestine, bladder and salivary gland) being either undetectable, or at significantly lower levels. One of these clones, having the sequence as provided in SEQ ID NO: 420 (clone #19014), shows homology to a previously identified clone, L773P. Clone L773P has the full-length cDNA sequence provided in SEQ ID NO: 171 and the amino acid sequence provided in SEQ ID NO: 172 The isolation of clone #19014 is also described in co-pending U.S. patent application Ser. No. 09/285,479, filed Apr. 2, 1999.

Example 5

Synthesis of Polypeptides

Polypeptides may be synthesized on a Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support is carried out using the following cleavage mixture: trifluoroacetic acid:ethanedithiol:thioanisole:water:phenol (40:1:2:2:3). After cleaving for 2 hours, the peptides are precipitated in cold methyl-t-butyl-ether. The peptide pellets are then dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides are characterized using electrospray or other types of mass spectrometry and by amino acid analysis.

Example 6

PREPARATION OF ANTIBODIES AGAINST LUNG CANCER ANTIGENS

Polyclonal antibodies against the lung cancer antigens L514S, L528S, L531S, L523 and L773P (SEQ ID NO: 155, 225, 112, 176 and 171, respectively) were prepared as follows.

Rabbits were immunized with recombinant protein expressed in and purified from *E. coli* as described below. For the initial immunization, 400 $\mu$g of antigen combined with muramyl dipeptide (MDP) was injected subcutaneously (S.C.). Animals were boosted S.C. 4 weeks later with 200 $\mu$g of antigen mixed with incomplete Freund's Adjuvant (IFA). Subsequent boosts of 100 $\mu$g of antigen mixed with IFA were injected S.C. as necessary to induce high antibody titer responses. Serum bleeds from immunized rabbits were tested for antigen-specific reactivity using ELISA assays with purified protein. Polyclonal antibodies against L514S, L528S, L531S, L523S and L773P were affinity purified from high titer polyclonal sera using purified protein attached to a solid support.

Immunohistochemical analysis using polyclonal antibodies against L514S was performed on a panel of 5 lung tumor samples, 5 normal lung tissue samples and normal colon, kidney, liver, brain and bone marrow. Specifically, tissue samples were fixed in formalin solution for 24 hours and embedded in paraffin before being sliced into micron sections. Tissue sections were permeabilized and incubated with antibody for 1 hr. HRP-labeled anti-mouse followed by incubation with DAB chromogen was used to visualize L514S immunoreactivity. L514S was found to be highly expressed in lung tumor tissue with little or no expression being observed in normal lung, brain or bone marrow. Light staining was observed in colon (epithelial crypt cells positive) and kidney (tubules positive). Staining was seen in normal liver but no mRNA has been detected in this tissue making this result suspect.

Using the same procedure, immunohistochemical analysis using polyclonal antibodies against L528S demonstrated staining in lung tumor and normal lung samples, light staining in colon and kidney, and no staining in liver and heart.

Inmunohistochemical analysis using polyclonal antibodies against L531S demonstrated staining in lung tumor samples, light membrane staining in most normal lung samples, epithelial staining in colon, tubule staining in kidney, ductal epithelial staining in liver and no staining in heart.

Immunohistochemical analysis using polyclonal antibodies against L523S demonstrated staining in all lung cancer samples tested but no staining in normal lung, kidney, liver, colon, bone marrow or cerebellum.

Generation of polyclonal anti-sera against L762P (SEQ ID NO: 169 and 170) was performed as follows. 400 micrograms of lung antigen was combined with 100 micrograms of muramyldipeptide (MDP). An equal volume of Incomplete Freund's Adjuvant (IFA) was added and then mixed until an emulsion was formed. Rabbits were injected subcutaneously (S.C.). After four weeks the animals were injected S.C. with 200 micrograms of antigen mixed with an equal volume of IFA. Every four weeks animals were boosted with 100 micrograms of antigen. Seven days following each boost the animal was bled. Sera was generated by incubating the blood at 4° C. for 12–24 hours followed by centrifugation.

Characterization of polyclonal antisera was carried out as follows. Ninety-six well plates were coated with antigen by incubing with 50 microliters (typically 1 microgram) at 4° C. for 20 hrs. 250 microliters of BSA blocking buffer was added to the wells and incubated at room temperature for 2 hrs. Plates were washed 6 times with PBS/0.01% Tween. Rabbit sera was diluted in PBS and 50 microliters of diluted sera was added to each well and incubated at room temperature for 30 min. Plates were washed as described above before addition of 50 microliters of goat anti-rabbit horse radish peroxidase (HRP) at a 1:10000 dilution and incubation at room temperature for 30 min. Plates were washed as described above and 100 $\mu$l of TMB Microwell Peroxidase Substrate was added to each well. Following a 15 minute incubation in the dark at room temperature, the calorimetric reaction was stopped with 100 $\mu$l 1N $H_2SO_4$ and read immediately at 450 nm. Antisera showed strong reactivity to antigen L762P.

Immunohistochemical analysis using polyclonal antibodies against L762P demonstrated staining in all lung cancer samples tested, some light staining in the bronchiole epithelium of normal lung, tubule staining in kidney, light epithelial staining in colon and no staining in heart or liver.

In order to evaluate L773P protein expression in various tissues, immunohistochemistry (IHC) analysis was performed using an affinity purified L773P polyclonal antibody. Briefly, tissue samples were fixed in formalin solution for 12–24 hrs and embedded in paraffin before being sliced into 8 micron sections. Steam heat induced epitope retrieval (SHIER) in 0.1 M sodiuym citrate buffer (pH 6.0) was used for optimal staining conditions. Sections were incubated with 10% serum/PBS for 5 minutes. Primary antibody was added to each section for 25 minutes at indicated concentrations followed by 25 minute incubation with either anti-rabbit or anti-mouse biotinylated antibody. Endogenous peroxidase activitiy was blocked by three 1.5 minute incubations with hydrogen peroxidase. The avidin biotin complex/horse radish peroxidase (ABC/HRP) system was used along with DAB chromogen to visualize L773P expression. Slides were counterstainied with hematoxylin to visualize cell nuclei. Using this approach, L773P protein was detected in 6/8 lung tumors, 4/6 normal lung samples (very light staining in some cases), 1/1 kidney samples (very light staining), 0/1 heart samples, 1/1 colon samples (very light staining) and 0/1 liver samples.

Example 7

PEPTIDE PRIMING OF MICE AND PROPAGATION OF CTL LINES

Immunogenic peptides from the lung cancer antigen L762P (SEQ ID NO: 161) for HLA-A2/$K^b$-restricted CD8+ T cells were identified as follows.

The location of HLA-A2 binding peptides within the lung cancer antigen L762P (SEQ ID NO: 161) was predicted using a computer program which predicts peptides sequences likely to being to HIA-A*0201 by fitting to the known peptide binding motif for HLA-A*0201 (Rupert et al. (1993) *Cell* 74:929; Rammensee et al. (1995) *Immunogenetics* 41:178–228). A series of 19 synthetic peptides corresponding to a selected subset of the predicted HLA-A*0201 binding peptides was prepared as described above.

Mice expressing the transgene for human HLA A2/$K^b$ (provided by Dr L. Sherman, The Scripps Research Institute, La Jolla, Calif.) were immunized with the synthetic peptides, as described by Theobald et al., *Proc. Natl. Acad.*

*Sci. USA* 92:11993–11997, 1995, with the following modifications. Mice were immunized with 50 μg of L726P peptide and 120 μg of an I-$A^b$ binding peptide derived from hepatitis B virus protein emulsified in incomplete Freund's adjuvant. Three weeks later these mice were sacrificed and single cell suspensions prepared. Cells were then resuspended at 7×$10^6$ cells/ml in complete media (RPMI-1640; Gibco BRL, Gaithersburg, Md.) containing 10% FCS, 2 mM Glutamine (Gibco BRL), sodium pyruvate (Gibco BRL), non-essential amino acids (Gibco BRL), 2×$10^{-5}$ M 2-mercaptoethanol, 50 U/ml penicillin and streptomycin, and cultured in the presence of irradiated (3000 rads) L762P peptide- (5 μg/ml) and 10 mg/ml $B_2$-microglobulin-(3 μg/ml) LPS blasts (A2 transgenic spleens cells cultured in the presence of 7 μg/ml dextran sulfate and 25 μg/ml LPS for 3 days). After six days, cells (5×$10^5$/ml) were restimulated with 2.5×$10^6$/ml peptide-pulsed irradiated (20,000 rads) EL4A2Kb cells (Sherman et al, *Science* 258:815–818, 1992) and 5×$10^6$/ml irradiated (3000 rads) A2/$K^b$-transgenic spleen feeder cells. Cells were cultured in the presence of 10 U/ml IL-2. Cells were restimulated on a weekly basis as described, in preparation for cloning the line.

Peptide-specific cell lines were cloned by limiting dilution analysis with irradiated (20,000 rads) L762P peptide-pulsed EL4 A2Kb tumor cells (1×$10^4$ cells/well) as stimulators and irradiated (3000 rads) A2/$K^b$-transgenic spleen cells as feeders (5×$10^5$ cells/well) grown in the presence of 10 U/ml IL-2. On day 7, cells were restimulated as before. On day 14, clones that were growing were isolated and maintained in culture.

Cell lines specific for the peptides L762P-87 (SEQ ID NO: 226; corresponding to amino acids 87–95 of SEQ ID NO: 161), L762P-145 (SEQ ID NO: 227; corresponding to amino acids 145–153 of SEQ ID NO: 161), L762P-585 (SEQ ID NO: 228; corresponding to amino acids 585–593 of SEQ ID NO: 161), L762P-425 (SEQ ID NO: 229; corresponding to amino acids 425–433 of SEQ ID NO: 161), L762P(10)-424 (SEQ ID NO: 230; corresponding to amino acids 424–433 of SEQ ID NO: 161) and L762P(10)-458 (SEQ ID NO: 231; corresponding to amino acids 458–467 of SEQ ID NO: 161) demonstrated significantly higher reactivity (as measured by percent specific lysis) against L762P peptide-pulsed EL4-A2/$K^b$ tumor target cells than control peptide-pulsed EL4-A2/$K^b$ tumor target cells.

Example 8

Identification of CD4 Immunogenic T Cell Epitopes Derived From the Lung Cancer Antigen L762p CD4 T cell lines specific for the antigen L762P (SEQ ID NO: 161) were generated as follows.

A series of 28 overlapping peptides were synthesized that spanned approximately 50% of the L762P sequence. For priming, peptides were combined into pools of 4–5 peptides, pulsed at 20 micrograms/ml into dendritic cells for 24 hours. The dendritic cells were then washed and mixed with positively selected CD4+ T cells in 96 well U-bottomed plates. Forty cultures were generated for each peptide pool. Cultures were restimulated weekly with fresh dendritic cells loaded with peptide pools. Following a total of 3 stimulation cycles, cells were rested for an additional week and tested for specificity to antigen presenting cells (APC) pulsed with peptide pools using interferon-gamma ELISA and proliferation assays. For these assays, adherent monocytes loaded with either the relevant peptide pool or an irrelevant peptide were used as APC. T cell lines that appeared to specifically recognize L762P peptide pools both by cytokine release and proliferation were identified for each pool. Emphasis was placed on identifying T cells with proliferative responses. T cell lines that demonstrated either both L762P-specific cytokine secretion and proliferation, or strong proliferation alone were further expanded to be tested for recognition of individual peptides from the pools, as well as for recognition of recombinant L762P. The source of recombinant L762P was *E. coli*, and the material was partially purified and endotoxin positive. These studies employed 10 micrograms of individual peptides, 10 or 2 micrograms of an irrelevant peptide, and 2 or 0.5 micrograms of either L762P protein or an irrelevant, equally impure, *E. coli* generated recombinant protein. Significant interferon-gamma production and CD4 T cell proliferation was induced by a number of L762P-derived peptides in each pool. The amino acid sequences for these peptides are provided in SEQ ID NO: 232–251. These peptides correspond to amino acids 661–680, 676–696, 526–545, 874–893, 811–830, 871–891, 856–875, 826–845, 795–815, 736–755, 706–725, 706–725, 691–710, 601–620, 571–590, 556–575, 616–635, 646–665, 631–650, 541–560 and 586–605, respectively, of SEQ ID NO: 161.

CD4 T cell lines that demonstrated specificity for individual L762P-derived peptides were further expanded by stimulation with the relevant peptide at 10 micrograms/ml. Two weeks post-stimulation, T cell lines were tested using both proliferation and IFN-gamma ELISA assays for recognition of the specific peptide. A number of previously identified T cells continued to demonstrate IL762P-peptide specific activity. Each of these lines was further expanded en the relevant peptide and, following two weeks of expansion, tested for specific recognition of the L762P-peptide in titration experiments, as well as for recognition of recombinant *E. coli*-derived L762P protein. For these experiments, autologous adherent monocytes were pulsed with either the relevant L762P-derived peptide, an irrelevant mammaglobin-derived peptide, recombinant *E. coli*-derived L762P (approx. 50% pure), or an irrelevant *E. coli*-derived protein. The majority of T cell lines were found to show low affinity for the relevant peptide, since specific proliferation and IFN-gamma ratios dramatically decreased as L762P peptide was diluted. However, four lines were identified that demonstrated significant activity even at 0.1 micrograms/ml peptide. Each of these lines (referred to as A/D5, D/F5, E/A7 and E/B6) also appeared to specifically proliferate in response to the *E. coli*-derived L762P protein preparation, but not in response to the irrelevant, protein preparation. The amino acid sequences of the L762P-derived peptides recognized by these lines are provided in SEQ ID NO: 234, 249, 236 and 245, respectively. No protein specific IFN-gamma was detected for any of the lines. Lines A/D5, E/A7 and E/B6 were cloned on autologous adherent monocytes pulsed with the relevant peptide at 0.1 (A/D5 and E/A7) or 1 (D/F5) microgram/ml. Following growth, clones were tested for specificity for the relevant peptide. Numerous clones specific for the relevant peptide were identified for lines A/D5 and E/A7.

Example 9

Protein Expression of Lung Tumor-Specific Antigens a) Expression of L514S in *E. coli*

The lung tumor antigen L514S (SEQ ID NO: 89) was subcloned into the expression vector pE32b at NcoI and NotI sites, and transformed into *E. coli* using standard techniques. The protein was expressed from residues 3–153 of SEQ ID NO: 89. The expressed amino acid sequence and the corresponding DNA sequence are provided in SEQ ID NO: 252 and 253, respectively.

b) Expression of L762P

Amino acids 32–944 of the lung tumor antigen L762P (SEQ ID NO: 161), with a 6× His Tag, were subcloned into a modified pET28 expression vector, using kanamycin resistance, and transformed into BL21 CodonPlus using standard techniques. Low to moderate levels of expression were observed. The determined DNA sequence of the L762P expression construct is provided in SEQ ID NO: 254.

Example 10

Identification of MHC class II Restricting Allele for L762P Peptide-Specific Responses A panel of HLA mismatched antigen presenting cells (APC) were used to identify the MHC class II restricting allele for the 1,762P-peptide specific responses of CD4 T cell clones derived from lines that recognized L762P peptide and recombinant protein. Clones from two lines, AD-5 and EA-7, were tested as described below. The AD-5 derived clones were found to be restricted by the HLA-DRB-1101 allele, and an EA-7 derived clone was found to be restricted by the HULA DRB-0701 or DQB1-0202 allele. Identification of the restriction allele allows targeting of vaccine therapies using the defined peptide to individuals that express the relevant class II allele. Knowing the relevant restricting allele will also enable clinical monitoring for responses to the defined peptide since only individuals that express the relevant allele will be monitored.

CD4 T cell clones derived from line AD-5 and EA-7 were stimulated on autologous APC pulsed with the specific peptide at 10 $\mu$g/ml, and tested for recognition of autologous APC (from donor D72) as well as against a panel of APC partially matched with D72 at class II alleles. Table 2 shows the HLA class typing of the APC tested. Adherent monocytes (generated by 2 hour adherence) from four different donors, referred to as D45, D187, D208, and D326, were used as APC in these experiments. Autologous APC were not included in the experiment. Each of the APC were pulsed with the relevant peptide (5a for AD-5 and 3e for 3A-7) or the irrelevant mammoglobin peptide at 10 $\mu$g/ml, and cultures were established for 10,000 T cells and about 20,000 APC/well. As shown in Table 3, specific proliferation and cytokine production could be detected only when partially matched donor cells were used as APC. Based on the MHC typing analysis, these results strongly suggest that the restricting allele for the 1,762-specific response of the AD-5 derived clones is HLA-DRB-1101 and for the EA-7 derived clone the restricting allele is HLA DRB-0701 or DQB1-0202.

TABLE 2

| | HLA Typing of APC | | | |
|---|---|---|---|---|
| DONOR | DR | DR | DQ | DQ |
| D72 | B1-1101 | B1-0701 | B1-0202 | B1-0301 |
| D45 | −3 | −15 | B1-0201 | B1-0602 |
| D187 | −4 | −15 | −1 | −7 |
| D208 | B1-1101 | B1-0407 | −3 | −3 |
| D326 | B1-0301 | B1-0701 | B1-0202 | B1-0201 |

TABLE 3

L762P Peptide Responses Map to HLA DR Alleles

| | AD-5 | | | | | | | | | | | | | |
|---|---|---|---|---|---|---|---|---|---|---|---|---|---|---|
| | A11 | | B10 | | C10 | | C11 | | E6 | | F1 | | F9 | |
| Donor | Prol | γ-IFN | Prol | γ-IFN | Prol | γ-IFN | Prol | γ-IFN | Prol | γ-IFN | Prol | γ-IFN | Prol | γ-IFN |
| D72 DR-0701, -1101, DQ-0202, -7 | 46 | | 31 | | 34 | | 24 | | 31 | | 40 | | 55 | |
| D45 DR-3, -15, DQ-1, -0201 | 3.2 | 1.7 | 5.5 | 1.2 | 3.3 | 1 | 1.0 | 1.5 | 1.1 | 1.1 | 1.6 | 1.1 | 1.4 | 1.3 |
| D187 DR-4, -15, DQ-1, -7 | 1.4 | 1.2 | 1.3 | 1 | 1.4 | 1.1 | 1.4 | 1.7 | 1.0 | 1.1 | 1.4 | 1.2 | 1.2 | 1.1 |
| D208 DR-4, -1101, DQ-3 | 138 | 13 | 38 | 5.4 | 18.8 | 10 | 14.6 | 4.6 | 15.3 | 6.1 | 45.9 | 8.6 | 73.3 | 14.1 |
| D326 DR-3, -0701, DQ-0202 | 0.7 | 4 | 0.3 | 1 | 0.3 | 1.4 | 1.0 | 2 | 0.8 | 1.1 | 0.3 | 1.1 | 0.7 | 1.1 |

| | AD-5 | | | | | | EA-7 | |
|---|---|---|---|---|---|---|---|---|
| | G8 | | G9 | | G10 | | G12 | |
| Donor | Prol | γ-IFN | Prol | γ-IFN | Prol | γ-IFN | Prol | γ-IFN |

TABLE 3-continued

L762P Peptide Responses Map to HLA DR Alleles

| | | | | | | | | |
|---|---|---|---|---|---|---|---|---|
| D72 DR-0701, -1101, DQ-0202, -7 | 45 | | 43 | | 91 | | 10 | |
| D45 DR-3, -15, DQ-1, -0201 | 0.2 | 1.1 | 1.1 | 1.1 | 1.2 | 1.5 | 0.8 | 1.1 |
| D187 DR-4, -15, DQ-1, -7 | 0.9 | 1 | 1.0 | 1 | 1.0 | 1.6 | 0.5 | 1 |
| D208 DR-4, -1101, DQ-3 | 38.0 | 7.7 | 174.3 | 16.1 | 113.6 | 19.6 | 0.8 | 1 |
| D326 DR-3, -0701, DQ-0202 | 0.6 | 1.2 | 0.4 | 1 | 1.2 | 5 | 14.1 | 6.8 |

Example 11

Fusion Proteins of N-Terminal and C-Terminal Portions of L763P

In another embodiment, a *Mycobacterium tuberculosis*-derived polynucleotide, referred to as Ra12, is linked to at least an immunogenic portion of a polynucleotide of this invention. Ra12 compositions and methods for their use in enhancing expression of heterologous polynucleotide sequences are described in U.S. Patent Application 60/158,585, the disclosure of which is incorporated herein by reference in its entirety. Briefly, Ra12 refers to a polynucleotide region that is a subsequence of a *Mycobacterium tuberculosis* MTB32A nucleic acid. MTB32A is a serine protease of 32 KD molecular weight encoded by a gene in virulent and avirulent strains of *M. tuberculosis*. The nucleotide sequence and amino acid sequence of MTB32A have been described (for example, U.S. patent application No. 60/158,585; see also, Skeiky et al., *Infection and Immun.* (1999) 67:3998–4007, incorporated herein by reference). Surprisingly, it was discovered that a 14 KD C-terminal fragment of the MTB32A coding sequence expresses at high levels on its own and remains as a soluble protein throughout the purification process. Moreover, this fragment may enhance the immunogenicity of heterologous antigenic polypeptides with which it is fused. This 14 KD C-terminal fragment of the MTB32A is referred to herein as Ra12 and represents a fragment comprising some or all of amino acid residues 192 to 323 of MTB32A.

Recombinant nucleic acids which encode a fusion polypeptide comprising a Ra12 polypeptide and a heterologous lung tumor polypeptide of interest, can be readily constructed by conventional genetic engineering techniques. Recombinant nucleic acids are constructed so that, preferably, a Ra12 polynucleotide sequence is located 5' to a selected heterologous lung tumor polynucleotide sequence. It may also be appropriate to place a Ra12 polynucleotide sequence 3' to a selected heterologous polynucleotide sequence or to insert a heterologous polynucleotide sequence into a site within a Ra12 polynucleotide sequence.

In addition, any suitable polynucleotide that encodes a Ra12 or a portion or other variant thereof can be used in constructing recombinant fusion polynucleotides comprising Ra12 and one or more lung tumor polynucleotides disclosed herein. Preferred Ra12 polynucleotides generally comprise at least about 15 consecutive nucleotides, at least about 30 nucleotides, at least about 60 nucleotides, at least about 100 nucleotides, at least about 200 nucleotides, or at least about 300 nucleotides that encode a portion of a Ra12 polypeptide.

Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants preferably exhibit at least about 70% identity, more preferably at least about 80% identity and most preferably at least about 90% identity to a polynucleotide sequence that encodes a native Ra12 polypeptide or a portion thereof.

Two specific embodiments of fusions between Ra12 and antigens of the present invention are described in this example.

A. N-Terminal Portion of L763P

A fusion protein of full-length Ra12 and the N-terminal portion of L763P (referred to as L763P-N; amino acid residues 1–130 of SEQ ID NO: 159) was expressed as a single recombinant protein in *E. coli*. The cDNA for the N-terminal portion was obtained by PCR with a cDNA for the full length L763P and primers L763F3 (5' GGCGAATTCATGGATTGGGGGACGCTGC; SEQ ID NO: 383) and 1763RV3 (5' GGCCTCGAGTCACCCCTCTATCCGAACCTTCTGC; SEQ ID NO: 384). The PCR product with expected size was recovered from agarose gel, digested with restriction enzymes EcoRI and XhoI, and cloned into the corresponding sites in the expression vector pCRX1. The sequence for the fusion of full-length of Ra12 and L763P-N was confirmed by DNA sequencing. The determined cDNA sequence is provided in SEQ ID NO:351, with the corresponding amino acid sequence being provided in SEQ ID NO: 352).

B. C-Terminal Portion of L763P

A fusion protein of full-length Ra12 and the C-terminal portion of L763P (referred to as L763P-C; amino acid residues 100–262 of SEQ ID NO: 159) was expressed as a single recombinant protein in *E. coli*. The cDNA of the C-terminal portion of L763P was obtained by PCR with a cDNA for the full length of L763P and primers L763F4 (5' CGGCGAATTCCACGAACCACTCGCAAGTTCAG; SEQ ID NO: 385) and L763RV4 (5' CGGCTCGAG-TTAGCTTGGGCCTGTGATTGC; SEQ ID NO: 386). The PCR product with expected size was recovered from agarose gel, digested with restriction enzymes EcoRI and XhoI, and cloned into the corresponding sites in the expression vector pCRX1. The sequence for the fusion of full-length Ra12 and L763P-C was confirmed by DNA sequencing. The determined DNA sequence is provided in SEQ ID NO: 353, with the corresponding amino acid sequence being provided in SEQ ID NO:354.

The recombinant proteins described in this example are useful for the preparation of vaccines, for antibody therapeutics, and for diagnosis of lung tumors.

Example 12

Expression in *E. coli* of L762P His Tag Fusion Protein

PCR was performed on the L762P coding region with the following primers:

Forward primer starting at amino acid 32.

PDM-278 5'ggagtacagcttcaagacaatggg 3' (SEQ ID NO:355) Tm 57° C.

Reverse primer including natural stop codon after amino acid 920, creating EcoRI site PDM-280 5'ccatgggaattcattataataattttgttcc 3' (SEQ ID NO:356) TM55° C.

The PCR product was digested with EcoRI restriction enzyme, gel purified and then cloned into pPDM His, a modified pET28 vector with a His tag in frame, which had been digested with Eco72I and EcoRI restriction enzymes. The correct construct was confirmed by DNA sequence analysis and then transformed into BL21 (DE3) pLys S and BL21 (DE3) CodonPlus RIL expression hosts.

The protein sequence of expressed recombinant L762P is shown in SEQ ID NO:357, and the DNA sequence is shown in SEQ ID NO:358.

Example 13

Expression in *E. coli* of a L773PA His Tag Fusion Protein

The L773PA coding region (encoding amino acids 2–71 of SEQ ID NO: 172) was PCR amplified using the following primers:

Forward primer for L773PA starting at amino acid 2:

PDM-299 5'tggcagcccctcttcttcaagtggc 3' (SEQ ID NO:359) Tm63° C.

Reverse primer for L773PA creating artificial stop codon after amino acid 70:

PDM-355 5'cgccagaattcatcaaacaaatctgttagcacc 3' (SEQ ID NO:360) Tm62° C.

The resulting PCR product was digested with EcoRI restriction enzyme, gel purified and then cloned into pPDM His, a modified pET28 vector with a His tag in frame, which had been digested with Eco72I and EcoRI restriction enzymes. The correct construct was confirmed by DNA sequence analysis and transformed into BL21 (DE3) pLys S and BL21 (DE3) CodonPlus RIL expression hosts.

The protein sequence of expressed recombinant L773PA is shown in SEQ ID NO:361, and the DNA sequence is shown in SEQ ID NO:362.

Example 14

Identification of Epitopes Derived From Lung Tumor Specific Polypeptides

A series of peptides from the L773P amino acid sequence (SEQ ID NO: 172) were synthesized and used in in vitro priming experiments to generate peptide-specific CD4 T cells. These peptides were 20-mers that overlapped by 15 amino acids and corresponded to amino acids 1–69 of the L773P protein. This region has been demonstrated to be tumor-specific. Following three in vitro stimulations, CD4 T cell lines were identified that produced IFNγ in response to the stimulating peptide but not the control peptide. Some of these T cell lines demonstrated recognition of recombinant L773P and L773PA (tumor-specific region) proteins.

To perform the experiments, a total of eleven 20-mer peptides (SEQ ID NO: 363, 365 and 387–395) overlapping by 15 amino acids and derived from the N-terminal tumor-specific region of L773P (corresponding to amino acids 1–69 of SEQ ID NO: 172) were generated by standard procedures. Dendritic cells were derived from PBMC of a normal donor using GMCSF and IL-4 by standard protocol. Purified CD4 T cells were generated from the same donor as the dendritic cells using MACS beads and negative selection of PBMCs. Dendritic cells were pulsed overnight with the individual 20-mer peptides at a concentration of 10 μg/ml. Pulsed dendritic cells were washed and plated at $1\times10^4$/well of a 96-well U-bottom plates, and purified CD4 cells were added at $1\times10^5$ well. Cultures were supplemented with 10 ng/ml IL-6 and 5 ng/ml IL-12, and incubated at 37° C. Cultures were re-stimulated as above on a weekly basis using as APC dendritic cells generated and pulsed as above, supplemented with 5 ng/ml IL-7 and 10 μg/ml IL-2. Following 3 in vitro stimulation cycles, cell lines (each corresponding to one well) were tested for cytokine production in response to the stimulating peptide vs. an irrelevant peptide.

A small number of individual CD4 T cell lines (9/528) demonstrated cytokine release (IFNγ) in response to the stimulating peptide but not to control peptide. The CD4 T cell lines that demonstrated specific activity were restimulated on the appropriate L773P peptide and reassayed using autologous dendritic cells pulsed with 10 μg/ml of the appropriate L773P peptide, an irrelevant control peptide, recombinant L773P protein (amino acids 2–364, made in *E. coli*), recombinant L773PA (amino acids 2–71, made in *E. coli*), or an appropriate control protein (L3E, made in *E. coli*). Three of the nine lines tested (1-3C, 1-6G, and 4-12B) recognized the appropriate L773P peptide as well as recombinant L773P and L773PA. Four of the lines tested (4-8A, 4-8E, 4-12D, and 4-12E) recognized the appropriate L773P peptide only. Two of the lines tested (5-6F and 9-3B) demonstrated non-specific activity.

These results demonstrate that the peptide sequences MWQPLFFKWLLSCCPGSSQI (amino acids 1–20 of SEQ ID NO: 172; SEQ ID NO:363) and GSSQIAAAASTQPED-DINTQ (amino acids 16–35 of SEQ ID NO: 172; SEQ ID NO: 365) may represent naturally processed epitopes of L773P, which are capable of stimulating human class II MHC-restricted CD4 T cell responses.

In subsequent studies, the above epitope mapping experiment was repeated using a different donor. Again, some of the resulting T cell lines were found to respond to peptide and recombinant protein. An additional peptide was found to be naturally processed. Specifically, purified CD4 cells were stimulated on a total of eleven 20-mer peptides overlapping by 15 amino acids (SEQ ID NO: 363, 387, 388, 365 and 389–395, respectively). The priming was carried out as described above, except that a peptide concentration of 0.5 ug/mL rather than 10 μg/mL was employed. In the initial screen of the cell lines 9 of the 528 lines released at least a three-fold greater level of IFN-gamma with stimulating peptide vs. control peptide. These 9 lines were restimulated on the appropriate peptide and then tested on dendritic cells pulsed with a titration of appropriate peptide (10 μg/mL, 1 μg/mL and 0.1 μg/mL), and 10 μg/mL of a control peptide. Six of the 9 lines recognized recombinant L773P as well as peptide. The six lines referred to as 1-1E, 1-2E, 1-4H, 1-6A, 1-6G and 2-12B recognized L773PA and the appropriate peptide. These results demonstrate that the peptides of SEQ ID NO: 363 and 387 represent naturally processed epitopes of L773P.

Using the procedures described above, CD4+ T cell responses were generated from PBMC of normal donors using dendritic cells pulsed with overlapping 20-mer peptides (SEQ ID NO: 396–419) spanning the L523S polypeptide sequence (SEQ ID NO: 176). A number of CD4+ T cells demonstrated reactivity with the priming peptides as well as with L523S recombinant protein, with the dominant reactivity of these lines being within the peptides 4, 7 and 21 (SEQ ID NO: 399, 402 and 416; corresponding to amino acids 30–39, 60–79 and 200–219, respectively, of SEQ ID NO: 176).

Epitopes within the scope of the invention include epitopes restricted by other class II MHC molecules. In addition, variants of the peptide can be produced wherein one or more amino acids are altered such that there is no effect on the ability of the peptides to bind to MHC molecules, no effect on their ability to elicit T cell responses, and no effect on the ability of the elicited T cells to recognize recombinant protein.

Example 15

Surface Expression of L762P AND Antibody Epitopes Thereof

Rabbits were immunized with full-length histidine-tagged L762P protein generated in *E. coli*. Sera was isolated from rabbits and screened for specific recognition of L762P in ELISA assays. One polyclonal serum, referred to as 2692L, was identified that specifically recognized recombinant L762P protein. The 2692L anti-L762P polyclonal antibodies were purified from the serum by affinity purification using L762P affinity columns. Although L762P is expressed in a subset of primary lung tumor samples, expression appears to be lost in established lung tumor cell lines. Therefore, to characterize surface expression of L762P, a retrovirus construct that expresses L762P was used to transduce primary human fibroblasts as well as 3 lung tumor cell lines (522–23, HTB, and 343T). Transduced lines were selected and expanded to examine L762P surface expression by FACS analysis. For this analysis, non-transduced and transduced cells were harvested using cell dissociation medium, and incubated with 10–50 micrograms/ml of either affinity purified anti-L762P or irrelevant antisera. Following a 30 minute incubation on ice, cells were washed and incubated with a secondary, FITC conjugated, anti rabbit IgG antibody as above. Cells were washed, resuspended in buffer with Propidium Iodide (PI) and examined by FACS using an Excalibur fluorescence activated cell sorter. For FACS analysis, PI-positive (i.e. dead/permeabilized cells) were excluded. The polyclonal anti-L762P sera specifically recognized and bound to the surface of L762P-transduced cells but not the non-transduced counterparts. These results demonstrate that L762P is localized to the cell surface of both fibroblasts as well as lung tumor cells.

To identify the peptide epitopes recognized by 2692L, an epitope mapping approach was pursued. A series of overlapping 19–21 mers (5 amino acid overlap) was synthesized that spanned the C terminal portion of L762P (amino acids 481–894 of SEQ ID NO: 161). In an initial experiment peptides were tested in pools. Specific reactivity with the L762P antiserum was observed with pools A, B, C, and E. To identify the specific peptides recognized by the antiserum, flat bottom 96 well microtiter plates were coated with individual peptides at 10 microgram/ml for 2 hours at 37° C. Wells were then aspirated and blocked with phosphate buffered saline containing 5% (w/v) milk for 2 hours at 37° C., and subsequently washed in PBS containing 0.1% Tween 20 (PBST). Purified rabbit anti-L762P serum 2692L was added at 200 or 20 ng/well to triplicate wells in PBST and incubated overnight at room temperature. This was followed by washing 6 times with PBST and subsequently incubating with HRP-conjugated donkey anti rabbit IgG (H+L)Affinipure F(ab') fragment at 1:2,000 for 60 minutes. Plates were then washed, and incubated in tetramethyl benzidine substrate. Reactions were stopped by the addition of 1N sulfuric acid and plates were read at 450/570 nm using an ELISA plate reader.

The resulting data, presented in Table 4 below, demonstrates that the L762P antisera recognized at least 6 distinct peptide epitopes from the 3' half of L762P.

TABLE 4

| | | ELISA activity (OD 450–570) | |
|---|---|---|---|
| Peptide (starting amino acid of L762P) | pool | 200 ng polyclonal serum | 20 ng polyclonal serum |
| A (481) | A | 1.76 | 1.0 |
| B (495) | A | 0.14 | .06 |
| C (511) | E | 0.47 | 0.18 |
| D (526) | E | 0.11 | 0.09 |
| E (541) | A | 0.11 | 0.04 |
| F (556) | A | 0.04 | 0.02 |
| G (571) | A | 0.06 | 0.02 |
| H (586) | B | 0.1 | 0.03 |
| I (601) | B | 0.25 | 0.06 |
| J (616) | B | 0.1 | 0.03 |
| K (631) | E | 0.1 | 0.08 |
| L (646) | B | 0.28 | 0.12 |
| M (661) | B | 0.14 | 0.03 |
| N (676) | C | 0.12 | 0.1 |
| O (691) | C | 1.1 | 0.23 |
| P (706) | C | 0.1 | 0.03 |
| Q (721) | C | 0.11 | 0.05 |
| R (736) | E | 0.12 | 0.04 |

TABLE 4-continued

| Peptide (starting amino acid of L762P) | pool | ELISA activity (OD 450–570) 200 ng polyclonal serum | 20 ng polyclonal serum |
|---|---|---|---|
| S (751) | C | 0.15 | 0.06 |
| U (781) | D | 0.12 | 0.06 |
| V (795) | F | 0.07 | 0.05 |
| X (826) | D | 0.1 | 0.03 |
| Y (841) | D | 0.17 | 0.07 |
| Z (856) | D | 0.16 | 0.08 |
| AA (871) | F | 0.17 | 0.05 |
| BB (874) | F | 0.14 | 0.11 |
| No peptide | | 0.15 | 0.045 |

Individual peptides were identified from each of the pools, and additionally a weak reactivity was identified with peptide BB from pool F. The relevant peptide epitopes are summarized in the Table 5 below The amino acid sequences for peptides BB, O, L, I, A and C are provided in SEQ ID NO: 376–381, respectively, with the corresponding cDNA sequences being provided in SEQ ID NO: 373, 370, 372, 374, 371 and 375, respectively.

TABLE 5

| Peptide | Nucleotides of L762P | Amino acids of L762P | Sequence | pool | ELISA activity (OD 450–570) 200 ng | 20 ng |
|---|---|---|---|---|---|---|
| A | 1441–1500 | 481–500 | SRISSGTGDIFQQHIQLEST | A | 1.76 | 1.0 |
| C | 1531–1590 | 511–530 | KNTVTVDNTVGNDTMFLVTW | E | 0.47 | 0.18 |
| I | 1801–1860 | 601–620 | AVPPATVEAFVERDSLHFPH | B | 0.25 | 0.06 |
| L | 1936–1955 | 646–665 | PETGDPVTLRLLDDGAGADV | B | 0.28 | 0.12 |
| O | 2071–2130 | 691–710 | VNHSPSISTPAHSIPGSHAMIL | C | 1.1 | 0.23 |
| BB | 2620–2679 | 874–893 | LQSAVSNIAQAPLFIPPNSD | F | 0.14 | 0.11 |
| None | — | — | — | — | 0.15 | 0.05 |

Example 16

DETECTION OF ANTIBODIES AGAINST LUNG TUMOR ANTIGENS IN PATIENT SERA

Antibodies specific for the lung tumor antigens L773PA (SEQ ID NO:361), L514S (SEQ ID NO:155 and 156), L523S (SEQ ID NO:176), L762P (SEQ ID NO:161) and L763P (SEQ ID NO:159) were shown to be present in effusion fluid or sera of lung cancer patients but not in normal donors. More specifically, the presence of antibodies against L773PA, L514S, L523S, L762P and L763P in effusion fluid obtained from lung cancer patients and in sera from normal donors was detected by ELISA using recombinant proteins and HRP-conjugated anti-human Ig. Briefly, each protein (100 ng) was coated in 96-well plate at pH 9.5. In parallel, BSA (bovine serum albumin) was also coated as a control protein. The signals ([S], absorbance measured at 405 nm) against BSA ([N]) were determined. The results of these studies are shown in Table 6, wherein – represents [S]/[N]<2; +/– represents [S]/[N]>2; ++ represents [S]/[N] >3; and +++ represents [S]/[N]>5.

TABLE 6

Detection of Antibodies Against Lung Tumor Antigens

| | L514S | L523S | L762P | L763P | L773PA |
|---|---|---|---|---|---|
| Effusion fluid | | | | | |
| #1 | +++ | ++ | ++ | – | ++ |
| #2 | – | – | +/– | ++ | +/– |
| #3 | – | – | – | – | +/– |
| #4 | +/– | ++ | +/– | – | +/– |
| #5 | +/– | +++ | +/– | +/– | ++ |
| #7 | – | +/– | – | – | +/– |
| #8 | – | +++ | – | – | ++ |
| #10 | – | ++ | +/– | +/– | – |
| #11 | +/– | ++ | ++ | – | ++ |
| #12 | +++ | +/– | – | +/– | +/– |
| #13 | – | +/– | – | – | +/– |
| #14 | – | +++ | +/– | +/– | ++ |
| #15 | +/– | ++ | +/– | – | ++ |
| #17 | – | +/– | – | – | +/– |
| #18 | – | ++ | – | – | – |
| #19 | – | +/– | – | – | +/– |
| #20 | +/– | +/– | +/– | – | +/– |
| Normalsera | | | | | |
| #21 | – | +/– | – | – | – |
| #22 | – | – | – | – | – |
| #23 | – | – | – | – | +/– |
| #24 | – | +/– | – | – | – |
| #25 | +/– | +/– | – | – | +/– |

Using Western blot analyses, antibodies against L523S were found to be present in 3 out of 4 samples of effusion fluid from lung cancer patients, with no L523S antibodies being detected in the three samples of normal sera tested.

Example 17

EXPRESSION IN *E. COLI* OF A L514S HIS TAG FUSION PROTEIN

PCR was performed on the L514S-13160 coding region with the following primers:

Forward primer PDM-278 5' cacactagtgtccgcgtggcggcctac 3' (SEQ ID NO:421) Tm 67° C.

Reverse primer PDM-280 5' catgagaattcatcacatgccctgaaggctccc 3' (SEQ ID NO:422) TM 66° C.

The PCR conditions were as follows:

10 μl 10×Pfu buffer 1.0 μl 10 mM dNTPs 2.0 μl 10 μM each primer

83 μl sterile water 1.5 μl Pfu DNA polymerase (Stratagene, La Jolla, Calif.)

50 ηg DNA

96° C. for 2 minutes, 96° C. for 20 seconds, 66° C. for 15 seconds, 72° C. for 1 minute with 40 cycles and then 72° C. for 4 minutes.

The PCR product was digested with EcoRI restriction enzyme, gel purified and then cloned into pPDM His, a modified pET28 vector with a His tag in frame, which had been digested with Eco72I and EcoRI restriction enzymes. The correct construct was confirmed by DNA sequence analysis and then transformed into BL21 CodonPlus (Stratagene, La Jolla, Calif.) cells for expression.

The amino acid sequence of expressed recombinant L514S is shown in SEQ ID NO:423, and the DNA coding region sequence is shown in SEQ ID NO:424.

Example 18

Expression in *E. coli* of a L523S His Tag Fusion Protein

PCR was performed on the L523S coding region with the following primers:

Forward primer PDM-414 5' aacaaactgtatatcggaaacct-cagcgagaa 3' (SEQ ID NO:425) Tm 62° C.

Reverse primer PDM-415 5' ccatagaattcattacftccgtct-tgactgagg 3' (SEQ ID NO:426) TM 62° C.

The PCR conditions were as follows:

10 μl 10×Pfu buffer 1.0 μl 10 mM dNTPs 2.0 μl 10 μM each primer

83 μl sterile water 1.5 μl Pfu DNA polymerase (Stratagene, La Jolla, Calif.)

50 ηg DNA

96° C. for 2 minutes, 96° C. for 20 seconds, 62° C. for 15 seconds, 72° C. for 4 minutes with 40 cycles and then 72° C. for 4 minutes.

The PCR product was digested with EcoRI restriction enzyme, gel purified and then cloned into pPDM His, a modified pET28 vector with a His tag in frame, which had been digested with Eco72I and EcoRI restriction enzymes. The correct construct was confirmed by DNA sequence analysis and then transformed into BL21 CodonPlus (Stratagene, La Jolla, Calif.) cells for expression.

The amino acid sequence of expressed recombinant L523S is shown in SEQ ID NO:427, and the DNA coding region sequence is shown in SEQ ID NO:428.

Example 19

Expression in *E. coli* of a L762PA His Tag Fusion Protein

PCR was performed on the L762PA coding region (L762PA is missing the signal sequence, the C-terminal transmembrane domain and the cytoplasmic tail) with the following primers:

Forward primer PDM-278 5'ggagtacagcttcaagacaatggg 3' (SEQ ID NO:355) Tm 57° C.

Reverse primer PDM-279 5'ccatggaattcattatttcaatataa-gataatctc 3' (SEQ ID NO:429) TM56° C.

The PCR conditions were as follows:

10 μl 10×Pfu buffer 1.0 μl 10 mM dNTPs 2.0 μl 10 μM each primer

83 μl sterile water 1.5 μl Pfu DNA polymerase (Stratagene, La Jolla, Calif.)

50 ηg DNA

96° C. for 2 minutes, 96° C. for 20 seconds, 55° C. for 15 seconds, 72° C. for 5 minutes with 40 cycles and then 72° C. for 4 minutes.

The PCR product was digested with EcoRI restriction enzyme, gel purified and then cloned into pPDM His, a modified pET28 vector with a His tag in frame, which had been digested with Eco72I and EcoRI restriction enzymes. The correct construct was confirmed by DNA sequence analysis and then transformed into BL21 pLys S (Novagen, Madison, Wis.) cells for expression.

The amino acid sequence of expressed recombinant L762PA is shown in SEQ ID NO:430, and the DNA coding region sequence is shown in SEQ ID NO:431.

Example 20

Expression in *E. coli* of a L773P His Tag Fusion Protein

PCR was performed on the L773P coding region with the following primers:

Forward primer PDM-299 5' tggcagcccctcttcttcaagtggc 3' (SEQ ID NO: 359) Tm 63° C.

Reverse primer PDM-300 5' cgcctgctcgagtcattaatattcatca-gaaaatgg 3' (SEQ ID NO:432) TM 63° C.

The PCR conditions were as follows:

10 μl 10×Pfu buffer 1.0 μl 10 mM dNTPs 2.0 μl 10 μM each primer

83 μl sterile water 1.5 μl Pfu DNA polymerase (Stratagene, La Jolla, Calif.)

50 ηg DNA

96° C. for 2 minutes, 96° C. for 20 seconds, 63° C. for 15 seconds, 72° C. for 2 minutes 15 seconds with 40 cycles and then 72° C. for 4 minutes.

The PCR product was digested with EcoRI restriction enzyme, gel purified and then cloned into pPDM His, a modified pET28 vector With a His tag in frame, which had been digested with Eco72I and EcoRI restriction enzymes. The correct construct was confirmed by DNA sequence analysis and then transformed into BL21 pLys S (Novagen, Madison, Wis.) and BL21 CodonPlus (Stratagene, La Jolla, Calif.) cells for expression.

The amino acid sequence of expressed recombinant L773P is shown in SEQ ID NO:433, and the DNA coding region sequence is shown in SEQ ID NO:434.

Example 21

Cloning and Sequencing of a T-Cell Receptor Clone for the Lung Specific Antigen L762P T cell receptor (TCR) alpha and beta chains from a CD4 T cell clone specific for the lung specific antigen L762P were cloned and sequence. Basically, total mRNA from $2\times10^6$ cells from CTL clone 4H6 was isolated using Trizol reagent and cDNA was synthesized using Ready-to go kits (Pharmacia). To determine Valpha and Vbeta sequences of this clone, a panel of Valpha and Vbeta subtype specific primers was synthesized and used in RT-PCR reactions with cDNA generated from each of the clones. The RT-PCR reactions demonstrated that each of the clones expressed a common Vbeta sequence that corresponded to the Vbeta8 subfamily and a Valpha sequence that corresponded to the Valpha8 subfamily. To clone the full TCR alpha and beta chains from clone 4H6, primers were designed that spanned the initiator and terminator-coding TCR nucleotides. The primers were as follows:

forward primer for TCR Valpha8 5' ggatccgccgccaccatgacatccattcgagctgta 3' (SEQ ID NO:435; has a BamHI site inserted);

Kozak reverse primer for TCR Valpha8 (antisense) 5' gtcgactcagctggaccacagccgcag 3' (SEQ ID NO:436; has a SalI site inserted plus the TCR alpha constant sequence);

forward primer for TCR Vbeta8 (sense) 5' ggatccgccgccaccatggactcctggaccttctgct 3' (SEQ ID NO:437; has a BamHI site inserted); and Kozak reverse primer for TCR Vbeta 5' gtcgactcagaaatcctttctcttgac 3' (SEQ ID NO:438; has a SalI site inserted plus the TCR beta constant sequence).

Standard 35 cycle RT-PCR reactions were established using the cDNA synthesized from the CTL clone and the above primers utilizing the proofreading thermostable polymerase, PWO (Roche). The resultant PCR band, about 850 bp for Valpha and about 950 for Vbeta, was ligated into a PCR blunt vector (Invitrogen) and transformed into *E. coli*. *E. coli* transformed with plasmids having full-length alpha and beta chains were identified. Large scale preparations of the corresponding plasmids were generated, and these plasmids were sequenced. The Valpha sequence (SEQ ID NO:439) was shown by nucleotide sequence alignment to be homologous to Valpha8.1, while the Vbeta sequence (SEQ ID NO:440) was shown by nucleotide sequence alignment to be homologous to Vbeta8.2.

Example 22

Recombinant Expression of Full Length L762P in Mammalian Cells

Full length L762P cDNA was subcloned into the mammalian expression vectors VR1012 and pCEP4 (Invitrogen). Both expression vectors had previously been modified to contain a FLAG epitope tag. These constructs were transfected into HEK293 and CHL-1 cells (ATCC) using Lipofectamine 2000 reagent (Gibco). Briefly, both the HEK and CHL-1 cells were plated at a density of 100,000 cells/ml in DMEM (Gibco) containing 10% FBS (Hyclone) and grown overnight. The following day, 4 $\mu$l of Lipofectamine 2000 was added to 100 $\mu$l of DMEM containing no FBS and incubated for 5 minutes at room temperature. The Lipofectamine/DMEM mixture was then added to 1 $\mu$g of L762P Flag/pCEP4 or L762P Flag/VR1012 plasmid DNA resuspended in 100 $\mu$l DMEM and incubated for 15 minutes at room temperature. The Lipofectamine/DNA mix was then added to the HEK293 and CHL-1 cells and incubated for 48–72 hours at 37° C. with 7% $CO_2$. Cells were rinsed with PBS, then collected and pelleted by centrifugation. L672P expression was detected in the transfected HEK293 and CHL-1 cell lysates by Western blot analysis and was detected on the surface of transfected HEK cells by flow cytometry analysis.

For Western blot analysis, whole cell lysates were generated by incubating the cells in Triton-X100 containing lysis buffer for 30 minutes on ice. Lysates were then cleared by centrifugation at 10,000 rpm for 5 minutes at 4° C. Samples were diluted with SDS-PAGE loading buffer containing beta-mercaptoethanol, then boiled for 10 minutes prior to loading the SDS-PAGE gel. The protein was transferred to nitrocellulose and probed using 1 $\mu$g/ml purified anti-L762P rabbit polyclonal sera (lot #690/73) or non-diluted anti-L762P mAb 153.20.1 supernatant. Blots were revealed using either goat anti-rabbit Ig coupled to HRP or goat anti-mouse Ig coupled to HRP followed by incubation in ECL substrate.

For flow cytometric analysis, cells were washed further with ice cold staining buffer (PBS+1% BSA+Azide). Next, the cells were incubated for 30 minutes on ice with 10 ug/ml of purified anti-L762P polyclonal sera (lot #690/73) or a 1:2 dilution of anti-L762P mAb 153.20.1 supernatant. The cells were washed 3 times with staining buffer and then incubated with a 1:100 dilution of goat anti-rabbit Ig(H+L)-FITC or goat anti-mouse Ig(H+L)-FITC reagent (Southern Biotechnology) for 30 minutes on ice. After 3 washes, the cells were resuspended in staining buffer containing propidium iodide (PI), a vital stain that allows for the exclusion of permeable cells, and analyzed by flow cytometry.

Example 23

Generation of Polyclonal Antibodies to Lung Tumor Antigens

Three lung antigens, L523S (SEQ ID NO:176), L763P (SEQ ID NO:159) and L763 peptide #2684 (SEQ ID NO:441), were expressed and purified for use in antibody generation.

L523S and L763P were expressed in an *E. coli* recombinant expression system and grown overnight in LB Broth with the appropriate antibiotics at 37° C. in a shaking incubator. The next morning, 10 ml of the overnight culture was added to 500 ml of 2×YT with the appropriate antibiotics in a 2 L-baffled Erlenmeyer flask. When the optical density of the culture reached 0.4–0.6 at 560 nanometers, the cells were induced with IPTG (1 mM). Four hours after induction with IPTG, the cells were harvested by centrifugation.

The cells were then washed with phosphate buffered saline and centrifuged again. The supernatant was discarded and the cells were either frozen for future use or immediately processed. Twenty milliliters of lysis buffer was added to the cell pellets and vortexed. To break open the *E. coli* cells, this mixture was then run through a french press at a pressure of 16,000 psi. The cells were then centrifuged again and the supernatant and pellet were checked by SDS-PAGE for the partitioning of the recombinant protein.

For proteins that localized to the cell pellet, the pellet was resuspended in 10 mM Tris pH 8.0, 1% CHAPS and the inclusion body pellet was washed and centrifuged again. This procedure was repeated twice more. The washed inclusion body pellet was solubilized with either 8M urea or 6M guanidine HCl containing 10 mM Tris pH 8.0 plus 10 mM imidazole. The solubilized protein was added to 5 ml of nickel-chelate resin (Qiagen) and incubated for 45 minutes to 1 hour at room temperature with continuous agitation.

After incubation, the resin and protein mixture was poured through a disposable column and the flow through was collected. The column was then washed with 10–20 column volumes of the solubilization buffer. The antigen was then eluted from the column using 8M urea, 10 mM Tris pH 8.0 and 300 mM imidazole and collected in 3 ml fractions. A SDS-PAGE gel was run to determine which fractions to pool for further purification.

As a final purification step, a strong anion exchange resin, in this case Hi-Prep Q (Biorad), was equilibrated with the appropriate buffer and the pooled fractions from above were loaded onto the column. Each antigen was eluted off the column with an increasing salt gradient. Fractions were collected as the column was run and another SDS-PAGE gel was run to determine which fractions from the column to pool.

The pooled fractions were dialyzed against 10 mM Tris pH 8.0. The release criteria were purity as determined by SDS-PAGE or HPLC, concentration as determined by Lowry assay or Amino Acid Analysis, identity as determined by amino terminal protein sequence, and endotoxin level was determined by the Limulus (LAL) assay. The proteins were then put in vials after filtration through a 0.22-micron filter and the antigens were frozen until needed for immunization.

The L763 peptide #2684 was synthesized and conjugated to KLH and froze until needed for immunization.

The polyclonal antisera were generated using 400 micrograms of each lung antigen combined with 100 micrograms of muramyldipeptide (MDP). An equal volume of Incomplete Freund's Adjuvant (IFA) was added and then mixed and injected subcutaneously (S.C.) into a rabbit. After four weeks, the rabbit was S.C. boosted with 200 micrograms of antigen mixed with an equal volume of IFA. Thereafter the rabbit was I.V. boosted with 100 micrograms of antigen. The animal was bled seven days following each boost. The blood was then incubated at 4° C. for 12–24 hours followed by centrifugation to generate the sera.

The polyclonal antisera were characterized using 96 well plates coated with antigen and incubated with 50 microliters (typically 1 microgram/microliter) of the polyclonal antisera at 4° C. for 20 hours. Basically, 250 microliters of BSA blocking buffer was added to the wells and incubated at room temperature for 2 hours. Plates were washed 6 times with PBS/0.1% Tween. The rabbit sera were diluted in PBS/0.1% Tween/0.1% BSA. 50 microliters of diluted sera was added to each well and incubated at room temperature for 30 minutes. The plates were washed as described above, and then 50 microliters of goat anti-rabbit horseradish peroxidase (HRP) at a 1:10000 dilution was added and incubated at room temperature for 30 minutes.

The plates were washed as described above, and 100 microliters of TMB Microwell Peroxidase Substrate was added to each well. Following a 15-minute incubation in the dark at room temperature, the colorimetric reaction was stopped with 100 microliters of 1N $H_2SO_4$ and read immediately at 450 nm. All the polyclonal antibodies showed immunoreactivity to the appropriate antigen. Tables 7–9 show the antibody reactivity of rabbit antisera in serial dilution to the three lung antigens, L523S, L763P and L763 peptide #2684. The first column shows the antibody dilutions. The columns "Pre-immune sera" indicate ELISA data for two experiments using pre-immune sera. These results are averaged in the fourth column. The columns "anti-L523S, L763P or #2684" indicate ELISA data for two experiments using sera from rabbits immunized as described in this Example, using the respective antigen, referred to as either L523S, L763P or #2684 in the tables.

TABLE 7

| Antibody dilution | Pre-immune sera (1) | Pre-immune sera (2) | Average | Anti-L523S (1) | Anti-L523S (2) | Average |
|---|---|---|---|---|---|---|
| 1:1000 | 0.14 | 0.14 | 0.14 | 2.36 | 2.37 | 2.37 |
| 1:2000 | 0.12 | 0.10 | 0.11 | 2.29 | 2.23 | 2.26 |
| 1:4000 | 0.10 | 0.09 | 0.10 | 2.11 | 2.17 | 2.14 |
| 1:8000 | 0.09 | 0.09 | 0.09 | 1.98 | 2.00 | 1.99 |
| 1:16000 | 0.09 | 0.09 | 0.09 | 1.73 | 1.76 | 1.75 |
| 1:32000 | 0.09 | 0.09 | 0.09 | 1.35 | 1.40 | 1.37 |
| 1:64000 | 0.09 | 0.11 | 0.10 | 0.94 | 0.98 | 0.96 |
| 1:128000 | 0.09 | 0.08 | 0.08 | 0.61 | 0.61 | 0.61 |
| 1:256000 | 0.08 | 0.08 | 0.08 | 0.38 | 0.38 | 0.38 |
| 1:512000 | 0.09 | 0.08 | 0.08 | 0.24 | 0.25 | 0.25 |
| 1:1024000 | 0.08 | 0.08 | 0.08 | 0.17 | 0.17 | 0.17 |
| 1:2048000 | 0.08 | 0.08 | 0.08 | 0.14 | 0.13 | 0.13 |

TABLE 8

| Antibody dilution | Pre-immune sera (1) | Pre-immune sera (2) | Average | Anti-L763P (1) | Anti-L763P (2) | Average |
|---|---|---|---|---|---|---|
| 1:1000 | 0.09 | 0.11 | 0.10 | 1.97 | 1.90 | 1.93 |
| 1:2000 | 0.07 | 0.07 | 0.07 | 1.86 | 1.84 | 1.85 |
| 1:4000 | 0.06 | 0.06 | 0.06 | 1.82 | 1.81 | 1.81 |
| 1:8000 | 0.06 | 0.06 | 0.06 | 1.83 | 1.81 | 1.82 |
| 1:16000 | 0.06 | 0.05 | 0.06 | 1.79 | 1.74 | 1.76 |
| 1:32000 | 0.06 | 0.06 | 0.06 | 1.56 | 1.51 | 1.53 |
| 1:64000 | 0.06 | 0.05 | 0.05 | 1.35 | 1.34 | 1.35 |
| 1:128000 | 0.05 | 0.05 | 0.05 | 1.01 | 0.98 | 0.99 |
| 1:256000 | 0.06 | 0.05 | 0.05 | 0.69 | 0.70 | 0.70 |
| 1:512000 | 0.06 | 0.05 | 0.05 | 0.47 | 0.44 | 0.46 |
| 1:1024000 | 0.06 | 0.05 | 0.06 | 0.27 | 0.27 | 0.27 |
| 1:2048000 | 0.05 | 0.05 | 0.05 | 0.16 | 0.15 | 0.16 |

TABLE 9

| Antibody dilution | Pre-immune sera (1) | Pre-immune sera (2) | Average | Anti-#2684 (1) | Anti-#2684 (2) | Average |
|---|---|---|---|---|---|---|
| 1:1000 | 0.07 | 0.07 | 0.07 | 2.10 | 2.00 | 2.05 |
| 1:2000 | 0.07 | 0.06 | 0.06 | 1.95 | 1.96 | 1.95 |
| 1:4000 | 0.06 | 0.06 | 0.06 | 1.77 | 1.82 | 1.79 |
| 1:8000 | 0.06 | 0.06 | 0.06 | 1.79 | 1.81 | 1.80 |
| 1:16000 | 0.06 | 0.06 | 0.06 | 1.54 | 1.50 | 1.52 |
| 1:32000 | 0.06 | 0.06 | 0.06 | 1.27 | 1.20 | 1.24 |
| 1:64000 | 0.06 | 0.06 | 0.06 | 0.85 | 0.82 | 0.83 |
| 0 | 0.06 | 0.06 | 0.06 | 0.06 | 0.06 | 0.06 |

Tables 10–12 show the affinity purification of, he respective antibodies to the three lung antigens, L523S, L763P and L763 peptide #2684.

TABLE 10

| Antibody conc. (μg/ml) | Affinity pure (salt peak) | Affinity pure (salt peak) | Average | Affinity pure (acid peak) | Affinity pure (acid peak) | Average |
|---|---|---|---|---|---|---|
| 1.0 | 2.38 | 2.35 | 2.36 | 2.25 | 2.31 | 2.28 |
| 0.5 | 2.24 | 2.22 | 2.23 | 2.19 | 2.18 | 2.18 |
| 0.25 | 2.05 | 2.09 | 2.07 | 2.01 | 2.03 | 2.02 |
| 0.13 | 1.70 | 1.81 | 1.75 | 1.74 | 1.74 | 1.74 |
| 0.063 | 1.44 | 1.44 | 1.44 | 1.43 | 1.38 | 1.40 |
| 0.031 | 1.05 | 1.05 | 1.05 | 0.99 | 0.99 | 0.99 |
| 0.016 | 0.68 | 0.67 | 0.68 | 0.65 | 0.64 | 0.64 |
| 0.0078 | 0.43 | 0.42 | 0.42 | 0.39 | 0.39 | 0.39 |
| 0.0039 | 0.27 | 0.26 | 0.27 | 0.24 | 0.26 | 0.25 |
| 0.0020 | 0.18 | 0.20 | 0.19 | 0.19 | 0.18 | 0.19 |

TABLE 10-continued

| Antibody conc. (μg/ml) | Affinity pure (salt peak) | Affinity pure (salt peak) | Average | Affinity pure (acid peak) | Affinity pure (acid peak) | Average |
|---|---|---|---|---|---|---|
| 0.0010 | 0.13 | 0.14 | 0.13 | 0.13 | 0.14 | 0.13 |
| 0.00 | 0.11 | 0.12 | 0.11 | 0.10 | 0.12 | 0.11 |

TABLE 11

| Antibody dilution | Affinity pure | Affinity pure | Average |
|---|---|---|---|
| 1:1000 | 1.64 | 1.77 | 1.70 |
| 1:2000 | 1.59 | 1.76 | 1.68 |
| 1:4000 | 1.48 | 1.62 | 1.55 |
| 1:8000 | 1.35 | 1.43 | 1.39 |
| 1:16000 | 1.09 | 1.19 | 1.14 |
| 1:32000 | 0.81 | 0.89 | 0.85 |
| 1:64000 | 0.55 | 0.58 | 0.56 |
| 1:128000 | 0.31 | 0.35 | 0.33 |
| 1:256000 | 0.18 | 0.20 | 0.19 |
| 1:512000 | 0.11 | 0.12 | 0.11 |
| 1:1024000 | 0.07 | 0.07 | 0.07 |
| 1:2048000 | 0.06 | 0.06 | 0.06 |

TABLE 12

| Antibody conc. (μg/ml) | Affinity pure | Affinity pure | Average |
|---|---|---|---|
| 1.0 | 2.00 | 2.02 | 2.01 |
| 0.5 | 2.01 | 1.93 | 1.97 |
| 0.25 | 1.84 | 1.83 | 1.84 |
| 0.13 | 1.80 | 1.83 | 1.81 |
| 0.06 | 1.39 | 1.60 | 1.50 |
| 0.03 | 1.33 | 1.35 | 1.34 |
| 0.02 | 0.94 | 0.93 | 0.94 |
| 0.00 | 0.06 | 0.06 | 0.06 |

Example 24

Full-Length cDNA Sequence Encoding L529S

The isolation of a partial sequence (SEQ ID NO:106) for lung antigen L529S was previously provided in Example 2. This partial sequence was used as a query to identify potential full length cDNA and protein sequences by searching against publicly available databases. The predicted full-length cDNA sequence for the isolated cloned sequence of SEQ ID NO:106 is provided in SEQ ID NO:442. The deduced amino acid sequence of the antigen encoded by SEQ ID NO:442 is provided in SEQ ID NO:443. It was previously disclosed in Example 2 that L529S shows similarity to connexin 26, a gap junction protein.

Example 25

Expression in Megaterium of a Histidine Tag-Free L523S Fusion Protein

PCR was performed on the L523S coding region with the following primers:

Forward primer PDM-734 5' caatcaggcatgcacaacaaactg-tatatcggaaac 3' (SEQ ID NO:444) Tm 63° C.

Reverse primer PDM-735 5' cgtcaagatcttcattacttccgtct-tgac 3' (SEQ ID NO:445) TM 60° C.

The PCR conditions were as follows:

10 μl 10×Pfu buffer 1.0 μl 10 mM dNTPs 2.0 μl 10 μM each primer

83 μl sterile water 1.5 μl Pfu DNA polymerase (Stratagene, La Jolla, Calif.)

50 ηg DNA

96° C. for 2 minutes, 96° C. for 20 seconds, 62° C. for 15 seconds, 72° C. for 4 minute with 40 cycles and then 72° C. for 4 minutes.

The PCR product was digested with SphI and BglII restriction enzymes, gel purified and then cloned into pMEG-3, which had been digested with Sphli and BglII restriction enzymes. The correct construct was confirmed by DNA sequence analysis and then transformed into Megaterium cells for expression.

The amino acid sequence of expressed recombinant L523S is shown in SEQ ID NO:446, and the DNA coding region sequence is shown in SEQ ID NO:447.

Example 26

Expression in *E. coli* of a Histidine Tag-Free L523S Fusion Protein

PCR was performed on the L552S coding region with the following primers:

Forward primer PDM-733 5' cgtactagcatatgaacaaactg-tatatcggaaac 3' (SEQ ID NO:448) Tm 64° C.

Reverse primer PDM-415 5' ccatagaattcattacttccgtct-tgactgagg 3' (SEQ ID NO:426) TM 62° C.

The PCR conditions were as follows:

10 μl 10×Pfu buffer 1.0 μl 10 mM dNTPs 2.0 μl 10 μM each primer

83 μl sterile water 1.5 μl Pfu DNA polymerase (Stratagene, La Jolla, Calif.)

50 ηg DNA

96° C. for 2 minutes, 96° C. for 20 seconds, 62° C. for 15 seconds, 72° C. for 4 minute with 40 cycles and then 72° C. for 4 minutes.

The PCR product was digested with NdeI and EcoRI restriction enzymes, gel purified and then cloned into pPDM, a modified pET28 vector, which had been digested with NdeI and EcoRI restriction enzymes. The correct construct was confirmed by DNA sequence analysis and then transformed into BLR pLys S and HMS 174 pLys S cells for expression.

The amino acid sequence of expressed recombinant L523S is shown in SEQ ID NO:449, and the DNA coding region sequence is shown in SEQ ID NO:450.

Example 27

Epitope-Analysis of L514S and L523S-Specific Antibodies

Peptides of candidate antigens can be used for the evaluation of antibody responses in both preclinical and clinical studies. These data allow one to further confirm the antibody response against a certain candidate antigen. Protein-based ELISA with and without competitive peptides and peptide-based ELISA can be used to evaluate these antibody responses. Peptide ELISA is especially useful since it can further exclude the false positive of the antibody titer observed in protein-based ELISA as well as to provide the simplest assay system to test antibody responses to candidate antigens. In this example, data was obtained using both L514S- and L523S-peptides that show that individual cancer patients produce L514S- and L523S-specific antibodies. The L514S-specific antibodies recognize primarily the following epitope of L514S:

aa86–110: LGKEVRDAKITPEAFEKLGFPAAKE (SED ID NO:451).

This epitope is the common epitope in humans. A rabbit antibody specific for L514S recognizes two addition epitopes of L514S:

```
(1) aa21–45:
KASDGDYYTLAVPMGDVPMDGISVA          (SEQ ID NO:452)

(2) aa121–135:
PDRDVNLTHQLNPKVK                   (SED ID NO:453)
```

It was further found that the SEQ ID NO:452 is common to both L514S isoforms, L514S-13160 and L514S-13166, whereas the other epitopes, SEQ ID NO:451 and SEQ ID NO:453, are probably specific to the isoform. L514S-13160.

The L523S-specific antibodies recognize primarily the following epitope of L523S:

aa440–460: KIAPAEAPDAKVRMVIITGP (SEQ ID NO:454).

This epitope is the common epitope in humans. A rabbit antibody specific for L523S recognizes two other epitopes:

```
(1) aa156–175
PDGAAQQNNNPLQQPRG                  (SEQ ID NO:455)

(2) aa326–345:
RTITVKGNVETCAKAEEEIM               (SED ID NO:456)
```

In further studies, it was determined by peptide based ELISAs that eight additional epitopes of L523S were recognized by L523S-specific antibodies:

```
(1) aa40–59
AFVDCPDESWALKAIEALS                (SEQ ID NO:457)

(2) aa80–99:
IRKLQIRNIPPHLQWEVLDS               (SED ID NO:458)

(3) aa160–179:
AQQNPLQQPRGRRGLGQRGS               (SEQ ID NO:459)

(4) aa180–199:
DVHRKENAGAAEKSITILST               (SED ID NO:460)

(5) aa320–339:
LYNPERTITVKGNVETCAKA               (SEQ ID NO:461)

(6) aa340–359:
EEEIMKKIRESYENDIASMN               (SED ID NO:462)

(7) aa370–389:
LNALGLFPPTSGMPPPTSGP               (SEQ ID NO:463)

(8) aa380–399:
KIAPAEAPDAKVRMVIITGP               (SED ID NO:464)
```

Out of these, six epitopes are common in both lung plural effusion fluid samples and in sera of lung patients. Of these six, SEQ ID NO:459 and SEQ ID NO:463 have no homology to other L523S-family proteins such as IGF-II mRNA-binding proteins 1 and 2. Accordingly, this indicates that these two peptides can be used as an assay system to determine the antibody response to L523S.

Example 28

Generation of L523S-Specific CTL Lines Using In Vitro Whole-Gene Priming

To determine if L523S is capable of generating a CD8$^+$ T cell immune response, CTLs were generated using in vitro whole-gene priming methodologies with tumor antigen-vaccinia infected DC (Yee et al, *The Journal of Immunology,* 157(9):4079–86, 1996), human CTL lines were derived that specifically recognize autologous fibroblasts transduced with the L552S tumor antigen, as determined by interferon-gamma ELISPOT analysis. Specifically, dendritic cells (DC) were differentiated from Percoll-purified monocytes derived from PBMC of normal human donors by plastic adherence and growing for five days in RPMI medium containing 10% human serum, 50 ng/ml human GM-CSF and 30 ng/ml human IL-4. Following the five days of culture, the DC were infected overnight with a recombinant adenovirus that expresses L523S at a multiplicity of infection (M.O.I) of 33, 66 and 100, and matured overnight by the addition of 2 μg/ml CD40 ligand. The virus was then inactivated by UV irradiation. In order to generate a CTL line, autologous PBMC were isolated and CD8+ T cells were enriched for by the negative selection using magnetic beads conjugated to CD4+, CD14+, CD16+, CD19+, CD34+ and CD56+ cells. CD8+ T cells specific for L523S were established in round bottom 96-well plates using 10,000 L523S expressing DCs and 100,000 CD8+ T cells per well in RPMI supplemented with 10% human serum, 10 ng/ml of IL-6 and Sng/ml of IL-12. The cultures were restimulated every 7–10 days using autologous primary fibroblasts retrovirally transduced with L523S, and the costimulatory molecule CD80 in the presence of IL-2. The cells were also stimulated with IFN-gamma to upregulate MHC Class I. The media was supplemented with 10 U/ml of IL-2 at the time of stimulation as well as on days 2 and 5 following stimulation. Following three stimulation cycles, ten L523S specific CD8+ T cell lines were identified using interferon-gamma ELISPOT analysis that specifically produce interferon-gamma when stimulated with the L523S tumor antigen-transduced autologous fibroblasts, but not with a control antigen.

One line, 6B1, was cloned using anti-CD3 and feeder cells. The clones were tested for specificity on L523S-transduced fibroblasts. In addition, using a panel of HLA-mismatched lines transduced with a vector expressing L523S and measuring interferon-gamma production by this CTL line in an ELISPOT assay, it was determined that this clone 6B1.4B8 is restricted by HLA-A0201.

Also using transfected Cos cells, it was shown that clone 6B1.4B8 recognizes Cos cells transfected with pcDNA3 HLA A0201/L523S in an HLA-restricted and antigen specific manner.

An epitope mapping study demonstrated the clone 6B1.4B8 recognizes HLA-A201 LCL loaded with peptide pool 3 (a polypeptide corresponding to amino acid positions 33–59 of L523S.

A peptide pool breakdown study demonstrated that clone 6B1.4B8 recognizes autologous B-LCL loaded with 15-mer peptides from amino acid positions 37–55 of L523S, TGYAFVCPDESWALKAIE (SEQ ID NO:465). A further peptide breakdown study demonstrated that clone 6B1.4B8 recognizes T2 cells loaded with the same 15-mer peptides.

A peptide recognition study demonstrated that clone 6B1.4B8 prefers T2 cells loaded with the peptide FVDCPESWAL (SEQ ID NO:466) which is corresponds to the amino acid sequence at positions 41–51 of L523S and is encoded by the DNA sequence of SEQ ID NO:467.

Example 29

L523S Expression in Other Human Cancers

It was previously disclosed in Example 2 that L523S is expressed in lung cancers including squamous, adenocarcinoma and small cell carcinoma. To further evaluate the expression profile of this antigen an electronic express profiling was performed. This was done by searching a L523S-specific sequence against a public EST database. Results of this profiling indicate that L523S may also be present in colon adenocarcinomas, prostate adenocarcinomas, CML, AML, Burkitt's Lymphoma, brain tumors, retinoblastomas, ovarian tumors, teratocarcinomas, uterus myosarcomas, germ cell tumors as well as pancreatic and cervical tumor cell lines.

Example 30

Immunohistochemistry Analysis of L523S

In order to determine which tissues express the lung tumor antigen L523S, immunohistochemistry (IHC) analysis was performed on a diverse range of tissue types. Polyclonal antibodies specific for L523S (SEQ ID NO:176) were generated as described in Example 23. IHC was performed essentially as described in Example 6. Briefly, tissue samples were fixed in formalin solution for 12–24 hours and embedded in paraffin before being sliced into 8 micron sections. Steam heat induced epitope retrieval (SHIER) in 0.1 sodium citrate buffer (pH 6.0) was used for optimal staining conditions. Sections were incubated with 10% serum in PBS for 5 minutes. The primary L523S antibody was added to each section for 25 minutes followed by a 25 minute incubation with anti-rabbit biotinylated antibody. Endogenous peroxidase activity was blocked by three 1.5 minute incubations with hydrogen peroxidase. The avidin biotin complex/horse radish peroxidase (ABC/HRP) system was used along with DAB chromogen to visualize antigen expression. Slides were counterstained with hematoxylin to visualize the cell nuclei.

IHC analysis of L523S expression revealed that of the lung cancer tissues tested over 90% of tissue samples demonstrated high over-expression of the lung tumor antigen (10/11 adenocaricomas and 8/9 squamous). Of the normal tissues tested, all were negative for expression of L523S, with the exception of weak staining in normal bronchus, testis, liver, and trachea.

Example 31

Generation and Characterization of L762 Human Monoclonal Antibodies

Cell supernatants from hybridoma fusions from the Xenomouse strain of transgenic mice were screened for ability to bind to L762P. All results are shown in Table 13. The primary screen was to test monoclonal supernatants for reactivity to L762P by ELISA analysis using recombinant bacterial expressed protein. We next tested the human supernatants for reactivity to surface expressed L762P by whole cell ELISA using fluorimetry analysis. Specific reactivity of the humab supernatants was confirmed by performing FACS analysis on cells transfected with either an irrelevant plasmid or a plasmid expressing L762P. FI/CFI is the relative fold increase in fluorescence intensity (FI) of the anti-L762P humab primary antibody to irrelevant human primary antibody. FI/CFI/A20 is the relative fold increase in fluorescence intensity (FI) of the anti-L762P humab primary antibody to irrelevant human primary antibody over the FI of the anti-L762P mouse monoclonal antibody 153A20.1. FI/CFI/R690 is the relative fold increase in fluorescence intensity (FI) of the anti-L762P humab primary antibody to irrelevant human primary antibody over the FI of the anti-L762P rabbit polyclonal antibody. FACS VRL762 is the percentage of cells transfected with plasmid expressing L762P that were positive following staining with indicated monoclonal antibody. FACS VR(−) is the percentage of cells transfected with irrelevant plasmid that were positive following staining with indicated monoclonal antibody. ELISA is the O.D. values of the indicated monoclonal antibody to recombinant L762P protein. The shaded rows in Table 13 indicate those antibodies that will be further cloned and characterized.

TABLE 13

Human Monoclonal Antibodies Against L762P

| L762PHumAb | FI/CFI | FI/CFI/A20 | FI/CFI/R690 | FACSVRL762 | FACS VR (−) | ELISA | L762/VR1013 |
|---|---|---|---|---|---|---|---|
| R-690 | 4.59 | | 1.00 | | | | |
| M-A20 | 2.88 | 1.00 | | | | | |
| 1.176 | 0.51 | 0.18 | 0.11 | | | 0.38 | |
| 1.178 | 1.42 | 0.49 | 0.31 | | | 0.35 | |
| 1.179 | 0.47 | 0.16 | 0.10 | | | 0.07 | |
| 1.180 | 1.50 | 0.52 | 0.33 | | | 0.26 | |
| 1.182 | 1.45 | 0.50 | 0.32 | | | 0.26 | |
| 1.183 | 0.75 | 0.26 | 0.16 | | | 0.24 | |
| 1.185 | 0.89 | 0.31 | 0.19 | | | 0.46 | |
| 1.186 | 3.45 | 1.20 | 0.75 | 32.68 | 7.14 | 1.22 | 1.93 |
| 1.187 | 0.36 | 0.13 | 0.08 | | | 0.06 | |
| 1.188 | 0.26 | 0.09 | 0.06 | | | 0.23 | |
| 1.189 | 0.50 | 0.17 | 0.11 | | | 0.44 | |
| 1.190 | 0.53 | 0.18 | 0.12 | | | 0.42 | |
| 1.191 | 3.12 | 1.08 | 0.68 | 41.44 | 17.90 | 0.86 | 1.29 |
| 1.192 | 1.91 | 0.66 | 0.42 | | | 0.12 | |
| 1.193 | 2.87 | 1.00 | 0.63 | 17.82 | 6.43 | 0.13 | 1.06 |
| 1.194 | 1.55 | 0.54 | 0.34 | | | 0.28 | |
| 1.195 | 0.14 | 0.05 | 0.03 | | | 0.37 | |
| 1.196 | 1.97 | 0.68 | 0.43 | | | 0.89 | 1.64 |
| 1.197 | 0.43 | 0.15 | 0.09 | | | 0.08 | |
| 1.198 | 0.54 | 0.19 | 0.12 | | | 0.33 | |
| 1.199 | 0.70 | 0.24 | 0.15 | | | 0.40 | |
| 1.200 | 2.00 | 0.69 | 0.44 | | | 0.38 | 1.56 |

TABLE 13-continued

| Human Monoclonal Antibodies Against L762P | | | | | | | |
|---|---|---|---|---|---|---|---|
| L762PHumAb | FI/CFI | FI/CFI/A20 | FI/CFI/R690 | FACSVRL762 | FACS VR (−) | ELISA | L762/VR1013 |
| 1.201 | 1.62 | 0.56 | 0.35 | | | 0.29 | |
| 1.202 | 0.86 | 0.30 | 0.19 | | | 0.36 | |
| 1.203 | 1.56 | 0.27 | 0.18 | | | 0.14 | |
| 1.204 | 3.32 | 0.58 | 0.38 | 24.83 | 6.60 | 0.17 | 1.91 |
| 1.205 | 2.13 | 0.37 | 0.25 | | | 0.09 | |
| 1.206 | 0.45 | 0.08 | 0.05 | | | 0.23 | |
| 1.207 | 0.60 | 0.10 | 0.07 | | | 0.39 | |
| 1.208 | 0.12 | 0.02 | 0.01 | | | 0.36 | |
| 1.209 | 15.52 | 2.71 | 1.80 | 27.54 | 9.54 | 0.16 | 0.77 |
| 1.210 | 0.92 | 0.16 | 0.11 | | | 0.16 | |
| 1.211 | 2.83 | 0.49 | 0.33 | | | 0.42 | |
| 1.212 | 3.40 | 0.59 | 0.39 | 21.68 | 11.36 | 0.14 | 2.47 |
| 1.213 | 2.32 | 0.40 | 0.27 | | | 0.38 | |
| 1.214 | 0.80 | 0.14 | 0.09 | | | 0.34 | |
| 1.215 | 3.96 | 0.69 | 0.46 | 38.87 | 13.17 | 0.33 | 1.80 |
| 1.216 | 1.26 | 0.22 | 0.15 | | | 0.20 | |
| 1.217 | 1.99 | 0.35 | 0.23 | | | 0.26 | |
| 1.218 | 2.29 | 0.40 | 0.27 | | | 0.10 | |
| 1.219 | 0.15 | 0.03 | 0.02 | | | 0.06 | |
| 1.220 | 0.82 | 0.14 | 0.09 | | | 0.21 | |
| 1.221 | 2.29 | 0.40 | 0.27 | | | 0.12 | |
| 1.222 | 0.57 | 0.10 | 0.07 | | | 0.45 | |
| 1.223 | 0.11 | 0.02 | 0.01 | | | 0.11 | |
| 1.224 | 2.08 | 0.36 | 0.24 | | | 0.25 | |
| 1.225 | 0.95 | 0.17 | 0.11 | | | 0.22 | |
| 1.226 | −0.32 | −0.06 | −0.04 | | | 0.06 | |
| R-690 | 8.62 | | 1.00 | 72.34 | 39.83 | | |
| M-A20 | 5.73 | 1.00 | | 50.23 | 6.34 | | |
| M-A12 | | | 67.43 | 25.15 | | | |
| M-Irr | | | 7.74 | 7.35 | | | |
| R-Irr | | | 30.09 | 24.80 | | | |
| H-Irr | | | 25.52 | 39.14 | | | |
| R-690 | 3.20 | | 1.00 | | | | |
| M-A20 | 2.33 | 1.00 | | | | | |
| 1.250 | 0.15 | 0.06 | 0.05 | | | 0.28 | |
| 1.228 | 0.38 | 0.16 | 0.12 | | | 0.08 | |
| 1.229 | 0.39 | 0.17 | 0.12 | | | 0.44 | |
| 1.230 | 1.78 | 0.76 | 0.56 | | | 0.13 | 1.35 |
| 1.231 | 0.42 | 0.18 | 0.13 | | | 0.47 | |
| 1.232 | 0.34 | 0.15 | 0.11 | | | 0.25 | |
| 1.233 | 7.07 | 3.04 | 2.21 | 68.84 | 38.60 | 0.43 | 0.75 |
| 1.234 | 2.54 | 1.09 | 0.79 | 33.96 | 10.94 | 0.73 | 1.68 |
| 1.235 | 1.53 | 0.65 | 0.48 | | | 0.19 | 1.45 |
| 1.236 | 0.17 | 0.07 | 0.05 | | | 0.44 | |
| 1.237 | 0.35 | 0.15 | 0.11 | | | 0.06 | |
| 1.238 | 0.38 | 0.16 | 0.12 | | | 0.06 | |
| 1.239 | 0.40 | 0.17 | 0.13 | | | 0.06 | |
| 1.240 | 2.05 | 0.88 | 0.64 | 28.70 | 7.44 | 0.33 | 1.70 |
| 1.241 | 0.41 | 0.18 | 0.13 | | | 0.41 | |
| 1.242 | 0.52 | 0.23 | 0.16 | | | 0.05 | |
| 1.243 | 2.34 | 1.00 | 0.73 | 30.94 | 28.13 | 0.16 | 1.33 |
| 1.244 | 0.94 | 0.40 | 0.29 | | | 0.23 | |
| 1.245 | 0.37 | 0.16 | 0.11 | | | 0.31 | |
| 1.246 | 2.10 | 0.90 | 0.66 | 13.97 | 28.92 | 0.52 | 1.21 |
| 1.247 | 0.33 | 0.14 | 0.10 | | | 0.37 | |
| 1.248 | 1.80 | 0.77 | 0.56 | | | 0.76 | |
| 1.249 | 2.77 | 1.19 | 0.86 | 28.76 | 12.37 | 1.15 | 2.38 |
| 1.251 | 0.22 | 0.09 | 0.07 | | | 0.47 | |
| 1.252 | 1.16 | 0.27 | 0.17 | | | 0.37 | |
| 1.253 | 0.07 | 0.02 | 0.01 | | | 0.43 | |
| 1.254 | 2.05 | 0.48 | 0.30 | | | 0.14 | |
| 1.255 | 0.09 | 0.02 | 0.01 | | | 0.08 | |
| 1.256 | 1.17 | 0.27 | 0.17 | | | 0.13 | |
| 1.257 | 0.42 | 0.10 | 0.06 | | | 0.06 | |
| 1.258 | 0.48 | 0.11 | 0.07 | | | 0.40 | |
| 1.259 | 4.82 | 1.13 | 0.69 | 40.24 | 11.92 | 0.38 | 1.78 |
| 1.260 | 1.80 | 0.42 | 0.26 | | | 0.38 | |
| 2.1 | 2.70 | 0.63 | 0.39 | | | 0.14 | 1.35 |
| 2.3 | 0.06 | 0.01 | 0.01 | | | 0.57 | |
| 2.4 | 3.08 | 0.72 | 0.44 | 31.28 | 11.43 | 0.73 | 1.95 |
| 2.5 | 0.70 | 0.16 | 0.10 | | | 0.45 | |
| 2.6 | 1.26 | 0.29 | 0.18 | | | 0.22 | |
| 2.8 | 0.59 | 0.14 | 0.09 | | | 0.31 | |
| 2.9 | 7.48 | 1.75 | 1.08 | 45.72 | 17.57 | 0.95 | 1.53 |
| 2.10 | 0.35 | 0.08 | 0.05 | | | 0.42 | |

TABLE 13-continued

Human Monoclonal Antibodies Against L762P

| L762PHumAb | FI/CFI | FI/CFI/A20 | FI/CFI/R690 | FACSVRL762 | FACS VR (−) | ELISA | L762/VR1013 |
|---|---|---|---|---|---|---|---|
| 2.11 | 2.71 | 0.63 | 0.39 | | | 0.60 | 1.58 |
| 2.12 | 6.04 | 1.41 | 0.87 | 52.50 | 19.59 | | 1.40 |
| 2.13 | 5.50 | 1.28 | 0.79 | 39.78 | 15.24 | | 1.39 |
| 2.14 | 0.68 | 0.16 | 0.10 | | | | |
| 2.15 | 6.51 | 1.52 | 0.94 | 49.90 | 15.36 | | 1.72 |
| 2.16 | 4.58 | 1.07 | 0.66 | 28.62 | 13.02 | | 1.51 |
| 2.17 | 8.10 | 1.89 | 1.17 | 48.76 | 18.24 | | 3.06 |
| R-690 | 6.94 | | 1.00 | | | | |
| M-A20 | 4.28 | 1.00 | | 56.40 | 5.00 | | |
| R-690 | 4.34 | 1.65 | 1.00 | | | | |
| M-A20 | 2.63 | 1.00 | 0.61 | | | | |
| 2.18 | 2.29 | 0.87 | 0.53 | | | 1.27 | 1.95 |
| 2.20 | 1.85 | 0.70 | 0.43 | | | 0.52 | 2.75 |
| 2.21 | 0.09 | 0.03 | 0.02 | | | 0.40 | |
| 2.22 | 3.26 | 1.24 | 0.75 | 29.4 | 6.2 | 1.45 | 1.8 |
| 2.23 | 0.31 | 0.12 | 0.07 | | | 0.12 | |
| 2.24 | 1.21 | 0.46 | 0.28 | | | 0.65 | |
| 2.25 | 3.47 | 1.32 | 0.80 | 32.5 | 7.1 | 1.35 | 1.46 |
| 2.26 | 4.42 | 1.68 | 1.02 | 35.9 | 5.5 | 0.77 | 1.55 |
| 2.27 | 1.42 | 0.54 | 0.33 | | | 0.22 | |
| 2.28 | 3.00 | 1.14 | 0.69 | 28.6 | 5.4 | 1.21 | 1.26 |
| 2.29 | 1.41 | 0.53 | 0.32 | | | 0.58 | |
| 2.30 | 0.42 | 0.16 | 0.10 | | | 0.43 | |
| 2.31 | 0.09 | 0.03 | 0.02 | | | 0.07 | |
| 2.34 | 1.94 | 0.74 | 0.45 | | | 1.17 | 1.23 |
| 2.38 | 1.14 | 0.43 | 0.26 | | | 0.09 | |
| 2.39 | 2.50 | 0.95 | 0.57 | 28.2 | 4.8 | 0.78 | 1.14 |
| 2.40 | 2.02 | 0.77 | 0.46 | | | 0.47 | 0.99 |
| 2.41 | 1.16 | 0.44 | 0.27 | | | 0.08 | |
| 2.42 | 0.41 | 0.16 | 0.09 | | | 0.24 | |
| 2.46 | 2.46 | 0.93 | 0.57 | 16.1 | 4.6 | 1.07 | 1.3 |
| 2.47 | 1.83 | 0.69 | 0.42 | | | 0.31 | 1.54 |
| 2.48 | 2.50 | 0.95 | 0.58 | | | 1.36 | 1.76 |
| 2.49 | 0.50 | 0.19 | 0.12 | | | 0.74 | |
| 2.50 | 2.93 | 1.11 | 0.68 | 15.8 | 4.7 | 0.52 | 1.54 |
| 2.51 | 0.13 | 0.10 | 0.07 | | | 0.30 | |
| 2.52 | 1.11 | 0.79 | 0.56 | 22.1 | 5 | 1.14 | 1.93 |
| 2.53 | 1.87 | 1.34 | 0.94 | 29.8 | 7.8 | 0.58 | 2.84 |
| 2.54 | 1.85 | 1.32 | 0.92 | 15.9 | 8.5 | 0.12 | 2.56 |
| 2.55 | 0.83 | 0.60 | 0.42 | | | 0.32 | |
| 2.58 | 0.46 | 0.33 | 0.23 | | | 0.15 | |
| 2.60 | 0.99 | 0.71 | 0.50 | | | 0.35 | |
| 2.61 | 2.16 | 1.54 | 1.08 | 30.7 | 7.9 | 1.34 | 2.88 |
| 2.62 | 0.36 | 0.26 | 0.18 | | | 0.58 | |
| 2.63 | 0.37 | 0.26 | 0.18 | | | 0.41 | |
| 2.64 | 1.60 | 1.14 | 0.80 | 25.7 | 6.1 | 1.39 | 2.85 |
| 2.65 | 0.63 | 0.45 | 0.31 | | | 0.16 | |
| 2.66 | 0.08 | 0.06 | 0.04 | | | 0.06 | |
| 2.67 | 1.34 | 0.96 | 0.67 | 23.3 | 4.5 | 1.32 | 1.34 |
| 2.68 | 0.66 | 0.47 | 0.33 | | | 0.38 | |
| 2.69 | 2.79 | 1.99 | 1.39 | 46.3 | 9.7 | 1.47 | 1.68 |
| 2.73 | 1.47 | 1.05 | 0.73 | 28.5 | 7.2 | 1.04 | 1.85 |
| 2.74 | 1.99 | 1.43 | 1.00 | 39.5 | 19.1 | 1.22 | 1.69 |
| 2.75 | 1.46 | 1.04 | 0.73 | 25.6 | 7.5 | 0.68 | 1.55 |
| 2.76 | 1.61 | 1.15 | 0.81 | 27.7 | 7.7 | 0.98 | 1.79 |
| 2.77 | 1.59 | 1.13 | 0.79 | 27.7 | 4.9 | 1.11 | 1.53 |
| 2.78 | 1.55 | 1.11 | 0.77 | 13.9 | 8 | 1.51 | 2.64 |
| 2.79 | 0.33 | 0.24 | 0.16 | 10 | 5.4 | 0.43 | |
| 2.80 | 1.47 | 1.05 | 0.73 | 15.9 | 8.8 | 0.46 | 0.95 |
| R-690 | 2.00 | 1.43 | 1.00 | | | | |
| M-A20 | 1.40 | 1.00 | | 56.4 | 5 | | |
| R-690 | 3.76 | 3.44 | 1.00 | | | | |
| M-A20 | 1.09 | 1.00 | | | | | |
| 2.81 | 0.25 | 0.23 | 0.07 | | | 0.17 | |
| 2.82 | 0.44 | 0.40 | 0.12 | | | 0.49 | |
| 2.83 | 0.63 | 0.58 | 0.17 | | | 0.80 | |
| 2.84 | 0.13 | 0.12 | 0.04 | | | 0.55 | |
| 2.85 | 0.62 | 0.57 | 0.16 | | | 0.19 | |
| 2.86 | 0.87 | 0.79 | 0.23 | | | 0.16 | |
| 2.87 | 0.84 | 0.77 | 0.22 | | | 0.22 | |
| 2.89 | 5.88 | 5.37 | 1.56 | 45.9 | 37.9 | 0.07 | 0.73 |
| 2.90 | 0.23 | 0.21 | 0.06 | | | 0.60 | |
| 2.91 | −0.37 | −0.34 | −0.10 | | | 0.43 | |
| 2.92 | 0.59 | 0.54 | 0.16 | | | 0.14 | |
| 2.93 | 0.28 | 0.26 | 0.08 | | | 0.44 | |

TABLE 13-continued

Human Monoclonal Antibodies Against L762P

| L762PHumAb | FI/CFI | FI/CFI/A20 | FI/CFI/R690 | FACSVRL762 | FACS VR (−) | ELISA | L762/VR1013 |
|---|---|---|---|---|---|---|---|
| 2.94 | 0.32 | 0.29 | 0.08 | | | 0.46 | |
| 2.95 | 0.39 | 0.36 | 0.10 | | | 0.51 | |
| 2.96 | 0.36 | 0.33 | 0.10 | | | 0.26 | |
| 2.97 | 1.26 | 1.15 | 0.33 | 36.8 | 14.1 | 1.01 | 0.89 |
| 2.98 | 0.92 | 0.84 | 0.24 | | | 0.84 | |
| 2.99 | 1.38 | 1.26 | 0.37 | 91.2 | 81.8 | 0.29 | |
| 2.100 | 0.94 | 0.86 | 0.25 | | | 1.40 | |
| 2.102 | 0.77 | 0.70 | 0.21 | | | 0.17 | |
| 2.104 | 1.37 | 1.25 | 0.36 | 10.2 | 7.4 | 0.14 | |
| 2.105 | 0.63 | 0.58 | 0.17 | | | 1.04 | |
| 2.106 | 0.79 | 0.72 | 0.21 | | | 0.84 | |
| 2.107 | 0.81 | 0.74 | 0.22 | | | 0.06 | |
| 2.109 | 0.66 | 1.24 | 0.32 | 19.2 | 6.1 | 0.45 | 0.89 |
| 2.110 | 1.58 | 3.00 | 0.77 | 36.4 | 14.2 | 0.89 | 1.11 |
| 2.112 | 0.80 | 1.52 | 0.39 | 28.8 | 6.4 | 1.16 | 1.35 |
| 2.113 | 0.57 | 1.07 | 0.27 | 31.4 | 10.7 | 0.66 | 1.17 |
| 2.114 | 0.52 | 0.99 | 0.25 | | | 0.32 | |
| 2.115 | 1.02 | 1.94 | 0.50 | 19.9 | 10.7 | 0.63 | 1.13 |
| 2.116 | 0.52 | 0.98 | 0.25 | | | 0.86 | |
| 2.118 | 0.19 | 0.36 | 0.09 | | | 0.06 | |
| 2.119 | 0.78 | 1.48 | 0.38 | 20.4 | 5.3 | 1.22 | 1.16 |
| 2.120 | 0.76 | 1.44 | 0.37 | 21.8 | 6 | 1.29 | 0.97 |
| 2.121 | 1.24 | 2.36 | 0.60 | 28.7 | 10.7 | 0.30 | 1.17 |
| 2.122 | 1.20 | 2.29 | 0.58 | 31.3 | 8.3 | 1.13 | 1.14 |
| 2.123 | 0.67 | 1.27 | 0.33 | 17.7 | 6.8 | 0.74 | 1.27 |
| R-690 | 2.06 | 3.91 | 1.00 | | | | |
| M-A20 | 0.53 | 1.00 | | 56.4 | 5 | | |
| R-690 | 3.51 | | 1.00 | | | | |
| M-A20 | 2.91 | 1.00 | | | | | |
| 1.1 | 1.05 | 0.36 | 0.30 | | | 0.16 | |
| 1.2 | −0.42 | −0.14 | −0.12 | | | 0.40 | |
| 1.3 | 1.04 | 0.36 | 0.30 | | | 1.31 | |
| 1.4 | 0.77 | 0.26 | 0.22 | | | 0.43 | |
| 1.5 | 0.19 | 0.06 | 0.05 | | | 0.13 | |
| 1.6 | 1.07 | 0.37 | 0.30 | | | 0.42 | |
| 1.7 | 0.09 | 0.03 | 0.03 | | | 0.33 | 0.80 |
| 1.8 | 2.93 | 1.01 | 0.83 | 54.70 | 45.60 | 0.59 | |
| 1.9 | 1.17 | 0.40 | 0.33 | | | 0.93 | |
| 1.10 | −0.04 | −0.02 | −0.01 | | | 0.08 | |
| 1.11 | −0.30 | −0.10 | −0.09 | | | 0.16 | |
| 1.12 | 0.11 | 0.04 | 0.03 | | | 0.25 | |
| 1.13 | 1.60 | 0.55 | 0.46 | | | 0.08 | |
| 1.14 | 0.69 | 0.24 | 0.20 | | | 0.13 | |
| 1.15 | 0.30 | 0.10 | 0.09 | | | 0.08 | |
| 1.16 | 1.44 | 0.49 | 0.41 | | | 0.08 | |
| 1.17 | −0.31 | −0.10 | −0.09 | | | 0.36 | |
| 1.18 | 0.05 | 0.02 | 0.01 | | | 0.17 | |
| 1.19 | −0.34 | −0.12 | −0.10 | | | 0.29 | |
| 1.20 | 0.84 | 0.29 | 0.24 | | | 0.45 | |
| 1.21 | −0.20 | −0.07 | −0.06 | | | 0.28 | |
| 1.22 | 0.14 | 0.05 | 0.04 | | | 0.06 | |
| 1.23 | 0.14 | 0.05 | 0.04 | | | 0.08 | |
| 1.24 | 1.02 | 0.35 | 0.29 | | | 0.16 | |
| 1.25 | 0.27 | 0.28 | 0.16 | | | 0.20 | |
| 1.26 | 1.06 | 1.09 | 0.62 | | | 0.31 | |
| 1.27 | 1.07 | 1.10 | 0.63 | | | 0.96 | |
| 1.28 | 2.14 | 2.21 | 1.26 | 3.60 | ND | 0.06 | 0.73 |
| 1.29 | 1.11 | 1.15 | 0.65 | | | 0.44 | 1.64 |
| 1.30 | 0.79 | 0.81 | 0.46 | | | 0.19 | |
| 1.31 | 1.42 | 1.46 | 0.84 | | | 0.23 | 1.27 |
| 1.32 | 1.37 | 1.42 | 0.81 | | | 0.11 | 1.91 |
| 1.33 | 0.29 | 0.30 | 0.17 | | | 0.18 | |
| 1.34 | 1.59 | 1.64 | 0.94 | 37.53 | 8.98 | 1.31 | 2.61 |
| 1.35 | 0.37 | 0.38 | 0.21 | | | 0.32 | |
| 1.36 | 0.70 | 0.72 | 0.41 | | | 0.17 | |
| 1.37 | 1.21 | 1.24 | 0.71 | | | 0.69 | |
| 1.38 | 0.63 | 0.65 | 0.37 | | | 0.38 | |
| 1.39 | 0.87 | 0.90 | 0.51 | | | 0.07 | |
| 1.40 | 0.71 | 0.73 | 0.42 | | | 0.26 | |
| 1.41 | 1.36 | 1.40 | 0.80 | 43.82 | 13.65 | 0.37 | 2.03 |
| 1.42 | 0.64 | 0.66 | 0.38 | | | 1.10 | |
| 1.43 | 0.46 | 0.47 | 0.27 | | | 0.09 | |
| 1.44 | 0.52 | 0.54 | 0.31 | | | 0.28 | |
| 1.45 | 0.74 | 0.76 | 0.44 | | | 0.15 | |
| 1.46 | 0.81 | 0.83 | 0.48 | | | 0.07 | |

TABLE 13-continued

| Human Monoclonal Antibodies Against L762P | | | | | | | |
|---|---|---|---|---|---|---|---|
| L762PHumAb | FI/CFI | FI/CFI/A20 | FI/CFI/R690 | FACSVRL762 | FACS VR (−) | ELISA | L762/VR1013 |
| 1.47 | 0.46 | 0.47 | 0.27 | | | 0.24 | |
| 1.48 | 0.62 | 0.63 | 0.36 | | | 0.27 | |
| R-690 | 1.70 | | 1.00 | | | | |
| M-A20 | 0.97 | 1.00 | | | | | |
| R-690 | 1.84 | | 1.00 | | | | |
| M-A20 | 2.82 | 1.00 | | | | | |
| 1.49 | 0.76 | 0.27 | 0.41 | | | 0.14 | |
| 1.50 | −0.22 | −0.08 | −0.12 | | | 0.36 | |
| 1.51 | −0.35 | −0.12 | −0.19 | | | 0.45 | |
| 1.52 | 1.84 | 0.65 | 1.00 | 45.74 | 9.90 | 1.40 | 2.44 |
| 1.53 | 1.77 | 0.63 | 0.96 | 42.79 | 24.70 | 0.89 | |
| 1.54 | 1.08 | 0.38 | 0.59 | | | 0.80 | |
| 1.55 | 0.81 | 0.29 | 0.44 | | | 0.35 | |
| 1.56 | 1.26 | 0.45 | 0.69 | | | 0.30 | |
| 1.57 | 3.26 | 1.16 | 1.77 | 22.20 | ND | 1.31 | 2.69 |
| 1.58 | 0.81 | 0.29 | 0.44 | | | 0.80 | |
| 1.59 | 2.22 | 0.79 | 1.21 | 24.50 | ND | 1.28 | 2.40 |
| 1.60 | 0.55 | 0.19 | 0.30 | | | 0.23 | |
| 1.61 | 0.13 | 0.04 | 0.07 | | | 0.06 | |
| 1.62 | 0.75 | 0.27 | 0.41 | 24.89 | 10.25 | 0.25 | |
| 1.63 | 0.99 | 0.35 | 0.54 | | | 0.12 | |
| 1.64 | 3.60 | 1.28 | 1.96 | | | 0.06 | 0.88 |
| 1.65 | 0.32 | 0.11 | 0.18 | | | 0.29 | |
| 1.66 | 0.01 | 0.00 | 0.00 | | | 0.30 | |
| 1.67 | 2.00 | 0.71 | 1.09 | 9.30 | ND | 0.38 | |
| 1.68 | 0.86 | 0.30 | 0.47 | | | 0.21 | |
| 1.69 | 3.31 | 1.17 | 1.80 | 8.50 | ND | 0.22 | 2.39 |
| 1.70 | 3.66 | 1.30 | 1.99 | 24.96 | 12.00 | 0.84 | 2.08 |
| 1.71 | 2.01 | 0.71 | 1.09 | | | 0.21 | |
| 1.72 | 6.49 | 2.30 | 3.53 | 6.50 | ND | 0.21 | 1.89 |
| 1.73 | 19.95 | 0.28 | 0.21 | 3.20 | ND | 0.31 | |
| 1.74 | 19.33 | 0.27 | 0.21 | 5.50 | ND | 0.20 | |
| 1.75 | 22.25 | 0.31 | 0.24 | | | 0.10 | |
| 1.76 | 11.42 | 0.16 | 0.12 | | | 0.37 | |
| 1.77 | −15.90 | −0.23 | −0.17 | | | 0.08 | |
| 1.78 | −4.60 | −0.07 | −0.05 | | | 0.26 | |
| 1.79 | 18.78 | 0.27 | 0.20 | | | 0.25 | |
| 1.80 | 35.51 | 0.50 | 0.38 | 9.00 | ND | 0.71 | |
| 1.81 | −4.15 | −0.06 | −0.04 | | | 0.33 | |
| 1.82 | −37.51 | −0.53 | −0.40 | | | 0.17 | |
| 1.83 | 7.11 | 0.10 | 0.08 | | | 0.08 | |
| 1.84 | −21.33 | −0.30 | −0.23 | | | 0.06 | |
| 1.85 | −3.61 | −0.05 | −0.04 | | | 0.13 | |
| 1.86 | −19.68 | −0.28 | −0.21 | | | 0.06 | |
| 1.87 | −3.39 | −0.05 | −0.04 | | | 0.30 | |
| 1.88 | 55.61 | 0.79 | 0.59 | 5.50 | ND | 0.10 | 1.25 |
| 1.89 | −6.73 | −0.10 | −0.07 | | | 0.17 | |
| 1.90 | 11.18 | 0.16 | 0.12 | | | 0.10 | |
| 1.91 | −31.50 | −0.45 | −0.33 | | | 0.13 | |
| 1.92 | −7.56 | −0.11 | −0.08 | | | 0.13 | |
| 1.93 | −12.37 | −0.18 | −0.13 | | | 0.11 | |
| 1.94 | 49.60 | 0.70 | 0.53 | 14.10 | ND | 1.39 | 2.33 |
| 1.95 | 10.68 | 0.15 | 0.11 | | | 0.16 | |
| 1.96 | 144.63 | 2.05 | | 63.24 | 74.75 | 0.75 | 0.80 |
| R-690 | 94.09 | 1.33 | 1.00 | | | | |
| M-A20 | 70.64 | 1.00 | | | | | |
| R-690 | 7.59 | | 1.00 | | | | |
| M-A20 | 5.33 | 1.00 | | | | | |
| 1.97 | 1.47 | 0.28 | 0.19 | | | 0.37 | |
| 1.98 | 3.69 | 0.69 | 0.49 | 38.67 | 16.57 | 0.43 | 1.69 |
| 1.99 | 4.32 | 0.81 | 0.57 | 38.31 | 18.76 | 0.40 | 1.48 |
| 1.100 | 0.22 | 0.04 | 0.03 | | | 0.32 | |
| 1.101 | 2.06 | 0.39 | 0.27 | | | 0.49 | |
| 1.102 | 0.23 | 0.04 | 0.03 | | | 0.12 | |
| 1.103 | 0.33 | 0.06 | 0.04 | | | 0.28 | |
| 1.104 | 0.45 | 0.08 | 0.06 | | | 0.08 | |

TABLE 13-continued

Human Monoclonal Antibodies Against L762P

| L762PHumAb | FI/CFI | FI/CFI/A20 | FI/CFI/R690 | FACSVRL762 | FACS VR (−) | ELISA | L762/VR1013 |
|---|---|---|---|---|---|---|---|
| 1.105 | 4.19 | 0.79 | 0.55 | 37.19 | 12.41 | 0.25 | 2.18 |
| 1.106 | 4.22 | 0.79 | 0.56 | 46.24 | 30.59 | 1.21 | 1.58 |
| 1.107 | 0.15 | 0.03 | 0.02 | | | 0.06 | |
| 1.108 | 0.08 | 0.01 | 0.01 | | | 0.31 | |
| 1.109 | 2.70 | 0.51 | 0.36 | 6.5 | 6 | 0.07 | |
| 1.110 | 1.02 | 0.19 | 0.13 | | | 0.35 | |
| 1.111 | 2.55 | 0.48 | 0.34 | | | 0.10 | |
| 1.112 | 3.58 | 0.67 | 0.47 | 18.6 | 4.2 | 1.25 | 1.74 |
| 1.113 | 0.37 | 0.07 | 0.05 | | | 0.35 | |
| 1.114 | −0.06 | −0.01 | −0.01 | | | 0.27 | |
| 1.115 | 0.55 | 0.10 | 0.07 | | | 0.13 | |
| 1.116 | 2.24 | 0.42 | 0.30 | | | 0.44 | |
| 1.117 | 0.56 | 0.10 | 0.07 | | | 0.27 | |
| 1.118 | 0.77 | 0.14 | 0.10 | | | 0.43 | |
| 1.119 | 0.78 | 0.15 | 0.10 | | | 0.41 | |
| 1.120 | 0.73 | 0.14 | 0.10 | | | 0.58 | |
| 1.121 | 0.21 | 0.05 | 0.03 | | | 0.40 | |
| 1.122 | 0.11 | 0.03 | 0.02 | | | 0.29 | |
| 1.123 | 0.41 | 0.11 | 0.07 | | | 0.07 | |
| 1.124 | 3.66 | 0.95 | 0.61 | 41.27 | 34.83 | 0.28 | 1.85 |
| 1.125 | 2.67 | 0.69 | 0.44 | | | 0.27 | 1.55 |
| 1.126 | 2.36 | 0.61 | 0.39 | | | 0.86 | 1.71 |
| 1.127 | 0.70 | 0.18 | 0.12 | | | 0.11 | |
| 1.128 | 2.99 | 0.77 | 0.50 | | | 0.13 | 1.45 |
| 1.129 | 0.33 | 0.09 | 0.06 | | | 0.39 | |
| 1.130 | 0.40 | 0.10 | 0.07 | | | 0.18 | |
| 1.131 | 1.45 | 0.38 | 0.24 | | | 0.52 | |
| 1.132 | 0.33 | 0.08 | 0.05 | | | 0.25 | |
| 1.133 | 0.17 | 0.04 | 0.03 | | | 0.24 | |
| 1.134 | 0.86 | 0.22 | 0.14 | | | 0.15 | |
| 1.135 | 1.75 | 0.45 | 0.29 | | | 0.30 | |
| 1.136 | 1.35 | 0.35 | 0.23 | | | 0.07 | |
| 1.137 | 2.30 | 0.59 | 0.38 | | | 0.83 | 1.30 |
| 1.138 | 0.83 | 0.21 | 0.14 | | | 0.60 | |
| 1.139 | 1.57 | 0.41 | 0.26 | | | 0.55 | |
| 1.140 | 1.40 | 0.36 | 0.23 | | | 1.28 | |
| 1.142 | −0.10 | −0.03 | −0.02 | | | 0.26 | |
| 1.143 | 1.46 | 0.38 | 0.24 | | | 0.16 | |
| 1.144 | 2.41 | 0.62 | 0.40 | | | 0.76 | |
| R-690 | 6.00 | | 1.00 | | | | |
| M-A20 | 3.86 | 1.00 | | 56.4 | 5 | | |
| R-690 | 2.58 | 3.22 | 1.00 | | | | |
| M-A20 | 0.80 | 1.00 | | | | | |
| 1.145 | 0.23 | 0.29 | 0.09 | | | 0.18 | |
| 1.146 | −0.12 | −0.15 | −0.05 | | | 0.41 | |
| 1.147 | 0.14 | 0.18 | 0.06 | | | 0.31 | |
| 1.148 | 0.09 | 0.11 | 0.03 | | | 0.43 | |
| 1.149 | 0.39 | 0.49 | 0.15 | | | 0.37 | |
| 1.150 | 2.23 | 2.79 | 0.87 | 17.3 | 5.4 | 0.70 | 1.46 |
| 1.151 | 0.13 | 0.16 | 0.05 | | | 0.29 | |
| 1.152 | 0.55 | 0.69 | 0.21 | | | 0.33 | |
| 1.154 | −0.20 | −0.25 | −0.08 | | | 0.41 | |
| 1.155 | 0.16 | 0.19 | 0.06 | | | 0.23 | |
| 1.156 | 0.06 | 0.07 | 0.02 | | | 0.31 | |
| 1.158 | 0.54 | 0.67 | 0.21 | | | 0.58 | |
| 1.159 | 0.78 | 0.98 | 0.30 | | | 0.09 | |
| 1.160 | 0.23 | 0.29 | 0.09 | | | 0.08 | |
| 1.162 | 0.63 | 0.78 | 0.24 | | | 0.11 | |
| 1.163 | 0.20 | 0.25 | 0.08 | | | 0.10 | |
| 1.164 | 0.22 | 0.27 | 0.08 | | | 0.09 | |
| 1.166 | 1.41 | 1.76 | 0.55 | 22.9 | 5.3 | 0.52 | 2.41 |
| 1.167 | 0.32 | 0.40 | 0.12 | | | 0.08 | |
| 1.168 | 0.88 | 1.10 | 0.34 | 15.9 | 5.1 | 0.48 | 1.90 |
| 1.170 | 0.22 | 0.42 | 0.11 | | | 0.21 | |
| 1.171 | 0.40 | 0.76 | 0.19 | | | 0.38 | |

TABLE 13-continued

| Human Monoclonal Antibodies Against L762P | | | | | | | |
|---|---|---|---|---|---|---|---|
| L762PHumAb | FI/CFI | FI/CFI/A20 | FI/CFI/R690 | FACSVRL762 | FACS VR (−) | ELISA | L762/VR1013 |
| 1.172 | 0.09 | 0.17 | 0.04 | | | 0.12 | |
| 1.174 | 0.23 | 0.43 | 0.11 | | | 0.15 | |
| 1.175 | 0.14 | 0.26 | 0.07 | | | 0.20 | |
| R-690 | 2.06 | 3.91 | 1.00 | | | | |
| M-A20 | 0.53 | 1.00 | | 56.4 | 5 | | |

for 1.170 to 1.175
FI - fluorescence intensity of primary antibody
CFI - fluorescence intensity of human irrelevant primary antibody.
A20 - mouse anti-L762P monoclonal antibody
R690 - rabbit anti-L762P affinity purified polyclonal antibody
FACS VRL762 - percent positive cells from transient transfection of VR1013/L762 expression plasmid
FACS VR (−) - percent positive cells from transient transfection of empty VR1013 expression plasmid

Example 32

Epitope Mapping and Purification of hL523S-specific Antibodies

This Example describes the purification of L523S antibodies that can distinguish between human and mouse L523S homologs and will likely distinguish between hL523S and hL523S-family members such as hIMP-1 and hIMP-2.

L523S (full-length cDNA and amino acid sequence set forth in SEQ ID NO:347 and 348, respectively) is one of a family of proteins that includes hIMP-1 and hIMP-2. The members of this family of proteins have a high degree of similarity one to the other and are also highly similar between species. Thus, generating antibodies that specifically recognize human L523S (hL523S) and not other members of the protein family in humans or the mouse homologs, has been problematic. However, in order to evaluate preclinical and clinical L523S DNA/Adenoviral vaccines by detecting the protein expression of L523S, human L523S-specific antibodies are critical.

Polyclonal antibodies specific for hL523S were generated as described in Example 23. These antibodies were used to map epitopes. The epitope analysis showed 2 particular peptides of hL523S that were recognized, peptide 16/17 and peptide 32.

The amino acid sequences of both hL523S and mouse L523S (mL523S) peptide 16/17 and peptide 32 were then compared. Peptide 32/33 is identical between hL523S and mL523S. However, as the alignment below indicates, peptide 16/17 has 5 amino acid differences between the human and mouse homologs (underlined).

```
hL523S (16/17):
IPDEMAAQQNPLQQPRGRRGLGQR          (SEQ ID NO:468)

mL523S (16/17):
IPDETAAQQNPSPQLRGRRGPGQR          (SEQ ID NO:469)
```

Moreover, peptide-based ELISAs showed that peptide 17 is specifically recognized by lung cancer patient sera #197, and a homology search of peptide 17 between human IMP (hIMP) family members shows that there is little similarity in this region between family members. The hL523S peptide 17 (and 16/17) has less than 50% similarity to hL523S family members such as hIMP-1 and hIMP-2.

Based upon the epitope mapping of L523S-specific antibodies and the data from the homology search, hL523S or mL523S peptide 16/17-conjugated ligands were then used to purify human or mouse L523S-specific antibodies from rabbit polyclonal antibodies generated against hL523S protein as described in Example 23. The data from the antibodies purified by affinity chromatography using ligands conjugated with either hL523S-peptide 16/17 or mL523S-peptide 16/17 suggested that the affinity of antibodies specific to hL523S-peptide 16/17 is much higher than that of antibodies to mL523S-peptide 16/17 since they bind more strongly to hL523S-peptide 16/17 than to mL523S-peptide 16/17. The difference in affinity between the purified antibodies to human and mouse L523S-peptide 16/17 was confirmed by peptide-based ELISA. The antibodies purified by hL523S-peptide 16/17 selectively bind to human L523S-peptide 16/17 but bind much less or not at all to mL523S-peptide 16/17.

In order to further characterize the original polyclonal antibodies and antibodies purified by hL523S-peptide 16/17, immunoblot analysis was conducted using both human lung adenocarcinoma line as a source of hL523S protein and mouse whole body embryo (day 17 gestation) as the source of mL523S protein. This analysis showed that polyclonal antibodies specific for hL523S recognize hL523S protein expressed in the tumor cell line as well as mL523S protein expressed in whole body embryos of day 17 gestation. However, the addition of hL523S peptide 32/33 blocks binding of antibodies to human and mouse L523S proteins. Thus, the crossreactivity of the polyclonal antibodies to mL523S protein is due to the existence of antibodies specific to hL523S peptide 32/33. In marked contrast, the purified antibodies specific to hL523S peptide 16/17 do not bind mL523S protein expressed in mice embryos but do recognize hL523S protein expressed in human lung adenocarcinoma cells. These data confirm the ELISA data using hL523S-peptide 16/17 and mL523S-peptide 16/17 described above.

The amino acid sequence of hL523S peptide 16/17 used to purify the antibodies is about 60–70% similar to that of the mL523S-peptide 16/17 which is not recognized by hL523S-specific antibodies by Western blot analysis and peptide-based ELISA. The hL523S peptide 16/17 has less than 50% similarity to hL523S family members such as hIMP-1 and hIMP-2. Taken together, these data suggest that it is highly probable that the antibodies purified by hL523S peptide 16/17 described herein will also distinguish hL523S protein from the other hL523S family members.

In summary, antibodies purified with the hL523S peptide 16/17 do not recognize the mouse L523S homolog. The amino acid sequence of peptide 16/17 between hL523S family members is less similar than between human and mouse L523S. Thus, the hL523S-specific antibodies described above can be used to distinguish between human and mouse L523S and between members of the hL523S family of proteins and can therefore be used for the accurate detection of hL523S protein expression in animals and humans.

Example 33

In Vivo Immunogenecity of Lung Tumor Antigen L523

This example describes two in vivo immunogenicity studies to evaluate the vaccination of mice with either an adenovirus containing L523 or with L523 naked DNA followed by a second immunization with an adenovirus containing L523.

The first study involved the immunization of two strains of mice with L523 adenovirus. The C57B16 strain of mice is homozygous for HLA-type H-$2^b$, while strain B6D2(F1) is heterozygous for the HLA-type, H-$2^{b/d}$. Table 14 describes the initial immunization strategy employed.

TABLE 14

Immunization with L523 Adenovirus alone: Experimental Design

| Group | Immunization | Strain (4/group) |
|---|---|---|
| 1 | $10^8$ PFU Ad L523 A | C57BL6 |
| 2 | $10^7$ PFU Ad hrGFP A | C57BL6 |
| 3 | $10^8$ PFU Ad L523 A | B6D2(F1) |
| 4 | $10^7$ PFU Ad hrGFP A | B6D2(F1) |
| 5 | Naïve | C57BL6 |
| 6 | Naïve | B6D2(F1) |

PFU = plaque forming unit; GFP = green fluorescent protein; Ad = adenovirus.

Mice were immunized intradermally with either $10^8$ PFU of L523-adenovirus or $10^7$ PFU of an irrelevant adenovirus (hrGFP). Three weeks following immunization, IgG1 and IgG2a antibody responses to L523 were examined in all groups of mice. Briefly, recombinant full length L523 (rL523) was coated onto ELISA plates and serum, at multiple dilutions, was added to the wells. Following a 60-minute incubation, the serum was washed from the wells and a secondary antibody, either specific for an IgG1 or IgG2a was added to the plates. Both antibodies were directly conjugated to horseradish peroxide (HRP). The levels of L523 antibodies, either IgG1 or IgG2a, were measured in all groups. In the C57BL6 mice, little to no L523-specific antibodies were detected following immunization. However, in the B6D2(F1) strain of mice immunized with L523 adenovirus, both IgG1 and IgG2a L523-specific antibodies were detected at serum dilution as low as 1/1000.

In addition to detecting L523-specific antibodies in the serum, interferon-gamma (IFN-γ) responses were assayed from immune spleen cells following in vitro stimulation with rL523 protein. Briefly, spleen cells were harvested from all mice groups and cultured for 3 days in 96-well plates. Culture conditions included, media alone, 1 or 10 μg/ml of rL523 protein, or 5 μg/ml of concanavalin A (Con A). After 3 days, the supernatants were harvested and assayed for IFN-γ levels in the supernatants.

Immunization with L523-adenovirus, but not an irrelevant adenovirus, elicited a strong IFN-γ response from the spleen cells which were stimulated with rL523. In general, responses were stronger in the B6D2(F1) mouse strain, as evidenced by both a higher level of IFN-γ production, as well as the fact that stimulation with a lower antigen concentration (1 μg/ml) elicited an equally strong response as seen with the higher antigen concentration (10 μg/ml).

Finally, T cell proliferation responses were assayed from immune spleen cells by stimulation in vitro with rL523 protein. Briefly, spleen cells were cultured for 4 days in 96-well plates with, media alone, 1 or 10 μg/ml of rL523 protein, or Con A. The cultures were then pulsed with 3H-thymidine for the final 8 hours of culture. Results are represented as the stimulation index (SI) in the presence of antigen relative to stimulation with media alone. Results were consistent with those obtained in the IFN-γ assay. Immunization with L523-adenovirus, but not an irrelevant adenovirus, elicited a proliferation response in spleen cells stimulated with rL523. A strong SI (average of>20) was observed in spleen cells harvested from the B6D2(F1) mouse strain, with similar levels of proliferation observed at both protein concentrations. Little or no T cell proliferation was observed in the C57BL6 mouse strain.

A second study involved the immunization of two strains of mice initially with L523 naked DNA followed by a second immunization with L523 adenovirus two weeks later. The mice were harvested 3 weeks after the boost. Table 15 describes the immunization regimen the second study.

TABLE 15

Immunization with L523 DNA followed by a second immunization with L523-Adenovirus: Experimental Design

| Group | Immunization | Strain (4/group) |
|---|---|---|
| 1 | L523 DNA + $10^8$ PFU Ad L523 A | C57BL6 |
| 2 | $10^9$ PFU Ad L523 A | C57BL6 |
| 3 | Irrelevant DNA + $10^7$ PFU Ad hrGFP A | C57BL6 |
| 4 | $10^7$ PFU Ad hrGFP A | C57BL6 |
| 5 | Naïve | C57BL6 |
| 6 | L523 DNA + $10^8$ PFU Ad L523 A | B6D2(F1) |
| 7 | $10^8$ PFU Ad L523 A | B6D2(F1) |
| 8 | Irrelevant DNA +$10^7$ PFU Ad hrGFP A | B6D2(F1) |
| 9 | $10^7$ PFU Ad hrGFPA | B6D2(F1) |
| 10 | Naïve | B6D2(F1) |

PFU = plaque forming unit; GFP = green fluorescent protein; Ad = adenovirus.

As described in the first study, strong IgG1 and IgG2a antibody responses were observed in B6D2(F1) mice following immunization with L523-adenovirus. Immunizing with L523 DNA appeared to increase the overall L523-specific antibody response compared to responses achieved with immunization with L523-adenovirus alone. C57BL6 mice elicited little or no L523-specific antibody responses following immunization with L523-adenovirus, but were some slightly positive responses were detected in mice immunized with L523 DNA followed by a second immunization with L523-adenovirus.

IFN-γ responses were assayed from immune spleen cells by stimulation in vitro with rL523 protein. These results confirm those observed in the initial study demonstrating the immunogenecity of L523 in animals. The results also suggest that initially immunizing the animals with L523 DNA, prior to immunization with L523-adeonvirus, does not significantly increase the CD4 response. As with the initial study, responses appear to be stronger in the B6D2(F1) strain of mice than the C57BL6 strain.

As with the initial study, T cell proliferation responses were assayed from immune spleen cells by stimulation in vitro with rL523 protein. The results from using two rounds of immunization are consistent with those obtained from the first study. Immunization with L523 DNA prior to a second round of immunization with L523-adenovirus did not significantly increase the proliferation responses generated in the mice. As with the first study, responses were stronger in the B6D2(F1) mouse strain than in the C57BL6 strain.

The difference in HLA types between the two strains of mice could explain variations in the extent of the immune responses detected. As described above, the C57BL6 strain is homozygous for H-$2^b$, while the B6D2(F1) is heterozygous for H-$2^{b/d}$. The increased diversity of the B6D2(F1) strains HLA type allows for a greater number of epitopes derived from the L523 protein to be presented. In this strain, epitopes specific for both H-$2^b$ and H-$2^d$ can be presented, while only H-$2^b$ epitopes can be presented by the C57BL6 strain.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed:

1. A method for inducing an immune response in an animal, comprising:

administering to the animal a composition comprising a polynucleotide encoding at least an immunogenic portion of a lung carcinoma polynucleotide wherein the polynucleotide comprises the polynucleotide set forth in SEQ ID NO:347;

thereby inducing an immune response in the animal.

2. The method of claim 1, wherein said composition further comprises a component selected from the group consisting of a physiologically acceptable carrier or an adjuvant.

3. The method according to claim 1, wherein said polynucleotide is delivered by a viral based delivery system.

4. The method according to claim 3, wherein the viral based delivery system is an adenovirus.

5. The method of claim 1, wherein the immune response induced is a CD4+ T helper response.

6. The method of claim 1, wherein the immune response induced is a CD8+ cytotoxic T lymphocyte response.

7. The method of claim 1, wherein the immune response induced is both a CD4+ T helper and CD8+ cytotoxic T cell immune response.

* * * * *

UNITED STATES PATENT AND TRADEMARK OFFICE

CERTIFICATE OF CORRECTION

PATENT NO. : 6,960,570 B2
DATED : November 1, 2005
INVENTOR(S) : Tongtong Wang et al.

It is certified that error appears in the above-identified patent and that said Letters Patent is hereby corrected as shown below:

<u>Column 557,</u>
Line 6, "polynucleotide" should read -- polypeptide --.

Signed and Sealed this

Third Day of January, 2006

JON W. DUDAS
*Director of the United States Patent and Trademark Office*

SEQUENCE LISTING

```
<160> NUMBER OF SEQ ID NOS: 469

<210> SEQ ID NO 1
<211> LENGTH: 315
<212> TYPE: DNA
<213> ORGANISM: Homo sapiens
<220> FEATURE:
<221> NAME/KEY: misc_feature
<222> LOCATION: 236, 241
<223> OTHER INFORMATION: n = A,T,C or G

<400> SEQUENCE: 1

gcagagacag actggtggtt gaacctggag gtgccaaaaa agccagctgc gggcccagga     60

cagctgccgt gagactcccg atgtcacagg cagtctgtgt ggttacagcg cccctcagtg    120

ttcatctcca gcagagacaa cggaggaggc tcccaccagg acggttctca ttatttatat    180

gttaatatgt ttgtaaactc atgtacagtt ttttttgggg gggaagcaat gggaanggta    240

naaattacaa atagaatcat ttgctgtaat ccttaaatgg caaacggtca ggccacgtga    300

aaaaaaaaaa aaaaa                                                      315


<210> SEQ ID NO 2
<211> LENGTH: 380
<212> TYPE: DNA
<213> ORGANISM: Homo sapiens

<400> SEQUENCE: 2

atttaggctt aagattttgt ttacccttgt tactaaggag caaattagta ttaaagtata     60

atatatataa acaaatacaa aaagttttga gtggttcagc ttttttattt tttttaatgg    120

cataactttt aacaacactg ctctgtaatg ggttgaactg tggtactcag actgagataa    180

ctgaaatgag tggatgtata gtgttattgc ataattatcc cactatgaag caaagggact    240

ggataaattc ccagtctaga ttattagcct ttgttaacca tcaagcacct agaagaagaa    300

ttattggaaa ttttgtcctc tgtaactggc actttggggt gtgacttatc ttttgccttt    360

gtaaaaaaaa aaaaaaaaaa                                                 380


<210> SEQ ID NO 3
<211> LENGTH: 346
<212> TYPE: DNA
<213> ORGANISM: Homo sapiens
<220> FEATURE:
<221> NAME/KEY: misc_feature
<222> LOCATION: 316, 317, 318, 322, 323, 326, 329, 330, 331, 336, 337,
      339, 340, 342, 343
<223> OTHER INFORMATION: n = A,T,C or G

<400> SEQUENCE: 3

ttgtaagtat acaattttag aaaggattaa atgttattga tcattttact gaatactgca     60
```

-continued

```
catcctcacc atacaccatc cactttccaa taacatttaa tcctttctaa aattgtaagt    120

atacaattgt actttctttg gattttcata acaaatatac catagactgt taattttatt    180

gaagtttcct taatggaatg agtcattttt gtcttgtgct tttgaggtta cctttgcttt    240

gacttccaac aatttgatca tatagtgttg agctgtggaa atctttaagt ttattctata    300

gcaataattt ctattnnnag annccnggnn naaaannann annaaa                   346


<210> SEQ ID NO 4
<211> LENGTH: 372
<212> TYPE: DNA
<213> ORGANISM: Homo sapiens
<220> FEATURE:
<221> NAME/KEY: misc_feature
<222> LOCATION: 297, 306, 332
<223> OTHER INFORMATION: n = A,T,C or G

<400> SEQUENCE: 4

actagtctca ttactccaga attatgctct tgtacctgtg tggctgggtt tcttagtcgt     60

tggtttggtt tggtttttg aactggtatg tagggtggtt cacagttcta atgtaagcac    120

tctcttctcc aagttgtgct ttgtggggac aatcattctt tgaacattag agaggaaggc    180

agttcaagct gttgaaaaga ctattgctta tttttgtttt taaagaccta cttgacgtca    240

tgtggacagt gcacgtgcct tacgctacat cttgttttct aggaagaagg ggatgcnggg    300

aaggantggg tgctttgtga tggataaaac gnctaaataa cacaccttta cattttgaaa    360

aaaacaaaac aa                                                        372


<210> SEQ ID NO 5
<211> LENGTH: 698
<212> TYPE: DNA
<213> ORGANISM: Homo sapiens
<220> FEATURE:
<221> NAME/KEY: misc_feature
<222> LOCATION: 8, 345, 422, 430, 433, 436, 438, 472, 481, 486, 515,
      521, 536, 549, 553, 556, 557, 559, 568, 593, 597, 605, 611, 613,
      616, 618, 620, 628, 630, 632, 634, 635, 639, 643, 647, 648,
      649, 652, 654, 658, 664, 690
<223> OTHER INFORMATION: n = A,T,C or G

<400> SEQUENCE: 5

actagtanga tagaaacact gtgtcccgag agtaaggaga gaagctacta ttgattagag     60

cctaacccag gttaactgca agaagaggcg ggatactttc agctttccat gtaactgtat    120

gcataaagcc aatgtagtcc agtttctaag atcatgttcc aagctaactg aatcccactt    180

caatacacac tcatgaactc ctgatggaac aataacaggc ccaagcctgt ggtatgatgt    240

gcacacttgc tagactcaga aaaaatacta ctctcataaa tgggtgggag tattttgggt    300

gacaacctac tttgcttggc tgagtgaagg aatgatattc atatnttcat ttattccatg    360

gacatttagt tagtgctttt tatataccag gcatgatgct gagtgacact cttgtgtata    420

tntccaaatn ttngtncngt cgctgcacat atctgaaatc ctatattaag antttcccaa    480

natgangtcc ctggtttttc cacgccactt gatcngtcaa ngatctcacc tctgtntgtc    540

ctaaaaccnt ctnctnnang gttagacngg acctctcttc tcccttcccg aanaaatnaag    600

tgtgngaaga nanccncncn cccccctncn tncnncctng ccngctnnnc cncntgtngg    660

gggngccgcc cccgcggggg gaccccccn ttttcccc                             698


<210> SEQ ID NO 6
<211> LENGTH: 740
<212> TYPE: DNA
```

-continued

<213> ORGANISM: Homo sapiens
<220> FEATURE:
<221> NAME/KEY: misc_feature
<222> LOCATION: 82, 406, 426, 434, 462, 536, 551, 558, 563, 567, 582,
584, 592, 638, 651, 660, 664, 673, 675, 697, 706, 711, 715, 716,
717, 723, 724, 725, 733
<223> OTHER INFORMATION: n = A,T,C or G

<400> SEQUENCE: 6

```
actagtcaaa aatgctaaaa taatttggga gaaaatattt tttaagtagt gttatagttt     60

catgtttatc ttttattatg tnttgtgaag ttgtgtcttt tcactaatta cctatactat    120

gccaatattt ccttatatct atccataaca tttatactac atttgtaaga gaatatgcac    180

gtgaaactta acactttata aggtaaaaat gaggtttcca agatttaata atctgatcaa    240

gttcttgtta tttccaaata gaatggactt ggtctgttaa ggggctaagg gagaagaaga    300

agataaggtt aaaagttgtt aatgaccaaa cattctaaaa gaaatgcaaa aaaaaattta    360

ttttcaagcc ttcgaactat ttaaggaaag caaaatcatt tcctanatgc atatcatttg    420

tgagantttc tcantaatat cctgaatcat tcatttcagc tnaggcttca tgttgactcg    480

atatgtcatc tagggaaagt ctatttcatg gtccaaacct gttgccatag ttggtnaggc    540

tttcctttaa ntgtgaanta ttnacangaa attttctctt tnanagttct tnatagggtt    600

aggggtgtgg gaaaagcttc taacaatctg tagtgttncg tgttatctgt ncagaaccan    660

aatnacggat cgnangaagg actgggtcta tttacangaa cgaatnatct ngttnnntgt    720

gtnnncaact ccngggagcc                                                740
```

<210> SEQ ID NO 7
<211> LENGTH: 670
<212> TYPE: DNA
<213> ORGANISM: Homo sapiens
<220> FEATURE:
<221> NAME/KEY: misc_feature
<222> LOCATION: 265, 268, 457, 470, 485, 546, 553, 566, 590, 596, 613,
624, 639, 653, 659, 661
<223> OTHER INFORMATION: n = A,T,C or G

<400> SEQUENCE: 7

```
gctggggagc tcggcatggc ggtccccgct gcagccatgg ggccctcggc gttgggccag     60

agcggccccg gctcgatggc cccgtggtgc tcagtgagca gcggcccgtc gcgctacgtg    120

cttgggatgc aggagctgtt ccggggccac agcaagaccg cgagttcctg gcgcacagcg    180

ccaaggtgca ctcggtggcc tggagttgcg acgggcgtcg cctacctcgg ggtcttcgac    240

aagacgccac gtcttcttgc tgganaanga ccgttggtca aagaaaacaa ttatcgggga    300

catggggata gtgtggacca ctttgttggc atccaagtaa tcctgaccta tttgttacgg    360

cgtctggaga taaaaccatt cgcatctggg atgtgaggac tacaaaatgc attgccactg    420

tgaacactaa aggggagaac attaatatct gctggantcc tgatgggcan accattgctg    480

tagcnacaag gatgatgtgg tgactttatt gatgccaaga aaccccgttc caaagcaaaa    540

aaacanttcc aanttcgaag tcaccnaaat ctcctggaac aatgaacatn aatatnttct    600

tcctgacaat ggnccttggg tgtntcacat cctcagctnc cccaaaactg aancctgtnc    660

natccacccc                                                           670
```

<210> SEQ ID NO 8
<211> LENGTH: 689
<212> TYPE: DNA
<213> ORGANISM: Homo sapiens
<220> FEATURE:

-continued

<221> NAME/KEY: misc_feature
<222> LOCATION: 253, 335, 410, 428, 448, 458, 466, 479, 480, 482, 483,
485, 488, 491, 492, 495, 499, 500, 502, 503, 512, 516, 524, 525,
526, 527, 530, 540, 546, 550, 581, 593, 594, 601, 606, 609,
610, 620, 621, 622, 628, 641, 646, 656, 673
<223> OTHER INFORMATION: n = A,T,C or G

<400> SEQUENCE: 8

```
actagtatct aggaatgaac agtaaaagag gagcagttgg ctacttgatt acaacagagt     60

aaatgaagta ctggatttgg gaaaacctgg ttttattaga acatatggaa tgaaagccta    120

cacctagcat tgcctactta gccccctgaa ttaacagagc ccaattgaga caaacccctg    180

gcaacaggaa attcaaggga gaaaaagtaa gcaacttggg ctaggatgag ctgactccct    240

tagagcaaag ganagacagc ccccattacc aaataccatt tttgcctggg gcttgtgcag    300

ctggcagtgt tcctgcccca gcatggcacc ttatngtttt gatagcaact tcgttgaatt    360

ttcaccaact tattacttga aattataata tagcctgtcc gtttgctgtn tccaggctgt    420

gatatatntt cctagtggtt tgactttnaa aataaatnag gtttantttt ctcccccnn    480

cnntnctncc nntcnctcnn cnntcccccc cnctcngtcc tccnnnnttn gggggggccn    540

cccccncggn ggaccccct ttggtccctt agtggaggtt natggcccct ggnnttatcc    600

nggccntann tttccccgtn nnaaatgntt ccccctccca ntcccnccac ctcaanccgg    660

aagcctaagt ttntaccctg ggggtcccc                                     689
```

<210> SEQ ID NO 9
<211> LENGTH: 674
<212> TYPE: DNA
<213> ORGANISM: Homo sapiens
<220> FEATURE:
<221> NAME/KEY: misc_feature
<222> LOCATION: 602, 632, 639, 668
<223> OTHER INFORMATION: n = A,T,C or G

<400> SEQUENCE: 9

```
gtccactctc ctttgagtgt actgtcttac tgtgcactct gtttttcaac tttctagata     60

taaaaaatgc ttgttctata gtggagtaag agctcacaca cccaaggcag caagataact    120

gaaaaaagcg aggctttttt gccaccttgg taaaggccag ttcactgcta tagaactgct    180

ataagcctga agggaagtag ctatgagact ttccattttt cttagttctc ccaataggct    240

ccttcatgga aaaaggcttc ctgtaataat tttcacctaa tgaattagca gtgtgattat    300

ttctgaaata agagacaaat tgggccgcag agtcttcctg tgatttaaaa taaacaaccc    360

aaagttttgt ttggtcttca ccaaaggaca tactctaggg ggtatgttgt tgaagacatt    420

caaaaacatt agctgttctg tctttcaatt tcaagttatt ttggagactg cctccatgtg    480

agttaattac tttgctctgg aactagcatt attgtcatta tcatcacatt ctgtcatcat    540

catctgaata atattgtgga tttccccctc tgcttgcatc ttcttttgac tcctctggga    600

anaaatgtca aaaaaaaagg tcgatctact cngcaaggnc catctaatca ctgcgctgga    660

aggacccnct gccc                                                      674
```

<210> SEQ ID NO 10
<211> LENGTH: 346
<212> TYPE: DNA
<213> ORGANISM: Homo sapiens
<220> FEATURE:
<221> NAME/KEY: misc_feature
<222> LOCATION: 320, 321, 322, 325, 326, 328, 329, 330, 332, 333, 334,
335, 342
<223> OTHER INFORMATION: n = A,T,C or G -continued

<400> SEQUENCE: 10

```
actagtctgc tgatagaaag cactatacat cctattgttt ctttctttcc aaaatcagcc     60
ttctgtctgt aacaaaaatg tactttatag agatggagga aaaggtctaa tactacatag    120
ccttaagtgt ttctgtcatt gttcaagtgt attttctgta acagaaacat atttggaatg    180
tttttctttt ccccttataa attgtaattc ctgaaatact gctgctttaa aaagtcccac    240
tgtcagatta tattatctaa caattgaata ttgtaaatat acttgtctta cctctcaata    300
aaagggtact tttctattan nnagnngnnn gnnnnataaa anaaaa                   346
```

<210> SEQ ID NO 11
<211> LENGTH: 602
<212> TYPE: DNA
<213> ORGANISM: Homo sapiens

<400> SEQUENCE: 11

```
actagtaaaa agcagcattg ccaaataatc cctaattttc cactaaaaat ataatgaaat     60

gatgttaagc tttttgaaaa gtttaggtta aacctactgt tgttagatta atgtatttgt    120

tgcttccctt tatctggaat gtggcattag ctttttttatt ttaaccctct ttaattctta    180

ttcaattcca tgacttaagg ttggagagct aaacactggg atttttggat aacagactga    240

cagttttgca taattataat cggcattgta catagaaagg atatggctac cttttgttaa    300

atctgcactt tctaaatatc aaaaaaggga aatgaagtta taaatcaatt tttgtataat    360

ctgtttgaaa catgagtttt atttgcttaa tattagggct ttgccccttt tctgtaagtc    420

tcttgggatc ctgtgtagaa ctgttctcat taaacaccaa acagttaagt ccattctctg    480

gtactagcta caaattcggt ttcatattct acttaacaat ttaaataaac tgaaatattt    540

ctagatggtc tacttctgtt catataaaaa caaaacttga tttccaaaaa aaaaaaaaaa    600

aa                                                                   602
```

<210> SEQ ID NO 12
<211> LENGTH: 685
<212> TYPE: DNA
<213> ORGANISM: Homo sapiens
<220> FEATURE:
<221> NAME/KEY: misc_feature
<222> LOCATION: 170, 279, 318, 321, 322, 422, 450, 453, 459, 467, 468, 470, 473, 475, 482, 485, 486, 491, 498, 503, 506, 509, 522, 526, 527, 528, 538, 542, 544, 551, 567, 568, 569, 574, 576, 582, 587, 588, 589, 590, 592, 593, 598, 599, 603, 605, 608
<223> OTHER INFORMATION: n = A,T,C or G
<221> NAME/KEY: misc_feature
<222> LOCATION: 633, 634, 635, 644, 646, 648, 651, 655, 660, 662, 663, 672, 674, 675, 682, 683
<223> OTHER INFORMATION: n = A,T,C or G

<400> SEQUENCE: 12

```
actagtcctg tgaaagtaca actgaaggca gaaagtgtta ggattttgca tctaatgttc     60

attatcatgg tattgatgga cctaagaaaa taaaaattag actaagcccc caaataagct    120

gcatgcattt gtaacatgat tagtagattt gaatatatag atgtagtatn ttgggtatct    180

aggtgtttta tcattatgta aaggaattaa agtaaaggac tttgtagttg tttttattaa    240

atatgcatat agtagagtgc aaaaatatag caaaaatana aactaaaggt agaaaagcat    300

tttagatatg ccttaatnta nnaactgtgc caggtggccc tcggaataga tgccaggcag    360

agaccagtgc ctgggtggtg cctccccttg tctgcccccc tgaagaactt ccctcacgtg    420

angtagtgcc ctcgtaggtg tcacgtggan tantggganc aggccgnncn gtnanaagaa    480

ancanngtga nagtttcncc gtngangcng aactgtccct gngccnnnac gctcccanaa    540

cntntccaat ngacaatcga gtttccnnnc tccngnaacc tngccgnnnn cnngcccnnc    600
```

-continued cantntgnta accccgcgcc cggatcgctc tcnnntcgtt ctcncncnaa ngggntttcn 660
cnnccgccgt cncnnccccg cnncc 685

<210> SEQ ID NO 13
<211> LENGTH: 694
<212> TYPE: DNA
<213> ORGANISM: Homo sapiens
<220> FEATURE:
<221> NAME/KEY: misc_feature
<222> LOCATION: 503, 546, 599, 611, 636, 641, 643, 645, 656, 658, 662, 676, 679, 687
<223> OTHER INFORMATION: n = A,T,C or G

<400> SEQUENCE: 13
cactagtcac tcattagcgt tttcaatagg gctcttaagt ccagtagatt acgggtagtc 60
agttgacgaa gatctggttt acaagaacta attaaatgtt tcattgcatt tttgtaagaa 120
cagaataatt ttataaaatg tttgtagttt ataattgccg aaaataattt aaagacactt 180
tttctctgtg tgtgcaaatg tgtgtttgtg atccattttt tttttttttt taggacacct 240
gtttactagc tagctttaca atatgccaaa aaaggatttc tccctgaccc catccgtggt 300
tcacctcttt ttccccccat gctttttgcc ctagtttata acaaaggaat gatgatgatt 360
taaaaagtag ttctgtatct tcagtatctt ggtcttccag aaccctctgg ttgggaaggg 420
gatcattttt tactggtcat ttccctttgg agtgtactac tttaacagat ggaaagaact 480
cattggccat ggaaacagcc gangtgttgg gagccagcag tgcatggcac cgtccggcat 540
ctggcntgat tggtctggct gccgtcattg tcagcacagt gccatgggac atggggaana 600
ctgactgcac ngccaatggt tttcatgaag aatacngcat ncncngtgat cacgtnancc 660
angacgctat gggggncana gggccanttg cttc 694

<210> SEQ ID NO 14
<211> LENGTH: 679
<212> TYPE: DNA
<213> ORGANISM: Homo sapiens
<220> FEATURE:
<221> NAME/KEY: misc_feature
<222> LOCATION: 29, 68, 83, 87, 94, 104, 117, 142, 145, 151, 187, 201, 211, 226, 229, 239, 241, 245, 252, 255, 259, 303, 309, 359, 387, 400, 441, 446, 461, 492, 504, 505, 512, 525, 527, 533, 574, 592, 609, 610, 618, 620, 626, 627, 633, 639, 645, 654
<223> OTHER INFORMATION: n = A,T,C or G

<400> SEQUENCE: 14
cagccgcctg catctgtatc cagcgccang tcccgccagt cccagctgcg cgcgcccccc 60
agtcccgnac ccgttcggcc cangctnagt tagncctcac catnccggtc aaaggangca 120
ccaagtgcat caaatacctg cngtncggat ntaaattcat cttctggctt gccgggattg 180
ctgtccntgc cattggacta nggctccgat ncgactctca gaccanganc atcttcganc 240
naganactaa tnatnattnt tccagcttct acacaggagt ctatattctg atcggatccg 300
gcnccctcnt gatgctggtg ggcttcctga gctgctgcgg ggctgtgcaa gagtcccant 360
gcatgctggg actgttcttc ggcttcntct tggtgatatn cgccattgaa atacctgcgg 420
ccatctgggg atattccact ncgatnatgt gattaaggaa ntccacggag ttttacaagg 480
acacgtacaa cnacctgaaa accnnggatg anccccaccg ggaancnctg aangccatcc 540
actatgcgtt gaactgcaat ggtttggctg gggnccttga acaatttaat cncatacatc 600
tggccccann aaaggacntn ctcganncct tcnccgtgna attcngttct gatnccatca 660
cagaagtctc gaacaatcc 679

-continued

<210> SEQ ID NO 15
<211> LENGTH: 695
<212> TYPE: DNA
<213> ORGANISM: Homo sapiens
<220> FEATURE:
<221> NAME/KEY: misc_feature
<222> LOCATION: 105, 172, 176, 179, 189, 203, 212, 219, 221, 229, 231, 238, 242, 261, 266, 270, 278, 285, 286, 298, 311, 324, 337, 350, 363, 384, 391, 395, 405, 411, 424, 427, 443, 448, 453, 455, 458, 463, 467, 470, 479, 482, 484, 493, 499, 505, 518
<223> OTHER INFORMATION: n = A,T,C or G
<221> NAME/KEY: misc_feature
<222> LOCATION: 520, 523, 531, 540, 584, 595, 597, 609, 611, 626, 628, 651, 652, 657, 661, 665, 669, 672, 681, 683, 691, 693
<223> OTHER INFORMATION: n = A,T,C or G

<400> SEQUENCE: 15

```
actagtggat aaaggccagg gatgctgctc aacctcctac catgtacagg gacgtctccc     60
cattacaact acccaatccg aagtgtcaac tgtgtcagga ctaanaaacc ctggttttga    120
ttaaaaaagg gcctgaaaaa aggggagcca caaatctgtc tgcttcctca cnttantcnt    180
tggcaaatna gcattctgtc tcnttggctg cngcctcanc ncaaaaaanc ngaactcnat    240
cnggcccagg aatacatctc ncaatnaacn aaattganca aggcnntggg aaatgccnga    300
tgggattatc ntccgcttgt tganctteta agtttcnttc ccttcattcn accctgccag    360
ccnagttctg ttagaaaaat gccngaattc naacnccggt tttcntactc ngaatttaga    420
tctncanaaa cttcctggcc acnattcnaa ttnanggnca cgnacanatn ccttccatna    480
ancncacccc acntttgana gccangacaa tgactgcntn aantgaaggc ntgaaggaan    540
aactttgaaa ggaaaaaaaa ctttgtttcc ggccccttcc aacncttctg tgttnancac    600
tgccttctng naaccctgga agcccngnga cagtgttaca tgttgttcta nnaaacngac    660
ncttnaatnt cnatcttccc nanaacgatt ncncc                                695
```

<210> SEQ ID NO 16
<211> LENGTH: 669
<212> TYPE: DNA
<213> ORGANISM: Homo sapiens
<220> FEATURE:
<221> NAME/KEY: misc_feature
<222> LOCATION: 299, 354, 483, 555, 571, 573, 577, 642, 651, 662, 667
<223> OTHER INFORMATION: n = A,T,C or G

<400> SEQUENCE: 16

```
cgccgaagca gcagcgcagg ttgtccccgt ttcccctccc ccttcccttc tccggttgcc     60
ttcccgggcc ccttacactc cacagtcccg gtcccgccat gtcccagaaa caagaagaag    120
agaaccctgc ggaggagacc ggcgaggaga agcaggacac gcaggagaaa gaaggtattc    180
tgcctgagag agctgaagag gcaaagctaa aggccaaata cccaagccta ggacaaaagc    240
ctggaggctc cgacttcctc atgaagagac tccagaaagg gcaaaagtac tttgactcng    300
gagactacaa catggccaaa gccaacatga agaataagca gctgccaagt gcangaccag    360
acaagaacct ggtgactggt gatcacatcc ccacccccaca ggatctgccc agagaaagtc    420
ctcgctcgtc accagcaagc ttgcgggtgg ccaagttgaa tgatgctgcc ggggctctgc    480
canatctgag acgcttccct ccctgcccca cccgggtcct gtgctggctc ctgcccttcc    540
tgcttttgca gccangggtc aggaagtggc ncnggtngtg gctggaaagc aaaacccttt    600
cctgttggtg tcccacccat ggagcccctg gggcgagccc angaacttga ncctttttgt    660
tntcttncc                                                             669
```

-continued

```
<210> SEQ ID NO 17
<211> LENGTH: 697
<212> TYPE: DNA
<213> ORGANISM: Homo sapiens
<220> FEATURE:
<221> NAME/KEY: misc_feature
<222> LOCATION: 33, 48, 50, 55, 59, 60, 76, 77, 78, 90, 113, 118, 130,
      135, 141, 143, 150, 156, 166, 167, 170, 172, 180, 181, 190, 192,
      194, 199, 201, 209, 212, 224, 225, 226, 230, 233, 234, 236,
      242, 244, 251, 253, 256, 268, 297, 305, 308, 311, 314
<223> OTHER INFORMATION: n = A,T,C or G
<221> NAME/KEY: misc_feature
<222> LOCATION: 315, 317, 322, 324, 327, 333, 337, 343, 362, 364, 367,
      368, 373, 384, 388, 394, 406, 411, 413, 423, 429, 438, 449, 450,
      473, 476, 479, 489, 491, 494, 499, 505, 507, 508, 522, 523,
      527, 530, 533, 535, 538, 539, 545, 548, 550, 552, 555
<223> OTHER INFORMATION: n = A,T,C or G
<221> NAME/KEY: misc_feature
<222> LOCATION: 562, 563, 566, 568, 572, 577, 578, 580, 581, 591, 594,
      622, 628, 632, 638, 642, 644, 653, 658, 662, 663, 665, 669, 675,
      680, 686, 689
<223> OTHER INFORMATION: n = A,T,C or G

<400> SEQUENCE: 17

gcaagatatg gacaactaag tgagaaggta atnctctact gctctagntn ctccnggcnn      60

gacgcgctga ggagannnac gctggcccan ctgccggcca cacacgggga tcntggtnat     120

gcctgcccan gggancccca ncnctcggan cccatntcac acccgnnccn tncgcccacn     180

ncctggctcn cncngcccng nccagctcnc gncccccctcc gccnnnctcn ttnncntctc     240

cncnccctcc ncnacnacct cctacccncg gctccctccc cagccccccc ccgcaancct     300

ccacnacncc ntcnncncga ancnccnctc gcnctcngcc ccngccccct gccccccgcc     360

cncnacnncg cgntcccccg cgcncgcngc ctcncccccct cccacnacag ncncacccgc     420

agncacgcnc tccgcccnct gacgccccnn cccgccgcgc tcaccttcat ggnccnacng     480

ccccgctcnc nccnctgcnc gccgncnngg cgccccgccc cnnccgngtn ccncncgnng     540

ccccngcngn angcngtgcg cnncangncc gngccgnncn ncaccctccg nccnccgccc     600

cgcccgctgg gggctcccgc cncgcggntc antccccncc cntncgccca ctntccgntc     660

cnncnctcnc gctcngcgcn cgcccnccnc ccccccc                              697


<210> SEQ ID NO 18
<211> LENGTH: 670
<212> TYPE: DNA
<213> ORGANISM: Homo sapiens
<220> FEATURE:
<221> NAME/KEY: misc_feature
<222> LOCATION: 234, 292, 329, 437, 458, 478, 487, 524, 542, 549, 550,
      557, 576, 597, 603, 604, 646, 665
<223> OTHER INFORMATION: n = A,T,C or G

<400> SEQUENCE: 18

ctcgtgtgaa gggtgcagta cctaagccgg agcggggtag aggcgggccg gcaccccctt      60

ctgacctcca gtgccgccgg cctcaagatc agacatggcc cagaacttga acgacttggc     120

gggacggctg cccgccgggc cccggggcat gggcacggcc ctgaagctgt tgctgggggc     180

cggcgccgtg gcctacggtg tgcgcgaatc tgtgttcacc gtggaaggcg ggcncagagc     240

catcttcttc aatcggatcg gtggagtgca caggacacta tcctgggccg anggccttca     300

cttcaggatc cttggttcca gtaccccanc atctatgaca ttcgggccag acctcgaaaa     360

aatctcctcc ctacaggctc caaagaccta cagatggtga atatctccct gcgagtgttg     420

tctcgaccaa tgctcangaa cttcctaaca tgttccancg cctaagggct ggactacnaa     480
```

-continued gaacgantgt tgccgtccat tgtcacgaag tgctcaagaa tttnggtggc caagttcaat 540
gncctcacnn ctgatcnccc agcggggcca agttanccct ggttgatccc cggggganctg 600 acnnaaaagg gccaaggact tcccctcatc ctggataatg tggccntcac aaagctcaac 660 tttanccacc 670

<210> SEQ ID NO 19
<211> LENGTH: 606
<212> TYPE: DNA
<213> ORGANISM: Homo sapiens
<220> FEATURE:
<221> NAME/KEY: misc_feature
<222> LOCATION: 506
<223> OTHER INFORMATION: n = A,T,C or G

<400> SEQUENCE: 19
actagtgcca acctcagctc ccaggccagt tctctgaatg tcgaggagtt ccaggatctc 60
tggcctcagt tgtccttggt tattgatggg ggacaaattg gggatggcca gagccccgag 120
tgtcgccttg gctcaactgt ggttgatttg tctgtgcccg gaaagtttgg catcattcgt 180
ccaggctgtg ccctggaaag tactacagcc atcctccaac agaagtacgg actgctcccc 240
tcacatgcgt cctacctgtg aaactctggg aagcaggaag gcccaagacc tggtgctgga 300
tactatgtgt ctgtccactg acgactgtca aggcctcatt tgcagaggcc accggagcta 360
gggcactagc ctgactttta aggcagtgtg tctttctgag cactgtagac caagcccttg 420
gagctgctgg tttagccttg cacctgggga aaggatgtat ttatttgtat tttcatatat 480
cagccaaaag ctgaatggaa aagttnagaa cattcctagg tggccttatt ctaataagtt 540
tcttctgtct gttttgtttt tcaattgaaa agttattaaa taacagattt agaatctagt 600
gagacc 606

<210> SEQ ID NO 20
<211> LENGTH: 449
<212> TYPE: DNA
<213> ORGANISM: Homo sapiens

<400> SEQUENCE: 20
actagtaaac aacagcagca gaaacatcag tatcagcagc gtcgccagca ggagaatatg 60
cagcgccaga gccgaggaga acccccgctc cctgaggagg acctgtccaa actcttcaaa 120
ccaccacagc cgcctgccag gatggactcg ctgctcattg caggccagat aaacacttac 180
tgccagaaca tcaaggagtt cactgcccaa aacttaggca agctcttcat ggcccaggct 240
cttcaagaat acaacaacta agaaaaggaa gtttccagaa aagaagttaa catgaactct 300
tgaagtcaca ccagggcaac tcttggaaga aatatatttg catattgaaa agcacagagg 360
atttctttag tgtcattgcc gattttggct ataacagtgt ctttctagcc ataataaaat 420
aaaacaaaat cttgactgct tgctcaaaa 449

<210> SEQ ID NO 21
<211> LENGTH: 409
<212> TYPE: DNA
<213> ORGANISM: Homo sapiens

<400> SEQUENCE: 21
tatcaatcaa ctggtgaata attaaacaat gtgtggtgtg atcatacaaa gggtaccact 60
caatgataaa aggaacaagc tgcctatatg tggaacaaca tggatgcatt tcagaaactt 120

-continued

```
tatgttgagt gaaagaacaa acacggagaa catactatgt ggttctcttt atgtaacatt    180

acagaaataa aaacagaggc aaccaccttt gaggcagtat ggagtgagat agactggaaa    240

aaggaaggaa ggaaactcta cgctgatgga aatgtctgtg tcttcattgg gtggtagtta    300

tgtggggata tacatttgtc aaaatttatt gaactatata ctaaagaact ctgcatttta    360

ttgggatgta aataatacct caattaaaaa gacaaaaaaa aaaaaaaaa                409
```

<210> SEQ ID NO 22
<211> LENGTH: 649
<212> TYPE: DNA
<213> ORGANISM: Homo sapiens
<220> FEATURE:
<221> NAME/KEY: misc_feature
<222> LOCATION: 263, 353, 610, 635, 646
<223> OTHER INFORMATION: n = A,T,C or G

<400> SEQUENCE: 22

```
acaattttca ttatcttaag cacattgtac atttctacag aacctgtgat tattctcgca     60

tgataaggat ggtacttgca tatggtgaat tactactgtt gacagtttcc gcagaaatcc    120

tatttcagtg gaccaacatt gtggcatggc agcaaatgcc aacattttgt ggaatagcag    180

caaatctaca agagaccctg gttggttttt cgttttgttt tctttgtttt ttccccccttc   240

tcctgaatca gcagggatgg aangagggta gggaagttat gaattactcc ttccagtagt    300

agctctgaag tgtcacattt aatatcagtt ttttttaaac atgattctag ttnaatgtag    360

aagagagaag aaagaggaag tgttcacttt tttaatacac tgatttagaa atttgatgtc    420

ttatatcagt agttctgagg tattgatagc ttgctttatt tctgccttta cgttgacagt    480

gttgaagcag ggtgaataac taggggcata tatatttttt ttttttgtaa gctgtttcat    540

gatgttttct ttggaatttc cggataagtt caggaaaaca tctgcatgtt gttatctagt    600

ctgaagttcn tatccatctc attacaacaa aaacncccag aacggnttg                649
```

<210> SEQ ID NO 23
<211> LENGTH: 669
<212> TYPE: DNA
<213> ORGANISM: Homo sapiens
<220> FEATURE:
<221> NAME/KEY: misc_feature
<222> LOCATION: 642, 661
<223> OTHER INFORMATION: n = A,T,C or G

<400> SEQUENCE: 23

```
actagtgccg tactggctga aatccctgca ggaccaggaa gagaaccagt tcagactttg     60

tactctcagt caccagctct ggaattagat aaattccttg aagatgtcag gaatgggatc    120

tatcctctga cagcctttgg gctgcctcgg ccccagcagc cacagcagga ggaggtgaca    180

tcacctgtcg tgccccccctc tgtcaagact ccgacacctg aaccagctga ggtggagact   240

cgcaaggtgg tgctgatgca gtgcaacatt gagtcggtgg aggagggagt caaacaccac    300

ctgacacttc tgctgaagtt ggaggacaaa ctgaaccggc acctgagctg tgacctgatg    360

ccaaatgaga atatccccga gttggcggct gagctggtgc agctgggctt cattagtgag    420

gctgaccaga gccggttgac ttctctgcta gaagagactt gaacaagttc aattttgcca    480

ggaacagtac cctcaactca gccgctgtca ccgtctcctc ttagagctca ctcgggccag    540

gccctgatct gcgctgtggc tgtcctggac gtgctgcacc ctctgtcctt ccccccagtc    600

agtattacct gtgaagccct tccctccttt attattcagg anggctgggg gggctccttg    660

nttctaacc                                                            669
```

-continued

<210> SEQ ID NO 24
<211> LENGTH: 442
<212> TYPE: DNA
<213> ORGANISM: Homo sapiens

<400> SEQUENCE: 24
actagtacca tcttgacaga ggatacatgc tcccaaaacg tttgttacca cacttaaaaa 60
tcactgccat cattaagcat cagtttcaaa attatagcca ttcatgattt actttttcca 120
gatgactatc attattctag tcctttgaat ttgtaagggg aaaaaaaaca aaaacaaaaa 180
cttacgatgc acttttctcc agcacatcag atttcaaatt gaaaattaaa gacatgctat 240
ggtaatgcac ttgctagtac tacacacttt ggtacaacaa aaaacagagg caagaaacaa 300
cggaaagaga aaagccttcc tttgttggcc cttaaactga gtcaagatct gaaatgtaga 360
gatgatctct gacgatacct gtatgttctt attgtgtaaa taaaattgct ggtatgaaat 420
gacctaaaaa aaaaaaaaga aa 442

<210> SEQ ID NO 25
<211> LENGTH: 656
<212> TYPE: DNA
<213> ORGANISM: Homo sapiens
<220> FEATURE:
<221> NAME/KEY: misc_feature
<222> LOCATION: 330, 342, 418, 548, 579, 608
<223> OTHER INFORMATION: n = A,T,C or G

<400> SEQUENCE: 25
tgcaagtacc acacactgtt tgaattttgc acaaaaagtg actgtaggat caggtgatag 60
ccccggaatg tacagtgtct tggtgcacca agatgccttc taaaggctga cataccttgg 120
accctaatgg ggcagagagt atagccctag cccagtggtg acatgaccac tccctttggg 180
aggcctgagg tagaggggag tggtatgtgt tttctcagtg gaagcagcac atgagtgggt 240
gacaggatgt tagataaagg ctctagttag ggtgtcattg tcatttgaga gactgacaca 300
ctcctagcag ctggtaaagg ggtgctggan gccatggagg anctctagaa acattagcat 360
gggctgatct gattacttcc tggcatcccg ctcactttta tgggaagtct tattagangg 420
atgggacagt tttccatatc cttgctgtgg agctctggaa cactctctaa atttccctct 480
attaaaaatc actgccctaa ctacacttcc tccttgaagg aatagaaatg gaactttctc 540
tgacatantt cttggcatgg ggagccagcc acaaatgana atctgaacgt gtccaggttt 600
ctcctganac tcatctacat agaattggtt aaaccctccc ttggaataag gaaaaa 656

<210> SEQ ID NO 26
<211> LENGTH: 434
<212> TYPE: DNA
<213> ORGANISM: Homo sapiens
<220> FEATURE:
<221> NAME/KEY: misc_feature
<222> LOCATION: 395
<223> OTHER INFORMATION: n = A,T,C or G

<400> SEQUENCE: 26
actagttcag actgccacgc caaccccaga aaatacccca catgccagaa aagtgaagtc 60
ctaggtgttt ccatctatgt ttcaatctgt ccatctacca ggcctcgcga taaaaacaaa 120
acaaaaaaac gctgccaggt tttagaagca gttctggtct caaaaccatc aggatcctgc 180
caccagggtt cttttgaaat agtaccacat gtaaaaggga atttggcttt cacttcatct 240

-continued

```
aataactgaa ttgtcaggct ttgattgata attgtagaaa taagtagcct tctgttgtgg    300

gaataagtta taatcagtat tcatctcttt gttttttgtc actcttttct ctctaattgt    360

gtcatttgta ctgtttgaaa aatatttctt ctatnaaatt aaactaacct gccttaaaaa    420

aaaaaaaaaa aaaa                                                      434


<210> SEQ ID NO 27
<211> LENGTH: 654
<212> TYPE: DNA
<213> ORGANISM: Homo sapiens
<220> FEATURE:
<221> NAME/KEY: misc_feature
<222> LOCATION: 505, 533, 563, 592, 613, 635, 638
<223> OTHER INFORMATION: n = A,T,C or G

<400> SEQUENCE: 27

actagtccaa cacagtcaga aacattgttt tgaatcctct gtaaaccaag gcattaatct     60

taataaacca ggatccattt aggtaccact tgatataaaa aggatatcca taatgaatat    120

tttatactgc atcctttaca ttagccacta aatacgttat tgcttgatga agacctttca    180

cagaatccta tggattgcag catttcactt ggctacttca tacccatgcc ttaaagaggg    240

gcagtttctc aaaagcagaa acatgccgcc agttctcaag ttttcctcct aactccattt    300

gaatgtaagg gcagctggcc cccaatgtgg ggaggtccga acattttctg aattcccatt    360

ttcttgttcg cggctaaatg acagtttctg tcattactta gattccgatc tttcccaaag    420

gtgttgattt acaaagaggc cagctaatag cagaaatcat gaccctgaaa gagagatgaa    480

attcaagctg tgagccaggc agganctcag tatggcaaag gtcttgagaa tcngccattt    540

ggtacaaaaa aaattttaaa gcntttatgt tataccatgg aaccatagaa anggcaaggg    600

aattgttaag aanaatttta agtgtccaga cccanaanga aaaaaaaaaa aaaa          654


<210> SEQ ID NO 28
<211> LENGTH: 670
<212> TYPE: DNA
<213> ORGANISM: Homo sapiens
<220> FEATURE:
<221> NAME/KEY: misc_feature
<222> LOCATION: 101, 226, 274, 330, 385, 392, 397, 402, 452, 473, 476,
      532, 534, 538, 550, 583, 595, 604, 613, 622, 643, 669
<223> OTHER INFORMATION: n = A,T,C or G

<400> SEQUENCE: 28

cgtgtgcaca tactgggagg atttccacag ctgcacggtc acagccctta cggattgcca     60

ggaaggggcg aaagatatgt gggataaact gagaaaagaa nccaaaaacc tcaacatcca    120

aggcagctta ttcgaactct gcggcagcgg caacggggcg gcggggtccc tgctcccggc    180

gttcccggtg ctcctggtgt ctctctcggc agctttagcg acctgncttt ccttctgagc    240

gtggggccag ctccccccgc ggcgcccacc cacnctcact ccatgctccc ggaaatcgag    300

aggaagatca ttagttcttt ggggacgttn gtgattctct gtgatgctga aaaacactca    360

tatagggaat gtgggaaatc ctganctctt tnttatntcg tntgatttct tgtgttttat    420

ttgccaaaat gttaccaatc agtgaccaac cnagcacagc caaaaatcgg acntcngctt    480

tagtccgtct tcacacacag aataagaaaa cggcaaaccc accccacttt tnantttnat    540

tattactaan tttttctgt tgggcaaaag aatctcagga acngccctgg ggccnccgta    600

ctanagttaa ccnagctagt tncatgaaaa atgatgggct ccncctcaat gggaaagcca    660

agaaaaagnc                                                           670
```

-continued

<210> SEQ ID NO 29
<211> LENGTH: 551
<212> TYPE: DNA
<213> ORGANISM: Homo sapiens
<220> FEATURE:
<221> NAME/KEY: misc_feature
<222> LOCATION: 336, 474, 504, 511, 522, 523, 524, 540, 547
<223> OTHER INFORMATION: n = A,T,C or G

<400> SEQUENCE: 29
actagtcctc cacagcctgt gaatcccccct agacctttca agcatagtga gcggagaaga 60
agatctcagc gtttagccac cttacccatg cctgatgatt ctgtagaaaa ggtttcttct 120
ccctctccag ccactgatgg gaaagtattc tccatcagtt ctcaaaatca gcaagaatct 180
tcagtaccag aggtgcctga tgttgcacat ttgccacttg agaagctggg accctgtctc 240
cctcttgact taagtcgtgg ttcagaagtt acagcaccgg tagcctcaga ttcctcttac 300
cgtaatgaat gtcccagggc agaaaaagag gatacncaga tgcttccaaa tccttcttcc 360
aaagcaatag ctgatgggaa gaggagctcc agcagcagca ggaatatcga aaacagaaaa 420
aaaagtgaaa ttgggaagac aaaagctcaa cagcatttgg taaggagaaa aganaagatg 480
aggaaggaag agagaagaga gacnaagatc nctacggacc gnnncggaag aagaagaagn 540
aaaaaanaaa a 551

<210> SEQ ID NO 30
<211> LENGTH: 684
<212> TYPE: DNA
<213> ORGANISM: Homo sapiens
<220> FEATURE:
<221> NAME/KEY: misc_feature
<222> LOCATION: 545, 570, 606, 657, 684
<223> OTHER INFORMATION: n = A,T,C or G

<400> SEQUENCE: 30
actagttcta tctggaaaaa gcccgggttg gaagaagctg tggagagtgc gtgtgcaatg 60
cgagactcat ttcttggaag catccctggc aaaaatgcag ctgagtacaa ggttatcact 120
gtgatagaac ctggactgct ttttgagata atagagatgc tgcagtctga agagacttcc 180
agcacctctc agttgaatga attaatgatg gcttctgagt caactttact ggctcaggaa 240
ccacgagaga tgactgcaga tgtaatcgag cttaaaggga aattcctcat caacttagaa 300
ggtggtgata ttcgtgaaga gtcttcctat aaagtaattg tcatgccgac tacgaaagaa 360
aaatgccccc gttgttggaa gtatacagcg ggagtcttca gatacactgt gtcctcgatg 420
tgcagaagtt gtcagtggga aaatagtatt aacagctcac tcgagcaaga accctcctga 480
cagtactggg ctagaagttt ggatggatta tttacaatat aggaaagaaa gccaagaatt 540
aggtnatgag tggatgagta aatggtggan gatggggaat tcaaatcaga attatggaag 600
aagttnttcc tgttactata gaaaggaatt atgtttattt acatgcagaa aatatanatg 660
tgtggtgtgt accgtggatg gaan 684

<210> SEQ ID NO 31
<211> LENGTH: 654
<212> TYPE: DNA
<213> ORGANISM: Homo sapiens
<220> FEATURE:
<221> NAME/KEY: misc_feature
<222> LOCATION: 326, 582, 651
<223> OTHER INFORMATION: n = A,T,C or G

<400> SEQUENCE: 31

-continued

```
gcgcagaaaa ggaaccaata tttcagaaac aagcttaata ggaacagctg cctgtacatc     60

aacatcttct cagaatgacc cagaagttat catcgtggga gctggcgtgc ttggctctgc    120

tttggcagct gtgctttcca gagatggaag aaaggtgaca gtcattgaga gagacttaaa    180

agagcctgac agaatagttg gagaattcct gcagccgggt ggttatcatg ttctcaaaga    240

ccttggtctt ggagatacag tggaaggtct tgatgcccag gttgtaaatg gttacatgat    300

tcatgatcag ggaaagcaaa tcagangttc agattcctta ccctctgtca gaaaacaatc    360

aagtgcagag tggaagagct ttccatcacg gaagattcat catgagtctc cggaaagcag    420

ctatggcaga gcccaatgca aagtttattg aaggtgttgt gttacagtta ttagaggaag    480

atgatgttgt gatgggagtt cagtacaagg ataaagagac tgggagatat caaggaactc    540

catgctccac tgactgttgt tgcagatggg cttttctcca anttcaggaa aagcctggtc    600

tcaataaagt ttctgtatca ctcatttggt tggcttctta tgaagaatgc nccc          654
```

<210> SEQ ID NO 32
<211> LENGTH: 673
<212> TYPE: DNA
<213> ORGANISM: Homo sapiens
<220> FEATURE:
<221> NAME/KEY: misc_feature
<222> LOCATION: 376, 545, 627
<223> OTHER INFORMATION: n = A,T,C or G

<400> SEQUENCE: 32

```
actagtgaag aaaaagaaat tctgatacgg gacaaaaatg ctcttcaaaa catcattctt     60

tatcacctga caccaggagt tttcattgga aaaggatttg aacctggtgt tactaacatt    120

ttaaagacca cacaaggaag caaaatcttt ctgaaagaag taaatgatac acttctggtg    180

aatgaattga aatcaaaaga atctgacatc atgacaacaa atggtgtaat tcatgttgta    240

gataaactcc tctatccagc agacacacct gttggaaatg atcaactgct ggaaatactt    300

aataaattaa tcaaatacat ccaaattaag tttgttcgtg gtagcacctt caaagaaatc    360

cccgtgactg tctatnagcc aattattaaa aaatacacca aaatcattga tgggagtgcc    420

tgtgggaaat aactgaaaaa gagaccgaga agaacgaatc attacaggtc ctgaaataaa    480

atacctagga tttctactgg aggtggagaa acagaagaac tctgaagaaa ttgttacaag    540

aagangtccc aaggtcacca aattcattga aggtggtgat ggtctttatt tgaagatgaa    600

gaaattaaaa gacgcttcag ggagacnccc catgaaggaa ttgccagcca caaaaaaatt    660

cagggattag aaa                                                       673
```

<210> SEQ ID NO 33
<211> LENGTH: 673
<212> TYPE: DNA
<213> ORGANISM: Homo sapiens
<220> FEATURE:
<221> NAME/KEY: misc_feature
<222> LOCATION: 325, 419, 452, 532, 538, 542, 571, 600, 616, 651, 653,
672
<223> OTHER INFORMATION: n = A,T,C or G

<400> SEQUENCE: 33

```
actagttatt tactttcctc cgcttcagaa ggtttttcag actgagagcc taagcatact     60

ggatctgttg tttcttttgg gtctcacctc atcagtgtgc atagtggcag aaattataaa    120

gaaggttgaa aggagcaggg aaaagatcca gaagcatgtt agttcgacat catcatcttt    180

tcttgaagta tgatgcatat tgcattattt tatttgcaaa ctaggaattg cagtctgagg    240
```

-continued

```
atcatttaga agggcaagtt caagaggata tgaagatttg agaacttttt aactattcat    300

tgactaaaaa tgaacattaa tgttnaagac ttaagacttt aacctgctgg cagtcccaaa    360

tgaaattatg caactttgat atcatattcc ttgatttaaa ttgggctttt gtgattgant    420

gaaactttat aaagcatatg gtcagttatt tnattaaaaa ggcaaaacct gaaccacctt    480

ctgcacttaa agaagtctaa cagtacaaat acctatctat cttagatgga tntatttntt    540

tntattttta aatattgtac tatttatggt nggtggggct ttcttactaa tacacaaatn    600

aatttatcat ttcaanggca ttctatttgg gtttagaagt tgattccaag nantgcatat    660

ttcgctactg tnt                                                       673
```

```
<210> SEQ ID NO 34
<211> LENGTH: 684
<212> TYPE: DNA
<213> ORGANISM: Homo sapiens
<220> FEATURE:
<221> NAME/KEY: misc_feature
<222> LOCATION: 414, 472, 480, 490, 503, 507, 508, 513, 523, 574, 575,
      598, 659, 662, 675
<223> OTHER INFORMATION: n = A,T,C or G

<400> SEQUENCE: 34

actagtttat tcaagaaaag aacttactga ttcctctgtt cctaaagcaa gagtggcagg     60

tgatcagggc tggtgtagca tccggttcct ttagtgcagc taactgcatt tgtcactgat    120

gaccaaggag gaaatcacta agacatttga gaagcagtgg tatgaacgtt cttggacaag    180

ccacagttct gagccttaac cctgtagttt gcacacaaga acgagctcca cctccccttc    240

ttcaggagga atctgtgcgg atagattggc tggacttttc aatggttctg ggttgcaagt    300

gggcactgtt atggctgggt atggagcgga cagccccagg aatcagagcc tcagcccggc    360

tgcctggttg gaaggtacag gtgttcagca ccttcggaaa aagggcataa agtngtgggg    420

gacaattctc agtccaagaa gaatgcattg accattgctg gctatttgct tncctagtan    480

gaattggatn catttttgac cangatnntt ctnctatgct ttnttgcaat gaaatcaaat    540

cccgcattat ctacaagtgg tatgaagtcc tgcnnccccc agagaggctg ttcaggcnat    600

gtcttccaag ggcagggtgg gttacaccat tttacctccc ctctccccccc agattatgna    660

cncagaagga atttntttcc tccc                                           684
```

```
<210> SEQ ID NO 35
<211> LENGTH: 614
<212> TYPE: DNA
<213> ORGANISM: Homo sapiens
<220> FEATURE:
<221> NAME/KEY: misc_feature
<222> LOCATION: 17, 20, 152, 223, 267, 287, 304, 306, 316, 319, 321,
      355, 365, 382, 391, 407, 419, 428, 434, 464, 467, 477, 480, 495,
      499, 505, 515, 516, 522, 524, 527, 542, 547, 549, 567, 572,
      576, 578
<223> OTHER INFORMATION: n = A,T,C or G

<400> SEQUENCE: 35

actagtccaa cgcgttngcn aatattcccc tggtagccta cttccttacc cccgaatatt     60

ggtaagatcg agcaatggct tcaggacatg ggttctcttc tcctgtgatc attcaagtgc    120

tcactgcatg aagactggct tgtctcagtg tntcaacctc accagggctg tctcttggtc    180

cacacctcgc tccctgttag tgccgtatga cagcccccat canatgacct tggccaagtc    240

acggtttctc tgtggtcaat gttggtnggc tgattggtgg aaagtanggt ggaccaaagg    300
```

-continued aagncncgtg agcagncanc nccagttctg caccagcagc gcctccgtcc tactngggtg 360
ttccngtttc tcctggccct gngtgggcta nggcctgatt cgggaanatg cctttgcang 420 gaagggganga taantgggat ctaccaattg attctggcaa aacnatntct aagattnttn 480
tgctttatgt ggganacana tctanctctc atttnntgct gnanatnaca ccctactcgt 540
gntcgancnc gtcttcgatt ttcgganaca cnccantnaa tactggcgtt ctgttgttaa 600
aaaaaaaaaa aaaa 614

<210> SEQ ID NO 36
<211> LENGTH: 686
<212> TYPE: DNA
<213> ORGANISM: Homo sapiens
<220> FEATURE:
<221> NAME/KEY: misc_feature
<222> LOCATION: 222, 224, 237, 264, 285, 548, 551, 628, 643, 645, 665, 674
<223> OTHER INFORMATION: n = A,T,C or G

<400> SEQUENCE: 36
gtggctggcc cggttctccg cttctcccca tcccctactt tcctccctcc ctccctttcc 60
ctccctcgtc gactgttgct tgctggtcgc agactccctg acccctccct cacccctccc 120
taacctcggt gccaccggat tgcccttctt ttcctgttgc ccagcccagc cctagtgtca 180
gggcgggggc ctggagcagc ccgaggcact gcagcagaag ananaaaaga cacgacnaac 240
ctcagctcgc cagtccggtc gctngcttcc cgccgcatgg caatnagaca gacgccgctc 300
acctgctctg ggcacacgcg acccgtggtt gatttggcct tcagtggcat caccccttatg 360 ggtatttctt aatcagcgct tgcaaagatg gttaacctat gctacgccag ggagatacag 420
gagactggat tggaacattt ttggggtcta aaggtctgtt tggggtgcaa cactgaataa 480
ggatgccacc aaagcagcta cagcagctgc agatttcaca gcccaagtgt gggatgctgt 540 ctcaggganat naattgataa cctggctcat aacacattgt caagaatgtg gatttcccca 600
ggatattatt atttgtttac cgggggganag gataactgtt tcncntattt taattgaaca 660
aactnaaaca aaanctaagg aaatcc 686

<210> SEQ ID NO 37
<211> LENGTH: 681
<212> TYPE: DNA
<213> ORGANISM: Homo sapiens
<220> FEATURE:
<221> NAME/KEY: misc_feature
<222> LOCATION: 7, 10, 11, 19, 25, 32, 46, 53, 77, 93, 101, 103, 109, 115, 123, 128, 139, 157, 175, 180, 192, 193, 194, 212, 218, 226, 227, 233, 240, 241, 259, 260, 267, 289, 296, 297, 298, 312, 313, 314, 320, 325, 330, 337, 345, 346, 352, 353, 356
<223> OTHER INFORMATION: n = A,T,C or G
<221> NAME/KEY: misc_feature
<222> LOCATION: 382, 385, 400, 427, 481, 484, 485, 491, 505, 515, 533, 542, 544, 554, 557, 560, 561, 564, 575, 583, 589, 595, 607, 619, 628, 634, 641, 645, 658, 670
<223> OTHER INFORMATION: n = A,T,C or G

<400> SEQUENCE: 37
gagacanacn naacgtcang agaanaaaag angcatggaa cacaanccag gcncgatggc 60
caccttccca ccagcancca gcgcccccca gcngccccca ngnccggang accangactc 120
cancctgnat caatctganc tctattcctg gcccatncct acctcggagg tggangccgn 180
aaaggtcgca cnnncagaga agctgctgcc ancaccancc gccccnnccc tgncgggctn 240
nataggaaac tggtgaccnn gctgcanaat tcatacagga gcacgcgang ggcacnnnct 300

-continued

```
cacactgagt tnnngatgan gcctnaccan ggacctnccc cagcnnattg annacnggac    360

tgcggaggaa ggaagacccc gnacnggatc ctggccggcn tgccaccccc ccacccctag    420

gattatnccc cttgactgag tctctgaggg gctacccgaa cccgcctcca ttccctacca    480

natnntgctc natcgggact gacangctgg ggatnggagg ggctatcccc cancatcccc    540

tnanaccaac agcnacngan natnggggct ccccngggtc ggngcaacnc tcctncaccc    600

cggcgcnggc cttcggtgnt gtcctccntc aacnaattcc naaanggcgg gccccccngt    660

ggactcctcn ttgttccctc c                                              681


<210> SEQ ID NO 38
<211> LENGTH: 687
<212> TYPE: DNA
<213> ORGANISM: Homo sapiens
<220> FEATURE:
<221> NAME/KEY: misc_feature
<222> LOCATION: 3, 30, 132, 151, 203, 226, 228, 233, 252, 264, 279, 306,
      308, 320, 340, 347, 380, 407, 429, 437, 440, 445, 448, 491,
      559, 567, 586, 589, 593, 596, 603, 605, 606, 609, 626, 639,
      655, 674, 682
<223> OTHER INFORMATION: n = A,T,C or G

<400> SEQUENCE: 38

canaaaaaaa aaaacatggc cgaaaccagn aagctgcgcg atggcgccac ggcccctctt     60

ctcccggcct gtgtccggaa ggtttccctc cgaggcgccc cggctcccgc aagcggagga    120

gagggcggga cntgccgggg ccggagctca naggccctgg ggccgctctg ctctcccgcc    180

atcgcaaggg cggcgctaac ctnaggcctc cccgcaaagg tccccnangc ggnggcggcg    240

gggggctgtg anaaccgcaa aaanaacgct gggcgcgcng cgaacccgtc cacccccgcg    300

aaggananac ttccacagan gcagcgtttc cacagcccan agccacnttt ctagggtgat    360

gcaccccagt aagttcctgn cggggaagct caccgctgtc aaaaaanctc ttcgctccac    420

cggcgcacna aggggangan ggcangangc tgccgcccgc acaggtcatc tgatcacgtc    480

gcccgcccta ntctgctttt gtgaatctcc actttgttca accccacccg ccgttctctc    540

ctccttgcgc cttcctctna ccttaanaac cagcttcctc tacccnatng tanttnctct    600

gcncnngtng aaattaattc ggtccnccgg aacctcttnc ctgtggcaac tgctnaaaga    660

aactgctgtt ctgnttactg cngtccc                                        687


<210> SEQ ID NO 39
<211> LENGTH: 695
<212> TYPE: DNA
<213> ORGANISM: Homo sapiens
<220> FEATURE:
<221> NAME/KEY: misc_feature
<222> LOCATION: 300, 401, 423, 429, 431, 437, 443, 448, 454, 466, 492,
      515, 523, 524, 536, 538, 541, 552, 561, 566, 581, 583, 619, 635,
      636, 641, 649, 661, 694
<223> OTHER INFORMATION: n = A,T,C or G

<400> SEQUENCE: 39

actagtctgg cctacaatag tgtgattcat gtaggacttc tttcatcaat tcaaaacccc     60

tagaaaaacg tatacagatt atataagtag ggataagatt tctaacattt ctgggctctc    120

tgacccctgc gctagactgt ggaaagggag tattattata gtatacaaca ctgctgttgc    180

cttattagtt ataacatgat aggtgctgaa ttgtgattca caatttaaaa acactgtaat    240

ccaaactttt ttttttaact gtagatcatg catgtgaatg ttaatgttaa tttgttcaan    300

gttgttatgg gtagaaaaaa ccacatgcct taaaatttta aaaagcaggg cccaaactta    360
```

-continued

```
ttagtttaaa attaggggta tgtttccagt ttgttattaa ntggttatag ctctgtttag    420

aanaaatcna ngaacangat ttngaaantt aagntgacat tatttnccag tgacttgtta    480

atttgaaatc anacacggca ccttccgttt tggtnctatt ggnntttgaa tccaancngg    540

ntccaaatct tnttggaaac ngtccnttta actttttac nanatcttat ttttttattt    600

tggaatggcc ctatttaang ttaaaagggg ggggnnccac naccattcnt gaataaaact    660

naatatatat ccttggtccc ccaaaattta aggng                               695
```

<210> SEQ ID NO 40
<211> LENGTH: 674
<212> TYPE: DNA
<213> ORGANISM: Homo sapiens
<220> FEATURE:
<221> NAME/KEY: misc_feature
<222> LOCATION: 403, 428, 432, 507, 530, 543, 580, 583, 591, 604, 608,
621, 624, 626, 639, 672
<223> OTHER INFORMATION: n = A,T,C or G

<400> SEQUENCE: 40

```
actagtagtc agttgggagt ggttgctata ccttgacttc atttatatga atttccactt     60

tattaaataa tagaaaagaa aatcccggtg cttgcagtag agttatagga cattctatgc    120

ttacagaaaa tatagccatg attgaaatca aatagtaaag gctgttctgg ctttttatct    180

tcttagctca tcttaaataa gtagtacact tgggatgcag tgcgtctgaa gtgctaatca    240

gttgtaacaa tagcacaaat cgaacttagg atgtgtttct tctcttctgt gtttcgattt    300

tgatcaattc tttaattttg ggaacctata atacagtttt cctattcttg gagataaaaa    360

ttaaatggat cactgatatt taagtcattc tgcttctcat ctnaatattc catattctgt    420

attagganaa antacctccc agcacagccc cctctcaaac cccacccaaa accaagcatt    480

tggaatgagt ctcctttatt tccgaantgt ggatggtata acccatatcn ctccaatttc    540

tgnttgggtt gggtattaat ttgaactgtg catgaaaagn ggnaatcttt nctttgggtc    600

aaantttncc ggttaatttg nctngncaaa tccaatttnc tttaagggtg tctttataaa    660

atttgctatt cngg                                                      674
```

<210> SEQ ID NO 41
<211> LENGTH: 657
<212> TYPE: DNA
<213> ORGANISM: Homo sapiens
<220> FEATURE:
<221> NAME/KEY: misc_feature
<222> LOCATION: 243, 247, 251, 261, 267, 272, 298, 312, 315, 421, 432,
434, 501, 524, 569, 594, 607, 650
<223> OTHER INFORMATION: n = A,T,C or G

<400> SEQUENCE: 41

```
gaaacatgca agtaccacac actgtttgaa ttttgcacaa aaagtgactg tagggatcag     60

gtgatagccc cggaatgtac agtgtcttgg tgcaccaaga tgccttctaa aggctgacat    120

accttgggac cctaatgggg cagagagtat agccctagcc cagtggtgac atgaccactc    180

cctttgggag gctgaagtta aagggaatgg tatgtgtttt ctcatggaag cagcacatga    240

atnggtnaca ngatgttaaa ntaaggntct antttgggtg tcttgtcatt tgaaaaantg    300

acacactcct ancanctggt aaaggggtgc tggaagccat ggaagaactc taaaaacatt    360

agcatgggct gatctgatta cttcctggca tcccgctcac ttttatggga agtcttatta    420

naaggatggg anantttcc atatccttgc tgttggaact ctggaacact ctctaaattt    480

ccctctatta aaaatcactg nccttactac acttcctcct tganggaata gaaatggacc    540
```

-continued

```
tttctctgac ttagttcttg gcatgggganc cagcccaaat taaaatctga cttntccggt    600

ttctccngaa ctcacctact tgaattggta aaacctcctt tggaattagn aaaaacc       657


<210> SEQ ID NO 42
<211> LENGTH: 389
<212> TYPE: DNA
<213> ORGANISM: Homo sapiens
<220> FEATURE:
<221> NAME/KEY: misc_feature
<222> LOCATION: 179, 317, 320
<223> OTHER INFORMATION: n = A,T,C or G

<400> SEQUENCE: 42

actagtgctg aggaatgtaa acaagtttgc tgggccttgc gagacttcac caggttgttt     60

cgatagctca cactcctgca ctgtgcctgt cacccaggaa tgtctttttt aattagaaga    120

caggaagaaa acaaaaacca gactgtgtcc cacaatcaga aacctccgtt gtggcagang    180

ggccttcacc gccaccaggg tgtcccgcca gacagggaga gactccagcc ttctgaggcc    240

atcctgaaga attcctgttt gggggttgtg aaggaaaatc acccggattt aaaaagatgc    300

tgttgcctgc ccgcgtngtn gggaagggac tggtttcctg gtgaatttct taaaagaaaa    360

atattttaag ttaagaaaaa aaaaaaaaa                                      389


<210> SEQ ID NO 43
<211> LENGTH: 279
<212> TYPE: DNA
<213> ORGANISM: Homo sapiens

<400> SEQUENCE: 43

actagtgaca agctcctggt cttgagatgt cttctcgtta aggagatggg ccttttggag     60

gtaaaggata aaatgaatga gttctgtcat gattcactat tctagaactt gcatgacctt    120

tactgtgtta gctctttgaa tgttcttgaa attttagact ttctttgtaa acaaataata    180

tgtccttatc attgtataaa agctgttatg tgcaacagtg tggagatcct tgtctgattt    240

aataaaatac ttaaacactg aaaaaaaaaa aaaaaaaaa                           279


<210> SEQ ID NO 44
<211> LENGTH: 449
<212> TYPE: DNA
<213> ORGANISM: Homo sapiens
<220> FEATURE:
<221> NAME/KEY: misc_feature
<222> LOCATION: 245, 256, 264, 266, 273, 281, 323, 325, 337, 393
<223> OTHER INFORMATION: n = A,T,C or G

<400> SEQUENCE: 44

actagtagca tcttttctac aacgttaaaa ttgcagaagt agcttatcat taaaaaacaa     60

caacaacaac aataacaata aatcctaagt gtaaatcagt tattctaccc cctaccaagg    120

atatcagcct gttttttccc tttttctcc tgggaataat tgtgggcttc ttcccaaatt     180

tctacagcct ctttcctctt ctcatgcttg agcttccctg tttgcacgca tgcgttgtgc    240

aagantgggc tgtttngctt ggantncggt ccnagtggaa ncatgctttc ccttgttact    300

gttggaagaa actcaaacct tcnancccta ggtgttncca ttttgtcaag tcatcactgt    360

atttttgtac tggcattaac aaaaaaagaa atnaaatatt gttccattaa actttaataa    420

aactttaaaa gggaaaaaaa aaaaaaaaa                                      449


<210> SEQ ID NO 45
```

-continued

```
<211> LENGTH: 559
<212> TYPE: DNA
<213> ORGANISM: Homo sapiens
<220> FEATURE:
<221> NAME/KEY: misc_feature
<222> LOCATION: 263
<223> OTHER INFORMATION: n = A,T,C or G

<400> SEQUENCE: 45

actagtgtgg gggaatcacg gacacttaaa gtcaatctgc gaaataattc ttttattaca     60

cactcactga agtttttgag tcccagagag ccattctatg tcaaacattc caagtactct    120

ttgagagccc agcattacat caacatgccc gtgcagttca aaccgaagtc cgcaggcaaa    180

tttgaagctt tgcttgtcat tcaaacagat gaaggcaaga gtattgctat tcgactaatt    240

ggtgaagctc ttggaaaaaa ttnactagaa tactttttgt gttaagttaa ttacataagt    300

tgtattttgt taactttatc tttctacact acaattatgc ttttgtatat atattttgta    360

tgatggatat ctataattgt agattttgtt tttacaagct aatactgaag actcgactga    420

aatattatgt atctagccca tagtattgta cttaactttt acagggtgaa aaaaaaattc    480

tgtgtttgca ttgattatga tattctgaat aaatatggga atatatttta atgtgggtaa    540

aaaaaaaaaa aaaaaggaa                                                 559


<210> SEQ ID NO 46
<211> LENGTH: 731
<212> TYPE: DNA
<213> ORGANISM: Homo sapiens
<220> FEATURE:
<221> NAME/KEY: misc_feature
<222> LOCATION: 270, 467, 477, 502, 635, 660, 671, 688, 695, 697, 725
<223> OTHER INFORMATION: n = A,T,C or G

<400> SEQUENCE: 46

actagttcta gtaccatggc tgtcatagat gcaaccatta tattccattt agtttcttcc     60

tcaggttccc taacaattgt ttgaaactga atatatatgt ttatgtatgt gtgtgtgttc    120

actgtcatgt atatggtgta tatgggatgt gtgcagtttt cagttatata tatattcata    180

tatacatatg catatatatg tataatatac atatatacat gcatacactt gtataatata    240

catatatata cacatatatg cacacatatn atcactgagt tccaaagtga gtctttattt    300

ggggcaattg tattctctcc ctctgtctgc tcactgggcc tttgcaagac atagcaattg    360

cttgatttcc tttggataag agtcttatct tcggcactct tgactctagc cttaacttta    420

gatttctatt ccagaatacc tctcatatct atcttaaaac ctaaganggg taaagangtc    480

ataagattgt agtatgaaag antttgctta gttaaattat atctcaggaa actcattcat    540

ctacaaatta aattgtaaaa tgatggtttg ttgtatctga aaaaatgttt agaacaagaa    600

atgtaactgg gtacctgtta tatcaaagaa cctcnattta ttaagtctcc tcatagccan    660

atccttatat ngccctctct gacctgantt aatananact tgaataatga atagttaatt    720

taggnttggg c                                                         731


<210> SEQ ID NO 47
<211> LENGTH: 640
<212> TYPE: DNA
<213> ORGANISM: Homo sapiens
<220> FEATURE:
<221> NAME/KEY: misc_feature
<222> LOCATION: 5, 28, 106, 153, 158, 173, 176, 182, 189, 205, 210, 214,
      225, 226, 229, 237, 260, 263, 269, 277, 281, 282, 322, 337,
      338, 354, 365, 428, 441, 443, 456, 467, 476, 484, 503, 508,
      554, 567, 575, 579, 588, 601, 606, 609, 611, 621, 636
```

-continued

<223> OTHER INFORMATION: n = A,T,C or G

<400> SEQUENCE: 47
tgcgngccgg tttggccctt ctttgtanga cactttcatc cgccctgaaa tcttcccgat 60
cgttaataac tcctcaggtc cctgcctgca cagggttttt tcttantttg ttgcctaaca 120
gtacaccaaa tgtgacatcc tttcaccaat atngattnct tcataccaca tcntcnatgg 180
anacgactnc aacaattttt tgatnacccn aaanactggg ggctnnaana agtacantct 240
ggagcagcat ggacctgtcn gcnactaang gaacaanagt nntgaacatt tacacaacct 300
ttggtatgtc ttactgaaag anagaaacat gcttctnncc ctagaccacg aggncaaccg 360
caganattgc caatgccaag tccgagcggt tagatcaggt aatacattcc atggatgcat 420
tacatacntt gtccccgaaa nanaagatgc cctaanggct tcttcanact ggtccngaaa 480
acanctacac ctggtgcttg ganaacanac tctttggaag atcatctggc acaagttccc 540
cccagtgggt tttnccttgg cacctanctt accanatcna ttcggaancc attctttgcc 600
ntggcnttnt nttgggacca ntcttctcac aactgnaccc 640

<210> SEQ ID NO 48
<211> LENGTH: 257
<212> TYPE: DNA
<213> ORGANISM: Homo sapiens

<400> SEQUENCE: 48
actagtatat gaaaatgtaa atatcacttg tgtactcaaa caaaagttgg tcttaagctt 60
ccaccttgag cagccttgga aacctaacct gcctctttta gcataatcac attttctaaa 120
tgattttctt tgttcctgaa aaagtgattt gtattagttt tacatttgtt ttttggaaga 180
ttatatttgt atatgtatca tcataaaata tttaaataaa aagtatcttt agagtgaaaa 240
aaaaaaaaaa aaaaaaa 257

<210> SEQ ID NO 49
<211> LENGTH: 652
<212> TYPE: DNA
<213> ORGANISM: Homo sapiens
<220> FEATURE:
<221> NAME/KEY: misc_feature
<222> LOCATION: 410, 428, 496, 571, 647
<223> OTHER INFORMATION: n = A,T,C or G

<400> SEQUENCE: 49
actagttcag atgagtggct gctgaagggg ccccccttgtc attttcatta taacccaatt 60
tccacttatt tgaactctta agtcataaat gtataatgac ttatgaatta gcacagttaa 120
gttgacacta gaaactgccc atttctgtat tacactatca aataggaaac attggaaaga 180
tggggaaaaa aatcttattt taaaatggct tagaaagttt tcagattact ttgaaaattc 240
taaacttctt tctgtttcca aaacttgaaa atatgtagat ggactcatgc attaagactg 300
ttttcaaagc tttcctcaca tttttaaagt gtgattttcc ttttaatata catatttatt 360
ttctttaaag cagctatatc ccaacccatg actttggaga tatacctatn aaaccaatat 420
aacagcangg ttattgaagc agctttctca aatgttgctt cagatgtgca agttgcaaat 480
tttattgtat ttgtanaata caatttttgt tttaaactgt atttcaatct atttctccaa 540
gatgcttttc atatagagtg aaatatccca ngataactgc ttctgtgtcg tcgcatttga 600
cgcataactg cacaaatgaa cagtgtatac ctcttggttg tgcattnacc cc 652

-continued

<210> SEQ ID NO 50
<211> LENGTH: 650
<212> TYPE: DNA
<213> ORGANISM: Homo sapiens
<220> FEATURE:
<221> NAME/KEY: misc_feature
<222> LOCATION: 237, 270, 311, 443, 454, 488, 520, 535, 539, 556, 567, 594, 603, 634
<223> OTHER INFORMATION: n = A,T,C or G

<400> SEQUENCE: 50

```
ttgcgctttg attttttag ggcttgtgcc ctgtttcact tatagggtct agaatgcttg      60

tgttgagtaa aaaggagatg cccaatattc aaagctgcta aatgttctct ttgccataaa     120

gactccgtgt aactgtgtga acacttggga tttttctcct ctgtcccgag gtcgtcgtct     180

gctttctttt ttgggttctt tctagaagat tgagaaatgc atatgacagg ctgagancac     240

ctccccaaac acacaagctc tcagccacan gcagcttctc cacagcccca gcttcgcaca     300

ggctcctgga nggctgcctg ggggaggcag acatgggagt gccaaggtgg ccagatggtt     360

ccaggactac aatgtcttta tttttaactg tttgccactg ctgccctcac ccctgcccgg     420

ctctggagta ccgtctgccc canacaagtg ggantgaaat gggggtgggg gggaacactg     480

attcccantt agggggtgcc taactgaaca gtagggatan aaggtgtgaa cctgngaant     540

gcttttataa attatnttcc ttgttanatt tattttttaa tttaatctct gttnaactgc     600

ccngggaaaa ggggaaaaaa aaaaaaaaat tctntttaaa cacatgaaca                650
```

<210> SEQ ID NO 51
<211> LENGTH: 545
<212> TYPE: DNA
<213> ORGANISM: Homo sapiens
<220> FEATURE:
<221> NAME/KEY: misc_feature
<222> LOCATION: 66, 159, 195, 205, 214, 243, 278, 298, 306, 337, 366, 375, 382, 405, 446, 477, 492, 495, 503, 507, 508, 521, 537
<223> OTHER INFORMATION: n = A,T,C or G

<400> SEQUENCE: 51

```
tggcgtgcaa ccagggtagc tgaagtttgg gtctgggact ggagattggc cattaggcct      60

cctganattc cagctccctt ccaccaagcc cagtcttgct acgtggcaca gggcaaacct     120

gactcccttt gggcctcagt ttcccctccc cttcatgana tgaaaagaat actacttttt     180

cttgttggtc taacnttgct ggacncaaag tgtngtcatt attgttgtat tgggtgatgt     240

gtncaaaact gcagaagctc actgcctatg agaggaanta agagagatag tggatganag     300

ggacanaagg agtcattatt tggtatagat ccacccntcc caacctttct ctcctcagtc     360

cctgcncctc atgtntctgg tntggtgagt cctttgtgcc accanccatc atgctttgca     420

ttgctgccat cctgggaagg gggtgnatcg tctcacaact tgttgtcatc gtttganatg     480

catgctttct tnatnaaaca aanaaannaa tgtttgacag ngtttaaaat aaaaaanaaa     540

caaaa                                                                 545
```

<210> SEQ ID NO 52
<211> LENGTH: 678
<212> TYPE: DNA
<213> ORGANISM: Homo sapiens
<220> FEATURE:
<221> NAME/KEY: misc_feature
<222> LOCATION: 98, 119, 121, 131, 136, 139, 140, 142, 143, 163, 168, 172, 176, 184, 189, 190, 191, 200, 201, 205, 207, 221, 223, 229, 230, 237, 240, 241, 255, 264, 266, 267, 276, 280, 288, 289, 291, 297, 301, 306, 308, 314, 315, 326, 332, 335, 337
<223> OTHER INFORMATION: n = A,T,C or G -continued
<221> NAME/KEY: misc_feature
<222> LOCATION: 339, 341, 343, 344, 345, 347, 350, 355, 356, 358, 362, 363, 372, 379, 395, 397, 398, 400, 403, 412, 414, 421, 423, 431, 435, 438, 439, 450, 457, 463, 467, 471, 474, 480, 483, 484, 487, 490, 491, 492, 493, 499, 500, 504, 508, 518, 536
<223> OTHER INFORMATION: n = A,T,C or G
<221> NAME/KEY: misc_feature
<222> LOCATION: 538, 549, 551, 552, 554, 556, 557, 562, 563, 567, 571, 572, 576, 579, 590, 592, 595, 598, 606, 609, 613, 620, 622, 624, 626, 631, 634, 638, 641, 647, 654, 660, 661, 674
<223> OTHER INFORMATION: n = A,T,C or G

<400> SEQUENCE: 52

```
actagtagaa gaactttgcc gcttttgtgc ctctcacagg cgcctaaagt cattgccatg     60

ggaggaagac gatttggggg gggagggggg gggggcangg tccgtggggc tttccctant    120

ntatctccat ntccantgnn cnntgtcgcc tcttccctcg tcncattnga anttantccc    180

tggnccccnn nccctctccn ncctncncct cccccctccg ncncctccnn ctttttntan    240

ncttccccat ctccntcccc cctnanngtc ccaacnccgn cagcaatnnc ncacttnctc    300

nctccncncc tccnnccgtt cttctnttct cnacntntnc ncnnntnccn tgccnntnaa    360

annctctccc cnctgcaanc gattctctcc ctccncnnan ctntccactc cntncttctc    420

ncncgctcct nttcntcnnc ccacctctcn ccttcgnccc cantacnctc nccnccccttn   480

cgnntcnttn nnntcctcnn accnccccncc tcccttcncc cctcttctcc ccggtntntc   540

tctctcccnc nncncnncct cnncccntcc nngcgnccnt ttccgccccn cnccnccntt    600

ccttcntcnc cantccatcn cntntnccat nctncctncc nctcacnccc gctncccccn    660

ntctctttca cacngtcc                                                  678
```

<210> SEQ ID NO 53
<211> LENGTH: 502
<212> TYPE: DNA
<213> ORGANISM: Homo sapiens
<220> FEATURE:
<221> NAME/KEY: misc_feature
<222> LOCATION: 139, 146, 215, 217, 257, 263, 289, 386, 420, 452, 457, 461, 466, 482, 486
<223> OTHER INFORMATION: n = A,T,C or G

<400> SEQUENCE: 53

```
tgaagatcct ggtgtcgcca tgggccgccg ccccgcccgt tgttaccggt attgtaagaa     60

caagccgtac ccaaagtctc gcttctgccg aggtgtccct gatgccaaaa ttcgcatttt    120

tgacctgggg cggaaaaang caaaantgga tgagtctccg ctttgtggcc acatggtgtc    180

agatcaatat gagcagctgt cctctgaagc cctgnangct gcccgaattt gtgccaataa    240

gtacatggta aaaagtngtg gcnaagatgc ttccatatcc gggtgcggnt ccacccccttc   300

cacgtcatcc gcatcaacaa gatgttgtcc tgtgctgggg ctgacaggct cccaacaggc    360

atgcgaagtg cctttggaaa acccanggca ctgtggccag ggttcacatt gggccaattn    420

atcatgttca tccgcaccaa ctgcagaaca angaacntgt naattnaagc cctgcccagg    480

gncaanttca aatttcccgg cc                                             502
```

<210> SEQ ID NO 54
<211> LENGTH: 494
<212> TYPE: DNA
<213> ORGANISM: Homo sapiens
<220> FEATURE:
<221> NAME/KEY: misc_feature
<222> LOCATION: 431, 442, 445
<223> OTHER INFORMATION: n = A,T,C or G -continued

<400> SEQUENCE: 54

```
actagtccaa gaaaaatatg cttaatgtat attacaaagg ctttgtatat gttaacctgt     60

tttaatgcca aaagtttgct ttgtccacaa tttccttaag acctcttcag aaagggattt    120

gtttgcctta atgaatactg ttgggaaaaa acacagtata atgagtgaaa agggcagaag    180

caagaaattt ctacatctta gcgactccaa gaagaatgag tatccacatt tagatggcac    240

attatgagga ctttaatctt tccttaaaca caataatgtt ttcttttttc ttttattcac    300

atgatttcta agtatatttt tcatgcagga cagtttttca accttgatgt acagtgactg    360

tgttaaattt ttctttcagt ggcaacctct ataatcttta aaatatggtg agcatcttgt    420

ctgttttgaa ngggatatga cnatnaatct atcagatggg aaatcctgtt tccaagttag    480

aaaaaaaaaa aaaa                                                      494
```

<210> SEQ ID NO 55
<211> LENGTH: 606
<212> TYPE: DNA
<213> ORGANISM: Homo sapiens
<220> FEATURE:
<221> NAME/KEY: misc_feature
<222> LOCATION: 375, 395, 511, 542, 559, 569, 578, 581
<223> OTHER INFORMATION: n = A,T,C or G

<400> SEQUENCE: 55

```
actagtaaaa agcagcattg ccaaataatc cctaattttc cactaaaaat ataatgaaat     60

gatgttaagc tttttgaaaa gtttaggtta aacctactgt tgttagatta atgtatttgt    120

tgcttccctt tatctggaat gtggcattag ctttttttatt ttaaccctct ttaattctta    180

ttcaattcca tgacttaagg ttggagagct aaacactggg atttttggat aacagactga    240

cagttttgca taattataat cggcattgta catagaaagg atatggctac cttttgttaa    300

atctgcactt tctaaatatc aaaaaaggga aatgaagtat aaatcaattt ttgtataatc    360

tgtttgaaac atganttttta tttgcttaat attanggctt tgccctttttc tgttagtctc    420

ttgggatcct gtgtaaaact gttctcatta aacaccaaac agttaagtcc attctctggt    480

actagctaca aattccgttt catattctac ntaacaattt aaattaactg aaatatttct    540

anatggtcta cttctgtcnt ataaaaacna aacttgantt nccaaaaaaa aaaaaaaaaa    600

aaaaaa                                                               606
```

<210> SEQ ID NO 56
<211> LENGTH: 183
<212> TYPE: DNA
<213> ORGANISM: Homo sapiens

<400> SEQUENCE: 56

```
actagtatat ttaaacttac aggcttattt gtaatgtaaa ccaccatttt aatgtactgt     60

aattaacatg gttataatac gtacaatcct tccctcatcc catcacacaa cttttttttgt   120

gtgtgataaa ctgattttgg tttgcaataa aaccttgaaa aataaaaaaa aaaaaaaaaa    180

aaa                                                                  183
```

<210> SEQ ID NO 57
<211> LENGTH: 622
<212> TYPE: DNA
<213> ORGANISM: Homo sapiens
<220> FEATURE:
<221> NAME/KEY: misc_feature
<222> LOCATION: 358, 368, 412, 414, 425, 430, 453, 455, 469, 475, 495,
499, 529, 540, 564, 575, 590

-continued

<223> OTHER INFORMATION: n = A,T,C or G

<400> SEQUENCE: 57
actagtcact actgtcttct ccttgtagct aatcaatcaa tattcttccc ttgcctgtgg 60
gcagtggaga gtgctgctgg gtgtacgctg cacctgccca ctgagttggg gaaagaggat 120
aatcagtgag cactgttctg ctcagagctc ctgatctacc ccacccccta ggatccagga 180
ctgggtcaaa gctgcatgaa accaggccct ggcagcaacc tgggaatggc tggaggtggg 240
agagaacctg acttctcttt ccctctccct cctccaacat tactggaact ctatcctgtt 300
agggatcttc tgagcttgtt tccctgctgg gtgggacaga agacaaagga gaagggangg 360
tctacaanaa gcagcccttc tttgtcctct ggggttaatg agcttgacct ananttcatg 420
gaganaccan aagcctctga tttttaattt ccntnaaatg tttgaagtnt atatntacat 480
atatatattt ctttnaatnt ttgagtcttt gatatgtctt aaaatccant ccctctgccn 540
gaaacctgaa ttaaaaccat gaanaaaaat gtttncctta aagatgttan taattaattg 600
aaacttgaaa aaaaaaaaaa aa 622

<210> SEQ ID NO 58
<211> LENGTH: 433
<212> TYPE: DNA
<213> ORGANISM: Homo sapiens

<400> SEQUENCE: 58
gaacaaattc tgattggtta tgtaccgtca aaagacttga agaaatttca tgattttgca 60
gtgtggaagc gttgaaaatt gaaagttact gcttttccac ttgctcatat agtaaaggga 120
tcctttcagc tgccagtgtt gaataatgta tcatccagag tgatgttatc tgtgacagtc 180
accagcttta agctgaacca ttttatgaat accaaataaa tagacctctt gtactgaaaa 240
catatttgtg actttaatcg tgctgcttgg atagaaatat ttttactggt tcttctgaat 300
tgacagtaaa cctgtccatt atgaatggcc tactgttcta ttatttgttt tgacttgaat 360
ttatccacca aagacttcat ttgtgtatca tcaataaagt tgtatgtttc aactgaaaaa 420
aaaaaaaaaa aaa 433

<210> SEQ ID NO 59
<211> LENGTH: 649
<212> TYPE: DNA
<213> ORGANISM: Homo sapiens
<220> FEATURE:
<221> NAME/KEY: misc_feature
<222> LOCATION: 22, 190, 217, 430, 433, 484, 544, 550, 577, 583, 594
<223> OTHER INFORMATION: n = A,T,C or G

<400> SEQUENCE: 59
actagttatt atctgacttt cnggttataa tcattctaat gagtgtgaag tagcctctgg 60
tgtcatttgg atttgcattt ctctgatgag tgatgctatc aagcaccttt gctggtgctg 120
ttggccatat gtgtatgttc cctggagaag tgtctgtgct gagccttggc ccacttttta 180
attaggcgtn tgtcttttta ttactgagtt gtaaganttc tttatatatt ctggattcta 240
gacccttatc agatacatgg tttgcaaata ttttctccca ttctgtgggt tgtgttttca 300
ctttatcgat aatgtcctta gacatataat aaatttgtat tttaaaagtg acttgatttg 360
ggctgtgcaa ggtgggctca cgcttgtaat cccagcactt tgggagactg aggtgggtgg 420
atcatatgan gangctagga gttcgaggtc agcctggcca gcatagcgaa aacttgtctc 480
tacnaaaaat acaaaaatta gtcaggcatg gtggtgcacg tctgtaatac cagcttctca 540

-continued

```
ggangctgan gcacaaggat cacttgaacc ccagaangaa gangttgcag tganctgaag    600

atcatgccag ggcaacaaaa atgagaactt gtttaaaaaa aaaaaaaaa               649


<210> SEQ ID NO 60
<211> LENGTH: 423
<212> TYPE: DNA
<213> ORGANISM: Homo sapiens
<220> FEATURE:
<221> NAME/KEY: misc_feature
<222> LOCATION: 209, 222, 277, 389, 398
<223> OTHER INFORMATION: n = A,T,C or G

<400> SEQUENCE: 60

actagttcag gccttccagt tcactgacaa acatggggaa gtgtgcccag ctggctggaa     60

acctggcagt gataccatca agcctgatgt ccaaaagagc aaagaatatt tctccaagca    120

gaagtgagcg ctgggctgtt ttagtgccag gctgcggtgg gcagccatga gaacaaaacc    180

tcttctgtat tttttttttc cattagtana acacaagact cngattcagc cgaattgtgg    240

tgtcttacaa ggcagggctt tcctacaggg ggtggganaaa acagcctttc ttcctttggt   300

aggaatggcc tgagttggcg ttgtgggcag gctactggtt tgtatgatgt attagtagag    360

caacccatta atcttttgta gtttgtatna aacttganct gagaccttaa acaaaaaaaa    420

aaa                                                                  423


<210> SEQ ID NO 61
<211> LENGTH: 423
<212> TYPE: DNA
<213> ORGANISM: Homo sapiens
<220> FEATURE:
<221> NAME/KEY: misc_feature
<222> LOCATION: 195, 285, 295, 329, 335, 340, 347, 367, 382, 383, 391,
      396, 418
<223> OTHER INFORMATION: n = A,T,C or G

<400> SEQUENCE: 61

cgggactgga atgtaaagtg aagttcggag ctctgagcac gggctcttcc cgccgggtcc     60

tccctcccca gaccccagag ggagaggccc accccgccca gccccgcccc agcccctgct    120

caggtctgag tatggctggg agtcgggggc cacaggcctc tagctgtgct gctcaagaag    180

actggatcag ggtanctaca agtggccggg ccttgccttt gggattctac cctgttccta    240

atttggtgtt ggggtgcggg gtccctggcc ccctttttcca cactncctcc ctccngacag   300

caacctccct tggggcaatt gggcctggnt ctccncccgn tgttgcnacc ctttgttggt    360

ttaaggnctt taaaaatgtt anntttttccc ntgccngggt taaaaaagga aaaaactnaa   420

aaa                                                                  423


<210> SEQ ID NO 62
<211> LENGTH: 683
<212> TYPE: DNA
<213> ORGANISM: Homo sapiens
<220> FEATURE:
<221> NAME/KEY: misc_feature
<222> LOCATION: 218, 291, 305, 411, 416, 441, 443, 453, 522, 523, 536,
      542, 547, 566, 588, 592, 595, 603, 621, 628, 630, 632, 644, 645,
      648, 655, 660, 672, 674, 676, 677, 683
<223> OTHER INFORMATION: n = A,T,C or G

<400> SEQUENCE: 62

gctggagagg ggtacggact ttcttggagt tgtcccaggt tggaatgaga ctgaactcaa     60

gaagagaccc taagagactg gggaatggtt cctgccttca ggaaagtgaa agacgcttag    120
```

-continued

```
gctgtcaaca cttaaaggaa gtccccttga agcccagagt ggacagacta gacccattga    180

tggggccact ggccatggtc cgtggacaag acattccngt gggccatggc acaccggggg    240

ggatcaaaat gtgtacttgt ggggtctcgc cccttgccaa aaccaaacca ntcccactcc    300

tgtcnttgga ctttcttccc attccctcct ccccaaatgc acttcccctc ctccctctgc    360

ccctcctgtg tttttggaat tctgtttccc tcaaaattgt taattttttta nttttngacc    420

atgaacttat gtttggggtc nangttcccc ttnccaatgc atactaatat attaatggtt    480

atttattttt gaaatatttt ttaatgaact tggaaaaaat tnntggaatt tccttncttc    540

cnttttnttt gggggggggtg gggggntggg ttaaaatttt tttggaancc cnatnggaaa    600

ttnttacttg gggcccccct naaaaaantn anttccaatt cttnnatngc ccctnttccn    660

ctaaaaaaaa ananannaaa aan                                             683
```

<210> SEQ ID NO 63
<211> LENGTH: 731
<212> TYPE: DNA
<213> ORGANISM: Homo sapiens
<220> FEATURE:
<221> NAME/KEY: misc_feature
<222> LOCATION: 237, 249, 263, 288, 312, 317, 323, 326, 337, 352, 362, 370, 377, 400, 411, 414, 434, 436, 446, 457, 473, 486, 497, 498, 502, 512, 531, 546, 554, 563, 565, 566, 588, 597, 608, 611, 613, 615, 627, 632, 640, 641, 644, 654, 660, 663, 665
<223> OTHER INFORMATION: n = A,T,C or G
<221> NAME/KEY: misc_feature
<222> LOCATION: 671, 678, 692, 697, 698, 699, 704, 705, 712, 714, 717, 718, 719, 723, 725, 730, 731
<223> OTHER INFORMATION: n = A,T,C or G

<400> SEQUENCE: 63

```
actagtcata aagggtgtgc gcgtcttcga cgtggcggtc ttggcgccac tgctgcgaga     60

cccggccctg gacctcaagg tcatccactt ggtgcgtgat ccccgcgcgg tggcgagttc    120

acggatccgc tcgcgccacg gcctcatccg tgagagccta caggtggtgc gcagccgaga    180

ccgcgagctc accgcatgcc cttcttggag gccgcgggcc acaagcttgg cgcccanaaa    240

gaaggcgtng ggggcccgca aantaccacg ctctgggcgc tatggaangt cctcttgcaa    300

taatattggt tnaaaanctg canaanagcc cctgcanccc cctgaactgg gntgcagggc    360

cncttacctn gtttggntgc ggttacaaag aacctgtttn ggaaaaccct nccnaaaacc    420

ttccgggaaa attntncaaa tttttnttgg ggaattnttg ggtaaacccc ccnaaaatgg    480

gaaacntttt tgccctnnaa antaaaccat tnggttccgg gggccccccc ncaaaaccct    540

tttttntttt tttntgcccc cantnncccc ccggggcccc ttttttttngg ggaaaanccc    600

ccccccctncc nanantttta aaagggnggg anaatttttn nttnccccccc gggnccccccn    660

ggngntaaaa nggtttcncc cccccgaggg gnggggnnnc ctcnnaaacc cntntcnnna    720

ccncnttttn n                                                          731
```

<210> SEQ ID NO 64
<211> LENGTH: 313
<212> TYPE: DNA
<213> ORGANISM: Homo sapiens
<220> FEATURE:
<221> NAME/KEY: misc_feature
<222> LOCATION: 240
<223> OTHER INFORMATION: n = A,T,C or G

<400> SEQUENCE: 64

```
actagttgtg caaaccacga ctgaagaaag acgaaaagtg ggaaataact tgcaacgtct     60
```

-continued

```
gttagagatg gttgctacac atgttgggtc tgtagagaaa catcttgagg agcagattgc    120

taaagttgat agagaatatg aagaatgcat gtcagaagat ctctcggaaa atattaaaga    180

gattagagat aagtatgaga agaaagctac tctaattaag tcttctgaag aatgaagatn    240

aaatgttgat catgtatata tatccatagt gaataaaatt gtctcagtaa agttgtaaaa    300

aaaaaaaaaa aaa                                                       313
```

```
<210> SEQ ID NO 65
<211> LENGTH: 420
<212> TYPE: DNA
<213> ORGANISM: Homo sapiens
<220> FEATURE:
<221> NAME/KEY: misc_feature
<222> LOCATION: 400, 402, 403, 404, 405, 406, 409, 411, 412, 414, 415,
      416
<223> OTHER INFORMATION: n = A,T,C or G

<400> SEQUENCE: 65

actagttccc tggcaggcaa gggcttccaa ctgaggcagt gcatgtgtgg cagagagagg     60

caggaagctg gcagtggcag cttctgtgtc tagggagggg tgtggctccc tccttccctg    120

tctgggaggt tggagggaag aatctaggcc ttagcttgcc ctcctgccac ccttcccctt    180

gtagatactg ccttaacact ccctcctctc tcagctgtgg ctgccaccca agccaggttt    240

ctccgtgctc actaatttat ttccaggaaa ggtgtgtgga agacatgagc cgtgtataat    300

atttgtttta acattttcat tgcaagtatt gaccatcatc cttggttgtg tatcgttgta    360

acacaaatta atgatattaa aaagcatcca aacaaagccn annnnnaana nnannngaaa    420
```

```
<210> SEQ ID NO 66
<211> LENGTH: 676
<212> TYPE: DNA
<213> ORGANISM: Homo sapiens
<220> FEATURE:
<221> NAME/KEY: misc_feature
<222> LOCATION: 328, 454, 505, 555, 586, 612, 636, 641
<223> OTHER INFORMATION: n = A,T,C or G

<400> SEQUENCE: 66

actagtttcc tatgatcatt aaactcattc tcagggttaa gaaaggaatg taaatttctg     60

cctcaatttg tacttcatca ataagttttt gaagagtgca gatttttagt caggtcttaa    120

aaataaactc acaaatctgg atgcatttct aaattctgca aatgtttcct ggggtgactt    180

aacaaggaat aatcccacaa tatacctagc tacctaatac atggagctgg ggctcaaccc    240

actgttttta aggatttgcg cttacttgtg gctgaggaaa aataagtagt tccgagggaa    300

gtagttttta aatgtgagct tatagatngg aaacagaata tcaacttaat tatggaaatt    360

gttagaaacc tgttctcttg ttatctgaat cttgattgca attactattg tactggatag    420

actccagccc attgcaaagt ctcagatatc ttanctgtgt agttgaattc cttggaaatt    480

ctttttaaga aaaaattgga gtttnaaaga aataaacccc tttgttaaat gaagcttggc    540

tttttggtga aaaanaatca tcccgcaggg cttattgttt aaaaanggaa ttttaagcct    600

ccctggaaaa anttgttaat taaatgggga aaatgntggg naaaaattat ccgttagggt    660

ttaaagggaa aactta                                                    676
```

```
<210> SEQ ID NO 67
<211> LENGTH: 620
<212> TYPE: DNA
<213> ORGANISM: Homo sapiens
```

-continued

<220> FEATURE:
<221> NAME/KEY: misc_feature
<222> LOCATION: 419, 493, 519, 568, 605, 610
<223> OTHER INFORMATION: n = A,T,C or G

<400> SEQUENCE: 67
caccattaaa gctgcttacc aagaacttcc ccagcatttt gacttccttg tttgatagct 60
gaattgtgag caggtgatag aagagccttt ctagttgaac atacagataa tttgctgaat 120
acattccatt taatgaaggg gttacatctg ttacgaagct actaagaagg agcaagagca 180
taggggaaaa aaatctgatc agaacgcatc aaactcacat gtgccccctc tactacaaac 240
agattgtagt gctgtggtgg tttattccgt tgtgcagaac ttgcaagctg agtcactaaa 300
cccaaagaga ggaaattata ggttagttaa acattgtaat cccaggaact aagtttaatt 360
cacttttgaa gtgttttgtt ttttattttt ggtttgtctg atttactttg ggggaaaang 420
ctaaaaaaaa agggatatca atctctaatt cagtgcccac taaaagttgt ccctaaaaag 480
tctttactgg aanttatggg actttttaag ctccaggtnt tttggtcctc caaattaacc 540
ttgcatgggc cccttaaaat tgttgaangg cattcctgcc tctaagtttg gggaaaattc 600
ccccnttttn aaaatttgga 620

<210> SEQ ID NO 68
<211> LENGTH: 551
<212> TYPE: DNA
<213> ORGANISM: Homo sapiens
<220> FEATURE:
<221> NAME/KEY: misc_feature
<222> LOCATION: 286, 464, 480, 501, 502, 518, 528, 533, 536, 537, 538,
539, 540, 541, 543, 544, 545, 547, 548, 549
<223> OTHER INFORMATION: n = A,T,C or G

<400> SEQUENCE: 68
actagtagct ggtacataat cactgaggag ctatttctta acatgctttt atagaccatg 60
ctaatgctag accagtattt aagggctaat ctcacacctc cttagctgta agagtctggc 120
ttagaacaga cctctctgtg caataacttg tggccactgg aaatccctgg gccggcattt 180
gtattggggt tgcaatgact cccaagggcc aaaagagtta aaggcacgac tgggatttct 240
tctgagactg tggtgaaact ccttccaagg ctgagggggt cagtangtgc tctgggaggg 300
actcggcacc actttgatat tcaacaagcc acttgaagcc caattataaa attgttattt 360
tacagctgat ggaactcaat ttgaaccttc aaaactttgt tagtttatcc tattatattg 420
ttaaacctaa ttacatttgt ctagcattgg atttggttcc tgtngcatat gttttttttcn 480 cctatgtgct cccctccccc nnatcttaat ttaaaccnca attttgcnat tcnccnnnnn 540
nannnannna a 551

<210> SEQ ID NO 69
<211> LENGTH: 396
<212> TYPE: DNA
<213> ORGANISM: Homo sapiens
<220> FEATURE:
<221> NAME/KEY: misc_feature
<222> LOCATION: 235, 310, 323, 381
<223> OTHER INFORMATION: n = A,T,C or G

<400> SEQUENCE: 69
cagaaatgga aagcagagtt ttcatttctg tttataaacg tctccaaaca aaaatggaaa 60
gcagagtttt cattaaatcc ttttaccttt tttttttctt ggtaatcccc tcaaataaca 120
gtatgtggga tattgaatgt taaagggata tttttttcta ttatttttat aattgtacaa 180

-continued

```
aattaagcaa atgttaaaag ttttatatgc tttattaatg ttttcaaaag gtatnataca    240

tgtgatacat tttttaagct tcagttgctt gtcttctggt actttctgtt atgggctttt    300

ggggagccan aaaccaatct acnatctctt tttgtttgcc aggacatgca ataaaattta    360

aaaaataaat aaaaactatt nagaaattga aaaaaa                              396
```

<210> SEQ ID NO 70
<211> LENGTH: 536
<212> TYPE: DNA
<213> ORGANISM: Homo sapiens
<220> FEATURE:
<221> NAME/KEY: misc_feature
<222> LOCATION: 388, 446, 455
<223> OTHER INFORMATION: n = A,T,C or G

<400> SEQUENCE: 70

```
actagtgcaa aagcaaatat aaacatcgaa aaggcgttcc tcacgttagc tgaagatatc     60

cttcgaaaga cccctgtaaa agagcccaac agtgaaaatg tagatatcag cagtggagga    120

ggcgtgacag gctggaagag caaatgctgc tgagcattct cctgttccat cagttgccat    180

ccactacccc gttttctctt cttgctgcaa aataaaccac tctgtccatt tttaactcta    240

aacagatatt tttgtttctc atcttaacta tccaagccac ctattttatt tgttctttca    300

tctgtgactg cttgctgact ttatcataat tttcttcaaa caaaaaaatg tatagaaaaa    360

tcatgtctgt gacttcattt ttaaatgnta cttgctcagc tcaactgcat ttcagttgtt    420

ttatagtcca gttcttatca acattnaaac ctatngcaat catttcaaat ctattctgca    480

aattgtataa gaataaaagt tagaatttaa caattaaaaa aaaaaaaaaa aaaaaa        536
```

<210> SEQ ID NO 71
<211> LENGTH: 865
<212> TYPE: DNA
<213> ORGANISM: Homo sapiens
<220> FEATURE:
<221> NAME/KEY: misc_feature
<222> LOCATION: 22, 35, 39, 56, 131, 138, 146, 183, 194, 197, 238, 269,
      277, 282, 297, 316, 331, 336, 340, 341, 346, 349, 370, 376, 381,
      382, 392, 396, 397, 401, 433, 444, 445, 454, 455, 469, 472,
      477, 480, 482, 489, 497, 499, 511, 522, 526, 527
<223> OTHER INFORMATION: n = A,T,C or G
<221> NAME/KEY: misc_feature
<222> LOCATION: 545, 553, 556, 567, 574, 580, 610, 613, 634, 638, 639,
      663, 672, 689, 693, 694, 701, 704, 713, 723, 729, 732, 743, 744,
      749, 761, 765, 767, 769, 772, 774, 780, 783, 788, 792, 803,
      810, 824, 840, 848
<223> OTHER INFORMATION: n = A,T,C or G

<400> SEQUENCE: 71

```
gacaaagcgt taggagaaga anagaggcag ggaanactnc ccaggcacga tggccncctt     60

cccaccagca accagcgccc cccaccagcc cccaggcccg gacgacgaag actccatcct    120

ggattaatct nacctctntc gcctgnccca ttcctacctc ggaggtggag gccggaaagg    180

tcncaccaag aganaanctg ctgccaacac caaccgcccc agccctggcg ggcacganag    240

gaaactggtg accaatctgc agaattctna gaggaanaag cnaggggccc cgcgctnaga    300

cagagctgga tatgangcca gaccatggac nctacncccn ncaatncana cgggactgcg    360

gaagatggan gacccncgac nngatcaggc cngctnncca ncccccacc cctatgaatt    420

attcccgctg aangaatctc tganngcctt ccannaaagc gcctccccnc cnaacgnaan    480

tncaacatng ggattanang ctgggaactg naaggggcaa ancctnnaat atccccagaa    540

acaanctctc ccnaanaaac tggggcncct catnggtggn accaactatt aactaaaccg    600
```

-continued

```
cacgccaagn aantataaaa gggggggcccc tccncggnng accccctttt gtcccttaat    660

ganggttatc cnccttgcgt accatggtnc ccnnttctgt ntgnatgttt ccnctcccct    720

ccncctatnt cnagccgaac tcnnatttnc ccgggggtgc natcnantng tncnccttttn    780

ttngttgncc cngccctttc cgncggaacn cgtttccccg ttantaacgg cacccggggn    840

aagggtgntt ggccccctcc ctccc                                            865
```

<210> SEQ ID NO 72
<211> LENGTH: 560
<212> TYPE: DNA
<213> ORGANISM: Homo sapiens
<220> FEATURE:
<221> NAME/KEY: misc_feature
<222> LOCATION: 83, 173, 183, 186, 209, 211, 215, 255, 321, 322, 323, 335, 344, 357, 361, 368, 394, 412, 415, 442, 455, 469, 472, 475, 487, 513, 522, 528, 531, 534, 546
<223> OTHER INFORMATION: n = A,T,C or G

<400> SEQUENCE: 72

```
cctggacttg tcttggttcc agaacctgac gacccggcga cggcgacgtc tcttttgact     60

aaaagacagt gtccagtgct ccngcctagg agtctacggg gaccgcctcc cgcgccgcca    120

ccatgcccaa cttctctggc aactggaaaa tcatccgatc ggaaaacttc gangaattgc    180

tcnaantgct gggggtgaat gtgatgctna ngaanattgc tgtggctgca gcgtccaagc    240

cagcagtgga gatcnaacag gagggagaca ctttctacat caaaacctcc accaccgtgc    300

gcaccacaaa gattaacttc nnngttgggg agganttga gganccaaact gtggatngga    360

ngcctgtnaa aacctggtga aatgggagaa tganaataaa atggtctgtg ancanaaact    420

cctgaaagga gaaggccccc anaactcctg gaccngaaaa actgacccnc cnatnggga    480

actgatnctt gaaccctgaa cgggcgggat ganccttttt tnttgccncc naangggttc    540

tttccntttc cccaaaaaaa                                                   560
```

<210> SEQ ID NO 73
<211> LENGTH: 379
<212> TYPE: DNA
<213> ORGANISM: Homo sapiens
<220> FEATURE:
<221> NAME/KEY: misc_feature
<222> LOCATION: 8, 17, 18, 21, 26, 29, 30, 32, 53, 56, 67, 71, 81, 102, 104, 111, 112, 114, 119, 122, 124, 125, 134, 144, 146, 189, 190, 214, 215, 219, 220, 235, 237, 246, 280, 288, 302, 310, 313, 319, 322, 343, 353, 354
<223> OTHER INFORMATION: n = A,T,C or G

<400> SEQUENCE: 73

```
ctggggancc ggcggtnngc nccatntcnn gncgcgaagg tggcaataaa aanccnctga     60

aaccgcncaa naaacatgcc naagatatgg acgaggaaga tngngctttc nngnacaanc    120

gnanngagga acanaacaaa ctcnangagc tctcaagcta atgccgcggg gaaggggccc    180

ttggccacnn gtggaattaa gaaatctggc aaanngtann tgttccttgt gcctnangag    240

ataagngacc ctttatttca tctgtattta aacctctctn ttccctgnca taacttcttt    300

tnccacgtan agntggaant anttgttgtc ttggactgtt gtncatttta gannaaactt    360

ttgttcaaaa aaaaaataa                                                    379
```

<210> SEQ ID NO 74
<211> LENGTH: 437
<212> TYPE: DNA
<213> ORGANISM: Homo sapiens -continued
<220> FEATURE:
<221> NAME/KEY: misc_feature
<222> LOCATION: 145, 355
<223> OTHER INFORMATION: n = A,T,C or G

<400> SEQUENCE: 74
actagttcag actgccacgc caaccccaga aaatacccca catgccagaa aagtgaagtc 60
ctaggtgttt ccatctatgt ttcaatctgt ccatctacca ggcctcgcga taaaaacaaa 120
acaaaaaaac gctgccaggt tttanaagca gttctggtct caaaaccatc aggatcctgc 180
caccagggtt cttttgaaat agtaccacat gtaaaaggga atttggcttt cacttcatct 240
aatcactgaa ttgtcaggct ttgattgata attgtagaaa taagtagcct tctgttgtgg 300
gaataagtta taatcagtat tcatctcttt gttttttgtc actcttttct ctctnattgt 360
gtcatttgta ctgtttgaaa aatatttctt ctataaaatt aaactaacct gccttaaaaa 420
aaaaaaaaaa aaaaaaa 437

<210> SEQ ID NO 75
<211> LENGTH: 579
<212> TYPE: DNA
<213> ORGANISM: Homo sapiens
<220> FEATURE:
<221> NAME/KEY: misc_feature
<222> LOCATION: 440, 513, 539, 551
<223> OTHER INFORMATION: n = A,T,C or G

<400> SEQUENCE: 75
ctccgtcgcc gccaagatga tgtgcggggc gccctccgcc acgcagccgg ccaccgccga 60
gacccagcac atcgccgacc aggtgaggtc ccagcttgaa gagaaagaaa acaagaagtt 120
ccctgtgttt aaggccgtgt cattcaagag ccaggtggtc gcggggacaa actacttcat 180
caaggtgcac gtcggcgacg aggacttcgt acacctgcga gtgttccaat ctctccctca 240
tgaaaacaag cccttgacct tatctaacta ccagaccaac aaagccaagc atgatgagct 300
gacctatttc tgatcctgac tttggacaag gcccttcagc cagaagactg acaaagtcat 360
cctccgtcta ccagagcgtg cacttgtgat cctaaaataa gcttcatctc cgggctgtgc 420
ccttggggtg gaaggggcan gatctgcact gcttttgcat ttctcttcct aaatttcatt 480
gtgttgattc tttccttcca ataggtgatc ttnattactt tcagaatatt ttccaaatna 540
gatatatttt naaaatcctt aaaaaaaaaa aaaaaaaaa 579

<210> SEQ ID NO 76
<211> LENGTH: 666
<212> TYPE: DNA
<213> ORGANISM: Homo sapiens
<220> FEATURE:
<221> NAME/KEY: misc_feature
<222> LOCATION: 411, 470, 476, 491, 506, 527, 560, 570, 632, 636, 643,
650, 654, 658
<223> OTHER INFORMATION: n = A,T,C or G

<400> SEQUENCE: 76
gtttatccta tctctccaac cagattgtca gctccttgag ggcaagagcc acagtatatt 60
tccctgtttc ttccacagtg cctaataata ctgtggaact aggttttaat aattttttaa 120
ttgatgttgt tatgggcagg atggcaacca gaccattgtc tcagagcagg tgctggctct 180
ttcctggcta ctccatgttg gctagcctct ggtaacctct tacttattat cttcaggaca 240
ctcactacag ggaccaggga tgatgcaaca tccttgtctt tttatgacag gatgtttgct 300
cagcttctcc aacaataaaa agcacgtggt aaaacacttg cggatattct ggactgtttt 360

-continued

```
taaaaaatat acagtttacc gaaaatcata ttatcttaca atgaaaagga ntttatagat    420

cagccagtga acaacctttt cccaccatac aaaaattcct tttcccgaan gaaaanggct    480

ttctcaataa ncctcacttt cttaanatct tacaagatag ccccganatc ttatcgaaac    540

tcattttagg caaatatgan ttttattgtn cgttacttgt ttcaaaattt ggtattgtga    600

atatcaatta ccaccccccat ctcccatgaa anaaanggga aanggtgaan ttcntaancg    660

cttaaa                                                               666
```

<210> SEQ ID NO 77
<211> LENGTH: 396
<212> TYPE: DNA
<213> ORGANISM: Homo sapiens
<220> FEATURE:
<221> NAME/KEY: misc_feature
<222> LOCATION: 31, 54, 125, 128, 136, 163, 168, 198
<223> OTHER INFORMATION: n = A,T,C or G

<400> SEQUENCE: 77

```
ctgcagcccg ggggatccac taatctacca nggttatttg gcagctaatt ctanatttgg     60

atcattgccc aaagttgcac ttgctggtct cttgggattt ggccttggaa aggtatcata    120

catanganta tgccanaata aattccattt ttttgaaaat canctccntg gggctggttt    180

tggtccacag cataacangc actgcctcct tacctgtgag gaatgcaaaa taaagcatgg    240

attaagtgag aagggagact ctcagccttc agcttcctaa attctgtgtc tgtgactttc    300

gaagtttttt aaacctctga atttgtacac atttaaaatt tcaagtgtac tttaaaataa    360

aatacttcta atgggaacaa aaaaaaaaaa aaaaaa                              396
```

<210> SEQ ID NO 78
<211> LENGTH: 793
<212> TYPE: DNA
<213> ORGANISM: Homo sapiens
<220> FEATURE:
<221> NAME/KEY: misc_feature
<222> LOCATION: 309, 492, 563, 657, 660, 703, 708, 710, 711, 732, 740,
748, 758, 762, 765, 787
<223> OTHER INFORMATION: n = A,T,C or G

<400> SEQUENCE: 78

```
gcatcctagc cgccgactca cacaaggcag gtgggtgagg aaatccagag ttgccatgga     60

gaaaattcca gtgtcagcat tcttgctcct tgtggccctc tcctacactc tggccagaga    120

taccacagtc aaacctggag ccaaaaagga cacaaaggac tctcgaccca aactgcccca    180

gaccctctcc agaggttggg gtgaccaact catctggact cagacatatg aagaagctct    240

atataaatcc aagacaagca acaaaccctt gatgattatt catcacttgg atgagtgccc    300

acacagtcna gctttaaaga aagtgtttgc tgaaaataaa gaaatccaga aattggcaga    360

gcagtttgtc ctcctcaatc tggtttatga aacaactgac aaacaccttt ctcctgatgg    420

ccagtatgtc ccaggattat gtttgttgac ccatctctga cagttgaagc cgatatcctg    480

ggaagatatt cnaaccgtct ctatgcttac aaactgcaga tacgctctgt tgcttgacac    540

atgaaaaagc tctcaagttg ctnaaaatga attgtaagaa aaaaaatctc cagccttctg    600

tctgtcggct tgaaaattga aaccagaaaa atgtgaaaaa tggctattgt ggaacanatn    660

gacacctgat taggttttgg ttatgttcac cactattttt aanaaaanan nttttaaaat    720

ttggttcaat tntctttttn aaacaatntg tttctacntt gnganctgat ttctaaaaaa    780

aataatnttt ggc                                                       793
```

<210> SEQ ID NO 79
<211> LENGTH: 456
<212> TYPE: DNA
<213> ORGANISM: Homo sapiens
<220> FEATURE:
<221> NAME/KEY: misc_feature
<222> LOCATION: 89, 195, 255, 263, 266, 286, 353, 384, 423, 425, 436, 441
<223> OTHER INFORMATION: n = A,T,C or G

<400> SEQUENCE: 79
actagtatgg ggtgggaggc cccacccttc tcccctaggc gctgttcttg ctccaaaggg 60
ctccgtggag agggactggc agagctgang ccacctgggg ctggggatcc cactcttctt 120
gcagctgttg agcgcaccta accactggtc atgcccccac ccctgctctc cgcacccgct 180
tcctcccgac cccangacca ggctacttct cccctcctct tgcctccctc ctgcccctgc 240
tgcctctgat cgtangaatt gangantgtc ccgccttgtg gctganaatg gacagtggca 300
ggggctggaa atgggtgtgt gtgtgtgtgt gtgtgtgtgt gtgtgtgtgt gcncccccc 360 tgcaagaccg agattgaggg aaancatgtc tgctgggtgt gaccatgttt cctctccata 420
aantncccct gtgacnctca naaaaaaaaa aaaaaa 456

<210> SEQ ID NO 80
<211> LENGTH: 284
<212> TYPE: DNA
<213> ORGANISM: Homo sapiens
<220> FEATURE:
<221> NAME/KEY: misc_feature
<222> LOCATION: 283
<223> OTHER INFORMATION: n = A,T,C or G

<400> SEQUENCE: 80
ctttgtacct ctagaaaaga taggtattgt gtcatgaaac ttgagtttaa attttatata 60
taaaactaaa agtaatgctc actttagcaa cacatactaa aattggaacc atactgagaa 120
gaatagcatg acctccgtgc aaacaggaca agcaaatttg tgatgtgttg attaaaaaga 180
aataaataaa tgtgtatatg tgtaacttgt atgtttatgt ggaatacaga ttgggaaata 240
aaatgtattt cttactgtga aaaaaaaaaa aaaaaaaaaa aana 284

<210> SEQ ID NO 81
<211> LENGTH: 671
<212> TYPE: DNA
<213> ORGANISM: Homo sapiens
<220> FEATURE:
<221> NAME/KEY: misc_feature
<222> LOCATION: 388, 505, 600, 603, 615, 642, 644, 660
<223> OTHER INFORMATION: n = A,T,C or G

<400> SEQUENCE: 81
gccaccaaca ttccaagcta ccctgggtac ctttgtgcag tagaagctag tgagcatgtg 60
agcaagcggt gtgcacacgg agactcatcg ttataattta ctatctgcca agagtagaaa 120
gaaaggctgg ggatatttgg gttggcttgg ttttgatttt ttgcttgttt gtttgttttg 180
tactaaaaca gtattatctt ttgaatatcg tagggacata agtatataca tgttatccaa 240
tcaagatggc tagaatggtg cctttctgag tgtctaaaac ttgacacccc tggtaaatct 300
ttcaacacac ttccactgcc tgcgtaatga agttttgatt catttttaac cactggaatt 360
tttcaatgcc gtcattttca gttagatnat tttgcacttt gagattaaaa tgccatgtct 420
atttgattag tcttattttt ttatttttac aggcttatca gtctcactgt tggctgtcat 480

-continued

```
tgtgacaaag tcaaataaac ccccnaggac aacacacagt atgggatcac atattgtttg    540

acattaagct ttggccaaaa aatgttgcat gtgttttacc tcgacttgct aaatcaatan    600

canaaaggct ggctnataat gttggtggtg aaataattaa tnantaacca aaaaaaaaan    660

aaaaaaaaaa a                                                         671


<210> SEQ ID NO 82
<211> LENGTH: 217
<212> TYPE: DNA
<213> ORGANISM: Homo sapiens
<220> FEATURE:
<221> NAME/KEY: misc_feature
<222> LOCATION: 35
<223> OTHER INFORMATION: n = A,T,C or G

<400> SEQUENCE: 82

ctgcagatgt ttcttgaatg ctttgtcaaa ttaanaaagt taaagtgcaa taatgtttga     60

agacaataag tggtggtgta tcttgtttct aataagataa actttttttgt ctttgcttta   120

tcttattagg gagttgtatg tcagtgtata aaacatactg tgtggtataa caggcttaat    180

aaattcttta aaaggaaaaa aaaaaaaaaa aaaaaaa                             217


<210> SEQ ID NO 83
<211> LENGTH: 460
<212> TYPE: DNA
<213> ORGANISM: Homo sapiens
<220> FEATURE:
<221> NAME/KEY: misc_feature
<222> LOCATION: 104, 118, 172, 401, 422, 423, 444, 449
<223> OTHER INFORMATION: n = A,T,C or G

<400> SEQUENCE: 83

cgcgagtggg agcaccagga tctcgggctc ggaacgagac tgcacggatt gttttaagaa     60

aatggcagac aaaccagaca tgggggaaat cgccagcttc gatnaggcca agctgaanaa    120

aacggagacg caggagaaga acaccctgcc gaccaaagag accattgagc angagaagcg    180

gagtgaaatt tcctaagatc ctggaggatt tcctaccccc gtcctcttcg agaccccagt    240

cgtgatgtgg aggaagagcc acctgcaaga tggacacgag ccacaagctg cactgtgaac    300

ctgggcactc cgcgccgatg ccaccggcct gtgggtctct gaagggaccc cccccaatcg    360

gactgccaaa ttctccggtt tgccccggga tattatacaa nattatttgt atgaataatg    420

annataaaac acacctcgtg gcancaaana aaaaaaaaaa                          460


<210> SEQ ID NO 84
<211> LENGTH: 323
<212> TYPE: DNA
<213> ORGANISM: Homo sapiens
<220> FEATURE:
<221> NAME/KEY: misc_feature
<222> LOCATION: 70, 138, 178, 197, 228, 242, 244, 287, 311
<223> OTHER INFORMATION: n = A,T,C or G

<400> SEQUENCE: 84

tggtggatct tggctctgtg gagctgctgg gacgggatct aaaagactat tctggaagct     60

gtggtccaan gcattttgct ggcttaacgg gtcccggaac aaaggacacc agctctctaa    120

aattgaagtt tacccganat aacaatcttt tgggcagaga tgcctatttt aacaaacncc    180

gtccctgcgc aacaacnaac aatctctggg aaataccggc catgaacntg ctgtctcaat    240

cnancatctc tctagctgac cgatcatatc gtcccagatt actacanatc ataataattg    300
```

-continued

```
atttcctgta naaaaaaaaa aaa                                            323


<210> SEQ ID NO 85
<211> LENGTH: 771
<212> TYPE: DNA
<213> ORGANISM: Homo sapiens
<220> FEATURE:
<221> NAME/KEY: misc_feature
<222> LOCATION: 63, 426, 471, 497, 521, 554, 583, 586, 606, 609, 615,
      652, 686, 691, 694, 695, 706, 713, 730, 732, 743, 751
<223> OTHER INFORMATION: n = A,T,C or G

<400> SEQUENCE: 85

aaactgggta ctcaacactg agcagatctg ttctttgagc taaaaaccat gtgctgtacc     60

aanagtttgc tcctggctgc tttgatgtca gtgctgctac tccacctctg cggcgaatca    120

gaagcaagca actttgactg ctgtcttgga tacacagacc gtattcttca tcctaaattt    180

attgtgggct tcacacggca gctggccaat gaaggctgtg acatcaatgc tatcatcttt    240

cacacaaaga aaaagttgtc tgtgtgcgca aatccaaaac agacttgggt gaaatatatt    300

gtgcgtctcc tcagtaaaaa agtcaagaac atgtaaaaac tgtggctttt ctggaatgga    360

attggacata gcccaagaac agaaagaact tgctggggtt ggaggtttca cttgcacatc    420

atgganggtt tagtgcttat cttatttgtg cctcctggac ttgtccaatt natgaagtta    480

atcatattgc atcatanttt gctttgttta acatcacatt naaattaaac tgtattttat    540

gttatttata gctntaggtt ttctgtgttt aactttttat acnaantttc ctaaactatt    600

ttggtntant gcaanttaaa aattatattt ggggggggaa taaatattgg antttctgca    660

gccacaagct ttttttaaaa aaccantaca nccnngttaa atggtnggtc ccnaatggtt    720

tttgcttttn antagaaaat ttnttagaac natttgaaaa aaaaaaaaaa a             771


<210> SEQ ID NO 86
<211> LENGTH: 628
<212> TYPE: DNA
<213> ORGANISM: Homo sapiens
<220> FEATURE:
<221> NAME/KEY: misc_feature
<222> LOCATION: 162, 249, 266, 348, 407, 427, 488, 518, 545, 566, 569,
      597, 598, 611, 617, 621, 624
<223> OTHER INFORMATION: n = A,T,C or G

<400> SEQUENCE: 86

actagtttgc tttacatttt tgaaaagtat tatttttgtc caagtgctta tcaactaaac     60

cttgtgttag gtaagaatgg aatttattaa gtgaatcagt gtgacccttc ttgtcataag    120

attatcttaa agctgaagcc aaaatatgct tcaaaagaaa angactttat tgttcattgt    180

agttcataca ttcaaagcat ctgaactgta gtttctatag caagccaatt acatccataa    240

gtggagaang aaatagatta atgtcnaagt atgattggtg gagggagcaa ggttgaagat    300

aatctggggt tgaaattttc tagttttcat tctgtacatt tttagttnga catcagattt    360

gaaatattaa tgtttacctt tcaatgtgtg gtatcagctg gactcantaa cacccctttc    420

ttccctnggg gatggggaat ggattattgg aaaatggaaa gaaaaaagta cttaaagcct    480

tcctttcnca gtttctggct cctaccctac tgatttancc agaataagaa aacattttat    540

catcntctgc tttattccca ttaatnaant tttgatgaat aaatctgctt ttatgcnnac    600

ccaaggaatt nagtggnttc ntcnttgt                                       628


<210> SEQ ID NO 87
<211> LENGTH: 518
```

-continued

<212> TYPE: DNA
<213> ORGANISM: Homo sapiens
<220> FEATURE:
<221> NAME/KEY: misc_feature
<222> LOCATION: 384, 421, 486
<223> OTHER INFORMATION: n = A,T,C or G

<400> SEQUENCE: 87

```
tttttattt tttttagaga gtagttcagc ttttatttat aaatttattg cctgttttat     60
tataacaaca ttatactgtt tatggtttaa tacatatggt tcaaaatgta taatacatca    120
agtagtacag ttttaaaatt ttatgcttaa aacaagtttt gtgtaaaaaa tgcagataca    180
ttttacatgg caaatcaatt tttaagtcat cctaaaaatt gatttttttt tgaaatttaa    240
aaacacattt aatttcaatt tctctcttat ataaccttta ttactatagc atggtttcca    300
ctacagttta acaatgcagc aaaattccca tttcacggta aattgggttt taagcggcaa    360
ggttaaaatg ctttgaggat cctnaatacc ctttgaactt caaatgaagg ttatggttgt    420
naatttaacc ctcatgccat aagcagaagc acaagtttag ctgcattttg ctctaaactg    480
taaaancgag ccccccgttg aaaaagcaaa agggaccc                            518
```

<210> SEQ ID NO 88
<211> LENGTH: 1844
<212> TYPE: DNA
<213> ORGANISM: Homo sapiens

<400> SEQUENCE: 88

```
gagacagtga atcctagtat caaaggattt ttggcctcag aaaaagttgt tgattatttt     60
tattttattt tatttttcga gactccgtct caaaaaaaaa aaaaaaaaaa agaatcacaa    120
ggtatttgct aaagcatttt gagctgcttg gaaaaaggga agtagttgca gtagagtttc    180
ttccatcttc ttggtgctgg gaagccatat atgtgtcttt tactcaagct aaggggtata    240
agcttatgtg ttgaatttgc tacatctata tttcacatat tctcacaata agagaatttt    300
gaaatagaaa tatcatagaa catttaagaa agtttagtat aaataatatt ttgtgtgttt    360
taatcccttt gaagggatct atccaaagaa aatattttac actgagctcc ttcctacacg    420
tctcagtaac agatcctgtg ttagtctttg aaaatagctc attttttaaa tgtcagtgag    480
tagatgtagc atacatatga tgtataatga cgtgtattat gttaacaatg tctgcagatt    540
ttgtaggaat acaaaacatg gccttttttta taagcaaaac gggccaatga ctagaataac    600
acatagggca atctgtgaat atgtattata agcagcattc cagaaaagta gttggtgaaa    660
taattttcaa gtcaaaaagg gatatggaaa gggaattatg agtaacctct attttttaag    720
ccttgctttt aaattaaacg ctacagccat ttaagccttg aggataataa agcttgagag    780
taataatgtt aggttagcaa aggtttagat gtatcacttc atgcatgcta ccatgatagt    840
aatgcagctc ttcgagtcat ttctggtcat tcaagatatt caccctttttg cccatagaaa    900
gcaccctacc tcacctgctt actgacattg tcttagctga tcacaagatc attatcagcc    960
tccattattc cttactgtat ataaaataca gagttttata ttttcctttc ttcgtttttc   1020
accatattca aaacctaaat ttgtttttgc agatggaatg caaagtaatc aagtgttcgt   1080
gctttcacct agaagggtgt ggtcctgaag gaaagaggtc cctaaatatc ccccaccctg   1140
ggtgctcctc cttccctggt accctgacta ccagaagtca ggtgctagag cagctggaga   1200
agtgcagcag cctgtgcttc cacagatggg ggtgctgctg caacaaggct ttcaatgtgc   1260
ccatcttagg gggagaagct agatcctgtg cagcagcctg gtaagtcctg aggaggttcc   1320
```

-continued

```
attgctcttc ctgctgctgt cctttgcttc tcaacggggc tcgctctaca gtctagagca   1380

catgcagcta acttgtgcct ctgcttatgc atgagggtta aattaacaac cataaccttc   1440

atttgaagtt caaaggtgta ttcaggatcc tcaaagcatt ttaaccttgc cgcttaaaac   1500

ccaatttacc gtgaaatggg aattttgctg cattgttaaa ctgtagtgga aaccatgcta   1560

tagtaataaa ggttatataa gagagaaatt gaaattaaat gtgtttttaa atttcaaaaa   1620

aaaatcaatc tttaggatga cttaaaaatt gatttgccat gtaaaatgta tctgcatttt   1680

ttacacaaaa cttgttttaa gcataaaatt ttaaaactgt actacttgat gtattataca   1740

ttttgaacca tatgtattaa accataaaca gtataatgtt gttataataa aacaggcaat   1800

aaatttataa ataaaagctg aaaaaaaaaa aaaaaaaaaa aaaa                    1844


<210> SEQ ID NO 89
<211> LENGTH: 523
<212> TYPE: DNA
<213> ORGANISM: Homo sapiens
<220> FEATURE:
<221> NAME/KEY: misc_feature
<222> LOCATION: 288, 352, 369, 398, 475, 511, 513
<223> OTHER INFORMATION: n = A,T,C or G

<400> SEQUENCE: 89

tttttttttt tttttttagt caatccacat ttattgatca cttattatgt accaggcact     60

gggataaaga tgactgttag tcactcacag taaggaagaa aactagcaaa taagacgatt    120

acaatatgat gtagaaaatg ctaagccaga gatatagaaa ggtcctattg ggtccttctg    180

tcaccttgtc tttccacatc cctacccttc acaggccttc cctccagctt cctgcccccg    240

ctccccactg cagatcccct gggattttgc ctagagctaa acgagganat gggccccctg    300

gccctggcat gacttgaacc caaccacaga ctgggaaagg gagcctttcg anagtggatc    360

actttgatna gaaaacacat agggaattga agagaaantc cccaaatggc cacccgtgct    420

ggtgctcaag aaaagtttgc agaatggata aatgaaggat caagggaatt aatanatgaa    480

taattgaatg gtggctcaat aagaatgact ncnttgaatg acc                      523


<210> SEQ ID NO 90
<211> LENGTH: 604
<212> TYPE: DNA
<213> ORGANISM: Homo sapiens
<220> FEATURE:
<221> NAME/KEY: misc_feature
<222> LOCATION: 563
<223> OTHER INFORMATION: n = A,T,C or G

<400> SEQUENCE: 90

ccagtgtggt ggaatgcaaa gattaccccg gaagctttcg agaagctggg attccctgca     60

gcaaaggaaa tagccaatat gtgtcgtttc tatgaaatga agccagaccg agatgtcaat    120

ctcacccacc aactaaatcc caaagtcaaa agcttcagcc agtttatctc agagaaccag    180

gggagccttc aagggcatgt agaaaatcag ctgttcagat aggcctctgc accacacagc    240

ctctttcctc tctgatcctt ttcctcttta cggcacaaca ttcatgtttg acagaacatg    300

ctggaatgca attgtttgca acaccgaagg atttcctgcg gtcgcctctt cagtaggaag    360

cactgcattg gtgataggac acggtaattt gattcacatt taacttgcta gttagtgata    420

aggggtggta cacctgtttg gtaaaatgag aagcctcgga aacttgggag cttctctcct    480

accactaatg gggagggcag attattactg ggatttctcc tggggtgaat taatttcaag    540

ccctaattgc tgaaattccc ctnggcaggc tccagttttc tcaactgcat tgcaaaattc    600
```

-continued

```
cccc                                                               604


<210> SEQ ID NO 91
<211> LENGTH: 858
<212> TYPE: DNA
<213> ORGANISM: Homo sapiens
<220> FEATURE:
<221> NAME/KEY: misc_feature
<222> LOCATION: 570, 591, 655, 664, 667, 683, 711, 759, 760, 765, 777,
      787, 792, 794, 801, 804, 809, 817, 820
<223> OTHER INFORMATION: n = A,T,C or G

<400> SEQUENCE: 91

tttttttttt ttttttttta tgattattat ttttttttatt gatctttaca tcctcagtgt     60

tggcagagtt tctgatgctt aataaacatt tgttctgatc agataagtgg aaaaaattgt    120

catttcctta ttcaagccat gcttttctgt gatattctga tcctagttga acatacagaa    180

ataaatgtct aaaacagcac ctcgattctc gtctataaca ggactaagtt cactgtgatc    240

ttaaataagc ttggctaaaa tgggacatga gtggaggtag tcacacttca gcgaagaaag    300

agaatctcct gtataatctc accaggagat tcaacgaatt ccaccacact ggactagtgg    360

atcccccggg ctgcaggaat tcgatatcaa gcttatcgat accgtcgacc tcgagggggg    420

gcccggtacc caattcgccc tatagtgagt cgtattacgc gcgctcactg gccgtcgttt    480

tacaacgtcg tgactgggaa aaccctggcg ttacccaact taatcgcctt gcagcacatc    540

cccctttcgc cagctggcgt aatagcgaan agcccgcacc gatcgccctt ncaacagttg    600

cgcagcctga atggcgaatg ggacgcgccc tgtagcggcg cattaaagcg cggcngggtg    660

tggnggntcc cccacgtgac cgntacactt ggcagcgcct tacgccggtc nttcgctttc    720

ttcccttcct ttctcgcacc gttcgccggg tttccccgnn agctnttaat cgggggnctc    780

cctttanggg tncnaattaa nggnttacng gaccttngan cccaaaaact ttgattaggg    840

ggaaggtccc cgaagggg                                                  858


<210> SEQ ID NO 92
<211> LENGTH: 585
<212> TYPE: DNA
<213> ORGANISM: Homo sapiens
<220> FEATURE:
<221> NAME/KEY: misc_feature
<222> LOCATION: 317, 319, 320, 321, 325, 327, 328, 330, 331, 332, 460,
      462, 483, 485, 487, 523, 538, 566, 584
<223> OTHER INFORMATION: n = A,T,C or G

<400> SEQUENCE: 92

gttgaatctc ctggtgagat tatacaggag attctctttc ttcgctgaag tgtgactacc     60

tccactcatg tcccatttta gccaagctta tttaagatca cagtgaactt agtcctgtta    120

tagacgagaa tcgaggtgct gttttagaca tttatttctg tatgttcaac taggatcaga    180

atatcacaga aaagcatggc ttgaataagg aaatgacaat tttttccact tatctgatca    240

gaacaaatgt ttattaagca tcagaaactc tgccaacact gaggatgtaa agatcaataa    300

aaaaaataat aatcatnann naaanannan nngaagggcg gccgccaccg cggtggagct    360

ccagcttttg ttccctttag tgagggttaa ttgcgcgctt ggcgttaatc atggtcatag    420

ctgtttcctg tgtgaaattg ttatccggct cacaattccn cncaacatac gagccgggaa    480

gcntnangtg taaaagcctg gggtgcctaa attgagtgag ctnactcaca ttaattgngt    540

tgcgctccac ttgcccgctt ttccantccg ggaaacctgt tcgnc                    585
```

-continued

<210> SEQ ID NO 93
<211> LENGTH: 567
<212> TYPE: DNA
<213> ORGANISM: Homo sapiens
<220> FEATURE:
<221> NAME/KEY: misc_feature
<222> LOCATION: 82, 158, 230, 232, 253, 266, 267, 268, 269, 270, 271, 272, 273, 274, 275, 276, 277, 278, 279, 280, 281, 282, 283, 284, 285, 286, 287, 295, 303, 307, 314, 349, 352, 354, 356, 366, 369, 379, 382, 386, 393, 404, 427, 428, 446, 450, 452
<223> OTHER INFORMATION: n = A,T,C or G
<221> NAME/KEY: misc_feature
<222> LOCATION: 453, 454, 459, 462, 480, 481, 483, 488, 493, 501, 509, 511, 512, 518, 520, 525, 526, 532, 541, 557
<223> OTHER INFORMATION: n = A,T,C or G

<400> SEQUENCE: 93
cggcagtgtt gctgtctgcg tgtccacctt ggaatctggc tgaactggct gggaggacca 60
agactgcggc tggggtgggc anggaaggga accgggggct gctgtgaagg atcttggaac 120
ttccctgtac ccaccttccc cttgcttcat gtttgtanag gaaccttgtg ccggccaagc 180
ccagtttcct tgtgtgatac actaatgtat ttgctttttt tgggaaatan anaaaaatca 240
attaaattgc tantgtttct ttgaannnnn nnnnnnnnnn nnnnnnnggg ggggncgccc 300
ccncggngga aacncccccct tttgttccct ttaattgaaa ggttaattng cncncntggc 360
gttaanccnt gggccaaanc tngttncccg tgntgaaatt gttnatcccc tcccaaattc 420
ccccccnncc ttccaaaccc ggaaancctn annntgttna ancccggggg gttgcctaan 480
ngnaattnaa ccnaaccccc ntttaaatng nntttgcncn ccacnngccc cnctttccca 540
nttcggggaa aaccctntcc gtgccca 567

<210> SEQ ID NO 94
<211> LENGTH: 620
<212> TYPE: DNA
<213> ORGANISM: Homo sapiens
<220> FEATURE:
<221> NAME/KEY: misc_feature
<222> LOCATION: 169, 171, 222, 472, 528, 559, 599
<223> OTHER INFORMATION: n = A,T,C or G

<400> SEQUENCE: 94
actagtcaaa aatgctaaaa taatttggga gaaaatattt tttaagtagt gttatagttt 60
catgtttatc ttttattatg ttttgtgaag ttgtgtcttt tcactaatta cctatactat 120
gccaatattt ccttatatct atccataaca tttatactac atttgtaana naatatgcac 180
gtgaaactta acactttata aggtaaaaat gaggtttcca anatttaata atctgatcaa 240
gttcttgtta tttccaaata gaatggactt ggtctgttaa gggctaagga gaagaggaag 300
ataaggttaa aagttgttaa tgaccaaaca ttctaaaaga aatgcaaaaa aaaagtttat 360
tttcaagcct tcgaactatt taaggaaagc aaaatcattt cctaaatgca tatcatttgt 420
gagaatttct cattaatatc ctgaatcatt catttcacta aggctcatgt tnactccgat 480
atgtctctaa gaaagtacta tttcatggtc caaacctggt tgccatantt gggtaaaggc 540
tttcccttaa gtgtgaaant atttaaaatg aaattttcct ctttttaaaa attctttana 600
agggttaagg gtgttgggga 620

<210> SEQ ID NO 95
<211> LENGTH: 470
<212> TYPE: DNA
<213> ORGANISM: Homo sapiens
<220> FEATURE:

-continued

<221> NAME/KEY: misc_feature
<222> LOCATION: 61, 67, 79, 89, 106, 213, 271, 281, 330, 354, 387, 432, 448
<223> OTHER INFORMATION: n = A,T,C or G

<400> SEQUENCE: 95
ctcgaccttc tctgcacagc ggatgaaccc tgagcagctg aagaccagaa aagccactat 60
nactttntgc ttaattcang agcttacang attcttcaaa gagtgngtcc agcatccttt 120
gaaacatgag ttcttaccag cagaagcaga cctttacccc accacctcag cttcaacagc 180
agcaggtgaa acaacccatc cagcctccac ctnaggaaat atttgttccc acaaccaagg 240
agccatgcca ctcaaaggtt ccacaacctg naaacacaaa nattccagag ccaggctgta 300
ccaaggtccc tgagccaggg ctgtaccaan gtccctgagc caggttgtac caangtccct 360
gagccaggat gtaccaaggt ccctgancca ggttgtccaa ggtccctgag ccaggctaca 420
ccaagggcct gngccaggca gcatcaangt ccctgaccaa ggcttatcaa 470

<210> SEQ ID NO 96
<211> LENGTH: 660
<212> TYPE: DNA
<213> ORGANISM: Homo sapiens
<220> FEATURE:
<221> NAME/KEY: misc_feature
<222> LOCATION: 299, 311, 360, 426, 538, 540, 542, 553, 563, 565, 592, 603, 604, 618, 633, 647, 649, 651, 653
<223> OTHER INFORMATION: n = A,T,C or G

<400> SEQUENCE: 96
tttttttttt tttttttttt ggaattaaaa gcaatttaat gagggcagag caggaaacat 60
gcatttcttt tcattcgaat cttcagatga accctgagca gccgaagacc agaaaagcca 120
tgaagacttt ctgcttaatt caggggctta caggattctt cagagtgtgt gtgaacaaaa 180
gctttatagt acgtattttt aggatacaaa taagagagag actatggctt ggggtgagaa 240
tgtactgatt acaaggtcta cagacaatta agacacagaa acagatggga agagggtgnc 300
cagcatctgg nggttggctt ctcaagggct tgtctgtgca ccaaattact tctgcttggn 360
cttctgctga gctgggcctg gagtgaccgt tgaaggacat ggctctggta cctttgtgta 420
gcctgncaca ggaactttgg tgtatccttg ctcaggaact ttgatggcac ctggctcagg 480
aaacttgatg aagccttggt caagggacct tgatgcttgc tggctcaggg accttggngn 540
ancctgggct canggacctt tgncncaacc ttggcttcaa gggacccttg gnacatcctg 600
gcnnagggac ccttgggncc aaccctgggc ttnagggacc ctttggntnc nanccttggc 660

<210> SEQ ID NO 97
<211> LENGTH: 441
<212> TYPE: DNA
<213> ORGANISM: Homo sapiens
<220> FEATURE:
<221> NAME/KEY: misc_feature
<222> LOCATION: 12, 308
<223> OTHER INFORMATION: n = A,T,C or G

<400> SEQUENCE: 97
gggaccatac anagtattcc tctcttcaca ccaggaccag ccactgttgc agcatgagtt 60
cccagcagca gaagcagccc tgcatcccac cccctcagct tcagcagcag caggtgaaac 120
agccttgcca gcctccacct caggaaccat gcatccccaa aaccaaggag ccctgccacc 180
ccaaggtgcc tgagccctgc caccccaaag tgcctgagcc ctgccagccc aaggttccag 240
agccatgcca ccccaaggtg cctgagccct gcccttcaat agtcactcca gcaccagccc 300

-continued agcagaanac caagcagaag taatgtggtc cacagccatg cccttgagga gccggccacc 360
agatgctgaa tcccctatcc cattctgtgt atgagtccca tttgccttgc aattagcatt 420
ctgtctcccc caaaaaaaaa a 441

<210> SEQ ID NO 98
<211> LENGTH: 600
<212> TYPE: DNA
<213> ORGANISM: Homo sapiens
<220> FEATURE:
<221> NAME/KEY: misc_feature
<222> LOCATION: 295, 349, 489, 496, 583
<223> OTHER INFORMATION: n = A,T,C or G

<400> SEQUENCE: 98
gtattcctct cttcacacca ggaccagcca ctgttgcagc atgagttccc agcagcagaa 60
gcagccctgc atcccacccc ctcagcttca gcagcagcag gtgaaacagc cttgccagcc 120
tccacctcag gaaccatgca tccccaaaac caaggagccc tgccacccca aggtgcctga 180
gccctgccac cccaaagtgc ctgagccctg ccagcccaag gttccagagc catgccaccc 240
caaggtgcct gagccctgcc cttcaatagt cactccagca ccagcccagc agaanaccaa 300
gcagaagtaa tgtggtccac agccatgccc ttgaggagcc ggccaccana tgctgaatcc 360
cctatcccat tctgtgtatg agtcccattt gccttgcaat tagcattctg tctcccccaa 420
aaaagaatgt gctatgaagc tttctttcct acacactctg agtctctgaa tgaagctgaa 480
ggtcttaant acaganctag ttttcagctg ctcagaattc tctgaagaaa agatttaaga 540
tgaaaggcaa atgattcagc tccttattac cccattaaat tcnctttcaa ttccaaaaaa 600

<210> SEQ ID NO 99
<211> LENGTH: 667
<212> TYPE: DNA
<213> ORGANISM: Homo sapiens
<220> FEATURE:
<221> NAME/KEY: misc_feature
<222> LOCATION: 345, 562, 635
<223> OTHER INFORMATION: n = A,T,C or G

<400> SEQUENCE: 99
actagtgact gagttcctgg caaagaaatt tgacctggac cagttgataa ctcatgtttt 60
accatttaaa aaaatcagtg aaggatttga gctgctcaat tcaggacaaa gcattcgaac 120
ggtcctgacg ttttgagatc caaagtggca ggaggtctgt gttgtcatgg tgaactggag 180
tttctcttgt gagagttccc tcatctgaaa tcatgtatct gtctcacaaa tacaagcata 240
agtagaagat ttgttgaaga catagaaccc ttataaagaa ttattaacct ttataaacat 300
ttaaagtctt gtgagcacct gggaattagt ataataacaa tgttnatatt tttgatttac 360
attttgtaag gctataattg tatcttttaa gaaaacatac cttggatttc tatgttgaaa 420
tggagatttt taagagtttt aaccagctgc tgcagatata ttactcaaaa cagatatagc 480
gtataaagat atagtaaatg catctcctag agtaatattc acttaacaca ttggaaacta 540
ttatttttta gatttgaata tnaatgttat tttttaaaca cttgttatga gttacttggg 600
attacatttt gaaatcagtt cattccatga tgcanattac tgggattaga ttaagaaaga 660
cggaaaa 667

<210> SEQ ID NO 100
<211> LENGTH: 583
<212> TYPE: DNA

-continued

<213> ORGANISM: Homo sapiens
<220> FEATURE:
<221> NAME/KEY: misc_feature
<222> LOCATION: 404, 506, 514, 527, 528, 538, 548, 556, 568, 569
<223> OTHER INFORMATION: n = A,T,C or G

<400> SEQUENCE: 100
gttttgtttg taagatgatc acagtcatgt tacactgatc taaaggacat atatataacc 60
ctttaaaaaa aaaatcactg cctcattctt atttcaagat gaatttctat acagactaga 120
tgtttttctg aagatcaatt agacattttg aaaatgattt aaagtgtttt ccttaatgtt 180
ctctgaaaac aagtttcttt tgtagtttta accaaaaaag tgcccttttt gtcactggat 240
tctcctagca ttcatgattt ttttttcata caatgaaatt aaaattgcta aaatcatgga 300
ctggctttct ggttggattt caggtaagat gtgtttaagg ccagagcttt tctcagtatt 360
tgattttttt ccccaatatt tgattttta aaaatataca catnggtgct gcatttatat 420
ctgctggttt aaaattctgt catatttcac ttctagcctt ttagttatgg caaatcatat 480
tttactttta cttaaagcat ttggtnattt ggantatctg gttctannct aaaaaaanta 540
attctatnaa ttgaantttt ggtactcnnc catatttgga tcc 583

<210> SEQ ID NO 101
<211> LENGTH: 592
<212> TYPE: DNA
<213> ORGANISM: Homo sapiens
<220> FEATURE:
<221> NAME/KEY: misc_feature
<222> LOCATION: 218, 497, 502, 533, 544, 546, 548, 550, 555
<223> OTHER INFORMATION: n = A,T,C or G

<400> SEQUENCE: 101
gtggagacgt acaaagagca gccgctcaag acacctggga agaaaaagaa aggcaagccc 60
gggaaacgca aggagcagga aaagaaaaaa cggcgaactc gctctgcctg gttagactct 120
ggagtgactg ggagtgggct agaaggggac cacctgtctg acacctccac aacgtcgctg 180
gagctcgatt cacggaggca ttgaaatttt cagcaganac cttccaagga catattgcag 240
gattctgtaa tagtgaacat atggaaagta ttagaaatat ttattgtctg taaatactgt 300
aaatgcattg gaataaaact gtctcccccca ttgctctatg aaactgcaca ttggtcattg 360
tgaatatttt tttttttgcc aaggctaatc caattattat tatcacattt accataattt 420
attttgtcca ttgatgtatt tattttgtaa atgtatcttg gtgctgctga atttctatat 480
tttttgtaca taatgcnttt anatatacct atcaagtttg ttgataaatg acncaatgaa 540
gtgncncnan ttggnggttg aatttaatga atgcctaatt ttattatccc aa 592

<210> SEQ ID NO 102
<211> LENGTH: 587
<212> TYPE: DNA
<213> ORGANISM: Homo sapiens
<220> FEATURE:
<221> NAME/KEY: misc_feature
<222> LOCATION: 91, 131, 256, 263, 332, 392, 400, 403, 461, 496, 497, 499, 510, 511, 518, 519, 539, 554, 560, 576
<223> OTHER INFORMATION: n = A,T,C or G

<400> SEQUENCE: 102
cgtcctaagc acttagacta catcagggaa gaacacagac cacatccctg tcctcatgcg 60
gcttatgttt tctggaagaa agtggagacc nagtccttgg ctttagggct ccccggctgg 120
gggctgtgca ntccggtcag ggcgggaagg gaaatgcacc gctgcatgtg aacttacagc 180

-continued

```
ccaggcggat gccccttccc ttagcactac ctggcctcct gcatcccctc gcctcatgtt    240

cctcccacct tcaaanaatg aanaacccca tgggcccagc cccttgccct ggggaaccaa    300

ggcagccttc caaaactcag gggctgaagc anactattag ggcaggggct gactttgggt    360

gacactgccc attccctctc agggcagctc angtcacccn ggnctcttga acccagcctg    420

ttcctttgaa aaagggcaaa actgaaaagg gcttttccta naaaaagaaa aaccagggaa    480

ctttgccagg gcttcnntnt taccaaaacn ncttctcnng gatttttaat tccccattng    540

gcctccactt accnggggcn atgccccaaa attaanaatt tcccatc                  587


<210> SEQ ID NO 103
<211> LENGTH: 496
<212> TYPE: DNA
<213> ORGANISM: Homo sapiens
<220> FEATURE:
<221> NAME/KEY: misc_feature
<222> LOCATION: 2, 17, 66, 74, 82, 119, 164, 166, 172, 200, 203, 228,
      232, 271, 273, 415, 423, 445, 446, 473
<223> OTHER INFORMATION: n = A,T,C or G

<400> SEQUENCE: 103

anaggactgg ccctacntgc tctctctcgt cctacctatc aatgcccaac atggcagaac     60

ctgcanccct tggncactgc anatggaaac ctctcagtgt cttgacatca ccctacccnt    120

gcggtgggtc tccaccacaa ccactttgac tctgtggtcc ctgnanggtg gnttctcctg    180

actggcagga tggaccttan ccnacatatc cctctgttcc ctctgctnag anaaagaatt    240

cccttaacat gatataatcc acccatgcaa ntngctactg gcccagctac catttaccat    300

ttgcctacag aatttcattc agtctacact ttggcattct ctctggcgat agagtgtggc    360

tgggctgacc gcaaaaggtg ccttacacac tggccccccac cctcaaccgt tgacncatca    420

gangcttgcc tcctccttct gattnncccc catgttggat atcagggtgc tcnagggatt    480

ggaaaagaaa caaaac                                                    496


<210> SEQ ID NO 104
<211> LENGTH: 575
<212> TYPE: DNA
<213> ORGANISM: Homo sapiens
<220> FEATURE:
<221> NAME/KEY: misc_feature
<222> LOCATION: 18, 19, 45, 68, 77, 132, 155, 174, 219, 226, 238, 259,
      263, 271, 273, 306, 323, 339, 363, 368, 370, 378, 381, 382, 436,
      440, 449, 450, 456, 481, 485, 496, 503, 510, 512, 515, 528,
      542, 552
<223> OTHER INFORMATION: n = A,T,C or G

<400> SEQUENCE: 104

gcacctgctc tcaatccnnc tctcaccatg atcctccgcc tgcanaaact cctctgccaa     60

ctatggangt ggtttcnggg gtggctcttg ccaactggga agaagccgtg gtgtctctac    120

ctgttcaact cngtttgtgt ctgggggatc aactnggggc tatggaagcg gctnaactgt    180

tgttttggtg gaagggctgg taattggctt tgggaagtng cttatngaag ttggcctngg    240

gaagttgcta ttgaaagtng ccntggaagt ngntttggtg gggggttttg ctggtggcct    300

ttgttnaatt tgggtgcttt gtnaatggcg gccccctcnc ctgggcaatg aaaaaaatca    360

ccnatgcngn aaacctcnac nnaacagcct gggcttccct cacctcgaaa aaagttgctc    420

cccccccaaa aaaggncaan cccctcaann tggaangttg aaaaaatcct cgaatgggga    480

ncccnaaaac aaaaancccc ccntttcccn gnaanggggg aaataccncc cccccactta    540

cnaaaaccct tntaaaaaac cccccgggaa aaaaa                               575
```

-continued

<210> SEQ ID NO 105
<211> LENGTH: 619
<212> TYPE: DNA
<213> ORGANISM: Homo sapiens
<220> FEATURE:
<221> NAME/KEY: misc_feature
<222> LOCATION: 260, 527, 560, 564, 566, 585, 599
<223> OTHER INFORMATION: n = A,T,C or G

<400> SEQUENCE: 105
cactagtagg atagaaacac tgtgtcccga gagtaaggag agaagctact attgattaga 60
gcctaaccca ggttaactgc aagaagaggc gggatacttt cagctttcca tgtaactgta 120
tgcataaagc caatgtagtc cagtttctaa gatcatgttc caagctaact gaatcccact 180
tcaatacaca ctcatgaact cctgatggaa caataacagg cccaagcctg tggtatgatg 240
tgcacacttg ctagactcan aaaaaatact actctcataa atgggtggga gtattttggt 300
gacaacctac tttgcttggc tgagtgaagg aatgatattc atatattcat ttattccatg 360
gacatttagt tagtgctttt tatataccag gcatgatgct gagtgacact cttgtgtata 420
tttccaaatt tttgtacagt cgctgcacat atttgaaatc atatattaag acttccaaaa 480
aatgaagtcc ctggtttttc atggcaactt gatcagtaaa ggattcncct ctgtttggta 540
cttaaaacat ctactatatn gttnanatga aattcctttt ccccncctcc cgaaaaaana 600
aagtggtggg gaaaaaaaa 619

<210> SEQ ID NO 106
<211> LENGTH: 506
<212> TYPE: DNA
<213> ORGANISM: Homo sapiens
<220> FEATURE:
<221> NAME/KEY: misc_feature
<222> LOCATION: 8, 21, 31, 32, 58, 75, 89, 96, 99, 103, 122, 126, 147,
150, 158, 195, 210, 212, 219, 226, 246, 248, 249, 255, 258, 261,
263, 265, 275, 304, 317, 321, 331, 337, 340, 358, 371, 377,
380, 396, 450, 491
<223> OTHER INFORMATION: n = A,T,C or G

<400> SEQUENCE: 106
cattggtnct ttcatttgct ntggaagtgt nnatctctaa cagtggacaa agttcccngt 60
gccttaaact ctgtnacact tttgggaant gaaaanttng tantatgata ggttattctg 120
angtanagat gttctggata ccattanatn tgcccccngt gtcagaggct catattgtgt 180
tatgtaaatg gtatntcatt cgctactatn antcaattng aaatanggtc tttgggttat 240
gaatantnng cagcncanct nanangctgt ctgtngtatt cattgtggtc atagcacctc 300
acancattgt aacctcnatc nagtgagaca nactagnaan ttcctagtga tggctcanga 360
ttccaaatgg nctcatntcn aatgtttaaa agttanttaa gtgtaagaaa tacagactgg 420
atgttccacc aactagtacc tgtaatgacn ggcctgtccc aacacatctc ccttttccat 480
gactgtggta ncccgcatcg gaaaaa 506

<210> SEQ ID NO 107
<211> LENGTH: 452
<212> TYPE: DNA
<213> ORGANISM: Homo sapiens
<220> FEATURE:
<221> NAME/KEY: misc_feature
<222> LOCATION: 289, 317, 378
<223> OTHER INFORMATION: n = A,T,C or G

<400> SEQUENCE: 107

-continued

```
gttgagtctg tactaaacag taagatatct caatgaacca taaattcaac tttgtaaaaa     60
tcttttgaag catagataat attgtttggt aaatgtttct tttgtttggt aaatgtttct    120
tttaaagacc ctcctattct ataaaactct gcatgtagag gcttgtttac ctttctctct    180
ctaaggttta caataggagt ggtgatttga aaaatataaa attatgagat tggttttcct    240
gtggcataaa ttgcatcact gtatcatttt ctttttttaac cggtaagant ttcagtttgt    300
tggaaagtaa ctgtganaac ccagtttccc gtccatctcc cttagggact acccatagaa    360
catgaaaagg tccccacnga agcaagaaga taagtctttc atggctgctg gttgcttaaa    420
ccactttaaa accaaaaaat tccccttgga aa                                  452
```

<210> SEQ ID NO 108
<211> LENGTH: 502
<212> TYPE: DNA
<213> ORGANISM: Homo sapiens
<220> FEATURE:
<221> NAME/KEY: misc_feature
<222> LOCATION: 22, 31, 126, 168, 183, 205, 219, 231, 236, 259, 283, 295, 296, 298, 301, 340, 354, 378, 383, 409, 433, 446, 455, 466, 488
<223> OTHER INFORMATION: n = A,T,C or G

<400> SEQUENCE: 108

```
atcttcttcc cttaattagt tnttatttat ntattaaatt ttattgcatg tcctggcaaa     60
caaaaagaga ttgtagattg gcttctggct ccccaaaagc ccataacaga aagtaccaca    120
agaccncaac tgaagcttaa aaaatctatc acatgtataa tacctttnga agaacattaa    180
tanagcatat aaaactttta acatntgctt aatgttgtnc aattataaaa ntaatngaaa    240
aaaatgtccc tttaacatnc aatatcccac atagtgttat ttnaggggat taccnngnaa    300
naaaaaaagg gtagaaggga tttaatgaaa actctgcttn ccatttctgt ttanaaacgt    360
ctccagaaca aaaacttntc aantctttca gctaaccgca tttgagctna ggccactcaa    420
aaactccatt agncccactt tctaanggtc tctanagctt actaancctt ttgacccctt    480
accctggnta ctcctgccct ca                                             502
```

<210> SEQ ID NO 109
<211> LENGTH: 1308
<212> TYPE: DNA
<213> ORGANISM: Homo sapiens

<400> SEQUENCE: 109

```
acccgaggtc tcgctaaaat catcatggat tcacttggcg ccgtcagcac tcgacttggg     60
tttgatcttt tcaaagagct gaagaaaaca aatgatggca acatcttctt ttcccctgtg    120
ggcatcttga ctgcaattgg catggtcctc ctggggaccc gaggagccac cgcttcccag    180
ttggaggagg tgtttcactc tgaaaaagag acgaagagct caagaataaa ggctgaagaa    240
aaagaggtga ttgagaacac agaagcagta catcaacaat tccaaaagtt tttgactgaa    300
ataagcaaac tcactaatga ttatgaactg aacataacca acaggctgtt tggagaaaaa    360
acatacctct tccttcaaaa atacttagat tatgttgaaa aatattatca tgcatctctg    420
gaacctgttg attttgtaaa tgcagccgat gaaagtcgaa agaagattaa ttcctgggtt    480
gaaagcaaaa caaatgaaaa aatcaaggac ttgttcccag atggctctat tagtagctct    540
accaagctgg tgctggtgaa catggtttat tttaaagggc aatgggacag ggagtttaag    600
aaagaaaata ctaaggaaga gaaattttgg atgaataaga gcacaagtaa atctgtacag    660
```

-continued

```
atgatgacac agagccattc ctttagcttc actttcctgg aggacttgca ggccaaaatt    720

ctagggattc catataaaaa caacgaccta agcatgtttg tgcttctgcc caacgacatc    780

gatggcctgg agaagataat agataaaata agtcctgaga aattggtaga gtggactagt    840

ccagggcata tggaagaaag aaaggtgaat ctgcacttgc cccggtttga ggtggaggac    900

agttacgatc tagaggcggt cctggctgcc atggggatgg gcgatgcctt cagtgagcac    960

aaagccgact actcgggaat gtcgtcaggc tccgggttgt acgcccagaa gttcctgcac   1020

agttcctttg tggcagtaac tgaggaaggc accgaggctg cagctgccac tggcataggc   1080

tttactgtca catccgcccc aggtcatgaa aatgttcact gcaatcatcc cttcctgttc   1140

ttcatcaggc acaatgaatc caacagcatc ctcttcttcg gcagattttc ttctccttaa   1200

gatgatcgtt gccatggcat tgctgctttt agcaaaaaac aactaccagt gttactcata   1260

tgattatgaa aatcgtccat tcttttaaat ggtggctcac ttgcattt                1308
```

<210> SEQ ID NO 110
<211> LENGTH: 391
<212> TYPE: PRT
<213> ORGANISM: Homo sapiens

<400> SEQUENCE: 110

```
Met Asp Ser Leu Gly Ala Val Ser Thr Arg Leu Gly Phe Asp Leu Phe
 1               5                  10                  15

Lys Glu Leu Lys Lys Thr Asn Asp Gly Asn Ile Phe Phe Ser Pro Val
            20                  25                  30

Gly Ile Leu Thr Ala Ile Gly Met Val Leu Leu Gly Thr Arg Gly Ala
        35                  40                  45

Thr Ala Ser Gln Leu Glu Glu Val Phe His Ser Glu Lys Glu Thr Lys
    50                  55                  60

Ser Ser Arg Ile Lys Ala Glu Glu Lys Glu Val Ile Glu Asn Thr Glu
65                  70                  75                  80

Ala Val His Gln Gln Phe Gln Lys Phe Leu Thr Glu Ile Ser Lys Leu
                85                  90                  95

Thr Asn Asp Tyr Glu Leu Asn Ile Thr Asn Arg Leu Phe Gly Glu Lys
            100                 105                 110

Thr Tyr Leu Phe Leu Gln Lys Tyr Leu Asp Tyr Val Glu Lys Tyr Tyr
        115                 120                 125

His Ala Ser Leu Glu Pro Val Asp Phe Val Asn Ala Ala Asp Glu Ser
    130                 135                 140

Arg Lys Lys Ile Asn Ser Trp Val Glu Ser Lys Thr Asn Glu Lys Ile
145                 150                 155                 160

Lys Asp Leu Phe Pro Asp Gly Ser Ile Ser Ser Ser Thr Lys Leu Val
                165                 170                 175

Leu Val Asn Met Val Tyr Phe Lys Gly Gln Trp Asp Arg Glu Phe Lys
            180                 185                 190

Lys Glu Asn Thr Lys Glu Glu Lys Phe Trp Met Asn Lys Ser Thr Ser
        195                 200                 205

Lys Ser Val Gln Met Met Thr Gln Ser His Ser Phe Ser Phe Thr Phe
    210                 215                 220

Leu Glu Asp Leu Gln Ala Lys Ile Leu Gly Ile Pro Tyr Lys Asn Asn
225                 230                 235                 240

Asp Leu Ser Met Phe Val Leu Leu Pro Asn Asp Ile Asp Gly Leu Glu
                245                 250                 255

Lys Ile Ile Asp Lys Ile Ser Pro Glu Lys Leu Val Glu Trp Thr Ser
```

-continued

```
            260                 265                 270

Pro Gly His Met Glu Glu Arg Lys Val Asn Leu His Leu Pro Arg Phe
        275                 280                 285

Glu Val Glu Asp Ser Tyr Asp Leu Glu Ala Val Leu Ala Ala Met Gly
    290                 295                 300

Met Gly Asp Ala Phe Ser Glu His Lys Ala Asp Tyr Ser Gly Met Ser
305                 310                 315                 320

Ser Gly Ser Gly Leu Tyr Ala Gln Lys Phe Leu His Ser Ser Phe Val
                325                 330                 335

Ala Val Thr Glu Glu Gly Thr Glu Ala Ala Ala Ala Thr Gly Ile Gly
            340                 345                 350

Phe Thr Val Thr Ser Ala Pro Gly His Glu Asn Val His Cys Asn His
        355                 360                 365

Pro Phe Leu Phe Phe Ile Arg His Asn Glu Ser Asn Ser Ile Leu Phe
    370                 375                 380

Phe Gly Arg Phe Ser Ser Pro
385                 390


<210> SEQ ID NO 111
<211> LENGTH: 1419
<212> TYPE: DNA
<213> ORGANISM: Homo sapiens

<400> SEQUENCE: 111

ggagaactat aaattaagga tcccagctac ttaattgact tatgcttcct agttcgttgc     60

ccagccacca ccgtctctcc aaaaacccga ggtctcgcta aaatcatcat ggattcactt    120

ggcgccgtca gcactcgact tgggtttgat cttttcaaag agctgaagaa aacaaatgat    180

ggcaacatct tcttttcccc tgtgggcatc ttgactgcaa ttggcatggt cctcctgggg    240

acccgaggag ccaccgcttc ccagttggag gaggtgtttc actctgaaaa agagacgaag    300

agctcaagaa taaaggctga agaaaaagag gtggtaagaa taaaggctga aggaaaagag    360

attgagaaca cagaagcagt acatcaacaa ttccaaaagt tttgactga aataagcaaa     420

ctcactaatg attatgaact gaacataacc aacaggctgt ttggagaaaa aacatacctc    480

ttccttcaaa aatacttaga ttatgttgaa aaatattatc atgcatctct ggaacctgtt    540

gattttgtaa atgcagccga tgaaagtcga aagaagatta attcctgggt tgaaagcaaa    600

acaaatgaaa aaatcaagga cttgttccca gatggctcta ttagtagctc taccaagctg    660

gtgctggtga acatggttta ttttaaaggg caatgggaca gggagtttaa gaaagaaaat    720

actaaggaag agaaattttg gatgaataag agcacaagta aatctgtaca gatgatgaca    780

cagagccatt cctttagctt cactttcctg gaggacttgc aggccaaaat tctagggatt    840

ccatataaaa acaacgacct aagcatgttt gtgcttctgc ccaacgacat cgatggcctg    900

gagaagataa tagataaaat aagtcctgag aaattggtag agtggactag tccagggcat    960

atggaagaaa gaaaggtgaa tctgcacttg ccccggtttg aggtggagga cagttacgat   1020

ctagaggcgg tcctggctgc catggggatg ggcgatgcct tcagtgagca caaagccgac   1080

tactcgggaa tgtcgtcagg ctccgggttg tacgcccaga agttcctgca cagttccttt   1140

gtggcagtaa ctgaggaagg caccgaggct gcagctgcca ctggcatagg ctttactgtc   1200

acatccgccc caggtcatga aaatgttcac tgcaatcatc ccttcctgtt cttcatcagg   1260

cacaatgaat ccaacagcat cctcttcttc ggcagatttt cttctcctta agatgatcgt   1320

tgccatggca ttgctgcttt tagcaaaaaa caactaccag tgttactcat atgattatga   1380
```

-continued aaatcgtcca ttcttttaaa tggtggctca cttgcattt 1419

<210> SEQ ID NO 112
<211> LENGTH: 400
<212> TYPE: PRT
<213> ORGANISM: Homo sapiens

<400> SEQUENCE: 112

```
Met Asp Ser Leu Gly Ala Val Ser Thr Arg Leu Gly Phe Asp Leu Phe
 1               5                  10                  15

Lys Glu Leu Lys Lys Thr Asn Asp Gly Asn Ile Phe Phe Ser Pro Val
            20                  25                  30

Gly Ile Leu Thr Ala Ile Gly Met Val Leu Leu Gly Thr Arg Gly Ala
        35                  40                  45

Thr Ala Ser Gln Leu Glu Glu Val Phe His Ser Glu Lys Glu Thr Lys
    50                  55                  60

Ser Ser Arg Ile Lys Ala Glu Glu Lys Glu Val Val Arg Ile Lys Ala
65                  70                  75                  80

Glu Gly Lys Glu Ile Glu Asn Thr Glu Ala Val His Gln Gln Phe Gln
                85                  90                  95

Lys Phe Leu Thr Glu Ile Ser Lys Leu Thr Asn Asp Tyr Glu Leu Asn
            100                 105                 110

Ile Thr Asn Arg Leu Phe Gly Glu Lys Thr Tyr Leu Phe Leu Gln Lys
        115                 120                 125

Tyr Leu Asp Tyr Val Glu Lys Tyr Tyr His Ala Ser Leu Glu Pro Val
    130                 135                 140

Asp Phe Val Asn Ala Ala Asp Glu Ser Arg Lys Lys Ile Asn Ser Trp
145                 150                 155                 160

Val Glu Ser Lys Thr Asn Glu Lys Ile Lys Asp Leu Phe Pro Asp Gly
                165                 170                 175

Ser Ile Ser Ser Ser Thr Lys Leu Val Leu Val Asn Met Val Tyr Phe
            180                 185                 190

Lys Gly Gln Trp Asp Arg Glu Phe Lys Lys Glu Asn Thr Lys Glu Glu
        195                 200                 205

Lys Phe Trp Met Asn Lys Ser Thr Ser Lys Ser Val Gln Met Met Thr
    210                 215                 220

Gln Ser His Ser Phe Ser Phe Thr Phe Leu Glu Asp Leu Gln Ala Lys
225                 230                 235                 240

Ile Leu Gly Ile Pro Tyr Lys Asn Asn Asp Leu Ser Met Phe Val Leu
                245                 250                 255

Leu Pro Asn Asp Ile Asp Gly Leu Glu Lys Ile Ile Asp Lys Ile Ser
            260                 265                 270

Pro Glu Lys Leu Val Glu Trp Thr Ser Pro Gly His Met Glu Glu Arg
        275                 280                 285

Lys Val Asn Leu His Leu Pro Arg Phe Glu Val Glu Asp Ser Tyr Asp
    290                 295                 300

Leu Glu Ala Val Leu Ala Ala Met Gly Met Gly Asp Ala Phe Ser Glu
305                 310                 315                 320

His Lys Ala Asp Tyr Ser Gly Met Ser Ser Gly Ser Gly Leu Tyr Ala
                325                 330                 335

Gln Lys Phe Leu His Ser Ser Phe Val Ala Val Thr Glu Glu Gly Thr
            340                 345                 350

Glu Ala Ala Ala Ala Thr Gly Ile Gly Phe Thr Val Thr Ser Ala Pro
        355                 360                 365
```

-continued

```
Gly His Glu Asn Val His Cys Asn His Pro Phe Leu Phe Phe Ile Arg
    370                 375                 380

His Asn Glu Ser Asn Ser Ile Leu Phe Phe Gly Arg Phe Ser Ser Pro
385                 390                 395                 400
```

<210> SEQ ID NO 113
<211> LENGTH: 957
<212> TYPE: DNA
<213> ORGANISM: Homo sapiens

<400> SEQUENCE: 113

```
ctcgaccttc tctgcacagc ggatgaaccc tgagcagctg aagaccagaa aagccactat      60

gactttctgc ttaattcagg agcttacagg attcttcaaa gagtgtgtcc agcatccttt     120

gaaacatgag ttcttaccag cagaagcaga cctttacccc accacctcag cttcaacagc     180

agcaggtgaa acaacccagc cagcctccac ctcaggaaat atttgttccc acaaccaagg     240

agccatgcca ctcaaaggtt ccacaacctg gaaacacaaa gattccagag ccaggctgta     300

ccaaggtccc tgagccaggc tgtaccaagg tccctgagcc aggttgtacc aaggtccctg     360

agccaggatg taccaaggtc cctgagccag gttgtaccaa ggtccctgag ccaggctaca     420

ccaaggtccc tgagccaggc agcatcaagg tccctgacca aggcttcatc aagtttcctg     480

agccaggtgc catcaaagtt cctgagcaag gatacaccaa agttcctgtg ccaggctaca     540

caaaggtacc agagccatgt ccttcaacgg tcactccagg cccagctcag cagaagacca     600

agcagaagta atttggtgca cagacaagcc cttgagaagc caaccaccag atgctggaca     660

ccctcttccc atctgtttct gtgtcttaat tgtctgtaga ccttgtaatc agtacattct     720

caccccaagc catagtctct ctcttatttg tatcctaaaa atacggtact ataaagcttt     780

tgttcacaca cactctgaag aatcctgtaa gcccctgaat taagcagaaa gtcttcatgg     840

cttttctggt cttcggctgc tcagggttca tctgaagatt cgaatgaaaa gaaatgcatg     900

tttcctgctc tgccctcatt aaattgcttt taattccaaa aaaaaaaaaa aaaaaaa        957
```

<210> SEQ ID NO 114
<211> LENGTH: 161
<212> TYPE: PRT
<213> ORGANISM: Homo sapiens

<400> SEQUENCE: 114

```
Met Ser Ser Tyr Gln Gln Lys Gln Thr Phe Thr Pro Pro Pro Gln Leu
 1               5                  10                  15

Gln Gln Gln Gln Val Lys Gln Pro Ser Gln Pro Pro Pro Gln Glu Ile
            20                  25                  30

Phe Val Pro Thr Thr Lys Glu Pro Cys His Ser Lys Val Pro Gln Pro
        35                  40                  45

Gly Asn Thr Lys Ile Pro Glu Pro Gly Cys Thr Lys Val Pro Glu Pro
    50                  55                  60

Gly Cys Thr Lys Val Pro Glu Pro Gly Cys Thr Lys Val Pro Glu Pro
65                  70                  75                  80

Gly Cys Thr Lys Val Pro Glu Pro Gly Cys Thr Lys Val Pro Glu Pro
                85                  90                  95

Gly Tyr Thr Lys Val Pro Glu Pro Gly Ser Ile Lys Val Pro Asp Gln
            100                 105                 110

Gly Phe Ile Lys Phe Pro Glu Pro Gly Ala Ile Lys Val Pro Glu Gln
        115                 120                 125
```

-continued

```
Gly Tyr Thr Lys Val Pro Val Pro Gly Tyr Thr Lys Val Pro Glu Pro
    130                 135                 140

Cys Pro Ser Thr Val Thr Pro Gly Pro Ala Gln Gln Lys Thr Lys Gln
145                 150                 155                 160

Lys


<210> SEQ ID NO 115
<211> LENGTH: 506
<212> TYPE: DNA
<213> ORGANISM: Homo sapiens
<220> FEATURE:
<221> NAME/KEY: misc_feature
<222> LOCATION: 8, 21, 31, 32, 58, 75, 89, 96, 99, 103, 122, 126, 147,
      150, 158, 195, 210, 212, 219, 226, 246, 248, 249, 255, 258, 261,
      263, 265, 275, 304, 317, 321, 331, 337, 340, 358, 371, 377,
      380, 396, 450, 491
<223> OTHER INFORMATION: n = A,T,C or G

<400> SEQUENCE: 115

cattggtnct ttcatttgct ntggaagtgt nnatctctaa cagtggacaa agttcccngt     60

gccttaaact ctgtnacact tttgggaant gaaaanttng tantatgata ggttattctg    120

angtanagat gttctggata ccattanatn tgcccccngt gtcagaggct catattgtgt    180

tatgtaaatg gtatntcatt cgctactatn antcaattng aaatanggtc tttgggttat    240

gaatantnng cagcncanct nanangctgt ctgtngtatt cattgtggtc atagcacctc    300

acancattgt aacctcnatc nagtgagaca nactagnaan ttcctagtga tggctcanga    360

ttccaaatgg nctcatntcn aatgtttaaa agttanttaa gtgtaagaaa tacagactgg    420

atgttccacc aactagtacc tgtaatgacn ggcctgtccc aacacatctc ccttttccat    480

gactgtggta ncccgcatcg gaaaaa                                         506


<210> SEQ ID NO 116
<211> LENGTH: 3079
<212> TYPE: DNA
<213> ORGANISM: Homo sapiens

<400> SEQUENCE: 116

ggatccccgg gtttcctaaa ccccccacag agtcctgccc aggccaaaga gcaaggaaaa     60

ggtcaaaggg cagaaaaaat gctgagttag gaggagctat ggaaggataa acctggcctt    120

aaagaggtca aagtggttta tagggggcgc tgagggcttc ccacattctc tggcctaaac    180

cttgcaggca gatctgccca gtgggctctg ggatagctgt gccttcccta acaaaaaaat    240

tgtgcacaaa aggatgaaac tctattttcc ctctagcaca taaccaagaa tataaggcta    300

cagattgcct ttcccagagg gaaaaccctg cagcaacctg ctgcctggaa aagtgtaaga    360

gcagatcact ggggaatcgt ttgccccccg ctgatggaca gcttccccaa gctccaaggg    420

caggtgctca gcatgtaccg tactgggatg gttgtcaata ctcctggtcc tgtaagagtc    480

ccaggacact gccatgccaa tgccccctca gttcctggca tcctttttgg gctgctcaca    540

gccccagcct ctatggtgaa gacatacttg ctagcagcgt caccaacttg ttgccaagag    600

atcagtgctc gaaggcaagg ttatttctaa ctgagcagag cctgccagga agaaagcgtt    660

tgcaccccac accactgtgc aggtgtgacc ggtgagctca cagctgcccc ccaggcatgc    720

ccagcccact taatcatcac agctcgacag ctctctcgcc cagcccagtt ctggaaggga    780

taaaaagggg catcaccgtt cctgggtaac agagccacct tctgcgtcct gctgagctct    840

gttctctcca gcacctccca acccactagt gcctggttct cttgctccac caggaacaag    900
```

-continued

```
ccaccatgtc tcgccagtca agtgtgtctt ccggagcggg gggcagtcgt agcttcagca    960

ccgcctctgc catcaccccg tctgtctccc gcaccagctt cacctccgtg tcccggtccg   1020

ggggtggcgg tggtggtggc ttcggcaggg tcagccttgc gggtgcttgt ggagtgggtg   1080

gctatggcag ccggagcctc tacaacctgg ggggctccaa gaggatatcc atcagcacta   1140

gtggtggcag cttcaggaac cggtttggtg ctggtgctgg aggcggctat ggctttggag   1200

gtggtgccgg tagtggattt ggtttcggcg gtggagctgg tggtggcttt gggctcggtg   1260

gcggagctgg ctttggaggt ggcttcggtg gccctggctt tcctgtctgc cctcctggag   1320

gtatccaaga ggtcactgtc aaccagagtc tcctgactcc cctcaacctg caaatcgacc   1380

ccagcatcca gagggtgagg accgaggagc gcgagcagat caagaccctc aacaataagt   1440

ttgcctcctt catcgacaag gtgcggttcc tggagcagca gaacaaggtt ctggaaacaa   1500

agtggaccct gctgcaggag cagggcacca agactgtgag gcagaacctg gagccgttgt   1560

tcgagcagta catcaacaac ctcaggaggc agctggacag catcgtgggg gaacggggcc   1620

gcctggactc agagctgaga aacatgcagg acctggtgga agacttcaag aacaagtatg   1680

aggatgaaat caacaagcgt accactgctg agaatgagtt tgtgatgctg aagaaggatg   1740

tagatgctgc ctacatgaac aaggtggagc tggaggccaa ggttgatgca ctgatggatg   1800

agattaactt catgaagatg ttctttgatg cggagctgtc ccagatgcag acgcatgtct   1860

ctgacacctc agtggtcctc tccatggaca acaaccgcaa cctggacctg gatagcatca   1920

tcgctgaggt caaggcccag tatgaggaga ttgccaaccg cagccggaca gaagccgagt   1980

cctggtatca gaccaagtat gaggagctgc agcagacagc tggccggcat ggcgatgacc   2040

tccgcaacac caagcatgag atctctgaga tgaaccggat gatccagagg ctgagagccg   2100

agattgacaa tgtcaagaaa cagtgcgcca atctgcagaa cgccattgcg gatgccgagc   2160

agcgtgggga gctggccctc aaggatgcca ggaacaagct ggccgagctg gaggaggccc   2220

tgcagaaggc caagcaggac atggcccggc tgctgcgtga gtaccaggag ctcatgaaca   2280

ccaagctggc cctggacgtg gagatcgcca cttaccgcaa gctgctggag ggcgaggaat   2340

gcagactcag tggagaagga gttggaccag tcaacatctc tgttgtcaca agcagtgttt   2400

cctctggata tggcagtggc agtggctatg gcggtggcct cggtggaggt cttggcggcg   2460

gcctcggtgg aggtcttgcc ggaggtagca gtggaagcta ctactccagc agcagtgggg   2520

gtgtcggcct aggtggtggg ctcagtgtgg ggggctctgg cttcagtgca agcagtagcc   2580

gagggctggg ggtgggcttt ggcagtggcg gggggtagcag ctccagcgtc aaatttgtct   2640

ccaccacctc ctcctcccgg aagagcttca agagctaaga acctgctgca agtcactgcc   2700

ttccaagtgc agcaacccag cccatggaga ttgcctcttc taggcagttg ctcaagccat   2760

gttttatcct tttctggaga gtagtctaga ccaagccaat tgcagaacca cattctttgg   2820

ttcccaggag agccccattc ccagccccctg gtctcccgtg ccgcagttct atattctgct   2880

tcaaatcagc cttcaggttt cccacagcat ggcccctgct gacacgagaa cccaaagttt   2940

tcccaaatct aaatcatcaa aacagaatcc ccaccccaat cccaaatttt gttttggttc   3000

taactacctc cagaatgtgt tcaataaaat gttttataat ataagctggt gtgcagaatt   3060

gttttttttt tctacccaa                                                3079
```

<210> SEQ ID NO 117
<211> LENGTH: 6921
<212> TYPE: DNA
<213> ORGANISM: Homo sapiens -continued

<400> SEQUENCE: 117

```
gaattctgac tgtccactca aaacttctat tccgatcaaa gctatctgtg actacagaca     60
aattgagata accatttaca aagacgatga atgtgttttg gcgaataact ctcatcgtgc    120
taaatggaag gtcattagtc ctactgggaa tgaggctatg gtcccatctg tgtgcttcac    180
cgttcctcca ccaaacaaag aagcggtgga ccttgccaac agaattgagc aacagtatca    240
gaatgtcctg actctttggc atgagtctca cataaacatg aagagtgtag tatcctggca    300
ttatctcatc aatgaaattg atagaattcg agctagcaat gtggcttcaa taaagacaat    360
gctacctggt gaacatcagc aagttctaag taatctacaa tctcgttttg aagattttct    420
ggaagatagc caggaatccc aagtcttttc aggctcagat ataacacaac tggaaaagga    480
ggttaatgta tgtaagcagt attatcaaga acttcttaaa tctgcagaaa gagaggagca    540
agaggaatca gtttataatc tctacatctc tgaagttcga aacattagac ttcggttaga    600
gaactgtgaa gatcggctga ttagacagat tcgaactccc ctggaaagag atgatttgca    660
tgaaagtgtg ttcagaatca cagaacagga gaaactaaag aaagagctgg aacgacttaa    720
agatgatttg ggaacaatca caaataagtg tgaggagttt ttcagtcaag cagcagcctc    780
ttcatcagtc cctaccctac gatcagagct taatgtggtc cttcagaaca tgaaccaagt    840
ctattctatg tcttccactt acatagataa gttgaaaact gttaacttgg tgttaaaaaa    900
cactcaagct gcagaagccc tcgtaaaact ctatgaaact aaactgtgtg aagaagaagc    960
agttatagct gacaagaata atattgagaa tctaataagt actttaaagc aatggagatc   1020
tgaagtagat gaaaagagac aggtattcca tgccttagag gatgagttgc agaaagctaa   1080
agccatcagt gatgaaatgt ttaaaacgta taaagaacgg gaccttgatt ttgactggca   1140
caaagaaaaa gcagatcaat tagttgaaag gtggcaaaat gttcatgtgc agattgacaa   1200
caggttacgg gacttagagg gcattggcaa atcactgaag tactacagag acacttacca   1260
tcctttagat gattggatcc agcaggttga aactactcag agaaagattc aggaaaatca   1320
gcctgaaaat agtaaaaccc tagccacaca gttgaatcaa cagaagatgc tggtgtccga   1380
aatagaaatg aaacagagca aaatggacga gtgtcaaaaa tatgcagaac agtactcagc   1440
tacagtgaag gactatgaat tacaaacaat gacctaccgg gccatggtag attcacaaca   1500
aaaatctcca gtgaaacgcc gaagaatgca gagttcagca gatctcatta ttcaagagtt   1560
catggaccta aggactcgat atactgccct ggtcactctc atgacacaat atattaaatt   1620
tgctggtgat tcattgaaga ggctggaaga ggaggagatt aaaaggtgta aggagacttc   1680
tgaacatggg gcatattcag atctgcttca gcgtcagaag gcaacagtgc ttgagaatag   1740
caaacttaca ggaaagataa gtgagttgga aagaatggta gctgaactaa agaaacaaaa   1800
gtcccgagta gaggaagaac ttccgaaggt cagggaggct gcagaaaatg aattgagaaa   1860
gcagcagaga aatgtagaag atatctctct gcagaagata agggctgaaa gtgaagccaa   1920
gcagtaccgc agggaacttg aaaccattgt gagagagaag gaagccgctg aaagagaact   1980
ggagcgggtg aggcagctca ccatagaggc cgaggctaaa agagctgccg tggaagagaa   2040
cctcctgaat tttcgcaatc agttggagga aaacaccttt accagacgaa cactggaaga   2100
tcatcttaaa agaaaagatt taagtctcaa tgatttggag caacaaaaaa ataaattaat   2160
ggaagaatta agaagaaaga gagacaatga ggaagaactc ttgaagctga taaagcagat   2220
ggaaaaagac cttgcatttc agaaacaggt agcagagaaa cagttgaaag aaaagcagaa   2280
```

-continued

```
aattgaattg gaagcaagaa gaaaaataac tgaaattcag tatacatgta gagaaaatgc   2340
attgccagtg tgtccgatca cacaggctac atcatgcagg gcagtaacgg gtctccagca   2400
agaacatgac aagcagaaag cagaagaact caaacagcag gtagatgaac taacagctgc   2460
caatagaaag gctgaacaag acatgagaga gctgacatat gaacttaatg ccctccagct   2520
tgaaaaaacg tcatctgagg aaaaggctcg tttgctaaaa gataaactag atgaaacaaa   2580
taatacactc agatgcctta agttggagct ggaaaggaag gatcaggcgg agaaagggta   2640
ttctcaacaa ctcagagagc ttggtaggca attgaatcaa accacaggta aagctgaaga   2700
agccatgcaa gaagctagtg atctcaagaa aataaagcgc aattatcagt tagaattaga   2760
atctcttaat catgaaaaag ggaaactaca aagagaagta gacagaatca caagggcaca   2820
tgctgtagct gagaagaata ttcagcattt aaattcacaa attcattctt ttcgagatga   2880
gaaagaatta gaaagactac aaatctgcca gagaaaatca gatcatctaa aagaacaatt   2940
tgagaaaagc catgagcagt tgcttcaaaa tatcaaagct gaaaaagaaa ataatgataa   3000
aatccaaagg ctcaatgaag aattggagaa aagtaatgag tgtgcagaga tgctaaaaca   3060
aaaagtagag gagcttacta ggcagaataa tgaaaccaaa ttaatgatgc agagaattca   3120
ggcagaatca gagaatatag ttttagagaa acaaactatc cagcaaagat gtgaagcact   3180
gaaaattcag gcagatggtt ttaaagatca gctacgcagc acaaatgaac acttgcataa   3240
acagacaaaa acagagcagg attttcaaag aaaaattaaa tgcctagaag aagacctggc   3300
gaaaagtcaa aatttggtaa gtgaatttaa gcaaaagtgt gaccaacaga acattatcat   3360
ccagaatacc aagaaagaag ttagaaatct gaatgcggaa ctgaatgctt ccaaagaaga   3420
gaagcgacgc ggggagcaga aagttcagct acaacaagct caggtgcaag agttaaataa   3480
caggttgaaa aaagtacaag acgaattaca cttaaagacc atagaggagc agatgaccca   3540
cagaaagatg gttctgtttc aggaagaatc tggtaaattc aaacaatcag cagaggagtt   3600
tcggaagaag atggaaaaat taatggagtc caaagtcatc actgaaaatg atatttcagg   3660
cattaggctt gactttgtgt ctcttcaaca agaaaactct agagcccaag aaaatgctaa   3720
gctttgtgaa acaaacatta aagaacttga aagacagctt caacagtatc gtgaacaaat   3780
gcagcaaggg cagcacatgg aagcaaatca ttaccaaaaa tgtcagaaac ttgaggatga   3840
gctgatagcc cagaagcgtg aggttgaaaa cctgaagcaa aaaatggacc aacagatcaa   3900
agagcatgaa catcaattag ttttgctcca gtgtgaaatt caaaaaaaga gcacagccaa   3960
agactgtacc ttcaaaccag attttgagat gacagtgaag gagtgccagc actctggaga   4020
gctgtcctct agaaacactg gacaccttca cccaacaccc agatcccctc tgttgagatg   4080
gactcaagaa ccacagccat tggaagagaa gtggcagcat cgggttgttg aacagatacc   4140
caaagaagtc caattccagc caccaggggc tccactcgag aaagagaaaa gccagcagtg   4200
ttactctgag tacttttctc agacaagcac cgagttacag ataacttttg atgagacaaa   4260
ccccattaca agactgtctg aaattgagaa gataagagac caagccctga acaattctag   4320
accacctgtt aggtatcaag ataacgcatg tgaaatggaa ctggtgaagg ttttgacacc   4380
cttagagata gctaagaaca agcagtatga tatgcataca gaagtcacaa cattaaaaca   4440
agaaaagaac ccagttccca gtgctgaaga atggatgctt gaagggtgca gagcatctgg   4500
tggactcaag aaaggggatt tccttaagaa gggcttagaa ccagagacct tccagaactt   4560
tgatggtgat catgcatgtt cagtcaggga tgatgaattt aaattccaag ggcttaggca   4620
cactgtgact gccaggcagt tggtggaagc taagcttctg gacatgagaa caattgagca   4680
```

-continued

```
gctgcgactc ggtcttaaga ctgttgaaga agttcagaaa actcttaaca agtttctgac   4740
gaaagccacc tcaattgcag ggctttacct agaatctaca aaagaaaaga tttcatttgc   4800
ctcagcggcc gagagaatca taatagacaa aatggtggct ttggcatttt tagaagctca   4860
ggctgcaaca ggttttataa ttgatcccat ttcaggtcag acatattctg ttgaagatgc   4920
agttcttaaa ggagttgttg accccgaatt cagaattagg cttcttgagg cagagaaggc   4980
agctgtggga tattcttatt cttctaagac attgtcagtg tttcaagcta tggaaaatag   5040
aatgcttgac agacaaaaag gtaaacatat cttggaagcc cagattgcca gtgggggtgt   5100
cattgaccct gtgagaggca ttcgtgttcc tccagaaatt gctctgcagc aggggttgtt   5160
gaataatgcc atcttacagt ttttacatga gccatccagc aacacaagag ttttccctaa   5220
tcccaataac aagcaagctc tgtattactc agaattactg cgaatgtgtg tatttgatgt   5280
agagtcccaa tgctttctgt ttccatttgg ggagaggaac atttccaatc tcaatgtcaa   5340
gaaaacacat agaatttctg tagtagatac taaaacagga tcagaattga ccgtgtatga   5400
ggctttccag agaaacctga ttgagaaaag tatatatctt gaactttcag ggcagcaata   5460
tcagtggaag gaagctatgt tttttgaatc ctatgggcat tcttctcata tgctgactga   5520
tactaaaaca ggattacact tcaatattaa tgaggctata gagcagggaa caattgacaa   5580
agccttggtc aaaaagtatc aggaaggcct catcacactt acagaacttg ctgattcttt   5640
gctgagccgg ttagtcccca agaaagattt gcacagtcct gttgcagggt attggctgac   5700
tgctagtggg gaaaggatct ctgtactaaa agcctcccgt agaaatttgg ttgatcggat   5760
tactgccctc cgatgccttg aagcccaagt cagtacaggg ggcataattg atcctcttac   5820
tggcaaaaag taccgggtgg ccgaagcttt gcatagaggc ctggttgatg aggggtttgc   5880
ccagcagctg cgacagtgtg aattagtaat cacagggatt ggccatccca tcactaacaa   5940
aatgatgtca gtggtggaag ctgtgaatgc aaatattata aataaggaaa tgggaatccg   6000
atgtttggaa tttcagtact tgacaggagg gttgatagag ccacaggttc actctcggtt   6060
atcaatagaa gaggctctcc aagtaggtat tatagatgtc ctcattgcca caaaactcaa   6120
agatcaaaag tcatatgtca gaaatataat atgccctcag acaaaaagaa agttgacata   6180
taaagaagcc ttagaaaaag ctgattttga tttccacaca ggacttaaac tgttagaagt   6240
atctgagccc ctgatgacag gaatttctag cctctactat tcttcctaat gggacatgtt   6300
taaataactg tgcaaggggt gatgcaggct ggttcatgcc actttttcag agtatgatga   6360
tatcggctac atatgcagtc tgtgaattat gtaacatact ctatttcttg agggctgcaa   6420
attgctaagt gctcaaaata gagtaagttt taaattgaaa attacataag atttaatgcc   6480
cttcaaatgg tttcatttag ccttgagaat ggtttttttga aacttggcca cactaaaatg   6540
tttttttttt tttacgtaga atgtgggata aacttgatga actccaagtt cacagtgtca   6600
tttcttcaga actccccttc attgaatagt gatcatttat taaatgataa attgcactcg   6660
ctgaaagagc acgtcatgaa gcaccatgga atcaaagaga aagatataaa ttcgttccca   6720
cagccttcaa gctgcagtgt tttagattgc ttcaaaaaat gaaaaagttt tgcctttttc   6780
gatatagtga ccttctttgc atattaaaat gtttaccaca atgtcccatt tctagttaag   6840
tcttcgcact tgaaagctaa cattatgaat attatgtgtt ggaggagggg aaggattttc   6900
ttcattctgt gtattttccg g                                              6921
```

<210> SEQ ID NO 118

-continued

<211> LENGTH: 946
<212> TYPE: DNA
<213> ORGANISM: Homo sapiens

<400> SEQUENCE: 118
cttctgactg ggctcaggct gacaggtaga gctcaccatg gcttcttgtg tccttgtccc 60
ctccccatca cagctgtggt gcagtccacc gtctccagtg gctatggcgg tgccagtggt 120
gtcggcagtg gcttaggcct gggtggagga agcagctact cctatggcag tggtcttggc 180
gttggaggtg gcttcagttc cagcagtggc agagccattg gggggtggcct cagctctgtt 240 ggaggcggca gttccaccat caagtacacc accacctcct cctccagcag gaagagctat 300
aagcactaaa gtgcgtctgc tagctctcgg tcccacagtc ctcaggcccc tctctggctg 360
cagagccctc tcctcaggtt gcctgtcctc tcctggcctc cagtctcccc tgctgtccca 420
ggtagagctg gggatgaatg cttagtgccc tcacttcttc tctctctctc tataccatct 480
gagcacccat tgctcaccat cagatcaacc tctgatttta catcatgatg taatcaccac 540
tggagcttca ctgttactaa attattaatt tcttgcctcc agtgttctat ctctgaggct 600
gagcattata agaaaatgac ctctgctcct tttcattgca gaaaattgcc aggggcttat 660
ttcagaacaa cttccactta ctttccactg gctctcaaac tctctaactt ataagtgttg 720 tgaacccccca cccaggcagt atccatgaaa gcacaagtga ctagtcctat gatgtacaaa 780
gcctgtatct ctgtgatgat ttctgtgctc ttcactgttt gcaattgcta aataaagcag 840
atttataata catatattct tttactttgc cttgctttgg ggccaaagtt ttgggcttaa 900 actttttat ctgataagtg aatagttgtt tttaaaagat aatcta 946

<210> SEQ ID NO 119
<211> LENGTH: 8948
<212> TYPE: DNA
<213> ORGANISM: Homo sapiens

<400> SEQUENCE: 119
tcaacagccc ctgctccttg ggcccctcca tgccatgccg taatctctcc cacccgacca 60
acaccaacac ccagctccga cgcagctcct ctgcgccctt gccgccctcc gagccacagc 120
tttcctcccg ctcctgcccc cggcccgtcg ccgtctccgc gctcgcagcg gcctcgggag 180
ggcccaggta gcgagcagcg acctcgcgag ccttccgcac tcccgcccgg ttccccggcc 240
gtccgcctat ccttggcccc ctccgctttc tccgcgccgg cccgcctcgc ttatgcctcg 300
gcgctgagcc gctctcccga ttgcccgccg acatgagctg caacggaggc tcccacccgc 360
ggatcaacac tctgggccgc atgatccgcg ccgagtctgg cccggacctg cgctacgagg 420
tgaccagcgg cggcgggggc accagcagga tgtactattc tcggcgcggc gtgatcaccg 480
accagaactc ggacggctac tgtcaaaccg gcacgatgtc caggcaccag aaccagaaca 540
ccatccagga gctgctgcag aactgctccg actgcttgat gcgagcagag ctcatcgtgc 600
agcctgaatt gaagtatgga gatggaatac aactgactcg gagtcgagaa ttggatgagt 660
gttttgccca ggccaatgac caaatggaaa tcctcgacag cttgatcaga gagatgcggc 720
agatgggcca gccctgtgat gcttaccaga aaaggcttct tcagctccaa gagcaaatgc 780
gagcccttta taaagccatc agtgtccctc gagtccgcag ggccagctcc aagggtggtg 840
gaggctacac ttgtcagagt ggctctggct gggatgagtt caccaaacat gtcaccagtg 900
aatgtttggg gtggatgagg cagcaaaggg cggagatgga catggtggcc tggggtgtgg 960
acctggcctc agtggagcag cacattaaca gccaccgggg catccacaac tccatcggcg 1020

-continued

```
actatcgctg gcagctggac aaaatcaaag ccgacctgcg cgagaaatct gcgatctacc   1080
agttggagga ggagtatgaa aacctgctga aagcgtcctt tgagaggatg gatcacctgc   1140
gacagctgca gaacatcatt caggccacgt ccagggagat catgtggatc aatgactgcg   1200
aggaggagga gctgctgtac gactggagcg acaagaacac caacatcgct cagaaacagg   1260
aggccttctc catacgcatg agtcaactgg aagttaaaga aaaagagctc aataagctga   1320
aacaagaaag tgaccaactt gtcctcaatc agcatccagc ttcagacaaa attgaggcct   1380
atatggacac tctgcagacg cagtggagtt ggattcttca gatcaccaag tgcattgatg   1440
ttcatctgaa agaaaatgct gcctactttc agtttttga agaggcgcag tctactgaag   1500
catacctgaa ggggctccag gactccatca ggaagaagta cccctgcgac aagaacatgc   1560
ccctgcagca cctgctggaa cagatcaagg agctggagaa agaacgagag aaaatccttg   1620
aatacaagcg tcaggtgcag aacttggtaa acaagtctaa gaagattgta cagctgaagc   1680
ctcgtaaccc agactacaga agcaataaac ccattattct cagagctctc tgtgactaca   1740
aacaagatca gaaaatcgtg cataaggggg atgagtgtat cctgaaggac aacaacgagc   1800
gcagcaagtg gtacgtgacg ggcccgggag gcgttgacat gcttgttccc tctgtggggc   1860
tgatcatccc tcctccgaac ccactggccg tggacctctc ttgcaagatt gagcagtact   1920
acgaagccat cttggctctg tggaaccagc tctacatcaa catgaagagc ctggtgtcct   1980
ggcactactg catgattgac atagagaaga tcagggccat gacaatcgcc aagctgaaaa   2040
caatgcggca ggaagattac atgaagacga tagccgacct tgagttacat taccaagagt   2100
tcatcagaaa tagccaaggc tcagagatgt ttggagatga tgacaagcgg aaaatacagt   2160
ctcagttcac cgatgcccag aagcattacc agaccctggt cattcagctc cctggctatc   2220
cccagcacca gacagtgacc acaactgaaa tcactcatca tggaacctgc caagatgtca   2280
accataataa agtaattgaa accaacagag aaaatgacaa gcaagaaaca tggatgctga   2340
tggagctgca gaagattcgc aggcagatag agcactgcga gggcaggatg actctcaaaa   2400
acctccctct agcagaccag gggtcttctc accacatcac agtgaaaatt aacgagctta   2460
agagtgtgca gaatgattca caagcaattg ctgaggttct caaccagctt aaagatatgc   2520
ttgccaactt cagaggttct gaaaagtact gctatttaca gaatgaagta tttggactat   2580
ttcagaaact ggaaaatatc aatggtgtta cagatggcta cttaaatagc ttatgcacag   2640
taagggcact gctccaggct attctccaaa cagaagacat gttaaaggtt tatgaagcca   2700
ggctcactga ggaggaaact gtctgcctgg acctggataa agtggaagct taccgctgtg   2760
gactgaagaa aataaaaaat gacttgaact tgaagaagtc gttgttggcc actatgaaga   2820
cagaactaca gaaagcccag cagatccact ctcagacttc acagcagtat ccactttatg   2880
atctggactt gggcaagttc ggtgaaaaag tcacacagct gacagaccgc tggcaaagga   2940
tagataaaca gatcgacttt agattatggg acctggagaa acaaatcaag caattgagga   3000
attatcgtga taactatcag gctttctgca agtggctcta tgatcgtaaa cgccgccagg   3060
attccttaga atccatgaaa tttggagatt ccaacacagt catgcggttt ttgaatgagc   3120
agaagaactt gcacagtgaa atatctggca aacgagacaa atcagaggaa gtacaaaaaa   3180
ttgctgaact ttgcgccaat tcaattaagg attatgagct ccagctggcc tcatacacct   3240
caggactgga aactctgctg aacataccta tcaagaggac catgattcag tccccttctg   3300
gggtgattct gcaagaggct gcagatgttc atgctcggta cattgaacta cttacaagat   3360
```

-continued

```
ctggagacta ttacaggttc ttaagtgaga tgctgaagag tttggaagat ctgaagctga   3420
aaaataccaa gatcgaagtt ttggaagagg agctcagact ggcccgagat gccaactcgg   3480
aaaactgtaa taagaacaaa ttcctggatc agaacctgca gaaataccag gcagagtgtt   3540
cccagttcaa agcgaagctt gcgagcctgg aggagctgaa gagacaggct gagctggatg   3600
ggaagtcggc taagcaaaat ctagacaagt gctacggcca aataaaagaa ctcaatgaga   3660
agatcacccg actgacttat gagattgaag atgaaaagag aagaagaaaa tctgtggaag   3720
acagatttga ccaacagaag aatgactatg accaactgca gaaagcaagg caatgtgaaa   3780
aggagaacct tggttggcag aaattagagt ctgagaaagc catcaaggag aaggagtacg   3840
agattgaaag gttgagggtt ctactgcagg aagaaggcac ccggaagaga gaatatgaaa   3900
atgagctggc aaaggtaaga aaccactata atgaggagat gagtaattta aggaacaagt   3960
atgaaacaga gattaacatt acgaagacca ccatcaagga gatatccatg caaaaagagg   4020
atgattccaa aaatcttaga aaccagcttg atagactttc aagggaaaat cgagatctga   4080
aggatgaaat tgtcaggctc aatgacagca tcttgcaggc cactgagcag cgaaggcgag   4140
ctgaagaaaa cgcccttcag caaaaggcct gtggctctga gataatgcag aagaagcagc   4200
atctggagat agaactgaag caggtcatgc agcagcgctc tgaggacaat gcccggcaca   4260
agcagtccct ggaggaggct gccaagacca ttcaggacaa aaataaggag atcgagagac   4320
tcaaagctga gtttcaggag gaggccaagc gccgctggga atatgaaaat gaactgagta   4380
aggtaagaaa caattatgat gaggagatca ttagcttaaa aaatcagttt gagaccgaga   4440
tcaacatcac caagaccacc atccaccagc tcaccatgca gaaggaagag gataccagtg   4500
gctaccgggc tcagatagac aatctcaccc gagaaaacag gagcttatct gaagaaataa   4560
agaggctgaa gaacactcta acccagacca cagagaatct caggagggtg gaagaagaca   4620
tccaacagca aaaggccact ggctctgagg tgtctcagag gaaacagcag ctggaggttg   4680
agctgagaca agtcactcag atgcgaacag aggagagcgt aagatataag caatctcttg   4740
atgatgctgc caaaaccatc caggataaaa acaaggagat agaaaggtta aaacaactga   4800
tcgacaaaga aacaaatgac cggaaatgcc tggaagatga aaacgcgaga ttacaaaggg   4860
tccagtatga cctgcagaaa gcaaacagta gtgcgacgga gacaataaac aaactgaagg   4920
ttcaggagca agaactgaca cgcctgagga tcgactatga aagggtttcc caggagagga   4980
ctgtgaagga ccaggatatc acgcggttcc agaactctct gaaagagctg cagctgcaga   5040
agcagaaggt ggaagaggag ctgaatcggc tgaagaggac cgcgtcagaa gactcctgca   5100
agaggaagaa gctggaggaa gagctggaag gcatgaggag gtcgctgaag gagcaagcca   5160
tcaaaatcac caacctgacc cagcagctgg agcaggcatc cattgttaag aagaggagtg   5220
aggatgacct ccggcagcag agggacgtgc tggatggcca cctgagggaa aagcagagga   5280
cccaggaaga gctgaggagg ctctcttctg aggtcgaggc cctgaggcgg cagttactcc   5340
aggaacagga aagtgtcaaa caagctcact tgaggaatga gcatttccag aaggcgatag   5400
aagataaaag cagaagctta aatgaaagca aaatagaaat tgagaggctg cagtctctca   5460
cagagaacct gaccaaggag cacttgatgt tagaagaaga actgcggaac ctgaggctgg   5520
agtacgatga cctgaggaga ggacgaagcg aagcggacag tgataaaaat gcaaccatct   5580
tggaactaag gagccagctg cagatcagca acaaccggac cctggaactg caggggctga   5640
ttaatgattt acagagagag agggaaaatt tgagacagga aattgagaaa ttccaaaagc   5700
aggctttaga ggcatctaat aggattcagg aatcaaagaa tcagtgtact caggtggtac   5760
```

-continued

```
aggaaagaga gagccttctg gtgaaaatca aagtcctgga gcaagacaag gcaaggctgc   5820
agaggctgga ggatgagctg aatcgtgcaa aatcaactct agaggcagaa accagggtga   5880
aacagcgcct ggagtgtgag aaacagcaaa ttcagaatga cctgaatcag tggaagactc   5940
aatattcccg caaggaggag gctattagga agatagaatc ggaaagagaa aagagtgaga   6000
gagagaagaa cagtcttagg agtgagatcg aaagactcca agcagagatc aagagaattg   6060
aagagaggtg caggcgtaag ctggaggatt ctaccaggga gacacagtca cagttagaaa   6120
cagaacgctc ccgatatcag agggagattg ataaactcag acagcgccca tatgggtccc   6180
atcgagagac ccagactgag tgtgagtgga ccgttgacac ctccaagctg gtgtttgatg   6240
ggctgaggaa gaaggtgaca gcaatgcagc tctatgagtg tcagctgatc gacaaaacaa   6300
ccttggacaa actattgaag gggaagaagt cagtggaaga agttgcttct gaaatccagc   6360
cattccttcg gggtgcagga tctatcgctg gagcatctgc ttctcctaag gaaaaatact   6420
ctttggtaga ggccaagaga aagaaattaa tcagcccaga atccacagtc atgcttctgg   6480
aggcccaggc agctacaggt ggtataattg atccccatcg gaatgagaag ctgactgtcg   6540
acagtgccat agctcgggac ctcattgact tcgatgaccg tcagcagata tatgcagcag   6600
aaaaagctat cactggtttt gatgatccat tttcaggcaa gacagtatct gtttcagaag   6660
ccatcaagaa aaatttgatt gatagagaaa ccggaatgcg cctgctggaa gcccagattg   6720
cttcaggggg tgtagtagac cctgtgaaca gtgtcttttt gccaaaagat gtcgccttgg   6780
cccgggggct gattgataga gatttgtatc gatccctgaa tgatccccga gatagtcaga   6840
aaaactttgt ggatccagtc accaaaaaga aggtcagtta cgtgcagctg aaggaacggt   6900
gcagaatcga accacatact ggtctgctct tgctttcagt acagaagaga agcatgtcct   6960
tccaaggaat cagacaacct gtgaccgtca ctgagctagt agattctggt atattgagac   7020
cgtccactgt caatgaactg gaatctggtc agatttctta tgacgaggtt ggtgagagaa   7080
ttaaggactt cctccagggt tcaagctgca tagcaggcat atacaatgag accacaaaac   7140
agaagcttgg catttatgag gccatgaaaa ttggcttagt ccgacctggt actgctctgg   7200
agttgctgga agcccaagca gctactggct ttatagtgga tcctgttagc aacttgaggt   7260
taccagtgga ggaagcctac aagagaggtc tggtgggcat tgagttcaaa gagaagctcc   7320
tgtctgcaga acgagctgtc actgggtata atgatcctga aacaggaaac atcatctctt   7380
tgttccaagc catgaataag gaactcatcg aaaagggcca cggtattcgc ttattagaag   7440
cacagatcgc aaccgggggg atcattgacc caaaggagag ccatcgttta ccagttgaca   7500
tagcatataa gaggggctat ttcaatgagg aactcagtga gattctctca gatccaagtg   7560
atgataccaa aggatttttt gaccccaaca ctgaagaaaa tcttacctat ctgcaactaa   7620
aagaaagatg cattaaggat gaggaaacag ggctctgtct tctgcctctg aaagaaaaga   7680
agaaacaggt gcagacatca caaaagaata ccctcaggaa gcgtagagtg gtcatagttg   7740
acccagaaac caataaagaa atgtctgttc aggaggccta caagaagggc ctaattgatt   7800
atgaaacctt caaagaactg tgtgagcagg aatgtgaatg ggaagaaata accatcacgg   7860
gatcagatgg ctccaccagg gtggtcctgg tagatagaaa gacaggcagt cagtatgata   7920
ttcaagatgc tattgacaag ggccttgttg acaggaagtt ctttgatcag taccgatccg   7980
gcagcctcag cctcactcaa tttgctgaca tgatctcctt gaaaaatggt gtcggcacca   8040
gcagcagcat gggcagtggt gtcagcgatg atgtttttag cagctcccga catgaatcag   8100
```

-continued

```
taagtaagat ttccaccata tccagcgtca ggaatttaac cataaggagc agctcttttt   8160

cagacaccct ggaagaatcg agccccattg cagccatctt tgacacagaa aacctggaga   8220

aaatctccat tacagaaggt atagagcggg gcatcgttga cagcatcacg ggtcagaggc   8280

ttctggaggc tcaggcctgc acaggtggca tcatccaccc aaccacgggc cagaagctgt   8340

cacttcagga cgcagtctcc cagggtgtga ttgaccaaga catggccacc agcgtgaagc   8400

ctgctcagaa agccttcata ggcttcgagg gtgtgaaggg aaagaagaag atgtcagcag   8460

cagaggcagt gaaagaaaaa tggctcccgt atgaggctgg ccagcgcttc ctggagttcc   8520

agtacctcac gggaggtctt gttgacccgg aagtgcatgg gaggataagc accgaagaag   8580

ccatccggaa ggggttcata gatggccgcg ccgcacagag gctgcaagac accagcagct   8640

atgccaaaat cctgacctgc cccaaaacca aattaaaaat atcctataag gatgccataa   8700

atcgctccat ggtagaagat atcactgggc tgcgccttct ggaagccgcc tccgtgtcgt   8760

ccaagggctt acccagccct tacaacatgt cttcggctcc ggggtcccgc tccggctccc   8820

gctcgggatc tcgctccgga tctcgctccg ggtcccgcag tgggtcccgg agaggaagct   8880

ttgacgccac agggaattct tcctactctt attcctactc atttagcagt agttctattg   8940

ggcactag                                                            8948
```

<210> SEQ ID NO 120
<211> LENGTH: 587
<212> TYPE: DNA
<213> ORGANISM: Homo sapiens
<220> FEATURE:
<221> NAME/KEY: misc_feature
<222> LOCATION: 91, 131, 256, 263, 332, 392, 400, 403, 461, 496, 497, 499, 510, 511, 518, 519, 539, 554, 560, 576
<223> OTHER INFORMATION: n = A,T,C or G

<400> SEQUENCE: 120

```
cgtcctaagc acttagacta catcagggaa gaacacagac cacatccctg tcctcatgcg     60

gcttatgttt tctggaagaa agtggagacc nagtccttgg ctttagggct ccccggctgg    120

gggctgtgca ntccggtcag ggcgggaagg gaaatgcacc gctgcatgtg aacttacagc    180

ccaggcggat gccccttccc ttagcactac ctggcctcct gcatcccctc gcctcatgtt    240

cctcccacct tcaaanaatg aanaacccca tgggcccagc cccttgccct ggggaaccaa    300

ggcagccttc caaaactcag gggctgaagc anactattag ggcaggggct gactttgggt    360

gacactgccc attccctctc agggcagctc angtcacccn ggnctcttga acccagcctg    420

ttcctttgaa aaagggcaaa actgaaaagg gcttttccta naaaaagaaa aaccagggaa    480

ctttgccagg gcttcnntnt taccaaaacn ncttctcnng gatttttaat tccccattng    540

gcctccactt accnggggcn atgccccaaa attaanaatt tcccatc                 587
```

<210> SEQ ID NO 121
<211> LENGTH: 619
<212> TYPE: DNA
<213> ORGANISM: Homo sapiens
<220> FEATURE:
<221> NAME/KEY: misc_feature
<222> LOCATION: 260, 527, 560, 564, 566, 585, 599
<223> OTHER INFORMATION: n = A,T,C or G

<400> SEQUENCE: 121

```
cactagtagg atagaaacac tgtgtcccga gagtaaggag agaagctact attgattaga     60

gcctaaccca ggttaactgc aagaagaggc gggatacttt cagctttcca tgtaactgta    120
```

-continued

```
tgcataaagc caatgtagtc cagtttctaa gatcatgttc caagctaact gaatcccact    180

tcaatacaca ctcatgaact cctgatggaa caataacagg cccaagcctg tggtatgatg    240

tgcacacttg ctagactcan aaaaaatact actctcataa atgggtggga gtattttggt    300

gacaacctac tttgcttggc tgagtgaagg aatgatattc atatattcat ttattccatg    360

gacatttagt tagtgctttt tatataccag gcatgatgct gagtgacact cttgtgtata    420

tttccaaatt tttgtacagt cgctgcacat atttgaaatc atatattaag acttccaaaa    480

aatgaagtcc ctggtttttc atggcaactt gatcagtaaa ggattcncct ctgtttggta    540

cttaaaacat ctactatatn gttnanatga aattcctttt ccccncctcc cgaaaaaana    600

aagtggtggg gaaaaaaaa                                                 619
```

<210> SEQ ID NO 122
<211> LENGTH: 1475
<212> TYPE: DNA
<213> ORGANISM: Homo sapiens

<400> SEQUENCE: 122

```
tccacctgtc cccgcagcgc cggctcgcgc cctcctgccg cagccaccga gccgccgtct     60

agcgccccga cctcgccacc atgagagccc tgctggcgcg cctgcttctc tgcgtcctgg    120

tcgtgagcga ctccaaaggc agcaatgaac ttcatcaagt tccatcgaac tgtgactgtc    180

taaatggagg aacatgtgtg tccaacaagt acttctccaa cattcactgg tgcaactgcc    240

caaagaaatt cggagggcag cactgtgaaa tagataagtc aaaaacctgc tatgagggga    300

atggtcactt ttaccgagga aaggccagca ctgacaccat gggccggccc tgcctgccct    360

ggaactctgc cactgtcctt cagcaaacgt accatgccca cagatctgat gctcttcagc    420

tgggcctggg gaaacataat tactgcagga acccagacaa ccggaggcga ccctggtgct    480

atgtgcaggt gggcctaaag ccgcttgtcc aagagtgcat ggtgcatgac tgcgcagatg    540

gaaaaaagcc ctcctctcct ccagaagaat taaaatttca gtgtggccaa aagactctga    600

ggccccgctt taagattatt gggggagaat tcaccaccat cgagaaccag ccctggtttg    660

cggccatcta caggaggcac cggggggggct ctgtcaccta cgtgtgtgga ggcagcctca    720

tcagcccttg ctgggtgatc agcgccacac actgcttcat tgattaccca aagaaggagg    780

actacatcgt ctacctgggt cgctcaaggc ttaactccaa cacgcaaggg gagatgaagt    840

ttgaggtgga aaacctcatc ctacacaagg actacagcgc tgacacgctt gctcaccaca    900

acgacattgc cttgctgaag atccgttcca aggagggcag gtgtgcgcag ccatcccgga    960

ctatacagac catctgcctg ccctcgatgt ataacgatcc ccagtttggc acaagctgtg   1020

agatcactgg ctttggaaaa gagaattcta ccgactatct ctatccggag cagctgaaga   1080

tgactgttgt gaagctgatt tcccaccggg agtgtcagca gccccactac tacggctctg   1140

aagtcaccac caaaatgctg tgtgctgctg acccacagtg gaaaacagat tcctgccagg   1200

gagactcagg gggacccctc gtctgttccc tccaaggccg catgactttg actggaattg   1260

tgagctgggg ccgtggatgt gccctgaagg acaagccagg cgtctacacg agagtctcac   1320

acttcttacc ctggatccgc agtcacacca aggaagagaa tggcctggcc ctctgagggt   1380

ccccagggag gaaacgggca ccacccgctt tcttgctggt tgtcattttt gcagtagagt   1440

catctccatc agctgtaaga agagactggg aagat                              1475
```

<210> SEQ ID NO 123
<211> LENGTH: 2294

<212> TYPE: DNA
<213> ORGANISM: Homo sapiens

<400> SEQUENCE: 123
cagcgccggc tcgcgccctc ctgccgcagc caccgagccg ccgtctagcg ccccgacctc 60
gccaccatga gagccctgct ggcgcgcctg cttctctgcg tcctggtcgt gagcgactcc 120
aaaggcagca atgaacttca tcaagttcca tcgaactgtg actgtctaaa tggaggaaca 180
tgtgtgtcca acaagtactt ctccaacatt cactggtgca actgcccaaa gaaattcgga 240
gggcagcact gtgaaataga taagtcaaaa acctgctatg aggggaatgg tcacttttac 300
cgaggaaagg ccagcactga caccatgggc cggccctgcc tgccctggaa ctctgccact 360
gtccttcagc aaacgtacca tgcccacaga tctgatgctc ttcagctggg cctgggggaaa 420 cataattact gcaggaaccc agacaaccgg aggcgaccct ggtgctatgt gcaggtgggc 480
ctaaagccgc ttgtccaaga gtgcatggtg catgactgcg cagatggaaa aaagccctcc 540
tctcctccag aagaattaaa atttcagtgt ggccaaaaga ctctgaggcc ccgctttaag 600
attattgggg gagaattcac caccatcgag aaccagccct ggtttgcggc catctacagg 660
aggcaccggg ggggctctgt cacctacgtg tgtggaggca gcctcatcag cccttgctgg 720
gtgatcagcg ccacacactg cttcattgat tacccaaaga aggaggacta catcgtctac 780
ctgggtcgct caaggcttaa ctccaacacg caaggggaga tgaagtttga ggtggaaaac 840
ctaatcctac acaaggacta cagcgctgac acgcttgctc accacaacga cattgccttg 900
ctgaagatcc gttccaagga gggcaggtgt gcgcagccat cccggactat acagaccatc 960
tgcctgccct cgatgtataa cgatccccag tttggcacaa gctgtgagat cactggcttt 1020
ggaaaagaga attctaccga ctatctctat ccggagcagc tgaaaatgac tgttgtgaag 1080
ctgatttccc accgggagtg tcagcagccc cactactacg gctctgaagt caccaccaaa 1140
atgctgtgtg ctgctgaccc acagtggaaa acagattcct gccagggaga ctcaggggga 1200
cccctcgtct gttccctcca aggccgcatg actttgactg gaattgtgag ctggggccgt 1260
ggatgtgccc tgaaggacaa gccaggcgtc tacacgagag tctcacactt cttaccctgg 1320
atccgcagtc acaccaagga agagaatggc ctggccctct gagggtcccc agggaggaaa 1380
cgggcaccac ccgctttctt gctggttgct attttgcagt agagtcatct ccatcagctg 1440
taagaagagc tgggaatata ggctctgcac agatggattt gcctgtgcca ccaccagggc 1500
gaacgacaat agctttaccc tcaggcatag gcctgggtgc tggctgccca gacccctctg 1560
gccaggatgg aggggtggtc ctgactcaac atgttactga ccagcaactt gtctttttct 1620
ggactgaagc ctgcaggagt taaaaagggc agggcatctc ctgtgcatgg gctcgaaggg 1680
agagccagct cccccgaccg gtgggcattt gtgaggccca tggttgagaa atgaataatt 1740
tcccaattag gaagtgtaag cagctgaggt ctcttgaggg agcttagcca atgtgggagc 1800
agcggtttgg ggagcagaga cactaacgac ttcagggcag ggctctgata ttccatgaat 1860
gtatcaggaa atatatatgt gtgtgtatgt ttgcacactt gtgtgtgggc tgtgagtgta 1920
agtgtgagta agagctggtg tctgattgtt aagtctaaat atttccttaa actgtgtgga 1980
ctgtgatgcc acacagagtg gtctttctgg agaggttata ggtcactcct ggggcctctt 2040
gggtccccca cgtgacagtg cctgggaatg tattattctg cagcatgacc tgtgaccagc 2100
actgtctcag tttcactttc acatagatgt ccctttcttg gccagttatc ccttcctttt 2160
agcctagttc atccaatcct cactgggtgg ggtgaggacc actcctgtac actgaatatt 2220

-continued

```
tatatttcac tatttttatt tatatttttg taattttaaa taaaagtgat caataaaatg   2280

tgatttttct gatg                                                     2294


<210> SEQ ID NO 124
<211> LENGTH: 956
<212> TYPE: DNA
<213> ORGANISM: Homo sapiens

<400> SEQUENCE: 124

gatgagttcc gcaccaagtt tgagacagac caggccctgc gcctgagtgt ggaggccgac     60

atcaatggcc tgcgcagggt gctggatgag ctgaccctgg ccagagccga cctggagatg    120

cagattgaga acctcaagga ggagctggcc tacctgaaga agaaccacga ggaggagatg    180

aacgccctgc gaggccaggt gggtggtgag atcaatgtgg agatggacgc tgccccaggc    240

gtggacctga gccgcatcct caacgagatg cgtgaccagt atgagaagat ggcagagaag    300

aaccgcaagg atgccgagga ttggttcttc agcaagacag aggaactgaa ccgcgaggtg    360

gccaccaaca gtgagctggt gcagagtggc aagagtgaga tctcggagct ccggcgcacc    420

atgcaggcct tggagataga gctgcagtcc cagctcagca tgaaagcatc cctggagggc    480

aacctggcgg agacagagaa ccgctactgc gtgcagctgt cccagatcca ggggctgatt    540

ggcagcgtgg aggagcagct ggcccagctt cgctgcgaga tggagcagca gaaccaggaa    600

tacaaaatcc tgctggatgt gaagacgcgg ctggagcagg agattgccac ctaccgccgc    660

ctgctggagg gagaggatgc ccacctgact cagtacaaga aagaaccggt gaccacccgt    720

caggtgcgta ccattgtgga agaggtccag gatggcaagg tcatctcctc ccgcgagcag    780

gtccaccaga ccacccgctg aggactcagc taccccggcc ggccacccag gaggcaggga    840

cgcagccgcc ccatctgccc cacagtctcc ggcctctcca gcctcagccc cctgcttcag    900

tcccttcccc atgcttcctt gcctgatgac aataaaagct tgttgactca gctatg        956


<210> SEQ ID NO 125
<211> LENGTH: 486
<212> TYPE: DNA
<213> ORGANISM: Homo sapiens
<220> FEATURE:
<221> NAME/KEY: misc_feature
<222> LOCATION: 16
<223> OTHER INFORMATION: n = A,T,C or G

<400> SEQUENCE: 125

aaattatata tagtgnttca gctcccattg tggtgttcat agtcttctag gaacagataa     60

acttaagtat tcaattcact cttggcattt tttctttaat ataggctttt tagcctattt    120

ttggaaaact gcttttcttc tgagaacctt attctgaatg tcatcaactt taccaaacct    180

tctaagtcca gagctaactt agtactgttt aagttactat tgactgaatt ttcttcattt    240

tctgtttagc cagtgttacc aaggtaagct ggggaatgaa gtataccaac ttctttcaga    300

gcattttagg acattatggc agctttagaa ggctgtcttg tttctagcca agggagagcc    360

agcgcaggtt ttggatacta gagaaagtca tttgcttgta ctattgccat tttagaaagc    420

tctgatgtga attcaaattt tacctctgtt acttaaagcc aacaatttta aggcagtagt    480

tttact                                                               486


<210> SEQ ID NO 126
<211> LENGTH: 3552
<212> TYPE: DNA
<213> ORGANISM: Homo sapiens
```

-continued

<400> SEQUENCE: 126
cggcaggcag gtctcgtctc ggcaccctcc cggcgcccgc gttctcctgg ccctgcccgg 60
catcccgatg gccgccgctg ggccccggcg ctccgtgcgc ggagccgtct gcctgcatct 120
gctgctgacc ctcgtgatct tcagtcgtgc tggtgaagcc tgcaaaaagg tgatacttaa 180
tgtaccttct aaactagagg cagacaaaat aattggcaga gttaatttgg aagagtgctt 240
caggtctgca gacctcatcc ggtcaagtga tcctgatttc agagttctaa atgatgggtc 300
agtgtacaca gccagggctg ttgcgctgtc tgataagaaa agatcattta ccatatggct 360
ttctgacaaa aggaaacaga cacagaaaga ggttactgtg ctgctagaac atcagaagaa 420
ggtatcgaag acaagacaca ctagagaaac tgttctcagg cgtgccaaga ggagatgggc 480
acctattcct tgctctatgc aagagaattc cttgggccct ttcccattgt ttcttcaaca 540
agttgaatct gatgcagcac agaactatac tgtcttctac tcaataagtg gacgtggagt 600
tgataaagaa cctttaaatt tgttttatat agaaagagac actggaaatc tattttgcac 660
tcggcctgtg gatcgtgaag aatatgatgt ttttgatttg attgcttatg cgtcaactgc 720
agatggatat tcagcagatc tgccccctccc actacccatc agggtagagg atgaaaatga 780
caaccaccct gttttcacag aagcaattta taattttgaa gttttggaaa gtagtagacc 840
tggtactaca gtgggggtgg tttgtgccac agacagagat gaaccggaca caatgcatac 900
gcgcctgaaa tacagcattt tgcagcagac accaaggtca cctgggctct tttctgtgca 960
tcccagcaca ggcgtaatca ccacagtctc tcattatttg gacagagagg ttgtagacaa 1020
gtactcattg ataatgaaag tacaagacat ggatggccag tttttggat tgataggcac 1080
atcaacttgt atcataacag taacagattc aaatgataat gcacccactt tcagacaaaa 1140
tgcttatgaa gcatttgtag aggaaaatgc attcaatgtg gaaatcttac gaatacctat 1200
agaagataag gatttaatta acactgccaa ttggagagtc aattttacca ttttaaaggg 1260
aaatgaaaat ggacatttca aaatcagcac agacaaagaa actaatgaag gtgttctttc 1320
tgttgtaaag ccactgaatt atgaagaaaa ccgtcaagtg aacctggaaa ttggagtaaa 1380
caatgaagcg ccatttgcta gagatattcc cagagtgaca gccttgaaca gagccttggt 1440
tacagttcat gtgagggatc tggatgaggg gcctgaatgc actcctgcag cccaatatgt 1500
gcggattaaa gaaaacttag cagtggggtc aaagatcaac ggctataagg catatgaccc 1560
cgaaaataga aatggcaatg gtttaaggta caaaaaattg catgatccta aaggttggat 1620
caccattgat gaaatttcag ggtcaatcat aacttccaaa atcctggata gggaggttga 1680
aactcccaaa aatgagttgt ataatattac agtcctggca atagacaaag atgatagatc 1740
atgtactgga acacttgctg tgaacattga agatgtaaat gataatccac cagaaatact 1800
tcaagaatat gtagtcattt gcaaaccaaa aatggggtat accgacattt tagctgttga 1860
tcctgatgaa cctgtccatg gagctccatt ttatttcagt ttgcccaata cttctccaga 1920
aatcagtaga ctgtggagcc tcaccaaagt taatgataca gctgcccgtc tttcatatca 1980
gaaaaatgct ggatttcaag aatataccat tcctattact gtaaaagaca gggccggcca 2040
agctgcaaca aaattattga gagttaatct gtgtgaatgt actcatccaa ctcagtgtcg 2100
tgcgacttca aggagtacag gagtaatact tggaaaatgg gcaatccttg caatattact 2160
gggtatagca ctgctctttt ctgtattgct aactttagta tgtggagttt ttggtgcaac 2220
taaagggaaa cgttttcctg aagatttagc acagcaaaac ttaattatat caaacacaga 2280

-continued

```
agcacctgga gacgatagag tgtgctctgc caatggattt atgacccaaa ctaccaacaa   2340

ctctagccaa ggtttttgtg gtactatggg atcaggaatg aaaaatggag ggcaggaaac   2400

cattgaaatg atgaaaggag gaaaccagac cttggaatcc tgccgggggg ctgggcatca   2460

tcataccctg gactcctgca ggggaggaca cacggaggtg gacaactgca gatacactta   2520

ctcggagtgg cacagtttta ctcaaccccg tctcggtgaa aaattgcatc gatgtaatca   2580

gaatgaagac cgcatgccat cccaagatta tgtcctcact tataactatg agggaagagg   2640

atctccagct ggttctgtgg gctgctgcag tgaaaagcag gaagaagatg gccttgactt   2700

tttaaataat ttggaaccca aatttattac attagcagaa gcatgcacaa agagataatg   2760

tcacagtgct acaattaggt ctttgtcaga cattctggag gtttccaaaa ataatattgt   2820

aaagttcaat ttcaacatgt atgtatatga tgattttttt ctcaattttg aattatgcta   2880

ctcaccaatt tatattttta aagcaagttg ttgcttatct tttccaaaaa gtgaaaaatg   2940

ttaaaacaga caactggtaa atctcaaact ccagcactgg aattaaggtc tctaaagcat   3000

ctgctctttt ttttttttac agatatttta gtaataaata tgctggataa atattagtcc   3060

aacaatagct aagttatgct aatatcacat tattatgtat tcactttaag tgatagttta   3120

aaaaataaac aagaaatatt gagtatcact atgtgaagaa agttttggaa aagaaacaat   3180

gaagactgaa ttaaattaaa aatgttgcag ctcataaaga attggactca cccctactgc   3240

actaccaaat tcatttgact ttggaggcaa aatgtgttga agtgccctat gaagtagcaa   3300

ttttctatag gaatatagtt ggaaataaat gtgtgtgtgt atattattat taatcaatgc   3360

aatatttaaa tgaaatgaga acaaagagga aaatggtaaa aacttgaaat gaggctgggg   3420

tatagtttgt cctacaatag aaaaaagaga gagcttccta ggcctgggct cttaaatgct   3480

gcattataac tgagtctatg aggaaatagt tcctgtccaa tttgtgtaat ttgtttaaaa   3540

ttgtaaataa at                                                      3552
```

```
<210> SEQ ID NO 127
<211> LENGTH: 754
<212> TYPE: DNA
<213> ORGANISM: Homo sapiens

<400> SEQUENCE: 127

tttttttttt ttgtcattgt tcattgattt taatgagaaa gctaagagag gaaataagta     60

gcctttcaaa ggtcacacag aagtaagtga cagatccagg attcatatcc aagcattctg    120

gctctagtgt ccatgcttct caaccattat gacccaatat tcaaccaaat caatactgaa    180

ggacacgtga aatgtatccg gtattttact attacaaaca aaaatccaat gaacattctt    240

gaagacatac acaaaaataa tggttacaat agaagttact ggaattgaaa ttttggttca    300

acctatatta aaatgtaagg cttttgatat agctaataga tttttgaaat gatcagtctt    360

aacgtttgta ggggagcaca ctcctgcatg gggaaaagat tcactgtgaa gcacagagca    420

cctttatggt tggatcatct tgtcattaaa gttcaggcgt tatctatcct gtaagtggca    480

gaatcaagac tgcaatatcg cctgcttttc tttttaactc atgttttccc ttgactacac    540

tggtcctcaa agtaaaaccc ctgtgtcagt gtactattca tggaatactc tgcaattata    600

accaccttct aatactttta atacccaatc aaaatttatt atacatatgt atcatagata    660

ctcatctgta aagctgtgct tcaaaatagt gatctcttcc caacattaca atatatatta    720

atgatgtcga acctgcccgg gcggccgctc gaag                                754
```

-continued

<210> SEQ ID NO 128
<211> LENGTH: 374
<212> TYPE: DNA
<213> ORGANISM: Homo sapiens

<400> SEQUENCE: 128
aggttttgat taaaaaggca aatgatttta ttgttcgata atcttttaaa aaaataagag 60
gaaggagtaa aattaaagat gaaagatgat ttttatttcc ttgtgacctc tatatccccc 120
ttcccctgcc cttggtaagt aactcttgat ggagaaagga ttaaagactc ttatttaacc 180
aaaaaacaga gccagctaat catttccaaa ggttagtatc tccctgctga cctcttcttt 240
ggtttaattg aataaaacta tatgttcata tatgtattaa aacaactcag aataacatct 300
tttcttcctt agttaaggca ttataagggc tatactatca tccataataa ccaaggcaat 360
aacttaaaaa gctg 374

<210> SEQ ID NO 129
<211> LENGTH: 546
<212> TYPE: DNA
<213> ORGANISM: Homo sapiens

<400> SEQUENCE: 129 gtgtgatgg atatctgcag aattcgggct aagcgtggtc gcggcccgag gtctggaact 60
tcccagcacy tgaaaaggag cctcctgagc tgactcggct aaagccccac tttcgctcct 120
cctcatttct gcctactgat ttccttggag cattcatctg aatattaccg tttgctgtgt 180
aacctggtac atacatagca tgactccctg gaatagagtg ggctggggtg cttatgctgg 240
gagagtgatt gacatgcact ttcaagctat atctaccatt tgcagcaaag gagaaaaaat 300
acctcgagta aattccatca ttttttataa catcagcacc tgctccatca tcaaggagtc 360
tcagcgtaac aggatctcca gtctctggct caactgtggc agtgacagtg gcattaagaa 420
tgggataaaa tccctgtttc acattggcat aaatcatcac aggatgagga aaatggaggc 480
tgtctctttc cacaaaggct tccacagtgg ctgggggcac agacctgccc gggcggccgc 540
tcgaaa 546

<210> SEQ ID NO 130
<211> LENGTH: 5156
<212> TYPE: DNA
<213> ORGANISM: Homo sapiens

<400> SEQUENCE: 130
accaaccgag gcgccgggca gcgacccctg cagcggagac agagactgag cggcccggca 60
ccgccatgcc tgcgctctgg ctgggctgct gcctctgctt gtcgctcctc ctgcccgcag 120
cccgggccac ctccaggagg gaagtctgtg attgcaatgg gaagtccagg cagtgtatct 180
ttgatcggga acttcacaga caaactggta atggattccg ctgcctcaac tgcaatgaca 240
acactgatgg cattcactgc gagaagtgca agaatggctt ttaccggcac agagaaaggg 300
accgctgttt gccctgcaat tgtaactcca aaggttctct tagtgctcga tgtgacaact 360
ccggacggtg cagctgtaaa ccaggtgtga caggagccag atgcgaccga tgtctgccag 420
gcttccacat gctcacggat gcggggtgca cccaagacca gagactgcta gactccaagt 480
gtgactgtga cccagctggc atcgcagggc cctgtgacgc gggccgctgt gtctgcaagc 540
cagctgtcac tggagaacgc tgtgataggt gtcgatcagg ttactataat ctggatgggg 600
ggaaccctga gggctgtacc cagtgtttct gctatgggca ttcagccagc tgccgcagct 660

-continued

```
ctgcagaata cagtgtccat aagatcacct ctacctttca tcaagatgtt gatggctgga    720
aggctgtcca acgaaatggg tctcctgcaa agctccaatg gtcacagcgc catcaagatg    780
tgtttagctc agcccaacga ctagaccctg tctattttgt ggctcctgcc aaatttcttg    840
ggaatcaaca ggtgagctat ggtcaaagcc tgtcctttga ctaccgtgtg gacagaggag    900
gcagacaccc atctgcccat gatgtgattc tggaaggtgc tggtctacgg atcacagctc    960
ccttgatgcc acttggcaag acactgcctt gtgggctcac caagacttac acattcaggt   1020
taaatgagca tccaagcaat aattggagcc cccagctgag ttactttgag tatcgaaggt   1080
tactgcggaa tctcacagcc ctccgcatcc gagctacata tggagaatac agtactgggt   1140
acattgacaa tgtgaccctg atttcagccc gccctgtctc tggagcccca gcaccctggg   1200
ttgaacagtg tatatgtcct gttgggtaca aggggcaatt ctgccaggat tgtgcttctg   1260
gctacaagag agattcagcg agactggggc cttttggcac ctgtattcct tgtaactgtc   1320
aaggggggagg ggcctgtgat ccagacacag gagattgtta ttcaggggat gagaatcctg   1380
acattgagtg tgctgactgc ccaattggtt tctacaacga tccgcacgac ccccgcagct   1440
gcaagccatg tccctgtcat aacgggttca gctgctcagt gatgccggag acggaggagg   1500
tggtgtgcaa taactgccct cccggggtca ccggtgcccg ctgtgagctc tgtgctgatg   1560
gctactttgg ggaccccttt ggtgaacatg gcccagtgag gccttgtcag ccctgtcaat   1620
gcaacaacaa tgtggacccc agtgcctctg ggaattgtga ccggctgaca ggcaggtgtt   1680
tgaagtgtat ccacaacaca gccggcatct actgcgacca gtgcaaagca ggctacttcg   1740
gggacccatt ggctcccaac ccagcagaca agtgtcgagc ttgcaactgt aaccccatgg   1800
gctcagagcc tgtaggatgt cgaagtgatg gcacctgtgt ttgcaagcca ggatttggtg   1860
gccccaactg tgagcatgga gcattcagct gtccagcttg ctataatcaa gtgaagattc   1920
agatggatca gtttatgcag cagcttcaga gaatggaggc cctgatttca aaggctcagg   1980
gtggtgatgg agtagtacct gatacagagc tggaaggcag gatgcagcag gctgagcagg   2040
cccttcagga cattctgaga gatgcccaga tttcagaagg tgctagcaga tcccttggtc   2100
tccagttggc caaggtgagg agccaagaga acagctacca gagccgcctg gatgacctca   2160
agatgactgt ggaaagagtt cgggctctgg gaagtcagta ccagaaccga gttcgggata   2220
ctcacaggct catcactcag atgcagctga gcctggcaga aagtgaagct tccttgggaa   2280
acactaacat tcctgcctca gaccactacg tggggccaaa tggctttaaa agtctggctc   2340
aggaggccac aagattagca gaaagccacg ttgagtcagc cagtaacatg gagcaactga   2400
caagggaaac tgaggactat tccaaacaag ccctctcact ggtgcgcaag gccctgcatg   2460
aaggagtcgg aagcggaagc ggtagcccgg acggtgctgt ggtgcaaggg cttgtggaaa   2520
aattggagaa aaccaagtcc ctggcccagc agttgacaag ggaggccact caagcggaaa   2580
ttgaagcaga taggtcttat cagcacagtc tccgcctcct ggattcagtg tctcggcttc   2640
agggagtcag tgatcagtcc tttcaggtgg aagaagcaaa gaggatcaaa caaaaagcgg   2700
attcactctc aagcctggta accaggcata tggatgagtt caagcgtaca cagaagaatc   2760
tgggaaactg gaaagaagaa gcacagcagc tcttacagaa tggaaaaagt gggagagaga   2820
aatcagatca gctgctttcc cgtgccaatc ttgctaaaag cagagcacaa gaagcactga   2880
gtatgggcaa tgccactttt tatgaagttg agagcatcct taaaaacctc agagagtttg   2940
acctgcaggt ggacaacaga aaagcagaag ctgaagaagc catgaagaga ctctcctaca   3000
tcagccagaa ggtttcagat gccagtgaca agacccagca agcagaaaga gccctgggga   3060
```

-continued gcgctgctgc tgatgcacag agggcaaaga atggggccgg ggaggccctg gaaatctcca 3120
gtgagattga acaggagatt gggagtctga acttggaagc caatgtgaca gcagatggag 3180
ccttggccat ggaaaaggga ctggcctctc tgaagagtga gatgagggaa gtggaaggag 3240
agctggaaag gaaggagctg gagtttgaca cgaatatgga tgcagtacag atggtgatta 3300
cagaagccca gaaggttgat accagagcca agaacgctgg ggttacaatc caagacacac 3360
tcaacacatt agacggcctc ctgcatctga tggaccagcc tctcagtgta gatgaagagg 3420
ggctggtctt actggagcag aagctttccc gagccaagac ccagatcaac agccaactgc 3480
ggcccatgat gtcagagctg gaagagaggg cacgtcagca gaggggccac ctccatttgc 3540
tggagacaag catagatggg attctggctg atgtgaagaa cttggagaac attagggaca 3600
acctgccccc aggctgctac aatacccagg ctcttgagca acagtgaagc tgccataaat 3660
atttctcaac tgaggttctt gggatacaga tctcagggct cgggagccat gtcatgtgag 3720
tgggtgggat ggggacattt gaacatgttt aatgggtatg ctcaggtcaa ctgacctgac 3780
cccattcctg atcccatggc caggtggttg tcttattgca ccatactcct tgcttcctga 3840
tgctgggcaa tgaggcagat agcactgggt gtgagaatga tcaaggatct ggaccccaaa 3900
gaatagactg gatggaaaga caaactgcac aggcagatgt ttgcctcata atagtcgtaa 3960
gtggagtcct ggaatttgga caagtgctgt tgggatatag tcaacttatt ctttgagtaa 4020
tgtgactaaa ggaaaaaact ttgactttgc ccaggcatga aattcttcct aatgtcagaa 4080
cagagtgcaa cccagtcaca ctgtggccag taaaatacta ttgcctcata ttgtcctctg 4140
caagcttctt gctgatcaga gttcctccta cttacaaccc agggtgtgaa catgttctcc 4200
attttcaagc tggaagaagt gagcagtgtt ggagtgagga cctgtaaggc aggcccattc 4260
agagctatgg tgcttgctgg tgcctgccac cttcaagttc tggacctggg catgacatcc 4320
tttcttttaa tgatgccatg gcaacttaga gattgcattt ttattaaagc atttcctacc 4380
agcaaagcaa atgttgggaa agtatttact ttttcggttt caaagtgata gaaaagtgtg 4440
gcttgggcat tgaaagaggt aaaattctct agatttatta gtcctaattc aatcctactt 4500
ttagaacacc aaaaatgatg cgcatcaatg tattttatct tattttctca atctcctctc 4560
tctttcctcc acccataata agagaatgtt cctactcaca cttcagctgg gtcacatcca 4620
tccctccatt catccttcca tccatctttc catccattac ctccatccat ccttccaaca 4680
tatatttatt gagtacctac tgtgtgccag gggctggtgg gacagtggtg acatagtctc 4740
tgccctcata gagttgattg tctagtgagg aagacaagca tttttaaaaa ataaatttaa 4800
acttacaaac tttgtttgtc acaagtggtg tttattgcaa taaccgcttg gtttgcaacc 4860
tctttgctca acagaacata tgttgcaaga ccctcccatg ggggcacttg agttttggca 4920
aggctgacag agctctgggt tgtgcacatt tctttgcatt ccagctgtca ctctgtgcct 4980
ttctacaact gattgcaaca gactgttgag ttatgataac accagtggga attgctggag 5040
gaaccagagg cacttccacc ttggctggga agactatggt gctgccttgc ttctgtattt 5100
ccttggattt tcctgaaagt gtttttaaat aaagaacaat tgttagaaaa aaaaaa 5156

<210> SEQ ID NO 131
<211> LENGTH: 671
<212> TYPE: DNA
<213> ORGANISM: Homo sapiens

<400> SEQUENCE: 131

-continued

```
aggtctggag ggcccacagc cggatgtggg acaccgggaa aaagtggtca tagcacacat     60
ttttgcatcc cggttgcagt gtgttgcaga cgaagtcctc ttgctcgtca ccccacactt    120
cctgggcagc caycacgagg atcatgactc ggaaaataaa gatgactgtg atccacacct    180
tcccgatgct ggtggagtgt ttgttgacac ccccgatgaa agtgtgcagc gtcccccaat    240
ccattgcgct ggtttatccc tgagtcctgt ttccaacgac tgccagtgtt tcagacccaa    300
agaatgaggg caagatccct ctgcgagggt ttcagacctc cttctcctac cccactggag    360
tgcctagaag ccaatgggtg cacagtgatg atacgaatgt caatctttgc tcggtcagtg    420
aggatgtcgc ctggaatatt caaattgaat tacagatgca tgaagagggc gtacaagtta    480
gaatttttct ttcgccatac agaaattgtt tagccagatc ttctgtactt cttttccttc    540
cctgaccctt cctgctcccc aggaagggag gtcagccccg tttgcaaaac acaggatgcc    600
cgtgacaccg gagacaggtc ttcttcaccg acaggaagtg ccttctggtg cctgcacgtt    660
ttaactgcta t                                                         671
```

<210> SEQ ID NO 132
<211> LENGTH: 590
<212> TYPE: DNA
<213> ORGANISM: Homo sapiens

<400> SEQUENCE: 132

```
ctgaatggaa aagcttatgg ctctgtgatg atattagtga ccagcggaga tgataagctt     60
cttggcaatt gcttacccac tgtgctcagc agtggttcaa caattcactc cattgccctg    120
ggttcatctg cagccccaaa tctggaggaa ttatcacgtc ttacaggagg tttaaagttc    180
tttgttccag atatatcaaa ctccaatagc atgattgatg ctttcagtag aatttcctct    240
ggaactggag acattttcca gcaacatatt cagcttgaaa gtacaggtga aaatgtcaaa    300
cctcaccatc aattgaaaaa cacagtgact gtggataata ctgtgggcaa cgacactatg    360
tttctagtta cgtggcaggc cagtggtcct cctgagatta tattatttga tcctgatgga    420
cgaaaatact acacaaataa ttttatcacc aatctaactt ttcggacagc tagtctttgg    480
attccaggaa cagctaagcc tgggcactgg acttacaccc tgaacaatac ccatcattct    540
ctgcaagccc tgaaagtgac agtgacctct cgcgcctcca actcagacct                590
```

<210> SEQ ID NO 133
<211> LENGTH: 581
<212> TYPE: DNA
<213> ORGANISM: Homo sapiens

<400> SEQUENCE: 133

```
aggtcctgtc cgggggcact gagaactccc tctggaattc ttggggggtg ttggggagag     60
actgtgggcc tggagataaa acttgtctcc tctaccacca ccctgtaccc tagcctgcac    120
ctgtcctcat ctctgcaaag ttcagcttcc ttccccaggt ctctgtgcac tctgtcttgg    180
atgctctggg gagctcatgg gtggaggagt ctccaccaga gggaggctca ggggactggt    240
tgggccaggg atgaatattt gagggataaa aattgtgtaa gagccaaaga attggtagta    300
gggggagaac agagaggagc tgggctatgg gaaatgattt gaataatgga gctgggaata    360
tggctggata tctggtacta aaaaagggtc tttaagaacc tacttcctaa tctcttcccc    420
aatccaaacc atagctgtct gtccagtgct ctcttcctgc ctccagctct gccccaggct    480
cctcctagac tctgtccctg ggctagggca ggggaggagg gagagcaggg ttgggggaga    540
ggctgaggag agtgtgacat gtggggagag gaccagacct c                        581
```

-continued

<210> SEQ ID NO 134
<211> LENGTH: 4797
<212> TYPE: DNA
<213> ORGANISM: Homo sapiens
<220> FEATURE:
<221> NAME/KEY: misc_feature
<222> LOCATION: 135, 501, 4421, 4467, 4468, 4698
<223> OTHER INFORMATION: n = A,T,C or G

<400> SEQUENCE: 134

```
cctgggacca aagtgctgcc cagagctgag ggtcctggag ccacatgaga aggcttctcc     60
ctgtgtacct gtgcagcaca gggtagggtg agtccactca gctgtctagg agaggaccca    120
ggagcagcag agacncgcca agcctttact cataccatat tctgatcctt ttccagcaaa    180
ttgtggctac taatttgccc cctgaagatc aagatggctc tggggatgac tctgacaact    240
tctccggctc aggtgcaggt gaggttgtca tgggggcccc ccccacccaa gacggcaaca    300
ggtcatgcct gggggcagtg gtcaggcagt ctcctgtgtt tactgagcat gtactgagtg    360
caccctgcct gccctgtctc cacccagctg gctccaaagg gcaatgctga ggagaggaat    420
ggggtcgtga gctgctgtta aggagagctc atgcttggag gtgaggtgaa ggctgtgagc    480
tccagaaggc cccagggcgc nctgctgcac gcaggctcat attcactagg aatagcttta    540
ctcactaaga aacctctgga accccttca gaaggttatt tgactcctga gcctctattt    600
tctcatctgc aaaatgggaa taataccttg acctgataag cttgtggagc tgtaaggcag    660
cacagagcca gctggggtgt agctcttcca tccaagctcc cttccttact tcccctttcc    720
tgtggggact gggggagaga agtccctgag ctggaggtgg tcagggaagc ttcacagagg    780
aggtggctct tgagtggacc tcaggaagag gggtgagaga gctaaggaag gaggctgagg    840
tcatccctgg ggaagtgacc tagcggaggc ctgagagctg caaggtagga tatctgttgt    900
tggaagtgtc tgttgttgga agtgggggcc ttttttttcag ggagggtggg gccagagaag    960
tgtgtgccct gggataagta ggataaccac agtagttatg cccctaaggg atgcccaccc   1020
cacccctgtg gtcacagaaa agctttccca ggtggcctag gcacctgtct cgtggctcca   1080
gagacaggct gcacctgaca cacacaatgg aaggacagct ctccttgtcc attttccaag   1140
gagcttagcc tcagctgcct tgtccaggta ctagcctccc tcatagcctg agcttggcca   1200
gcccaggtgc tctggagcct cccccgaccc acccaacaca ctctgcttct ggtcctcccc   1260
acccccacc tccccaacac actctgcttc tggtcctgca ggtgctttgc aagatatcac   1320
cttgtcacag cagacccct ccacttggaa ggacacgcag ctcctgacgg ctattcccac   1380
gtctccagaa cccaccggcc tggaggctac agctgcctcc acctccaccc tgccggctgg   1440
agaggggccc aaggagggag aggctgtagt cctgccagaa gtggagcctg gcctcaccgc   1500
ccgggagcag gaggccaccc cccgacccag ggagaccaca cagctcccga ccactcatca   1560
ggcctcaacg accacagcca ccacggccca ggagcccgcc acctcccacc cccacaggga   1620
catgcagcct ggccaccatg agacctcaac ccctgcagga cccagccaag ctgaccttca   1680
cactccccac acagaggatg gaggtccttc tgccaccgag agggctgctg aggatggagc   1740
ctccagtcag ctcccagcag cagagggctc tggggagcag gtgagtggcc tctgcattcc   1800
ttgggaaatt gagtgggttg gtcctaatgc ctggcacttg gcaggcccta cacctgtgcc   1860
ctgcgcgatc tcgtattcct caccaggaag acagggcaca ggggccgcct tcccctaccc   1920
ccagggcctc gcagagcagg acagactaac tatgagatca gagcagaagc acccttaaag   1980
```

-continued

```
atcacccaag agagggctcc caaactcaca atccaaactt gcagccctcg tcgaagagtg   2040
aacgttatac cagtcatttt atttatagct tcgtggattt acgcttacac taaatagtct   2100
gctattcata caaaatgtgt gctttgtatc actttttgtg atatccatgc catggtccag   2160
ccagggtccg gagttgatgt ggcaagaagg cctggctttc gggccctgtg cgatcctggt   2220
ttgggtgcat ctgagtgggt ggtggcaaag atcagggagg caggagctgc ttctgggtct   2280
gtagtggagc tggttgctgc tgctggcggt gacctggcca acccaatctg cccctgccct   2340
cccacaggac ttcacctttg aaacctcggg ggagaatacg gctgtagtgg ccgtggagcc   2400
tgaccgccgg aaccagtccc cagtggatca gggggccacg gggcctcac agggcctcct    2460
ggacaggaaa gaggtgctgg gaggtgagtt ttctttcagg ggggtagttt ggggtgaatt   2520
gctgctgtgg ggtcagggtg gggctgacca cagccaaggc cactgctttg ggagggtctg   2580
cacgagagcc caaggagccg ctgagctgag ctggccccgt ctacctgccc taggggtcat   2640
tgccggaggc ctcgtggggc tcatctttgc tgtgtgcctg gtgggtttca tgctgtaccg   2700
catgaagaag aaggacgaag gcagctactc cttggaggag ccgaaacaag ccaacggcgg   2760
ggcctaccag aagcccacca aacaggagga attctatgcc tgacgcggga gccatgcgcc   2820
ccctccgccc tgccactcac taggccccca cttgcctctt ccttgaagaa ctgcaggccc   2880
tggcctcccc tgccaccagg ccacctcccc agcattccag cccctctggt cgctcctgcc   2940
cacggagtcg tgggtgtgct gggagctcca ctctgcttct ctgacttctg cctggagact   3000
tagggcacca ggggtttctc gcataggacc tttccaccac agccagcacc tggcatcgca   3060
ccattctgac tcggtttctc caaactgaag cagcctctcc ccaggtccag ctctggaggg   3120
gagggggatc cgactgcttt ggacctaaat ggcctcatgt ggctggaaga tcctgcgggt   3180
ggggcttggg gctcacacac ctgtagcact tactggtagg accaagcatc ttggggggt    3240
ggccgctgag tggcagggga caggagtcac tttgtttcgt ggggaggtct aatctagata   3300
tcgacttgtt tttgcacatg tttcctctag ttctttgttc atagcccagt agaccttgtt   3360
acttctgagg taagttaagt aagttgattc ggtatccccc catcttgctt ccctaatcta   3420
tggtcgggag acagcatcag ggttaagaag actttttttt tttttttaa actaggagaa    3480
ccaaatctgg aagccaaaat gtaggcttag tttgtgtgtt gtctcttgag tttgtcgctc   3540
atgtgtgcaa cagggtatgg actatctgtc tggtggcccc gttctggtgg tctgttggca   3600
ggctggccag tccaggctgc cgtggggccg ccgcctcttt caagcagtcg tgcctgtgtc   3660
catgcgctca gggccatgct gaggcctggg ccgctgccac gttggagaag cccgtgtgag   3720
aagtgaatgc tgggactcag ccttcagaca gagaggactg tagggagggc ggcaggggcc   3780
tggagatcct cctgcaggct cacgcccgtc ctcctgtggc gccgtctcca ggggctgctt   3840
cctcctggaa attgacgagg ggtgtcttgg gcagagctgg ctctgagcgc ctccatccaa   3900
ggccaggttc tccgttagct cctgtggccc caccctgggc cctgggctgg aatcaggaat   3960
attttccaaa gagtgatagt cttttgcttt tggcaaaact ctacttaatc caatgggttt   4020
ttccctgtac agtagatttt ccaaatgtaa taaactttaa tataaagtag tctgtgaatg   4080
ccactgcctt cgcttcttgc ctctgtgctg tgtgtgacgt gaccggactt ttctgcaaac   4140
accaacatgt tgggaaactt ggctcgaatc tctgtgcctt cgtctttccc atggggaggg   4200
attctggttc cagggtccct ctgtgtattt gctttttgt tttggctgaa attctcctgg    4260
aggtcggtag gttcagccaa ggttttataa ggctgatgtc aatttctgtg ttgccaagct   4320
ccaagcccat cttctaaatg gcaaaggaag gtggatggcc ccagcacagc ttgacctgag   4380
```

-continued gctgtggtca cagcggaggt gtggagccga ggcctacccc ncagacacct tggacatcct 4440
cctcccaccc ggctgcagag gccagannccc agcccagggt cctgcactta cttgcttatt 4500
tgacaacgtt tcagcgactc cgttggccac tccgagagtg ggccagtctg tggatcagag 4560
atgcaccacc aagccaaggg aacctgtgtc cggtattcga tactgcgact ttctgcctgg 4620
agtgtatgac tgcacatgac tcgggggtgg ggaaaggggt cggctgacca tgctcatctg 4680
ctggtccgtg ggacggtncc caagccagag gtgggttcat ttgtgtaacg acaataaacg 4740
gtacttgtca tttcgggcaa cggctgctgt ggtggtggtt gagtctcttc ttggcct 4797

<210> SEQ ID NO 135
<211> LENGTH: 2856
<212> TYPE: DNA
<213> ORGANISM: Homo sapiens

<400> SEQUENCE: 135
tagtcgcggg tccccgagtg agcacgccag ggagcaggag accaaacgac gggggtcgga 60
gtcagagtcg cagtgggagt ccccggaccg gagcacgagc ctgagcggga gagcgccgct 120
cgcacgcccg tcgccacccg cgtacccggc gcagccagag ccaccagcgc agcgctgcca 180
tggagcccag cagcaagaag ctgacgggtc gcctcatgct ggctgtggga ggagcagtgc 240
ttggctccct gcagtttggc tacaacactg gagtcatcaa tgcccccag aaggtgatcg 300 aggagttcta caaccagaca tgggtccacc gctatgggga gagcatcctg cccaccacgc 360
tcaccacgct ctggtccctc tcagtggcca tcttttctgt tgggggcatg attggctcct 420
tctctgtggg cctttttcgtt aaccgctttg gccggcggaa ttcaatgctg atgatgaacc 480
tgctggcctt cgtgtccgcc gtgctcatgg gcttctcgaa actgggcaag tcctttgaga 540
tgctgatcct gggccgcttc atcatcggtg tgtactgcgg cctgaccaca ggcttcgtgc 600
ccatgtatgt gggtgaagtg tcacccacag cctttcgtgg ggccctgggc accctgcacc 660
agctgggcat cgtcgtcggc atcctcatcg cccaggtgtt cggcctggac tccatcatgg 720
gcaacaagga cctgtggccc ctgctgctga gcatcatctt catcccggcc ctgctgcagt 780
gcatcgtgct gcccttctgc cccgagagtc cccgcttcct gctcatcaac cgcaacgagg 840
agaaccgggc caagagtgtg ctaaagaagc tgcgcgggac agctgacgtg acccatgacc 900
tgcaggagat gaaggaagag agtcggcaga tgatgcggga gaagaaggtc accatcctgg 960
agctgttccg ctcccccgcc taccgccagc ccatcctcat cgctgtggtg ctgcagctgt 1020
cccagcagct gtctggcatc aacgctgtct tctattactc cacgagcatc ttcgagaagg 1080
cgggggtgca gcagcctgtg tatgccacca ttggctccgg tatcgtcaac acggccttca 1140
ctgtcgtgtc gctgtttgtg gtggagcgag caggccggcg gaccctgcac ctcataggcc 1200
tcgctggcat ggcgggttgt gccatactca tgaccatcgc gctagcactg ctggagcagc 1260
taccctggat gtcctatctg agcatcgtgg ccatctttgg ctttgtggcc ttctttgaag 1320
tgggtcctgg ccccatccca tggttcatcg tggctgaact cttcagccag ggtccacgtc 1380
cagctgccat tgccgttgca ggcttctcca actggacctc aaatttcatt gtgggcatgt 1440
gcttccagta tgtggagcaa ctgtgtggtc cctacgtctt catcatcttc actgtgctcc 1500
tggttctgtt cttcatcttc acctacttca aagttcctga gactaaaggc cggaccttcg 1560
atgagatcgc ttccggcttc cggcaggggg gagccagcca aagtgataag acacccgagg 1620
agctgttcca tcccctgggg gctgattccc aagtgtgagt cgccccagat caccagcccg 1680

-continued

```
gcctgctccc agcagcccta aggatctctc aggagcacag gcagctggat gagacttcca   1740

aacctgacag atgtcagccg agccgggcct ggggctcctt tctccagcca gcaatgatgt   1800

ccagaagaat attcaggact taacggctcc aggattttaa caaaagcaag actgttgctc   1860

aaatctattc agacaagcaa caggttttat aatttttttta ttactgattt tgttattttt   1920

atatcagcct gagtctcctg tgcccacatc ccaggcttca ccctgaatgg ttccatgcct   1980

gagggtggag actaagccct gtcgagacac ttgccttctt cacccagcta atctgtaggg   2040

ctggacctat gtcctaagga cacactaatc gaactatgaa ctacaaagct tctatcccag   2100

gaggtggcta tggccacccg ttctgctggc ctggatctcc ccactctagg ggtcaggctc   2160

cattaggatt tgccccttcc catctcttcc tacccaacca ctcaaattaa tctttcttta   2220

cctgagacca gttgggagca ctggagtgca gggaggagag gggaagggcc agtctgggct   2280

gccgggttct agtctccttt gcactgaggg ccacactatt accatgagaa gagggcctgt   2340

gggagcctgc aaactcactg ctcaagaaga catggagact cctgccctgt tgtgtataga   2400

tgcaagatat ttatatatat ttttggttgt caatattaaa tacagacact aagttatagt   2460

atatctggac aagccaactt gtaaatacac cacctcactc ctgttactta cctaaacaga   2520

tataaatggc tggtttttag aaacatggtt ttgaaatgct tgtggattga gggtaggagg   2580

tttggatggg agtgagacag aagtaagtgg ggttgcaacc actgcaacgg cttagacttc   2640

gactcaggat ccagtccctt acacgtacct ctcatcagtg tcctcttgct caaaaatctg   2700

tttgatccct gttacccaga gaatatatac attctttatc ttgacattca aggcatttct   2760

atcacatatt tgatagttgg tgttcaaaaa aacactagtt ttgtgccagc cgtgatgctc   2820

aggcttgaaa tcgcattatt ttgaatgtga agggaa                             2856
```

<210> SEQ ID NO 136
<211> LENGTH: 356
<212> TYPE: DNA
<213> ORGANISM: Homo sapiens

<400> SEQUENCE: 136

```
ggtggagcca aatgaagaaa atgaagatga aagagacaga cacctcagtt tttctggatc     60

aggcattgat gatgatgaag attttatctc cagcaccatt tcaaccacac cacgggcttt    120

tgaccacaca aaacagaacc aggactggac tcagtggaac ccaagccatt caaatccgga    180

agtgctactt cagacaacca caaggatgac tgatgtagac agaaatggca ccactgctta    240

tgaaggaaac tggaacccag aagcacaccc tcccctcatt caccatgagc atcatgagga    300

agaagagacc ccacattcta caagcacaat ccaggcaact cctagtagta caacgg        356
```

<210> SEQ ID NO 137
<211> LENGTH: 356
<212> TYPE: DNA
<213> ORGANISM: Homo sapiens
<220> FEATURE:
<221> NAME/KEY: misc_feature
<222> LOCATION: 254, 264, 279, 281, 290, 328, 342
<223> OTHER INFORMATION: n = A,T,C or G

<400> SEQUENCE: 137

```
gcaggtggag aagacatttt attgttcctg gggtctctgg aggcccattg gtggggctgg     60

gtcactggct gcccccggaa cagggcgctg ctccatggct ctgcttgtgg tagtctgtgg    120

ctatgtctcc cagcaaggac agaaactcag aaaaatcaat cttcttatcc tcattcttgt    180

cctttttctc aaagacatcg gcgaggtaat ttgtgccctt tttacctcgg cccgcgacca    240
```

-continued cgctaaggcc aaanttccag acanayggcc gggccggtnc nataggggan cccaacttgg 300
ggacccaaac tctggcgcgg aaacacangg gcataagctt gnttcctgtg gggaaa 356

<210> SEQ ID NO 138
<211> LENGTH: 353
<212> TYPE: DNA
<213> ORGANISM: Homo sapiens

<400> SEQUENCE: 138
aggtccagtc ctccacttgg cctgatgaga gtggggagtg gcaagggacg tttctcctgc 60
aatagacact tagatttctc tcttgtggga agaaaccacc tgtccatcca ctgactcttc 120
tacattgatg tggaaattgc tgctgctacc accacctcct gaagaggctt ccctgatgcc 180
aatgccagcc atcttggcat cctggccctc gagcaggctg cggtaagtag cgatctcctg 240
ctccagccgt gtctttatgt caagcagcat cttgtactcc tggttctgag cctccatctc 300
gcatcggagc tcactcagac ctcgsccgsg mssmcgctam gccgaattcc agc 353

<210> SEQ ID NO 139
<211> LENGTH: 371
<212> TYPE: DNA
<213> ORGANISM: Homo sapiens

<400> SEQUENCE: 139
agcgtggtcg cggccgaggt ccatccgaag caagattgca gatggcagtg tgaagagaga 60
agacatattc tacacttcaa agctttggtg caattcccat cgaccagagt tggtccgacc 120
agccttggaa aggtcactga aaaatcttca attggattat gttgacctct accttattca 180
ttttccagtg tctgtaaagc caggtgagga agtgatccca aaagatgaaa atggaaaaat 240
actatttgac acagtggatc tctgtgccac gtgggaggcc gtggagaagt gtaaagatgc 300
aggattggac ctgcccgggc ggccgctcga aagccgaatt ccagcacact ggcggccgtt 360
actagtggat c 371

<210> SEQ ID NO 140
<211> LENGTH: 370
<212> TYPE: DNA
<213> ORGANISM: Homo sapiens

<400> SEQUENCE: 140
tagcgtggtc gcggccgagg tccatctccc tttgggaact aggggggctgc tggtgggaaa 60 tgggagccag ggcagatgtt gcattccttt gtgtccctgt aaatgtggga ctacaagaag 120
aggagctgcc tgagtggtac tttctcttcc tggtaatcct ctggcccagc ctcatggcag 180
aatagaggta tttttaggct atttttgtaa tatggcttct ggtcaaaatc cctgtgtagc 240
tgaattccca agccctgcat tgtacagccc cccactcccc tcaccaccta ataaaggaat 300
agttaacact caaaaaaaaa aaaaaaacctg cccgggcggc cgctcgaaag ccgaattcca 360
gcacactggc 370

<210> SEQ ID NO 141
<211> LENGTH: 371
<212> TYPE: DNA
<213> ORGANISM: Homo sapiens

<400> SEQUENCE: 141
tagcgtggtc gcggccgagg tcctctgtgc tgcctgtcac agcccgatgg taccagcgca 60

-continued

```
gggtgtaggc agtgcaggag ccctcatcca gtggcaggga acaggggtca tcactatccc    120

aaggagcttc agggtcctgg tactcctcca cagaatactc ggagtattca gagtactcat    180

catcctcagg gggtacccgc tcttcctcct ctgcatgaga gacgcggagc acaggcacag    240

catggagctg ggagccggca gtgtctgcag cataactagg gaggggtcgt gatccagatg    300

cgatgaactg gccctggcag gcacagtgct gactcatctc ttggcgacct gcccgggcgg    360

ccgctcgaag c                                                          371


<210> SEQ ID NO 142
<211> LENGTH: 343
<212> TYPE: DNA
<213> ORGANISM: Homo sapiens

<400> SEQUENCE: 142

gcgttttgag gccaatggtg taaaaggaaa tatcttcaca taaaaactag atggaagcat     60

tgtcagaaac ctctttgtga tgtttgcttt caactcacag agttgaacat tccttttcat    120

agagcagttt tgaaacactc ttttgtagaa tttgcaagcg gatgattgga tcgctatgag    180

gtcttcattg gaaacgggat acctttacat aaaaactaga cagtagcatt ctcagaaatt    240

tctttgggat gtgggcattc aacccacaga ggagaacttc atttgataga gcagttttga    300

aacacccttt ttgtagaatc tacaggtgga catttagagt gct                      343


<210> SEQ ID NO 143
<211> LENGTH: 354
<212> TYPE: DNA
<213> ORGANISM: Homo sapiens

<400> SEQUENCE: 143

aggtctgatg gcagaaaaac tcagactgtc tgcaacttta cagatggtgc attggttcag     60

catcaggagt gggatgggaa ggaaagcaca ataacaagaa aattgaaaga tgggaaatta    120

gtggtggagt gtgtcatgaa caatgtcacc tgtactcgga tctatgaaaa agtagaataa    180

aaattccatc atcactttgg acaggagtta attaagagaa tgaccaagct cagttcaatg    240

agcaaatctc catactgttt ctttcttttt tttttcatta ctgtgttcaa ttatctttat    300

cataaacatt ttacatgcag ctatttcaaa gtgtgttgga ttaattagga tcat          354


<210> SEQ ID NO 144
<211> LENGTH: 353
<212> TYPE: DNA
<213> ORGANISM: Homo sapiens

<400> SEQUENCE: 144

ggtcaaggac ctgggggacc cccaggtcca gcagccacat gattctgcag cagacaggga     60

cctagagcac atctggatct cagccccacc cctggcaacc tgcctgccta gagaactccc    120

aagatgacag actaagtagg attctgccat ttagaataat tctggtatcc tgggcgttgc    180

gttaagttgc ttaactttca ttctgtctta cgatagtctt cagaggtggg aacagatgaa    240

gaaaccatgc cccagagaag gttaagtgac ttcctcttta tggagccagt gttccaacct    300

aggtttgcct gataccagac ctgtggcccc acctcccatg caggtctctg tgg           353


<210> SEQ ID NO 145
<211> LENGTH: 371
<212> TYPE: DNA
<213> ORGANISM: Homo sapiens

<400> SEQUENCE: 145
```

-continued

```
caggtctgtc ataaactggt ctggagtttc tgacgactcc ttgttcacca aatgcaccat     60

ttcctgagac ttgctggcct ctccgttgag tccacttggc tttctgtcct ccacagctcc    120

attgccactg ttgatcacta gctttttctt ctgcccacac cttcttcgac tgttgactgc    180

aatgcaaact gcaagaatca aagccaaggc caagagggat gccaagatga tcagccattc    240

tggaatttgg ggtgtcctta taggaccaga ggttgtgttt gctccacctt cttgactccc    300

atgtgagacc tcggccgcga ccacgctaag ccgaattcca gcacactggc ggcccgttac    360

tagtggatcc g                                                         371
```

<210> SEQ ID NO 146
<211> LENGTH: 355
<212> TYPE: DNA
<213> ORGANISM: Homo sapiens

<400> SEQUENCE: 146

```
ggtcctccgt cctcttccca gaggtgtcgg ggcttggccc cagcctccat cttcgtctct     60

caggatggcg agtagcagcg gctccaaggc tgaattcatt gtcggaggga aatataaact    120

ggtacggaag atcgggtctg gctccttcgg ggacatctat ttggcgatca acatcaccaa    180

cggcgaggaa gtggcagtga agctagaatc tcagaaggcc aggcatcccc agttgctgta    240

cgagagcaag ctctataaga ttcttcaagg tggggttggc atcccccaca tacggtggta    300

tggtcaggaa aaagactaca atgtactagt catggatctt ctgggaccta gcctc         355
```

<210> SEQ ID NO 147
<211> LENGTH: 355
<212> TYPE: DNA
<213> ORGANISM: Homo sapiens

<400> SEQUENCE: 147

```
ggtctgttac aaaatgaaga cagacaacac aacatttact ctgtggagat atcctactca     60

tactatgcac gtgctgtgat tttgaacata actcgtccca aaaacttgtc acgatcatcc    120

tgacttttta ggttggctga tccatcaatc ttgcactcaa ctgttacttc tttcccagtg    180

ttgttaggag caaagctgac ctgaacagca accaatggct gtagataccc aacatgcagt    240

tttttcccat aatatgggaa atattttaag tctatcattc cattatgagg ataaactgct    300

acatttggta tatcttcatt ctttgaaaca caatctatcc ttggcactcc ttcag         355
```

<210> SEQ ID NO 148
<211> LENGTH: 369
<212> TYPE: DNA
<213> ORGANISM: Homo sapiens

<400> SEQUENCE: 148

```
aggtctctct ccccctctcc ctctcctgcc agccaagtga agacatgctt acttcccctt     60

caccttcctt catgatgtgg gaagagtgct gcaacccagc cctagccaac accgcatgag    120

agggagtgtg ccgagggctt ctgagaaggt ttctctcaca tctagaaaga agcgcttaag    180

atgtggcagc ccctcttctt caagtggctc ttgtcctgtt gccctgggag ttctcaaatt    240

gctgcagcag cctccatcca gcctgaggat gacatcaata cacagaggaa gaagagtcag    300

gaaaagatga gagaagttac agactctcct gggcgacccc gagagcttac cattcctcag    360

acttcttca                                                            369
```

<210> SEQ ID NO 149

-continued

<211> LENGTH: 620
<212> TYPE: DNA
<213> ORGANISM: Homo sapiens
<220> FEATURE:
<221> NAME/KEY: misc_feature
<222> LOCATION: 169, 171, 222, 472, 528, 559, 599
<223> OTHER INFORMATION: n = A,T,C or G

<400> SEQUENCE: 149
actagtcaaa aatgctaaaa taatttggga gaaaatattt tttaagtagt gttatagttt 60
catgtttatc ttttattatg ttttgtgaag ttgtgtcttt tcactaatta cctatactat 120
gccaatattt ccttatatct atccataaca tttatactac atttgtaana naatatgcac 180
gtgaaactta acactttata aggtaaaaat gaggtttcca anatttaata atctgatcaa 240
gttcttgtta tttccaaata gaatggactt ggtctgttaa gggctaagga gaagaggaag 300
ataaggttaa aagttgttaa tgaccaaaca ttctaaaaga aatgcaaaaa aaaagtttat 360
tttcaagcct tcgaactatt taaggaaagc aaaatcattt cctaaatgca tatcatttgt 420
gagaatttct cattaatatc ctgaatcatt catttcacta aggctcatgt tnactccgat 480
atgtctctaa gaaagtacta tttcatggtc caaacctggt tgccatantt gggtaaaggc 540
tttcccttaa gtgtgaaant atttaaaatg aaattttcct ctttttaaaa attctttana 600
agggttaagg gtgttgggga 620

<210> SEQ ID NO 150
<211> LENGTH: 371
<212> TYPE: DNA
<213> ORGANISM: Homo sapiens

<400> SEQUENCE: 150
ggtccgatca aaacctgcta cctccccaag actttactag tgccgataaa ctttctcaaa 60
gagcaaccag tatcacttcc ctgtttataa aacctctaac catctctttg ttctttgaac 120
atgctgaaaa ccacctggtc tgcatgtatg cccgaatttg yaattctttt ctctcaaatg 180
aaaatttaat tttagggatt catttctata ttttcacata tgtagtatta ttatttcctt 240
atatgtgtaa ggtgaaattt atggtatttg agtgtgcaag aaaatatatt tttaaagctt 300
tcatttttcc cccagtgaat gatttagaat tttttatgta aatatacaga atgttttttc 360
ttacttttat a 371

<210> SEQ ID NO 151
<211> LENGTH: 4655
<212> TYPE: DNA
<213> ORGANISM: Homo sapiens

<400> SEQUENCE: 151
gggacttgag ttctgttatc ttcttaagta gattcatatt gtaagggtct cggggtgggg 60
gggttggcaa aatcctggag ccagaagaaa ggacagcagc attgatcaat cttacagcta 120
acatgttgta cctggaaaac aatgcccaga ctcaatttag tgagccacag tacacgaacc 180
tggggctcct gaacagcatg gaccagcaga ttcagaacgg ctcctcgtcc accagtccct 240
ataacacaga ccacgcgcag aacagcgtca cggcgccctc gccctacgca cagcccagct 300
ccaccttcga tgctctctct ccatcacccg ccatcccctc caacaccgac tacccaggcc 360
cgcacagttt cgacgtgtcc ttccagcagt cgagcaccgc caagtcggcc acctggacgt 420
attccactga actgaagaaa ctctactgcc aaattgcaaa gacatgcccc atccagatca 480
aggtgatgac cccacctcct cagggagctg ttatccgcgc catgcctgtc tacaaaaaag 540

-continued

```
ctgagcacgt cacggaggtg gtgaagcggt gccccaacca tgagctgagc cgtgaattca    600
acgagggaca gattgcccct yctagtcatt tgattcgagt agaggggaac agccatgccc    660
agtatgtaga agatcccatc acaggaagac agagtgtgct ggtaccttat gagccacccc    720
aggttggcac tgaattcacg acagtcttgt acaatttcat gtgtaacagc agttgtgttg    780
gagggatgaa ccgccgtcca attttaatca ttgttactct ggaaaccaga gatgggcaag    840
tcctgggccg acgctgcttt gaggcccgga tctgtgcttg cccaggaaga gacaggaagg    900
cggatgaaga tagcatcaga aagcagcaag tttcggacag tacaaagaac ggtgatggta    960
cgaagcgccc gtttcgtcag aacacacatg gtatccagat gacatccatc aagaaacgaa   1020
gatccccaga tgatgaactg gtatacttac cagtgagggg ccgtgagact tatgaaatgc   1080
tggtgaagat caaagagtcc ctggaactca tgcagtacct tcttcagcac acaattgaaa   1140
cgtacaggca acagcaacag cagcagcacc agcacttact tcagaaacag acctcaatac   1200
agtctccatc ttcatatggt aacagctccc cacctctgaa caaaatgaac agcatgaaca   1260
agctgccttc tgtgagccag cttatcaacc ctcagcagcg caacgccctc actcctacaa   1320
ccattcctga tggcatggga gccaacattc ccatgatggg cacccacatg ccaatggctg   1380
gagacatgaa tggactcagc cccacccagg cactccctcc cccactctcc atgccatcca   1440
cctcccactg cacacccccca cctccgtatc ccacagattg cagcattgtc agtttcttag   1500
cgaggttggg ctgttcatca tgtctggact atttcacgac ccagggggctg accaccatct   1560
atcagattga gcattactcc atggatgatc tggcaagtct gaaaatccct gagcaatttc   1620
gacatgcgat ctggaagggc atcctggacc accggcagct ccacgaattc tcctcccctt   1680
ctcatctcct gcggacccca agcagtgcct ctacagtcag tgtgggctcc agtgagaccc   1740
ggggtgagcg tgttattgat gctgtgcgat tcaccctccg ccagaccatc tctttcccac   1800
cccgagatga gtggaatgac ttcaactttg acatggatgc tcgccgcaat aagcaacagc   1860
gcatcaaaga ggaggggggag tgagcctcac catgtgagct cttcctatcc ctctcctaac   1920
tgccagcccc ctaaaagcac tcctgcttaa tcttcaaagc cttctcccta gctcctcccc   1980
ttcctcttgt ctgatttctt aggggaagga gaagtaagag gcttacttct taccctaacc   2040
atctgacctg gcatctaatt ctgattctgg ctttaagcct tcaaaactat agcttgcaga   2100
actgtagctt gccatggcta ggtagaagtg agcaaaaaag agttgggtgt ctccttaagc   2160
tgcagagatt tctcattgac ttttataaag catgttcacc cttatagtct aagactatat   2220
atataaatgt ataaatatac agtatagatt tttgggtggg ggcattgag tattgtttaa   2280
aatgtaattt aaatgaaaga aaattgagtt gcacttattg accatttttt aatttacttg   2340
ttttggatgg cttgtctata ctccttccct taaggggtat catgtatggt gataggtatc   2400
tagagcttaa tgctacatgt gagtgacgat gatgtacaga ttctttcagt tctttggatt   2460
ctaaatacat gccacatcaa acctttgagt agatccattt ccattgctta ttatgtaggt   2520
aagactgtag atatgtattc ttttctcagt gttggtatat tttatattac tgacatttct   2580
tctagtgatg atggttcacg ttggggtgat ttaatccagt tataagaaga agttcatgtc   2640
caaacgtcct ctttagtttt tggttgggaa tgaggaaaat tcttaaaagg cccatagcag   2700
ccagttcaaa aacacccgac gtcatgtatt tgagcatatc agtaacccccc ttaaatttaa   2760
taccagatac cttatcttac aatattgatt gggaaaacat ttgctgccat tacagaggta   2820
ttaaaactaa atttcactac tagattgact aactcaaata cacatttgct actgttgtaa   2880
```

-continued gaattctgat tgatttgatt gggatgaatg ccatctatct agttctaaca gtgaagtttt 2940
actgtctatt aatattcagg gtaaatagga atcattcaga aatgttgagt ctgtactaaa 3000
cagtaagata tctcaatgaa ccataaattc aactttgtaa aaatcttttg aagcatagat 3060
aatattgttt ggtaaatgtt tcttttgttt ggtaaatgtt tcytttaaag accctcctat 3120
tctataaaac tctgcatgta gaggcttgtt tacctttctc tctctaaggt ttacaatagg 3180
agtggtgatt tgaaaaatat aaaattatga gattggtttt cctgtggcat aaattgcatc 3240
actgtatcat tttctttttt aaccggtaag agtttcagtt tgttggaaag taactgtgag 3300
aacccagttt cccgtccatc tcccttaggg actacccata gacatgaaag gtccccacag 3360
agcaagagat aagtctttca tggctgctgt tgcttaaacc acttaaacga agagttccct 3420
tgaaactttg ggaaaacatg ttaatgacaa tattccagat ctttcagaaa tataacacat 3480
ttttttgcat gcatgcaaat gagctctgaa atcttcccat gcattctggt caagggctgt 3540
cattgcacat aagcttccat tttaatttta aagtgcaaaa gggccagcgt ggctctaaaa 3600
ggtaatgtgt ggattgcctc tgaaaagtgt gtatatattt tgtgtgaaat tgcatacttt 3660
gtattttgat tatttttttt ttcttcttgg gatagtggga tttccagaac cacacttgaa 3720
accttttttt atcgtttttg tattttcatg aaaataccat ttagtaagaa taccacatca 3780
aataagaaat aatgctacaa ttttaagagg ggagggaagg gaaagttttt tttttttatta 3840 ttttttaaa attttgtatg ttaaagagaa tgagtccttg atttcaaagt tttgttgtac 3900
ttaaatggta ataagcactg taaacttctg caacaagcat gcagctttgc aaacccatta 3960
aggggaagaa tgaaagctgt tccttggtcc tagtaagaag acaaactgct tcccttactt 4020
tgctgagggt ttgaataaac ctaggacttc cgagctatgt cagtactatt caggtaacac 4080
tagggccttg gaaatccctg tactgtgtct catggatttg gcactagcca aagcgaggca 4140
ccccttactg gcttacctcc tcatggcagc ctactctcct tgagtgtatg agtagccagg 4200
gtaaggggta aaaggatagt aagcatagaa accactagaa agtgggctta atggagttct 4260
tgtggcctca gctcaatgca gttagctgaa gaattgaaaa gtttttgttt ggagacgttt 4320
ataaacagaa atggaaagca gagttttcat taaatccttt taccttttt ttttcttggt 4380 aatcccctaa aataacagta tgtgggatat tgaatgttaa agggatattt ttttctatta 4440
tttttataat tgtacaaaat taagcaaatg ttaaaagttt tatatgcttt attaatgttt 4500
tcaaaaggta ttatacatgt gatacatttt ttaagcttca gttgcttgtc ttctggtact 4560
ttctgttatg ggcttttggg gagccagaag ccaatctaca atctcttttt gtttgccagg 4620
acatgcaata aaatttaaaa aataaataaa aacta 4655

<210> SEQ ID NO 152
<211> LENGTH: 586
<212> TYPE: PRT
<213> ORGANISM: Homo sapiens

<400> SEQUENCE: 152

Met Leu Tyr Leu Glu Asn Asn Ala Gln Thr Gln Phe Ser Glu Pro Gln
1               5                   10                  15

Tyr Thr Asn Leu Gly Leu Leu Asn Ser Met Asp Gln Gln Ile Gln Asn
            20                  25                  30

Gly Ser Ser Ser Thr Ser Pro Tyr Asn Thr Asp His Ala Gln Asn Ser
        35                  40                  45

Val Thr Ala Pro Ser Pro Tyr Ala Gln Pro Ser Ser Thr Phe Asp Ala
    50                  55                  60

-continued

```
Leu Ser Pro Ser Pro Ala Ile Pro Ser Asn Thr Asp Tyr Pro Gly Pro
65                  70                  75                  80

His Ser Phe Asp Val Ser Phe Gln Gln Ser Ser Thr Ala Lys Ser Ala
                85                  90                  95

Thr Trp Thr Tyr Ser Thr Glu Leu Lys Lys Leu Tyr Cys Gln Ile Ala
            100                 105                 110

Lys Thr Cys Pro Ile Gln Ile Lys Val Met Thr Pro Pro Pro Gln Gly
        115                 120                 125

Ala Val Ile Arg Ala Met Pro Val Tyr Lys Lys Ala Glu His Val Thr
    130                 135                 140

Glu Val Val Lys Arg Cys Pro Asn His Glu Leu Ser Arg Glu Phe Asn
145                 150                 155                 160

Glu Gly Gln Ile Ala Pro Ser Ser His Leu Ile Arg Val Glu Gly Asn
                165                 170                 175

Ser His Ala Gln Tyr Val Glu Asp Pro Ile Thr Gly Arg Gln Ser Val
            180                 185                 190

Leu Val Pro Tyr Glu Pro Pro Gln Val Gly Thr Glu Phe Thr Thr Val
        195                 200                 205

Leu Tyr Asn Phe Met Cys Asn Ser Ser Cys Val Gly Gly Met Asn Arg
    210                 215                 220

Arg Pro Ile Leu Ile Ile Val Thr Leu Glu Thr Arg Asp Gly Gln Val
225                 230                 235                 240

Leu Gly Arg Arg Cys Phe Glu Ala Arg Ile Cys Ala Cys Pro Gly Arg
                245                 250                 255

Asp Arg Lys Ala Asp Glu Asp Ser Ile Arg Lys Gln Gln Val Ser Asp
            260                 265                 270

Ser Thr Lys Asn Gly Asp Gly Thr Lys Arg Pro Phe Arg Gln Asn Thr
        275                 280                 285

His Gly Ile Gln Met Thr Ser Ile Lys Lys Arg Arg Ser Pro Asp Asp
    290                 295                 300

Glu Leu Val Tyr Leu Pro Val Arg Gly Arg Glu Thr Tyr Glu Met Leu
305                 310                 315                 320

Val Lys Ile Lys Glu Ser Leu Glu Leu Met Gln Tyr Leu Leu Gln His
                325                 330                 335

Thr Ile Glu Thr Tyr Arg Gln Gln Gln Gln Gln His Gln His Leu
            340                 345                 350

Leu Gln Lys Gln Thr Ser Ile Gln Ser Pro Ser Ser Tyr Gly Asn Ser
        355                 360                 365

Ser Pro Pro Leu Asn Lys Met Asn Ser Met Asn Lys Leu Pro Ser Val
    370                 375                 380

Ser Gln Leu Ile Asn Pro Gln Gln Arg Asn Ala Leu Thr Pro Thr Thr
385                 390                 395                 400

Ile Pro Asp Gly Met Gly Ala Asn Ile Pro Met Met Gly Thr His Met
                405                 410                 415

Pro Met Ala Gly Asp Met Asn Gly Leu Ser Pro Thr Gln Ala Leu Pro
            420                 425                 430

Pro Pro Leu Ser Met Pro Ser Thr Ser His Cys Thr Pro Pro Pro Pro
        435                 440                 445

Tyr Pro Thr Asp Cys Ser Ile Val Ser Phe Leu Ala Arg Leu Gly Cys
    450                 455                 460

Ser Ser Cys Leu Asp Tyr Phe Thr Thr Gln Gly Leu Thr Thr Ile Tyr
465                 470                 475                 480
```

-continued

```
Gln Ile Glu His Tyr Ser Met Asp Asp Leu Ala Ser Leu Lys Ile Pro
                485                 490                 495

Glu Gln Phe Arg His Ala Ile Trp Lys Gly Ile Leu Asp His Arg Gln
            500                 505                 510

Leu His Glu Phe Ser Ser Pro Ser His Leu Leu Arg Thr Pro Ser Ser
        515                 520                 525

Ala Ser Thr Val Ser Val Gly Ser Ser Glu Thr Arg Gly Glu Arg Val
    530                 535                 540

Ile Asp Ala Val Arg Phe Thr Leu Arg Gln Thr Ile Ser Phe Pro Pro
545                 550                 555                 560

Arg Asp Glu Trp Asn Asp Phe Asn Phe Asp Met Asp Ala Arg Arg Asn
                565                 570                 575

Lys Gln Gln Arg Ile Lys Glu Glu Gly Glu
            580                 585
```

<210> SEQ ID NO 153
<211> LENGTH: 2007
<212> TYPE: DNA
<213> ORGANISM: Homo sapiens

<400> SEQUENCE: 153

```
gaattcgtcg ctgctccagg gaaagttctg ttactccact gactctctct tttcctgata     60

acatggccag caagaaagta attacagtgt ttggagcaac aggagctcaa ggtggctctg    120

tggccagggc aattttggag agcaaaaaat ttgcagtgag agcagtgacc agggatgtga    180

cttgaccaaa tgccctggag ctccagcgcc ttggagctga ggtggtcaaa ggtgacctga    240

atgataaagc atcggtggac agtgccttaa aaggtgtcta tggggccttc ttggtgacca    300

acttctggga ccctctcaac caagataagg aagtgtgtcg gggaagctg gtggcagact    360

ccgccaagca cctgggtctg aagcacgtgg tgtacagcgg cctggagaac gtcaagcgac    420

tgacggatgg caagctggag gtgccgcact ttgacagcaa gggcgaggtg gaggagtact    480

tctggtccat tggcatcccc atgaccagtg tccgcgtggc ggcctacttt gaaaactttc    540

tcgcggcgtg gcggcccgtg aaagcctctg atggagatta ctacaccttg gctgtaccga    600

tgggagatgt accaatggat ggtatctctg ttgctgatat tggagcagcc gtctctagca    660

tttttaattc tccagaggaa tttttaggca aggccgtggg gctcagtgca gaagcactaa    720

caatacagca atatgctgat gttttgtcca aggctttggg gaaagaagtc cgagatgcaa    780

agattacccc ggaagctttc gagaagctgg gattccctgc agcaaaggaa atagccaata    840

tgtgtcgttt ctatgaaatg aagccagacc gagatgtcaa tctcacccac caactaaatc    900

ccaaagtcaa aagcttcagc cagtttatct cagagaacca gggagccttc aagggcatgt    960

agaaaatcag ctgttcagat aggcctctgc accacacagc ctctttcctc tctgatcctt   1020

ttcctcttta cggcacaaca ttcatgttga cagaacatgc tggaatgcaa ttgtttgcaa   1080

caccgaagga tttcctgcgg tcgcctcttc agtaggaagc actgcattgg tgataggaca   1140

cggtaatttg attcacattt aacttgctag ttagtgataa gggtggtaca actgtttggt   1200

aaaatgagaa gcctcggaac ttggagcttc tctcctacca ctaatgggag ggcagattat   1260

actgggattt ctcctgggtg agtaatttca agccctaatg ctgaaattcc cctaggcagc   1320

tccagttttc tcaactgcat tgcaaaattc ccagtgaact tttaagtact tttaacttaa   1380

aaaaatgaac atctttgtag agaattttct ggggaacatg gtgttcaatg aacaagcaca   1440

agcattggaa atgctaaaat tcagttttgc ctcaagattg gaagtttatt ttctgactca   1500
```

-continued

```
ttcatgaagt catctattga gccaccattc aattattcat ctattaattc cttgatcctt   1560

catttatcca ttctgcaaac ttttcttgag caccagcacg ggtggccatt tgtggacttc   1620

tcttcattcc tatgtgtttt cttatcaaag tgatccactc tcgaaaggct cctttccagt   1680

ctgtggttgg gttcaagtca tgccagggcc aggggcccca tctcctcgtt tagctctagg   1740

caaaatccag gggatctgca gtggggagcg ggggcaggaa gctggaggga aggcctgtga   1800

agggtaggga tgtggaaaga caaggtgaca gaaggaccca ataggacctt tctatatctc   1860

tggcttagca ttttctacat catattgtaa tcgtcttatt tgctagtttt cttccttact   1920

gtgagtgact aacagtcatc tttatcccag tgcctggtac ataataagtg atcaataaat   1980

gttgattgac taaaaaaaaa aaaaaaa                                       2007
```

<210> SEQ ID NO 154
<211> LENGTH: 2148
<212> TYPE: DNA
<213> ORGANISM: Homo sapiens

<400> SEQUENCE: 154

```
gaattcgtcg ctgctccagg gaaagttctg ttactccact gactctctct tttcctgata     60

acatggccag caagaaagta attacagtgt ttggagcaac aggagctcaa ggtggctctg    120

tggccagggc aattttggag agcaaaaaat ttgcagtgag agcagtgacc agggatgtga    180

cttgaccaaa tgccctggag ctccagcgcc ttggagctga ggtggtcaaa ggtgacctga    240

atgataaagc atcggtggac agtgccttaa aaggggaagc tggtggcaga ctccgccaag    300

cacctgggtc tgaagcacgt ggtgtacagc ggcctggaga acgtcaagcg actgacggat    360

ggcaagctgg aggtgccgca ctttgacagc aagggcgagg tggaggagta cttctggtcc    420

attggcatcc ccatgaccag tgtccgcgtg gcggcctact ttgaaaactt tctcgcggcg    480

tggcggcccg tgaaagcctc tgatggagat tactacacct tggctgtacc gatgggagat    540

gtaccaatgg atggtatctc tgttgctgat attggagcag ccgtctctag catttttaat    600

tctccagagg aatttttagg caaggccgtg gggctcagtg cagaagcact aacaatacag    660

caatatgctg atgttttgtc caaggctttg gggaaagaag tccgagatgc aaagactatc    720

tgtgctatag atgaccagaa aacagtggaa gaaggtttca tggaagacgt gggcttgagt    780

tggtccttga gggaacatga ccatgtatag acagaggagg catcaagaag gctggcctgg    840

ctaattctgg aataaacacg acaaaccaga ggcagtacgg gaaggaggca aattctggct    900

ctgcctctat ccttgattac cccggaagct ttcgagaagc tgggattccc tgcagcaaag    960

gaaatagcca atatgtgtcg tttctatgaa atgaagccag accgagatgt caatctcacc   1020

caccaactaa atcccaaagt caaaagcttc agccatttta tctcagagaa ccagggagcc   1080

ttcaagggca tgtagaaaat cagctgttca gataggcctc tgcaccacac agcctctttc   1140

ctctctgatc cttttcctct ttacggcaca acattcatgt tgacagaaca tgctggaatg   1200

caattgtttg caacaccgaa ggatttcctg cggtcgcctc ttcagtagga agcactgcat   1260

tggtgatagg acacggtaat ttgattcaca tttaacttgc tagttagtga taagggtggt   1320

acaactgttt ggtaaaatga gaagcctcgg aacttggagc ttctctccta ccactaatgg   1380

gagggcagat tatactggga tttctcctgg gtgagtaatt tcaagcccta atgctgaaat   1440

tcccctaggc agctccagtt ttctcaactg cattgcaaaa ttcccagtga acttttaagt   1500

acttttaact taaaaaaatg aacatctttg tagagaattt tctggggaac atggtgttca   1560

atgaacaagc acaagcattg gaaatgctaa aattcagttt tgcctcaaga ttggaagttt   1620
```

-continued

```
atttctgac tcattcatga agtcatctat tgagccacca ttcaattatt catctattaa   1680

ttccttgatc cttcatttat ccattctgca aacttttctt gagcaccagc acgggtggcc   1740

atttgtggac ttctcttcat tcctatgtgt tttcttatca aagtgatcca ctctcgaaag   1800

gctcctttcc agtctgtggt tgggttcaag tcatgccagg gccagggggc ccatctcctc   1860

gtttagctct aggcaaaatc caggggatct gcagtgggga gcgggggcag gaagctggag   1920

ggaaggcctg tgaagggtag ggatgtggaa agacaaggtg acagaaggac ccaataggac   1980

ctttctatat ctctggctta gcattttcta catcatattg taatcgtctt atttgctagt   2040

tttcttcctt actgtgagtg actaacagtc atctttatcc cagtgcctgg tacataataa   2100

gtgatcaata aatgttgatt gactaaatga aaaaaaaaaa aaaaaaaa                2148


<210> SEQ ID NO 155
<211> LENGTH: 153
<212> TYPE: PRT
<213> ORGANISM: Homo sapiens

<400> SEQUENCE: 155

Met Thr Ser Val Arg Val Ala Ala Tyr Phe Glu Asn Phe Leu Ala Ala
 1               5                  10                  15

Trp Arg Pro Val Lys Ala Ser Asp Gly Asp Tyr Tyr Thr Leu Ala Val
            20                  25                  30

Pro Met Gly Asp Val Pro Met Asp Gly Ile Ser Val Ala Asp Ile Gly
        35                  40                  45

Ala Ala Val Ser Ser Ile Phe Asn Ser Pro Glu Glu Phe Leu Gly Lys
    50                  55                  60

Ala Val Gly Leu Ser Ala Glu Ala Leu Thr Ile Gln Gln Tyr Ala Asp
65                  70                  75                  80

Val Leu Ser Lys Ala Leu Gly Lys Glu Val Arg Asp Ala Lys Ile Thr
                85                  90                  95

Pro Glu Ala Phe Glu Lys Leu Gly Phe Pro Ala Ala Lys Glu Ile Ala
            100                 105                 110

Asn Met Cys Arg Phe Tyr Glu Met Lys Pro Asp Arg Asp Val Asn Leu
        115                 120                 125

Thr His Gln Leu Asn Pro Lys Val Lys Ser Phe Ser Gln Phe Ile Ser
    130                 135                 140

Glu Asn Gln Gly Ala Phe Lys Gly Met
145                 150


<210> SEQ ID NO 156
<211> LENGTH: 128
<212> TYPE: PRT
<213> ORGANISM: Homo sapiens

<400> SEQUENCE: 156

Met Thr Ser Val Arg Val Ala Ala Tyr Phe Glu Asn Phe Leu Ala Ala
 1               5                  10                  15

Trp Arg Pro Val Lys Ala Ser Asp Gly Asp Tyr Tyr Thr Leu Ala Val
            20                  25                  30

Pro Met Gly Asp Val Pro Met Asp Gly Ile Ser Val Ala Asp Ile Gly
        35                  40                  45

Ala Ala Val Ser Ser Ile Phe Asn Ser Pro Glu Glu Phe Leu Gly Lys
    50                  55                  60

Ala Val Gly Leu Ser Ala Glu Ala Leu Thr Ile Gln Gln Tyr Ala Asp
65                  70                  75                  80
```

-continued

```
Val Leu Ser Lys Ala Leu Gly Lys Glu Val Arg Asp Ala Lys Thr Ile
                85                  90                  95

Cys Ala Ile Asp Asp Gln Lys Thr Val Glu Glu Gly Phe Met Glu Asp
            100                 105                 110

Val Gly Leu Ser Trp Ser Leu Arg Glu His Asp His Val Ala Gly Ala
        115                 120                 125
```

<210> SEQ ID NO 157
<211> LENGTH: 424
<212> TYPE: DNA
<213> ORGANISM: Homo sapiens
<220> FEATURE:
<221> NAME/KEY: misc_feature
<222> LOCATION: 320, 322
<223> OTHER INFORMATION: n = A,T,C or G

<400> SEQUENCE: 157

```
ctgcagcccg gggatccac tagtccagtg tggtggaatt cattggtctt tacaagactt     60

ggatacatta cagcagacat ggaaatataa ttttaaaaaa tttctctcca acctccttca    120

aattcagtca ccactgttat attaccttct ccaggaaccc tccagtgggg aaggctgcga    180

tattagattt ccttgtatgc aaagtttttg ttgaaagctg tgctcagagg aggtgagagg    240

agaggaagga gaaaactgca tcataacttt acagaattga atctagagtc ttccccgaaa    300

agcccagaaa cttctctgcn gnatctggct tgtccatctg gtctaaggtg gctgcttctt    360

ccccagccat cgagtcagtt tgtgcccatg aataatacac gacctgctat ttcccatgac    420

tgct                                                                 424
```

<210> SEQ ID NO 158
<211> LENGTH: 2099
<212> TYPE: DNA
<213> ORGANISM: Homo sapiens

<400> SEQUENCE: 158

```
ccgcggttaa aaggcgcagc aggtgggagc cggggccttc acccgaaacc cgacgagagc     60

ccgacagccg gcggcgcccg agcccgacct gcctgcccag ccggagcgaa gggcgccgcc    120

ccgcgcagag cccgcgccag ggccgccggc cgcagagcag ttaaaacgtg caggcaccag    180

aaggcacttc ctgtcggtga agaagacctg tctccggtgt cacgggcatc ctgtgttttg    240

caaacggggc tgacctccct tcctggggag caggaagggt cagggaagga aaagaagtac    300

agaagatctg gctaaacaat ttctgtatgg cgaaagaaaa attctaactt gtacgccctc    360

ttcatgcatc tttaattcaa tttgaatatt ccaggcgaca tcctcactga ccgagcaaag    420

attgacattc gtatcatcac tgtgcaccat tggcttctag gcactccagt ggggtaggag    480

aaggaggtct gaaaccctcg cagagggatc ttgccctcat tctttgggtc tgaaacactg    540

gcagtcgttg gaaacaggac tcagggataa accagcgcaa tggattgggg gacgctgcac    600

actttcatcg gggtgtcaa caaacactcc accagcatcg ggaaggtgtg gatcacagtc    660

atctttattt tccgagtcat gatcctcgtg gtggctgccc aggaagtgtg gggtgacgag    720

caagaggact tcgtctgcaa cacactgcaa ccgggatgca aaaatgtgtg ctatgaccac    780

tttttcccgg tgtcccacat ccggctgtgg gccctccagc tgatcttcgt ctccacccca    840

gcgctgctgg tggccatgca tgtggcctac tacaggcacg aaaccactcg caagttcagg    900

cgaggagaga agaggaatga tttcaaagac atagaggaca ttaaaaagca gaaggttcgg    960

atagaggggt cgctgtggtg gacgtacacc agcagcatct ttttccgaat catctttgaa   1020
```

-continued

```
gcagccttta tgtatgtgtt ttacttcctt tacaatgggt accacctgcc ctgggtgttg   1080

aaatgtggga ttgacccctg ccccaacctt gttgactgct ttatttctag gccaacagag   1140

aagaccgtgt ttaccatttt tatgatttct gcgtctgtga tttgcatgct gcttaacgtg   1200

gcagagttgt gctacctgct gctgaaagtg tgttttagga gatcaaagag agcacagacg   1260

caaaaaaatc accccaatca tgccctaaag gagagtaagc agaatgaaat gaatgagctg   1320

atttcagata gtggtcaaaa tgcaatcaca ggttcccaag ctaaacattt caaggtaaaa   1380

tgtagctgcg tcataaggag acttctgtct tctccagaag gcaataccaa cctgaaagtt   1440

ccttctgtag cctgaagagt ttgtaaatga ctttcataat aaatagacac ttgagttaac   1500

tttttgtagg atacttgctc cattcataca caacgtaatc aaatatgtgg tccatctctg   1560

aaaacaagag actgcttgac aaaggagcat tgcagtcact ttgacaggtt ccttttaagt   1620

ggactctctg acaaagtggg tactttctga aaatttatat aactgttgtt gataaggaac   1680

atttatccag gaattgatac gtttattagg aaaagatatt tttataggct tggatgtttt   1740

tagttctgac tttgaattta tataaagtat ttttataatg actggtcttc cttacctgga   1800

aaaacatgcg atgttagttt tagaattaca ccacaagtat ctaaatttgg aacttacaaa   1860

gggtctatct tgtaaatatt gttttgcatt gtctgttggc aaatttgtga actgtcatga   1920

tacgcttaag gtggaaagtg ttcattgcac aatatatttt tactgctttc tgaatgtaga   1980

cggaacagtg tggaagcaga aggctttttt aactcatccg tttgccaatc attgcaaaca   2040

actgaaatgt ggatgtgatt gcctcaataa agctcgtccc cattgcttaa aaaaaaaaa    2099


<210> SEQ ID NO 159
<211> LENGTH: 291
<212> TYPE: PRT
<213> ORGANISM: Homo sapiens

<400> SEQUENCE: 159

Met Asp Trp Gly Thr Leu His Thr Phe Ile Gly Gly Val Asn Lys His
 1               5                  10                  15

Ser Thr Ser Ile Gly Lys Val Trp Ile Thr Val Ile Phe Ile Phe Arg
            20                  25                  30

Val Met Ile Leu Val Val Ala Ala Gln Glu Val Trp Gly Asp Glu Gln
        35                  40                  45

Glu Asp Phe Val Cys Asn Thr Leu Gln Pro Gly Cys Lys Asn Val Cys
    50                  55                  60

Tyr Asp His Phe Phe Pro Val Ser His Ile Arg Leu Trp Ala Leu Gln
65                  70                  75                  80

Leu Ile Phe Val Ser Thr Pro Ala Leu Leu Val Ala Met His Val Ala
                85                  90                  95

Tyr Tyr Arg His Glu Thr Thr Arg Lys Phe Arg Arg Gly Glu Lys Arg
            100                 105                 110

Asn Asp Phe Lys Asp Ile Glu Asp Ile Lys Lys Gln Lys Val Arg Ile
        115                 120                 125

Glu Gly Ser Leu Trp Trp Thr Tyr Thr Ser Ser Ile Phe Phe Arg Ile
    130                 135                 140

Ile Phe Glu Ala Ala Phe Met Tyr Val Phe Tyr Phe Leu Tyr Asn Gly
145                 150                 155                 160

Tyr His Leu Pro Trp Val Leu Lys Cys Gly Ile Asp Pro Cys Pro Asn
                165                 170                 175

Leu Val Asp Cys Phe Ile Ser Arg Pro Thr Glu Lys Thr Val Phe Thr
```

-continued

```
            180                 185                 190

Ile Phe Met Ile Ser Ala Ser Val Ile Cys Met Leu Leu Asn Val Ala
        195                 200                 205

Glu Leu Cys Tyr Leu Leu Leu Lys Val Cys Phe Arg Arg Ser Lys Arg
    210                 215                 220

Ala Gln Thr Gln Lys Asn His Pro Asn His Ala Leu Lys Glu Ser Lys
225                 230                 235                 240

Gln Asn Glu Met Asn Glu Leu Ile Ser Asp Ser Gly Gln Asn Ala Ile
                245                 250                 255

Thr Gly Ser Gln Ala Lys His Phe Lys Val Lys Cys Ser Cys Val Ile
            260                 265                 270

Arg Arg Leu Leu Ser Ser Pro Glu Gly Asn Thr Asn Leu Lys Val Pro
        275                 280                 285

Ser Val Ala
    290
```

<210> SEQ ID NO 160
<211> LENGTH: 3951
<212> TYPE: DNA
<213> ORGANISM: Homo sapiens

<400> SEQUENCE: 160

```
tctgcatcca tattgaaaac ctgacacaat gtatgcagca ggctcagtgt gagtgaactg     60

gaggcttctc tacaacatga cccaaaggag cattgcaggt cctatttgca acctgaagtt    120

tgtgactctc ctggttgcct taagttcaga actcccattc ctgggagctg gagtacagct    180

tcaagacaat gggtataatg gattgctcat tgcaattaat cctcaggtac ctgagaatca    240

gaacctcatc tcaaacatta aggaaatgat aactgaagct tcattttacc tatttaatgc    300

taccaagaga agagtatttt tcagaaatat aaagatttta atacctgcca catggaaagc    360

taataataac agcaaaataa aacaagaatc atatgaaaag gcaaatgtca tagtgactga    420

ctggtatggg gcacatggag atgatccata caccctacaa tacagagggt gtggaaaaga    480

gggaaaatac attcatttca cacctaattt cctactgaat gataacttaa cagctggcta    540

cggatcacga ggccgagtgt ttgtccatga atgggcccac ctccgttggg gtgtgttcga    600

tgagtataac aatgacaaac ctttctacat aaatgggcaa aatcaaatta aagtgacaag    660

gtgttcatct gacatcacag gcatttttgt gtgtgaaaaa ggtccttgcc cccaagaaaa    720

ctgtattatt agtaagcttt ttaaagaagg atgcaccttt atctacaata gcacccaaaa    780

tgcaactgca tcaataatgt tcatgcaaag tttatcttct gtggttgaat tttgtaatgc    840

aagtacccac aaccaagaag caccaaacct acagaaccag atgtgcagcc tcagaagtgc    900

atgggatgta atcacagact ctgctgactt tcaccacagc tttcccatga acgggactga    960

gcttccacct cctcccacat tctcgcttgt agaggctggt gacaaagtgg tctgtttagt   1020

gctggatgtg tccagcaaga tggcagaggc tgacagactc cttcaactac aacaagccgc   1080

agaattttat ttgatgcaga ttgttgaaat tcataccttc gtgggcattg ccagtttcga   1140

cagcaaagga gagatcagag cccagctaca ccaaattaac agcaatgatg atcgaaagtt   1200

gctggtttca tatctgccca ccactgtatc agctaaaaca gacatcagca tttgttcagg   1260

gcttaagaaa ggatttgagg tggttgaaaa actgaatgga aaagcttatg gctctgtgat   1320

gatattagtg accagcggag atgataagct tcttggcaat tgcttaccca ctgtgctcag   1380

cagtggttca acaattcact ccattgccct gggttcatct gcagccccaa atctggagga   1440
```

-continued

```
attatcacgt cttacaggag gtttaaagtt ctttgttcca gatatatcaa actccaatag   1500
catgattgat gctttcagta gaatttcctc tggaactgga gacattttcc agcaacatat   1560
tcagcttgaa agtacaggtg aaaatgtcaa acctcaccat caattgaaaa acacagtgac   1620
tgtggataat actgtgggca acgacactat gtttctagtt acgtggcagg ccagtggtcc   1680
tcctgagatt atattatttg atcctgatgg acgaaaatac tacacaaata attttatcac   1740
caatctaact tttcggacag ctagtctttg gattccagga acagctaagc ctgggcactg   1800
gacttacacc ctgaacaata cccatcattc tctgcaagcc ctgaaagtga cagtgacctc   1860
tcgcgcctcc aactcagctg tgcccccagc cactgtggaa gcctttgtgg aaagagacag   1920
cctccatttt cctcatcctg tgatgattta tgccaatgtg aaacagggat tttatcccat   1980
tcttaatgcc actgtcactg ccacagttga gccagagact ggagatcctg ttacgctgag   2040
actccttgat gatggagcag gtgctgatgt tataaaaaat gatggaattt actcgaggta   2100
tttttctcc tttgctgcaa atggtagata tagcttgaaa gtgcatgtca atcactctcc   2160
cagcataagc accccagccc actctattcc agggagtcat gctatgtatg taccaggtta   2220
cacagcaaac ggtaatattc agatgaatgc tccaaggaaa tcagtaggca gaaatgagga   2280
ggagcgaaag tggggcttta gccgagtcag ctcaggaggc tccttttcag tgctgggagt   2340
tccagctggc ccccaccctg atgtgtttcc accatgcaaa attattgacc tggaagctgt   2400
aaaagtagaa gaggaattga ccctatcttg gacagcacct ggagaagact ttgatcaggg   2460
ccaggctaca agctatgaaa taagaatgag taaaagtcta cagaatatcc aagatgactt   2520
taacaatgct attttagtaa atacatcaaa gcgaaatcct cagcaagctg gcatcaggga   2580
gatatttacg ttctcacccc aaatttccac gaatggacct gaacatcagc caaatggaga   2640
aacacatgaa agccacagaa tttatgttgc aatacgagca atggatagga actccttaca   2700
gtctgctgta tctaacattg cccaggcgcc tctgtttatt ccccccaatt ctgatcctgt   2760
acctgccaga gattatctta tattgaaagg agttttaaca gcaatgggtt tgataggaat   2820
catttgcctt attatagttg tgacacatca tactttaagc aggaaaaaga gagcagacaa   2880
gaaagagaat ggaacaaaat tattataaat aaatatccaa agtgtcttcc ttcttagata   2940
taagacccat ggccttcgac tacaaaaaca tactaacaaa gtcaaattaa catcaaaact   3000
gtattaaaat gcattgagtt tttgtacaat acagataaga tttttacatg gtagatcaac   3060
aaattctttt tgggggtaga ttagaaaacc cttacacttt ggctatgaac aaataataaa   3120
aattattctt taaagtaatg tctttaaagg caaagggaag ggtaaagtcg gaccagtgtc   3180
aaggaaagtt tgttttattg aggtggaaaa atagccccaa gcagagaaaa ggagggtagg   3240
tctgcattat aactgtctgt gtgaagcaat catttagtta ctttgattaa tttttctttt   3300
ctccttatct gtgcagaaca ggttgcttgt ttacaactga agatcatgct atatttcata   3360
tatgaagccc ctaatgcaaa gctctttacc tcttgctatt ttgttatata tattacagat   3420
gaaatctcac tgctaatgct cagagatctt ttttcactgt aagaggtaac ctttaacaat   3480
atgggtatta cctttgtctc ttcataccgg ttttatgaca aaggtctatt gaatttattt   3540
gtttgtaagt ttctactccc atcaaagcag ctttttaagt tattgccttg gttattatgg   3600
atgatagtta tagcccttat aatgccttaa ctaaggaaga aaagatgtta ttctgagttt   3660
gttttaatac atatatgaac atatagtttt attcaattaa accaaagaag aggtcagcag   3720
ggagatacta acctttggaa atgattagct ggctctgttt tttggttaaa taagagtctt   3780
taatcctttc tccatcaaga gttacttacc aagggcaggg gaagggggat atagaggtcc   3840
```

-continued caaggaaata aaaatcatct ttcatcttta attttactcc ttcctcttat ttttttaaaa 3900
gattatcgaa caataaaatc atttgccttt ttaattaaaa acataaaaaa a 3951

<210> SEQ ID NO 161
<211> LENGTH: 943
<212> TYPE: PRT
<213> ORGANISM: Homo sapiens

<400> SEQUENCE: 161

Met Thr Gln Arg Ser Ile Ala Gly Pro Ile Cys Asn Leu Lys Phe Val
1 5 10 15

Thr Leu Leu Val Ala Leu Ser Ser Glu Leu Pro Phe Leu Gly Ala Gly
20 25 30

Val Gln Leu Gln Asp Asn Gly Tyr Asn Gly Leu Leu Ile Ala Ile Asn
35 40 45

Pro Gln Val Pro Glu Asn Gln Asn Leu Ile Ser Asn Ile Lys Glu Met
50 55 60

Ile Thr Glu Ala Ser Phe Tyr Leu Phe Asn Ala Thr Lys Arg Arg Val
65 70 75 80

Phe Phe Arg Asn Ile Lys Ile Leu Ile Pro Ala Thr Trp Lys Ala Asn
85 90 95

Asn Asn Ser Lys Ile Lys Gln Glu Ser Tyr Glu Lys Ala Asn Val Ile
100 105 110

Val Thr Asp Trp Tyr Gly Ala His Gly Asp Asp Pro Tyr Thr Leu Gln
115 120 125

Tyr Arg Gly Cys Gly Lys Glu Gly Lys Tyr Ile His Phe Thr Pro Asn
130 135 140

Phe Leu Leu Asn Asp Asn Leu Thr Ala Gly Tyr Gly Ser Arg Gly Arg
145 150 155 160

Val Phe Val His Glu Trp Ala His Leu Arg Trp Gly Val Phe Asp Glu
165 170 175

Tyr Asn Asn Asp Lys Pro Phe Tyr Ile Asn Gly Gln Asn Gln Ile Lys
180 185 190

Val Thr Arg Cys Ser Ser Asp Ile Thr Gly Ile Phe Val Cys Glu Lys
195 200 205

Gly Pro Cys Pro Gln Glu Asn Cys Ile Ile Ser Lys Leu Phe Lys Glu
210 215 220

Gly Cys Thr Phe Ile Tyr Asn Ser Thr Gln Asn Ala Thr Ala Ser Ile
225 230 235 240

Met Phe Met Gln Ser Leu Ser Ser Val Val Glu Phe Cys Asn Ala Ser
245 250 255

Thr His Asn Gln Glu Ala Pro Asn Leu Gln Asn Gln Met Cys Ser Leu
260 265 270

Arg Ser Ala Trp Asp Val Ile Thr Asp Ser Ala Asp Phe His His Ser
275 280 285

Phe Pro Met Asn Gly Thr Glu Leu Pro Pro Pro Pro Thr Phe Ser Leu
290 295 300

Val Glu Ala Gly Asp Lys Val Val Cys Leu Val Leu Asp Val Ser Ser
305 310 315 320

Lys Met Ala Glu Ala Asp Arg Leu Leu Gln Leu Gln Gln Ala Ala Glu
325 330 335

Phe Tyr Leu Met Gln Ile Val Glu Ile His Thr Phe Val Gly Ile Ala
340 345 350

-continued

```
Ser Phe Asp Ser Lys Gly Glu Ile Arg Ala Gln Leu His Gln Ile Asn
        355                 360                 365

Ser Asn Asp Asp Arg Lys Leu Leu Val Ser Tyr Leu Pro Thr Thr Val
    370                 375                 380

Ser Ala Lys Thr Asp Ile Ser Ile Cys Ser Gly Leu Lys Lys Gly Phe
385                 390                 395                 400

Glu Val Val Glu Lys Leu Asn Gly Lys Ala Tyr Gly Ser Val Met Ile
                405                 410                 415

Leu Val Thr Ser Gly Asp Asp Lys Leu Leu Gly Asn Cys Leu Pro Thr
            420                 425                 430

Val Leu Ser Ser Gly Ser Thr Ile His Ser Ile Ala Leu Gly Ser Ser
        435                 440                 445

Ala Ala Pro Asn Leu Glu Glu Leu Ser Arg Leu Thr Gly Gly Leu Lys
    450                 455                 460

Phe Phe Val Pro Asp Ile Ser Asn Ser Asn Ser Met Ile Asp Ala Phe
465                 470                 475                 480

Ser Arg Ile Ser Ser Gly Thr Gly Asp Ile Phe Gln Gln His Ile Gln
                485                 490                 495

Leu Glu Ser Thr Gly Glu Asn Val Lys Pro His His Gln Leu Lys Asn
            500                 505                 510

Thr Val Thr Val Asp Asn Thr Val Gly Asn Asp Thr Met Phe Leu Val
        515                 520                 525

Thr Trp Gln Ala Ser Gly Pro Pro Glu Ile Ile Leu Phe Asp Pro Asp
    530                 535                 540

Gly Arg Lys Tyr Tyr Thr Asn Asn Phe Ile Thr Asn Leu Thr Phe Arg
545                 550                 555                 560

Thr Ala Ser Leu Trp Ile Pro Gly Thr Ala Lys Pro Gly His Trp Thr
                565                 570                 575

Tyr Thr Leu Asn Asn Thr His His Ser Leu Gln Ala Leu Lys Val Thr
            580                 585                 590

Val Thr Ser Arg Ala Ser Asn Ser Ala Val Pro Pro Ala Thr Val Glu
        595                 600                 605

Ala Phe Val Glu Arg Asp Ser Leu His Phe Pro His Pro Val Met Ile
    610                 615                 620

Tyr Ala Asn Val Lys Gln Gly Phe Tyr Pro Ile Leu Asn Ala Thr Val
625                 630                 635                 640

Thr Ala Thr Val Glu Pro Glu Thr Gly Asp Pro Val Thr Leu Arg Leu
                645                 650                 655

Leu Asp Asp Gly Ala Gly Ala Asp Val Ile Lys Asn Asp Gly Ile Tyr
            660                 665                 670

Ser Arg Tyr Phe Phe Ser Phe Ala Ala Asn Gly Arg Tyr Ser Leu Lys
        675                 680                 685

Val His Val Asn His Ser Pro Ser Ile Ser Thr Pro Ala His Ser Ile
    690                 695                 700

Pro Gly Ser His Ala Met Tyr Val Pro Gly Tyr Thr Ala Asn Gly Asn
705                 710                 715                 720

Ile Gln Met Asn Ala Pro Arg Lys Ser Val Gly Arg Asn Glu Glu Glu
                725                 730                 735

Arg Lys Trp Gly Phe Ser Arg Val Ser Ser Gly Gly Ser Phe Ser Val
            740                 745                 750

Leu Gly Val Pro Ala Gly Pro His Pro Asp Val Phe Pro Pro Cys Lys
        755                 760                 765

Ile Ile Asp Leu Glu Ala Val Lys Val Glu Glu Glu Leu Thr Leu Ser
```

-continued

```
    770                 775                 780

Trp Thr Ala Pro Gly Glu Asp Phe Asp Gln Gly Gln Ala Thr Ser Tyr
785                 790                 795                 800

Glu Ile Arg Met Ser Lys Ser Leu Gln Asn Ile Gln Asp Asp Phe Asn
                805                 810                 815

Asn Ala Ile Leu Val Asn Thr Ser Lys Arg Asn Pro Gln Gln Ala Gly
            820                 825                 830

Ile Arg Glu Ile Phe Thr Phe Ser Pro Gln Ile Ser Thr Asn Gly Pro
        835                 840                 845

Glu His Gln Pro Asn Gly Glu Thr His Glu Ser His Arg Ile Tyr Val
    850                 855                 860

Ala Ile Arg Ala Met Asp Arg Asn Ser Leu Gln Ser Ala Val Ser Asn
865                 870                 875                 880

Ile Ala Gln Ala Pro Leu Phe Ile Pro Pro Asn Ser Asp Pro Val Pro
                885                 890                 895

Ala Arg Asp Tyr Leu Ile Leu Lys Gly Val Leu Thr Ala Met Gly Leu
            900                 905                 910

Ile Gly Ile Ile Cys Leu Ile Ile Val Val Thr His His Thr Leu Ser
        915                 920                 925

Arg Lys Lys Arg Ala Asp Lys Lys Glu Asn Gly Thr Lys Leu Leu
    930                 935                 940
```

<210> SEQ ID NO 162
<211> LENGTH: 498
<212> TYPE: DNA
<213> ORGANISM: Homo sapiens

<400> SEQUENCE: 162

```
tggagaacca cgtggacagc accatgaaca tgttgggcgg gggaggcagt gctggccgga     60

agcccctcaa gtcgggtatg aaggagctgg ccgtgttccg ggagaaggtc actgagcagc    120

accggcagat gggcaagggt ggcaagcatc accttggcct ggaggagccc aagaagctgc    180

gaccaccccc tgccaggact ccctgccaac aggaactgga ccaggtcctg gagcggatct    240

ccaccatgcg ccttccggat gagcggggcc ctctggagca cctctactcc ctgcacatcc    300

ccaactgtga caagcatggc ctgtacaacc tcaaacagtg gcaagatgtc tctgaacggg    360

cagcgtgggg agtgctggtg tgtgaacccc aacaccggga agctgatcca gggagccccc    420

accatccggg gggaccccga gtgtcatctc ttctacaatg agcagcagga ggctcgcggg    480

gtgcacaccc cagcggat                                                  498
```

<210> SEQ ID NO 163
<211> LENGTH: 1128
<212> TYPE: DNA
<213> ORGANISM: Homo sapiens

<400> SEQUENCE: 163

```
gccacctggc cctcctgatc gacgacacac gcacttgaaa cttgttctca gggtgtgtgg     60

aatcaacttt ccggaagcaa ccagcccacc agaggaggtc ccgagcgcga gcggagacga    120

tgcagcggag actggttcag cagtggagcg tcgcggtgtt cctgctgagc tacgcggtgc    180

cctcctgcgg gcgctcggtg gagggtctca gccgccgcct caaaagagct gtgtctgaac    240

atcagctcct ccatgacaag gggaagtcca tccaagattt acggcgacga ttcttccttc    300

accatctgat cgcagaaatc cacacagctg aaatcagagc tacctcggag gtgtccccta    360

actccaagcc ctctcccaac acaaagaacc accccgtccg atttgggtct gatgatgagg    420
```

-continued

```
gcagatacct aactcaggaa actaacaagg tggagacgta caaagagcag ccgctcaaga    480
cacctgggaa gaaaaagaaa ggcaagcccg ggaaacgcaa ggagcaggaa aagaaaaaac    540
ggcgaactcg ctctgcctgg ttagactctg gagtgactgg gagtgggcta gaaggggacc    600
acctgtctga cacctccaca acgtcgctgg agctcgattc acggaggcat tgaaattttc    660
agcagagacc ttccaaggac atattgcagg attctgtaat agtgaacata tggaaagtat    720
tagaaatatt tattgtctgt aaatactgta aatgcattgg aataaaactg tctcccccat    780
tgctctatga aactgcacat tggtcattgt gaatattttt ttttttgcca aggctaatcc    840
aattattatt atcacattta ccataattta ttttgtccat tgatgtattt attttgtaaa    900
tgtatcttgg tgctgctgaa tttctatatt ttttgtaaca taatgcactt tagatataca    960
tatcaagtat gttgataaat gacacaatga agtgtctcta ttttgtggtt gattttaatg   1020
aatgcctaaa tataattatc caaattgatt ttcctttgtg catgtaaaaa taacagtatt   1080
ttaaatttgt aaagaatgtc taataaaata taatctaatt acatcatg                1128
```

<210> SEQ ID NO 164
<211> LENGTH: 1310
<212> TYPE: DNA
<213> ORGANISM: Homo sapiens

<400> SEQUENCE: 164

```
gggcctggtt cgcaaagaag ctgacttcag agggggaaac tttcttcttt taggaggcgg     60
ttagccctgt tccacgaacc caggagaact gctggccaga ttaattagac attgctatgg    120
gagacgtgta aacacactac ttatcattga tgcatatata aaaccatttt attttcgcta    180
ttatttcaga ggaagcgcct ctgatttgtt tctttttttcc ctttttgctc tttctggctg    240
tgtggtttgg agaaagcaca gttggagtag ccggttgcta aataagtccc gagcgcgagc    300
ggagacgatg cagcggagac tggttcagca gtggagcgtc gcggtgttcc tgctgagcta    360
cgcggtgccc tcctgcgggc gctcggtgga gggtctcagc cgccgcctca aaagagctgt    420
gtctgaacat cagctcctcc atgacaaggg gaagtccatc caagatttac ggcgacgatt    480
cttccttcac catctgatcg cagaaatcca cacagctgaa atcagagcta cctcggaggt    540
gtcccctaac tccaagccct ctcccaacac aaagaaccac cccgtccgat ttgggtctga    600
tgatgagggc agatacctaa ctcaggaaac taacaaggtg gagacgtaca aagagcagcc    660
gctcaagaca cctgggaaga aaaagaaagg caagcccggg aaacgcaagg agcaggaaaa    720
gaaaaaacgg cgaactcgct ctgcctggtt agactctgga gtgactggga gtgggctaga    780
aggggaccac ctgtctgaca cctccacaac gtcgctggag ctcgattcac ggaggcattg    840
aaattttcag cagagacctt ccaaggacat attgcaggat tctgtaatag tgaacatatg    900
gaaagtatta gaaatattta ttgtctgtaa atactgtaaa tgcattggaa taaaactgtc    960
tcccccattg ctctatgaaa ctgcacattg gtcattgtga atattttttt ttttgccaag   1020
gctaatccaa ttattattat cacatttacc ataatttatt ttgtccattg atgtatttat   1080
tttgtaaatg tatcttggtg ctgctgaatt tctatatttt ttgtaacata atgcacttta   1140
gatatacata tcaagtatgt tgataaatga cacaatgaag tgtctctatt ttgtggttga   1200
ttttaatgaa tgcctaaata taattatcca aattgatttt cctttgtgcc cgtaaaaata   1260
acagtatttt aaatttgtaa agaatgtcta ataaaatata atctaattac              1310
```

<210> SEQ ID NO 165

-continued

<211> LENGTH: 177
<212> TYPE: PRT
<213> ORGANISM: Homo sapiens

<400> SEQUENCE: 165

```
Met Gln Arg Arg Leu Val Gln Gln Trp Ser Val Ala Val Phe Leu Leu
 1              5                   10                  15

Ser Tyr Ala Val Pro Ser Cys Gly Arg Ser Val Glu Gly Leu Ser Arg
            20                  25                  30

Arg Leu Lys Arg Ala Val Ser Glu His Gln Leu Leu His Asp Lys Gly
        35                  40                  45

Lys Ser Ile Gln Asp Leu Arg Arg Arg Phe Phe Leu His His Leu Ile
    50                  55                  60

Ala Glu Ile His Thr Ala Glu Ile Arg Ala Thr Ser Glu Val Ser Pro
65                  70                  75                  80

Asn Ser Lys Pro Ser Pro Asn Thr Lys Asn His Pro Val Arg Phe Gly
                85                  90                  95

Ser Asp Asp Glu Gly Arg Tyr Leu Thr Gln Glu Thr Asn Lys Val Glu
            100                 105                 110

Thr Tyr Lys Glu Gln Pro Leu Lys Thr Pro Gly Lys Lys Lys Lys Gly
        115                 120                 125

Lys Pro Gly Lys Arg Lys Glu Gln Glu Lys Lys Lys Arg Arg Thr Arg
    130                 135                 140

Ser Ala Trp Leu Asp Ser Gly Val Thr Gly Ser Gly Leu Glu Gly Asp
145                 150                 155                 160

His Leu Ser Asp Thr Ser Thr Thr Ser Leu Glu Leu Asp Ser Arg Arg
                165                 170                 175

His
```

<210> SEQ ID NO 166
<211> LENGTH: 177
<212> TYPE: PRT
<213> ORGANISM: Homo sapiens

<400> SEQUENCE: 166

```
Met Gln Arg Arg Leu Val Gln Gln Trp Ser Val Ala Val Phe Leu Leu
 1              5                   10                  15

Ser Tyr Ala Val Pro Ser Cys Gly Arg Ser Val Glu Gly Leu Ser Arg
            20                  25                  30

Arg Leu Lys Arg Ala Val Ser Glu His Gln Leu Leu His Asp Lys Gly
        35                  40                  45

Lys Ser Ile Gln Asp Leu Arg Arg Arg Phe Phe Leu His His Leu Ile
    50                  55                  60

Ala Glu Ile His Thr Ala Glu Ile Arg Ala Thr Ser Glu Val Ser Pro
65                  70                  75                  80

Asn Ser Lys Pro Ser Pro Asn Thr Lys Asn His Pro Val Arg Phe Gly
                85                  90                  95

Ser Asp Asp Glu Gly Arg Tyr Leu Thr Gln Glu Thr Asn Lys Val Glu
            100                 105                 110

Thr Tyr Lys Glu Gln Pro Leu Lys Thr Pro Gly Lys Lys Lys Lys Gly
        115                 120                 125

Lys Pro Gly Lys Arg Lys Glu Gln Glu Lys Lys Lys Arg Arg Thr Arg
    130                 135                 140

Ser Ala Trp Leu Asp Ser Gly Val Thr Gly Ser Gly Leu Glu Gly Asp
145                 150                 155                 160
```

-continued

His Leu Ser Asp Thr Ser Thr Thr Ser Leu Glu Leu Asp Ser Arg Arg
165 170 175

His

<210> SEQ ID NO 167
<211> LENGTH: 3362
<212> TYPE: DNA
<213> ORGANISM: Homo sapiens

<400> SEQUENCE: 167
cacaatgtat gcagcaggct cagtgtgagt gaactggagg cttctctaca acatgaccca 60
aaggagcatt gcaggtccta tttgcaacct gaagtttgtg actctcctgg ttgccttaag 120
ttcagaactc ccattcctgg gagctggagt acagcttcaa gacaatgggt ataatggatt 180
gctcattgca attaatcctc aggtacctga gaatcagaac ctcatctcaa acattaagga 240
aatgataact gaagcttcat tttacctatt taatgctacc aagagaagag tatttttcag 300
aaatataaag attttaatac ctgccacatg gaaagctaat aataacagca aaataaaaca 360
agaatcatat gaaaaggcaa atgtcatagt gactgactgg tatggggcac atggagatga 420
tccatacacc ctacaataca gagggtgtgg aaaagaggga aaatacattc atttcacacc 480
taatttccta ctgaatgata acttaacagc tggctacgga tcacgaggcc gagtgtttgt 540
ccatgaatgg gcccacctcc gttggggtgt gttcgatgag tataacaatg acaaaccttt 600
ctacataaat gggcaaaatc aaattaaagt gacaaggtgt tcatctgaca tcacaggcat 660
ttttgtgtgt gaaaaaggtc cttgccccca agaaaactgt attattagta agctttttaa 720
agaaggatgc acctttatct acaatagcac ccaaaatgca actgcatcaa taatgttcat 780
gcaaagttta tcttctgtgg ttgaattttg taatgcaagt acccacaacc aagaagcacc 840
aaacctacag aaccagatgt gcagcctcag aagtgcatgg gatgtaatca cagactctgc 900
tgactttcac cacagctttc ccatgaacgg gactgagctt ccacctcctc ccacattctc 960
gcttgtagag gctggtgaca aagtggtctg tttagtgctg gatgtgtcca gcaagatggc 1020
agaggctgac agactccttc aactacaaca agccgcagaa ttttatttga tgcagattgt 1080
tgaaattcat accttcgtgg gcattgccag tttcgacagc aaaggagaga tcagagccca 1140
gctacaccaa attaacagca atgatgatcg aaagttgctg gtttcatatc tgcccaccac 1200
tgtatcagct aaaacagaca tcagcatttg ttcagggctt aagaaaggat ttgaggtggt 1260
tgaaaaactg aatggaaaag cttatggctc tgtgatgata ttagtgacca gcggagatga 1320
taagcttctt ggcaattgct tacccactgt gctcagcagt ggttcaacaa ttcactccat 1380
tgccctgggt tcatctgcag ccccaaatct ggaggaatta tcacgtctta caggaggttt 1440
aaagttcttt gttccagata tatcaaactc caatagcatg attgatgctt tcagtagaat 1500
ttcctctgga actggagaca ttttccagca acatattcag cttgaaagta caggtgaaaa 1560
tgtcaaacct caccatcaat tgaaaaacac agtgactgtg gataatactg tgggcaacga 1620
cactatgttt ctagttacgt ggcaggccag tggtcctcct gagattatat tatttgatcc 1680
tgatggacga aaatactaca caaataattt tatcaccaat ctaacttttc ggacagctag 1740
tctttggatt ccaggaacag ctaagcctgg gcactggact tacaccctga tgtgtttcca 1800
ccatgcaaaa ttattgacct ggaagctgta aaagtagaag aggaattgac cctatcttgg 1860
acagcacctg gagaagactt tgatcagggc caggctacaa gctatgaaat aagaatgagt 1920
aaaagtctac agaatatcca agatgacttt aacaatgcta ttttagtaaa tacatcaaag 1980

-continued

```
cgaaatcctc agcaagctgg catcagggag atatttacgt tctcacccca aatttccacg   2040

aatggacctg aacatcagcc aaatggagaa acacatgaaa gccacagaat ttatgttgca   2100

atacgagcaa tggataggaa ctccttacag tctgctgtat ctaacattgc ccaggcgcct   2160

ctgtttattc cccccaattc tgatcctgta cctgccagag attatcttat attgaaagga   2220

gttttaacag caatgggttt gataggaatc atttgcctta ttatagttgt gacacatcat   2280

actttaagca ggaaaaagag agcagacaag aaagagaatg gaacaaaatt attataaata   2340

aatatccaaa gtgtcttcct tcttagatat aagacccatg gccttcgact acaaaaacat   2400

actaacaaag tcaaattaac atcaaaactg tattaaaatg cattgagttt ttgtacaata   2460

cagataagat ttttacatgg tagatcaaca aattcttttt gggggtagat tagaaaaccc   2520

ttacactttg gctatgaaca aataataaaa attattcttt aaagtaatgt ctttaaaggc   2580

aaagggaagg gtaaagtcgg accagtgtca aggaaagttt gttttattga ggtggaaaaa   2640

tagccccaag cagagaaaag gagggtaggt ctgcattata actgtctgtg tgaagcaatc   2700

atttagttac tttgattaat ttttcttttc tccttatctg tgcagaacag gttgcttgtt   2760

tacaactgaa gatcatgcta tatttcatat atgaagcccc taatgcaaag ctctttacct   2820

cttgctattt tgttatatat attacagatg aaatctcact gctaatgctc agagatcttt   2880

tttcactgta agaggtaacc tttaacaata tgggtattac ctttgtctct tcataccggt   2940

tttatgacaa aggtctattg aatttatttg tttgtaagtt tctactccca tcaaagcagc   3000

tttctaagtt attgccttgg ttattatgga tgatagttat agcccttata atgccttaac   3060

taaggaagaa aagatgttat tctgagtttg ttttaataca tatatgaaca tatagtttta   3120

ttcaattaaa ccaaagaaga ggtcagcagg gagatactaa cctttggaaa tgattagctg   3180

gctctgtttt ttggttaaat aagagtcttt aatcctttct ccatcaagag ttacttacca   3240

agggcagggg aagggggata tagaggtcac aaggaaataa aaatcatctt tcatctttaa   3300

ttttactcct tcctcttatt tttttaaaag attatcgaac aataaaatca tttgcctttt   3360

tt                                                                  3362
```

<210> SEQ ID NO 168
<211> LENGTH: 2784
<212> TYPE: DNA
<213> ORGANISM: Homo sapiens

<400> SEQUENCE: 168

```
tctgcatcca tattgaaaac ctgacacaat gtatgcagca ggctcagtgt gagtgaactg     60

gaggcttctc tacaacatga cccaaaggag cattgcaggt cctatttgca acctgaagtt    120

tgtgactctc ctggttgcct taagttcaga actcccattc ctgggagctg gagtacagct    180

tcaagacaat gggtataatg gattgctcat tgcaattaat cctcaggtac ctgagaatca    240

gaacctcatc tcaaacatta aggaaatgat aactgaagct tcattttacc tatttaatgc    300

taccaagaga agagtatttt tcagaaatat aaagatttta atacctgcca catggaaagc    360

taataataac agcaaaataa aacaagaatc atatgaaaag gcaaatgtca tagtgactga    420

ctggtatggg gcacatggag atgatccata caccctacaa tacagagggt gtggaaaaga    480

gggaaaatac attcatttca cacctaattt cctactgaat gataacttaa cagctggcta    540

cggatcacga ggccgagtgt ttgtccatga atgggcccac ctccgttggg gtgtgttcga    600

tgagtataac aatgacaaac ctttctacat aaatgggcaa aatcaaatta aagtgacaag    660

gtgttcatct gacatcacag gcatttttgt gtgtgaaaaa ggtccttgcc cccaagaaaa    720
```

-continued

```
ctgtattatt agtaagcttt ttaaagaagg atgcaccttt atctacaata gcacccaaaa    780
tgcaactgca tcaataatgt tcatgcaaag tttatcttct gtggttgaat tttgtaatgc    840
aagtacccac aaccaagaag caccaaacct acagaaccag atgtgcagcc tcagaagtgc    900
atgggatgta atcacagact ctgctgactt tcaccacagc tttcccatga acgggactga    960
gcttccacct cctcccacat tctcgcttgt agaggctggt gacaaagtgg tctgtttagt   1020
gctggatgtg tccagcaaga tggcagaggc tgacagactc cttcaactac aacaagccgc   1080
agaattttat ttgatgcaga ttgttgaaat tcataccttc gtgggcattg ccagtttcga   1140
cagcaaagga gagatcagag cccagctaca ccaaattaac agcaatgatg atcgaaagtt   1200
gctggtttca tatctgccca ccactgtatc agctaaaaca gacatcagca tttgttcagg   1260
gcttaagaaa ggatttgagg tggttgaaaa actgaatgga aaagcttatg gctctgtgat   1320
gatattagtg accagcggag atgataagct tcttggcaat tgcttaccca ctgtgctcag   1380
cagtggttca acaattcact ccattgccct gggttcatct gcagccccaa atctggagga   1440
attatcacgt cttacaggag gtttaaagtt ctttgttcca gatatatcaa actccaatag   1500
catgattgat gctttcagta gaatttcctc tggaactgga gacattttcc agcaacatat   1560
tcagcttgaa agtacaggtg aaaatgtcaa acctcaccat caattgaaaa acacagtgac   1620
tgtggataat actgtgggca acgacactat gtttctagtt acgtggcagg ccagtggtcc   1680
tcctgagatt atattatttg atcctgatgg acgaaaatac tacacaaata attttatcac   1740
caatctaact tttcggacag ctagtctttg gattccagga acagctaagc ctgggcactg   1800
gacttacacc ctgaacaata cccatcattc tctgcaagcc ctgaaagtga cagtgacctc   1860
tcgcgcctcc aactcagctg tgcccccagc cactgtggaa gcctttgtgg aaagagacag   1920
cctccatttt cctcatcctg tgatgattta tgccaatgtg aaacagggat tttatcccat   1980
tcttaatgcc actgtcactg ccacagttga gccagagact ggagatcctg ttacgctgag   2040
actccttgat gatggagcag gtgctgatgt tataaaaaat gatggaattt actcgaggta   2100
tttttctcc tttgctgcaa atggtagata tagcttgaaa gtgcatgtca atcactctcc   2160
cagcataagc accccagccc actctattcc agggagtcat gctatgtatg taccaggtta   2220
cacagcaaac ggtaatattc agatgaatgc tccaaggaaa tcagtaggca gaaatgagga   2280
ggagcgaaag tggggcttta gccgagtcag ctcaggaggc tccttttcag tgctgggagt   2340
tccagctggc ccccaccctg atgtgtttcc accatgcaaa attattgacc tggaagctgt   2400
aaatagaaga ggaattgacc ctatcttgga cagcacctgg agaagacttt gatcagggcc   2460
aggctacaag ctatgaaata agaatgagta aaagtctaca gaatatccaa gatgacttta   2520
acaatgctat tttagtaaat acatcaaagc gaaatcctca gcaagctggc atcagggaga   2580
tatttacgtt ctcaccccaa atttccacga atggacctga acatcagcca aatggagaaa   2640
cacatgaaag ccacagaatt tatgttgcaa tacgagcaat ggataggaac tccttacagt   2700
ctgctgtatc taacattgcc caggcgcctc tgtttattcc ccccaattct gatcctgtac   2760
ctgccagaga ttatcttata ttga                                          2784
```

<210> SEQ ID NO 169
<211> LENGTH: 592
<212> TYPE: PRT
<213> ORGANISM: Homo sapiens

<400> SEQUENCE: 169

-continued

```
Met Thr Gln Arg Ser Ile Ala Gly Pro Ile Cys Asn Leu Lys Phe Val
1               5                   10                  15

Thr Leu Leu Val Ala Leu Ser Ser Glu Leu Pro Phe Leu Gly Ala Gly
            20                  25                  30

Val Gln Leu Gln Asp Asn Gly Tyr Asn Gly Leu Leu Ile Ala Ile Asn
        35                  40                  45

Pro Gln Val Pro Glu Asn Gln Asn Leu Ile Ser Asn Ile Lys Glu Met
    50                  55                  60

Ile Thr Glu Ala Ser Phe Tyr Leu Phe Asn Ala Thr Lys Arg Arg Val
65                  70                  75                  80

Phe Phe Arg Asn Ile Lys Ile Leu Ile Pro Ala Thr Trp Lys Ala Asn
                85                  90                  95

Asn Asn Ser Lys Ile Lys Gln Glu Ser Tyr Glu Lys Ala Asn Val Ile
            100                 105                 110

Val Thr Asp Trp Tyr Gly Ala His Gly Asp Asp Pro Tyr Thr Leu Gln
        115                 120                 125

Tyr Arg Gly Cys Gly Lys Glu Gly Lys Tyr Ile His Phe Thr Pro Asn
    130                 135                 140

Phe Leu Leu Asn Asp Asn Leu Thr Ala Gly Tyr Gly Ser Arg Gly Arg
145                 150                 155                 160

Val Phe Val His Glu Trp Ala His Leu Arg Trp Gly Val Phe Asp Glu
                165                 170                 175

Tyr Asn Asn Asp Lys Pro Phe Tyr Ile Asn Gly Gln Asn Gln Ile Lys
            180                 185                 190

Val Thr Arg Cys Ser Ser Asp Ile Thr Gly Ile Phe Val Cys Glu Lys
        195                 200                 205

Gly Pro Cys Pro Gln Glu Asn Cys Ile Ile Ser Lys Leu Phe Lys Glu
    210                 215                 220

Gly Cys Thr Phe Ile Tyr Asn Ser Thr Gln Asn Ala Thr Ala Ser Ile
225                 230                 235                 240

Met Phe Met Gln Ser Leu Ser Ser Val Val Glu Phe Cys Asn Ala Ser
                245                 250                 255

Thr His Asn Gln Glu Ala Pro Asn Leu Gln Asn Gln Met Cys Ser Leu
            260                 265                 270

Arg Ser Ala Trp Asp Val Ile Thr Asp Ser Ala Asp Phe His His Ser
        275                 280                 285

Phe Pro Met Asn Gly Thr Glu Leu Pro Pro Pro Pro Thr Phe Ser Leu
    290                 295                 300

Val Glu Ala Gly Asp Lys Val Val Cys Leu Val Leu Asp Val Ser Ser
305                 310                 315                 320

Lys Met Ala Glu Ala Asp Arg Leu Leu Gln Leu Gln Gln Ala Ala Glu
                325                 330                 335

Phe Tyr Leu Met Gln Ile Val Glu Ile His Thr Phe Val Gly Ile Ala
            340                 345                 350

Ser Phe Asp Ser Lys Gly Glu Ile Arg Ala Gln Leu His Gln Ile Asn
        355                 360                 365

Ser Asn Asp Asp Arg Lys Leu Leu Val Ser Tyr Leu Pro Thr Thr Val
    370                 375                 380

Ser Ala Lys Thr Asp Ile Ser Ile Cys Ser Gly Leu Lys Lys Gly Phe
385                 390                 395                 400

Glu Val Val Glu Lys Leu Asn Gly Lys Ala Tyr Gly Ser Val Met Ile
                405                 410                 415

Leu Val Thr Ser Gly Asp Asp Lys Leu Leu Gly Asn Cys Leu Pro Thr
```

-continued

```
            420                 425                 430

Val Leu Ser Ser Gly Ser Thr Ile His Ser Ile Ala Leu Gly Ser Ser
        435                 440                 445

Ala Ala Pro Asn Leu Glu Glu Leu Ser Arg Leu Thr Gly Gly Leu Lys
    450                 455                 460

Phe Phe Val Pro Asp Ile Ser Asn Ser Asn Ser Met Ile Asp Ala Phe
465                 470                 475                 480

Ser Arg Ile Ser Ser Gly Thr Gly Asp Ile Phe Gln Gln His Ile Gln
                485                 490                 495

Leu Glu Ser Thr Gly Glu Asn Val Lys Pro His His Gln Leu Lys Asn
            500                 505                 510

Thr Val Thr Val Asp Asn Thr Val Gly Asn Asp Thr Met Phe Leu Val
        515                 520                 525

Thr Trp Gln Ala Ser Gly Pro Pro Glu Ile Ile Leu Phe Asp Pro Asp
    530                 535                 540

Gly Arg Lys Tyr Tyr Thr Asn Asn Phe Ile Thr Asn Leu Thr Phe Arg
545                 550                 555                 560

Thr Ala Ser Leu Trp Ile Pro Gly Thr Ala Lys Pro Gly His Trp Thr
                565                 570                 575

Tyr Thr Leu Met Cys Phe His His Ala Lys Leu Leu Thr Trp Lys Leu
            580                 585                 590


<210> SEQ ID NO 170
<211> LENGTH: 791
<212> TYPE: PRT
<213> ORGANISM: Homo sapiens

<400> SEQUENCE: 170

Met Thr Gln Arg Ser Ile Ala Gly Pro Ile Cys Asn Leu Lys Phe Val
 1               5                  10                  15

Thr Leu Leu Val Ala Leu Ser Ser Glu Leu Pro Phe Leu Gly Ala Gly
            20                  25                  30

Val Gln Leu Gln Asp Asn Gly Tyr Asn Gly Leu Leu Ile Ala Ile Asn
        35                  40                  45

Pro Gln Val Pro Glu Asn Gln Asn Leu Ile Ser Asn Ile Lys Glu Met
    50                  55                  60

Ile Thr Glu Ala Ser Phe Tyr Leu Phe Asn Ala Thr Lys Arg Arg Val
65                  70                  75                  80

Phe Phe Arg Asn Ile Lys Ile Leu Ile Pro Ala Thr Trp Lys Ala Asn
                85                  90                  95

Asn Asn Ser Lys Ile Lys Gln Glu Ser Tyr Glu Lys Ala Asn Val Ile
            100                 105                 110

Val Thr Asp Trp Tyr Gly Ala His Gly Asp Asp Pro Tyr Thr Leu Gln
        115                 120                 125

Tyr Arg Gly Cys Gly Lys Glu Gly Lys Tyr Ile His Phe Thr Pro Asn
    130                 135                 140

Phe Leu Leu Asn Asp Asn Leu Thr Ala Gly Tyr Gly Ser Arg Gly Arg
145                 150                 155                 160

Val Phe Val His Glu Trp Ala His Leu Arg Trp Gly Val Phe Asp Glu
                165                 170                 175

Tyr Asn Asn Asp Lys Pro Phe Tyr Ile Asn Gly Gln Asn Gln Ile Lys
            180                 185                 190

Val Thr Arg Cys Ser Ser Asp Ile Thr Gly Ile Phe Val Cys Glu Lys
        195                 200                 205
```

-continued

```
Gly Pro Cys Pro Gln Glu Asn Cys Ile Ile Ser Lys Leu Phe Lys Glu
    210                 215                 220

Gly Cys Thr Phe Ile Tyr Asn Ser Thr Gln Asn Ala Thr Ala Ser Ile
225                 230                 235                 240

Met Phe Met Gln Ser Leu Ser Ser Val Val Glu Phe Cys Asn Ala Ser
                245                 250                 255

Thr His Asn Gln Glu Ala Pro Asn Leu Gln Asn Gln Met Cys Ser Leu
            260                 265                 270

Arg Ser Ala Trp Asp Val Ile Thr Asp Ser Ala Asp Phe His His Ser
        275                 280                 285

Phe Pro Met Asn Gly Thr Glu Leu Pro Pro Pro Pro Thr Phe Ser Leu
    290                 295                 300

Val Glu Ala Gly Asp Lys Val Val Cys Leu Val Leu Asp Val Ser Ser
305                 310                 315                 320

Lys Met Ala Glu Ala Asp Arg Leu Leu Gln Leu Gln Gln Ala Ala Glu
                325                 330                 335

Phe Tyr Leu Met Gln Ile Val Glu Ile His Thr Phe Val Gly Ile Ala
            340                 345                 350

Ser Phe Asp Ser Lys Gly Glu Ile Arg Ala Gln Leu His Gln Ile Asn
        355                 360                 365

Ser Asn Asp Asp Arg Lys Leu Leu Val Ser Tyr Leu Pro Thr Thr Val
    370                 375                 380

Ser Ala Lys Thr Asp Ile Ser Ile Cys Ser Gly Leu Lys Lys Gly Phe
385                 390                 395                 400

Glu Val Val Glu Lys Leu Asn Gly Lys Ala Tyr Gly Ser Val Met Ile
                405                 410                 415

Leu Val Thr Ser Gly Asp Asp Lys Leu Leu Gly Asn Cys Leu Pro Thr
            420                 425                 430

Val Leu Ser Ser Gly Ser Thr Ile His Ser Ile Ala Leu Gly Ser Ser
        435                 440                 445

Ala Ala Pro Asn Leu Glu Glu Leu Ser Arg Leu Thr Gly Gly Leu Lys
    450                 455                 460

Phe Phe Val Pro Asp Ile Ser Asn Ser Asn Ser Met Ile Asp Ala Phe
465                 470                 475                 480

Ser Arg Ile Ser Ser Gly Thr Gly Asp Ile Phe Gln Gln His Ile Gln
                485                 490                 495

Leu Glu Ser Thr Gly Glu Asn Val Lys Pro His His Gln Leu Lys Asn
            500                 505                 510

Thr Val Thr Val Asp Asn Thr Val Gly Asn Asp Thr Met Phe Leu Val
        515                 520                 525

Thr Trp Gln Ala Ser Gly Pro Pro Glu Ile Ile Leu Phe Asp Pro Asp
    530                 535                 540

Gly Arg Lys Tyr Tyr Thr Asn Asn Phe Ile Thr Asn Leu Thr Phe Arg
545                 550                 555                 560

Thr Ala Ser Leu Trp Ile Pro Gly Thr Ala Lys Pro Gly His Trp Thr
                565                 570                 575

Tyr Thr Leu Asn Asn Thr His His Ser Leu Gln Ala Leu Lys Val Thr
            580                 585                 590

Val Thr Ser Arg Ala Ser Asn Ser Ala Val Pro Pro Ala Thr Val Glu
        595                 600                 605

Ala Phe Val Glu Arg Asp Ser Leu His Phe Pro His Pro Val Met Ile
    610                 615                 620

Tyr Ala Asn Val Lys Gln Gly Phe Tyr Pro Ile Leu Asn Ala Thr Val
```

-continued

```
625                 630                 635                 640

Thr Ala Thr Val Glu Pro Glu Thr Gly Asp Pro Val Thr Leu Arg Leu
                645                 650                 655

Leu Asp Asp Gly Ala Gly Ala Asp Val Ile Lys Asn Asp Gly Ile Tyr
            660                 665                 670

Ser Arg Tyr Phe Phe Ser Phe Ala Ala Asn Gly Arg Tyr Ser Leu Lys
        675                 680                 685

Val His Val Asn His Ser Pro Ser Ile Ser Thr Pro Ala His Ser Ile
    690                 695                 700

Pro Gly Ser His Ala Met Tyr Val Pro Gly Tyr Thr Ala Asn Gly Asn
705                 710                 715                 720

Ile Gln Met Asn Ala Pro Arg Lys Ser Val Gly Arg Asn Glu Glu Glu
                725                 730                 735

Arg Lys Trp Gly Phe Ser Arg Val Ser Ser Gly Gly Ser Phe Ser Val
            740                 745                 750

Leu Gly Val Pro Ala Gly Pro His Pro Asp Val Phe Pro Pro Cys Lys
        755                 760                 765

Ile Ile Asp Leu Glu Ala Val Asn Arg Arg Gly Ile Asp Pro Ile Leu
    770                 775                 780

Asp Ser Thr Trp Arg Arg Leu
785                 790


<210> SEQ ID NO 171
<211> LENGTH: 1491
<212> TYPE: DNA
<213> ORGANISM: Homo sapiens

<400> SEQUENCE: 171

cctcctgcca gccaagtgaa gacatgctta cttccccttc accttccttc atgatgtggg     60

aagagtgctg caacccagcc ctagccaacg ccgcatgaga gggagtgtgc cgagggcttc    120

tgagaaggtt tctctcacat ctagaaagaa gcgcttaaga tgtggcagcc cctcttcttc    180

aagtggctct tgtcctgttg ccctgggagt tctcaaattg ctgcagcagc ctccacccag    240

cctgaggatg acatcaatac acagaggaag aagagtcagg aaaagatgag agaagttaca    300

gactctcctg ggcgaccccg agagcttacc attcctcaga cttcttcaca tggtgctaac    360

agatttgttc ctaaaagtaa agctctagag gccgtcaaat tggcaataga agccgggttc    420

caccatattg attctgcaca tgtttacaat aatgaggagc aggttggact ggccatccga    480

agcaagattg cagatggcag tgtgaagaga gaagacatat tctacacttc aaagctttgg    540

agcaattccc atcgaccaga gttggtccga ccagccttgg aaaggtcact gaaaaatctt    600

caattggact atgttgacct ctatcttatt cattttccag tgtctgtaaa gccaggtgag    660

gaagtgatcc caaaagatga aaatggaaaa atactatttg acacagtgga tctctgtgcc    720

acatgggagg ccatggagaa gtgtaaagat gcaggattgg ccaagtccat cggggtgtcc    780

aacttcaacc acaggctgct ggagatgatc ctcaacaagc cagggctcaa gtacaagcct    840

gtctgcaacc aggtggaatg tcatccttac ttcaaccaga gaaaactgct ggatttctgc    900

aagtcaaaag acattgttct ggttgcctat agtgctctgg gatcccatcg agaagaacca    960

tgggtggacc cgaactcccc ggtgctcttg gaggacccag tcctttgtgc cttggcaaaa   1020

aagcacaagc gaaccccagc cctgattgcc ctgcgctacc agctgcagcg tggggttgtg   1080

gtcctggcca agagctacaa tgagcagcgc atcagacaga acgtgcaggt gtttgaattc   1140

cagttgactt cagaggagat gaaagccata gatggcctaa acagaaatgt gcgatatttg   1200
```

-continued

```
acccttgata tttttgctgg cccccctaat tatccatttt ctgatgaata ttaacatgga   1260

gggcattgca tgaggtctgc cagaaggccc tgcgtgtgga tggtgacaca gaggatggct   1320

ctatgctggt gactggacac atcgcctctg gttaaatctc tcctgcttgg cgacttcagt   1380

aagctacagc taagcccatc ggccggaaaa gaaagacaat aattttgttt ttcattttga   1440

aaaaattaaa tgctctctcc taaagattct tcacctaaaa aaaaaaaaaa a            1491


<210> SEQ ID NO 172
<211> LENGTH: 364
<212> TYPE: PRT
<213> ORGANISM: Homo sapiens

<400> SEQUENCE: 172

Met Trp Gln Pro Leu Phe Phe Lys Trp Leu Leu Ser Cys Cys Pro Gly
 1               5                  10                  15

Ser Ser Gln Ile Ala Ala Ala Ala Ser Thr Gln Pro Glu Asp Asp Ile
            20                  25                  30

Asn Thr Gln Arg Lys Lys Ser Gln Glu Lys Met Arg Glu Val Thr Asp
        35                  40                  45

Ser Pro Gly Arg Pro Arg Glu Leu Thr Ile Pro Gln Thr Ser Ser His
    50                  55                  60

Gly Ala Asn Arg Phe Val Pro Lys Ser Lys Ala Leu Glu Ala Val Lys
65                  70                  75                  80

Leu Ala Ile Glu Ala Gly Phe His His Ile Asp Ser Ala His Val Tyr
                85                  90                  95

Asn Asn Glu Glu Gln Val Gly Leu Ala Ile Arg Ser Lys Ile Ala Asp
            100                 105                 110

Gly Ser Val Lys Arg Glu Asp Ile Phe Tyr Thr Ser Lys Leu Trp Ser
        115                 120                 125

Asn Ser His Arg Pro Glu Leu Val Arg Pro Ala Leu Glu Arg Ser Leu
    130                 135                 140

Lys Asn Leu Gln Leu Asp Tyr Val Asp Leu Tyr Leu Ile His Phe Pro
145                 150                 155                 160

Val Ser Val Lys Pro Gly Glu Glu Val Ile Pro Lys Asp Glu Asn Gly
                165                 170                 175

Lys Ile Leu Phe Asp Thr Val Asp Leu Cys Ala Thr Trp Glu Ala Met
            180                 185                 190

Glu Lys Cys Lys Asp Ala Gly Leu Ala Lys Ser Ile Gly Val Ser Asn
        195                 200                 205

Phe Asn His Arg Leu Leu Glu Met Ile Leu Asn Lys Pro Gly Leu Lys
    210                 215                 220

Tyr Lys Pro Val Cys Asn Gln Val Glu Cys His Pro Tyr Phe Asn Gln
225                 230                 235                 240

Arg Lys Leu Leu Asp Phe Cys Lys Ser Lys Asp Ile Val Leu Val Ala
                245                 250                 255

Tyr Ser Ala Leu Gly Ser His Arg Glu Glu Pro Trp Val Asp Pro Asn
            260                 265                 270

Ser Pro Val Leu Leu Glu Asp Pro Val Leu Cys Ala Leu Ala Lys Lys
        275                 280                 285

His Lys Arg Thr Pro Ala Leu Ile Ala Leu Arg Tyr Gln Leu Gln Arg
    290                 295                 300

Gly Val Val Val Leu Ala Lys Ser Tyr Asn Glu Gln Arg Ile Arg Gln
305                 310                 315                 320
```

-continued

```
Asn Val Gln Val Phe Glu Phe Gln Leu Thr Ser Glu Glu Met Lys Ala
                325                 330                 335

Ile Asp Gly Leu Asn Arg Asn Val Arg Tyr Leu Thr Leu Asp Ile Phe
            340                 345                 350

Ala Gly Pro Pro Asn Tyr Pro Phe Ser Asp Glu Tyr
        355                 360
```

<210> SEQ ID NO 173
<211> LENGTH: 1988
<212> TYPE: DNA
<213> ORGANISM: Homo sapiens

<400> SEQUENCE: 173

```
cgggagccgc ctccccgcgg cctcttcgct tttgtggcgg cgcccgcgct cgcaggccac     60

tctctgctgt cgcccgtccc gcgcgctcct ccgacccgct ccgctccgct ccgctcggcc    120

ccgcgccgcc cgtcaacatg atccgctgcg gcctggcctg cgagcgctgc cgctggatcc    180

tgcccctgct cctactcagc gccatcgcct tcgacatcat cgcgctggcc ggccgcggct    240

ggttgcagtc tagcgaccac ggccagacgt cctcgctgtg gtggaaatgc tcccaagagg    300

gcggcggcag cgggtcctac gaggagggct gtcagagcct catggagtac gcgtggggta    360

gagcagcggc tgccatgctc ttctgtggct tcatcatcct ggtgatctgt ttcatcctct    420

ccttcttcgc cctctgtgga ccccagatgc ttgtcttcct gagagtgatt ggaggtctcc    480

ttgccttggc tgctgtgttc cagatcatct ccctggtaat ttaccccgtg aagtacaccc    540

agaccttcac ccttcatgcc aaccctgctg tcacttacat ctataactgg gcctacggct    600

ttgggtgggc agccacgatt atcctgatcg gctgtgcctt cttcttctgc tgcctcccca    660

actacgaaga tgaccttctg ggcaatgcca agcccaggta cttctacaca tctgcctaac    720

ttgggaatga atgtgggaga aaatcgctgc tgctgagatg gactccagaa gaagaaactg    780

tttctccagg cgactttgaa cccatttttt ggcagtgttc atattattaa actagtcaaa    840

aatgctaaaa taatttggga gaaaatattt tttaagtagt gttatagttt catgtttatc    900

ttttattatg ttttgtgaag ttgtgtcttt tcactaatta cctatactat gccaatattt    960

ccttatatct atccataaca tttatactac atttgtaaga gaatatgcac gtgaaactta   1020

acactttata aggtaaaaat gaggtttcca agatttaata atctgatcaa gttcttgtta   1080

tttccaaata gaatggactt ggtctgttaa gggctaagga gaagaggaag ataaggttaa   1140

aagttgttaa tgaccaaaca ttctaaaaga aatgcaaaaa aaaagtttat tttcaagcct   1200

tcgaactatt taaggaaagc aaaatcattt cctaaatgca tatcatttgt gagaatttct   1260

cattaatatc ctgaatcatt catttcagct aaggcttcat gttgactcga tatgtcatct   1320

aggaaagtac tatttcatgg tccaaacctg ttgccatagt tggtaaggct ttcctttaag   1380

tgtgaaatat ttagatgaaa ttttctcttt taaagttctt tatagggtta gggtgtggga   1440

aaatgctata ttaataaatc tgtagtgttt tgtgtttata tgttcagaac cagagtagac   1500

tggattgaaa gatggactgg gtctaattta tcatgactga tagatctggt taagttgtgt   1560

agtaaagcat taggagggtc attcytgtca caaaagtgcc actaaaacag cctcaggaga   1620

ataaatgact tgcttttcta aatctcaggt ttatctgggc tctatcatat agacaggctt   1680

ctgatagttt gcarctgtaa gcagaaacct acatatagtt aaaatcctgg tctttcttgg   1740

taaacagatt ttaaatgtct gatataaaac atgccacagg agaattcggg gatttgagtt   1800

tctctgaata gcatatatat gatgcatcgg ataggtcatt atgatttttt accatttcga   1860
```

-continued

```
cttacataat gaaaaccaat tcattttaaa tatcagatta ttattttgta agttgtggaa   1920

aaagctaatt gtagttttca ttatgaagtt ttcccaataa accaggtatt ctaaaaaaaa   1980

aaaaaaaa                                                            1988


<210> SEQ ID NO 174
<211> LENGTH: 238
<212> TYPE: PRT
<213> ORGANISM: Homo sapiens

<400> SEQUENCE: 174

Gly Ala Ala Ser Pro Arg Pro Leu Arg Phe Cys Gly Gly Ala Arg Ala
 1               5                  10                  15

Arg Arg Pro Leu Ser Ala Val Ala Arg Pro Ala Arg Ser Ser Asp Pro
            20                  25                  30

Leu Arg Ser Ala Pro Leu Gly Pro Ala Pro Pro Val Asn Met Ile Arg
        35                  40                  45

Cys Gly Leu Ala Cys Glu Arg Cys Arg Trp Ile Leu Pro Leu Leu Leu
    50                  55                  60

Leu Ser Ala Ile Ala Phe Asp Ile Ile Ala Leu Ala Gly Arg Gly Trp
65                  70                  75                  80

Leu Gln Ser Ser Asp His Gly Gln Thr Ser Ser Leu Trp Trp Lys Cys
                85                  90                  95

Ser Gln Glu Gly Gly Gly Ser Gly Ser Tyr Glu Glu Gly Cys Gln Ser
            100                 105                 110

Leu Met Glu Tyr Ala Trp Gly Arg Ala Ala Ala Ala Met Leu Phe Cys
        115                 120                 125

Gly Phe Ile Ile Leu Val Ile Cys Phe Ile Leu Ser Phe Phe Ala Leu
    130                 135                 140

Cys Gly Pro Gln Met Leu Val Phe Leu Arg Val Ile Gly Gly Leu Leu
145                 150                 155                 160

Ala Leu Ala Ala Val Phe Gln Ile Ile Ser Leu Val Ile Tyr Pro Val
                165                 170                 175

Lys Tyr Thr Gln Thr Phe Thr Leu His Ala Asn Pro Ala Val Thr Tyr
            180                 185                 190

Ile Tyr Asn Trp Ala Tyr Gly Phe Gly Trp Ala Ala Thr Ile Ile Leu
        195                 200                 205

Ile Gly Cys Ala Phe Phe Phe Cys Cys Leu Pro Asn Tyr Glu Asp Asp
    210                 215                 220

Leu Leu Gly Asn Ala Lys Pro Arg Tyr Phe Tyr Thr Ser Ala
225                 230                 235


<210> SEQ ID NO 175
<211> LENGTH: 4181
<212> TYPE: DNA
<213> ORGANISM: Homo sapiens
<220> FEATURE:
<221> NAME/KEY: misc_feature
<222> LOCATION: 3347, 3502, 3506, 3520, 3538, 3549, 3646, 3940, 3968,
      3974, 4036, 4056, 4062, 4080, 4088, 4115
<223> OTHER INFORMATION: n = A,T,C or G

<400> SEQUENCE: 175

ggtggatgcg tttgggttgt agctaggctt tttcttttct ttctctttta aaacacatct     60

agacaaggaa aaaacaagcc tcggatctga tttttcactc ctcgttcttg tgcttggttc    120

ttactgtgtt tgtgtatttt aaaggcgaga agacgagggg aacaaaacca gctggatcca    180

tccatcaccg tgggtggttt taatttttcg ttttttctcg ttattttttt ttaaacaacc    240
```

-continued

```
actcttcaca atgaacaaac tgtatatcgg aaacctcagc gagaacgccg ccccctcgga    300
cctagaaagt atcttcaagg acgccaagat cccggtgtcg ggacccttcc tggtgaagac    360
tggctacgcg ttcgtggact gcccggacga gagctgggcc ctcaaggcca tcgaggcgct    420
ttcaggtaaa atagaactgc acgggaaacc catagaagtt gagcactcgg tcccaaaaag    480
gcaaaggatt cggaaacttc agatacgaaa tatcccgcct catttacagt gggaggtgct    540
ggatagttta ctagtccagt atggagtggt ggagagctgt gagcaagtga acactgactc    600
ggaaactgca gttgtaaatg taacctattc cagtaaggac caagctagac aagcactaga    660
caaactgaat ggatttcagt tagagaattt caccttgaaa gtagcctata tccctgatga    720
aatggccgcc cagcaaaacc ccttgcagca gccccgaggt cgccgggggc ttgggcagag    780
gggctcctca aggcaggggt ctccaggatc cgtatccaag cagaaaccat gtgatttgcc    840
tctgcgcctg ctggttccca cccaatttgt tggagccatc ataggaaaag aaggtgccac    900
cattcggaac atcaccaaac agacccagtc taaaatcgat gtccaccgta aagaaaatgc    960
gggggctgct gagaagtcga ttactatcct ctctactcct gaaggcacct ctgcggcttg   1020
taagtctatt ctggagatta tgcataagga agctcaagat ataaaattca cagaagagat   1080
ccccttgaag attttagctc ataataactt tgttggacgt cttattggta aagaaggaag   1140
aaatcttaaa aaaattgagc aagacacaga cactaaaatc acgatatctc cattgcagga   1200
attgacgctg tataatccag aacgcactat tacagttaaa ggcaatgttg agacatgtgc   1260
caaagctgag gaggagatca tgaagaaaat cagggagtct tatgaaaatg atattgcttc   1320
tatgaatctt caagcacatt taattcctgg attaaatctg aacgccttgg gtctgttccc   1380
acccacttca gggatgccac ctcccacctc agggccccct tcagccatga ctcctcccta   1440
cccgcagttt gagcaatcag aaacggagac tgttcatcag tttatcccag ctctatcagt   1500
cggtgccatc atcggcaagc agggccagca catcaagcag ctttctcgct ttgctggagc   1560
ttcaattaag attgctccag cggaagcacc agatgctaaa gtgaggatgg tgattatcac   1620
tggaccacca gaggctcagt tcaaggctca gggaagaatt tatggaaaaa ttaaagaaga   1680
aaactttgtt agtcctaaag aagaggtgaa acttgaagct catatcagag tgccatcctt   1740
tgctgctggc agagttattg gaaaaggagg caaaacggtg aatgaacttc agaatttgtc   1800
aagtgcagaa gttgttgtcc ctcgtgacca gacacctgat gagaatgacc aagtggttgt   1860
caaaataact ggtcacttct atgcttgcca ggttgcccag agaaaaattc aggaaattct   1920
gactcaggta aagcagcacc aacaacagaa ggctctgcaa agtggaccac ctcagtcaag   1980
acggaagtaa aggctcagga aacagcccac cacagaggca gatgccaaac caaagacaga   2040
ttgcttaacc aacagatggg cgctgacccc ctatccagaa tcacatgcac aagtttttac   2100
ctagccagtt gtttctgagg accaggcaac ttttgaactc ctgtctctgt gagaatgtat   2160
actttatgct ctctgaaatg tatgacaccc agctttaaaa caaacaaaca aacaaacaaa   2220
aaaagggtgg gggagggagg gaaagagaag agctctgcac ttccctttgt tgtagtctca   2280
cagtataaca gatattctaa ttcttcttaa tattccccca taatgccaga aattggctta   2340
atgatgcttt cactaaattc atcaaataga ttgctcctaa atccaattgt taaaattgga   2400
tcagaataat tatcacagga acttaaatgt taagccatta gcatagaaaa actgttctca   2460
gttttatttt tacctaacac taacatgagt aacctaaggg aagtgctgaa tggtgttggc   2520
aggggtatta aacgtgcatt tttactcaac tacctcaggt attcagtaat acaatgaaaa   2580
```

-continued

```
gcaaaattgt tcctttttttt tgaaaatttt atatacttta taatgataga agtccaaccg   2640

tttttttaaaa aataaattta aaatttaaca gcaatcagct aacaggcaaa ttaagatttt   2700

tacttctggc tggtgacagt aaagctggaa aattaatttc agggtttttt gaggcttttg   2760

acacagttat tagttaaatc aaatgttcaa aaatacggag cagtgcctag tatctggaga   2820

gcagcactac catttattct ttcatttata gttgggaaag tttttgacgg tactaacaaa   2880

gtggtcgcag gagattttgg aacggctggt ttaaatggct tcaggagact tcagtttttt   2940

gtttagctac atgattgaat gcataataaa tgctttgtgc ttctgactat caatacctaa   3000

agaaagtgca tcagtgaaga gatgcaagac tttcaactga ctggcaaaaa gcaagcttta   3060

gcttgtctta taggatgctt agtttgccac tacacttcag accaatggga cagtcataga   3120

tggtgtgaca gtgtttaaac gcaacaaaag gctacatttc catggggcca gcactgtcat   3180

gagcctcact aagctatttt gaagattttt aagcactgat aaattaaaaa aaaaaaaaaa   3240

aaattagact ccaccttaag tagtaaagta taacaggatt tctgtatact gtgcaatcag   3300

ttctttgaaa aaaaagtcaa aagatagaga atacaagaaa agttttnggg atataatttg   3360

aatgactgtg aaaacatatg acctttgata acgaactcat ttgctcactc cttgacagca   3420

aagcccagta cgtacaattg tgttgggtgt gggtggtctc caaggccacg ctgctctctg   3480

aattgatttt ttgagttttg gnttgnaaga tgatcacagn catgttacac tgatcttnaa   3540

ggacatatnt tataaccctt taaaaaaaaa atcccctgcc tcattcttat ttcgagatga   3600

atttcgatac agactagatg tctttctgaa gatcaattag acattntgaa aatgatttaa   3660

agtgttttcc ttaatgttct ctgaaaacaa gtttcttttg tagttttaac caaaaaagtg   3720

cccttttgt cactggtttc tcctagcatt catgattttt ttttcacaca atgaattaaa   3780

attgctaaaa tcatggactg gctttctggt tggatttcag gtaagatgtg tttaaggcca   3840

gagcttttct cagtatttga ttttttccc caatatttga ttttttaaaa atatacacat   3900

aggagctgca tttaaaacct gctggtttaa attctgtcan atttcacttc tagcctttta   3960

gtatggcnaa tcanaattta cttttactta agcatttgta atttggagta tctggtacta   4020

gctaagaaat aattcnataa ttgagttttg tactcnccaa anatgggtca ttcctcatgn   4080

ataatgtncc cccaatgcag cttcattttc caganacctt gacgcaggat aaattttttc   4140

atcatttagg tccccaaaaa aaaaaaaaaa aaaaaaaaaa a                      4181
```

<210> SEQ ID NO 176
<211> LENGTH: 579
<212> TYPE: PRT
<213> ORGANISM: Homo sapiens

<400> SEQUENCE: 176

```
Met Asn Lys Leu Tyr Ile Gly Asn Leu Ser Glu Asn Ala Ala Pro Ser
 1               5                  10                  15

Asp Leu Glu Ser Ile Phe Lys Asp Ala Lys Ile Pro Val Ser Gly Pro
            20                  25                  30

Phe Leu Val Lys Thr Gly Tyr Ala Phe Val Asp Cys Pro Asp Glu Ser
        35                  40                  45

Trp Ala Leu Lys Ala Ile Glu Ala Leu Ser Gly Lys Ile Glu Leu His
    50                  55                  60

Gly Lys Pro Ile Glu Val Glu His Ser Val Pro Lys Arg Gln Arg Ile
65                  70                  75                  80

Arg Lys Leu Gln Ile Arg Asn Ile Pro Pro His Leu Gln Trp Glu Val
                85                  90                  95
```

-continued

```
Leu Asp Ser Leu Leu Val Gln Tyr Gly Val Val Glu Ser Cys Glu Gln
            100                 105                 110

Val Asn Thr Asp Ser Glu Thr Ala Val Val Asn Val Thr Tyr Ser Ser
        115                 120                 125

Lys Asp Gln Ala Arg Gln Ala Leu Asp Lys Leu Asn Gly Phe Gln Leu
    130                 135                 140

Glu Asn Phe Thr Leu Lys Val Ala Tyr Ile Pro Asp Glu Met Ala Ala
145                 150                 155                 160

Gln Gln Asn Pro Leu Gln Gln Pro Arg Gly Arg Arg Gly Leu Gly Gln
                165                 170                 175

Arg Gly Ser Ser Arg Gln Gly Ser Pro Gly Ser Val Ser Lys Gln Lys
            180                 185                 190

Pro Cys Asp Leu Pro Leu Arg Leu Leu Val Pro Thr Gln Phe Val Gly
        195                 200                 205

Ala Ile Ile Gly Lys Glu Gly Ala Thr Ile Arg Asn Ile Thr Lys Gln
    210                 215                 220

Thr Gln Ser Lys Ile Asp Val His Arg Lys Glu Asn Ala Gly Ala Ala
225                 230                 235                 240

Glu Lys Ser Ile Thr Ile Leu Ser Thr Pro Glu Gly Thr Ser Ala Ala
                245                 250                 255

Cys Lys Ser Ile Leu Glu Ile Met His Lys Glu Ala Gln Asp Ile Lys
            260                 265                 270

Phe Thr Glu Glu Ile Pro Leu Lys Ile Leu Ala His Asn Asn Phe Val
        275                 280                 285

Gly Arg Leu Ile Gly Lys Glu Gly Arg Asn Leu Lys Lys Ile Glu Gln
    290                 295                 300

Asp Thr Asp Thr Lys Ile Thr Ile Ser Pro Leu Gln Glu Leu Thr Leu
305                 310                 315                 320

Tyr Asn Pro Glu Arg Thr Ile Thr Val Lys Gly Asn Val Glu Thr Cys
                325                 330                 335

Ala Lys Ala Glu Glu Glu Ile Met Lys Lys Ile Arg Glu Ser Tyr Glu
            340                 345                 350

Asn Asp Ile Ala Ser Met Asn Leu Gln Ala His Leu Ile Pro Gly Leu
        355                 360                 365

Asn Leu Asn Ala Leu Gly Leu Phe Pro Pro Thr Ser Gly Met Pro Pro
    370                 375                 380

Pro Thr Ser Gly Pro Pro Ser Ala Met Thr Pro Pro Tyr Pro Gln Phe
385                 390                 395                 400

Glu Gln Ser Glu Thr Glu Thr Val His Gln Phe Ile Pro Ala Leu Ser
                405                 410                 415

Val Gly Ala Ile Ile Gly Lys Gln Gly Gln His Ile Lys Gln Leu Ser
            420                 425                 430

Arg Phe Ala Gly Ala Ser Ile Lys Ile Ala Pro Ala Glu Ala Pro Asp
        435                 440                 445

Ala Lys Val Arg Met Val Ile Ile Thr Gly Pro Pro Glu Ala Gln Phe
    450                 455                 460

Lys Ala Gln Gly Arg Ile Tyr Gly Lys Ile Lys Glu Glu Asn Phe Val
465                 470                 475                 480

Ser Pro Lys Glu Glu Val Lys Leu Glu Ala His Ile Arg Val Pro Ser
                485                 490                 495

Phe Ala Ala Gly Arg Val Ile Gly Lys Gly Gly Lys Thr Val Asn Glu
            500                 505                 510
```

-continued

```
Leu Gln Asn Leu Ser Ser Ala Glu Val Val Val Pro Arg Asp Gln Thr
        515                 520                 525

Pro Asp Glu Asn Asp Gln Val Val Val Lys Ile Thr Gly His Phe Tyr
    530                 535                 540

Ala Cys Gln Val Ala Gln Arg Lys Ile Gln Glu Ile Leu Thr Gln Val
545                 550                 555                 560

Lys Gln His Gln Gln Gln Lys Ala Leu Gln Ser Gly Pro Pro Gln Ser
                565                 570                 575

Arg Arg Lys
```

<210> SEQ ID NO 177
<211> LENGTH: 401
<212> TYPE: DNA
<213> ORGANISM: Homo sapiens

<400> SEQUENCE: 177

```
atgccccgta aatgtcttca gtgttcttca gggtagttgg gatctcaaaa gatttggttc     60

agatccaaac aaatacacat tctgtgtttt agctcagtgt tttctaaaaa aagaaactgc    120

cacacagcaa aaaattgttt actttgttgg acaaaccaaa tcagttctca aaaaatgacc    180

ggtgcttata aaaagttata aatatcgagt agctctaaaa caaaccacct gaccaagagg    240

gaagtgagct tgtgcttagt atttacattg gatgccagtt ttgtaatcac tgacttatgt    300

gcaaactggt gcagaaattc tataaactct ttgctgtttt tgatacctgc tttttgtttc    360

attttgtttt gttttgtaaa aatgataaaa cttcagaaaa t                        401
```

<210> SEQ ID NO 178
<211> LENGTH: 561
<212> TYPE: DNA
<213> ORGANISM: Homo sapiens

<400> SEQUENCE: 178

```
acgcctttca agggtgtacg caaagcactc attgataccc ttttggatgg ctatgaaaca     60

gcccgctatg ggacaggggt ctttggccag aatgagtacc tacgctatca ggaggccctg    120

agtgagctgg ccactgcggt taaagcacga attgggagct ctcagcgaca tcaccagtca    180

gcagccaaag acctaactca gtcccctgag gtctccccaa caaccatcca ggtgacatac    240

ctcccctcca gtcagaagag taaacgtgcc aagcacttcc ttgaattgaa gagctttaag    300

gataactata acacattgga gagtactctg tgacggagct gaaggactct tgccgtagat    360

taagccagtc agttgcaatg tgcaagacag gctgcttgcc gggccgccct cggaacatct    420

ggcccagcag gcccagactg tatccatcca agttcccgtt gtatccagag ttcttagagc    480

ttgtgtctaa agggtaattc cccaaccctt ccttatgagc atttttagaa cattggctaa    540

gactattttc ccccagtagc g                                              561
```

<210> SEQ ID NO 179
<211> LENGTH: 521
<212> TYPE: DNA
<213> ORGANISM: Homo sapiens

<400> SEQUENCE: 179

```
cccaacgcgt ttgcaaatat tcccctggta gcctacttcc ttacccccga atattggtaa     60

gatcgagcaa tggcttcagg acatgggttc tcttctcctg tgatcattca agtgctcact    120

gcatgaagac tggcttgtct cagtgtttca acctcaccag ggctgtctct tggtccacac    180

ctcgctccct gttagtgccg tatgacagcc cccatcaaat gaccttggcc aagtcacggt    240
```

-continued

```
ttctctgtgg tcaaggttgg ttggctgatt ggtggaaagt agggtggacc aaaggaggcc    300

acgtgagcag tcagcaccag ttctgcacca gcagcgcctc cgtcctagtg ggtgttcctg    360

tttctcctgg ccctgggtgg gctagggcct gattcgggaa gatgcctttg cagggagggg    420

aggataagtg ggatctacca attgattctg gcaaaacaat ttctaagatt tttttgcttt    480

atgtgggaaa cagatctaaa tctcatttta tgctgtattt t                        521
```

<210> SEQ ID NO 180
<211> LENGTH: 417
<212> TYPE: DNA
<213> ORGANISM: Homo sapiens

<400> SEQUENCE: 180

```
ggtggaattc gccgaagatg gcggaggtgc aggtcctggt gcttgatggt cgaggccatc     60

tcctgggccg cctggcggcc atcgtggcta aacaggtact gctgggccgg aaggtggtgg    120

tcgtacgctg tgaaggcatc aacatttctg gcaatttcta cagaaacaag ttgaagtacc    180

tggctttcct ccgcaagcgg atgaacacca acccttcccg aggcccctac cacttccggg    240

cccccagccg catcttctgg cggaccgtgc gaggtatgct gccccacaaa accaagcgag    300

gccaggccgc tctggaccgt ctcaaggtgt ttgacggcat cccaccgccc tacgacaaga    360

aaaagcggat ggtggttcct gctgccctca aggtcgtgcg tctgaagcct acaagaa       417
```

<210> SEQ ID NO 181
<211> LENGTH: 283
<212> TYPE: DNA
<213> ORGANISM: Homo sapiens
<220> FEATURE:
<221> NAME/KEY: misc_feature
<222> LOCATION: 35
<223> OTHER INFORMATION: n = A,T,C or G

<400> SEQUENCE: 181

```
gatttcttct aaataggatg taaaacttct ttcanattac tcttcctcag tcctgcctgc     60

caagaactca agtgtaactg tgataaaata acctttccca ggtatattgg caggtatgtg    120

tgtaatctca gaatacacag gtgacataga tatgatatga caactggtaa tggtggattc    180

atttacattg tttacacttc tatgaccagg ccttaaggga aggtcagttt tttaaaaaac    240

caagtagtgt cttcctacct atctccagat acatgtcaaa aaa                      283
```

<210> SEQ ID NO 182
<211> LENGTH: 401
<212> TYPE: DNA
<213> ORGANISM: Homo sapiens

<400> SEQUENCE: 182

```
atattcttgc tgcttatgca gctgacattg ttgccctccc taaagcaacc aagtagcctt     60

tatttcccac agtgaaagaa aacgctggcc tatcagttac attacaaaag gcagatttca    120

agaggattga gtaagtagtt ggatggcttt cataaaaaca agaattcaag aagaggattc    180

atgctttaag aaacatttgt tatacattcc tcacaaatta tacctgggat aaaaactatg    240

tagcaggcag tgtgttttcc ttccatgtct ctctgcacta cctgcagtgt gtcctctgag    300

gctgcaagtc tgtcctatct gaattcccag cagaagcact aagaagctcc accctatcac    360

ctagcagata aaactatggg gaaaacttaa atctgtgcat a                        401
```

<210> SEQ ID NO 183

-continued

<211> LENGTH: 366
<212> TYPE: DNA
<213> ORGANISM: Homo sapiens
<220> FEATURE:
<221> NAME/KEY: misc_feature
<222> LOCATION: 325
<223> OTHER INFORMATION: n = A,T,C or G

<400> SEQUENCE: 183
accgtgtcca agtttttaga acccttgtta gccagaccga ggtgtcctgg tcaccgtttc 60
accatcatgc tttgatgttc ccctgtcttt ctctcttctg ctctcaagag caaaggttaa 120
tttaaggaca aagatgaagt cactgtaaac taatctgtca ttgtttttac cttccttttc 180
tttttcagtg cagaaattaa aagtaagtat aaagcaccgt gattgggagt gtttttgcgt 240
gtgtcggaat cactggtaaa tgttggctga gaacaatccc tccccttgca cttgtgaaaa 300
cactttgagc gctttaagag attancctga gaaataatta aatatctttt ctcttcaaaa 360
aaaaaa 366

<210> SEQ ID NO 184
<211> LENGTH: 370
<212> TYPE: DNA
<213> ORGANISM: Homo sapiens

<400> SEQUENCE: 184
tcttacttca aaagaaaaat aaacataaaa aataagttgc tggttcctaa caggaaaaat 60
tttaataatt gtactgagag aaactgctta cgtacacatt gcagatcaaa tatttggagt 120
taaaatgtta gtctacatag atgggtgatt gtaactttat tgccattaaa agatttcaaa 180
ttgcattcat gcttctgtgt acacataatg aaaaatgggc aaataatgaa gatctctcct 240
tcagtctgct ctgtttaatt ctgctgtctg ctcttctcta atgctgcgtc cctaattgta 300
cacagtttag tgatatctag gagtataaag ttgtcgccca tcaataaaaa tcacaaagtt 360
ggtttaaaaa 370

<210> SEQ ID NO 185
<211> LENGTH: 107
<212> TYPE: DNA
<213> ORGANISM: Homo sapiens

<400> SEQUENCE: 185
ctcatattat tttccttttg agaaattgga aactctttct gttgctatta tattaataaa 60
gttggtgttt attttctggt agtcaccttc cccatttaaa aaaaaaa 107

<210> SEQ ID NO 186
<211> LENGTH: 309
<212> TYPE: DNA
<213> ORGANISM: Homo sapiens

<400> SEQUENCE: 186
gaaaggatgg ctctggttgc cacagagctg ggacttcatg ttcttctaga gagggccaca 60
agagggccac aggggtggcc gggagttgtc agctgatgcc tgctgagagg caggaattgt 120
gccagtgagt gacagtcatg agggagtgtc tcttcttggg gaggaaagaa ggtagagcct 180
ttctgtctga atgaaaggcc aaggctacag tacagggccc cgccccagcc agggtgttaa 240
tgcccacgta gtggaggcct ctggcagatc ctgcattcca aggtcactgg actgtacgtt 300
tttatggtt 309

-continued

<210> SEQ ID NO 187
<211> LENGTH: 477
<212> TYPE: DNA
<213> ORGANISM: Homo sapiens

<400> SEQUENCE: 187
ttcagtccta gcaagaagcg agaattctga gatcctccag aaagtcgagc agcacccacc 60
tccaacctcg ggccagtgtc ttcaggcttt actggggacc tgcgagctgg cctaatgtgg 120
tggcctgcaa gccaggccat ccctgggcgc cacagacgag ctccgagcca ggtcaggctt 180
cggaggccac aagctcagcc tcaggcccag gcactgattg tggcagaggg gccactaccc 240
aaggtctagc taggcccaag acctagttac ccagacagtg agaagcccct ggaaggcaga 300
aaagttggga gcatggcaga cagggaaggg aaacattttc agggaaaaga catgtatcac 360
atgtcttcag aagcaagtca ggtttcatgt aaccgagtgt cctcttgcgt gtccaaaagt 420
agcccagggc tgtagcacag gcttcacagt gattttgtgt tcagccgtga gtcacac 477

<210> SEQ ID NO 188
<211> LENGTH: 220
<212> TYPE: DNA
<213> ORGANISM: Homo sapiens

<400> SEQUENCE: 188
taaatatggt agatattaat attcctctta gatgaccagt gattccaatt gtcccaagtt 60
ttaaataagt accctgtgag tatgagataa attagtgaca atcagaacaa gtttcagtat 120
cagatgttca agaggaagtt gctattgcat tgattttaat atttgtacat aaacactgat 180
ttttttgagc attattttgt atttgttgta ctttaatacc 220

<210> SEQ ID NO 189
<211> LENGTH: 417
<212> TYPE: DNA
<213> ORGANISM: Homo sapiens
<220> FEATURE:
<221> NAME/KEY: misc_feature
<222> LOCATION: 76, 77
<223> OTHER INFORMATION: n = A,T,C or G

<400> SEQUENCE: 189
accatcttga cagaggatac atgctcccaa aacgtttgtt accacactta aaaatcactg 60
ccatcattaa gcatcnnttt caaaattata gccattcatg atttactttt tccagatgac 120
tatcattatt ctagtccttt gaatttgtaa ggggaaaaaa aacaaaaaca aaaacttacg 180
atgcactttt ctccagcaca tcagatttca aattgaaaat taaagacatg ctatggtaat 240
gcacttgcta gtactacaca ctttgtacaa caaaaaacag aggcaagaaa caacggaaag 300
agaaaagcct tcctttgttg gcccttaaac tgagtcaaga tctgaaatgt agagatgatc 360
tctgacgata cctgtatgtt cttattgtgt aaataaaatt gctggtatga aatgaca 417

<210> SEQ ID NO 190
<211> LENGTH: 497
<212> TYPE: DNA
<213> ORGANISM: Homo sapiens

<400> SEQUENCE: 190
gcactgcggc gctctcccgt cccgcggtgg ttgctgctgc tgccgctgct gctgggcctg 60
aacgcaggag ctgtcattga ctggcccaca gaggagggca aggaagtatg ggattatgtg 120
acggtccgca aggatgccta catgttctgg tggctctatt atgccaccaa ctcctgcaag 180

-continued aacttctcag aactgcccct ggtcatgtgg cttcagggcg gtccaggcgg ttctagcact 240
ggatttggaa actttgagga aattgggccc cttgacagtg atctcaaacc acggaaaacc 300
acctggctcc aggctgccag tctcctattt gtggataatc ccgtgggcac tgggttcagt 360
tatgtgaatg gtagtggtgc ctatgccaag gacctggcta tggtggcttc agacatgatg 420
gttctcctga agaccttctt cagttgccac aaagaattcc agacagttcc attctacatt 480
ttctcagagt cctatgg 497

<210> SEQ ID NO 191
<211> LENGTH: 175
<212> TYPE: DNA
<213> ORGANISM: Homo sapiens

<400> SEQUENCE: 191
atgttgaata ttttgcttat taactttgtt tattgtcttc tccctcgatt agaatattag 60
ctacttgagt acaaggattt gagcctgtta cattcactgc tgaattttag gctcctggaa 120
gatacccagc attcaataga gaccacacaa taaatatatg tcaaataaaa aaaaa 175

<210> SEQ ID NO 192
<211> LENGTH: 526
<212> TYPE: DNA
<213> ORGANISM: Homo sapiens

<400> SEQUENCE: 192
agtaaacatt attatttttt ttatatttgc aaaggaaaca tatctaatcc ttcctataga 60
aagaacagta ttgctgtaat tccttttctt ttcttcctca tttcctctgc cccttaaaag 120
attgaagaaa gagaaacttg tcaactcata tccacgttat ctagcaaagt acataagaat 180
ctatcactaa gtaatgtatc cttcagaatg tgttggttta ccagtgacac cccatattca 240
tcacaaaatt aaagcaagaa gtccatagta atttatttgc taatagtgga tttttaatgc 300
tcagagtttc tgaggtcaaa ttttatcttt tcacttacaa gctctatgat cttaaataat 360
ttacttaatg tattttggtg tattttcctc aaattaatat tggtgttcaa gactatatct 420
aattcctctg atcactttga gaaacaaact tttattaaat gtaaggcact tttctatgaa 480
ttttaaatat aaaaataaat attgttctga ttattactga aaaaaa 526

<210> SEQ ID NO 193
<211> LENGTH: 553
<212> TYPE: DNA
<213> ORGANISM: Homo sapiens
<220> FEATURE:
<221> NAME/KEY: misc_feature
<222> LOCATION: 290, 300, 411, 441
<223> OTHER INFORMATION: n = A,T,C or G

<400> SEQUENCE: 193
tccattgtgg tggaattcgc tctctggtaa aggcgtgcag gtgttggccg cggcctctga 60
gctgggatga gccgtgctcc cggtggaagc aagggagccc agccggagcc atggccagta 120
cagtggtagc agttggactg accattgctg ctgcaggatt tgcaggccgt tacgttttgc 180
aagccatgaa gcatatggag cctcaagtaa aacaagtttt tcaaagccta ccaaaatctg 240
ccttcagtgg tggctattat agaggtgggt ttgaacccaa aatgacaaan cgggaagcan 300
cattaatact aggtgtaagc cctactgcca ataaagggaa aataagagat gctcatcgac 360
gaattatgct tttaaatcat cctgacaaag gaggatctcc ttatatagca nccaaaatca 420
atgaagctaa agatttacta naaggtcaag ctaaaaaatg aagtaaatgt atgatgaatt 480

-continued ttaagttcgt attagtttat gtatatgagt actaagtttt tataataaaa tgcctcagag 540
ctacaatttt aaa 553

<210> SEQ ID NO 194
<211> LENGTH: 320
<212> TYPE: DNA
<213> ORGANISM: Homo sapiens

<400> SEQUENCE: 194
cccttcccaa tccatcagta aagaccccat ctgccttgtc catgccgttt cccaacaggg 60
atgtcacttg atatgagaat ctcaaatctc aatgccttat aagcattcct tcctgtgtcc 120
attaagactc tgataattgt ctcccctcca taggaatttc tcccaggaaa gaaatatatc 180
cccatctccg tttcatatca gaactaccgt ccccgatatt cccttcagag agattaaaga 240
ccagaaaaaa gtgagcctct tcatctgcac ctgtaatagt ttcagttcct attttcttcc 300
attgacccat atttatacct 320

<210> SEQ ID NO 195
<211> LENGTH: 320
<212> TYPE: DNA
<213> ORGANISM: Homo sapiens
<220> FEATURE:
<221> NAME/KEY: misc_feature
<222> LOCATION: 203, 218
<223> OTHER INFORMATION: n = A,T,C or G

<400> SEQUENCE: 195
aagcatgacc tggggaaatg gtcagacctt gtattgtgtt tttggccttg aaagtagcaa 60
gtgaccagaa tctgccatgg caacaggctt taaaaaagac ccttaaaaag acactgtctc 120
aactgtggtg ttagcaccag ccagctctct gtacatttgc tagcttgtag ttttctaaga 180
ctgagtaaac ttcttatttt tanaaagggg aggctggntt gtaactttcc ttgtacttaa 240
ttgggtaaaa gtcttttcca caaaccacca tctattttgt gaactttgtt agtcatcttt 300
tatttggtaa attatgaact 320

<210> SEQ ID NO 196
<211> LENGTH: 357
<212> TYPE: DNA
<213> ORGANISM: Homo sapiens
<220> FEATURE:
<221> NAME/KEY: misc_feature
<222> LOCATION: 36
<223> OTHER INFORMATION: n = A,T,C or G

<400> SEQUENCE: 196
atataaaata atacgaaact ttaaaaagca ttggantgtc agtatgttga atcagtagtt 60
tcactttaac tgtaaacaat ttcttaggac accatttggg ctagtttctg tgtaagtgta 120
aatactacaa aaacttattt atactgttct tatgtcattt gttatattca tagatttata 180
tgatgatatg acatctggct aaaaagaaat tattgcaaaa ctaaccacta tgtacttttt 240
tataaatact gtatggacaa aaaatggcat tttttatatt aaattgttta gctctggcaa 300
aaaaaaaaaa ttttaagagc tggtactaat aaaggattat tatgactgtt aaaaaaa 357

<210> SEQ ID NO 197
<211> LENGTH: 565
<212> TYPE: DNA
<213> ORGANISM: Homo sapiens
<220> FEATURE:

-continued

<221> NAME/KEY: misc_feature
<222> LOCATION: 27
<223> OTHER INFORMATION: n = A,T,C or G

<400> SEQUENCE: 197

```
tcagctgagt accatcagga tatttanccc tttaagtgct gttttgggag tagaaaacta     60

aagcaacaat acttcctctt gacagctttg attggaatgg ggttattaga tcattcacct    120

tggtcctaca ctttttagga tgcttggtga acataacacc acttataatg aacatccctg    180

gttcctatat tttgggctat gtgggtagga attgttactt gttactgcag cagcagccct    240

agaaagtaag cccagggctt cagatctaag ttagtccaaa agctaaatga tttaaagtca    300

agttgtaatg ctaggcataa gcactctata atacattaaa ttataggccg agcaattagg    360

gaatgtttct gaaacattaa acttgtattt atgtcactaa aattctaaca caaacttaaa    420

aaatgtgtct catacatatg ctgtactagg cttcatcatg catttctaaa tttgtgtatg    480

atttgaatat atgaaagaat ttatacaaga gtgttattta aaattattaa aaataaatgt    540

atataatttg tacctattgt aaaaa                                          565
```

<210> SEQ ID NO 198
<211> LENGTH: 484
<212> TYPE: DNA
<213> ORGANISM: Homo sapiens

<400> SEQUENCE: 198

```
tatgtaagta ttggtgtctg ctttaaaaaa ggagacccag acttcacctg tcctttttaa     60

acatttgaga acagtgttac tctgagcagt tgggccacct tcaccttatc cgacagctga    120

ctgttggatg tgtccattgt cgccagtttg gctgttgccc ggacaggaca ggacctccat    180

tgggcgcagc agcaggtggc aggggtgtgg cttgaggtgg gtggcagcgt ctggtcctcc    240

tctctggtgc tttctgagag ggtctctaaa gcagagtgtg gttggcctgg gggaaggcag    300

agcacgtatt tctcccctct agtacctctg catttgtgag tgttccctct ggctttctga    360

agggcagcag actcttgagt atactgcaga ggacatgctt tatcagtagg tcctgagggc    420

tccaggggct caactgacca agtaacacag aagttggggt atgtggccta tttgggtcgg    480

aaac                                                                 484
```

<210> SEQ ID NO 199
<211> LENGTH: 429
<212> TYPE: DNA
<213> ORGANISM: Homo sapiens
<220> FEATURE:
<221> NAME/KEY: misc_feature
<222> LOCATION: 77, 88, 134, 151, 189, 227, 274, 319
<223> OTHER INFORMATION: n = A,T,C or G

<400> SEQUENCE: 199

```
gcttatgttt tttgttttaa cttttgtttt ttaacattta gaatattaca ttttgtatta     60

tacagtacct ttctcanaca ttttgtanaa ttcatttcgg cagctcacta ggattttgct    120

gaacattaaa aagngtgata gcgatattag ngccaatcaa atggaaaaaa ggtagtctta    180

ataaacaana cacaacgttt ttatacaaca tactttaaaa tattaanaaa actccttaat    240

attgtttcct attaagtatt attctttggg caanattttc tgatgctttt gattttctct    300

caatttagca tttgctttng gttttttttct ctatttagca ttctgttaag gcacaaaaac    360

tatgtactgt atgggaaatg ttgtaaatat taccttttcc acattttaaa cagacaactt    420

tgaatccaa                                                            429
```

-continued

<210> SEQ ID NO 200
<211> LENGTH: 279
<212> TYPE: DNA
<213> ORGANISM: Homo sapiens

<400> SEQUENCE: 200
gcttttttga ggaattacag ggaagctcct ggaattgtac atggatatct ttatccctag 60
ggggaaatca aggagctggg cacccctaat tctttatgga agtgtttaaa actattttaa 120
ttttattaca agtattacta gagtagtggt tctactctaa gatttcaaaa gtgcatttaa 180
aatcatacat gttcccgcct gcaaatatat tgttattttg gtggagaaaa aaatagtata 240
ttctacataa aaaattaaag atattaacta agaaaaaaa 279

<210> SEQ ID NO 201
<211> LENGTH: 569
<212> TYPE: DNA
<213> ORGANISM: Homo sapiens

<400> SEQUENCE: 201
taggtcagta tttttagaaa ctcttaatag ctcatactct tgataccaaa agcagccctg 60
attgttaaag cacacacctg cacaagaagc agtgatggtt gcatttacat ttcctgggtg 120
cacaaaaaaa aattctcaaa aagcaaggac ttacgctttt tgcaaagcct ttgagaagtt 180
actggatcat aggaagctta taacaagaat ggaagattct taaataactc actttctttg 240
gtatccagta acagtagatg ttcaaaatat gtagctgatt aataccagca ttgtgaacgc 300
tgtacaacct tgtggttatt actaagcaag ttactactag cttctgaaaa gtagcttcat 360
aattaatgtt atttatacac tgccttccat gacttttact ttgccctaag ctaatctcca 420
aaatctgaaa tgctactcca atatcagaaa aaaaggggga ggtggaatta tatttcctgt 480
gattttaaga gtacagagaa tcatgcacat ctctgattag ttcatatatg tctagtgtgt 540
aataaaagtc aaagatgaac tctcaaaaa 569

<210> SEQ ID NO 202
<211> LENGTH: 501
<212> TYPE: DNA
<213> ORGANISM: Homo sapiens

<400> SEQUENCE: 202
attaataggc ttaataattg ttggcaagga tccttttgct ttctttggca tgcaagctcc 60
tagcatctgg cagtggggcc aagaaaataa ggtttatgca tgtatgatgg ttttcttctt 120
gagcaacatg attgagaacc agtgtatgtc aacaggtgca tttgagataa ctttaaatga 180
tgtacctgtg tggtctaagc tggaatctgg tcaccttcca tccatgcaac aacttgttca 240
aattcttgac aatgaaatga agctcaatgt gcatatggat tcaatcccac accatcgatc 300
atagcaccac ctatcagcac tgaaaactct tttgcattaa gggatcattg caagagcagc 360
gtgactgaca ttatgaaggc ctgtactgaa gacagcaagc tgttagtaca gaccagatgc 420
tttcttggca ggctcgttgt acctcttgga aaacctcaat gcaagatagt gtttcagtgc 480
tggcatattt tggaattctg c 501

<210> SEQ ID NO 203
<211> LENGTH: 261
<212> TYPE: DNA
<213> ORGANISM: Homo sapiens
<220> FEATURE:

-continued

<221> NAME/KEY: misc_feature
<222> LOCATION: 36, 96
<223> OTHER INFORMATION: n = A,T,C or G

<400> SEQUENCE: 203
gacaagctcc tggtcttgag atgtcttctc gttaangaga tgggcctttt ggaggtaaag 60
gataaaatga atgagttctg tcatgattca ctattntata acttgcatga cctttactgt 120
gttagctctt tgaatgttct tgaaatttta gactttcttt gtaaacaaat gatatgtcct 180
tatcattgta taaaagctgt tatgtgcaac agtgtggaga ttccttgtct gatttaataa 240
aatacttaaa cactgaaaaa a 261

<210> SEQ ID NO 204
<211> LENGTH: 421
<212> TYPE: DNA
<213> ORGANISM: Homo sapiens

<400> SEQUENCE: 204
agcatctttt ctacaacgtt aaaattgcag aagtagctta tcattaaaaa acaacaacaa 60
caacaataac aataaatcct aagtgtaaat cagttattct accccctacc aaggatatca 120
gcctgttttt tccctttttt ctcctgggaa taattgtggg cttcttccca aatttctaca 180
gcctctttcc tcttctcatg cttgagcttc cctgtttgca cgcatgcgtg tgcaggactg 240
gcttgtgtgc ttggactcgg ctccaggtgg aagcatgctt tcccttgtta ctgttggaga 300
aactcaaacc ttcaagccct aggtgtagcc attttgtcaa gtcatcaact gtatttttgt 360
actggcatta acaaaaaaag aagataaaat attgtaccat taaactttaa taaaacttta 420
a 421

<210> SEQ ID NO 205
<211> LENGTH: 460
<212> TYPE: DNA
<213> ORGANISM: Homo sapiens

<400> SEQUENCE: 205
tactctcaca atgaaggacc tggaatgaaa aatctgtgtc taaacaagtc ctctttagat 60
tttagtgcaa atccagagcc agcgtcggtt gcctcgagta attctttcat gggtaccttt 120
ggaaaagctc tcaggagacc tcacctagat gcctattcaa gctttggaca gccatcagat 180
tgtcagccaa gagcctttta tttgaaagct cattcttccc cagacttgga ctctgggtca 240
gaggaagatg ggaaagaaag gacagatttt caggaagaaa atcacatttg tacctttaaa 300
cagactttag aaaactacag gactccaaat tttcagtctt atgacttgga cacatagact 360
gaatgagacc aaaggaaaag cttaacatac tacctcaagg tgaactttta tttaaaagag 420
agagaatctt atgtttttta aatggagtta tgaattttaa 460

<210> SEQ ID NO 206
<211> LENGTH: 481
<212> TYPE: DNA
<213> ORGANISM: Homo sapiens

<400> SEQUENCE: 206
tgtggtggaa ttcgggacgc ccccagaccc tgactttttc ctgcgtgggc cgtctcctcc 60
tgcggaagca gtgacctctg acccctggtg accttcgctt tgagtgcctt ttgaacgctg 120
gtcccgcggg acttggtttt ctcaagctct gtctgtccaa agacgctccg gtcgaggtcc 180
cgcctgccct gggtggatac ttgaacccca gacgcccctc tgtgctgctg tgtccggagg 240

-continued

```
cggccttccc atctgcctgc ccacccggag ctctttccgc cggcgcaggg tcccaagccc    300

acctcccgcc ctcagtcctg cggtgtgcgt ctgggcacgt cctgcacaca caatgcaagt    360

cctggcctcc gcgcccgccc gcccacgcga gccgtacccg ccgccaactc tgttatttat    420

ggtgtgaccc cctggaggtg ccctcggccc accggggcta tttattgttt aatttatttg    480

t                                                                    481
```

```
<210> SEQ ID NO 207
<211> LENGTH: 605
<212> TYPE: DNA
<213> ORGANISM: Homo sapiens

<400> SEQUENCE: 207

acccttttttg gattcagggc tcctcacaat taaaatgagt gtaatgaaac aaggtgaaaa     60

tatagaagca tccctttgta tactgttttg ctacttacag tgtacttggc attgctttat    120

ctcactggat tctcacggta ggatttctga gatcttaatc taagctccaa agttgtctac    180

ttttttgatc ctagggtgct ccttttgttt tacagagcag ggtcacttga tttgctagct    240

ggtggcagaa ttggcaccat tacccaggtc tgactgacca ccagtcagag gcactttatt    300

tgtatcatga aatgatttga aatcattgta aagcagcgaa gtctgataat gaatgccagc    360

tttccttgtg ctttgataac aaagactcca aatattctgg agaacctgga taaaagtttg    420

aagggctaga ttgggatttg aagacaaaat tgtaggaaat cttacatttt tgcaataaca    480

aacattaatg aaagcaaaac attataaaag taattttaat tcaccacata cttatcaatt    540

tcttgatgct tccaaatgac atctaccaga tatggttttg tggacatctt tttctgttta    600

cataa                                                                605
```

```
<210> SEQ ID NO 208
<211> LENGTH: 655
<212> TYPE: DNA
<213> ORGANISM: Homo sapiens

<400> SEQUENCE: 208

ggcgttgttc tggattcccg tcgtaactta aagggaaact ttcacaatgt ccggagccct     60

tgatgtcctg caaatgaagg aggaggatgt ccttaagttc cttgcagcag gaacccactt    120

aggtggcacc aatcttgact tccagatgga acagtacatc tataaaagga aaagtgatgg    180

catctatatc ataaatctca agaggacctg ggagaagctt ctgctggcag ctcgtgcaat    240

tgttgccatt gaaaaccctg ctgatgtcag tgttatatcc tccaggaata ctggccagag    300

ggctgtgctg aagtttgctg ctgccactgg agccactcca attgctggcc gcttcactcc    360

tggaaccttc actaaccaga tccaggcagc cttccgggag ccacggcttc ttgtggttac    420

tgaccccagg gctgaccacc agcctctcac ggaggcatct tatgttaacc tacctaccat    480

tgcgctgtgt aacacagatt ctcctctgcg ctatgtggac attgccatcc catgcaacaa    540

caagggagct cactcagtgg gtttgatgtg gtggatgctg gctcgggaag ttctgcgcat    600

gcgtggcacc atttcccgtg aacacccatg ggaggtcatg cctgatctgt acttc         655
```

```
<210> SEQ ID NO 209
<211> LENGTH: 621
<212> TYPE: DNA
<213> ORGANISM: Homo sapiens

<400> SEQUENCE: 209
```

-continued

```
catttagaac atggttatca tccaagacta ctctaccctg caacattgaa ctcccaagag     60

caaatccaca ttcctcttga gttctgcagc ttctgtgtaa atagggcagc tgtcgtctat    120

gccgtagaat cacatgatct gaggaccatt catggaagct gctaaatagc ctagtctggg    180

gagtcttcca taaagttttg catggagcaa acaaacagga ttaaactagg tttggttcct    240

tcagccctct aaaagcatag ggcttagcct gcaggcttcc ttgggctttc tctgtgtgtg    300

tagttttgta aacactatag catctgttaa gatccagtgt ccatggaaac cttcccacat    360

gccgtgactc tggactatat cagtttttgg aaagcagggt tcctctgcct gctaacaagc    420

ccacgtggac cagtctgaat gtctttcctt tacacctatg tttttaaata gtcaaacttc    480

aagaaacaat ctaaacaagt ttctgttgca tatgtgtttg tgaacttgta tttgtattta    540

gtaggcttct atattgcatt taacttgttt ttgtaactcc tgattcttcc ttttcggata    600

ctattgatga ataaagaaat t                                               621
```

```
<210> SEQ ID NO 210
<211> LENGTH: 533
<212> TYPE: DNA
<213> ORGANISM: Homo sapiens
<220> FEATURE:
<221> NAME/KEY: misc_feature
<222> LOCATION: 20, 21, 61
<223> OTHER INFORMATION: n = A,T,C or G

<400> SEQUENCE: 210

cgccttgggg agccggcggn ngagtccggg acgtggagac ccggggtccc ggcagccggg     60

nggcccgcgg gcccagggtg gggatgcacc gccgcggggt gggagctggc gccatcgcca    120

agaagaaact tgcagaggcc aagtataagg agcgagggac ggtcttggct gaggaccagc    180

tagcccagat gtcaaagcag ttggacatgt tcaagaccaa cctggaggaa tttgccagca    240

aacacaagca ggagatccgg aagaatcctg agttccgtgt gcagttccag gacatgtgtg    300

caaccattgg cgtggatccg ctggcctctg gaaaaggatt ttggtctgag atgctgggcg    360

tgggggactt ctattacgaa ctaggtgtcc aaattatcga agtgtgcctg gcgctgaagc    420

atcggaatgg aggtctgata actttggagg aactacatca acaggtgttg aagggaaggg    480

gcaagttcgc ccaggatgtc agtcaagatg acctgatcag agccatcaag aaa           533
```

```
<210> SEQ ID NO 211
<211> LENGTH: 451
<212> TYPE: DNA
<213> ORGANISM: Homo sapiens

<400> SEQUENCE: 211

ttagcttgag ccgagaacga ggcgagaaag ctggagaccg aggagaccgc ctagagcgga     60

gtgaacgggg aggggaccgt ggggaccggc ttgatcgtgc gcggacacct gctaccaagc    120

ggagcttcag caaggaagtg gaggagcgga gtagagaacg gccctcccag cctgaggggc    180

tgcgcaaggc agctagcctc acggaggatc gggaccgtgg gcgggatgcc gtgaagcgag    240

aagctgccct acccccagtg agccccctga aggcggctct ctctgaggag gagttagaga    300

agaaatccaa ggctatcatt gaggaatatc tccatctcaa tgacatgaaa gaggcagtcc    360

agtgcgtgca ggagctggcc tcaccctcct tgctcttcat ctttgtacgg catggtgtcg    420

agtctacgct ggagcgcagt gccattgctc g                                    451
```

```
<210> SEQ ID NO 212
<211> LENGTH: 471
```

-continued

<212> TYPE: DNA
<213> ORGANISM: Homo sapiens
<220> FEATURE:
<221> NAME/KEY: misc_feature
<222> LOCATION: 54
<223> OTHER INFORMATION: n = A,T,C or G

<400> SEQUENCE: 212
gtgattattc ttgatcaggg agaagatcat ttagatttgt tttgcattcc ttanaatgga 60
gggcaacatt ccacagctgc cctggctgtg atgagtgtcc ttgcaggggc cggagtagga 120
gcactggggt gggggcggaa ttggggttac tcgatgtaag ggattccttg ttgttgtgtt 180
gagatccagt gcagttgtga tttctgtgga tcccagcttg gttccaggaa ttttgtgtga 240
ttggcttaaa tccagttttc aatcttcgac agctgggctg gaacgtgaac tcagtagctg 300
aacctgtctg acccggtcac gttcttggat cctcagaact ctttgctctt gtcggggtgg 360
gggtgggaac tcacgtgggg agcggtggct gagaaaatgt aaggattctg gaatacatat 420
tccatgggac tttccttccc tctcctgctt cctcttttcc tgctccctaa c 471

<210> SEQ ID NO 213
<211> LENGTH: 511
<212> TYPE: DNA
<213> ORGANISM: Homo sapiens
<220> FEATURE:
<221> NAME/KEY: misc_feature
<222> LOCATION: 27, 63, 337, 442
<223> OTHER INFORMATION: n = A,T,C or G

<400> SEQUENCE: 213
ctaattagaa acttgctgta ctttttnttt tcttttaggg gtcaaggacc ctctttatag 60
ctnccatttg cctacaataa attattgcag cagtttgcaa tactaaaata ttttttatag 120
actttatatt tttccttttg ataaagggat gctgcatagt agagttggtg taattaaact 180
atctcagccg tttccctgct ttcccttctg ctccatatgc ctcattgtcc ttccagggag 240
ctcttttaat cttaaagttc tacatttcat gctcttagtc aaattctgtt accttttttaa 300 taactcttcc cactgcatat ttccatcttg aattggnggt tctaaattct gaaactgtag 360
ttgagataca gctatttaat atttctggga gatgtgcatc cctcttcttt gtggttgccc 420
aaggttgttt tgcgtaactg anactccttg atatgcttca gagaatttag gcaaacactg 480
gccatggccg tgggagtact gggagtaaaa t 511

<210> SEQ ID NO 214
<211> LENGTH: 521
<212> TYPE: DNA
<213> ORGANISM: Homo sapiens

<400> SEQUENCE: 214
agcattgcca aataatccct aattttccac taaaaatata atgaaatgat gttaagcttt 60
ttgaaaagtt taggttaaac ctactgttgt tagattaatg tatttgttgc ttccctttat 120
ctggaatgtg gcattagctt ttttatttta accctcttta attcttattc aattccatga 180
cttaaggttg gagagctaaa cactgggatt tttggataac agactgacag ttttgcataa 240
ttataatcgg cattgtacat agaaaggata tggctacctt ttgttaaatc tgcactttct 300
aaatatcaaa aaagggaaat gaagtataaa tcaatttttg tataatctgt ttgaaacatg 360
agttttattt gcttaatatt agggctttgc cccttttctg taagtctctt gggatcctgt 420
gtagaagctg ttctcattaa acaccaaaca gttaagtcca ttctctggta ctagctacaa 480

-continued attcggtttc atattctact taacaattta aataaactga a 521

<210> SEQ ID NO 215
<211> LENGTH: 381
<212> TYPE: DNA
<213> ORGANISM: Homo sapiens
<220> FEATURE:
<221> NAME/KEY: misc_feature
<222> LOCATION: 17, 20, 60, 61, 365
<223> OTHER INFORMATION: n = A,T,C or G

<400> SEQUENCE: 215
gagcggagag cggaccngtn agagccctga gcagccccac cgccgccgcc ggcctagttn 60
ncatcacacc ccgggaggag ccgcagctgc cgcagccggc cccagtcacc atcaccgcaa 120
ccatgagcag cgaggccgag acccagcagc cgcccgccgc cccccccgcc gcccccgccc 180
tcagcgccgc cgacaccaag cccggcacta cgggcagcgg cgcagggagc ggtggcccgg 240
gcggcctcac atcggcggcg cctgccggcg gggacaagaa ggtcatcgca acgaaggttt 300
tgggaacagt aaaatggttc aatgtaagga acggatatgg tttcatcaac aggaatgaca 360
ccaangaaga tgtatttgta c 381

<210> SEQ ID NO 216
<211> LENGTH: 425
<212> TYPE: DNA
<213> ORGANISM: Homo sapiens

<400> SEQUENCE: 216
ttactaacta ggtcattcaa ggaagtcaag ttaacttaaa catgtcacct aaatgcactt 60
gatggtgttg aaatgtccac cttcttaaat ttttaagatg aacttagttc taaagaagat 120
aacaggccaa tcctgaaggt actccctgtt tgctgcagaa tgtcagatat tttggatgtt 180
gcataagagt cctatttgcc ccagttaatt caacttttgt ctgcctgttt tgtggactgg 240
ctggctctgt tagaactctg tccaaaaagt gcatggaata taacttgtaa agcttcccac 300
aattgacaat atatatgcat gtgtttaaac caaatccaga aagcttaaac aatagagctg 360
cataatagta tttattaaag aatcacaact gtaaacatga gaataactta aggattctag 420
tttag 425

<210> SEQ ID NO 217
<211> LENGTH: 181
<212> TYPE: DNA
<213> ORGANISM: Homo sapiens

<400> SEQUENCE: 217
gagaaaccaa atgataggtt gtagagcctg atgactccaa acaaagccat cacccgcatt 60
cttcctcctt cttctggtgc tacagctcca agggcccttc accttcatgt ctgaaatgga 120
actttggctt tttcagtgga agaatatgtt gaaggtttca ttttgttcta gaaaaaaaaa 180
a 181

<210> SEQ ID NO 218
<211> LENGTH: 405
<212> TYPE: DNA
<213> ORGANISM: Homo sapiens

<400> SEQUENCE: 218
caggccttcc agttcactga caaacatggg gaagtgtgcc cagctggctg gaaacctggc 60
agtgatacca tcaagcctga tgtccaaaag agcaaagaat atttctccaa gcagaagtga 120

-continued

```
gcgctgggct gttttagtgc caggctgcgg tgggcagcca tgagaacaaa acctcttctg    180

tatttttttt ttccattagt aaaacacaag acttcagatt cagccgaatt gtggtgtctt    240

acaaggcagg cctttcctac agggggtgga gagaccagcc tttcttcctt tggtaggaat    300

ggcctgagtt ggcgttgtgg gcaggctact ggtttgtatg atgtattagt agagcaaccc    360

attaatcttt tgtagtttgt attaaacttg aactgagaaa aaaaa                    405
```

<210> SEQ ID NO 219
<211> LENGTH: 216
<212> TYPE: DNA
<213> ORGANISM: Homo sapiens
<220> FEATURE:
<221> NAME/KEY: misc_feature
<222> LOCATION: 207, 210
<223> OTHER INFORMATION: n = A,T,C or G

<400> SEQUENCE: 219

```
actccaagag ttagggcagc agagtggagc gatttagaaa gaacatttta aaacaatcag     60

ttaatttacc atgtaaaatt gctgtaaatg ataatgtgta cagattttct gttcaaatat    120

tcaattgtaa acttcttgtt aagactgtta cgtttctatt gcttttgtat gggatattgc    180

aaaaataaaa aggaaagaac cctcttnaan aaaaaa                               216
```

<210> SEQ ID NO 220
<211> LENGTH: 380
<212> TYPE: DNA
<213> ORGANISM: Homo sapiens

<400> SEQUENCE: 220

```
cttacaaatt gcccccatgt gtaggggaca cagaaccctt tgagaaaact tagatttttg     60

tctgtacaaa gtctttgcct ttttccttct tcattttttt ccagtacatt aaatttgtca    120

atttcatctt tgagggaaac tgattagatg ggttgtgttt gtgttctgat ggagaaaaca    180

gcaccccaag gactcagaag atgattttaa cagttcagaa cagatgtgtg caatattggt    240

gcatgtaata atgttgagtg gcagtcaaaa gtcatgattt ttatcttagt tcttcattac    300

tgcattgaaa aggaaaacct gtctgagaaa atgcctgaca gtttaattta aaactatggt    360

gtaagtcttt gacaaaaaaa                                                 380
```

<210> SEQ ID NO 221
<211> LENGTH: 398
<212> TYPE: DNA
<213> ORGANISM: Homo sapiens

<400> SEQUENCE: 221

```
ggttagtaag ctgtcgactt tgtaaaaaag ttaaaaatga aaaaaaaagg aaaaatgaat     60

tgtatattta atgaatgaac atgtacaatt tgccactggg aggaggttcc tttttgttgg    120

gtgagtctgc aagtgaattt cactgatgtt gatattcatt gtgtgtagtt ttatttcggt    180

cccagccccg tttcctttta ttttggagct aatgccagct gcgtgtctag ttttgagtgc    240

agtaaaatag aatcagcaaa tcactcttat ttttcatcct tttccggtat tttttgggtt    300

gtttctgtgg gagcagtgta caccaactct tcctgtatat tgcctttttg ctggaaaatg    360

ttgtatgttg aataaaattt tctataaaaa ttaaaaaa                             398
```

<210> SEQ ID NO 222
<211> LENGTH: 301
<212> TYPE: DNA

<213> ORGANISM: Homo sapiens
<220> FEATURE:
<221> NAME/KEY: misc_feature
<222> LOCATION: 49, 64
<223> OTHER INFORMATION: n = A,T,C or G

<400> SEQUENCE: 222

```
ttcgataatt gatctcatgg gctttccctg gaggaaaggt tttttttgnt gtttattttt     60

taanaacttg aaacttgtaa actgagatgt ctgtagcttt tttgcccatc tgtagtgtat    120

gtgaagattt caaaacctga gagcactttt tctttgttta gaattatgag aaaggcacta    180

gatgacttta ggatttgcat ttttcccttt attgcctcat ttcttgtgac gccttgttgg    240

ggagggaaat ctgtttattt tttcctacaa ataaaaagct aagattctat atcgcaaaaa    300

a                                                                    301
```

<210> SEQ ID NO 223
<211> LENGTH: 200
<212> TYPE: DNA
<213> ORGANISM: Homo sapiens

<400> SEQUENCE: 223

```
gtaagtgctt aggaagaaac tttgcaaaca tttaatgagg atacactgtt catttttaaa     60

attccttcac actgtaattt aatgtgtttt atattctttt gtagtaaaac aacataactc    120

agatttctac aggagacagt ggttttattt ggattgtctt ctgtaatagg tttcaataaa    180

gctggatgaa cttaaaaaaa                                                200
```

<210> SEQ ID NO 224
<211> LENGTH: 385
<212> TYPE: DNA
<213> ORGANISM: Homo sapiens

<400> SEQUENCE: 224

```
gaaaggtttg atccggactc aaagaaagca aaggagtgtg agccgccatc tgctggagca     60

gctgtaactg caagacctgg acaagagatt cgtcagcgaa ctgcagctca aagaaacctt    120

tctccaacac cagcaagccc taaccagggc cctcctccac aagttccagt atctcctgga    180

ccaccaaagg acagttctgc ccctggtgga ccccccagaaa ggactgttac tccagcccta    240

tcatcaaatg tgttaccaag acatcttgga tcccctgcta cttcagtgcc tggaatgggt    300

aaacagagca cttaatgtta tttacagttt atattgtttt ctctggttac caataaaacg    360

ggccattttc aggtggtaaa aaaaa                                          385
```

<210> SEQ ID NO 225
<211> LENGTH: 560
<212> TYPE: PRT
<213> ORGANISM: Homo sapiens

<400> SEQUENCE: 225

```
Met Glu Cys Leu Tyr Tyr Phe Leu Gly Phe Leu Leu Leu Ala Ala Arg
 1               5                  10                  15

Leu Pro Leu Asp Ala Ala Lys Arg Phe His Asp Val Leu Gly Asn Glu
            20                  25                  30

Arg Pro Ser Ala Tyr Met Arg Glu His Asn Gln Leu Asn Gly Trp Ser
        35                  40                  45

Ser Asp Glu Asn Asp Trp Asn Glu Lys Leu Tyr Pro Val Trp Lys Arg
    50                  55                  60

Gly Asp Met Arg Trp Lys Asn Ser Trp Lys Gly Gly Arg Val Gln Ala
```

-continued

```
65                  70                  75                  80

Val Leu Thr Ser Asp Ser Pro Ala Leu Val Gly Ser Asn Ile Thr Phe
                85                  90                  95

Ala Val Asn Leu Ile Phe Pro Arg Cys Gln Lys Glu Asp Ala Asn Gly
            100                 105                 110

Asn Ile Val Tyr Glu Lys Asn Cys Arg Asn Glu Ala Gly Leu Ser Ala
        115                 120                 125

Asp Pro Tyr Val Tyr Asn Trp Thr Ala Trp Ser Glu Asp Ser Asp Gly
    130                 135                 140

Glu Asn Gly Thr Gly Gln Ser His His Asn Val Phe Pro Asp Gly Lys
145                 150                 155                 160

Pro Phe Pro His His Pro Gly Trp Arg Arg Trp Asn Phe Ile Tyr Val
                165                 170                 175

Phe His Thr Leu Gly Gln Tyr Phe Gln Lys Leu Gly Arg Cys Ser Val
            180                 185                 190

Arg Val Ser Val Asn Thr Ala Asn Val Thr Leu Gly Pro Gln Leu Met
        195                 200                 205

Glu Val Thr Val Tyr Arg Arg His Gly Arg Ala Tyr Val Pro Ile Ala
    210                 215                 220

Gln Val Lys Asp Val Tyr Val Val Thr Asp Gln Ile Pro Val Phe Val
225                 230                 235                 240

Thr Met Phe Gln Lys Asn Asp Arg Asn Ser Ser Asp Glu Thr Phe Leu
                245                 250                 255

Lys Asp Leu Pro Ile Met Phe Asp Val Leu Ile His Asp Pro Ser His
            260                 265                 270

Phe Leu Asn Tyr Ser Thr Ile Asn Tyr Lys Trp Ser Phe Gly Asp Asn
        275                 280                 285

Thr Gly Leu Phe Val Ser Thr Asn His Thr Val Asn His Thr Tyr Val
    290                 295                 300

Leu Asn Gly Thr Phe Ser Leu Asn Leu Thr Val Lys Ala Ala Ala Pro
305                 310                 315                 320

Gly Pro Cys Pro Pro Pro Pro Pro Pro Pro Arg Pro Ser Lys Pro Thr
                325                 330                 335

Pro Ser Leu Gly Pro Ala Gly Asp Asn Pro Leu Glu Leu Ser Arg Ile
            340                 345                 350

Pro Asp Glu Asn Cys Gln Ile Asn Arg Tyr Gly His Phe Gln Ala Thr
        355                 360                 365

Ile Thr Ile Val Glu Gly Ile Leu Glu Val Asn Ile Ile Gln Met Thr
    370                 375                 380

Asp Val Leu Met Pro Val Pro Trp Pro Glu Ser Ser Leu Ile Asp Phe
385                 390                 395                 400

Val Val Thr Cys Gln Gly Ser Ile Pro Thr Glu Val Cys Thr Ile Ile
                405                 410                 415

Ser Asp Pro Thr Cys Glu Ile Thr Gln Asn Thr Val Cys Ser Pro Val
            420                 425                 430

Asp Val Asp Glu Met Cys Leu Leu Thr Val Arg Arg Thr Phe Asn Gly
        435                 440                 445

Ser Gly Thr Tyr Cys Val Asn Leu Thr Leu Gly Asp Asp Thr Ser Leu
    450                 455                 460

Ala Leu Thr Ser Thr Leu Ile Ser Val Pro Asp Arg Asp Pro Ala Ser
465                 470                 475                 480

Pro Leu Arg Met Ala Asn Ser Ala Leu Ile Ser Val Gly Cys Leu Ala
                485                 490                 495
```

-continued

```
Ile Phe Val Thr Val Ile Ser Leu Leu Val Tyr Lys Lys His Lys Glu
            500                 505                 510

Tyr Asn Pro Ile Glu Asn Ser Pro Gly Asn Val Val Arg Ser Lys Gly
        515                 520                 525

Leu Ser Val Phe Leu Asn Arg Ala Lys Ala Val Phe Phe Pro Gly Asn
    530                 535                 540

Gln Glu Lys Asp Pro Leu Leu Lys Asn Gln Glu Phe Lys Gly Val Ser
545                 550                 555                 560
```

<210> SEQ ID NO 226
<211> LENGTH: 9
<212> TYPE: PRT
<213> ORGANISM: Homo sapiens

<400> SEQUENCE: 226

```
Ile Leu Ile Pro Ala Thr Trp Lys Ala
 1               5
```

<210> SEQ ID NO 227
<211> LENGTH: 9
<212> TYPE: PRT
<213> ORGANISM: Homo sapiens

<400> SEQUENCE: 227

```
Phe Leu Leu Asn Asp Asn Leu Thr Ala
 1               5
```

<210> SEQ ID NO 228
<211> LENGTH: 9
<212> TYPE: PRT
<213> ORGANISM: Homo sapiens

<400> SEQUENCE: 228

```
Leu Leu Gly Asn Cys Leu Pro Thr Val
 1               5
```

<210> SEQ ID NO 229
<211> LENGTH: 10
<212> TYPE: PRT
<213> ORGANISM: Homo sapiens

<400> SEQUENCE: 229

```
Lys Leu Leu Gly Asn Cys Leu Pro Thr Val
 1               5                  10
```

<210> SEQ ID NO 230
<211> LENGTH: 10
<212> TYPE: PRT
<213> ORGANISM: Homo sapiens

<400> SEQUENCE: 230

```
Arg Leu Thr Gly Gly Leu Lys Phe Phe Val
 1               5                  10
```

<210> SEQ ID NO 231
<211> LENGTH: 9
<212> TYPE: PRT
<213> ORGANISM: Homo sapiens

<400> SEQUENCE: 231

```
Ser Leu Gln Ala Leu Lys Val Thr Val
 1               5
```

-continued

<210> SEQ ID NO 232
<211> LENGTH: 20
<212> TYPE: PRT
<213> ORGANISM: Homo sapiens

<400> SEQUENCE: 232

```
Ala Gly Ala Asp Val Ile Lys Asn Asp Gly Ile Tyr Ser Arg Tyr Phe
 1               5                  10                  15

Phe Ser Phe Ala
            20
```

<210> SEQ ID NO 233
<211> LENGTH: 21
<212> TYPE: PRT
<213> ORGANISM: Homo sapiens

<400> SEQUENCE: 233

```
Phe Phe Ser Phe Ala Ala Asn Gly Arg Tyr Ser Leu Lys Val His Val
 1               5                  10                  15

Asn His Ser Pro Ser
            20
```

<210> SEQ ID NO 234
<211> LENGTH: 20
<212> TYPE: PRT
<213> ORGANISM: Homo sapiens

<400> SEQUENCE: 234

```
Phe Leu Val Thr Trp Gln Ala Ser Gly Pro Pro Glu Ile Ile Leu Phe
 1               5                  10                  15

Asp Pro Asp Gly
            20
```

<210> SEQ ID NO 235
<211> LENGTH: 20
<212> TYPE: PRT
<213> ORGANISM: Homo sapiens

<400> SEQUENCE: 235

```
Leu Gln Ser Ala Val Ser Asn Ile Ala Gln Ala Pro Leu Phe Ile Pro
 1               5                  10                  15

Pro Asn Ser Asp
            20
```

<210> SEQ ID NO 236
<211> LENGTH: 20
<212> TYPE: PRT
<213> ORGANISM: Homo sapiens

<400> SEQUENCE: 236

```
Ile Gln Asp Asp Phe Asn Asn Ala Ile Leu Val Asn Thr Ser Lys Arg
 1               5                  10                  15

Asn Pro Gln Gln
            20
```

<210> SEQ ID NO 237
<211> LENGTH: 21
<212> TYPE: PRT
<213> ORGANISM: Homo sapiens

<400> SEQUENCE: 237

```
Arg Asn Ser Leu Gln Ser Ala Val Ser Asn Ile Ala Gln Ala Pro Leu
```

-continued 1 5 10 15

Phe Ile Pro Pro Asn
20

<210> SEQ ID NO 238
<211> LENGTH: 20
<212> TYPE: PRT
<213> ORGANISM: Homo sapiens

<400> SEQUENCE: 238

Thr His Glu Ser His Arg Ile Tyr Val Ala Ile Arg Ala Met Asp Arg
1 5 10 15

Asn Ser Leu Gln
20

<210> SEQ ID NO 239
<211> LENGTH: 20
<212> TYPE: PRT
<213> ORGANISM: Homo sapiens

<400> SEQUENCE: 239

Arg Asn Pro Gln Gln Ala Gly Ile Arg Glu Ile Phe Thr Phe Ser Pro
1 5 10 15

Gln Ile Ser Thr
20

<210> SEQ ID NO 240
<211> LENGTH: 21
<212> TYPE: PRT
<213> ORGANISM: Homo sapiens

<400> SEQUENCE: 240

Gly Gln Ala Thr Ser Tyr Glu Ile Arg Met Ser Lys Ser Leu Gln Asn
1 5 10 15

Ile Gln Asp Asp Phe
20

<210> SEQ ID NO 241
<211> LENGTH: 20
<212> TYPE: PRT
<213> ORGANISM: Homo sapiens

<400> SEQUENCE: 241

Glu Arg Lys Trp Gly Phe Ser Arg Val Ser Ser Gly Gly Ser Phe Ser
1 5 10 15

Val Leu Gly Val
20

<210> SEQ ID NO 242
<211> LENGTH: 20
<212> TYPE: PRT
<213> ORGANISM: Homo sapiens

<400> SEQUENCE: 242

Gly Ser His Ala Met Tyr Val Pro Gly Tyr Thr Ala Asn Gly Asn Ile
1 5 10 15

Gln Met Asn Ala
20

<210> SEQ ID NO 243
<211> LENGTH: 20
<212> TYPE: PRT

-continued

<213> ORGANISM: Homo sapiens

<400> SEQUENCE: 243

```
Val Asn His Ser Pro Ser Ile Ser Thr Pro Ala His Ser Ile Pro Gly
 1               5                   10                  15

Ser His Ala Met
            20
```

<210> SEQ ID NO 244
<211> LENGTH: 20
<212> TYPE: PRT
<213> ORGANISM: Homo sapiens

<400> SEQUENCE: 244

```
Ala Val Pro Pro Ala Thr Val Glu Ala Phe Val Glu Arg Asp Ser Leu
 1               5                   10                  15

His Phe Pro His
            20
```

<210> SEQ ID NO 245
<211> LENGTH: 20
<212> TYPE: PRT
<213> ORGANISM: Homo sapiens

<400> SEQUENCE: 245

```
Lys Pro Gly His Trp Thr Tyr Thr Leu Asn Asn Thr His His Ser Leu
 1               5                   10                  15

Gln Ala Leu Lys
            20
```

<210> SEQ ID NO 246
<211> LENGTH: 20
<212> TYPE: PRT
<213> ORGANISM: Homo sapiens

<400> SEQUENCE: 246

```
Asn Leu Thr Phe Arg Thr Ala Ser Leu Trp Ile Pro Gly Thr Ala Lys
 1               5                   10                  15

Pro Gly His Trp
            20
```

<210> SEQ ID NO 247
<211> LENGTH: 20
<212> TYPE: PRT
<213> ORGANISM: Homo sapiens

<400> SEQUENCE: 247

```
Leu His Phe Pro His Pro Val Met Ile Tyr Ala Asn Val Lys Gln Gly
 1               5                   10                  15

Phe Tyr Pro Ile
            20
```

<210> SEQ ID NO 248
<211> LENGTH: 20
<212> TYPE: PRT
<213> ORGANISM: Homo sapiens

<400> SEQUENCE: 248

```
Pro Glu Thr Gly Asp Pro Val Thr Leu Arg Leu Leu Asp Asp Gly Ala
 1               5                   10                  15

Gly Ala Asp Val
            20
```

-continued

<210> SEQ ID NO 249
<211> LENGTH: 20
<212> TYPE: PRT
<213> ORGANISM: Homo sapiens

<400> SEQUENCE: 249

```
Gly Phe Tyr Pro Ile Leu Asn Ala Thr Val Thr Ala Thr Val Glu Pro
 1               5                  10                  15

Glu Thr Gly Asp
            20
```

<210> SEQ ID NO 250
<211> LENGTH: 20
<212> TYPE: PRT
<213> ORGANISM: Homo sapiens

<400> SEQUENCE: 250

```
Phe Asp Pro Asp Gly Arg Lys Tyr Tyr Thr Asn Asn Phe Ile Thr Asn
 1               5                  10                  15

Leu Thr Phe Arg
            20
```

<210> SEQ ID NO 251
<211> LENGTH: 20
<212> TYPE: PRT
<213> ORGANISM: Homo sapiens

<400> SEQUENCE: 251

```
Leu Gln Ala Leu Lys Val Thr Val Thr Ser Arg Ala Ser Asn Ser Ala
 1               5                  10                  15

Val Pro Pro Ala
            20
```

<210> SEQ ID NO 252
<211> LENGTH: 153
<212> TYPE: PRT
<213> ORGANISM: Homo sapiens

<400> SEQUENCE: 252

```
Met Ala Ser Val Arg Val Ala Ala Tyr Phe Glu Asn Phe Leu Ala Ala
 1               5                  10                  15

Trp Arg Pro Val Lys Ala Ser Asp Gly Asp Tyr Tyr Thr Leu Ala Val
            20                  25                  30

Pro Met Gly Asp Val Pro Met Asp Gly Ile Ser Val Ala Asp Ile Gly
        35                  40                  45

Ala Ala Val Ser Ser Ile Phe Asn Ser Pro Glu Glu Phe Leu Gly Lys
    50                  55                  60

Ala Val Gly Leu Ser Ala Glu Ala Leu Thr Ile Gln Gln Tyr Ala Asp
65                  70                  75                  80

Val Leu Ser Lys Ala Leu Gly Lys Glu Val Arg Asp Ala Lys Ile Thr
                85                  90                  95

Pro Glu Ala Phe Glu Lys Leu Gly Phe Pro Ala Ala Lys Glu Ile Ala
            100                 105                 110

Asn Met Cys Arg Phe Tyr Glu Met Lys Pro Asp Arg Asp Val Asn Leu
        115                 120                 125

Thr His Gln Leu Asn Pro Lys Val Lys Ser Phe Ser Gln Phe Ile Ser
    130                 135                 140

Glu Asn Gln Gly Ala Phe Lys Gly Met
```

-continued 145 150

<210> SEQ ID NO 253
<211> LENGTH: 462
<212> TYPE: DNA
<213> ORGANISM: Homo sapiens

<400> SEQUENCE: 253
atggccagtg tccgcgtggc ggcctacttt gaaaactttc tcgcggcgtg gcggcccgtg 60
aaagcctctg atggagatta ctacaccttg gctgtaccga tgggagatgt accaatggat 120
ggtatctctg ttgctgatat tggagcagcc gtctctagca tttttaattc tccagaggaa 180
tttttaggca aggccgtggg gctcagtgca gaagcactaa caatacagca atatgctgat 240
gttttgtcca aggctttggg gaaagaagtc cgagatgcaa agattacccc ggaagctttc 300
gagaagctgg gattccctgc agcaaaggaa atagccaata tgtgtcgttt ctatgaaatg 360
aagccagacc gagatgtcaa tctcacccac caactaaatc ccaaagtcaa aagcttcagc 420
cagtttatct cagagaacca gggagccttc aagggcatgt ag 462

<210> SEQ ID NO 254
<211> LENGTH: 8031
<212> TYPE: DNA
<213> ORGANISM: Homo sapiens

<400> SEQUENCE: 254
tggcgaatgg gacgcgccct gtagcggcgc attaagcgcg gcgggtgtgg tggttacgcg 60
cagcgtgacc gctacacttg ccagcgccct agcgcccgct cctttcgctt tcttcccttc 120
ctttctcgcc acgttcgccg gctttccccg tcaagctcta aatcgggggc tccctttagg 180
gttccgattt agtgctttac ggcacctcga ccccaaaaaa cttgattagg gtgatggttc 240
acgtagtggg ccatcgccct gatagacggt ttttcgccct ttgacgttgg agtccacgtt 300
ctttaatagt ggactcttgt tccaaactgg aacaacactc aaccctatct cggtctattc 360
ttttgattta taagggattt tgccgatttc ggcctattgg ttaaaaaatg agctgattta 420
acaaaaattt aacgcgaatt ttaacaaaat attaacgttt acaatttcag gtggcacttt 480
tcggggaaat gtgcgcggaa cccctatttg tttatttttc taaatacatt caaatatgta 540
tccgctcatg aattaattct tagaaaaact catcgagcat caaatgaaac tgcaatttat 600
tcatatcagg attatcaata ccatattttt gaaaaagccg tttctgtaat gaaggagaaa 660
actcaccgag gcagttccat aggatggcaa gatcctggta tcggtctgcg attccgactc 720
gtccaacatc aatacaacct attaatttcc cctcgtcaaa aataaggtta tcaagtgaga 780
aatcaccatg agtgacgact gaatccggtg agaatggcaa aagtttatgc atttctttcc 840
agacttgttc aacaggccag ccattacgct cgtcatcaaa atcactcgca tcaaccaaac 900
cgttattcat tcgtgattgc gcctgagcga gacgaaatac gcgatcgctg ttaaaaggac 960
aattacaaac aggaatcgaa tgcaaccggc gcaggaacac tgccagcgca tcaacaatat 1020
tttcacctga atcaggatat tcttctaata cctggaatgc tgttttcccg gggatcgcag 1080
tggtgagtaa ccatgcatca tcaggagtac ggataaaatg cttgatggtc ggaagaggca 1140
taaattccgt cagccagttt agtctgacca tctcatctgt aacatcattg gcaacgctac 1200
ctttgccatg tttcagaaac aactctggcg catcgggctt cccatacaat cgatagattg 1260
tcgcacctga ttgcccgaca ttatcgcgag cccatttata cccatataaa tcagcatcca 1320
tgttggaatt taatcgcggc ctagagcaag acgtttcccg ttgaatatgg ctcataacac 1380

-continued

```
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
```

-continued

```
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatgcagcat caccaccatc accacggagt   5100
acagcttcaa gacaatgggt ataatggatt gctcattgca attaatcctc aggtacctga   5160
gaatcagaac ctcatctcaa acattaagga aatgataact gaagcttcat tttacctatt   5220
taatgctacc aagagaagag tatttttcag aaatataaag attttaatac ctgccacatg   5280
gaaagctaat aataacagca aaataaaaca agaatcatat gaaaaggcaa atgtcatagt   5340
gactgactgg tatggggcac atggagatga tccatacacc ctacaataca gagggtgtgg   5400
aaaagaggga aaatacattc atttcacacc taatttccta ctgaatgata acttaacagc   5460
tggctacgga tcacgaggcc gagtgtttgt ccatgaatgg gcccacctcc gttggggtgt   5520
gttcgatgag tataacaatg acaaaccttt ctacataaat gggcaaaatc aaattaaagt   5580
gacaaggtgt tcatctgaca tcacaggcat tttgtgtgt gaaaaaggtc cttgccccca   5640
agaaaactgt attattagta agcttttttaa agaaggatgc acctttatct acaatagcac   5700
ccaaaatgca actgcatcaa taatgttcat gcaaagttta tcttctgtgg ttgaattttg   5760
taatgcaagt acccacaacc aagaagcacc aaacctacag aaccagatgt gcagcctcag   5820
aagtgcatgg gatgtaatca cagactctgc tgactttcac cacagctttc ccatgaacgg   5880
gactgagctt ccacctcctc ccacattctc gcttgtagag gctggtgaca aagtggtctg   5940
tttagtgctg gatgtgtcca gcaagatggc agaggctgac agactccttc aactacaaca   6000
agccgcagaa ttttatttga tgcagattgt tgaaattcat accttcgtgg gcattgccag   6060
tttcgacagc aaaggagaga tcagagccca gctacaccaa attaacagca atgatgatcg   6120
```

aaagttgctg gtttcatatc tgcccaccac tgtatcagct aaaacagaca tcagcatttg 6180
ttcagggctt aagaaaggat ttgaggtggt tgaaaaactg aatggaaaag cttatggctc 6240
tgtgatgata ttagtgacca gcggagatga taagcttctt ggcaattgct tacccactgt 6300
gctcagcagt ggttcaacaa ttcactccat tgccctgggt tcatctgcag ccccaaatct 6360
ggaggaatta tcacgtctta caggaggttt aaagttcttt gttccagata tatcaaactc 6420
caatagcatg attgatgctt tcagtagaat ttcctctgga actggagaca ttttccagca 6480
acatattcag cttgaaagta caggtgaaaa tgtcaaacct caccatcaat tgaaaaacac 6540
agtgactgtg gataatactg tgggcaacga cactatgttt ctagttacgt ggcaggccag 6600
tggtcctcct gagattatat tatttgatcc tgatggacga aaatactaca caaataattt 6660
tatcaccaat ctaacttttc ggacagctag tctttggatt ccaggaacag ctaagcctgg 6720
gcactggact tacaccctga acaataccca tcattctctg caagccctga aagtgacagt 6780
gacctctcgc gcctccaact cagctgtgcc cccagccact gtggaagcct ttgtggaaag 6840
agacagcctc cattttcctc atcctgtgat gatttatgcc aatgtgaaac agggatttta 6900
tcccattctt aatgccactg tcactgccac agttgagcca gagactggag atcctgttac 6960
gctgagactc cttgatgatg gagcaggtgc tgatgttata aaaaatgatg gaatttactc 7020
gaggtatttt ttctcctttg ctgcaaatgg tagatatagc ttgaaagtgc atgtcaatca 7080
ctctcccagc ataagcaccc cagcccactc tattccaggg agtcatgcta tgtatgtacc 7140
aggttacaca gcaaacggta atattcagat gaatgctcca aggaaatcag taggcagaaa 7200
tgaggaggag cgaaagtggg gctttagccg agtcagctca ggaggctcct tttcagtgct 7260
gggagttcca gctggccccc accctgatgt gtttccacca tgcaaaatta ttgacctgga 7320
agctgtaaaa gtagaagagg aattgaccct atcttggaca gcacctggag aagactttga 7380
tcagggccag gctacaagct atgaaataag aatgagtaaa agtctacaga atatccaaga 7440
tgactttaac aatgctattt tagtaaatac atcaaagcga aatcctcagc aagctggcat 7500
cagggagata tttacgttct caccccaaat ttccacgaat ggacctgaac atcagccaaa 7560
tggagaaaca catgaaagcc acagaattta tgttgcaata cgagcaatgg ataggaactc 7620
cttacagtct gctgtatcta acattgccca ggcgcctctg tttattcccc ccaattctga 7680
tcctgtacct gccagagatt atcttatatt gaaaggagtt ttaacagcaa tgggtttgat 7740
aggaatcatt tgccttatta tagttgtgac acatcatact ttaagcagga aaaagagagc 7800
agacaagaaa gagaatggaa caaaattatt ataatgaatt ctgcagatat ccatcacact 7860
ggcggccgct cgagcaccac caccaccacc actgagatcc ggctgctaac aaagcccgaa 7920
aggaagctga gttggctgct gccaccgctg agcaataact agcataaccc cttggggcct 7980
ctaaacgggt cttgaggggt tttttgctga aaggaggaac tatatccgga t 8031

<210> SEQ ID NO 255
<211> LENGTH: 401
<212> TYPE: DNA
<213> ORGANISM: Homo sapiens
<220> FEATURE:
<221> NAME/KEY: misc_feature
<222> LOCATION: 9, 67, 247, 275, 277, 397
<223> OTHER INFORMATION: n = A,T,C or G

<400> SEQUENCE: 255
gtggccagng actagaaggc gaggcgccgc gggaccatgg cggcggcggc ggacgagcgg 60

-continued

```
agtccanagg acggagaaga cgaggaagag gaggagcagt tggttctggt ggaattatca    120

ggaattattg attcagactt cctctcaaaa tgtgaaaata aatgcaaggt tttgggcatt    180

gacactgaga ggcccattct gcaagtggac agctgtgtct ttgctgggga gtatgaagac    240

actctangga cctgtgttat atttgaagaa aatgntnaac atgctgatac agaaggcaat    300

aataaaacag tgctaaaata taaatgccat acaatgaaga agctcagcat gacaagaact    360

ctcctgacag agaagaagga aggagaagaa aacatangtg g                        401


<210> SEQ ID NO 256
<211> LENGTH: 401
<212> TYPE: DNA
<213> ORGANISM: Homo sapiens
<220> FEATURE:
<221> NAME/KEY: misc_feature
<222> LOCATION: 7, 37, 51, 79, 96, 98, 103, 104, 107, 116, 167, 181,
      183, 194, 206, 276, 303, 307, 308, 310, 323, 332, 341, 353, 374,
      376
<223> OTHER INFORMATION: n = A,T,C or G

<400> SEQUENCE: 256

tggtggncct gggatgggga accgcggtgg cttccgngga ggtttcggca ntggcatccg     60

gggccggggt cgcggccgng gacggggccg gggccnangc cgnnganctc gcggangcaa    120

ggccgaggat aaggagtgga tgcccgtcac caacttgggc cgcttgncca aggacatgaa    180

nancaagccc ctgnaggaga tctatntctt cttccctgcc ccattaagga atcaagagat    240

catttgattt cttcctgggg gcctctctca aggatnaggt ttttgaagat tatgccagtg    300

canaaannan accccgttgc ccngtccatc tncacccaac ncttccaagg gcnatttttg    360

tttaggcctc attncngggg ggaaccttaa cccaatttgg g                        401


<210> SEQ ID NO 257
<211> LENGTH: 401
<212> TYPE: DNA
<213> ORGANISM: Homo sapiens
<220> FEATURE:
<221> NAME/KEY: misc_feature
<222> LOCATION: 382, 387
<223> OTHER INFORMATION: n = A,T,C or G

<400> SEQUENCE: 257

atgtatgtaa aacacttcat aaaatgtaaa gggctataac aaatatgtta taaagtgatt     60

ctctcagccc tgaggtatac agaatcattt gcctcagact gctgttggat tttaaaattt    120

ttaaaatatc tgctaagtaa tttgctatgt cttctcccac actatcaata tgcctgcttc    180

taacaggctc cccactttct tttaatgtgc tgttatgagc tttggacatg agataaccgt    240

gcctgttcag agtgtctaca gtaagagctg gacaaactct ggagggacac agtctttgag    300

acagctcttt tggttgcttt ccacttttct gaaaggttca cagtaacctt ctagataata    360

gaaactccca gttaaagcct angctancaa tttttttag t                         401


<210> SEQ ID NO 258
<211> LENGTH: 401
<212> TYPE: DNA
<213> ORGANISM: Homo sapiens

<400> SEQUENCE: 258

ggagcgctag gtcggtgtac gaccgagatt agggtgcgtg ccagctccgg gaggccgcgg     60

tgaggggccg ggcccaagct gccgacccga gccgatcgtc agggtcgcca gcgcctcagc    120

tctgtggagg agcagcagta gtcggagggt gcaggatatt agaaatggct actccccagt    180
```

-continued

```
caattttcat ctttgcaatc tgcattttaa tgataacaga attaattctg gcctcaaaaa    240

gctactatga tatcttaggt gtgccaaaat cggcatcaga gcgccaaatc aagaaggcct    300

ttcacaagtt ggccatgaag taccaccctg acaaaaataa gacccagatg ctgaagcaaa    360

attcagagag attgcagaag catatgaaac actctcagat g                        401
```

<210> SEQ ID NO 259
<211> LENGTH: 401
<212> TYPE: DNA
<213> ORGANISM: Homo sapiens

<400> SEQUENCE: 259

```
attgggtttg gagggaggat gatgacagag gaatgccctt tggccatcac ggttttgatt     60

ctccagaata ttgtgggttt gatcatcaat gcagtcatgt taggctgcat tttcatgaaa    120

acagctcagg ctcacagaag ggcagaaact ttgattttca gccgccatgc tgtgattgcc    180

gtccgaaatg gcaagctgtg cttcatgttc cgagtgggtg acctgaggaa aagcatgatc    240

attagtgcct ctgtgcgcat ccaggtggtc aagaaaacaa ctacacctga aggggaggtg    300

gttcctattc accaactgga cattcctgtt gataacccaa tcgagagcaa taacattttt    360

ctggtggccc ctttgatcat ctgccacgtg attgacaagc g                        401
```

<210> SEQ ID NO 260
<211> LENGTH: 363
<212> TYPE: DNA
<213> ORGANISM: Homo sapiens
<220> FEATURE:
<221> NAME/KEY: misc_feature
<222> LOCATION: 7, 9, 19, 41, 63, 73, 106, 111, 113, 116, 119, 156, 158, 162, 187, 247, 288, 289, 290, 292, 298, 299, 300, 340
<223> OTHER INFORMATION: n = A,T,C or G

<400> SEQUENCE: 260

```
aggaganang gagggggana tgaataggga tggagaggga natagtggat gagcagggca     60

canggagagg aancagaaag gagaggcaag acagggagac acacancaca nangangana    120

caggtggggg ctggggtggg gcatggagag cctttnangt cncccaggcc accctgctct    180

cgctggnctg ttgaaaccca ctccatggct tcctgccact gcagttgggc ccagggctgg    240

cttattnctg gaatgcaagt ggctgtggct tggagcctcc cctctggnnn anggaaannn    300

attgctccct tatctgcttg gaatatctga gtttttccan cccggaaata aaacacacac    360

aca                                                                  363
```

<210> SEQ ID NO 261
<211> LENGTH: 401
<212> TYPE: DNA
<213> ORGANISM: Homo sapiens
<220> FEATURE:
<221> NAME/KEY: misc_feature
<222> LOCATION: 114, 152
<223> OTHER INFORMATION: n = A,T,C or G

<400> SEQUENCE: 261

```
cggctctccg ccgctctccc ggggtttcgg ggcacttggg tcccacagtc tggtcctgct     60

tcaccttccc ctgacctgag tagtcgccat ggcacaggtt ctcagaggca ctgngactga    120

cttccctgga tttgatgagc gggctgatgc anaaactctt cggaaggcta tgaaaggctt    180

gggcacagat gaggagagca tcctgactct gttgacatcc cgaagtaatg ctcagcgcca    240

ggaaatctct gcagctttta agactctgtt tggcagggat cttctggatg acctgaaatc    300
```

-continued

```
agaactaact ggaaaatttg aaaaattaat tgtggctctg atgaaaccct ctcggcttta    360

tgatgcttat gaactgaaac atgccttgaa gggagctgga a                        401
```

<210> SEQ ID NO 262
<211> LENGTH: 401
<212> TYPE: DNA
<213> ORGANISM: Homo sapiens
<220> FEATURE:
<221> NAME/KEY: misc_feature
<222> LOCATION: 7, 26, 258, 305, 358, 373, 374, 378
<223> OTHER INFORMATION: n = A,T,C or G

<400> SEQUENCE: 262

```
agtctanaac atttctaata ttttgngctt tcatatatca aaggagatta tgtgaaacta     60

tttttaaata ctgtaaagtg acatatagtt ataagatata tttctgtaca gtagagaaag    120

agtttataac atgaagaata ttgtaccatt atacattttc attctcgatc tcataagaaa    180

ttcaaaagaa taatgataga ggtgaaaata tgtttacttt ctctaaatca agcctagttg    240

tcaactcaaa aattatgntg catagtttta ttttgaattt aggttttggg actacttttt    300

tccancttca atgagaaaat aaaatctaca actcaggagt tactacagaa gttctaanta    360

tttttttgct aannagcnaa aaatataaac atatgaaaat g                        401
```

<210> SEQ ID NO 263
<211> LENGTH: 401
<212> TYPE: DNA
<213> ORGANISM: Homo sapiens
<220> FEATURE:
<221> NAME/KEY: misc_feature
<222> LOCATION: 232, 290, 304, 326, 383
<223> OTHER INFORMATION: n = A,T,C or G

<400> SEQUENCE: 263

```
ctgtccgacc aagagaggcc ggccgagccc gaggcttggg cttttgcttt ctggcggagg     60

gatctgcggc ggtttaggag gcggcgctga tcctgggagg aagaggcagc tacggcggcg    120

gcggcggtgg cggctagggc ggcggcgaat aaaggggccg ccgccgggtg atgcggtgac    180

cactgcggca ggcccaggag ctgagtgggc cccggccctc agcccgtccc gncggacccg    240

ctttcctcaa ctctccatct tctcctgccg accgagatcg ccgaggcggn ctcaggctcc    300

ctanccccctt ccccgtccct tccccncccc cgtccccgcc ccgggggccg ccgccacccg    360

cctcccacca tggctctgaa ganaatccac aaggaattga a                        401
```

<210> SEQ ID NO 264
<211> LENGTH: 401
<212> TYPE: DNA
<213> ORGANISM: Homo sapiens

<400> SEQUENCE: 264

```
aacaccagcc actccaggac ccctgaaggc ctctaccagg tcaccagtgt tctgcgccta     60

aagccacccc ctggcagaaa cttcagctgt gtgttctgga atactcacgt gagggaactt    120

actttggcca gcattgacct tcaaagtcag atggaaccca ggacccatcc aacttggctg    180

cttcacattt tcatcccctc ctgcatcatt gctttcattt tcatagccac agtgatagcc    240

ctaagaaaac aactctgtca aaagctgtat tcttcaaaag acacaacaaa aagacctgtc    300

accacaacaa agagggaagt gaacagtgct gtgaatctga acctgtggtc ttgggagcca    360

gggtgacctg atatgacatc taaagaagct tctggactct g                        401
```

-continued

<210> SEQ ID NO 265
<211> LENGTH: 271
<212> TYPE: DNA
<213> ORGANISM: Homo sapiens
<220> FEATURE:
<221> NAME/KEY: misc_feature
<222> LOCATION: 59
<223> OTHER INFORMATION: n = A,T,C or G

<400> SEQUENCE: 265
gccacttcct gtggacatgg gcagagcgct gctgccagtt cctggtagcc ttgaccacna 60
cgctgggggg tctttgtgat ggtcatgggt ctcatttgca cttgggggtg tgggattcaa 120
gttagaagtt tctagatctg gccgggcgca gtggctcaca cctgtaatcc cagcacttta 180
ggaggctgag gcaggcggat catgaggtca ggagatcgag accgtcctgg ctaacacagt 240
gaaaccccgt ctctactaaa aatacaaaaa a 271

<210> SEQ ID NO 266
<211> LENGTH: 401
<212> TYPE: DNA
<213> ORGANISM: Homo sapiens
<220> FEATURE:
<221> NAME/KEY: misc_feature
<222> LOCATION: 45
<223> OTHER INFORMATION: n = A,T,C or G

<400> SEQUENCE: 266
attcataaat ttagctgaaa gatactgatt caatttgtat acagngaata taaatgagac 60
gacagcaaaa ttttcatgaa atgtaaaata tttttatagt ttgttcatac tatatgaggt 120
tctattttaa atgactttct ggattttaaa aaatttcttt aaatacaatc atttttgtaa 180
tatttatttt atgcttatga tctagataat tgcagaatat cattttatct gactctgtct 240
tcataagaga gctgtggccg aattttgaac atctgttata gggagtgatc aaattagaag 300
gcaatgtgga aaaacaattc tgggaaagat ttctttatat gaagtccctg ccactagcca 360
gccatcctaa ttgatgaaag ttatctgttc acaggcctgc a 401

<210> SEQ ID NO 267
<211> LENGTH: 401
<212> TYPE: DNA
<213> ORGANISM: Homo sapiens
<220> FEATURE:
<221> NAME/KEY: misc_feature
<222> LOCATION: 116, 247, 277, 296, 307, 313, 322, 323, 336, 342, 355,
365, 377, 378, 397
<223> OTHER INFORMATION: n = A,T,C or G

<400> SEQUENCE: 267
gaagaggcat cacctgatcc cggagacctt tggagttaag aggcggcgga agcgagggcc 60
tgtggagtcg gatcctcttc ggggtgagcc agggtcggcg cgcgcggctg tctcanaact 120
catgcagctg ttcccgcgag gcctgtttga ggacgcgctg ccgcccatcg tgctgaggag 180
ccaggtgtac agccttgtgc ctgacaggac cgtggccgac cggcagctga aggagcttca 240
agagcanggg gagacaaaat cgtccagctg ggcttcnact tggatgccca tggaanttat 300
tctttcnctt ganggactta cnngggaccc aagaanccct tncaaggggc ccttngtgga 360
tgggncccga aaccccnnta tttgcccttg ggggggncca a 401

<210> SEQ ID NO 268
<211> LENGTH: 223
<212> TYPE: DNA

-continued

<213> ORGANISM: Homo sapiens

<400> SEQUENCE: 268
tcgccatgtt ggccaggctg gtcttgaact cctgacttta agtgatccac ccgcctcaac 60
ctcccaaagt gctgggatta caggtgtgag ccaccgcgcc tggcctgata catactttta 120
gaatcaagta gtcacgcact ttttctgttc atttttctaa aaagtaaata tacaaatgtt 180 ttgtttttttg ttttttttgt ttgtttgttt ctgttttttt ttt 223

<210> SEQ ID NO 269
<211> LENGTH: 401
<212> TYPE: DNA
<213> ORGANISM: Homo sapiens

<400> SEQUENCE: 269
actatgtaaa ccacattgta cttttttttta ctttggcaac aaatatttat acatacaaga 60
tgctagttca tttgaatatt tctcccaact tatccaagga tctccagctc taacaaaatg 120
gtttattttt atttaaatgt caatagttgt tttttaaaat ccaaatcaga ggtgcaggcc 180
accagttaaa tgccgtctat caggttttgt gccttaagag actacagagt caaagctcat 240
ttttaaagga gtaggacaaa gttgtcacag gtttttgttg ttgtttttat tgcccccaaa 300
attacatgtt aatttccatt tatatcaggg attctattta cttgaagact gtgaagttgc 360
cattttgtct cattgttttc tttgacataa ctaggatcca t 401

<210> SEQ ID NO 270
<211> LENGTH: 401
<212> TYPE: DNA
<213> ORGANISM: Homo sapiens
<220> FEATURE:
<221> NAME/KEY: misc_feature
<222> LOCATION: 240, 382
<223> OTHER INFORMATION: n = A,T,C or G

<400> SEQUENCE: 270
tggctgttga ttcacctcag cactgcttgg tatctgcacc ctacctctct ttagaggctg 60
ccttgtcaac tgaaaaatgc acctgacttc gagcaagact ctttccttag gttctggatc 120
tgtttgagcc ccatggcact gagctggaat ctgagggtct tgttccaagg atgtgatgat 180
gtgggagaat gttctttgaa agagcagaaa tccagtctgc atggaaacag cctgtagagn 240
agaagtttcc agtgataagt gttcactgtt ctaaggaggt acaccacagc tacctgaatt 300
ttcccaaaat gagtgcttct gtgcgttaca actggccttt gtacttgact gtgatgactt 360 tgtttttttct tttcaattct anatgaacat gggaaaaaat g 401

<210> SEQ ID NO 271
<211> LENGTH: 329
<212> TYPE: DNA
<213> ORGANISM: Homo sapiens

<400> SEQUENCE: 271
ccacagcctc caagtcaggt ggggtggagt cccagagctg cacagggttt ggcccaagtt 60
tctaagggag gcacttcctc ccctcgccca tcagtgccag cccctgctgg ctggtgcctg 120
agcccctcag acagccccct gccccgcagg cctgccttct cagggacttc tgcggggcct 180
gaggcaagcc atggagtgag acccaggagc cggacacttc tcaggaaatg gcttttccca 240
acccccagcc cccacccggt ggttcttcct gttctgtgac tgtgtatagt gccaccacag 300
cttatggcat ctcattgagg acaaaaaaa 329

-continued

<210> SEQ ID NO 272
<211> LENGTH: 401
<212> TYPE: DNA
<213> ORGANISM: Homo sapiens
<220> FEATURE:
<221> NAME/KEY: misc_feature
<222> LOCATION: 1, 7, 12, 21, 61, 62, 66, 72, 78, 88, 90, 92, 98, 117, 119, 128, 130, 134, 142, 144, 151, 159, 162, 164, 168, 169, 177, 184, 185, 188, 194, 202, 204, 209, 213, 218, 223, 231, 260, 272, 299, 300, 306, 321, 322, 323, 331, 335, 336, 338
<223> OTHER INFORMATION: n = A,T,C or G
<221> NAME/KEY: misc_feature
<222> LOCATION: 341, 342, 343, 345, 346, 351, 358, 360, 362, 363, 387, 390, 392
<223> OTHER INFORMATION: n = A,T,C or G

<400> SEQUENCE: 272

```
nggctgntaa cntcggaggt nacttcctgg actatcctgg agaccccctc cgcttccacg     60

nncatnatat cnctcatngc tgggcccntn angacacnat cccactccaa cacctgngng    120

atgctggncn cctnggaacc ancntcagaa ngaccctgnt cntntgtnnt ccgcaanctg    180

aagnnaangc gggntacacc tncntgcant ggnccacnct gcngggaact ntacacacct    240

acgggatgtg gctgcgccan gagccaagag cntttctgga tgattcccca gcctcttgnn    300

agggantcta caacattgct nnntaccttt ntccnncngc nnntnntgga ntacaggngn    360

tnntaacact acatcttttt tactgcnccn tncttggtgg g                        401
```

<210> SEQ ID NO 273
<211> LENGTH: 401
<212> TYPE: DNA
<213> ORGANISM: Homo sapiens
<220> FEATURE:
<221> NAME/KEY: misc_feature
<222> LOCATION: 399
<223> OTHER INFORMATION: n = A,T,C or G

<400> SEQUENCE: 273

```
cagcaccatg aagatcaaga tcatcgcacc cccagagcgc aagtactcgg tgtggatcgg     60

tggctccatc ctggcctcac tgtccacctt ccagcagatg tggattagca agcaggagta    120

cgacgagtcg ggcccctcca tcgtccaccg caaatgcttc taaacggact cagcagatgc    180

gtagcatttg ctgcatgggt taattgagaa tagaaatttg cccctggcaa atgcacacac    240

ctcatgctag cctcacgaaa ctggaataag ccttcgaaaa gaaattgtcc ttgaagcttg    300

tatctgatat cagcactgga ttgtagaact tgttgctgat tttgaccttg tattgaagtt    360

aactgttccc cttggtatta acgtgtcagg gctgagtgnt c                        401
```

<210> SEQ ID NO 274
<211> LENGTH: 401
<212> TYPE: DNA
<213> ORGANISM: Homo sapiens

<400> SEQUENCE: 274

```
ccacccacac ccaccgcgcc ctcgttcgcc tcttctccgg gagccagtcc gcgccaccgc     60

cgccgcccag gccatcgcca ccctccgcag ccatgtccac caggtccgtg tcctcgtcct    120

cctaccgcag gatgttcggc ggcccgggca ccgcgagccg gccgagctcc agccggagct    180

acgtgactac gtccacccgc acctacagcc tgggcagcgc gctgcgcccc agcaccagcc    240

gcagcctcta cgcctcgtcc ccgggcggcg tgtatgccac gcgctcctct gccgtgcgcc    300

tgcggagcag cgtgcccggg gtgcggctcc tgcaggactc ggtggacttc tcgctggccg    360
```

-continued acgccatcaa caccgagttc aagaacaccc gcaccaacga g 401

<210> SEQ ID NO 275
<211> LENGTH: 401
<212> TYPE: DNA
<213> ORGANISM: Homo sapiens

<400> SEQUENCE: 275
ccacttccac cactttgtgg agcagtgcct tcagcgcaac ccggatgcca ggtatccctg 60
ctggcctggg cctgggcttc gggagagcag agggtgctca ggagggtaag gccagggtgt 120
gaagggactt acctcccaaa ggttctgcag gggaatctgg agctacacac aggagggatc 180
agctcctggg tgtgtcagag gccagcctgg ggagctctgg ccactgcttc ccatgagctg 240
agggagaggg agaggggacc cgaggctgag gcataagtgg caggatttcg ggaagctggg 300
gacacggcag tgatgctgcg gtctctcctc ccctttccct ccaggcccag tgccagcacc 360
ctcctgaacc actctttctt caagcagatc aagcgacgtg c 401

<210> SEQ ID NO 276
<211> LENGTH: 401
<212> TYPE: DNA
<213> ORGANISM: Homo sapiens
<220> FEATURE:
<221> NAME/KEY: misc_feature
<222> LOCATION: 11
<223> OTHER INFORMATION: n = A,T,C or G

<400> SEQUENCE: 276
tctgatattg ntacccttga gccacctaag ttagaagaaa ttggaaatca agaagttgtc 60
attgttgaag aagcacagag ttcagaagac tttaacatgg gctcttcctc tagcagccag 120
tatactttct gtcagccaga aactgtattt tcatctcagc ctagtgatga tgaatcaagt 180
agtgatgaaa ccagtaatca gcccagtcct gcctttagac gacgccgtgc taggaagaag 240
accgtttctg cttcagaatc tgaagaccgg ctagttggtg aacaagaaac tgaaccttct 300
aaggagttga gtaaacgtca gttcagtagt ggtctcaata agtgtgttat acttgctttg 360
gtgattgcaa tcagcatggg atttggccat ttctatggca c 401

<210> SEQ ID NO 277
<211> LENGTH: 401
<212> TYPE: DNA
<213> ORGANISM: Homo sapiens
<220> FEATURE:
<221> NAME/KEY: misc_feature
<222> LOCATION: 227, 333
<223> OTHER INFORMATION: n = A,T,C or G

<400> SEQUENCE: 277
aactttggca acatatctca gcaaaaacta cagctatgtt attcatgcca aaataaaagc 60
tgtgcagagg agtggctgca atgaggtcac aacggtggtg gatgtaaaag agatcttcaa 120
gtcctcatca cccatccctc gaactcaagt cccgctcatt acaaattctt cttgccagtg 180
tccacacatc ctgccccatc aagatgttct catcatgtgt tacgagnggc gctcaaggat 240
gatgcttctt gaaaattgct tagttgaaaa atggagagat cagcttagta aaagatccat 300
acagtgggaa gagaggctgc aggaacagcg ganaacagtt caggacaaga agaaaacagc 360
cgggcgcacc agtcgtagta atccccccaa accaaaggga a 401

<210> SEQ ID NO 278

-continued

<211> LENGTH: 401
<212> TYPE: DNA
<213> ORGANISM: Homo sapiens
<220> FEATURE:
<221> NAME/KEY: misc_feature
<222> LOCATION: 322, 354
<223> OTHER INFORMATION: n = A,T,C or G

<400> SEQUENCE: 278
aatgagtgtg agaccacaaa tgaatgccgg gaggatgaaa tgtgttggaa ttatcatggc 60
ggcttccgtt gttatccacg aaatccttgt caagatccct acattctaac accagagaac 120
cgatgtgttt gcccagtctc aaatgccatg tgccgagaac tgccccagtc aatagtctac 180
aaatacatga gcatccgatc tgataggtct gtgccatcag acatcttcca gatacaggcc 240
acaactattt atgccaacac catcaatact tttcggatta aatctggaaa tgaaaatgga 300
gagtctacct acgacaacaa ancccctgtaa gtgcaatgct tgtgctcgtg aagncattat 360
caggaccaag agaacatatc gtggacctgg agatgctgac a 401

<210> SEQ ID NO 279
<211> LENGTH: 401
<212> TYPE: DNA
<213> ORGANISM: Homo sapiens
<220> FEATURE:
<221> NAME/KEY: misc_feature
<222> LOCATION: 30, 35, 81, 88, 180, 212, 378, 384, 391
<223> OTHER INFORMATION: n = A,T,C or G

<400> SEQUENCE: 279
aaattattgc ctctgataca tacctaagtn aacanaacat taatacctaa gtaaacataa 60
cattacttgg agggttgcag nttctaantg aaactgtatt tgaaactttt aagtatactt 120
taggaaacaa gcatgaacgg cagtctagaa taccagaaac atctacttgg gtagcttggn 180
gccattatcc tgtggaatct gatatgtctg gnagcatgtc attgatggga catgaagaca 240
tctttggaaa tgatgagatt atttcctgtg ttaaaaaaaa aaaaaatctt aaattcctac 300
aatgtgaaac tgaaactaat aattttgatc ctgatgtatg ggacagcgta tctgtaccag 360
gctctaaata acaaaagnta gggngacaag nacatgttcc t 401

<210> SEQ ID NO 280
<211> LENGTH: 326
<212> TYPE: DNA
<213> ORGANISM: Homo sapiens

<400> SEQUENCE: 280
gaagtggaat tgtataattc aattcgataa ttgatctcat gggctttccc tggaggaaag 60
gttttttttg ttgttttttt tttaagaact tgaaacttgt aaactgagat gtctgtagct 120
tttttgccca tctgtagtgt atgtgaagat ttcaaaacct gagagcactt tttctttgtt 180
tagaattatg agaaaggcac tagatgactt taggatttgc atttttccct ttattgcctc 240
atttcttgtg acgccttgtt ggggagggaa atctgtttat tttttcctac aaataaaaag 300
ctaagattct atatcgcaaa aaaaaa 326

<210> SEQ ID NO 281
<211> LENGTH: 374
<212> TYPE: DNA
<213> ORGANISM: Homo sapiens

<400> SEQUENCE: 281
caacgcgttt gcaaatattc ccctggtagc ctacttcctt acccccgaat attggtaaga 60

-continued

```
tcgagcaatg gcttcaggac atgggttctc ttctcctgtg atcattcaag tgctcactgc    120

atgaagactg gcttgtctca gtgtttcaac ctcaccaggg ctgtctcttg gtccacacct    180

cgctccctgt tagtgccgta tgacagcccc catcaaatga ccttggccaa gtcacggttt    240

ctctgtggtc aaggttggtt ggctgattgg tggaaagtag ggtggaccaa aggaggccac    300

gtgagcagtc agcaccagtt ctgcaccagc agcgcctccg tcctagtggg tgttcctgtt    360

tctcctggcc ctgg                                                      374


<210> SEQ ID NO 282
<211> LENGTH: 404
<212> TYPE: DNA
<213> ORGANISM: Homo sapiens
<220> FEATURE:
<221> NAME/KEY: misc_feature
<222> LOCATION: 26, 27, 51, 137, 180, 222
<223> OTHER INFORMATION: n = A,T,C or G

<400> SEQUENCE: 282

agtgtggtgg aattcccgca tcctanncgc cgactcacac aaggcagagt ngccatggag     60

aaaattccag tgtcagcatt cttgctcctt gtggccctct cctacactct ggccagagat    120

accacagtca aacctgnagc caaaaaggac acaaaggact ctcgacccaa actgccccan    180

accctctcca gaggttgggg tgaccaactc atctggactc anacatatga agaagctcta    240

tataaatcca agacaagcaa caaacccttg atgattattc atcacttgga tgagtgccca    300

cacagtcaag ctttaaagaa agtgtttgct gaaaataaag aaatccagaa attggcagag    360

cagtttgtcc tcctcaatct ggtttatgaa acaactgaca aaca                     404


<210> SEQ ID NO 283
<211> LENGTH: 184
<212> TYPE: DNA
<213> ORGANISM: Homo sapiens
<220> FEATURE:
<221> NAME/KEY: misc_feature
<222> LOCATION: 26
<223> OTHER INFORMATION: n = A,T,C or G

<400> SEQUENCE: 283

agtgtggtgg aattcacttg cttaanttgt gggcaaaaga gaaaaagaag gattgatcag     60

agcattgtgc aatacagttt cattaactcc ttccctcgct cccccaaaaa tttgaatttt    120

tttttcaaca ctcttacacc tgttatggaa aatgtcaacc tttgtaagaa aaccaaaata    180

aaaa                                                                 184


<210> SEQ ID NO 284
<211> LENGTH: 421
<212> TYPE: DNA
<213> ORGANISM: Homo sapiens
<220> FEATURE:
<221> NAME/KEY: misc_feature
<222> LOCATION: 147, 149
<223> OTHER INFORMATION: n = A,T,C or G

<400> SEQUENCE: 284

ctattaatcc tgccacaata tttttaatta cgtacaaaga tctgacatgt cacccaggga     60

cccatttcac ccactgctct gtttggccgc cagtcttttg tctctctctt cagcaatggt    120

gaggcggata ccctttcctc ggggaanana aatccatggt ttgttgccct tgccaataac    180

aaaaatgttg gaaagtcgag tggcaaagct gttgccattg gcatctttca cgtgaaccac    240
```

-continued

```
gtcaaaagat ccagggtgcc tctctctgtt ggtgatcaca ccaattcttc ctaggttagc    300

acctccagtc accatacaca ggttaccagt gtcgaacttg atgaaatcag taatcttgcc    360

agtctctaaa tcaatctgaa tggtatcatt caccttgatg aggggatcgg ggtagcggat    420

g                                                                    421
```

<210> SEQ ID NO 285
<211> LENGTH: 361
<212> TYPE: DNA
<213> ORGANISM: Homo sapiens
<220> FEATURE:
<221> NAME/KEY: misc_feature
<222> LOCATION: 34, 188
<223> OTHER INFORMATION: n = A,T,C or G

<400> SEQUENCE: 285

```
ctgggtggta actctttatt tcattgtccg gaanaaagat gggagtggga acagggtgga     60

cactgtgcag gcttcagctt ccactccggg caggattcag gctatctggg accgcaggga    120

ctgccaggtg cacagccctg gctcccgagg caggcaggca aggtgacggg actggaagcc    180

cttttcanag ccttggagga gctggtccgt ccacaagcaa tgagtgccac tctgcagttt    240

gcaggggatg gataaacagg gaaacactgt gcattcctca cagccaacag tgtaggtctt    300

ggtgaagccc cggcgctgag ctaagctcag gctgttccag ggagccacga aactgcaggt    360

a                                                                    361
```

<210> SEQ ID NO 286
<211> LENGTH: 336
<212> TYPE: DNA
<213> ORGANISM: Homo sapiens
<220> FEATURE:
<221> NAME/KEY: misc_feature
<222> LOCATION: 40, 68, 75, 127, 262
<223> OTHER INFORMATION: n = A,T,C or G

<400> SEQUENCE: 286

```
tttgagtggc agcgccttta tttgtggggg ccttcaaggn agggtcgtgg ggggcagcgg     60

ggaggaanag ccganaaact gtgtgaccgg ggcctcaggt ggtgggcatt gggggctcct    120

cttgcanatg cccattggca tcaccggtgc agccattggt ggcagcgggt accggtcctt    180

tcttgttcaa catagggtag gtggcagcca cgggtccaac tcgcttgagg ctgggccctg    240

ggcgctccat tttgtgttcc angagcatgt ggttctgtgg cgggagcccc acgcaggccc    300

tgaggatgtt ctcgatgcag ctgcgctggc ggaaaa                              336
```

<210> SEQ ID NO 287
<211> LENGTH: 301
<212> TYPE: DNA
<213> ORGANISM: Homo sapiens
<220> FEATURE:
<221> NAME/KEY: misc_feature
<222> LOCATION: 15, 33, 44, 53, 76, 83, 107, 117, 154, 166, 192, 194,
      207, 215, 241, 246
<223> OTHER INFORMATION: n = A,T,C or G

<400> SEQUENCE: 287

```
tgggtaccaa atttntttat ttgaaggaat ggnacaaatc aaanaactta agnggatgtt     60

ttggtacaac ttatanaaaa ggnaaaggaa accccaacat gcatgcnctg ccttggngac    120

cagggaagtc accccacggc tatggggaaa ttancccgag gcttancttt cattatcact    180

gtctcccagg gngngcttgt caaaaanata ttccnccaag ccaaattcgg gcgctcccat    240
```

-continued

```
nttgcncaag ttggtcacgt ggtcacccaa ttctttgatg gctttcacct gctcattcag    300

g                                                                    301


<210> SEQ ID NO 288
<211> LENGTH: 358
<212> TYPE: DNA
<213> ORGANISM: Homo sapiens
<220> FEATURE:
<221> NAME/KEY: misc_feature
<222> LOCATION: 39, 143, 226
<223> OTHER INFORMATION: n = A,T,C or G

<400> SEQUENCE: 288

aagtttttaa actttttatt tgcatattaa aaaaattgng cattccaata attaaaatca     60

tttgaacaaa aaaaaaaatg gcactctgat taaactgcat tacagcctgc aggacacctt    120

gggccagctt ggttttactc tanatttcac tgtcgtccca ccccacttct tccaccccac    180

ttcttccttc accaacatgc aagttctttc cttccctgcc agccanatag atagacagat    240

gggaaaggca ggcgcggcct tcgttgtcag tagttctttg atgtgaaagg ggcagcacag    300

tcatttaaac ttgatccaac ctctttgcat cttacaaagt taaacagcta aaagaagt      358


<210> SEQ ID NO 289
<211> LENGTH: 462
<212> TYPE: DNA
<213> ORGANISM: Homo sapiens
<220> FEATURE:
<221> NAME/KEY: misc_feature
<222> LOCATION: 87, 141, 182, 220, 269, 327
<223> OTHER INFORMATION: n = A,T,C or G

<400> SEQUENCE: 289

ggcatcagaa atgctgttta tttctctgct gctcccaagc tggctggcct ttgcagagga     60

gcagacaaca gatgcatagt tggggganaa gggaggacag gttccaggat agagggtgca    120

ggctgaggga ggaagggtaa naggaaggaa ggccatcctg gatccccaca tttcagtctc    180

anatgaggac aaagggactc ccaagccccc aaatcatcan aaaacaccaa ggagcaggag    240

gagcttgagc aggccccagg gagcctcana gccataccag ccactgtcta cttcccatcc    300

tcctctccca ttccctgtct gcttcanacc acctcccagc taagccccag ctccattccc    360

ccaatcctgg cccttgccag cttgacagtc acagtgcctg gaattccacc actgaggctt    420

ctcccagttg gattaggacg tcgccctgtt agcatgctgc cc                       462


<210> SEQ ID NO 290
<211> LENGTH: 481
<212> TYPE: DNA
<213> ORGANISM: Homo sapiens
<220> FEATURE:
<221> NAME/KEY: misc_feature
<222> LOCATION: 44, 57, 122, 158, 304, 325, 352, 405
<223> OTHER INFORMATION: n = A,T,C or G

<400> SEQUENCE: 290

tactttccta aactttatta aagaaaaaag caataagcaa tggngggtaaa tctctanaac     60

atacccaatt ttctgggctt cctcccccga gaatgtgaca ttttgatttc caaacatgcc    120

anaagtgtat ggttcccaac tgtactaaag taggtganaa gctgaagtcc tcaagtgttc    180

atcttccaac ttttcccagt ctgtggtctg tctttggatc agcaataatt gcctgaacag    240

ctactatggc ttcgttgatt tttgtctgta gctctctgag ctcctctatg tgcagcaatc    300

gcanaatttg agcagcttca ttaanaactg catctcctgt gtcaaaacca anaatatgtt    360
```

-continued tgtctaaagc aacaggtaag ccctcttttg tttgatttgc cttancaact gcatcctgtg 420
tcaggcgctc ctgaaccaaa atccgaattg ccttaagcat taccaggtaa tcatcatgac 480
g 481

<210> SEQ ID NO 291
<211> LENGTH: 381
<212> TYPE: DNA
<213> ORGANISM: Homo sapiens
<220> FEATURE:
<221> NAME/KEY: misc_feature
<222> LOCATION: 79, 166, 187, 208, 219, 315
<223> OTHER INFORMATION: n = A,T,C or G

<400> SEQUENCE: 291
tcatagtaat gtaaaaccat ttgtttaatt ctaaatcaaa tcactttcac aacagtgaaa 60
attagtgact ggttaaggng tgccactgta catatcatca ttttctgact ggggtcagga 120
cctggtccta gtccacaagg gtggcaggag gagggtggag gctaanaaca cagaaaacac 180
acaaaanaaa ggaaagctgc cttggcanaa ggatgaggng gtgagcttgc cgaaggatgg 240
tgggaagggg gctccctgtt ggggccgagc caggagtccc aagtcagctc tcctgcctta 300
cttagctcct ggcanagggt gagtggggac ctacgaggtt caaaatcaaa tggcatttgg 360
ccagcctggc tttactaaca g 381

<210> SEQ ID NO 292
<211> LENGTH: 371
<212> TYPE: DNA
<213> ORGANISM: Homo sapiens
<220> FEATURE:
<221> NAME/KEY: misc_feature
<222> LOCATION: 32, 55, 72, 151, 189, 292
<223> OTHER INFORMATION: n = A,T,C or G

<400> SEQUENCE: 292
gaaaaaataa tccgtttaat tgaaaaacct gnaggatact attccactcc cccanatgag 60
gaggctgagg anaccaaacc cctacatcac ctcgtagcca cttctgatac tcttcacgag 120
gcagcaggca aagacaattc ccaaaacctc nacaaaagca attccaaggg ctgctgcagc 180
taccaccanc acatttttcc tcagccagcc cccaatcttc tccacacagc cctccttatg 240
gatcgccttc tcgttgaaat taatcccaca gcccacagta acattaatgc ancaggagtc 300
ggggactcgg ttcttcgaca tggaagggat tttctcccaa tctgtgtagt tagcagcccc 360
acagcactta a 371

<210> SEQ ID NO 293
<211> LENGTH: 361
<212> TYPE: DNA
<213> ORGANISM: Homo sapiens
<220> FEATURE:
<221> NAME/KEY: misc_feature
<222> LOCATION: 75, 196, 222
<223> OTHER INFORMATION: n = A,T,C or G

<400> SEQUENCE: 293
gatttaaaag aaaacacttt attgttcagc aattaaaagt tagccaaata tgtatttttc 60
tccataattt attgngatgt tatcaacatc aagtaaaatg ctcattttca tcatttgctt 120
ctgttcatgt tttcttgaac acgtcttcaa ttttccttcc aaaatgctgc atgccacact 180
tgaggtaacg aagcanaagt atttttaaac atgacagcta anaacattca tctacagcaa 240

-continued

```
cctatatgct caatacatgc cgcgtgatcc tagtagtttt ttcacaacct tctacaagtt    300

tttggaaaac atctgttatg atgactttca tacaccttca cctcaaaggc tttcttgcac    360

c                                                                    361


<210> SEQ ID NO 294
<211> LENGTH: 391
<212> TYPE: DNA
<213> ORGANISM: Homo sapiens
<220> FEATURE:
<221> NAME/KEY: misc_feature
<222> LOCATION: 26, 77, 96, 150, 203, 252, 254, 264, 276
<223> OTHER INFORMATION: n = A,T,C or G

<400> SEQUENCE: 294

tattttaaag tttaattatg attcanaaaa aatcgagcga ataactttct ctgaaaaaat     60

atattgactc tgtatanacc acagttattg gggganaagg gctggtaggt taaattatcc    120

tattttttat tctgaaaatg atattaatan aaagtcccgt ttccagtctg attataaaga    180

tacatatgcc caaaatggct ganaataaat acaacaggaa atgcaaaagc tgtaaagcta    240

agggcatgca ananaaaatc tcanaatacc caaagnggca acaaggaacg tttggctgga    300

atttgaagtt atttcagtca tctttgtctt tggctccatg tttcaggatg cgtgtgaact    360

cgatgtaatt gaaattcccc tttttatcaa t                                   391


<210> SEQ ID NO 295
<211> LENGTH: 343
<212> TYPE: DNA
<213> ORGANISM: Homo sapiens
<220> FEATURE:
<221> NAME/KEY: misc_feature
<222> LOCATION: 145, 174, 205, 232
<223> OTHER INFORMATION: n = A,T,C or G

<400> SEQUENCE: 295

ttcttttgtt ttattgataa cagaaactgt gcataattac agatttgatg aggaatctgc     60

aaataataaa gaatgtgtct actgccagca aaatacaatt attccatgcc ctctcaacat    120

acaaatatag agttcttcac accanatggc tctggtgtaa caaagccatt ttanatgttt    180

aattgtgctt ctacaaaacc ttcanagcat gaggtagttt cttttaccta cnatattttc    240

cacatttcca ttattacact tttagtgagc taaaatcctt ttaacatagc ctgcggatga    300

tctttcacaa aagccaagcc tcatttacaa agggtttatt tct                      343


<210> SEQ ID NO 296
<211> LENGTH: 241
<212> TYPE: DNA
<213> ORGANISM: Homo sapiens
<220> FEATURE:
<221> NAME/KEY: misc_feature
<222> LOCATION: 96, 98, 106, 185
<223> OTHER INFORMATION: n = A,T,C or G

<400> SEQUENCE: 296

ttcttggata ttggttgttt ttgtgaaaaa gtttttgttt ttcttctcag tcaactgaat     60

tatttctcta ctttgccctc ctgatgccca catgananaa cttaanataa tttctaacag    120

cttccacttt ggaaaaaaaa aaaacctgtt ttcctcatgg aaccccagga gttgaaagtg    180

gatanatcgc tctcaaaatc taaggctctg ttcagcttta cattatgtta cctgacgttt    240

t                                                                    241
```

-continued

<210> SEQ ID NO 297
<211> LENGTH: 391
<212> TYPE: DNA
<213> ORGANISM: Homo sapiens
<220> FEATURE:
<221> NAME/KEY: misc_feature
<222> LOCATION: 12, 130
<223> OTHER INFORMATION: n = A,T,C or G

<400> SEQUENCE: 297
gttgtggctg anaatgctgg agatgctcag ttctctccct cacaaggtag gccacaaatt 60
cttggtggtg ccctcacatc tggggtcttc aggcaccagc catgcctgcc gaggagtgct 120
gtcaggacan accatgtccg tgctaggccc aggcacagcc caaccactcc tcatccaagt 180
ctctcccagg tttctggtcc cgatgggcaa ggatgacccc tccagtggct ggtaccccac 240
catcccacta cccctcacat gctctcactc tccatcaggt ccccaatcct ggcttccctc 300
ttcacgaact ctcaaagaaa aggaaggata aaacctaaat aaaccagaca gaagcagctc 360
tggaaaagta caaaaagaca gccagaggtg t 391

<210> SEQ ID NO 298
<211> LENGTH: 321
<212> TYPE: DNA
<213> ORGANISM: Homo sapiens
<220> FEATURE:
<221> NAME/KEY: misc_feature
<222> LOCATION: 14, 30, 76, 116, 201, 288, 301
<223> OTHER INFORMATION: n = A,T,C or G

<400> SEQUENCE: 298
caagccaaac tgtntccagc tttattaaan atactttcca taaacaatca tggtatttca 60
ggcaggacat gggcanacaa tcgttaacag tatacaacaa ctttcaaact cccttnttca 120
atggactacc aaaaatcaaa aagccactat aaaacccaat gaagtcttca tctgatgctc 180
tgaacaggga aagtttaaag ngagggttga catttcacat ttagcatgtt gtttaacaac 240
ttttcacaag ccgaccctga ctttcaggaa gtgaaatgaa aatggcanaa tttatctgaa 300
natccacaat ctaaaaatgg a 321

<210> SEQ ID NO 299
<211> LENGTH: 401
<212> TYPE: DNA
<213> ORGANISM: Homo sapiens
<220> FEATURE:
<221> NAME/KEY: misc_feature
<222> LOCATION: 104, 268, 347
<223> OTHER INFORMATION: n = A,T,C or G

<400> SEQUENCE: 299
tatcataaag agtgttgaag tttatttatt atagcaccat tgagacattt tgaaattgga 60
attggtaaaa aaataaaaca aaaagcattt gaattgtatt tggnggaaca gcaaaaaaag 120
agaagtatca tttttctttg tcaaattata ctgtttccaa acattttgga aataaataac 180
tggaattttg tcggtcactt gcactggttg acaagattag aacaagagga acacatatgg 240
agttaaattt tttttgttgg gatttcanat agagtttggt ttataaaaag caaacagggc 300
caacgtccac accaaattct tgatcaggac caccaatgtc atagggngca atatctacaa 360
taggtagtct cacagccttg cgtgttcgat attcaaagac t 401

<210> SEQ ID NO 300
<211> LENGTH: 188
<212> TYPE: DNA

-continued

<213> ORGANISM: Homo sapiens
<220> FEATURE:
<221> NAME/KEY: misc_feature
<222> LOCATION: 48
<223> OTHER INFORMATION: n = A,T,C or G

<400> SEQUENCE: 300
tgaatgcttt gtcatattaa gaaagttaaa gtgcaataat gtttgaanac aataagtggt 60
ggtgtatctt gtttctaata agataaactt ttttgtcttt gctttatctt attagggagt 120
tgtatgtcag tgtataaaac atactgtgtg gtataacagg cttaataaat tctttaaaag 180
gaaaaaaa 188

<210> SEQ ID NO 301
<211> LENGTH: 291
<212> TYPE: DNA
<213> ORGANISM: Homo sapiens

<400> SEQUENCE: 301
aagattttgt tttattttat tatggctaga aagacactgt tatagccaaa atcggcaatg 60
acactaaaga aatcctctgt gcttttcaat atgcaaatat atttcttcca agagttgccc 120
tggtgtgact tcaagagttc atgttaactt cttttctgga aacttccttt tcttagttgt 180
tgtattcttg aagagcctgg gccatgaaga gcttgcctaa gttttgggca gtgaactcct 240
tgatgttctg gcagtaagtg tttatctggc ctgcaatgag cagcgagtcc a 291

<210> SEQ ID NO 302
<211> LENGTH: 341
<212> TYPE: DNA
<213> ORGANISM: Homo sapiens
<220> FEATURE:
<221> NAME/KEY: misc_feature
<222> LOCATION: 25
<223> OTHER INFORMATION: n = A,T,C or G

<400> SEQUENCE: 302
tgatttttca taattttatt aaatnatcac tgggaaaact aatggttcgc gtatcacaca 60
attacactac aatctgatag gagtggtaaa accagccaat ggaatccagg taaagtacaa 120
aaacgccacc ttttattgtc ctgtcttatt tctcgggaag gagggttcta ctttacacat 180
ttcatgagcc agcagtggac ttgagttaca atgtgtaggt tccttgtggt tatagctgca 240
gaagaagcca tcaaattctt gaggacttga catctctcgg aaagaagcaa actagtggat 300
cccccgggct gcaggaattc gatatcaagc ttatcgatac c 341

<210> SEQ ID NO 303
<211> LENGTH: 361
<212> TYPE: DNA
<213> ORGANISM: Homo sapiens
<220> FEATURE:
<221> NAME/KEY: misc_feature
<222> LOCATION: 15, 27, 92, 124, 127, 183, 198, 244, 320
<223> OTHER INFORMATION: n = A,T,C or G

<400> SEQUENCE: 303
tgcagacagt aaatnaattt tatttgngtt cacagaacat actaggcgat ctcgacagtc 60
gctccgtgac agcccaccaa cccccaaccc tntacctcgc agccacccta aaggcgactt 120
caanaanatg gaaggatctc acggatctca ttcctaatgg tccgccgaag tctcacacag 180
tanacagacg gagttganat gctggaggat gcagtcacct cctaaactta cgacccacca 240
ccanacttca tcccagccgg gacgtcctcc cccacccgag tcctccccat ttcttctcct 300

-continued

```
actttgccgc agttccaggn gtcctgcttc caccagtccc acaaagctca ataaatacca    360

a                                                                     361


<210> SEQ ID NO 304
<211> LENGTH: 301
<212> TYPE: DNA
<213> ORGANISM: Homo sapiens
<220> FEATURE:
<221> NAME/KEY: misc_feature
<222> LOCATION: 23, 104, 192
<223> OTHER INFORMATION: n = A,T,C or G

<400> SEQUENCE: 304

ctctttacaa cagcctttat ttncggccct tgatcctgct cggatgctgg tggaggccct     60

tagctccgcc cgccaggctc tgtgccgcct ccccgcaggc gcanattcat gaacacggtg    120

ctcaggggct tgaggccgta ctcccccagc gggagctggt cctccagggg cttcccctcg    180

aaggtcagcc anaacaggtc gtcctgcaca ccctccagcc cgctcacttg ctgcttcagg    240

tgggccacgg tctgcgtcag ccgcacctcg taggtgctgc tgcggccctt gttattcctc    300

a                                                                     301


<210> SEQ ID NO 305
<211> LENGTH: 331
<212> TYPE: DNA
<213> ORGANISM: Homo sapiens
<220> FEATURE:
<221> NAME/KEY: misc_feature
<222> LOCATION: 3, 36, 60, 193, 223
<223> OTHER INFORMATION: n = A,T,C or G

<400> SEQUENCE: 305

ganaggctag taacatcagt tttattgggt tggggnggca accatagcct ggctggggggn     60

ggggctggcc ctcacaggtt gttgagttcc agcagggtct ggtccaaggt ctggtgaatc    120

tcgacgttct cctccttggc actggccaag gtctcttcta ggtcatcgat ggttttctcc    180

aactttgcca canacctctc ggcaaactct gctcgggtct cancctcctt cagcttctcc    240

tccaacagtt tgatctcctc ttcatattta tcttctttgg gggaatactc ctcctctgag    300

gccatcaggg acttgagggc ctggtccatg g                                    331


<210> SEQ ID NO 306
<211> LENGTH: 457
<212> TYPE: DNA
<213> ORGANISM: Homo sapiens

<400> SEQUENCE: 306

aatatgtaaa ggtaataact tttattatat taaagacaat gcaaacgaaa aacagaattg     60

agcagtgcaa aatttaaagg actgttttgt tctcaaagtt gcaagtttca aagccaaaag    120

aattatatgt atcaaatata taagtaaaaa aaagttagac tttcaagcct gtaatcccag    180

cactttggga ggctgaggca ggtggatcac taacattaaa aagacaacat tagattttgt    240

cgatttatag caattttata aatatataac tttgtcactt ggatcctgaa gcaaaataat    300

aaagtgaatt tgggattttt gtacttggta aaaagtttaa caccctaaat tcacaactag    360

tggatccccc gggctgcagg aattcgatat caagcttatc gataccgtcg acctcgaggg    420

ggggcccggt acccaattcg ccctatagtg agtcgta                              457


<210> SEQ ID NO 307
```

-continued

<211> LENGTH: 491
<212> TYPE: DNA
<213> ORGANISM: Homo sapiens

<400> SEQUENCE: 307
gtgcttggac ggaacccggc gctcgttccc caccccggcc ggccgcccat agccagccct 60
ccgtcacctc ttcaccgcac cctcggactg ccccaaggcc cccgccgccg ctccagcgcc 120
gcgcagccac cgccgccgcc gccgcctctc cttagtcgcc gccatgacga ccgcgtccac 180
ctcgcaggtg cgccagaact accaccagga ctcagaggcc gccatcaacc gccagatcaa 240
cctggagctc tacgcctcct acgtttacct gtccatgtct tactactttg accgcgatga 300
tgtggctttg aagaactttg ccaaatactt tcttcaccaa tctcatgagg agagggaaca 360
tgctgagaaa ctgatgaagc tgcagaacca acgaggtggc cgaatcttcc ttcaggatat 420
caagaaacca gactgtgatg actgggagag cgggctgaat gcaatggagt gtgcattaca 480
tttggaaaaa a 491

<210> SEQ ID NO 308
<211> LENGTH: 421
<212> TYPE: DNA
<213> ORGANISM: Homo sapiens

<400> SEQUENCE: 308
ctcagcgctt cttctttctt ggtttgatcc tgactgctgt catggcgtgc cctctggaga 60
aggccctgga tgtgatggtg tccaccttcc acaagtactc gggcaaagag ggtgacaagt 120
tcaagctcaa caagtcagaa ctaaaggagc tgctgacccg ggagctgccc agcttcttgg 180
ggaaaaggac agatgaagct gctttccaga agctgatgag caacttggac agcaacaggg 240
acaacgaggt ggacttccaa gagtactgtg tcttcctgtc ctgcatcgcc atgatgtgta 300
acgaattctt tgaaggcttc ccagataagc agcccaggaa gaaatgaaaa ctcctctgat 360
gtggttgggg ggtctgccag ctggggccct ccctgtcgcc agtgggcact ttttttttc 420 c 421

<210> SEQ ID NO 309
<211> LENGTH: 321
<212> TYPE: DNA
<213> ORGANISM: Homo sapiens

<400> SEQUENCE: 309
accaaatggc ggatgacgcc ggtgcagcgg gggggcccgg gggccctggt ggccctggga 60
tggggaaccg cggtggcttc cgcggaggtt tcggcagtgg catccggggc cggggtcgcg 120
gccgtggacg gggccggggc cgaggccgcg gagctcgcgg aggcaaggcc gaggataagg 180
agtggatgcc cgtcaccaag ttgggccgct tggtcaagga catgaagatc aagtccctgg 240
aggagatcta tctcttctcc ctgcccatta aggaatcaga gatcattgat ttcttcctgg 300
gggcctctct caaggatgag g 321

<210> SEQ ID NO 310
<211> LENGTH: 381
<212> TYPE: DNA
<213> ORGANISM: Homo sapiens

<400> SEQUENCE: 310
ttaaccagcc atattggctc aataaatagc ttcggtaagg agttaatttc cttctagaaa 60
tcagtgccta tttttcctgg aaactcaatt ttaaatagtc caattccatc tgaagccaag 120

-continued ctgttgtcat tttcattcgg tgacattctc tcccatgaca cccagaaggg gcagaagaac 180
cacatttttc atttatagat gtttgcatcc tttgtattaa aattattttg aaggggttgc 240
ctcattggat ggcttttttt tttttcctcc agggagaagg ggagaaatgt acttggaaat 300
taatgtatgt ttacatctct ttgcaaattc ctgtacatag agatatattt tttaagtgtg 360
aatgtaacaa catactgtga a 381

<210> SEQ ID NO 311
<211> LENGTH: 538
<212> TYPE: DNA
<213> ORGANISM: Homo sapiens

<400> SEQUENCE: 311
tttgaattta caccaagaac ttctcaataa aagaaaatca tgaatgctcc acaatttcaa 60
cataccacaa gagaagttaa tttcttaaca ttgtgttcta tgattatttg taagaccttc 120
accaagttct gatatctttt aaagacatag ttcaaaattg cttttgaaaa tctgtattct 180
tgaaaatatc cttgttgtgt attaggtttt taaataccag ctaaaggatt acctcactga 240
gtcatcagta ccctcctatt cagctcccca agatgatgtg tttttgctta ccctaagaga 300
ggttttcttc ttatttttag ataattcaag tgcttagata aattatgttt tctttaagtg 360
tttatggtaa actcttttaa agaaaattta atatgttata gctgaatctt tttggtaact 420
ttaaatcttt atcatagact ctgtacatat gttcaaatta gctgcttgcc tgatgtgtgt 480
atcatcggtg ggatgacaga acaaacatat ttatgatcat gaataatgtg ctttgtaa 538

<210> SEQ ID NO 312
<211> LENGTH: 176
<212> TYPE: DNA
<213> ORGANISM: Homo sapiens

<400> SEQUENCE: 312
ggaggagcag ctgagagata gggtcagtga atgcggttca gcctgctacc tctcctgtct 60
tcatagaacc attgccttag aattattgta tgacacgttt tttgttggtt aagctgtaag 120
gttttgttct ttgtgaacat gggtattttg aggggagggt ggagggagta gggaag 176

<210> SEQ ID NO 313
<211> LENGTH: 396
<212> TYPE: DNA
<213> ORGANISM: Homo sapiens

<400> SEQUENCE: 313
ccagcacccc caggccctgg gggacctggg ttctcagact gccaaagaag ccttgccatc 60
tggcgctccc atggctcttg caacatctcc ccttcgtttt tgaggggggtc atgccggggg 120 agccaccagc ccctcactgg gttcggagga gagtcaggaa gggccaagca cgacaaagca 180
gaaacatcgg atttggggaa cgcgtgtcaa tcccttgtgc cgcagggctg ggcgggagag 240
actgttctgt tccttgtgta actgtgttgc tgaaagacta cctcgttctt gtcttgatgt 300
gtcaccgggg caactgcctg gggggcgggga tgggggcagg gtggaagcgg ctccccattt 360
tataccaaag gtgctacatc tatgtgatgg gtgggg 396

<210> SEQ ID NO 314
<211> LENGTH: 311
<212> TYPE: DNA
<213> ORGANISM: Homo sapiens -continued

<400> SEQUENCE: 314
cctcaacatc ctcagagagg actggaagcc agtccttacg ataaactcca taatttatgg 60
cctgcagtat ctcttcttgg agcccaaccc cgaggaccca ctgaacaagg aggccgcaga 120
ggtcctgcag aacaaccggc ggctgtttga gcagaacgtg cagcgctcca tgcggggtgg 180
ctacatcggc tccacctact ttgagcgctg cctgaaatag ggttggcgca tacccacccc 240
cgccacggcc acaagccctg gcatcccctg caaatattta ttgggggcca tgggtagggg 300 tttgggggc g 311

<210> SEQ ID NO 315
<211> LENGTH: 336
<212> TYPE: DNA
<213> ORGANISM: Homo sapiens

<400> SEQUENCE: 315
tttagaacat ggttatcatc caagactact ctaccctgca acattgaact cccaagagca 60
aatccacatt cctcttgagt tctgcagctt ctgtgtaaat agggcagctg tcgtctatgc 120
cgtagaatca catgatctga ggaccattca tggaagctgc taaatagcct agtctgggga 180
gtcttccata aagttttgca tggagcaaac aaacaggatt aaactaggtt tggttccttc 240
agccctctaa aagcataggg cttagcctgc aggcttcctt gggctttctc tgtgtgtgta 300
gttttgtaaa cactatagca tctgttaaga tccagt 336

<210> SEQ ID NO 316
<211> LENGTH: 436
<212> TYPE: DNA
<213> ORGANISM: Homo sapiens

<400> SEQUENCE: 316
aacatggtct gcgtgcctta agagagacgc ttcctgcaga acaggacctg actacaaaga 60
atgtttccat tggaattgtt ggtaaagact tggagtttac aatctatgat gatgatgatg 120
tgtctccatt cctggaaggt cttgaagaaa gaccacagag aaaggcacag cctgctcaac 180
ctgctgatga acctgcagaa aaggctgatg aaccaatgga acattaagtg ataagccagt 240
ctatatatgt attatcaaat atgtaagaat acaggcacca catactgatg acaataatct 300
atactttgaa ccaaaagttg cagagtggtg gaatgctatg ttttaggaat cagtccagat 360
gtgagttttt tccaagcaac ctcactgaaa cctatataat ggaatacatt tttctttgaa 420
agggtctgta taatca 436

<210> SEQ ID NO 317
<211> LENGTH: 196
<212> TYPE: DNA
<213> ORGANISM: Homo sapiens

<400> SEQUENCE: 317
tattccttgt gaagatgata tactattttt gttaagcgtg tctgtattta tgtgtgagga 60
gctgctggct tgcagtgcgc gtgcacgtgg agagctggtg cccggagatt ggacggcctg 120
atgctccctc ccctgccctg gtccagggaa gctggccgag ggtcctggct cctgaggggc 180
atctgcccct ccccca 196

<210> SEQ ID NO 318
<211> LENGTH: 381
<212> TYPE: DNA
<213> ORGANISM: Homo sapiens -continued
<220> FEATURE:
<221> NAME/KEY: misc_feature
<222> LOCATION: 8, 9, 102, 122, 167, 182, 193, 235, 253, 265, 266, 290, 321, 378
<223> OTHER INFORMATION: n = A,T,C or G

<400> SEQUENCE: 318
gacgcttnng ccgtaacgat gatcggagac atcctgctgt tcgggacgtt gctgatgaat 60
gccggggcgg tgctgaactt taagctgaaa aagaaggaca cncagggctt tggggaggag 120
tncagggagc ccaacacagg tgacaacatc cgggaattct tgctgancct cagatacttt 180
cnaatcttca tcnccctgtg gaacatcttc atgatgttct gcatgattgt gctgntcggc 240
tcttgaatcc cancgatgaa accannaact cactttcccg ggatgccgan tctccattcc 300
tccattcctg atgacttcaa naatgttttt gaccaaaaaa ccgacaacct tcccagaaag 360
tccaagctcg tggtgggngg a 381

<210> SEQ ID NO 319
<211> LENGTH: 506
<212> TYPE: DNA
<213> ORGANISM: Homo sapiens

<400> SEQUENCE: 319
ctaagcttta cgaatggggt gacaacttat gataaaaact agagctagtg aattagccta 60
tttgtaaata cctttgttat aattgatagg atacatcttg gacatggaat tgttaagcca 120
cctctgagca gtgtatgtca ggacttgttc attaggttgg cagcagaggg gcagaaggaa 180
ttatacaggt agagatgtat gcagatgtgt ccatatatgt ccatatttac attttgatag 240
ccattgatgt atgcatctct tggctgtact ataagaacac attaattcaa tggaaataca 300
ctttgctaat attttaatgg tatagatctg ctaatgaatt ctcttaaaaa catactgtat 360
tctgttgctg tgtgtttcat tttaaattga gcattaaggg aatgcagcat ttaaatcaga 420
actctgccaa tgcttttatc tagaggcgtg ttgccatttt tgtcttatat gaaatttctg 480
tcccaagaaa ggcaggatta catctt 506

<210> SEQ ID NO 320
<211> LENGTH: 351
<212> TYPE: DNA
<213> ORGANISM: Homo sapiens

<400> SEQUENCE: 320
ctgacctgca ggacgaaacc atgaagagcc tgatccttct tgccatcctg gccgccttag 60
cggtagtaac tttgtgttat gaatcacatg aaagcatgga atcttatgaa cttaatccct 120
tcattaacag gagaaatgca aataccttca tatcccctca gcagagatgg agagctaaag 180
tccaagagag gatccgagaa cgctctaagc ctgtccacga gctcaatagg gaagcctgtg 240
atgactacag actttgcgaa cgctacgcca tggtttatgg atacaatgct gcctataatc 300
gctacttcag gaagcgccga gggaccaaat gagactgagg gaagaaaaaa a 351

<210> SEQ ID NO 321
<211> LENGTH: 421
<212> TYPE: DNA
<213> ORGANISM: Homo sapiens

<400> SEQUENCE: 321
ctcggaggcg ttcagctgct tcaagatgaa gctgaacatc tccttcccag ccactggctg 60
ccagaaactc attgaagtgg acgatgaacg caaacttcgt actttctatg agaagcgtat 120

-continued

```
ggccacagaa gttgctgctg acgctctggg tgaagaatgg aagggttatg tggtccgaat    180

cagtggtggg aacgacaaac aaggtttccc catgaagcag ggtgtcttga cccatggccg    240

tgtccgcctg ctactgagta aggggcattc ctgttacaga ccaaggagaa ctggagaaag    300

aaagagaaaa tcagttcgtg gttgcattgt ggatgcaaat ctgagcgttc tcaacttggt    360

tattgtaaaa aaaggagaga aggatattcc tggactgact gatactacag tgcctcgccg    420

c                                                                    421
```

<210> SEQ ID NO 322
<211> LENGTH: 521
<212> TYPE: DNA
<213> ORGANISM: Homo sapiens

<400> SEQUENCE: 322

```
agcagctctc ctgccacagc tcctcacccc ctgaaaatgt tcgcctgctc caagtttgtc     60

tccactccct ccttggtcaa gagcacctca cagctgctga gccgtccgct atctgcagtg    120

gtgctgaaac gaccggagat actgacagat gagagcctca gcagcttggc agtctcatgt    180

ccccttacct cacttgtctc tagccgcagc ttccaaacca gcgccatttc aagggacatc    240

gacacagcag ccaagttcat tggagctggg gctgccacag ttggggtggc tggttctggg    300

gctgggattg gaactgtgtt tgggagcctc atcattggtt atgccaggaa cccttctctg    360

aagcaacagc tcttctccta cgccattctg ggctttgccc tctcggaggc catggggctc    420

ttttgtctga tggtagcctt tctcatcctc tttgccatgt gaaggagccg tctccacctc    480

ccatagttct cccgcgtctg gttggccccg tgtgttcctt t                        521
```

<210> SEQ ID NO 323
<211> LENGTH: 435
<212> TYPE: DNA
<213> ORGANISM: Homo sapiens

<400> SEQUENCE: 323

```
ccgaggtcgc acgcgtgaga cttctccgcc gcagacgccg ccgcgatgcg ctacgtcgcc     60

tcctacctgc tggctgccct agggggcaac tcctccccca gcgccaagga catcaagaag    120

atcttggaca gcgtgggtat cgaggcggac gacgaccggc tcaacaaggt tatcagtgag    180

ctgaatggaa aaaacattga agacgtcatt gcccagggta ttggcaagct tgccagtgta    240

cctgctggtg gggctgtagc cgtctctgct gccccaggct ctgcagcccc tgctgctggt    300

tctgcccctg ctgcagcaga ggagaagaaa gatgagaaga aggaggagtc tgaagagtca    360

gatgatgaca tgggatttgg ccttttttgat taaattcctg ctcccctgca aataaagcct    420

ttttacacat ctcaa                                                     435
```

<210> SEQ ID NO 324
<211> LENGTH: 521
<212> TYPE: DNA
<213> ORGANISM: Homo sapiens

<400> SEQUENCE: 324

```
aggagatcga ctttcggtgc ccgcaagacc agggctggaa cgccgagatc acgctgcaga     60

tggtgcagta caagaatcgt caggccatcc tggcggtcaa atccacgcgg cagaagcagc    120

agcacctggt ccagcagcag ccccccctcgc agccgcagcc gcagccgcag ctccagcccc   180

aaccccagcc tcagcctcag ccgcaacccc agccccaatc acaaccccag cctcagcccc    240
```

-continued

```
aacccaagcc tcagccccag cagctccacc cgtatccgca tccacatcca catccacact    300

ctcatcctca ctcgcaccca caccctcacc cgcacccgca tccgcaccaa ataccgcacc    360

cacacccaca gccgcactcg cagccgcacg ggcaccggct tctccgcagc acctccaact    420

ctgcctgaaa ggggcagctc ccgggcaaga caaggttttg aggacttgag gaagtgggac    480

gagcacattt ctattgtctt cacttggatc aaaagcaaaa c                        521


<210> SEQ ID NO 325
<211> LENGTH: 451
<212> TYPE: DNA
<213> ORGANISM: Homo sapiens

<400> SEQUENCE: 325

attttcattt ccattaacct ggaagctttc atgaatattc tcttctttta aaacatttta     60

acattattta aacagaaaaa gatgggctct ttctggttag ttgttacatg atagcagaga    120

tatttttact tagattactt tgggaatgag agattgttgt cttgaactct ggcactgtac    180

agtgaatgtg tctgtagttg tgttagtttg cattaagcat gtataacatt caagtatgtc    240

atccaaataa gaggcatata cattgaattg tttttaatcc tctgacaagt tgactcttcg    300

acccccaccc ccacccaaga cattttaata gtaaatagag agagagagaa gagttaatga    360

acatgaggta gtgttccact ggcaggatga cttttcaata gctcaaatca atttcagtgc    420

ctttatcact tgaattatta acttaatttg a                                   451


<210> SEQ ID NO 326
<211> LENGTH: 421
<212> TYPE: DNA
<213> ORGANISM: Homo sapiens
<220> FEATURE:
<221> NAME/KEY: misc_feature
<222> LOCATION: 296
<223> OTHER INFORMATION: n = A,T,C or G

<400> SEQUENCE: 326

cgcggtcgta agggctgagg atttttggtc cgcacgctcc tgctcctgac tcaccgctgt     60

tcgctctcgc cgaggaacaa gtcggtcagg aagcccgcgc gcaacagcca tggcttttaa    120

ggataccgga aaaacacccg tggagccgga ggtggcaatt caccgaattc gaatcaccct    180

aacaagccgc aacgtaaaat ccttggaaaa ggtgtgtgct gacttgataa gaggcgcaaa    240

agaaaagaat ctcaaagtga aaggaccagt tcgaatgcct accaagactt tgagantcac    300

tacaagaaaa actccttgtg gtgaaggttc taagacgtgg gatcgtttcc agatgagaat    360

tcacaagcga ctcattgact tgcacagtcc ttctgagatt gttaagcaga ttacttccat    420

c                                                                    421


<210> SEQ ID NO 327
<211> LENGTH: 456
<212> TYPE: DNA
<213> ORGANISM: Homo sapiens

<400> SEQUENCE: 327

atcttgacga ggctgcggtg tctgctgcta ttctccgagc ttcgcaatgc cgcctaagga     60

cgacaagaag aagaaggacg ctggaaagtc ggccaagaaa gacaaagacc cagtgaacaa    120

atccgggggc aaggccaaaa agaagaagtg gtccaaaggc aaagttcggg acaagctcaa    180

taacttagtc ttgtttgaca aagctaccta tgataaactc tgtaaggaag ttcccaacta    240

taaacttata accccagctg tggtctctga gagactgaag attcgaggct ccctggccag    300
```

-continued

```
ggcagccctt caggagctcc ttagtaaagg acttatcaaa ctggtttcaa agcacagagc    360

tcaagtaatt tacaccagaa ataccaaggg tggagatgct ccagctgctg gtgaagatgc    420

atgaataggt ccaaccagct gtacatttgg aaaaat                              456


<210> SEQ ID NO 328
<211> LENGTH: 471
<212> TYPE: DNA
<213> ORGANISM: Homo sapiens

<400> SEQUENCE: 328

gtggaagtga catcgtcttt aaaccctgcg tggcaatccc tgacgcaccg ccgtgatgcc     60

cagggaagac agggcgacct ggaagtccaa ctacttcctt aagatcatcc aactattgga    120

tgattatccg aaatgtttca ttgtgggagc agacaatgtg ggctccaagc agatgcagca    180

gatccgcatg tcccttcgcg ggaaggctgt ggtgctgatg ggcaagaaca ccatgatgcg    240

caaggccatc cgagggcacc tggaaaacaa cccagctctg gagaaactgc tgcctcatat    300

ccgggggaat gtgggctttg tgttcaccaa ggaggacctc actgagatca gggacatgtt    360

gctggccaat aaggtgccag ctgctgcccg tgctggtgcc attgccccat gtgaagtcac    420

tgtgccagcc cagaacactg gtctcgggcc cgagaagacc tcctttttcc a             471


<210> SEQ ID NO 329
<211> LENGTH: 278
<212> TYPE: DNA
<213> ORGANISM: Homo sapiens
<220> FEATURE:
<221> NAME/KEY: misc_feature
<222> LOCATION: 154, 204
<223> OTHER INFORMATION: n = A,T,C or G

<400> SEQUENCE: 329

gtttaaactt aagcttggta ccgagctcgg atccactagt ccagtgtggt ggaattctag     60

aaattgagat gcccccccag gccagcaaat gttccttttt gttcaaagtc tatttttatt    120

ccttgatatt tttcttttt tttttttttt ttgnggatgg ggacttgtga atttttctaa    180

aggtgctatt taacatggga gganagcgtg tgcggctcca gcccagcccg ctgctcactt    240

tccaccctct ctccacctgc ctctggcttc tcaggcct                            278


<210> SEQ ID NO 330
<211> LENGTH: 338
<212> TYPE: DNA
<213> ORGANISM: Homo sapiens

<400> SEQUENCE: 330

ctcaggcttc aacatcgaat acgccgcagg ccccttcgcc ctattcttca tagccgaata     60

cacaaacatt attataataa acaccctcac cactacaatc ttcctaggaa caacatatga    120

cgcactctcc cctgaactct acacaacata ttttgtcacc aagaccctac ttctaacctc    180

cctgttctta tgaattcgaa cagcataccc ccgattccgc tacgaccaac tcatacacct    240

cctatgaaaa aacttcctac cactcaccct agcattactt atatgatatg tctccatacc    300

cattacaatc tccagcattc cccctcaaac ctaaaaaa                            338


<210> SEQ ID NO 331
<211> LENGTH: 2820
<212> TYPE: DNA
<213> ORGANISM: Homo sapiens
```

-continued

<400> SEQUENCE: 331
tggcaaaatc ctggagccag aagaaaggac agcagcattg atcaatctta cagctaacat 60
gttgtacctg gaaaacaatg cccagactca atttagtgag ccacagtaca cgaacctggg 120
gctcctgaac agcatggacc agcagattcg gaacggctcc tcgtccacca gtccctataa 180
cacagaccac gcgcagaaca gcgtcacggc gccctcgccc tacgcacagc ccagccccac 240
cttcgatgct ctctctccat cacccgccat cccctccaac accgactacc caggcccgca 300
cagttccgac gtgtccttcc agcagtcgag caccgccaag tcggccacct ggacgtattc 360
cactgaactg aagaaactct actgccaaat tgcaaagaca tgccccatcc agatcaaggt 420
gatgacccca cctcctcagg gagctgttat ccgcgccatg cctgtctaca aaaaagctga 480
gcacgtcacg gaggtggtga agcggtgccc caaccatgag ctgagccgtg agttcaacga 540
gggacagatt gcccctccta gtcatttgat tcgagtagag gggaacagcc atgcccagta 600
tgtagaagat cccatcacag gaagacagag tgtgctggta ccttatgagc caccccaggt 660
tggcactgaa ttcacgacag tcttgtacaa tttcatgtgt aacagcagtt gtgttggagg 720
gatgaaccgc cgtccaattt taatcattgt tactctggaa accagagatg ggcaagtcct 780
gggccgacgc tgctttgagg cccggatctg tgcttgccca ggaagagaca ggaaggcgga 840
tgaagatagc atcagaaagc agcaagtttc ggacagtaca aagaacggtg atggtacgaa 900
gcgcccgttt cgtcagaaca cacatggtat ccagatgaca tccatcaaga aacgaagatc 960
cccagatgat gaactgttat acttaccagt gaggggccgt gagacttatg aaatgctgtt 1020
gaagatcaaa gagtccctgg aactcatgca gtaccttcct cagcacacaa ttgaaacgta 1080
caggcaacag caacagcagc agcaccagca cttacttcag aaacagacct caatacagtc 1140
tccatcttca tatggtaaca gctccccacc tctgaacaaa atgaacagca tgaacaagct 1200
gccttctgtg agccagctta tcaaccctca gcagcgcaac gccctcactc ctacaaccat 1260
tcctgatggc atgggagcca acattcccat gatgggcacc cacatgccaa tggctggaga 1320
catgaatgga ctcagcccca cccaggcact ccctcccccca ctctccatgc catccacctc 1380
ccactgcaca cccccacctc cgtatcccac agattgcagc attgtcagtt tcttagcgag 1440
gttgggctgt tcatcatgtc tggactattt cacgacccag ggctgacca ccatctatca 1500 gattgagcat tactccatgg atgatctggc aagtctgaaa atccctgagc aatttcgaca 1560
tgcgatctgg aagggcatcc tggaccaccg gcagctccac gaattctcct cccttctca 1620 tctcctgcgg accccaagca gtgcctctac agtcagtgtg ggctccagtg agacccgggg 1680
tgagcgtgtt attgatgctg tgcgattcac cctccgccag accatctctt tcccaccccg 1740
agatgagtgg aatgacttca actttgacat ggatgctcgc cgcaataagc aacagcgcat 1800
caaagaggag gggagtgag cctcaccatg tgagctcttc ctatccctct cctaactgcc 1860 agcccccctaa aagcactcct gcttaatctt caaagccttc tccctagctc ctccccttcc 1920
tcttgtctga tttcttaggg gaaggagaag taagaggcta cctcttacct aacatctgac 1980
ctggcatcta attctgattc tggctttaag ccttcaaaac tatagcttgc agaactgtag 2040
ctgccatggc taggtagaag tgagcaaaaa agagttgggt gtctccttaa gctgcagaga 2100
tttctcattg acttttataa agcatgttca cccttatagt ctaagactat atatataaat 2160
gtataaatat acagtataga tttttgggtg gggggcattg agtattgttt aaaatgtaat 2220
ttaaatgaaa gaaaattgag ttgcacttat tgaccatttt ttaatttact tgttttggat 2280
ggcttgtcta tactccttcc cttaaggggt atcatgtatg gtgataggta tctagagctt 2340

-continued

```
aatgctacat gtgagtgcga tgatgtacag attctttcag ttctttggat tctaaataca   2400
tgccacatca aacctttgag tagatccatt tccattgctt attatgtagg taagactgta   2460
gatatgtatt cttttctcag tgttggtata ttttatatta ctgacatttc ttctagtgat   2520
gatggttcac gttggggtga tttaatccag ttataagaag aagttcatgt ccaaacggtc   2580
ctctttagtt tttggttggg aatgaggaaa attcttaaaa ggcccatagc agccagttca   2640
aaaacacccg acgtcatgta tttgagcata tcagtaaccc ccttaaattt aatacccaga   2700
taccttatct tacaatgttg attgggaaaa catttgctgc ccattacaga ggtattaaaa   2760
ctaaatttca ctactagatt gactaactca aatacacatt tgctactgtt gtaagaattc   2820
```

<210> SEQ ID NO 332
<211> LENGTH: 2270
<212> TYPE: DNA
<213> ORGANISM: Homo sapiens

<400> SEQUENCE: 332

```
tcgttgatat caaagacagt tgaaggaaat gaattttgaa acttcacggt gtgccaccct     60
acagtactgc cctgaccctt acatccagcg tttcgtagaa acccagctca tttctcttgg    120
aaagaaagtt attaccgatc caccatgtcc cagagcacac agacaaatga attcctcagt    180
ccagaggttt tccagcatat ctgggatttt ctggaacagc ctatatgttc agttcagccc    240
attgacttga actttgtgga tgaaccatca gaagatggtg cgacaaacaa gattgagatt    300
agcatggact gtatccgcat gcaggactcg gacctgagtg accccatgtg gccacagtac    360
acgaacctgg ggctcctgaa cagcatggac cagcagattc agaacggctc ctcgtccacc    420
agtccctata acacagacca cgcgcagaac agcgtcacgg cgccctcgcc ctacgcacag    480
cccagctcca ccttcgatgc tctctctcca tcacccgcca tcccctccaa caccgactac    540
ccaggcccgc acagtttcga cgtgtccttc cagcagtcga gcaccgccaa gtcggccacc    600
tggacgtatt ccactgaact gaagaaactc tactgccaaa ttgcaaagac atgccccatc    660
cagatcaagg tgatgacccc acctcctcag ggagctgtta tccgcgccat gcctgtctac    720
aaaaaagctg agcacgtcac ggaggtggtg aagcggtgcc ccaaccatga gctgagccgt    780
gaattcaacg agggacagat tgcccctcct agtcatttga ttcgagtaga ggggaacagc    840
catgcccagt atgtagaaga tcccatcaca ggaagacaga gtgtgctggt accttatgag    900
ccaccccagg ttggcactga attcacgaca gtcttgtaca atttcatgtg taacagcagt    960
tgtgttggag ggatgaaccg ccgtccaatt ttaatcattg ttactctgga aaccagagat   1020
gggcaagtcc tgggccgacg ctgctttgag gcccggatct gtgcttgccc aggaagagac   1080
aggaaggcgg atgaagatag catcagaaag cagcaagttt cggacagtac aaagaacggt   1140
gatggtacga agcgcccgtt tcgtcagaac acacatggta tccagatgac atccatcaag   1200
aaacgaagat ccccagatga tgaactgtta tacttaccag tgaggggccg tgagacttat   1260
gaaatgctgt tgaagatcaa agagtccctg gaactcatgc agtaccttcc tcagcacaca   1320
attgaaacgt acaggcaaca gcaacagcag cagcaccagc acttacttca gaaacagacc   1380
tcaatacagt ctccatcttc atatggtaac agctccccac ctctgaacaa aatgaacagc   1440
atgaacaagc tgccttctgt gagccagctt atcaaccctc agcagcgcaa cgccctcact   1500
cctacaacca ttcctgatgg catgggagcc aacattccca tgatgggcac ccacatgcca   1560
atggctggag acatgaatgg actcagcccc acccaggcac tccctccccc actctccatg   1620
```

-continued

```
ccatccacct cccactgcac acccccacct ccgtatccaa cagattgcag cattgtcggt   1680

ttcttagcga ggttgggctg ttcatcatgt ctggactatt tcacgaccca ggggctgacc   1740

accatctatc agattgagca ttactccatg gatgatctgg caagtctgaa aatccctgag   1800

caatttcgac atgcgatctg gaagggcatc ctggaccacc ggcagctcca cgaattctcc   1860

tccccttctc atctcctgcg gaccccaagc agtgcctcta cagtcagtgt gggctccagt   1920

gagacccggg gtgagcgtgt tattgatgct gtgcgattca ccctccgcca gaccatctct   1980

ttcccacccc gagatgagtg gaatgacttc aactttgaca tggatgctcg ccgcaataag   2040

caacagcgca tcaaagagga gggggagtga gcctcaccat gtgagctctt cctatccctc   2100

tcctaactgc cagcccccta aaagcactcc tgcttaatct tcaaagcctt ctccctagct   2160

cctccccttc ctcttgtctg atttcttagg ggaaggagaa gtaagaggct acctcttacc   2220

taacatctga cctggcatct aattctgatt ctggctttaa gccttcaaaa              2270
```

<210> SEQ ID NO 333
<211> LENGTH: 2816
<212> TYPE: DNA
<213> ORGANISM: Homo sapiens

<400> SEQUENCE: 333

```
tcgttgatat caaagacagt tgaaggaaat gaattttgaa acttcacggt gtgccaccct     60

acagtactgc cctgaccctt acatccagcg tttcgtagaa acccagctca tttctcttgg    120

aaagaaagtt attaccgatc caccatgtcc cagagcacac agacaaatga attcctcagt    180

ccagaggttt tccagcatat ctgggatttt ctggaacagc ctatatgttc agttcagccc    240

attgacttga actttgtgga tgaaccatca gaagatggtg cgacaaacaa gattgagatt    300

agcatggact gtatccgcat gcaggactcg gacctgagtg accccatgtg gccacagtac    360

acgaacctgg ggctcctgaa cagcatggac cagcagattc agaacggctc ctcgtccacc    420

agtccctata acacagacca cgcgcagaac agcgtcacgg cgccctcgcc ctacgcacag    480

cccagctcca ccttcgatgc tctctctcca tcacccgcca tcccctccaa caccgactac    540

ccaggcccgc acagtttcga cgtgtccttc cagcagtcga gcaccgccaa gtcggccacc    600

tggacgtatt ccactgaact gaagaaactc tactgccaaa ttgcaaagac atgccccatc    660

cagatcaagg tgatgacccc acctcctcag ggagctgtta tccgcgccat gcctgtctac    720

aaaaaagctg agcacgtcac ggaggtggtg aagcggtgcc ccaaccatga gctgagccgt    780

gaattcaacg agggacagat tgcccctcct agtcatttga ttcgagtaga ggggaacagc    840

catgcccagt atgtagaaga tcccatcaca ggaagacaga gtgtgctggt accttatgag    900

ccaccccagg ttggcactga attcacgaca gtcttgtaca atttcatgtg taacagcagt    960

tgtgttggag ggatgaaccg ccgtccaatt ttaatcattg ttactctgga aaccagagat   1020

gggcaagtcc tgggccgacg ctgctttgag gcccggatct gtgcttgccc aggaagagac   1080

aggaaggcgg atgaagatag catcagaaag cagcaagttt cggacagtac aaagaacggt   1140

gatggtacga agcgcccgtt tcgtcagaac acacatggta tccagatgac atccatcaag   1200

aaacgaagat ccccagatga tgaactgtta tacttaccag tgaggggccg tgagacttat   1260

gaaatgctgt tgaagatcaa agagtccctg gaactcatgc agtaccttcc tcagcacaca   1320

attgaaacgt acaggcaaca gcaacagcag cagcaccagc acttacttca gaaacatctc   1380

ctttcagcct gcttcaggaa tgagcttgtg gagccccgga gagaaactcc aaaacaatct   1440

gacgtcttct ttagacattc caagccccca aaccgatcag tgtacccata gagccctatc   1500
```

-continued tctatatttt aagtgtgtgt gttgtatttc catgtgtata tgtgagtgtg tgtgtgtgta 1560
tgtgtgtgcg tgtgtatcta gccctcataa acaggacttg aagacacttt ggctcagaga 1620
cccaactgct caaaggcaca aagccactag tgagagaatc ttttgaaggg actcaaacct 1680
ttacaagaaa ggatgttttc tgcagatttt gtatccttag accggccatt ggtgggtgag 1740
gaaccactgt gtttgtctgt gagctttctg ttgtttcctg ggagggaggg gtcaggtggg 1800
gaaaggggca ttaagatgtt tattggaacc cttttctgtc ttcttctgtt gtttttctaa 1860
aattcacagg gaagcttttg agcaggtctc aaacttaaga tgtcttttta agaaaaggag 1920
aaaaaagttg ttattgtctg tgcataagta agttgtaggt gactgagaga ctcagtcaga 1980 ccctttttaat gctggtcatg taataatatt gcaagtagta agaaacgaag gtgtcaagtg 2040
tactgctggg cagcgaggtg atcattacca aaagtaatca actttgtggg tggagagttc 2100
tttgtgagaa cttgcattat ttgtgtcctc ccctcatgtg taggtagaac atttcttaat 2160
gctgtgtacc tgcctctgcc actgtatgtt ggcatctgtt atgctaaagt ttttcttgta 2220
catgaaaccc tggaagacct actacaaaaa aactgttgtt tggcccccat agcaggtgaa 2280
ctcattttgt gcttttaata gaaagacaaa tccaccccag taatattgcc cttacgtagt 2340
tgtttaccat tattcaaagc tcaaaataga atttgaagcc ctctcacaaa atctgtgatt 2400
aatttgctta attagagctt ctatccctca agcctaccta ccataaaacc agccatatta 2460
ctgatactgt tcagtgcatt tagccaggag acttacgttt tgagtaagtg agatccaagc 2520
agacgtgtta aaatcagcac tcctggactg gaaattaaag attgaaaggg tagactactt 2580
ttcttttttt tactcaaaag tttagagaat ctctgtttct ttccatttta aaaacatatt 2640
ttaagataat agcataaaga ctttaaaaat gttcctcccc tccatcttcc cacacccagt 2700
caccagcact gtattttctg tcaccaagac aatgatttct tgttattgag gctgttgctt 2760
ttgtggatgt gtgattttaa ttttcaataa acttttgcat cttggtttaa aagaaa 2816

<210> SEQ ID NO 334
<211> LENGTH: 2082
<212> TYPE: DNA
<213> ORGANISM: Homo sapiens

<400> SEQUENCE: 334
agatgctaca gcgactgcac acccaggctg tatgatacag cctattgctc ccgggctgca 60
aacctgtcca gcatgtgatg tggtgggata ctgaattgaa taccgaatac tgtaggcaat 120
tgtaacacag tggtaagtct ttgtgtatct aaacatagct aaacaccaaa aggtatagta 180
agaatatggt attataatct tatggaacta tcattgtata tgtggtttgt caaccagaat 240
gtagttatac agcacaggac tgtgcttatg atgtgccaag cacagctctc agtactaact 300
cctttaatct tcatatcaac cctaggaggt aacttcttaa gtagattcat attgtaaggg 360
tctcggggtg gggggttgg caaaatcctg gagccagaag aaaggacagc agcattgatc 420
aatcttacag ctaacatgtt gtacctggaa aacaatgccc agactcaatt tagtgagcca 480
cagtacacga acctggggct cctgaacagc atggaccagc agattcagaa cggctcctcg 540
tccaccagtc cctataacac agaccacgcg cagaacagcg tcacggcgcc ctcgccctac 600
gcacagccca gctccacctt cgatgctctc tctccatcac ccgccatccc ctccaacacc 660
gactacccag gcccgcacag tttcgacgtg tccttccagc agtcgagcac cgccaagtcg 720
gccacctgga cgtattccac tgaactgaag aaactctact gccaaattgc aaagacatgc 780

-continued

```
cccatccaga tcaaggtgat gaccccacct cctcagggag ctgttatccg cgccatgcct     840

gtctacaaaa aagctgagca cgtcacggag gtggtgaagc ggtgccccaa ccatgagctg     900

agccgtgaat tcaacgaggg acagattgcc cctcctagtc atttgattcg agtagagggg     960

aacagccatg cccagtatgt agaagatccc atcacaggaa gacagagtgt gctggtacct    1020

tatgagccac cccaggttgg cactgaattc acgacagtct tgtacaattt catgtgtaac    1080

agcagttgtg ttggagggat gaaccgccgt ccaattttaa tcattgttac tctggaaacc    1140

agagatgggc aagtcctggg ccgacgctgc tttgaggccc ggatctgtgc ttgcccagga    1200

agagacagga aggcggatga agatagcatc agaaagcagc aagtttcgga cagtacaaag    1260

aacggtgatg gtacgaagcg cccgtctcgt cagaacacac atggtatcca gatgacatcc    1320

atcaagaaac gaagatcccc agatgatgaa ctgttatact taccagtgag ggccgtgag     1380

acttatgaaa tgctgttgaa gatcaaagag tccctggaac tcatgcagta ccttcctcag    1440

cacacaattg aaacgtacag gcaacagcaa cagcagcagc accagcactt acttcagaaa    1500

cagtgagtgt atcaacgtgt cattttagga ggcatgagtg acggtgactt tatttggatc    1560

agcaataggg tgattgatga gcaatgtgga acataatggg agatagcaga ttgtcataga    1620

ttcagatgac ctggtatggc aaccctcttt cagttgcaac ctttttttacg tgtcttatta   1680

taaccttccc ttcagaattc cacttatgtt ctgaaattaa atacaaacca tttctggtga    1740

attacaaaga aactcacact aacagttctc ttctctatat gcctggtcca tacacactaa    1800

cagtaagtac acactctatt tggtagtgat gtgtatattt gaaaacatga aatcttttct    1860

catcccaatg gattgtctta taaatctcct gggatgcaca ctatccactt ttgggaataa    1920

cactgtagac cagggatagc aaataggctt tactataata taaagtgact tgtttgaatg    1980

ctgtaatgag aagaattctg agacctagtg catgataatt ggggaaatat ctgggtgcag    2040

aaggataagg tagcatcatg ttgccgtatt ttagcatctc tg                       2082
```

<210> SEQ ID NO 335
<211> LENGTH: 4849
<212> TYPE: DNA
<213> ORGANISM: Homo sapiens

<400> SEQUENCE: 335

```
cgttgatatc aaagacagtt gaaggaaatg aattttgaaa cttcacggtg tgccacccta      60

cagtactgcc ctgaccctta catccagcgt ttcgtagaaa ccccagctca tttctcttgg     120

aaagaaagtt attaccgatc caccatgtcc cagagcacac agacaaatga attcctcagt     180

ccagaggttt tccagcatat ctgggatttt ctggaacagc ctatatgttc agttcagccc     240

attgacttga actttgtgga tgaaccatca gaagatggtg cgacaaacaa gattgagatt     300

agcatggact gtatccgcat gcaggactcg gacctgagtg accccatgtg gccacagtac     360

acgaacctgg ggctcctgaa cagcatggac cagcagattc agaacggctc ctcgtccacc     420

agtccctata acacagacca cgcgcagaac agcgtcacgg cgccctcgcc ctacgcacag     480

cccagctcca ccttcgatgc tctctctcca tcacccgcca tcccctccaa caccgactac     540

ccaggcccgc acagtttcga cgtgtccttc cagcagtcga gcaccgccaa gtcggccacc     600

tggacgtatt ccactgaact gaagaaactc tactgccaaa ttgcaaagac atgccccatc     660

cagatcaagg tgatgacccc acctcctcag ggagctgtta tccgcgccat gcctgtctac     720

aaaaaagctg agcacgtcac ggaggtggtg aagcggtgcc ccaaccatga gctgagccgt     780

gaattcaacg agggacagat tgcccctcct agtcatttga ttcgagtaga ggggaacagc     840
```

-continued

```
catgcccagt atgtagaaga tcccatcaca ggaagacaga gtgtgctggt accttatgag    900
ccaccccagg ttggcactga attcacgaca gtcttgtaca atttcatgtg taacagcagt    960
tgtgttggag ggatgaaccg ccgtccaatt ttaatcattg ttactctgga aaccagagat   1020
gggcaagtcc tgggccgacg ctgctttgag gcccggatct gtgcttgccc aggaagagac   1080
aggaaggcgg atgaagatag catcagaaag cagcaagttt cggacagtac aaagaacggt   1140
gatggtacga agcgcccgtt tcgtcagaac acacatggta tccagatgac atccatcaag   1200
aaacgaagat ccccagatga tgaactgtta tacttaccag tgaggggccg tgagacttat   1260
gaaatgctgt tgaagatcaa agagtccctg gaactcatgc agtaccttcc tcagcacaca   1320
attgaaacgt acaggcaaca gcaacagcag cagcaccagc acttacttca gaaacagacc   1380
tcaatacagt ctccatcttc atatggtaac agctccccac ctctgaacaa aatgaacagc   1440
atgaacaagc tgccttctgt gagccagctt atcaaccctc agcagcgcaa cgccctcact   1500
cctacaacca ttcctgatgg catgggagcc aacattccca tgatgggcac ccacatgcca   1560
atggctggag acatgaatgg actcagcccc acccaggcac tccctccccc actctccatg   1620
ccatccacct cccagtgcac acccccacct ccgtatccca cagattgcag cattgtcagt   1680
ttcttagcga ggttgggctg ttcatcatgt ctggactatt tcacgaccca ggggctgacc   1740
accatctatc agattgagca ttactccatg gatgatctgg caagtctgaa aatccctgag   1800
caatttcgac atgcgatctg gaagggcatc ctggaccacc ggcagctcca cgaattctcc   1860
tccccttctc atctcctgcg gaccccaagc agtgcctcta cagtcagtgt gggctccagt   1920
gagacccggg gtgagcgtgt tattgatgct gtgcgattca ccctccgcca gaccatctct   1980
ttcccacccc gagatgagtg gaatgacttc aactttgaca tggatgctcg ccgcaataag   2040
caacagcgca tcaaagagga gggggagtga gcctcaccat gtgagctctt cctatccctc   2100
tcctaactgc cagcycccta aaagcactcc tgcttaatct tcaaagcctt ctccctagct   2160
cctccccttc ctcttgtctg atttcttagg ggaaggagaa gtaagaggct acctcttacc   2220
taacatctga cctggcatct aattctgatt ctggctttaa gccttcaaaa ctatagcttg   2280
cagaactgta gctgccatgg ctaggtagaa gtgagcaaaa aagagttggg tgtctcctta   2340
agctgcagag atttctcatt gacttttata aagcatgttc acccttatag tctaagacta   2400
tatatataaa tgtataaata tacagtatag atttttgggt gggggcatt gagtattgtt    2460
taaaatgtaa tttaaatgaa agaaaattga gttgcactta ttgaccattt tttaatttac   2520
ttgttttgga tggcttgtct atactccttc ccttaagggg tatcatgtat ggtgataggt   2580
atctagagct taatgctaca tgtgagtgac gatgatgtac agattctttc agttctttgg   2640
attctaaata catgccacat caaacctttg agtagatcca tttccattgc ttattatgta   2700
ggtaagactg tagatatgta ttcttttctc agtgttggta tattttatat tactgacatt   2760
tcttctagtg atgatggttc acgttggggt gatttaatcc agttataaga agaagttcat   2820
gtccaaacgt cctctttagt ttttggttgg gaatgaggaa aattcttaaa aggcccatag   2880
cagccagttc aaaaacaccc gacgtcatgt atttgagcat atcagtaacc cccttaaatt   2940
taataccaga taccttatct tacaatattg attgggaaaa catttgctgc cattacagag   3000
gtattaaaac taaatttcac tactagattg actaactcaa atacacattt gctactgttg   3060
taagaattct gattgatttg attgggatga atgccatcta tctagttcta acagtgaagt   3120
tttactgtct attaatattc agggtaaata ggaatcattc agaaatgttg agtctgtact   3180
```

-continued

```
aaacagtaag atatctcaat gaaccataaa ttcaactttg taaaaatctt ttgaagcata   3240

gataatattg tttggtaaat gtttcttttg tttggtaaat gtttctttta aagaccctcc   3300

tattctataa aactctgcat gtagaggctt gtttaccttt ctctctctaa ggtttacaat   3360

aggagtggtg atttgaaaaa tataaaatta tgagattggt tttcctgtgg cataaattgc   3420

atcactgtat catttttcttt tttaaccggt aagagtttca gtttgttgga aagtaactgt   3480

gagaacccag tttcccgtcc atctccctta gggactaccc atagacatga aaggtcccca   3540

cagagcaaga gataagtctt tcatggctgc tgttgcttaa accacttaaa cgaagagttc   3600

ccttgaaact ttgggaaaac atgttaatga caatattcca gatctttcag aaatataaca   3660

cattttttg catgcatgca aatgagctct gaaatcttcc catgcattct ggtcaagggc   3720

tgtcattgca cataagcttc cattttaatt tttaaagtgca aaagggccag cgtggctcta   3780

aaaggtaatg tgtggattgc ctctgaaaag tgtgtatata ttttgtgtga aattgcatac   3840

tttgtatttt gattattttt tttttcttct tgggatagtg ggatttccag aaccacactt   3900

gaaacctttt tttatcgttt ttgtattttc atgaaaatac catttagtaa gaataccaca   3960

tcaaataaga aataatgcta caattttaag aggggaggga agggaaagtt ttttttattt   4020

attttttttaa aattttgtat gttaaagaga atgagtcctt gatttcaaag ttttgttgta   4080

cttaaatggt aataagcact gtaaacttct gcaacaagca tgcagctttg caaacccatt   4140

aaggggaaga atgaaagctg ttccttggtc ctagtaagaa gacaaactgc ttcccttact   4200

ttgctgaggg tttgaataaa cctaggactt ccgagctatg tcagtactat tcaggtaaca   4260

ctagggcctt ggaaattcct gtactgtgtc tcatggattt ggcactagcc aaagcgaggc   4320

acccttactg gcttacctcc tcatggcagc ctactctcct tgagtgtatg agtagccagg   4380

gtaaggggta aaaggatagt aagcatagaa accactagaa agtgggctta atggagttct   4440

tgtggcctca gctcaatgca gttagctgaa gaattgaaaa gtttttgttt ggagacgttt   4500

ataaacagaa atggaaagca gagttttcat taaatccttt taccttttttt ttttcttggt   4560

aatcccctaa aataacagta tgtgggatat tgaatgttaa agggatattt tttttctatt   4620

atttttataa ttgtacaaaa ttaagcaaat gttaaaagtt ttatatgctt tattaatgtt   4680

ttcaaaaggt attatacatg tgatacattt tttaagcttc agttgcttgt cttctggtac   4740

tttctgttat gggcttttgg ggagccagaa gccaatctac aatctctttt tgtttgccag   4800

gacatgcaat aaaatttaaa aaataaataa aaactaatta agaaataaa               4849
```

<210> SEQ ID NO 336
<211> LENGTH: 1386
<212> TYPE: DNA
<213> ORGANISM: Homo sapiens

<400> SEQUENCE: 336

```
atgttgtacc tggaaaacaa tgcccagact caatttagtg agccacagta cacgaacctg     60

gggctcctga acagcatgga ccagcagatt cagaacggct cctcgtccac cagtccctat    120

aacacagacc acgcgcagaa cagcgtcacg gcgccctcgc cctacgcaca gcccagctcc    180

accttcgatg ctctctctcc atcacccgcc atcccctcca acaccgacta cccaggcccg    240

cacagtttcg acgtgtcctt ccagcagtcg agcaccgcca agtcggccac ctggacgtat    300

tccactgaac tgaagaaact ctactgccaa attgcaaaga catgccccat ccagatcaag    360

gtgatgaccc cacctcctca gggagctgtt atccgcgcca tgcctgtcta caaaaaagct    420

gagcacgtca cggaggtggt gaagcggtgc ccaaccatg agctgagccg tgaattcaac      480
```

-continued gagggacaga ttgcccctcc tagtcatttg attcgagtag aggggaacag ccatgcccag 540
tatgtagaag atcccatcac aggaagacag agtgtgctgg taccttatga gccaccccag 600
gttggcactg aattcacgac agtcttgtac aatttcatgt gtaacagcag ttgtgttgga 660
gggatgaacc gccgtccaat tttaatcatt gttactctgg aaaccagaga tgggcaagtc 720
ctgggccgac gctgctttga ggcccggatc tgtgcttgcc caggaagaga caggaaggcg 780
gatgaagata gcatcagaaa gcagcaagtt tcggacagta caaagaacgg tgatggtacg 840
aagcgcccgt ttcgtcagaa cacacatggt atccagatga catccatcaa gaaacgaaga 900
tccccagatg atgaactgtt atacttacca gtgaggggcc gtgagactta tgaaatgctg 960
ttgaagatca aagagtccct ggaactcatg cagtaccttc ctcagcacac aattgaaacg 1020
tacaggcaac agcaacagca gcagcaccag cacttacttc agaaacagac ctcaatacag 1080
tctccatctt catatggtaa cagctcccca cctctgaaca aaatgaacag catgaacaag 1140
ctgccttctg tgagccagct tatcaaccct cagcagcgca acgccctcac tcctacaacc 1200
attcctgatg gcatgggagc caacattccc atgatgggca cccacatgcc aatggctgga 1260
gacatgaatg gactcagccc cacccaggca ctccctcccc cactctccat gccatccacc 1320
tcccactgca cacccccacc tccgtatccc acagattgca gcattgtcag gatctggcaa 1380
gtctga 1386

<210> SEQ ID NO 337
<211> LENGTH: 1551
<212> TYPE: DNA
<213> ORGANISM: Homo sapiens

<400> SEQUENCE: 337
atgtcccaga gcacacagac aaatgaattc ctcagtccag aggttttcca gcatatctgg 60
gattttctgg aacagcctat atgttcagtt cagcccattg acttgaactt tgtggatgaa 120
ccatcagaag atggtgcgac aaacaagatt gagattagca tggactgtat ccgcatgcag 180
gactcggacc tgagtgaccc catgtggcca cagtacacga acctggggct cctgaacagc 240
atggaccagc agattcagaa cggctcctcg tccaccagtc cctataacac agaccacgcg 300
cagaacagcg tcacggcgcc ctcgccctac gcacagccca gctccacctt cgatgctctc 360
tctccatcac ccgccatccc ctccaacacc gactacccag gcccgcacag tttcgacgtg 420
tccttccagc agtcgagcac cgccaagtcg gccacctgga cgtattccac tgaactgaag 480
aaactctact gccaaattgc aaagacatgc cccatccaga tcaaggtgat gaccccacct 540
cctcagggag ctgttatccg cgccatgcct gtctacaaaa aagctgagca cgtcacggag 600
gtggtgaagc ggtgccccaa ccatgagctg agccgtgaat tcaacgaggg acagattgcc 660
cctcctagtc atttgattcg agtagagggg aacagccatg cccagtatgt agaagatccc 720
atcacaggaa gacagagtgt gctggtacct tatgagccac cccaggttgg cactgaattc 780
acgacagtct tgtacaattt catgtgtaac agcagttgtg ttggagggat gaaccgccgt 840
ccaattttaa tcattgttac tctggaaacc agagatgggc aagtcctggg ccgacgctgc 900
tttgaggccc ggatctgtgc ttgcccagga agagacagga aggcggatga agatagcatc 960
agaaagcagc aagtttcgga cagtacaaag aacggtgatg gtacgaagcg cccgtttcgt 1020
cagaacacac atggtatcca gatgacatcc atcaagaaac gaagatcccc agatgatgaa 1080
ctgttatact taccagtgag ggccgtgag acttatgaaa tgctgttgaa gatcaaagag 1140

-continued

```
tccctggaac tcatgcagta ccttcctcag cacacaattg aaacgtacag gcaacagcaa   1200

cagcagcagc accagcactt acttcagaaa cagacctcaa tacagtctcc atcttcatat   1260

ggtaacagct ccccacctct gaacaaaatg aacagcatga acaagctgcc ttctgtgagc   1320

cagcttatca accctcagca gcgcaacgcc ctcactccta caaccattcc tgatggcatg   1380

ggagccaaca ttcccatgat gggcacccac atgccaatgg ctggagacat gaatggactc   1440

agccccaccc aggcactccc tcccccactc tccatgccat ccacctccca ctgcacaccc   1500

ccacctccgt atcccacaga ttgcagcatt gtcaggatct ggcaagtctg a            1551


<210> SEQ ID NO 338
<211> LENGTH: 586
<212> TYPE: PRT
<213> ORGANISM: Homo sapiens

<400> SEQUENCE: 338

Met Leu Tyr Leu Glu Asn Asn Ala Gln Thr Gln Phe Ser Glu Pro Gln
 1               5                  10                  15

Tyr Thr Asn Leu Gly Leu Leu Asn Ser Met Asp Gln Gln Ile Arg Asn
            20                  25                  30

Gly Ser Ser Ser Thr Ser Pro Tyr Asn Thr Asp His Ala Gln Asn Ser
        35                  40                  45

Val Thr Ala Pro Ser Pro Tyr Ala Gln Pro Ser Pro Thr Phe Asp Ala
    50                  55                  60

Leu Ser Pro Ser Pro Ala Ile Pro Ser Asn Thr Asp Tyr Pro Gly Pro
65                  70                  75                  80

His Ser Ser Asp Val Ser Phe Gln Gln Ser Ser Thr Ala Lys Ser Ala
                85                  90                  95

Thr Trp Thr Tyr Ser Thr Glu Leu Lys Lys Leu Tyr Cys Gln Ile Ala
            100                 105                 110

Lys Thr Cys Pro Ile Gln Ile Lys Val Met Thr Pro Pro Pro Gln Gly
        115                 120                 125

Ala Val Ile Arg Ala Met Pro Val Tyr Lys Lys Ala Glu His Val Thr
    130                 135                 140

Glu Val Val Lys Arg Cys Pro Asn His Glu Leu Ser Arg Glu Phe Asn
145                 150                 155                 160

Glu Gly Gln Ile Ala Pro Pro Ser His Leu Ile Arg Val Glu Gly Asn
                165                 170                 175

Ser His Ala Gln Tyr Val Glu Asp Pro Ile Thr Gly Arg Gln Ser Val
            180                 185                 190

Leu Val Pro Tyr Glu Pro Pro Gln Val Gly Thr Glu Phe Thr Thr Val
        195                 200                 205

Leu Tyr Asn Phe Met Cys Asn Ser Ser Cys Val Gly Gly Met Asn Arg
    210                 215                 220

Arg Pro Ile Leu Ile Ile Val Thr Leu Glu Thr Arg Asp Gly Gln Val
225                 230                 235                 240

Leu Gly Arg Arg Cys Phe Glu Ala Arg Ile Cys Ala Cys Pro Gly Arg
                245                 250                 255

Asp Arg Lys Ala Asp Glu Asp Ser Ile Arg Lys Gln Gln Val Ser Asp
            260                 265                 270

Ser Thr Lys Asn Gly Asp Gly Thr Lys Arg Pro Phe Arg Gln Asn Thr
        275                 280                 285

His Gly Ile Gln Met Thr Ser Ile Lys Lys Arg Arg Ser Pro Asp Asp
    290                 295                 300
```

-continued

```
Glu Leu Leu Tyr Leu Pro Val Arg Gly Arg Glu Thr Tyr Glu Met Leu
305                 310                 315                 320

Leu Lys Ile Lys Glu Ser Leu Glu Leu Met Gln Tyr Leu Pro Gln His
                325                 330                 335

Thr Ile Glu Thr Tyr Arg Gln Gln Gln Gln Gln Gln His Gln His Leu
            340                 345                 350

Leu Gln Lys Gln Thr Ser Ile Gln Ser Pro Ser Ser Tyr Gly Asn Ser
        355                 360                 365

Ser Pro Pro Leu Asn Lys Met Asn Ser Met Asn Lys Leu Pro Ser Val
    370                 375                 380

Ser Gln Leu Ile Asn Pro Gln Gln Arg Asn Ala Leu Thr Pro Thr Thr
385                 390                 395                 400

Ile Pro Asp Gly Met Gly Ala Asn Ile Pro Met Met Gly Thr His Met
                405                 410                 415

Pro Met Ala Gly Asp Met Asn Gly Leu Ser Pro Thr Gln Ala Leu Pro
            420                 425                 430

Pro Pro Leu Ser Met Pro Ser Thr Ser His Cys Thr Pro Pro Pro Pro
        435                 440                 445

Tyr Pro Thr Asp Cys Ser Ile Val Ser Phe Leu Ala Arg Leu Gly Cys
    450                 455                 460

Ser Ser Cys Leu Asp Tyr Phe Thr Thr Gln Gly Leu Thr Thr Ile Tyr
465                 470                 475                 480

Gln Ile Glu His Tyr Ser Met Asp Asp Leu Ala Ser Leu Lys Ile Pro
                485                 490                 495

Glu Gln Phe Arg His Ala Ile Trp Lys Gly Ile Leu Asp His Arg Gln
            500                 505                 510

Leu His Glu Phe Ser Ser Pro Ser His Leu Leu Arg Thr Pro Ser Ser
        515                 520                 525

Ala Ser Thr Val Ser Val Gly Ser Ser Glu Thr Arg Gly Glu Arg Val
    530                 535                 540

Ile Asp Ala Val Arg Phe Thr Leu Arg Gln Thr Ile Ser Phe Pro Pro
545                 550                 555                 560

Arg Asp Glu Trp Asn Asp Phe Asn Phe Asp Met Asp Ala Arg Arg Asn
                565                 570                 575

Lys Gln Gln Arg Ile Lys Glu Glu Gly Glu
            580                 585


<210> SEQ ID NO 339
<211> LENGTH: 641
<212> TYPE: PRT
<213> ORGANISM: Homo sapiens

<400> SEQUENCE: 339

Met Ser Gln Ser Thr Gln Thr Asn Glu Phe Leu Ser Pro Glu Val Phe
 1               5                  10                  15

Gln His Ile Trp Asp Phe Leu Glu Gln Pro Ile Cys Ser Val Gln Pro
            20                  25                  30

Ile Asp Leu Asn Phe Val Asp Glu Pro Ser Glu Asp Gly Ala Thr Asn
        35                  40                  45

Lys Ile Glu Ile Ser Met Asp Cys Ile Arg Met Gln Asp Ser Asp Leu
    50                  55                  60

Ser Asp Pro Met Trp Pro Gln Tyr Thr Asn Leu Gly Leu Leu Asn Ser
65                  70                  75                  80

Met Asp Gln Gln Ile Gln Asn Gly Ser Ser Ser Thr Ser Pro Tyr Asn
                85                  90                  95
```

-continued

```
Thr Asp His Ala Gln Asn Ser Val Thr Ala Pro Ser Pro Tyr Ala Gln
            100                 105                 110

Pro Ser Ser Thr Phe Asp Ala Leu Ser Pro Ser Pro Ala Ile Pro Ser
        115                 120                 125

Asn Thr Asp Tyr Pro Gly Pro His Ser Phe Asp Val Ser Phe Gln Gln
    130                 135                 140

Ser Ser Thr Ala Lys Ser Ala Thr Trp Thr Tyr Ser Thr Glu Leu Lys
145                 150                 155                 160

Lys Leu Tyr Cys Gln Ile Ala Lys Thr Cys Pro Ile Gln Ile Lys Val
                165                 170                 175

Met Thr Pro Pro Pro Gln Gly Ala Val Ile Arg Ala Met Pro Val Tyr
            180                 185                 190

Lys Lys Ala Glu His Val Thr Glu Val Val Lys Arg Cys Pro Asn His
        195                 200                 205

Glu Leu Ser Arg Glu Phe Asn Glu Gly Gln Ile Ala Pro Pro Ser His
    210                 215                 220

Leu Ile Arg Val Glu Gly Asn Ser His Ala Gln Tyr Val Glu Asp Pro
225                 230                 235                 240

Ile Thr Gly Arg Gln Ser Val Leu Val Pro Tyr Glu Pro Pro Gln Val
                245                 250                 255

Gly Thr Glu Phe Thr Thr Val Leu Tyr Asn Phe Met Cys Asn Ser Ser
            260                 265                 270

Cys Val Gly Gly Met Asn Arg Arg Pro Ile Leu Ile Ile Val Thr Leu
        275                 280                 285

Glu Thr Arg Asp Gly Gln Val Leu Gly Arg Arg Cys Phe Glu Ala Arg
    290                 295                 300

Ile Cys Ala Cys Pro Gly Arg Asp Arg Lys Ala Asp Glu Asp Ser Ile
305                 310                 315                 320

Arg Lys Gln Gln Val Ser Asp Ser Thr Lys Asn Gly Asp Gly Thr Lys
                325                 330                 335

Arg Pro Phe Arg Gln Asn Thr His Gly Ile Gln Met Thr Ser Ile Lys
            340                 345                 350

Lys Arg Arg Ser Pro Asp Asp Glu Leu Leu Tyr Leu Pro Val Arg Gly
        355                 360                 365

Arg Glu Thr Tyr Glu Met Leu Leu Lys Ile Lys Glu Ser Leu Glu Leu
    370                 375                 380

Met Gln Tyr Leu Pro Gln His Thr Ile Glu Thr Tyr Arg Gln Gln Gln
385                 390                 395                 400

Gln Gln Gln His Gln His Leu Leu Gln Lys Gln Thr Ser Ile Gln Ser
                405                 410                 415

Pro Ser Ser Tyr Gly Asn Ser Ser Pro Pro Leu Asn Lys Met Asn Ser
            420                 425                 430

Met Asn Lys Leu Pro Ser Val Ser Gln Leu Ile Asn Pro Gln Gln Arg
        435                 440                 445

Asn Ala Leu Thr Pro Thr Thr Ile Pro Asp Gly Met Gly Ala Asn Ile
    450                 455                 460

Pro Met Met Gly Thr His Met Pro Met Ala Gly Asp Met Asn Gly Leu
465                 470                 475                 480

Ser Pro Thr Gln Ala Leu Pro Pro Pro Leu Ser Met Pro Ser Thr Ser
                485                 490                 495

His Cys Thr Pro Pro Pro Pro Tyr Pro Thr Asp Cys Ser Ile Val Gly
            500                 505                 510
```

-continued

```
Phe Leu Ala Arg Leu Gly Cys Ser Ser Cys Leu Asp Tyr Phe Thr Thr
        515                 520                 525

Gln Gly Leu Thr Thr Ile Tyr Gln Ile Glu His Tyr Ser Met Asp Asp
    530                 535                 540

Leu Ala Ser Leu Lys Ile Pro Glu Gln Phe Arg His Ala Ile Trp Lys
545                 550                 555                 560

Gly Ile Leu Asp His Arg Gln Leu His Glu Phe Ser Ser Pro Ser His
                565                 570                 575

Leu Leu Arg Thr Pro Ser Ser Ala Ser Thr Val Ser Val Gly Ser Ser
            580                 585                 590

Glu Thr Arg Gly Glu Arg Val Ile Asp Ala Val Arg Phe Thr Leu Arg
        595                 600                 605

Gln Thr Ile Ser Phe Pro Pro Arg Asp Glu Trp Asn Asp Phe Asn Phe
    610                 615                 620

Asp Met Asp Ala Arg Arg Asn Lys Gln Gln Arg Ile Lys Glu Glu Gly
625                 630                 635                 640

Glu


<210> SEQ ID NO 340
<211> LENGTH: 448
<212> TYPE: PRT
<213> ORGANISM: Homo sapiens

<400> SEQUENCE: 340

Met Ser Gln Ser Thr Gln Thr Asn Glu Phe Leu Ser Pro Glu Val Phe
 1               5                  10                  15

Gln His Ile Trp Asp Phe Leu Glu Gln Pro Ile Cys Ser Val Gln Pro
            20                  25                  30

Ile Asp Leu Asn Phe Val Asp Glu Pro Ser Glu Asp Gly Ala Thr Asn
        35                  40                  45

Lys Ile Glu Ile Ser Met Asp Cys Ile Arg Met Gln Asp Ser Asp Leu
    50                  55                  60

Ser Asp Pro Met Trp Pro Gln Tyr Thr Asn Leu Gly Leu Leu Asn Ser
65                  70                  75                  80

Met Asp Gln Gln Ile Gln Asn Gly Ser Ser Ser Thr Ser Pro Tyr Asn
                85                  90                  95

Thr Asp His Ala Gln Asn Ser Val Thr Ala Pro Ser Pro Tyr Ala Gln
            100                 105                 110

Pro Ser Ser Thr Phe Asp Ala Leu Ser Pro Ser Pro Ala Ile Pro Ser
        115                 120                 125

Asn Thr Asp Tyr Pro Gly Pro His Ser Phe Asp Val Ser Phe Gln Gln
    130                 135                 140

Ser Ser Thr Ala Lys Ser Ala Thr Trp Thr Tyr Ser Thr Glu Leu Lys
145                 150                 155                 160

Lys Leu Tyr Cys Gln Ile Ala Lys Thr Cys Pro Ile Gln Ile Lys Val
                165                 170                 175

Met Thr Pro Pro Pro Gln Gly Ala Val Ile Arg Ala Met Pro Val Tyr
            180                 185                 190

Lys Lys Ala Glu His Val Thr Glu Val Val Lys Arg Cys Pro Asn His
        195                 200                 205

Glu Leu Ser Arg Glu Phe Asn Glu Gly Gln Ile Ala Pro Pro Ser His
    210                 215                 220

Leu Ile Arg Val Glu Gly Asn Ser His Ala Gln Tyr Val Glu Asp Pro
225                 230                 235                 240
```

-continued

Ile Thr Gly Arg Gln Ser Val Leu Val Pro Tyr Glu Pro Pro Gln Val
245 250 255

Gly Thr Glu Phe Thr Thr Val Leu Tyr Asn Phe Met Cys Asn Ser Ser
260 265 270

Cys Val Gly Gly Met Asn Arg Arg Pro Ile Leu Ile Ile Val Thr Leu
275 280 285

Glu Thr Arg Asp Gly Gln Val Leu Gly Arg Arg Cys Phe Glu Ala Arg
290 295 300

Ile Cys Ala Cys Pro Gly Arg Asp Arg Lys Ala Asp Glu Asp Ser Ile
305 310 315 320

Arg Lys Gln Gln Val Ser Asp Ser Thr Lys Asn Gly Asp Gly Thr Lys
325 330 335

Arg Pro Phe Arg Gln Asn Thr His Gly Ile Gln Met Thr Ser Ile Lys
340 345 350

Lys Arg Arg Ser Pro Asp Asp Glu Leu Leu Tyr Leu Pro Val Arg Gly
355 360 365

Arg Glu Thr Tyr Glu Met Leu Leu Lys Ile Lys Glu Ser Leu Glu Leu
370 375 380

Met Gln Tyr Leu Pro Gln His Thr Ile Glu Thr Tyr Arg Gln Gln Gln
385 390 395 400

Gln Gln Gln His Gln His Leu Leu Gln Lys His Leu Leu Ser Ala Cys
405 410 415

Phe Arg Asn Glu Leu Val Glu Pro Arg Arg Glu Thr Pro Lys Gln Ser
420 425 430

Asp Val Phe Phe Arg His Ser Lys Pro Pro Asn Arg Ser Val Tyr Pro
435 440 445

<210> SEQ ID NO 341
<211> LENGTH: 356
<212> TYPE: PRT
<213> ORGANISM: Homo sapiens

<400> SEQUENCE: 341

Met Leu Tyr Leu Glu Asn Asn Ala Gln Thr Gln Phe Ser Glu Pro Gln
1 5 10 15

Tyr Thr Asn Leu Gly Leu Leu Asn Ser Met Asp Gln Gln Ile Gln Asn
20 25 30

Gly Ser Ser Ser Thr Ser Pro Tyr Asn Thr Asp His Ala Gln Asn Ser
35 40 45

Val Thr Ala Pro Ser Pro Tyr Ala Gln Pro Ser Ser Thr Phe Asp Ala
50 55 60

Leu Ser Pro Ser Pro Ala Ile Pro Ser Asn Thr Asp Tyr Pro Gly Pro
65 70 75 80

His Ser Phe Asp Val Ser Phe Gln Gln Ser Ser Thr Ala Lys Ser Ala
85 90 95

Thr Trp Thr Tyr Ser Thr Glu Leu Lys Lys Leu Tyr Cys Gln Ile Ala
100 105 110

Lys Thr Cys Pro Ile Gln Ile Lys Val Met Thr Pro Pro Pro Gln Gly
115 120 125

Ala Val Ile Arg Ala Met Pro Val Tyr Lys Lys Ala Glu His Val Thr
130 135 140

Glu Val Val Lys Arg Cys Pro Asn His Glu Leu Ser Arg Glu Phe Asn
145 150 155 160

Glu Gly Gln Ile Ala Pro Pro Ser His Leu Ile Arg Val Glu Gly Asn
165 170 175

-continued

```
Ser His Ala Gln Tyr Val Glu Asp Pro Ile Thr Gly Arg Gln Ser Val
            180                 185                 190

Leu Val Pro Tyr Glu Pro Pro Gln Val Gly Thr Glu Phe Thr Thr Val
        195                 200                 205

Leu Tyr Asn Phe Met Cys Asn Ser Ser Cys Val Gly Gly Met Asn Arg
    210                 215                 220

Arg Pro Ile Leu Ile Ile Val Thr Leu Glu Thr Arg Asp Gly Gln Val
225                 230                 235                 240

Leu Gly Arg Arg Cys Phe Glu Ala Arg Ile Cys Ala Cys Pro Gly Arg
                245                 250                 255

Asp Arg Lys Ala Asp Glu Asp Ser Ile Arg Lys Gln Gln Val Ser Asp
            260                 265                 270

Ser Thr Lys Asn Gly Asp Gly Thr Lys Arg Pro Ser Arg Gln Asn Thr
        275                 280                 285

His Gly Ile Gln Met Thr Ser Ile Lys Lys Arg Arg Ser Pro Asp Asp
    290                 295                 300

Glu Leu Leu Tyr Leu Pro Val Arg Gly Arg Glu Thr Tyr Glu Met Leu
305                 310                 315                 320

Leu Lys Ile Lys Glu Ser Leu Glu Leu Met Gln Tyr Leu Pro Gln His
                325                 330                 335

Thr Ile Glu Thr Tyr Arg Gln Gln Gln Gln Gln Gln His Gln His Leu
            340                 345                 350

Leu Gln Lys Gln
        355


<210> SEQ ID NO 342
<211> LENGTH: 680
<212> TYPE: PRT
<213> ORGANISM: Homo sapiens

<400> SEQUENCE: 342

Met Asn Phe Glu Thr Ser Arg Cys Ala Thr Leu Gln Tyr Cys Pro Asp
 1               5                  10                  15

Pro Tyr Ile Gln Arg Phe Val Glu Thr Pro Ala His Phe Ser Trp Lys
            20                  25                  30

Glu Ser Tyr Tyr Arg Ser Thr Met Ser Gln Ser Thr Gln Thr Asn Glu
        35                  40                  45

Phe Leu Ser Pro Glu Val Phe Gln His Ile Trp Asp Phe Leu Glu Gln
    50                  55                  60

Pro Ile Cys Ser Val Gln Pro Ile Asp Leu Asn Phe Val Asp Glu Pro
65                  70                  75                  80

Ser Glu Asp Gly Ala Thr Asn Lys Ile Glu Ile Ser Met Asp Cys Ile
                85                  90                  95

Arg Met Gln Asp Ser Asp Leu Ser Asp Pro Met Trp Pro Gln Tyr Thr
            100                 105                 110

Asn Leu Gly Leu Leu Asn Ser Met Asp Gln Gln Ile Gln Asn Gly Ser
        115                 120                 125

Ser Ser Thr Ser Pro Tyr Asn Thr Asp His Ala Gln Asn Ser Val Thr
    130                 135                 140

Ala Pro Ser Pro Tyr Ala Gln Pro Ser Ser Thr Phe Asp Ala Leu Ser
145                 150                 155                 160

Pro Ser Pro Ala Ile Pro Ser Asn Thr Asp Tyr Pro Gly Pro His Ser
                165                 170                 175

Phe Asp Val Ser Phe Gln Gln Ser Ser Thr Ala Lys Ser Ala Thr Trp
```

-continued

```
            180                 185                 190

Thr Tyr Ser Thr Glu Leu Lys Lys Leu Tyr Cys Gln Ile Ala Lys Thr
        195                 200                 205

Cys Pro Ile Gln Ile Lys Val Met Thr Pro Pro Pro Gln Gly Ala Val
    210                 215                 220

Ile Arg Ala Met Pro Val Tyr Lys Lys Ala Glu His Val Thr Glu Val
225                 230                 235                 240

Val Lys Arg Cys Pro Asn His Glu Leu Ser Arg Glu Phe Asn Glu Gly
                245                 250                 255

Gln Ile Ala Pro Pro Ser His Leu Ile Arg Val Glu Gly Asn Ser His
            260                 265                 270

Ala Gln Tyr Val Glu Asp Pro Ile Thr Gly Arg Gln Ser Val Leu Val
        275                 280                 285

Pro Tyr Glu Pro Pro Gln Val Gly Thr Glu Phe Thr Thr Val Leu Tyr
    290                 295                 300

Asn Phe Met Cys Asn Ser Ser Cys Val Gly Gly Met Asn Arg Arg Pro
305                 310                 315                 320

Ile Leu Ile Ile Val Thr Leu Glu Thr Arg Asp Gly Gln Val Leu Gly
                325                 330                 335

Arg Arg Cys Phe Glu Ala Arg Ile Cys Ala Cys Pro Gly Arg Asp Arg
            340                 345                 350

Lys Ala Asp Glu Asp Ser Ile Arg Lys Gln Gln Val Ser Asp Ser Thr
        355                 360                 365

Lys Asn Gly Asp Gly Thr Lys Arg Pro Phe Arg Gln Asn Thr His Gly
    370                 375                 380

Ile Gln Met Thr Ser Ile Lys Lys Arg Arg Ser Pro Asp Asp Glu Leu
385                 390                 395                 400

Leu Tyr Leu Pro Val Arg Gly Arg Glu Thr Tyr Glu Met Leu Leu Lys
                405                 410                 415

Ile Lys Glu Ser Leu Glu Leu Met Gln Tyr Leu Pro Gln His Thr Ile
            420                 425                 430

Glu Thr Tyr Arg Gln Gln Gln Gln Gln Gln His Gln His Leu Leu Gln
        435                 440                 445

Lys Gln Thr Ser Ile Gln Ser Pro Ser Ser Tyr Gly Asn Ser Ser Pro
    450                 455                 460

Pro Leu Asn Lys Met Asn Ser Met Asn Lys Leu Pro Ser Val Ser Gln
465                 470                 475                 480

Leu Ile Asn Pro Gln Gln Arg Asn Ala Leu Thr Pro Thr Thr Ile Pro
                485                 490                 495

Asp Gly Met Gly Ala Asn Ile Pro Met Met Gly Thr His Met Pro Met
            500                 505                 510

Ala Gly Asp Met Asn Gly Leu Ser Pro Thr Gln Ala Leu Pro Pro Pro
        515                 520                 525

Leu Ser Met Pro Ser Thr Ser Gln Cys Thr Pro Pro Pro Pro Tyr Pro
    530                 535                 540

Thr Asp Cys Ser Ile Val Ser Phe Leu Ala Arg Leu Gly Cys Ser Ser
545                 550                 555                 560

Cys Leu Asp Tyr Phe Thr Thr Gln Gly Leu Thr Thr Ile Tyr Gln Ile
                565                 570                 575

Glu His Tyr Ser Met Asp Asp Leu Ala Ser Leu Lys Ile Pro Glu Gln
            580                 585                 590

Phe Arg His Ala Ile Trp Lys Gly Ile Leu Asp His Arg Gln Leu His
        595                 600                 605
```

-continued

```
Glu Phe Ser Ser Pro Ser His Leu Leu Arg Thr Pro Ser Ser Ala Ser
    610                 615                 620

Thr Val Ser Val Gly Ser Ser Glu Thr Arg Gly Glu Arg Val Ile Asp
625                 630                 635                 640

Ala Val Arg Phe Thr Leu Arg Gln Thr Ile Ser Phe Pro Pro Arg Asp
                645                 650                 655

Glu Trp Asn Asp Phe Asn Phe Asp Met Asp Ala Arg Arg Asn Lys Gln
            660                 665                 670

Gln Arg Ile Lys Glu Glu Gly Glu
        675                 680


<210> SEQ ID NO 343
<211> LENGTH: 461
<212> TYPE: PRT
<213> ORGANISM: Homo sapiens

<400> SEQUENCE: 343

Met Leu Tyr Leu Glu Asn Asn Ala Gln Thr Gln Phe Ser Glu Pro Gln
 1               5                  10                  15

Tyr Thr Asn Leu Gly Leu Leu Asn Ser Met Asp Gln Gln Ile Gln Asn
            20                  25                  30

Gly Ser Ser Ser Thr Ser Pro Tyr Asn Thr Asp His Ala Gln Asn Ser
        35                  40                  45

Val Thr Ala Pro Ser Pro Tyr Ala Gln Pro Ser Ser Thr Phe Asp Ala
    50                  55                  60

Leu Ser Pro Ser Pro Ala Ile Pro Ser Asn Thr Asp Tyr Pro Gly Pro
65                  70                  75                  80

His Ser Phe Asp Val Ser Phe Gln Gln Ser Ser Thr Ala Lys Ser Ala
                85                  90                  95

Thr Trp Thr Tyr Ser Thr Glu Leu Lys Lys Leu Tyr Cys Gln Ile Ala
            100                 105                 110

Lys Thr Cys Pro Ile Gln Ile Lys Val Met Thr Pro Pro Pro Gln Gly
        115                 120                 125

Ala Val Ile Arg Ala Met Pro Val Tyr Lys Lys Ala Glu His Val Thr
    130                 135                 140

Glu Val Val Lys Arg Cys Pro Asn His Glu Leu Ser Arg Glu Phe Asn
145                 150                 155                 160

Glu Gly Gln Ile Ala Pro Pro Ser His Leu Ile Arg Val Glu Gly Asn
                165                 170                 175

Ser His Ala Gln Tyr Val Glu Asp Pro Ile Thr Gly Arg Gln Ser Val
            180                 185                 190

Leu Val Pro Tyr Glu Pro Pro Gln Val Gly Thr Glu Phe Thr Thr Val
        195                 200                 205

Leu Tyr Asn Phe Met Cys Asn Ser Ser Cys Val Gly Gly Met Asn Arg
    210                 215                 220

Arg Pro Ile Leu Ile Ile Val Thr Leu Glu Thr Arg Asp Gly Gln Val
225                 230                 235                 240

Leu Gly Arg Arg Cys Phe Glu Ala Arg Ile Cys Ala Cys Pro Gly Arg
                245                 250                 255

Asp Arg Lys Ala Asp Glu Asp Ser Ile Arg Lys Gln Gln Val Ser Asp
            260                 265                 270

Ser Thr Lys Asn Gly Asp Gly Thr Lys Arg Pro Phe Arg Gln Asn Thr
        275                 280                 285

His Gly Ile Gln Met Thr Ser Ile Lys Lys Arg Arg Ser Pro Asp Asp
```

-continued

```
    290                 295                 300

Glu Leu Leu Tyr Leu Pro Val Arg Gly Arg Glu Thr Tyr Glu Met Leu
305                 310                 315                 320

Leu Lys Ile Lys Glu Ser Leu Glu Leu Met Gln Tyr Leu Pro Gln His
                325                 330                 335

Thr Ile Glu Thr Tyr Arg Gln Gln Gln Gln Gln Gln His Gln His Leu
            340                 345                 350

Leu Gln Lys Gln Thr Ser Ile Gln Ser Pro Ser Ser Tyr Gly Asn Ser
        355                 360                 365

Ser Pro Pro Leu Asn Lys Met Asn Ser Met Asn Lys Leu Pro Ser Val
    370                 375                 380

Ser Gln Leu Ile Asn Pro Gln Gln Arg Asn Ala Leu Thr Pro Thr Thr
385                 390                 395                 400

Ile Pro Asp Gly Met Gly Ala Asn Ile Pro Met Met Gly Thr His Met
                405                 410                 415

Pro Met Ala Gly Asp Met Asn Gly Leu Ser Pro Thr Gln Ala Leu Pro
            420                 425                 430

Pro Pro Leu Ser Met Pro Ser Thr Ser His Cys Thr Pro Pro Pro Pro
        435                 440                 445

Tyr Pro Thr Asp Cys Ser Ile Val Arg Ile Trp Gln Val
    450                 455                 460
```

<210> SEQ ID NO 344
<211> LENGTH: 516
<212> TYPE: PRT
<213> ORGANISM: Homo sapiens

<400> SEQUENCE: 344

```
Met Ser Gln Ser Thr Gln Thr Asn Glu Phe Leu Ser Pro Glu Val Phe
 1               5                  10                  15

Gln His Ile Trp Asp Phe Leu Glu Gln Pro Ile Cys Ser Val Gln Pro
            20                  25                  30

Ile Asp Leu Asn Phe Val Asp Glu Pro Ser Glu Asp Gly Ala Thr Asn
        35                  40                  45

Lys Ile Glu Ile Ser Met Asp Cys Ile Arg Met Gln Asp Ser Asp Leu
    50                  55                  60

Ser Asp Pro Met Trp Pro Gln Tyr Thr Asn Leu Gly Leu Leu Asn Ser
65                  70                  75                  80

Met Asp Gln Gln Ile Gln Asn Gly Ser Ser Ser Thr Ser Pro Tyr Asn
                85                  90                  95

Thr Asp His Ala Gln Asn Ser Val Thr Ala Pro Ser Pro Tyr Ala Gln
            100                 105                 110

Pro Ser Ser Thr Phe Asp Ala Leu Ser Pro Ser Pro Ala Ile Pro Ser
        115                 120                 125

Asn Thr Asp Tyr Pro Gly Pro His Ser Phe Asp Val Ser Phe Gln Gln
    130                 135                 140

Ser Ser Thr Ala Lys Ser Ala Thr Trp Thr Tyr Ser Thr Glu Leu Lys
145                 150                 155                 160

Lys Leu Tyr Cys Gln Ile Ala Lys Thr Cys Pro Ile Gln Ile Lys Val
                165                 170                 175

Met Thr Pro Pro Pro Gln Gly Ala Val Ile Arg Ala Met Pro Val Tyr
            180                 185                 190

Lys Lys Ala Glu His Val Thr Glu Val Val Lys Arg Cys Pro Asn His
        195                 200                 205
```

-continued

```
Glu Leu Ser Arg Glu Phe Asn Glu Gly Gln Ile Ala Pro Pro Ser His
    210                 215                 220

Leu Ile Arg Val Glu Gly Asn Ser His Ala Gln Tyr Val Glu Asp Pro
225                 230                 235                 240

Ile Thr Gly Arg Gln Ser Val Leu Val Pro Tyr Glu Pro Pro Gln Val
                245                 250                 255

Gly Thr Glu Phe Thr Thr Val Leu Tyr Asn Phe Met Cys Asn Ser Ser
            260                 265                 270

Cys Val Gly Gly Met Asn Arg Arg Pro Ile Leu Ile Ile Val Thr Leu
        275                 280                 285

Glu Thr Arg Asp Gly Gln Val Leu Gly Arg Arg Cys Phe Glu Ala Arg
    290                 295                 300

Ile Cys Ala Cys Pro Gly Arg Asp Arg Lys Ala Asp Glu Asp Ser Ile
305                 310                 315                 320

Arg Lys Gln Gln Val Ser Asp Ser Thr Lys Asn Gly Asp Gly Thr Lys
                325                 330                 335

Arg Pro Phe Arg Gln Asn Thr His Gly Ile Gln Met Thr Ser Ile Lys
            340                 345                 350

Lys Arg Arg Ser Pro Asp Asp Glu Leu Leu Tyr Leu Pro Val Arg Gly
        355                 360                 365

Arg Glu Thr Tyr Glu Met Leu Leu Lys Ile Lys Glu Ser Leu Glu Leu
    370                 375                 380

Met Gln Tyr Leu Pro Gln His Thr Ile Glu Thr Tyr Arg Gln Gln Gln
385                 390                 395                 400

Gln Gln Gln His Gln His Leu Leu Gln Lys Gln Thr Ser Ile Gln Ser
                405                 410                 415

Pro Ser Ser Tyr Gly Asn Ser Ser Pro Pro Leu Asn Lys Met Asn Ser
            420                 425                 430

Met Asn Lys Leu Pro Ser Val Ser Gln Leu Ile Asn Pro Gln Gln Arg
        435                 440                 445

Asn Ala Leu Thr Pro Thr Thr Ile Pro Asp Gly Met Gly Ala Asn Ile
    450                 455                 460

Pro Met Met Gly Thr His Met Pro Met Ala Gly Asp Met Asn Gly Leu
465                 470                 475                 480

Ser Pro Thr Gln Ala Leu Pro Pro Pro Leu Ser Met Pro Ser Thr Ser
                485                 490                 495

His Cys Thr Pro Pro Pro Pro Tyr Pro Thr Asp Cys Ser Ile Val Arg
            500                 505                 510

Ile Trp Gln Val
        515
```

<210> SEQ ID NO 345
<211> LENGTH: 1800
<212> TYPE: DNA
<213> ORGANISM: Homo sapiens

<400> SEQUENCE: 345

```
gcgcctcatt gccactgcag tgactaaagc tgggaagacg ctggtcagtt cacctgcccc     60

actggttgtt ttttaaacaa attctgatac aggcgacatc ctcactgacc gagcaaagat    120

tgacattcgt atcatcactg tgcaccattg gcttctaggc actccagtgg ggtaggagaa    180

ggaggtctga aaccctcgca gagggatctt gccctcattc tttgggtctg aaacactggc    240

agtcgttgga aacaggactc agggataaac cagcgcaatg gattggggga cgctgcacac    300

tttcatcggg ggtgtcaaca aacactccac cagcatcggg aaggtgtgga tcacagtcat    360
```

-continued

```
ctttattttc cgagtcatga tcctagtggt ggctgcccag gaagtgtggg gtgacgagca    420

agaggacttc gtctgcaaca cactgcaacc gggatgcaaa aatgtgtgct atgaccactt    480

tttcccggtg tcccacatcc ggctgtgggc cctccagctg atcttcgtct ccaccccagc    540

gctgctggtg gccatgcatg tggcctacta caggcacgaa accactcgca agttcaggcg    600

aggagagaag aggaatgatt tcaaagacat agaggacatt aaaaagcaca aggttcggat    660

agaggggtcg ctgtggtgga cgtacaccag cagcatcttt ttccgaatca tctttgaagc    720

agcctttatg tatgtgtttt acttccttta caatgggtac cacctgccct gggtgttgaa    780

atgtgggatt gacccctgcc ccaaccttgt tgactgcttt atttctaggc caacagagaa    840

gaccgtgttt accattttta tgatttctgc gtctgtgatt tgcatgctgc ttaacgtggc    900

agagttgtgc tacctgctgc tgaaagtgtg ttttaggaga tcaaagagag cacagacgca    960

aaaaaatcac cccaatcatg ccctaaagga gagtaagcag aatgaaatga atgagctgat   1020

ttcagatagt ggtcaaaatg caatcacagg tttcccaagc taaacatttc aaggtaaaat   1080

gtagctgcgt cataaggaga cttctgtctt ctccagaagg caataccaac ctgaaagttc   1140

cttctgtagc ctgaagagtt tgtaaatgac tttcataata aatagacact tgagttaact   1200

ttttgtagga tacttgctcc attcatacac aacgtaatca aatatgtggt ccatctctga   1260

aaacaagaga ctgcttgaca aaggagcatt gcagtcactt tgacaggttc cttttaagtg   1320

gactctctga caaagtgggt actttctgaa aatttatata actgttgttg ataaggaaca   1380

tttatccagg aattgatacg tttattagga aaagatattt ttataggctt ggatgttttt   1440

agttccgact ttgaatttat ataaagtatt tttataatga ctggtcttcc ttacctggaa   1500

aaacatgcga tgttagtttt agaattacac cacaagtatc taaatttcca acttacaaag   1560

ggtcctatct tgtaaatatt gttttgcatt gtctgttggc aaatttgtga actgtcatga   1620

tacgcttaag gtgggaaagt gttcattgca caatatattt ttactgcttt ctgaatgtag   1680

acggaacagt gtggaagcag aaggcttttt taactcatcc gtttggccga tcgttgcaga   1740

ccactgggag atgtggatgt ggttgcctcc ttttgctcgt ccccgtggct taacccttct   1800
```

<210> SEQ ID NO 346
<211> LENGTH: 261
<212> TYPE: PRT
<213> ORGANISM: Homo sapiens

<400> SEQUENCE: 346

```
Met Asp Trp Gly Thr Leu His Thr Phe Ile Gly Gly Val Asn Lys His
 1               5                  10                  15

Ser Thr Ser Ile Gly Lys Val Trp Ile Thr Val Ile Phe Ile Phe Arg
            20                  25                  30

Val Met Ile Leu Val Val Ala Ala Gln Glu Val Trp Gly Asp Glu Gln
        35                  40                  45

Glu Asp Phe Val Cys Asn Thr Leu Gln Pro Gly Cys Lys Asn Val Cys
    50                  55                  60

Tyr Asp His Phe Phe Pro Val Ser His Ile Arg Leu Trp Ala Leu Gln
65                  70                  75                  80

Leu Ile Phe Val Ser Thr Pro Ala Leu Leu Val Ala Met His Val Ala
                85                  90                  95

Tyr Tyr Arg His Glu Thr Thr Arg Lys Phe Arg Arg Gly Glu Lys Arg
            100                 105                 110

Asn Asp Phe Lys Asp Ile Glu Asp Ile Lys Lys His Lys Val Arg Ile
```

-continued

```
        115                 120                 125

Glu Gly Ser Leu Trp Trp Thr Tyr Thr Ser Ser Ile Phe Phe Arg Ile
    130                 135                 140

Ile Phe Glu Ala Ala Phe Met Tyr Val Phe Tyr Phe Leu Tyr Asn Gly
145                 150                 155                 160

Tyr His Leu Pro Trp Val Leu Lys Cys Gly Ile Asp Pro Cys Pro Asn
                165                 170                 175

Leu Val Asp Cys Phe Ile Ser Arg Pro Thr Glu Lys Thr Val Phe Thr
            180                 185                 190

Ile Phe Met Ile Ser Ala Ser Val Ile Cys Met Leu Leu Asn Val Ala
        195                 200                 205

Glu Leu Cys Tyr Leu Leu Leu Lys Val Cys Phe Arg Arg Ser Lys Arg
    210                 215                 220

Ala Gln Thr Gln Lys Asn His Pro Asn His Ala Leu Lys Glu Ser Lys
225                 230                 235                 240

Gln Asn Glu Met Asn Glu Leu Ile Ser Asp Ser Gly Gln Asn Ala Ile
                245                 250                 255

Thr Gly Phe Pro Ser
            260
```

<210> SEQ ID NO 347
<211> LENGTH: 1740
<212> TYPE: DNA
<213> ORGANISM: Homo sapiens

<400> SEQUENCE: 347

```
atgaacaaac tgtatatcgg aaacctcagc gagaacgccg ccccctcgga cctagaaagt     60

atcttcaagg acgccaagat cccggtgtcg ggacccttcc tggtgaagac tggctacgcg    120

ttcgtggact gcccggacga gagctgggcc ctcaaggcca tcgaggcgct ttcaggtaaa    180

atagaactgc acgggaaacc catagaagtt gagcactcgg tcccaaaaag gcaaaggatt    240

cggaaacttc agatacgaaa tatcccgcct catttacagt gggaggtgct ggatagttta    300

ctagtccagt atggagtggt ggagagctgt gagcaagtga acactgactc ggaaactgca    360

gttgtaaatg taacctattc cagtaaggac caagctagac aagcactaga caaactgaat    420

ggatttcagt tagagaattt caccttgaaa gtagcctata tccctgatga aacggccgcc    480

cagcaaaacc ccttgcagca gccccgaggt cgccgggggc ttgggcagag gggctcctca    540

aggcaggggt ctccaggatc cgtatccaag cagaaaccat gtgatttgcc tctgcgcctg    600

ctggttccca cccaatttgt tggagccatc ataggaaaag aaggtgccac cattcggaac    660

atcaccaaac agacccagtc taaaatcgat gtccaccgta aagaaaatgc gggggctgct    720

gagaagtcga ttactatcct ctctactcct gaaggcacct ctgcggcttg taagtctatt    780

ctggagatta tgcataagga agctcaagat ataaaattca cagaagagat cccccttgaag    840

attttagctc ataataactt tgttggacgt cttattggta aagaaggaag aaatcttaaa    900

aaaattgagc aagacacaga cactaaaatc acgatatctc cattgcagga attgacgctg    960

tataatccag aacgcactat tacagttaaa ggcaatgttg agacatgtgc caaagctgag   1020

gaggagatca tgaagaaaat cagggagtct tatgaaaatg atattgcttc tatgaatctt   1080

caagcacatt taattcctgg attaaatctg aacgccttgg gtctgttccc acccacttca   1140

gggatgccac ctcccacctc agggccccct tcagccatga ctcctcccta cccgcagttt   1200

gagcaatcag aaacggagac tgttcatctg tttatcccag ctctatcagt cggtgccatc   1260
```

-continued

```
atcggcaagc agggccagca catcaagcag ctttctcgct ttgctggagc ttcaattaag   1320

attgctccag cggaagcacc agatgctaaa gtgaggatgg tgattatcac tggaccacca   1380

gaggctcagt tcaaggctca gggaagaatt tatggaaaaa ttaaagaaga aaactttgtt   1440

agtcctaaag aagaggtgaa acttgaagct catatcagag tgccatcctt tgctgctggc   1500

agagttattg gaaaaggagg caaaacggtg aatgaacttc agaatttgtc aagtgcagaa   1560

gttgttgtcc ctcgtgacca gacacctgat gagaatgacc aagtggttgt caaaataact   1620

ggtcacttct atgcttgcca ggttgcccag agaaaaattc aggaaattct gactcaggta   1680

aagcagcacc aacaacagaa ggctctgcaa agtggaccac ctcagtcaag acggaagtaa   1740
```

<210> SEQ ID NO 348
<211> LENGTH: 579
<212> TYPE: PRT
<213> ORGANISM: Homo sapiens

<400> SEQUENCE: 348

```
Met Asn Lys Leu Tyr Ile Gly Asn Leu Ser Glu Asn Ala Ala Pro Ser
 1               5                  10                  15

Asp Leu Glu Ser Ile Phe Lys Asp Ala Lys Ile Pro Val Ser Gly Pro
            20                  25                  30

Phe Leu Val Lys Thr Gly Tyr Ala Phe Val Asp Cys Pro Asp Glu Ser
        35                  40                  45

Trp Ala Leu Lys Ala Ile Glu Ala Leu Ser Gly Lys Ile Glu Leu His
    50                  55                  60

Gly Lys Pro Ile Glu Val Glu His Ser Val Pro Lys Arg Gln Arg Ile
65                  70                  75                  80

Arg Lys Leu Gln Ile Arg Asn Ile Pro Pro His Leu Gln Trp Glu Val
                85                  90                  95

Leu Asp Ser Leu Leu Val Gln Tyr Gly Val Val Glu Ser Cys Glu Gln
            100                 105                 110

Val Asn Thr Asp Ser Glu Thr Ala Val Val Asn Val Thr Tyr Ser Ser
        115                 120                 125

Lys Asp Gln Ala Arg Gln Ala Leu Asp Lys Leu Asn Gly Phe Gln Leu
    130                 135                 140

Glu Asn Phe Thr Leu Lys Val Ala Tyr Ile Pro Asp Glu Thr Ala Ala
145                 150                 155                 160

Gln Gln Asn Pro Leu Gln Gln Pro Arg Gly Arg Arg Gly Leu Gly Gln
                165                 170                 175

Arg Gly Ser Ser Arg Gln Gly Ser Pro Gly Ser Val Ser Lys Gln Lys
            180                 185                 190

Pro Cys Asp Leu Pro Leu Arg Leu Leu Val Pro Thr Gln Phe Val Gly
        195                 200                 205

Ala Ile Ile Gly Lys Glu Gly Ala Thr Ile Arg Asn Ile Thr Lys Gln
    210                 215                 220

Thr Gln Ser Lys Ile Asp Val His Arg Lys Glu Asn Ala Gly Ala Ala
225                 230                 235                 240

Glu Lys Ser Ile Thr Ile Leu Ser Thr Pro Glu Gly Thr Ser Ala Ala
                245                 250                 255

Cys Lys Ser Ile Leu Glu Ile Met His Lys Glu Ala Gln Asp Ile Lys
            260                 265                 270

Phe Thr Glu Glu Ile Pro Leu Lys Ile Leu Ala His Asn Asn Phe Val
        275                 280                 285

Gly Arg Leu Ile Gly Lys Glu Gly Arg Asn Leu Lys Lys Ile Glu Gln
```

-continued

```
    290                 295                 300

Asp Thr Asp Thr Lys Ile Thr Ile Ser Pro Leu Gln Glu Leu Thr Leu
305                 310                 315                 320

Tyr Asn Pro Glu Arg Thr Ile Thr Val Lys Gly Asn Val Glu Thr Cys
                325                 330                 335

Ala Lys Ala Glu Glu Glu Ile Met Lys Lys Ile Arg Glu Ser Tyr Glu
            340                 345                 350

Asn Asp Ile Ala Ser Met Asn Leu Gln Ala His Leu Ile Pro Gly Leu
        355                 360                 365

Asn Leu Asn Ala Leu Gly Leu Phe Pro Pro Thr Ser Gly Met Pro Pro
    370                 375                 380

Pro Thr Ser Gly Pro Pro Ser Ala Met Thr Pro Pro Tyr Pro Gln Phe
385                 390                 395                 400

Glu Gln Ser Glu Thr Glu Thr Val His Leu Phe Ile Pro Ala Leu Ser
                405                 410                 415

Val Gly Ala Ile Ile Gly Lys Gln Gly Gln His Ile Lys Gln Leu Ser
            420                 425                 430

Arg Phe Ala Gly Ala Ser Ile Lys Ile Ala Pro Ala Glu Ala Pro Asp
        435                 440                 445

Ala Lys Val Arg Met Val Ile Ile Thr Gly Pro Pro Glu Ala Gln Phe
    450                 455                 460

Lys Ala Gln Gly Arg Ile Tyr Gly Lys Ile Lys Glu Glu Asn Phe Val
465                 470                 475                 480

Ser Pro Lys Glu Glu Val Lys Leu Glu Ala His Ile Arg Val Pro Ser
                485                 490                 495

Phe Ala Ala Gly Arg Val Ile Gly Lys Gly Gly Lys Thr Val Asn Glu
            500                 505                 510

Leu Gln Asn Leu Ser Ser Ala Glu Val Val Val Pro Arg Asp Gln Thr
        515                 520                 525

Pro Asp Glu Asn Asp Gln Val Val Val Lys Ile Thr Gly His Phe Tyr
    530                 535                 540

Ala Cys Gln Val Ala Gln Arg Lys Ile Gln Glu Ile Leu Thr Gln Val
545                 550                 555                 560

Lys Gln His Gln Gln Gln Lys Ala Leu Gln Ser Gly Pro Pro Gln Ser
                565                 570                 575

Arg Arg Lys
```

<210> SEQ ID NO 349
<211> LENGTH: 207
<212> TYPE: DNA
<213> ORGANISM: Homo sapiens

<400> SEQUENCE: 349

```
atgtggcagc ccctcttctt caagtggctc ttgtcctgtt gccctgggag ttctcaaatt      60

gctgcagcag cctccaccca gcctgaggat gacatcaata cacagaggaa gaagagtcag     120

gaaaagatga gagaagttac agactctcct gggcgacccc gagagcttac cattcctcag     180

acttcttcac atggtgctaa cagattt                                          207
```

<210> SEQ ID NO 350
<211> LENGTH: 69
<212> TYPE: PRT
<213> ORGANISM: Homo sapiens

<400> SEQUENCE: 350

-continued

```
Met Trp Gln Pro Leu Phe Phe Lys Trp Leu Leu Ser Cys Cys Pro Gly
 1               5                  10                  15

Ser Ser Gln Ile Ala Ala Ala Ala Ser Thr Gln Pro Glu Asp Asp Ile
            20                  25                  30

Asn Thr Gln Arg Lys Lys Ser Gln Glu Lys Met Arg Glu Val Thr Asp
        35                  40                  45

Ser Pro Gly Arg Pro Arg Glu Leu Thr Ile Pro Gln Thr Ser Ser His
    50                  55                  60

Gly Ala Asn Arg Phe
65


<210> SEQ ID NO 351
<211> LENGTH: 1012
<212> TYPE: DNA
<213> ORGANISM: Homo sapiens

<400> SEQUENCE: 351

ccctctagaa ataattttgt ttaactttaa gaaggagata tacatatgca tcaccatcac     60

catcacacgg ccgcgtccga taacttccag ctgtcccagg gtgggcaggg attcgccatt    120

ccgatcgggc aggcgatggc gatcgcgggc cagatcaagc ttcccaccgt tcatatcggg    180

cctaccgcct tcctcggctt gggtgttgtc gacaacaacg gcaacggcgc acgagtccaa    240

cgcgtggtcg ggagcgctcc ggcggcaagt ctcggcatct ccaccggcga cgtgatcacc    300

gcggtcgacg gcgctccgat caactcggcc accgcgatgg cggacgcgct taacgggcat    360

catcccggtg acgtcatctc ggtgacctgg caaaccaagt cgggcggcac gcgtacaggg    420

aacgtgacat tggccgaggg acccccggcc gaattcatgg attgggggac gctgcacact    480

ttcatcgggg gtgtcaacaa acactccacc agcatcggga aggtgtggat cacagtcatc    540

tttattttcc gagtcatgat cctcgtggtg gctgcccagg aagtgtgggg tgacgagcaa    600

gaggacttcg tctgcaacac actgcaaccg ggatgcaaaa atgtgtgcta tgaccacttt    660

ttcccggtgt cccacatccg gctgtgggcc ctccagctga tcttcgtctc caccccagcg    720

ctgctggtgg ccatgcatgt ggcctactac aggcacgaaa ccactcgcaa gttcaggcga    780

ggagagaaga ggaatgattt caaagacata gaggacatta aaaagcagaa ggttcggata    840

gaggggtgac tcgagcacca ccaccaccac cactgagatc cggctgctaa caaagcccga    900

aaggaagctg agttggctgc tgccaccgct gagcaataac tagcataacc ccttggggcc    960

tctaaacggg tcttgagggg ttttttgctg aaaggaggaa ctatatccgg at           1012


<210> SEQ ID NO 352
<211> LENGTH: 267
<212> TYPE: PRT
<213> ORGANISM: Homo sapiens

<400> SEQUENCE: 352

Met His His His His His His Thr Ala Ala Ser Asp Asn Phe Gln Leu
 1               5                  10                  15

Ser Gln Gly Gly Gln Gly Phe Ala Ile Pro Ile Gly Gln Ala Met Ala
            20                  25                  30

Ile Ala Gly Gln Ile Lys Leu Pro Thr Val His Ile Gly Pro Thr Ala
        35                  40                  45

Phe Leu Gly Leu Gly Val Val Asp Asn Asn Gly Asn Gly Ala Arg Val
    50                  55                  60

Gln Arg Val Val Gly Ser Ala Pro Ala Ala Ser Leu Gly Ile Ser Thr
65                  70                  75                  80
```

-continued

```
Gly Asp Val Ile Thr Ala Val Asp Gly Ala Pro Ile Asn Ser Ala Thr
                85                  90                  95

Ala Met Ala Asp Ala Leu Asn Gly His His Pro Gly Asp Val Ile Ser
            100                 105                 110

Val Thr Trp Gln Thr Lys Ser Gly Gly Thr Arg Thr Gly Asn Val Thr
        115                 120                 125

Leu Ala Glu Gly Pro Pro Ala Glu Phe Met Asp Trp Gly Thr Leu His
    130                 135                 140

Thr Phe Ile Gly Gly Val Asn Lys His Ser Thr Ser Ile Gly Lys Val
145                 150                 155                 160

Trp Ile Thr Val Ile Phe Ile Phe Arg Val Met Ile Leu Val Val Ala
                165                 170                 175

Ala Gln Glu Val Trp Gly Asp Glu Gln Glu Asp Phe Val Cys Asn Thr
            180                 185                 190

Leu Gln Pro Gly Cys Lys Asn Val Cys Tyr Asp His Phe Phe Pro Val
        195                 200                 205

Ser His Ile Arg Leu Trp Ala Leu Gln Leu Ile Phe Val Ser Thr Pro
    210                 215                 220

Ala Leu Leu Val Ala Met His Val Ala Tyr Tyr Arg His Glu Thr Thr
225                 230                 235                 240

Arg Lys Phe Arg Arg Gly Glu Lys Arg Asn Asp Phe Lys Asp Ile Glu
                245                 250                 255

Asp Ile Lys Lys Gln Lys Val Arg Ile Glu Gly
            260                 265
```

<210> SEQ ID NO 353
<211> LENGTH: 900
<212> TYPE: DNA
<213> ORGANISM: Homo sapiens

<400> SEQUENCE: 353

```
atgcatcacc atcaccatca cacggccgcg tccgataact tccagctgtc ccagggtggg     60

cagggattcg ccattccgat cgggcaggcg atggcgatcg cgggccagat caagcttccc    120

accgttcata tcgggcctac cgccttcctc ggcttgggtg ttgtcgacaa caacggcaac    180

ggcgcacgag tccaacgcgt ggtcgggagc gctccggcgg caagtctcgg catctccacc    240

ggcgacgtga tcaccgcggt cgacggcgct ccgatcaact cggccaccgc gatggcggac    300

gcgcttaacg ggcatcatcc cggtgacgtc atctcggtga cctggcaaac caagtcgggc    360

ggcacgcgta cagggaacgt gacattggcc gagggacccc cggccgaatt ccacgaaacc    420

actcgcaagt tcaggcgagg agagaagagg aatgatttca aagacataga ggacattaaa    480

aagcagaagg ttcggataga ggggtcgctg tggtggacgt acaccagcag catctttttc    540

cgaatcatct ttgaagcagc ctttatgtat gtgttttact tcctttacaa tgggtaccac    600

ctgccctggg tgttgaaatg tgggattgac ccctgcccca accttgttga ctgctttatt    660

tctaggccaa cagagaagac cgtgtttacc atttttatga tttctgcgtc tgtgatttgc    720

atgctgctta acgtggcaga gttgtgctac ctgctgctga aagtgtgttt taggagatca    780

aagagagcac agacgcaaaa aaatcacccc aatcatgccc taaaggagag taagcagaat    840

gaaatgaatg agctgatttc agatagtggt caaaatgcaa tcacaggttt cccaagctaa    900
```

<210> SEQ ID NO 354
<211> LENGTH: 299
<212> TYPE: PRT

-continued

<213> ORGANISM: Homo sapiens

<400> SEQUENCE: 354

```
Met His His His His His His Thr Ala Ala Ser Asp Asn Phe Gln Leu
 1               5                  10                  15

Ser Gln Gly Gly Gln Gly Phe Ala Ile Pro Ile Gly Gln Ala Met Ala
            20                  25                  30

Ile Ala Gly Gln Ile Lys Leu Pro Thr Val His Ile Gly Pro Thr Ala
        35                  40                  45

Phe Leu Gly Leu Gly Val Val Asp Asn Asn Gly Asn Gly Ala Arg Val
    50                  55                  60

Gln Arg Val Val Gly Ser Ala Pro Ala Ala Ser Leu Gly Ile Ser Thr
65                  70                  75                  80

Gly Asp Val Ile Thr Ala Val Asp Gly Ala Pro Ile Asn Ser Ala Thr
                85                  90                  95

Ala Met Ala Asp Ala Leu Asn Gly His His Pro Gly Asp Val Ile Ser
            100                 105                 110

Val Thr Trp Gln Thr Lys Ser Gly Gly Thr Arg Thr Gly Asn Val Thr
        115                 120                 125

Leu Ala Glu Gly Pro Pro Ala Glu Phe His Glu Thr Thr Arg Lys Phe
    130                 135                 140

Arg Arg Gly Glu Lys Arg Asn Asp Phe Lys Asp Ile Glu Asp Ile Lys
145                 150                 155                 160

Lys Gln Lys Val Arg Ile Glu Gly Ser Leu Trp Trp Thr Tyr Thr Ser
                165                 170                 175

Ser Ile Phe Phe Arg Ile Ile Phe Glu Ala Ala Phe Met Tyr Val Phe
            180                 185                 190

Tyr Phe Leu Tyr Asn Gly Tyr His Leu Pro Trp Val Leu Lys Cys Gly
        195                 200                 205

Ile Asp Pro Cys Pro Asn Leu Val Asp Cys Phe Ile Ser Arg Pro Thr
    210                 215                 220

Glu Lys Thr Val Phe Thr Ile Phe Met Ile Ser Ala Ser Val Ile Cys
225                 230                 235                 240

Met Leu Leu Asn Val Ala Glu Leu Cys Tyr Leu Leu Leu Lys Val Cys
                245                 250                 255

Phe Arg Arg Ser Lys Arg Ala Gln Thr Gln Lys Asn His Pro Asn His
            260                 265                 270

Ala Leu Lys Glu Ser Lys Gln Asn Glu Met Asn Glu Leu Ile Ser Asp
        275                 280                 285

Ser Gly Gln Asn Ala Ile Thr Gly Phe Pro Ser
    290                 295
```

<210> SEQ ID NO 355
<211> LENGTH: 24
<212> TYPE: DNA
<213> ORGANISM: Artificial Sequence
<220> FEATURE:
<223> OTHER INFORMATION: PCR primer

<400> SEQUENCE: 355

```
ggagtacagc ttcaagacaa tggg                                            24
```

<210> SEQ ID NO 356
<211> LENGTH: 31
<212> TYPE: DNA
<213> ORGANISM: Artificial Sequence
<220> FEATURE:

<223> OTHER INFORMATION: PCR primer

<400> SEQUENCE: 356
ccatgggaat tcattataat aattttgttc c 31

<210> SEQ ID NO 357
<211> LENGTH: 920
<212> TYPE: PRT
<213> ORGANISM: Homo sapiens

<400> SEQUENCE: 357

```
Met Gln His His His His His His Gly Val Gln Leu Gln Asp Asn Gly
 1               5                  10                  15

Tyr Asn Gly Leu Leu Ile Ala Ile Asn Pro Gln Val Pro Glu Asn Gln
            20                  25                  30

Asn Leu Ile Ser Asn Ile Lys Glu Met Ile Thr Glu Ala Ser Phe Tyr
        35                  40                  45

Leu Phe Asn Ala Thr Lys Arg Arg Val Phe Phe Arg Asn Ile Lys Ile
    50                  55                  60

Leu Ile Pro Ala Thr Trp Lys Ala Asn Asn Asn Ser Lys Ile Lys Gln
65                  70                  75                  80

Glu Ser Tyr Glu Lys Ala Asn Val Ile Val Thr Asp Trp Tyr Gly Ala
                85                  90                  95

His Gly Asp Asp Pro Tyr Thr Leu Gln Tyr Arg Gly Cys Gly Lys Glu
            100                 105                 110

Gly Lys Tyr Ile His Phe Thr Pro Asn Phe Leu Leu Asn Asp Asn Leu
        115                 120                 125

Thr Ala Gly Tyr Gly Ser Arg Gly Arg Val Phe Val His Glu Trp Ala
    130                 135                 140

His Leu Arg Trp Gly Val Phe Asp Glu Tyr Asn Asn Asp Lys Pro Phe
145                 150                 155                 160

Tyr Ile Asn Gly Gln Asn Gln Ile Lys Val Thr Arg Cys Ser Ser Asp
                165                 170                 175

Ile Thr Gly Ile Phe Val Cys Glu Lys Gly Pro Cys Pro Gln Glu Asn
            180                 185                 190

Cys Ile Ile Ser Lys Leu Phe Lys Glu Gly Cys Thr Phe Ile Tyr Asn
        195                 200                 205

Ser Thr Gln Asn Ala Thr Ala Ser Ile Met Phe Met Gln Ser Leu Ser
    210                 215                 220

Ser Val Val Glu Phe Cys Asn Ala Ser Thr His Asn Gln Glu Ala Pro
225                 230                 235                 240

Asn Leu Gln Asn Gln Met Cys Ser Leu Arg Ser Ala Trp Asp Val Ile
                245                 250                 255

Thr Asp Ser Ala Asp Phe His His Ser Phe Pro Met Asn Gly Thr Glu
            260                 265                 270

Leu Pro Pro Pro Pro Thr Phe Ser Leu Val Glu Ala Gly Asp Lys Val
        275                 280                 285

Val Cys Leu Val Leu Asp Val Ser Ser Lys Met Ala Glu Ala Asp Arg
    290                 295                 300

Leu Leu Gln Leu Gln Gln Ala Ala Glu Phe Tyr Leu Met Gln Ile Val
305                 310                 315                 320

Glu Ile His Thr Phe Val Gly Ile Ala Ser Phe Asp Ser Lys Gly Glu
                325                 330                 335

Ile Arg Ala Gln Leu His Gln Ile Asn Ser Asn Asp Asp Arg Lys Leu
            340                 345                 350
```

-continued

```
Leu Val Ser Tyr Leu Pro Thr Thr Val Ser Ala Lys Thr Asp Ile Ser
        355                 360                 365

Ile Cys Ser Gly Leu Lys Lys Gly Phe Glu Val Val Glu Lys Leu Asn
    370                 375                 380

Gly Lys Ala Tyr Gly Ser Val Met Ile Leu Val Thr Ser Gly Asp Asp
385                 390                 395                 400

Lys Leu Leu Gly Asn Cys Leu Pro Thr Val Leu Ser Ser Gly Ser Thr
                405                 410                 415

Ile His Ser Ile Ala Leu Gly Ser Ser Ala Ala Pro Asn Leu Glu Glu
            420                 425                 430

Leu Ser Arg Leu Thr Gly Gly Leu Lys Phe Phe Val Pro Asp Ile Ser
        435                 440                 445

Asn Ser Asn Ser Met Ile Asp Ala Phe Ser Arg Ile Ser Ser Gly Thr
    450                 455                 460

Gly Asp Ile Phe Gln Gln His Ile Gln Leu Glu Ser Thr Gly Glu Asn
465                 470                 475                 480

Val Lys Pro His His Gln Leu Lys Asn Thr Val Thr Val Asp Asn Thr
                485                 490                 495

Val Gly Asn Asp Thr Met Phe Leu Val Thr Trp Gln Ala Ser Gly Pro
            500                 505                 510

Pro Glu Ile Ile Leu Phe Asp Pro Asp Gly Arg Lys Tyr Tyr Thr Asn
        515                 520                 525

Asn Phe Ile Thr Asn Leu Thr Phe Arg Thr Ala Ser Leu Trp Ile Pro
    530                 535                 540

Gly Thr Ala Lys Pro Gly His Trp Thr Tyr Thr Leu Asn Asn Thr His
545                 550                 555                 560

His Ser Leu Gln Ala Leu Lys Val Thr Val Thr Ser Arg Ala Ser Asn
                565                 570                 575

Ser Ala Val Pro Pro Ala Thr Val Glu Ala Phe Val Glu Arg Asp Ser
            580                 585                 590

Leu His Phe Pro His Pro Val Met Ile Tyr Ala Asn Val Lys Gln Gly
        595                 600                 605

Phe Tyr Pro Ile Leu Asn Ala Thr Val Thr Ala Thr Val Glu Pro Glu
    610                 615                 620

Thr Gly Asp Pro Val Thr Leu Arg Leu Leu Asp Asp Gly Ala Gly Ala
625                 630                 635                 640

Asp Val Ile Lys Asn Asp Gly Ile Tyr Ser Arg Tyr Phe Phe Ser Phe
                645                 650                 655

Ala Ala Asn Gly Arg Tyr Ser Leu Lys Val His Val Asn His Ser Pro
            660                 665                 670

Ser Ile Ser Thr Pro Ala His Ser Ile Pro Gly Ser His Ala Met Tyr
        675                 680                 685

Val Pro Gly Tyr Thr Ala Asn Gly Asn Ile Gln Met Asn Ala Pro Arg
    690                 695                 700

Lys Ser Val Gly Arg Asn Glu Glu Glu Arg Lys Trp Gly Phe Ser Arg
705                 710                 715                 720

Val Ser Ser Gly Gly Ser Phe Ser Val Leu Gly Val Pro Ala Gly Pro
                725                 730                 735

His Pro Asp Val Phe Pro Pro Cys Lys Ile Ile Asp Leu Glu Ala Val
            740                 745                 750

Lys Val Glu Glu Glu Leu Thr Leu Ser Trp Thr Ala Pro Gly Glu Asp
        755                 760                 765
```

-continued

```
Phe Asp Gln Gly Gln Ala Thr Ser Tyr Glu Ile Arg Met Ser Lys Ser
    770                 775                 780

Leu Gln Asn Ile Gln Asp Asp Phe Asn Asn Ala Ile Leu Val Asn Thr
785                 790                 795                 800

Ser Lys Arg Asn Pro Gln Gln Ala Gly Ile Arg Glu Ile Phe Thr Phe
                805                 810                 815

Ser Pro Gln Ile Ser Thr Asn Gly Pro Glu His Gln Pro Asn Gly Glu
            820                 825                 830

Thr His Glu Ser His Arg Ile Tyr Val Ala Ile Arg Ala Met Asp Arg
        835                 840                 845

Asn Ser Leu Gln Ser Ala Val Ser Asn Ile Ala Gln Ala Pro Leu Phe
    850                 855                 860

Ile Pro Pro Asn Ser Asp Pro Val Pro Ala Arg Asp Tyr Leu Ile Leu
865                 870                 875                 880

Lys Gly Val Leu Thr Ala Met Gly Leu Ile Gly Ile Ile Cys Leu Ile
                885                 890                 895

Ile Val Val Thr His His Thr Leu Ser Arg Lys Lys Arg Ala Asp Lys
            900                 905                 910

Lys Glu Asn Gly Thr Lys Leu Leu
        915                 920
```

<210> SEQ ID NO 358
<211> LENGTH: 2773
<212> TYPE: DNA
<213> ORGANISM: Homo sapiens

<400> SEQUENCE: 358

```
catatgcagc atcaccacca tcaccacgga gtacagcttc aagacaatgg gtataatgga     60

ttgctcattg caattaatcc tcaggtacct gagaatcaga acctcatctc aaacattaag    120

gaaatgataa ctgaagcttc attttaccta tttaatgcta ccaagagaag agtatttttc    180

agaaatataa agattttaat acctgccaca tggaaagcta ataataacag caaaataaaa    240

caagaatcat atgaaaaggc aaatgtcata gtgactgact ggtatggggc acatggagat    300

gatccataca ccctacaata cagagggtgt ggaaaagagg gaaaatacat tcatttcaca    360

cctaatttcc tactgaatga taacttaaca gctggctacg gatcacgagg ccgagtgttt    420

gtccatgaat gggcccacct ccgttggggt gtgttcgatg agtataacaa tgacaaacct    480

ttctacataa atgggcaaaa tcaaattaaa gtgacaaggt gttcatctga catcacaggc    540

atttttgtgt gtgaaaaagg tccttgcccc caagaaaact gtattattag taagcttttt    600

aaagaaggat gcacctttat ctacaatagc acccaaaatg caactgcatc aataatgttc    660

atgcaaagtt tatcttctgt ggttgaattt tgtaatgcaa gtacccacaa ccaagaagca    720

ccaaacctac agaaccagat gtgcagcctc agaagtgcat gggatgtaat cacagactct    780

gctgactttc accacagctt tcccatgaac gggactgagc ttccacctcc tcccacattc    840

tcgcttgtag aggctggtga caaagtggtc tgtttagtgc tggatgtgtc cagcaagatg    900

gcagaggctg acagactcct tcaactacaa caagccgcag aattttattt gatgcagatt    960

gttgaaattc ataccttcgt gggcattgcc agtttcgaca gcaaaggaga gatcagagcc   1020

cagctacacc aaattaacag caatgatgat cgaaagttgc tggtttcata tctgcccacc   1080

actgtatcag ctaaaacaga catcagcatt tgttcagggc ttaagaaagg atttgaggtg   1140

gttgaaaaac tgaatggaaa agcttatggc tctgtgatga tattagtgac cagcggagat   1200

gataagcttc ttggcaattg cttacccact gtgctcagca gtggttcaac aattcactcc   1260
```

-continued

```
attgccctgg gttcatctgc agccccaaat ctggaggaat tatcacgtct tacaggaggt   1320
ttaaagttct ttgttccaga tatatcaaac tccaatagca tgattgatgc tttcagtaga   1380
atttcctctg gaactggaga cattttccag caacatattc agcttgaaag tacaggtgaa   1440
aatgtcaaac ctcaccatca attgaaaaac acagtgactg tggataatac tgtgggcaac   1500
gacactatgt ttctagttac gtggcaggcc agtggtcctc ctgagattat attatttgat   1560
cctgatggac gaaaatacta cacaaataat tttatcacca atctaacttt tcggacagct   1620
agtctttgga ttccaggaac agctaagcct gggcactgga cttacaccct gaacaatacc   1680
catcattctc tgcaagccct gaaagtgaca gtgacctctc gcgcctccaa ctcagctgtg   1740
cccccagcca ctgtggaagc ctttgtggaa agagacagcc tccattttcc tcatcctgtg   1800
atgatttatg ccaatgtgaa acagggattt tatcccattc ttaatgccac tgtcactgcc   1860
acagttgagc cagagactgg agatcctgtt acgctgagac tccttgatga tggagcaggt   1920
gctgatgtta taaaaaatga tggaatttac tcgaggtatt ttttctcctt tgctgcaaat   1980
ggtagatata gcttgaaagt gcatgtcaat cactctccca gcataagcac cccagcccac   2040
tctattccag ggagtcatgc tatgtatgta ccaggttaca cagcaaacgg taatattcag   2100
atgaatgctc caaggaaatc agtaggcaga aatgaggagg agcgaaagtg gggctttagc   2160
cgagtcagct caggaggctc cttttcagtg ctgggagttc cagctggccc ccaccctgat   2220
gtgtttccac catgcaaaat tattgacctg gaagctgtaa aagtagaaga ggaattgacc   2280
ctatcttgga cagcacctgg agaagacttt gatcagggcc aggctacaag ctatgaaata   2340
agaatgagta aaagtctaca gaatatccaa gatgacttta acaatgctat tttagtaaat   2400
acatcaaagc gaaatcctca gcaagctggc atcagggaga tatttacgtt ctcaccccaa   2460
atttccacga atggacctga acatcagcca aatggagaaa cacatgaaag ccacagaatt   2520
tatgttgcaa tacgagcaat ggataggaac tccttacagt ctgctgtatc taacattgcc   2580
caggcgcctc tgtttattcc ccccaattct gatcctgtac ctgccagaga ttatcttata   2640
ttgaaaggag ttttaacagc aatgggtttg ataggaatca tttgccttat tatagttgtg   2700
acacatcata ctttaagcag gaaaaagaga gcagacaaga aagagaatgg aacaaaatta   2760
ttataatgaa ttc                                                      2773
```

<210> SEQ ID NO 359
<211> LENGTH: 25
<212> TYPE: DNA
<213> ORGANISM: Artificial Sequence
<220> FEATURE:
<223> OTHER INFORMATION: PCR primer

<400> SEQUENCE: 359

```
tggcagcccc tcttcttcaa gtggc                                           25
```

<210> SEQ ID NO 360
<211> LENGTH: 33
<212> TYPE: DNA
<213> ORGANISM: Artificial Sequence
<220> FEATURE:
<223> OTHER INFORMATION: PCR primer

<400> SEQUENCE: 360

```
cgccagaatt catcaaacaa atctgttagc acc                                  33
```

<210> SEQ ID NO 361

-continued

<211> LENGTH: 77
<212> TYPE: PRT
<213> ORGANISM: Homo sapiens

<400> SEQUENCE: 361

```
Met Gln His His His His His His Trp Gln Pro Leu Phe Phe Lys Trp
 1               5                  10                  15

Leu Leu Ser Cys Cys Pro Gly Ser Ser Gln Ile Ala Ala Ala Ala Ser
            20                  25                  30

Thr Gln Pro Glu Asp Asp Ile Asn Thr Gln Arg Lys Lys Ser Gln Glu
        35                  40                  45

Lys Met Arg Glu Val Thr Asp Ser Pro Gly Arg Pro Arg Glu Leu Thr
    50                  55                  60

Ile Pro Gln Thr Ser Ser His Gly Ala Asn Arg Phe Val
65                  70                  75
```

<210> SEQ ID NO 362
<211> LENGTH: 244
<212> TYPE: DNA
<213> ORGANISM: Homo sapiens

<400> SEQUENCE: 362

```
catatgcagc atcaccacca tcaccactgg cagcccctct tcttcaagtg gctcttgtcc     60

tgttgccctg ggagttctca aattgctgca gcagcctcca cccagcctga ggatgacatc    120

aatacacaga ggaagaagag tcaggaaaag atgagagaag ttacagactc tcctgggcga    180

ccccgagagc ttaccattcc tcagacttct tcacatggtg ctaacagatt tgtttgatga    240

attc                                                                 244
```

<210> SEQ ID NO 363
<211> LENGTH: 20
<212> TYPE: PRT
<213> ORGANISM: Homo sapiens

<400> SEQUENCE: 363

```
Met Trp Gln Pro Leu Phe Phe Lys Trp Leu Leu Ser Cys Cys Pro Gly
 1               5                  10                  15

Ser Ser Gln Ile
            20
```

<210> SEQ ID NO 364
<211> LENGTH: 60
<212> TYPE: DNA
<213> ORGANISM: Homo sapiens

<400> SEQUENCE: 364

```
atgtggcagc ccctcttctt caagtggctc ttgtcctgtt gccctgggag ttctcaaatt     60
```

<210> SEQ ID NO 365
<211> LENGTH: 20
<212> TYPE: PRT
<213> ORGANISM: Homo sapiens

<400> SEQUENCE: 365

```
Gly Ser Ser Gln Ile Ala Ala Ala Ala Ser Thr Gln Pro Glu Asp Asp
 1               5                  10                  15

Ile Asn Thr Gln
            20
```

<210> SEQ ID NO 366

-continued

<211> LENGTH: 60
<212> TYPE: DNA
<213> ORGANISM: Homo sapiens

<400> SEQUENCE: 366
gggagttctc aaattgctgc agcagcctcc acccagcctg aggatgacat caatacacag 60

<210> SEQ ID NO 367
<211> LENGTH: 20
<212> TYPE: PRT
<213> ORGANISM: Homo sapiens

<400> SEQUENCE: 367

Lys Pro Gly His Trp Thr Tyr Thr Leu Asn Asn Thr His His Ser Leu
1 5 10 15

Gln Ala Leu Lys
20

<210> SEQ ID NO 368
<211> LENGTH: 2343
<212> TYPE: DNA
<213> ORGANISM: Homo sapiens

<400> SEQUENCE: 368
attccggagc gtttgcggct tcgcttcatg gccgctctcc cgcccctcct gggatctgtg 60
gggagctggg gagcccgcag cggcccggag ccggagctgg cgagccgagc ggagacctgt 120
gcgccgcgcc tctgaggcgc agcatgtgaa gcggagacgg catccagtgg ggggcgagcc 180
tctcagccgg ccgggatggc taccacggcc gagctcttcg aggagccttt tgtggcagat 240
gaatatattg aacgtcttgt atggagaacc ccaggaggag gctctagagg tggacctgaa 300
gcttttgatc ctaaaagatt attagaagaa tttgtaaatc atattcagga actccagata 360
atggatgaaa ggattcagag gaaagtagag aaactagagc aacaatgtca gaaagaagcc 420
aaggaatttg ccaagaaggt acaagagctg cagaaaagca atcaggttgc cttccaacat 480
ttccaagaac tagatgagca cattagctat gtagcaacta aagtctgtca ccttggagac 540
cagttagagg gggtaaacac acccagacaa cgggcagtgg aggctcagaa attgatgaaa 600
tactttaatg agtttctaga tggagaattg aaatctgatg tttttacaaa ttctgaaaag 660
ataaaggaag cagcagacat cattcagaag ttgcacctaa ttgcccaaga gttacctttt 720
gatagatttt cagaagttaa atccaaaatt gcaagtaaat accatgattt agaatgccag 780
ctgattcagg agtttaccag tgctcaaaga agaggtgaaa tctccagaat gagagaagta 840
gcagcagttt tacttcattt taagggttat tcccattgtg ttgatgttta tataaagcag 900
tgccaggagg gtgcttattt gagaaatgat atatttgaag acgctggaat actctgtcaa 960
agagtgaaca aacaagttgg agatatcttc agtaatccag aaacagtcct ggctaaactt 1020
attcaaaatg tatttgaaat caaactacag agttttgtga aagagcagtt agaagaatgt 1080
aggaagtccg atgcagagca atatctcaaa aatctctatg atctgtatac aagaaccacc 1140
aatctttcca gcaagctgat ggagtttaat ttaggtactg ataaacagac tttcttgtct 1200
aagcttatca aatccatttt catttcctat ttggagaact atattgaggt ggagactgga 1260
tatttgaaaa gcagaagtgc tatgatccta cagcgctatt atgattcgaa aaaccatcaa 1320
aagagatcca ttggcacagg aggtattcaa gatttgaagg aaagaattag acagcgtacc 1380
aacttaccac ttgggccaag tatcgatact catggggaga cttttctatc ccaagaagtg 1440
gtggttaatc ttttacaaga aaccaaacaa gcctttgaaa gatgtcatag gctctctgat 1500

-continued ccttctgact taccaaggaa tgccttcaga atttttacca ttcttgtgga atttttatgt 1560
attgagcata ttgattatgc tttggaaaca ggacttgctg gaattccctc ttcagattct 1620
aggaatgcaa atctttattt tttggacgtt gtgcaacagg ccaatactat ttttcatctt 1680
tttgacaaac agtttaatga tcaccttatg ccactaataa gctcttctcc taagttatct 1740
gaatgccttc agaagaaaaa agaaataatt gaacaaatgg agatgaaatt ggatactggc 1800
attgatagga cattaaattg tatgattgga cagatgaagc atattttggc tgcagaacag 1860
aagaaaacag attttaagcc agaagatgaa aacaatgttt tgattcaata tactaatgcc 1920
tgtgtaaaag tctgtgctta cgtaagaaaa caagtggaga agattaaaaa ttccatggat 1980
gggaagaatg tggatacagt tttgatggaa cttggagtac gttttcatcg acttatctat 2040
gagcatcttc aacaatattc ctacagttgt atgggtggca tgttggccat ttgtgatgta 2100
gccgaatata ggaagtgtgc caaagacttc aagattccaa tggtattaca tctttttgat 2160
actctgcatg ctctttgcaa tcttctggta gttgccccag ataatttaaa gcaagtctgc 2220
tcaggagaac aacttgctaa tctggacaag aatatacttc actccttcgt acaacttcgt 2280
gctgattata gatctgcccg ccttgctcga cacttcagct gagattgaat ttacaaagga 2340
att 2343

<210> SEQ ID NO 369
<211> LENGTH: 708
<212> TYPE: PRT
<213> ORGANISM: Homo sapiens

<400> SEQUENCE: 369

Met Ala Thr Thr Ala Glu Leu Phe Glu Glu Pro Phe Val Ala Asp Glu
1 5 10 15

Tyr Ile Glu Arg Leu Val Trp Arg Thr Pro Gly Gly Gly Ser Arg Gly
20 25 30

Gly Pro Glu Ala Phe Asp Pro Lys Arg Leu Leu Glu Glu Phe Val Asn
35 40 45

His Ile Gln Glu Leu Gln Ile Met Asp Glu Arg Ile Gln Arg Lys Val
50 55 60

Glu Lys Leu Glu Gln Gln Cys Gln Lys Glu Ala Lys Glu Phe Ala Lys
65 70 75 80

Lys Val Gln Glu Leu Gln Lys Ser Asn Gln Val Ala Phe Gln His Phe
85 90 95

Gln Glu Leu Asp Glu His Ile Ser Tyr Val Ala Thr Lys Val Cys His
100 105 110

Leu Gly Asp Gln Leu Glu Gly Val Asn Thr Pro Arg Gln Arg Ala Val
115 120 125

Glu Ala Gln Lys Leu Met Lys Tyr Phe Asn Glu Phe Leu Asp Gly Glu
130 135 140

Leu Lys Ser Asp Val Phe Thr Asn Ser Glu Lys Ile Lys Glu Ala Ala
145 150 155 160

Asp Ile Ile Gln Lys Leu His Leu Ile Ala Gln Glu Leu Pro Phe Asp
165 170 175

Arg Phe Ser Glu Val Lys Ser Lys Ile Ala Ser Lys Tyr His Asp Leu
180 185 190

Glu Cys Gln Leu Ile Gln Glu Phe Thr Ser Ala Gln Arg Arg Gly Glu
195 200 205

Ile Ser Arg Met Arg Glu Val Ala Ala Val Leu Leu His Phe Lys Gly

-continued

```
    210                 215                 220

Tyr Ser His Cys Val Asp Val Tyr Ile Lys Gln Cys Gln Glu Gly Ala
225                 230                 235                 240

Tyr Leu Arg Asn Asp Ile Phe Glu Asp Ala Gly Ile Leu Cys Gln Arg
                245                 250                 255

Val Asn Lys Gln Val Gly Asp Ile Phe Ser Asn Pro Glu Thr Val Leu
            260                 265                 270

Ala Lys Leu Ile Gln Asn Val Phe Glu Ile Lys Leu Gln Ser Phe Val
        275                 280                 285

Lys Glu Gln Leu Glu Glu Cys Arg Lys Ser Asp Ala Glu Gln Tyr Leu
    290                 295                 300

Lys Asn Leu Tyr Asp Leu Tyr Thr Arg Thr Thr Asn Leu Ser Ser Lys
305                 310                 315                 320

Leu Met Glu Phe Asn Leu Gly Thr Asp Lys Gln Thr Phe Leu Ser Lys
                325                 330                 335

Leu Ile Lys Ser Ile Phe Ile Ser Tyr Leu Glu Asn Tyr Ile Glu Val
            340                 345                 350

Glu Thr Gly Tyr Leu Lys Ser Arg Ser Ala Met Ile Leu Gln Arg Tyr
        355                 360                 365

Tyr Asp Ser Lys Asn His Gln Lys Arg Ser Ile Gly Thr Gly Gly Ile
    370                 375                 380

Gln Asp Leu Lys Glu Arg Ile Arg Gln Arg Thr Asn Leu Pro Leu Gly
385                 390                 395                 400

Pro Ser Ile Asp Thr His Gly Glu Thr Phe Leu Ser Gln Glu Val Val
                405                 410                 415

Val Asn Leu Leu Gln Glu Thr Lys Gln Ala Phe Glu Arg Cys His Arg
            420                 425                 430

Leu Ser Asp Pro Ser Asp Leu Pro Arg Asn Ala Phe Arg Ile Phe Thr
        435                 440                 445

Ile Leu Val Glu Phe Leu Cys Ile Glu His Ile Asp Tyr Ala Leu Glu
    450                 455                 460

Thr Gly Leu Ala Gly Ile Pro Ser Ser Asp Ser Arg Asn Ala Asn Leu
465                 470                 475                 480

Tyr Phe Leu Asp Val Val Gln Gln Ala Asn Thr Ile Phe His Leu Phe
                485                 490                 495

Asp Lys Gln Phe Asn Asp His Leu Met Pro Leu Ile Ser Ser Ser Pro
            500                 505                 510

Lys Leu Ser Glu Cys Leu Gln Lys Lys Lys Glu Ile Ile Glu Gln Met
        515                 520                 525

Glu Met Lys Leu Asp Thr Gly Ile Asp Arg Thr Leu Asn Cys Met Ile
    530                 535                 540

Gly Gln Met Lys His Ile Leu Ala Ala Glu Gln Lys Lys Thr Asp Phe
545                 550                 555                 560

Lys Pro Glu Asp Glu Asn Asn Val Leu Ile Gln Tyr Thr Asn Ala Cys
                565                 570                 575

Val Lys Val Cys Ala Tyr Val Arg Lys Gln Val Glu Lys Ile Lys Asn
            580                 585                 590

Ser Met Asp Gly Lys Asn Val Asp Thr Val Leu Met Glu Leu Gly Val
        595                 600                 605

Arg Phe His Arg Leu Ile Tyr Glu His Leu Gln Gln Tyr Ser Tyr Ser
    610                 615                 620

Cys Met Gly Gly Met Leu Ala Ile Cys Asp Val Ala Glu Tyr Arg Lys
625                 630                 635                 640
```

-continued

```
Cys Ala Lys Asp Phe Lys Ile Pro Met Val Leu His Leu Phe Asp Thr
            645                 650                 655

Leu His Ala Leu Cys Asn Leu Leu Val Val Ala Pro Asp Asn Leu Lys
        660                 665                 670

Gln Val Cys Ser Gly Glu Gln Leu Ala Asn Leu Asp Lys Asn Ile Leu
    675                 680                 685

His Ser Phe Val Gln Leu Arg Ala Asp Tyr Arg Ser Ala Arg Leu Ala
    690                 695                 700

Arg His Phe Ser
705
```

<210> SEQ ID NO 370
<211> LENGTH: 60
<212> TYPE: DNA
<213> ORGANISM: Homo sapiens

<400> SEQUENCE: 370
gtcaatcact ctcccagcat aagcacccca gcccactcta ttccagggag tcatgctatg     60

<210> SEQ ID NO 371
<211> LENGTH: 60
<212> TYPE: DNA
<213> ORGANISM: Homo sapiens

<400> SEQUENCE: 371
agtagaattt cctctggaac tggagacatt ttccagcaac atattcagct tgaaagtaca     60

<210> SEQ ID NO 372
<211> LENGTH: 60
<212> TYPE: DNA
<213> ORGANISM: Homo sapiens

<400> SEQUENCE: 372
ccagagactg gagatcctgt tacgctgaga ctccttgatg atggagcagg tgctgatgtt     60

<210> SEQ ID NO 373
<211> LENGTH: 60
<212> TYPE: DNA
<213> ORGANISM: Homo sapiens

<400> SEQUENCE: 373
ttacagtctg ctgtatctaa cattgcccag gcgcctctgt ttattccccc caattctgat     60

<210> SEQ ID NO 374
<211> LENGTH: 60
<212> TYPE: DNA
<213> ORGANISM: Homo sapiens

<400> SEQUENCE: 374
gctgtgcccc cagccactgt ggaagccttt gtggaaagag acagcctcca ttttcctcat     60

<210> SEQ ID NO 375
<211> LENGTH: 60
<212> TYPE: DNA
<213> ORGANISM: Homo sapiens

<400> SEQUENCE: 375
aaaaacacag tgactgtgga taatactgtg ggcaacgaca ctatgtttct agttacgtgg     60

<210> SEQ ID NO 376
<211> LENGTH: 20

<212> TYPE: PRT
<213> ORGANISM: Homo sapiens

<400> SEQUENCE: 376

Leu Gln Ser Ala Val Ser Asn Ile Ala Gln Ala Pro Leu Phe Ile Pro
1 5 10 15

Pro Asn Ser Asp
20

<210> SEQ ID NO 377
<211> LENGTH: 20
<212> TYPE: PRT
<213> ORGANISM: Homo sapiens

<400> SEQUENCE: 377

Val Asn His Ser Pro Ser Ile Ser Thr Pro Ala His Ser Ile Pro Gly
1 5 10 15

Ser His Ala Met
20

<210> SEQ ID NO 378
<211> LENGTH: 20
<212> TYPE: PRT
<213> ORGANISM: Homo sapiens

<400> SEQUENCE: 378

Pro Glu Thr Gly Asp Pro Val Thr Leu Arg Leu Leu Asp Asp Gly Ala
1 5 10 15

Gly Ala Asp Val
20

<210> SEQ ID NO 379
<211> LENGTH: 20
<212> TYPE: PRT
<213> ORGANISM: Homo sapiens

<400> SEQUENCE: 379

Ala Val Pro Pro Ala Thr Val Glu Ala Phe Val Glu Arg Asp Ser Leu
1 5 10 15

His Phe Pro His
20

<210> SEQ ID NO 380
<211> LENGTH: 20
<212> TYPE: PRT
<213> ORGANISM: Homo sapiens

<400> SEQUENCE: 380

Ser Arg Ile Ser Ser Gly Thr Gly Asp Ile Phe Gln Gln His Ile Gln
1 5 10 15

Leu Glu Ser Thr
20

<210> SEQ ID NO 381
<211> LENGTH: 20
<212> TYPE: PRT
<213> ORGANISM: Homo sapiens

<400> SEQUENCE: 381

Lys Asn Thr Val Thr Val Asp Asn Thr Val Gly Asn Asp Thr Met Phe
1 5 10 15

Leu Val Thr Trp

-continued

20

<210> SEQ ID NO 382
<211> LENGTH: 20
<212> TYPE: PRT
<213> ORGANISM: Homo sapiens

<400> SEQUENCE: 382

Lys Pro Gly His Trp Thr Tyr Thr Leu Asn Asn Thr His His Ser Leu
1 5 10 15

Gln Ala Leu Lys
20

<210> SEQ ID NO 383
<211> LENGTH: 29
<212> TYPE: DNA
<213> ORGANISM: Artificial Sequence
<220> FEATURE:
<223> OTHER INFORMATION: PCR primer

<400> SEQUENCE: 383
cggcgaattc atggattggg ggacgctgc 29

<210> SEQ ID NO 384
<211> LENGTH: 35
<212> TYPE: DNA
<213> ORGANISM: Artificial Sequence
<220> FEATURE:
<223> OTHER INFORMATION: PCR primer

<400> SEQUENCE: 384
cggcctcgag tcacccctct atccgaacct tctgc 35

<210> SEQ ID NO 385
<211> LENGTH: 32
<212> TYPE: DNA
<213> ORGANISM: Artificial Sequence
<220> FEATURE:
<223> OTHER INFORMATION: PCR primer

<400> SEQUENCE: 385
cggcgaattc cacgaaccac tcgcaagttc ag 32

<210> SEQ ID NO 386
<211> LENGTH: 30
<212> TYPE: DNA
<213> ORGANISM: Artificial Sequence
<220> FEATURE:
<223> OTHER INFORMATION: PCR primer

<400> SEQUENCE: 386
cggctcgagt tagcttgggc ctgtgattgc 30

<210> SEQ ID NO 387
<211> LENGTH: 20
<212> TYPE: PRT
<213> ORGANISM: Homo sapiens

<400> SEQUENCE: 387

Phe Phe Lys Trp Leu Leu Ser Cys Cys Pro Gly Ser Ser Gln Ile Ala
1 5 10 15

Ala Ala Ala Ser
20

-continued

<210> SEQ ID NO 388
<211> LENGTH: 19
<212> TYPE: PRT
<213> ORGANISM: Homo sapiens

<400> SEQUENCE: 388

Leu Ser Cys Cys Pro Gly Ser Ser Gln Ile Ala Ala Ala Ser Thr Gln
1 5 10 15

Pro Glu Asp

<210> SEQ ID NO 389
<211> LENGTH: 20
<212> TYPE: PRT
<213> ORGANISM: Homo sapiens

<400> SEQUENCE: 389

Ala Ala Ala Ala Ser Thr Gln Pro Glu Asp Asp Ile Asn Thr Gln Arg
1 5 10 15

Lys Lys Ser Gln
20

<210> SEQ ID NO 390
<211> LENGTH: 20
<212> TYPE: PRT
<213> ORGANISM: Homo sapiens

<400> SEQUENCE: 390

Thr Gln Pro Glu Asp Asp Ile Asn Thr Gln Arg Lys Lys Ser Gln Glu
1 5 10 15

Lys Met Arg Glu
20

<210> SEQ ID NO 391
<211> LENGTH: 20
<212> TYPE: PRT
<213> ORGANISM: Homo sapiens

<400> SEQUENCE: 391

Asp Ile Asn Thr Gln Arg Lys Lys Ser Gln Glu Lys Met Arg Glu Val
1 5 10 15

Thr Asp Ser Pro
20

<210> SEQ ID NO 392
<211> LENGTH: 20
<212> TYPE: PRT
<213> ORGANISM: Homo sapiens

<400> SEQUENCE: 392

Arg Lys Lys Ser Gln Glu Lys Met Arg Glu Val Thr Asp Ser Pro Gly
1 5 10 15

Arg Pro Arg Glu
20

<210> SEQ ID NO 393
<211> LENGTH: 20
<212> TYPE: PRT
<213> ORGANISM: Homo sapiens

<400> SEQUENCE: 393

Glu Lys Met Arg Glu Val Thr Asp Ser Pro Gly Arg Pro Arg Glu Leu
1 5 10 15

-continued

```
Thr Ile Pro Gln
            20


<210> SEQ ID NO 394
<211> LENGTH: 20
<212> TYPE: PRT
<213> ORGANISM: Homo sapiens

<400> SEQUENCE: 394

Val Thr Asp Ser Pro Gly Arg Pro Arg Glu Leu Thr Ile Pro Gln Thr
 1               5                  10                  15

Ser Ser His Gly
            20


<210> SEQ ID NO 395
<211> LENGTH: 19
<212> TYPE: PRT
<213> ORGANISM: Homo sapiens

<400> SEQUENCE: 395

Gly Arg Pro Arg Glu Leu Thr Ile Pro Gln Thr Ser Ser His Gly Ala
 1               5                  10                  15

Asn Arg Phe


<210> SEQ ID NO 396
<211> LENGTH: 19
<212> TYPE: PRT
<213> ORGANISM: Homo sapiens

<400> SEQUENCE: 396

Met Asn Lys Leu Tyr Ile Gly Asn Leu Ser Glu Asn Ala Ala Pro Ser
 1               5                  10                  15

Asp Leu Glu


<210> SEQ ID NO 397
<211> LENGTH: 20
<212> TYPE: PRT
<213> ORGANISM: Homo sapiens

<400> SEQUENCE: 397

Ser Glu Asn Ala Ala Pro Ser Asp Leu Glu Ser Ile Phe Lys Asp Ala
 1               5                  10                  15

Lys Ile Pro Val
            20


<210> SEQ ID NO 398
<211> LENGTH: 20
<212> TYPE: PRT
<213> ORGANISM: Homo sapiens

<400> SEQUENCE: 398

Ser Ile Phe Lys Asp Ala Lys Ile Pro Val Ser Gly Pro Phe Leu Val
 1               5                  10                  15

Lys Thr Gly Tyr
            20


<210> SEQ ID NO 399
<211> LENGTH: 20
<212> TYPE: PRT
<213> ORGANISM: Homo sapiens

<400> SEQUENCE: 399
```

-continued

```
Ser Gly Pro Phe Leu Val Lys Thr Gly Tyr Ala Phe Val Asp Cys Pro
 1               5                  10                  15

Asp Glu Ser Trp
            20


<210> SEQ ID NO 400
<211> LENGTH: 20
<212> TYPE: PRT
<213> ORGANISM: Homo sapiens

<400> SEQUENCE: 400

Ala Phe Val Asp Cys Pro Asp Glu Ser Trp Ala Leu Lys Ala Ile Glu
 1               5                  10                  15

Ala Leu Ser Gly
            20


<210> SEQ ID NO 401
<211> LENGTH: 20
<212> TYPE: PRT
<213> ORGANISM: Homo sapiens

<400> SEQUENCE: 401

Ala Leu Lys Ala Ile Glu Ala Leu Ser Gly Lys Ile Glu Leu His Gly
 1               5                  10                  15

Lys Pro Ile Glu
            20


<210> SEQ ID NO 402
<211> LENGTH: 20
<212> TYPE: PRT
<213> ORGANISM: Homo sapiens

<400> SEQUENCE: 402

Lys Ile Glu Leu His Gly Lys Pro Ile Glu Val Glu His Ser Val Pro
 1               5                  10                  15

Lys Arg Gln Arg
            20


<210> SEQ ID NO 403
<211> LENGTH: 20
<212> TYPE: PRT
<213> ORGANISM: Homo sapiens

<400> SEQUENCE: 403

Val Glu His Ser Val Pro Lys Arg Gln Arg Ile Arg Lys Leu Gln Ile
 1               5                  10                  15

Arg Asn Ile Pro
            20


<210> SEQ ID NO 404
<211> LENGTH: 20
<212> TYPE: PRT
<213> ORGANISM: Homo sapiens

<400> SEQUENCE: 404

Ile Arg Lys Leu Gln Ile Arg Asn Ile Pro Pro His Leu Gln Trp Glu
 1               5                  10                  15

Val Leu Asp Ser
            20


<210> SEQ ID NO 405
<211> LENGTH: 20
```

-continued

<212> TYPE: PRT
<213> ORGANISM: Homo sapiens

<400> SEQUENCE: 405

Ala Val Val Asn Val Thr Tyr Ser Ser Lys Asp Gln Ala Arg Gln Ala
 1               5                   10                  15

Leu Asp Lys Leu
            20

<210> SEQ ID NO 406
<211> LENGTH: 20
<212> TYPE: PRT
<213> ORGANISM: Homo sapiens

<400> SEQUENCE: 406

Asp Gln Ala Arg Gln Ala Leu Asp Lys Leu Asn Gly Phe Gln Leu Glu
 1               5                   10                  15

Asn Phe Thr Leu
            20

<210> SEQ ID NO 407
<211> LENGTH: 20
<212> TYPE: PRT
<213> ORGANISM: Homo sapiens

<400> SEQUENCE: 407

Asn Gly Phe Gln Leu Glu Asn Phe Thr Leu Lys Val Ala Tyr Ile Pro
 1               5                   10                  15

Asp Glu Thr Ala
            20

<210> SEQ ID NO 408
<211> LENGTH: 20
<212> TYPE: PRT
<213> ORGANISM: Homo sapiens

<400> SEQUENCE: 408

Lys Val Ala Tyr Ile Pro Asp Glu Thr Ala Ala Gln Gln Asn Pro Leu
 1               5                   10                  15

Gln Gln Pro Arg
            20

<210> SEQ ID NO 409
<211> LENGTH: 20
<212> TYPE: PRT
<213> ORGANISM: Homo sapiens

<400> SEQUENCE: 409

Ala Gln Gln Asn Pro Leu Gln Gln Pro Arg Gly Arg Arg Gly Leu Gly
 1               5                   10                  15

Gln Arg Gly Ser
            20

<210> SEQ ID NO 410
<211> LENGTH: 20
<212> TYPE: PRT
<213> ORGANISM: Homo sapiens

<400> SEQUENCE: 410

Gly Arg Arg Gly Leu Gly Gln Arg Gly Ser Ser Arg Gln Gly Ser Pro
 1               5                   10                  15

Gly Ser Val Ser

-continued

20

<210> SEQ ID NO 411
<211> LENGTH: 20
<212> TYPE: PRT
<213> ORGANISM: Homo sapiens

<400> SEQUENCE: 411

Ser Arg Gln Gly Ser Pro Gly Ser Val Ser Lys Gln Lys Pro Cys Asp
1 5 10 15

Leu Pro Leu Arg
20

<210> SEQ ID NO 412
<211> LENGTH: 20
<212> TYPE: PRT
<213> ORGANISM: Homo sapiens

<400> SEQUENCE: 412

Lys Gln Lys Pro Cys Asp Leu Pro Leu Arg Leu Leu Val Pro Thr Gln
1 5 10 15

Phe Val Gly Ala
20

<210> SEQ ID NO 413
<211> LENGTH: 20
<212> TYPE: PRT
<213> ORGANISM: Homo sapiens

<400> SEQUENCE: 413

Leu Leu Val Pro Thr Gln Phe Val Gly Ala Ile Ile Gly Lys Glu Gly
1 5 10 15

Ala Thr Ile Arg
20

<210> SEQ ID NO 414
<211> LENGTH: 20
<212> TYPE: PRT
<213> ORGANISM: Homo sapiens

<400> SEQUENCE: 414

Ile Ile Gly Lys Glu Gly Ala Thr Ile Arg Asn Ile Thr Lys Gln Thr
1 5 10 15

Gln Ser Lys Ile
20

<210> SEQ ID NO 415
<211> LENGTH: 20
<212> TYPE: PRT
<213> ORGANISM: Homo sapiens

<400> SEQUENCE: 415

Asn Ile Thr Lys Gln Thr Gln Ser Lys Ile Asp Val His Arg Lys Glu
1 5 10 15

Asn Ala Gly Ala
20

<210> SEQ ID NO 416
<211> LENGTH: 20
<212> TYPE: PRT
<213> ORGANISM: Homo sapiens

<400> SEQUENCE: 416

-continued

```
Asp Val His Arg Lys Glu Asn Ala Gly Ala Ala Glu Lys Ser Ile Thr
 1               5                  10                  15

Ile Leu Ser Thr
            20
```

```
<210> SEQ ID NO 417
<211> LENGTH: 20
<212> TYPE: PRT
<213> ORGANISM: Homo sapiens

<400> SEQUENCE: 417

Ala Glu Lys Ser Ile Thr Ile Leu Ser Thr Pro Glu Gly Thr Ser Ala
 1               5                  10                  15

Ala Cys Lys Ser
            20


<210> SEQ ID NO 418
<211> LENGTH: 20
<212> TYPE: PRT
<213> ORGANISM: Homo sapiens

<400> SEQUENCE: 418

Pro Glu Gly Thr Ser Ala Ala Cys Lys Ser Ile Leu Glu Ile Met His
 1               5                  10                  15

Lys Glu Ala Gln
            20


<210> SEQ ID NO 419
<211> LENGTH: 20
<212> TYPE: PRT
<213> ORGANISM: Homo sapiens

<400> SEQUENCE: 419

Ile Leu Glu Ile Met His Lys Glu Ala Gln Asp Ile Lys Phe Thr Glu
 1               5                  10                  15

Glu Ile Pro Leu
            20


<210> SEQ ID NO 420
<211> LENGTH: 455
<212> TYPE: DNA
<213> ORGANISM: Homo sapiens

<400> SEQUENCE: 420

gaagacatgc ttacttcccc ttcaccttcc ttcatgatgt gggaagagtg ctgcaaccca      60

gccctagcca acgccgcatg agagggagtg tgccgagggc ttctgagaag gtttctctca     120

catctagaaa gaagcgctta agatgtggca gcccctcttc ttcaagtggc tcttgtcctg     180

ttgccctggg agttctcaaa ttgctgcagc agcctccacc cagcctgagg atgacatcaa     240

tacacagagg aagaagagtc aggaaaagat gagagaagtt acagactctc ctgggcgacc     300

ccgagagctt accattcctc agacttcttc acatggtgct aacagatttg ttcctaaaag     360

taaagctcta gaggccgtca aattggcaat agaagccggg ttccaccata ttgattctgc     420

acatgtttac aataatgagg agcaggttgg actgg                                455


<210> SEQ ID NO 421
<211> LENGTH: 24
<212> TYPE: DNA
<213> ORGANISM: Artificial Sequence
<220> FEATURE:
```

-continued

<223> OTHER INFORMATION: PCR primer

<400> SEQUENCE: 421
actagtgtcc gcgtggcggc ctac 24

<210> SEQ ID NO 422
<211> LENGTH: 34
<212> TYPE: DNA
<213> ORGANISM: Artificial Sequence
<220> FEATURE:
<223> OTHER INFORMATION: PCR primer

<400> SEQUENCE: 422
catgagaatt catcacatgc ccttgaaggc tccc 34

<210> SEQ ID NO 423
<211> LENGTH: 161
<212> TYPE: PRT
<213> ORGANISM: Homo sapiens

<400> SEQUENCE: 423

```
Met Gln His His His His His His His Thr Ser Val Arg Val Ala Ala
 1               5                  10                  15

Tyr Phe Glu Asn Phe Leu Ala Ala Trp Arg Pro Val Lys Ala Ser Asp
            20                  25                  30

Gly Asp Tyr Tyr Thr Leu Ala Val Pro Met Gly Asp Val Pro Met Asp
        35                  40                  45

Gly Ile Ser Val Ala Asp Ile Gly Ala Ala Val Ser Ser Ile Phe Asn
    50                  55                  60

Ser Pro Glu Glu Phe Leu Gly Lys Ala Val Gly Leu Ser Ala Glu Ala
65                  70                  75                  80

Leu Thr Ile Gln Gln Tyr Ala Asp Val Leu Ser Lys Ala Leu Gly Lys
                85                  90                  95

Glu Val Arg Asp Ala Lys Ile Thr Pro Glu Ala Phe Glu Lys Leu Gly
            100                 105                 110

Phe Pro Ala Ala Lys Glu Ile Ala Asn Met Cys Arg Phe Tyr Glu Met
        115                 120                 125

Lys Pro Asp Arg Asp Val Asn Leu Thr His Gln Leu Asn Pro Lys Val
    130                 135                 140

Lys Ser Phe Ser Gln Phe Ile Ser Glu Asn Gln Gly Ala Phe Lys Gly
145                 150                 155                 160

Met
```

<210> SEQ ID NO 424
<211> LENGTH: 489
<212> TYPE: DNA
<213> ORGANISM: Homo sapiens

<400> SEQUENCE: 424

```
atgcagcatc accaccatca ccaccacact agtgtccgcg tggcggccta ctttgaaaac     60

tttctcgcgg cgtggcggcc cgtgaaagcc tctgatggag attactacac cttggctgta    120

ccgatgggag atgtaccaat ggatggtatc tctgttgctg atattggagc agccgtctct    180

agcattttta attctccaga ggaattttta ggcaaggccg tggggctcag tgcagaagca    240

ctaacaatac agcaatatgc tgatgttttg tccaaggctt tggggaaaga agtccgagat    300

gcaaagatta ccccggaagc tttcgagaag ctgggattcc ctgcagcaaa ggaaatagcc    360

aatatgtgtc gtttctatga aatgaagcca gaccgagatg tcaatctcac ccaccaacta    420
```

-continued aatcccaaag tcaaaagctt cagccagttt atctcagaga accagggagc cttcaagggc 480
atgtgatga 489

<210> SEQ ID NO 425
<211> LENGTH: 32
<212> TYPE: DNA
<213> ORGANISM: Artificial Sequence
<220> FEATURE:
<223> OTHER INFORMATION: PCR primer

<400> SEQUENCE: 425
aacaaactgt atatcggaaa cctcagcgag aa 32

<210> SEQ ID NO 426
<211> LENGTH: 33
<212> TYPE: DNA
<213> ORGANISM: Artificial Sequence
<220> FEATURE:
<223> OTHER INFORMATION: PCR primer

<400> SEQUENCE: 426
ccatagaatt cattacttcc gtcttgactg agg 33

<210> SEQ ID NO 427
<211> LENGTH: 586
<212> TYPE: PRT
<213> ORGANISM: Homo sapiens

<400> SEQUENCE: 427

Met Gln His His His His His His Asn Lys Leu Tyr Ile Gly Asn Leu
1 5 10 15

Ser Glu Asn Ala Ala Pro Ser Asp Leu Glu Ser Ile Phe Lys Asp Ala
20 25 30

Lys Ile Pro Val Ser Gly Pro Phe Leu Val Lys Thr Gly Tyr Ala Phe
35 40 45

Val Asp Cys Pro Asp Glu Ser Trp Ala Leu Lys Ala Ile Glu Ala Leu
50 55 60

Ser Gly Lys Ile Glu Leu His Gly Lys Pro Ile Glu Val Glu His Ser
65 70 75 80

Val Pro Lys Arg Gln Arg Ile Arg Lys Leu Gln Ile Arg Asn Ile Pro
85 90 95

Pro His Leu Gln Trp Glu Val Leu Asp Ser Leu Leu Val Gln Tyr Gly
100 105 110

Val Val Glu Ser Cys Glu Gln Val Asn Thr Asp Ser Glu Thr Ala Val
115 120 125

Val Asn Val Thr Tyr Ser Ser Lys Asp Gln Ala Arg Gln Ala Leu Asp
130 135 140

Lys Leu Asn Gly Phe Gln Leu Glu Asn Phe Thr Leu Lys Val Ala Tyr
145 150 155 160

Ile Pro Asp Glu Thr Ala Ala Gln Gln Asn Pro Leu Gln Gln Pro Arg
165 170 175

Gly Arg Arg Gly Leu Gly Gln Arg Gly Ser Ser Arg Gln Gly Ser Pro
180 185 190

Gly Ser Val Ser Lys Gln Lys Pro Cys Asp Leu Pro Leu Arg Leu Leu
195 200 205

Val Pro Thr Gln Phe Val Gly Ala Ile Ile Gly Lys Glu Gly Ala Thr
210 215 220

-continued

```
Ile Arg Asn Ile Thr Lys Gln Thr Gln Ser Lys Ile Asp Val His Arg
225                 230                 235                 240

Lys Glu Asn Ala Gly Ala Ala Glu Lys Ser Ile Thr Ile Leu Ser Thr
                245                 250                 255

Pro Glu Gly Thr Ser Ala Ala Cys Lys Ser Ile Leu Glu Ile Met His
            260                 265                 270

Lys Glu Ala Gln Asp Ile Lys Phe Thr Glu Glu Ile Pro Leu Lys Ile
        275                 280                 285

Leu Ala His Asn Asn Phe Val Gly Arg Leu Ile Gly Lys Glu Gly Arg
    290                 295                 300

Asn Leu Lys Lys Ile Glu Gln Asp Thr Asp Thr Lys Ile Thr Ile Ser
305                 310                 315                 320

Pro Leu Gln Glu Leu Thr Leu Tyr Asn Pro Glu Arg Thr Ile Thr Val
                325                 330                 335

Lys Gly Asn Val Glu Thr Cys Ala Lys Ala Glu Glu Glu Ile Met Lys
            340                 345                 350

Lys Ile Arg Glu Ser Tyr Glu Asn Asp Ile Ala Ser Met Asn Leu Gln
        355                 360                 365

Ala His Leu Ile Pro Gly Leu Asn Leu Asn Ala Leu Gly Leu Phe Pro
    370                 375                 380

Pro Thr Ser Gly Met Pro Pro Pro Thr Ser Gly Pro Pro Ser Ala Met
385                 390                 395                 400

Thr Pro Pro Tyr Pro Gln Phe Glu Gln Ser Glu Thr Glu Thr Val His
                405                 410                 415

Leu Phe Ile Pro Ala Leu Ser Val Gly Ala Ile Ile Gly Lys Gln Gly
            420                 425                 430

Gln His Ile Lys Gln Leu Ser Arg Phe Ala Gly Ala Ser Ile Lys Ile
        435                 440                 445

Ala Pro Ala Glu Ala Pro Asp Ala Lys Val Arg Met Val Ile Ile Thr
    450                 455                 460

Gly Pro Pro Glu Ala Gln Phe Lys Ala Gln Gly Arg Ile Tyr Gly Lys
465                 470                 475                 480

Ile Lys Glu Glu Asn Phe Val Ser Pro Lys Glu Glu Val Lys Leu Glu
                485                 490                 495

Ala His Ile Arg Val Pro Ser Phe Ala Ala Gly Arg Val Ile Gly Lys
            500                 505                 510

Gly Gly Lys Thr Val Asn Glu Leu Gln Asn Leu Ser Ser Ala Glu Val
        515                 520                 525

Val Val Pro Arg Asp Gln Thr Pro Asp Glu Asn Asp Gln Val Val Val
    530                 535                 540

Lys Ile Thr Gly His Phe Tyr Ala Cys Gln Val Ala Gln Arg Lys Ile
545                 550                 555                 560

Gln Glu Ile Leu Thr Gln Val Lys Gln His Gln Gln Gln Lys Ala Leu
                565                 570                 575

Gln Ser Gly Pro Pro Gln Ser Arg Arg Lys
            580                 585
```

<210> SEQ ID NO 428
<211> LENGTH: 1764
<212> TYPE: DNA
<213> ORGANISM: Homo sapiens

<400> SEQUENCE: 428
atgcagcatc accaccatca ccacaacaaa ctgtatatcg gaaacctcag cgagaacgcc     60

-continued gccccctcgg acctagaaag tatcttcaag gacgccaaga tcccggtgtc gggacccttc 120
ctggtgaaga ctggctacgc gttcgtggac tgcccggacg agagctgggc cctcaaggcc 180
atcgaggcgc tttcaggtaa aatagaactg cacgggaaac ccatagaagt tgagcactcg 240
gtcccaaaaa ggcaaaggat tcggaaactt cagatacgaa atatcccgcc tcatttacag 300
tgggaggtgc tggatagttt actagtccag tatggagtgg tggagagctg tgagcaagtg 360
aacactgact cggaaactgc agttgtaaat gtaacctatt ccagtaagga ccaagctaga 420
caagcactag acaaactgaa tggatttcag ttagagaatt tcaccttgaa agtagcctat 480
atccctgatg aaacggccgc ccagcaaaac cccttgcagc agccccgagg tcgccggggg 540
cttgggcaga ggggctcctc aaggcagggg tctccaggat ccgtatccaa gcagaaacca 600
tgtgatttgc ctctgcgcct gctggttccc acccaatttg ttggagccat cataggaaaa 660
gaaggtgcca ccattcggaa catcaccaaa cagacccagt ctaaaatcga tgtccaccgt 720
aaagaaaatg cgggggctgc tgagaagtcg attactatcc tctctactcc tgaaggcacc 780
tctgcggctt gtaagtctat tctggagatt atgcataagg aagctcaaga tataaaattc 840
acagaagaga tccccttgaa gattttagct cataataact ttgttggacg tcttattggt 900
aaagaaggaa gaaatcttaa aaaaattgag caagacacag acactaaaat cacgatatct 960
ccattgcagg aattgacgct gtataatcca gaacgcacta ttacagttaa aggcaatgtt 1020
gagacatgtg ccaaagctga ggaggagatc atgaagaaaa tcagggagtc ttatgaaaat 1080
gatattgctt ctatgaatct tcaagcacat ttaattcctg gattaaatct gaacgccttg 1140
ggtctgttcc cacccacttc agggatgcca cctcccacct cagggccccc ttcagccatg 1200
actcctccct acccgcagtt tgagcaatca gaaacggaga ctgttcatct gtttatccca 1260
gctctatcag tcggtgccat catcggcaag cagggccagc acatcaagca gctttctcgc 1320
tttgctggag cttcaattaa gattgctcca gcggaagcac cagatgctaa agtgaggatg 1380
gtgattatca ctggaccacc agaggctcag ttcaaggctc agggaagaat ttatggaaaa 1440
attaaagaag aaaactttgt tagtcctaaa gaagaggtga aacttgaagc tcatatcaga 1500
gtgccatcct ttgctgctgg cagagttatt ggaaaaggag gcaaaacggt gaatgaactt 1560
cagaatttgt caagtgcaga agttgttgtc cctcgtgacc agacacctga tgagaatgac 1620
caagtggttg tcaaaataac tggtcacttc tatgcttgcc aggttgccca gagaaaaatt 1680
caggaaattc tgactcaggt aaagcagcac caacaacaga aggctctgca aagtggacca 1740
cctcagtcaa gacggaagta atga 1764

<210> SEQ ID NO 429
<211> LENGTH: 35
<212> TYPE: DNA
<213> ORGANISM: Artificial Sequence
<220> FEATURE:
<223> OTHER INFORMATION: PCR primer

<400> SEQUENCE: 429
ccatggaatt cattatttca atataagata atctc 35

<210> SEQ ID NO 430
<211> LENGTH: 881
<212> TYPE: PRT
<213> ORGANISM: Homo sapiens

<400> SEQUENCE: 430

Met Gln His His His His His His Gly Val Gln Leu Gln Asp Asn Gly

-continued

```
1               5                   10                  15

Tyr Asn Gly Leu Leu Ile Ala Ile Asn Pro Gln Val Pro Glu Asn Gln
            20                  25                  30

Asn Leu Ile Ser Asn Ile Lys Glu Met Ile Thr Glu Ala Ser Phe Tyr
        35                  40                  45

Leu Phe Asn Ala Thr Lys Arg Arg Val Phe Phe Arg Asn Ile Lys Ile
    50                  55                  60

Leu Ile Pro Ala Thr Trp Lys Ala Asn Asn Asn Ser Lys Ile Lys Gln
65                  70                  75                  80

Glu Ser Tyr Glu Lys Ala Asn Val Ile Val Thr Asp Trp Tyr Gly Ala
                85                  90                  95

His Gly Asp Asp Pro Tyr Thr Leu Gln Tyr Arg Gly Cys Gly Lys Glu
            100                 105                 110

Gly Lys Tyr Ile His Phe Thr Pro Asn Phe Leu Leu Asn Asp Asn Leu
        115                 120                 125

Thr Ala Gly Tyr Gly Ser Arg Gly Arg Val Phe Val His Glu Trp Ala
    130                 135                 140

His Leu Arg Trp Gly Val Phe Asp Glu Tyr Asn Asn Asp Lys Pro Phe
145                 150                 155                 160

Tyr Ile Asn Gly Gln Asn Gln Ile Lys Val Thr Arg Cys Ser Ser Asp
                165                 170                 175

Ile Thr Gly Ile Phe Val Cys Glu Lys Gly Pro Cys Pro Gln Glu Asn
            180                 185                 190

Cys Ile Ile Ser Lys Leu Phe Lys Glu Gly Cys Thr Phe Ile Tyr Asn
        195                 200                 205

Ser Thr Gln Asn Ala Thr Ala Ser Ile Met Phe Met Gln Ser Leu Ser
    210                 215                 220

Ser Val Val Glu Phe Cys Asn Ala Ser Thr His Asn Gln Glu Ala Pro
225                 230                 235                 240

Asn Leu Gln Asn Gln Met Cys Ser Leu Arg Ser Ala Trp Asp Val Ile
                245                 250                 255

Thr Asp Ser Ala Asp Phe His His Ser Phe Pro Met Asn Gly Thr Glu
            260                 265                 270

Leu Pro Pro Pro Pro Thr Phe Ser Leu Val Glu Ala Gly Asp Lys Val
        275                 280                 285

Val Cys Leu Val Leu Asp Val Ser Ser Lys Met Ala Glu Ala Asp Arg
    290                 295                 300

Leu Leu Gln Leu Gln Gln Ala Ala Glu Phe Tyr Leu Met Gln Ile Val
305                 310                 315                 320

Glu Ile His Thr Phe Val Gly Ile Ala Ser Phe Asp Ser Lys Gly Glu
                325                 330                 335

Ile Arg Ala Gln Leu His Gln Ile Asn Ser Asn Asp Asp Arg Lys Leu
            340                 345                 350

Leu Val Ser Tyr Leu Pro Thr Thr Val Ser Ala Lys Thr Asp Ile Ser
        355                 360                 365

Ile Cys Ser Gly Leu Lys Lys Gly Phe Glu Val Val Glu Lys Leu Asn
    370                 375                 380

Gly Lys Ala Tyr Gly Ser Val Met Ile Leu Val Thr Ser Gly Asp Asp
385                 390                 395                 400

Lys Leu Leu Gly Asn Cys Leu Pro Thr Val Leu Ser Ser Gly Ser Thr
                405                 410                 415

Ile His Ser Ile Ala Leu Gly Ser Ser Ala Ala Pro Asn Leu Glu Glu
            420                 425                 430
```

-continued

```
Leu Ser Arg Leu Thr Gly Gly Leu Lys Phe Phe Val Pro Asp Ile Ser
        435                 440                 445

Asn Ser Asn Ser Met Ile Asp Ala Phe Ser Arg Ile Ser Ser Gly Thr
    450                 455                 460

Gly Asp Ile Phe Gln Gln His Ile Gln Leu Glu Ser Thr Gly Glu Asn
465                 470                 475                 480

Val Lys Pro His His Gln Leu Lys Asn Thr Val Thr Val Asp Asn Thr
                485                 490                 495

Val Gly Asn Asp Thr Met Phe Leu Val Thr Trp Gln Ala Ser Gly Pro
            500                 505                 510

Pro Glu Ile Ile Leu Phe Asp Pro Asp Gly Arg Lys Tyr Tyr Thr Asn
        515                 520                 525

Asn Phe Ile Thr Asn Leu Thr Phe Arg Thr Ala Ser Leu Trp Ile Pro
    530                 535                 540

Gly Thr Ala Lys Pro Gly His Trp Thr Tyr Thr Leu Asn Asn Thr His
545                 550                 555                 560

His Ser Leu Gln Ala Leu Lys Val Thr Val Thr Ser Arg Ala Ser Asn
                565                 570                 575

Ser Ala Val Pro Pro Ala Thr Val Glu Ala Phe Val Glu Arg Asp Ser
            580                 585                 590

Leu His Phe Pro His Pro Val Met Ile Tyr Ala Asn Val Lys Gln Gly
        595                 600                 605

Phe Tyr Pro Ile Leu Asn Ala Thr Val Thr Ala Thr Val Glu Pro Glu
    610                 615                 620

Thr Gly Asp Pro Val Thr Leu Arg Leu Leu Asp Asp Gly Ala Gly Ala
625                 630                 635                 640

Asp Val Ile Lys Asn Asp Gly Ile Tyr Ser Arg Tyr Phe Phe Ser Phe
                645                 650                 655

Ala Ala Asn Gly Arg Tyr Ser Leu Lys Val His Val Asn His Ser Pro
            660                 665                 670

Ser Ile Ser Thr Pro Ala His Ser Ile Pro Gly Ser His Ala Met Tyr
        675                 680                 685

Val Pro Gly Tyr Thr Ala Asn Gly Asn Ile Gln Met Asn Ala Pro Arg
    690                 695                 700

Lys Ser Val Gly Arg Asn Glu Glu Glu Arg Lys Trp Gly Phe Ser Arg
705                 710                 715                 720

Val Ser Ser Gly Gly Ser Phe Ser Val Leu Gly Val Pro Ala Gly Pro
                725                 730                 735

His Pro Asp Val Phe Pro Pro Cys Lys Ile Ile Asp Leu Glu Ala Val
            740                 745                 750

Lys Val Glu Glu Glu Leu Thr Leu Ser Trp Thr Ala Pro Gly Glu Asp
        755                 760                 765

Phe Asp Gln Gly Gln Ala Thr Ser Tyr Glu Ile Arg Met Ser Lys Ser
    770                 775                 780

Leu Gln Asn Ile Gln Asp Asp Phe Asn Asn Ala Ile Leu Val Asn Thr
785                 790                 795                 800

Ser Lys Arg Asn Pro Gln Gln Ala Gly Ile Arg Glu Ile Phe Thr Phe
                805                 810                 815

Ser Pro Gln Ile Ser Thr Asn Gly Pro Glu His Gln Pro Asn Gly Glu
            820                 825                 830

Thr His Glu Ser His Arg Ile Tyr Val Ala Ile Arg Ala Met Asp Arg
        835                 840                 845
```

-continued

```
Asn Ser Leu Gln Ser Ala Val Ser Asn Ile Ala Gln Ala Pro Leu Phe
    850                 855                 860

Ile Pro Pro Asn Ser Asp Pro Val Pro Ala Arg Asp Tyr Leu Ile Leu
865                 870                 875                 880

Lys


<210> SEQ ID NO 431
<211> LENGTH: 2646
<212> TYPE: DNA
<213> ORGANISM: Homo sapiens

<400> SEQUENCE: 431

atgcagcatc accaccatca ccacggagta cagcttcaag acaatgggta taatggattg     60

ctcattgcaa ttaatcctca ggtacctgag aatcagaacc tcatctcaaa cattaaggaa    120

atgataactg aagcttcatt ttacctattt aatgctacca agagaagagt atttttcaga    180

aatataaaga ttttaatacc tgccacatgg aaagctaata ataacagcaa aataaaacaa    240

gaatcatatg aaaaggcaaa tgtcatagtg actgactggt atggggcaca tggagatgat    300

ccatacaccc tacaatacag agggtgtgga aaagagggaa aatacattca tttcacacct    360

aatttcctac tgaatgataa cttaacagct ggctacggat cacgaggccg agtgtttgtc    420

catgaatggg cccacctccg ttggggtgtg ttcgatgagt ataacaatga caaacctttc    480

tacataaatg ggcaaaatca aattaaagtg acaaggtgtt catctgacat cacaggcatt    540

tttgtgtgtg aaaaaggtcc ttgcccccaa gaaaactgta ttattagtaa gctttttaaa    600

gaaggatgca cctttatcta caatagcacc caaaatgcaa ctgcatcaat aatgttcatg    660

caaagtttat cttctgtggt tgaattttgt aatgcaagta cccacaacca agaagcacca    720

aacctacaga accagatgtg cagcctcaga agtgcatggg atgtaatcac agactctgct    780

gactttcacc acagctttcc catgaacggg actgagcttc cacctcctcc cacattctcg    840

cttgtagagg ctggtgacaa agtggtctgt ttagtgctgg atgtgtccag caagatggca    900

gaggctgaca gactccttca actacaacaa gccgcagaat ttatttgat gcagattgtt     960

gaaattcata ccttcgtggg cattgccagt ttcgacagca aaggagagat cagagcccag   1020

ctacaccaaa ttaacagcaa tgatgatcga aagttgctgg tttcatatct gcccaccact   1080

gtatcagcta aaacagacat cagcatttgt tcagggctta agaaaggatt tgaggtggtt   1140

gaaaaactga atggaaaagc ttatggctct gtgatgatat tagtgaccag cggagatgat   1200

aagcttcttg gcaattgctt acccactgtg ctcagcagtg gttcaacaat tcactccatt   1260

gccctgggtt catctgcagc cccaaatctg gaggaattat cacgtcttac aggaggttta   1320

aagttctttg ttccagatat atcaaactcc aatagcatga ttgatgcttt cagtagaatt   1380

tcctctggaa ctggagacat tttccagcaa catattcagc ttgaaagtac aggtgaaaat   1440

gtcaaacctc accatcaatt gaaaaacaca gtgactgtgg ataatactgt gggcaacgac   1500

actatgtttc tagttacgtg gcaggccagt ggtcctcctg agattatatt atttgatcct   1560

gatggacgaa aatactacac aaataatttt atcaccaatc taacttttcg gacagctagt   1620

ctttggattc caggaacagc taagcctggg cactggactt acaccctgaa caataccgat   1680

cattctctgc aagccctgaa agtgacagtg acctctcgcg cctccaactc agctgtgccc   1740

ccagccactg tggaagcctt tgtggaaaga gacagcctcc attttcctca tcctgtgatg   1800

atttatgcca atgtgaaaca gggattttat cccattctta atgccactgt cactgccaca   1860

gttgagccag agactggaga tcctgttacg ctgagactcc ttgatgatgg agcaggtgct   1920
```

-continued

```
gatgttataa aaaatgatgg aatttactcg aggtattttt tctcctttgc tgcaaatggt   1980

agatatagct tgaaagtgca tgtcaatcac tctcccagca taagcacccc agcccactct   2040

attccaggga gtcatgctat gtatgtacca ggttacacag caaacggtaa tattcagatg   2100

aatgctccaa ggaaatcagt aggcagaaat gaggaggagc gaaagtgggg ctttagccga   2160

gtcagctcag gaggctcctt ttcagtgctg ggagttccag ctggccccca ccctgatgtg   2220

tttccaccat gcaaaattat tgacctggaa gctgtaaaag tagaagagga attgacccta   2280

tcttggacag cacctggaga agactttgat cagggccagg ctacaagcta tgaaataaga   2340

atgagtaaaa gtctacagaa tatccaagat gactttaaca atgctatttt agtaaataca   2400

tcaaagcgaa atcctcagca agctggcatc agggagatat ttacgttctc accccaaatt   2460

tccacgaatg gacctgaaca tcagccaaat ggagaaacac atgaaagcca cagaatttat   2520

gttgcaatac gagcaatgga taggaactcc ttacagtctg ctgtatctaa cattgcccag   2580

gcgcctctgt ttattccccc caattctgat cctgtacctg ccagagatta tcttatattg   2640

aaataa                                                              2646


<210> SEQ ID NO 432
<211> LENGTH: 36
<212> TYPE: DNA
<213> ORGANISM: Artificial Sequence
<220> FEATURE:
<223> OTHER INFORMATION: PCR primer

<400> SEQUENCE: 432

cgcctgctcg agtcattaat attcatcaga aaatgg                                36


<210> SEQ ID NO 433
<211> LENGTH: 371
<212> TYPE: PRT
<213> ORGANISM: Homo sapiens

<400> SEQUENCE: 433

Met Gln His His His His His His Trp Gln Pro Leu Phe Phe Lys Trp
 1               5                  10                  15

Leu Leu Ser Cys Cys Pro Gly Ser Ser Gln Ile Ala Ala Ala Ala Ser
            20                  25                  30

Thr Gln Pro Glu Asp Asp Ile Asn Thr Gln Arg Lys Lys Ser Gln Glu
        35                  40                  45

Lys Met Arg Glu Val Thr Asp Ser Pro Gly Arg Pro Arg Glu Leu Thr
    50                  55                  60

Ile Pro Gln Thr Ser Ser His Gly Ala Asn Arg Phe Val Pro Lys Ser
65                  70                  75                  80

Lys Ala Leu Glu Ala Val Lys Leu Ala Ile Glu Ala Gly Phe His His
                85                  90                  95

Ile Asp Ser Ala His Val Tyr Asn Asn Glu Glu Gln Val Gly Leu Ala
            100                 105                 110

Ile Arg Ser Lys Ile Ala Asp Gly Ser Val Lys Arg Glu Asp Ile Phe
        115                 120                 125

Tyr Thr Ser Lys Leu Trp Ser Asn Ser His Arg Pro Glu Leu Val Arg
    130                 135                 140

Pro Ala Leu Glu Arg Ser Leu Lys Asn Leu Gln Leu Asp Tyr Val Asp
145                 150                 155                 160

Leu Tyr Leu Ile His Phe Pro Val Ser Val Lys Pro Gly Glu Glu Val
                165                 170                 175
```

-continued

```
Ile Pro Lys Asp Glu Asn Gly Lys Ile Leu Phe Asp Thr Val Asp Leu
            180                 185                 190

Cys Ala Thr Trp Glu Ala Met Glu Lys Cys Lys Asp Ala Gly Leu Ala
        195                 200                 205

Lys Ser Ile Gly Val Ser Asn Phe Asn His Arg Leu Leu Glu Met Ile
    210                 215                 220

Leu Asn Lys Pro Gly Leu Lys Tyr Lys Pro Val Cys Asn Gln Val Glu
225                 230                 235                 240

Cys His Pro Tyr Phe Asn Gln Arg Lys Leu Leu Asp Phe Cys Lys Ser
                245                 250                 255

Lys Asp Ile Val Leu Val Ala Tyr Ser Ala Leu Gly Ser His Arg Glu
            260                 265                 270

Glu Pro Trp Val Asp Pro Asn Ser Pro Val Leu Leu Glu Asp Pro Val
        275                 280                 285

Leu Cys Ala Leu Ala Lys Lys His Lys Arg Thr Pro Ala Leu Ile Ala
    290                 295                 300

Leu Arg Tyr Gln Leu Gln Arg Gly Val Val Val Leu Ala Lys Ser Tyr
305                 310                 315                 320

Asn Glu Gln Arg Ile Arg Gln Asn Val Gln Val Phe Glu Phe Gln Leu
                325                 330                 335

Thr Ser Glu Glu Met Lys Ala Ile Asp Gly Leu Asn Arg Asn Val Arg
            340                 345                 350

Tyr Leu Thr Leu Asp Ile Phe Ala Gly Pro Pro Asn Tyr Pro Phe Ser
        355                 360                 365

Asp Glu Tyr
    370
```

<210> SEQ ID NO 434
<211> LENGTH: 1119
<212> TYPE: DNA
<213> ORGANISM: Homo sapiens

<400> SEQUENCE: 434

```
atgcagcatc accaccatca ccactggcag cccctcttct tcaagtggct cttgtcctgt     60

tgccctggga gttctcaaat tgctgcagca gcctccaccc agcctgagga tgacatcaat    120

acacagagga agaagagtca ggaaaagatg agagaagtta cagactctcc tgggcgaccc    180

cgagagctta ccattcctca gacttcttca catggtgcta acagatttgt tcctaaaagt    240

aaagctctag aggccgtcaa attggcaata gaagccgggt tccaccatat tgattctgca    300

catgtttaca ataatgagga gcaggttgga ctggccatcc gaagcaagat tgcagatggc    360

agtgtgaaga gagaagacat attctacact tcaaagcttt ggagcaattc ccatcgacca    420

gagttggtcc gaccagcctt ggaaaggtca ctgaaaaatc ttcaattgga ctatgttgac    480

ctctatctta ttcattttcc agtgtctgta aagccaggtg aggaagtgat cccaaaagat    540

gaaaatggaa aaatactatt tgacacagtg gatctctgtg ccacatggga ggccatggag    600

aagtgtaaag atgcaggatt ggccaagtcc atcggggtgt ccaacttcaa ccacaggctg    660

ctggagatga tcctcaacaa gccagggctc aagtacaagc ctgtctgcaa ccaggtggaa    720

tgtcatcctt acttcaacca gagaaaactg ctggatttct gcaagtcaaa agacattgtt    780

ctggttgcct atagtgctct gggatcccat cgagaagaac catgggtgga cccgaactcc    840

ccggtgctct tggaggaccc agtcctttgt gccttggcaa aaaagcacaa gcgaacccca    900

gccctgattg ccctgcgcta ccagctgcag cgtggggttg tggtcctggc caagagctac    960
```

```
aatgagcagc gcatcagaca gaacgtgcag gtgtttgaat tccagttgac ttcagaggag    1020

atgaaagcca tagatggcct aaacagaaat gtgcgatatt tgacccttga tatttttgct    1080

ggccccccta attatccatt ttctgatgaa tattaatga                           1119

<210> SEQ ID NO 435
<211> LENGTH: 36
<212> TYPE: DNA
<213> ORGANISM: Artificial Sequence
<220> FEATURE:
<223> OTHER INFORMATION: Primer

<400> SEQUENCE: 435

ggatccgccg ccaccatgac atccattcga gctgta                              36

<210> SEQ ID NO 436
<211> LENGTH: 27
<212> TYPE: DNA
<213> ORGANISM: Artificial Sequence
<220> FEATURE:
<223> OTHER INFORMATION: Primer

<400> SEQUENCE: 436

gtcgactcag ctggaccaca gccgcag                                        27

<210> SEQ ID NO 437
<211> LENGTH: 37
<212> TYPE: DNA
<213> ORGANISM: Artificial Sequence
<220> FEATURE:
<223> OTHER INFORMATION: Primer

<400> SEQUENCE: 437

ggatccgccg ccaccatgga ctcctggacc ttctgct                             37

<210> SEQ ID NO 438
<211> LENGTH: 27
<212> TYPE: DNA
<213> ORGANISM: Artificial Sequence
<220> FEATURE:
<223> OTHER INFORMATION: Primer

<400> SEQUENCE: 438

gtcgactcag aaatcctttc tcttgac                                        27

<210> SEQ ID NO 439
<211> LENGTH: 933
<212> TYPE: DNA
<213> ORGANISM: Homo sapiens

<400> SEQUENCE: 439

atggactcct ggaccttctg ctgtgtgtcc ctttgcatcc tggtagcaaa gcacacagat    60

gctggagtta tccagtcacc ccggcacgag gtgacagaga tgggacaaga agtgactctg    120

agatgtaaac caatttcagg acacgactac cttttctggt acagacagac catgatgcgg    180

ggactggagt tgctcattta ctttaacaac aacgttccga tagatgattc agggatgccc    240

gaggatcgat tctcagctaa gatgcctaat gcatcattct ccactctgaa gatccagccc    300

tcagaaccca gggactcagc tgtgtacttc tgtgccagca gtttagttgg agcaaacact    360

gaagctttct ttggacaagg caccagactc acagttgtag aggacctgaa caaggtgttc    420

ccacccgagg tcgctgtgtt tgagccatca gaagcagaga tctcccacac ccaaaaggcc    480
```

-continued

```
acactggtgt gcctggccac aggcttcttc cctgaccacg tggagctgag ctggtgggtg    540

aatgggaagg aggtgcacag tggggtcagc acggacccgc agcccctcaa ggagcagccc    600

gccctcaatg actccagata ctgcctgagc agccgcctga gggtctcggc caccttctgg    660

cagaaccccc gcaaccactt ccgctgtcaa gtccagttct acgggctctc ggagaatgac    720

gagtggaccc aggatagggc caaacccgtc acccagatcg tcagcgccga ggcctggggt    780

agagcagact gtggctttac ctcggtgtcc taccagcaag ggtcctgtc tgccaccatc    840

ctctatgaga tcctgctagg gaaggccacc ctgtatgctg tgctggtcag cgcccttgtg    900

ttgatggcca tggtcaagag aaaggatttc tga                                 933
```

```
<210> SEQ ID NO 440
<211> LENGTH: 822
<212> TYPE: DNA
<213> ORGANISM: Homo sapiens

<400> SEQUENCE: 440

atgacatcca ttcgagctgt atttatattc ctgtggctgc agctggactt ggtgaatgga     60

gagaatgtgg agcagcatcc ttcaaccctg agtgtccagg agggagacag cgctgttatc    120

aagtgtactt attcagacag tgcctcaaac tacttccctt ggtataagca agaacttgga    180

aaaagacctc agcttattat agacattcgt tcaaatgtgg gcgaaaagaa agaccaacga    240

attgctgtta cattgaacaa gacagccaaa catttctccc tgcacatcac agagacccaa    300

cctgaagact cggctgtcta cttctgtgca gcaagtatac tgaacaccgg taaccagttc    360

tattttggga cagggacaag tttgacggtc attccaaata tccagaaccc tgaccctgcc    420

gtgtaccagc tgagagactc taaatccagt gacaagtctg tctgcctatt caccgatttt    480

gattctcaaa caaatgtgtc acaaagtaag gattctgatg tgtatatcac agacaaaact    540

gtgctagaca tgaggtctat ggacttcaag agcaacagtg ctgtggcctg gagcaacaaa    600

tctgactttg catgtgcaaa cgccttcaac aacagcatta ttccagaaga caccttcttc    660

cccagcccag aaagttcctg tgatgtcaag ctggtcgaga aaagctttga aacagatacg    720

aacctaaact ttcaaaacct gtcagtgatt gggttccgaa tcctcctcct gaaagtggcc    780

gggtttaatc tgctcatgac gctgcggctg tggtccagct ga                       822
```

```
<210> SEQ ID NO 441
<211> LENGTH: 2311
<212> TYPE: DNA
<213> ORGANISM: Homo sapiens

<400> SEQUENCE: 441

gatttaatcc tatgacaaac taagttggtt ctgtcttcac ctgttttggt gaggttgtgt     60

aagagttggt gtttgctcag gaagagattt aagcatgctt gcttacccag actcagagaa    120

gtctccctgt tctgtcctag ctatgttcct gtgttgtgtg cattcgtctt ttccagagca    180

aaccgcccag agtagaagat ggattggggc acgctgcaga cgatcctggg gggtgtgaac    240

aaacactcca ccagcattgg aaagatctgg ctcaccgtcc tcttcatttt tcgcattatg    300

atcctcgttg tggctgcaaa ggaggtgtgg ggagatgagc aggccgactt tgtctgcaac    360

accctgcagc caggctgcaa gaacgtgtgc tacgatcact acttccccat ctcccacatc    420

cggctatggg ccctgcagct gatcttcgtg tccagcccag cgctcctagt ggccatgcac    480

gtggcctacc ggagacatga gaagaagagg aagttcatca aggggggagat aaagagtgaa    540

tttaaggaca tcgaggagat caaaacccag aaggtccgca tcgaaggctc cctgtggtgg    600
```

```
acctacacaa gcagcatctt cttccgggtc atcttcgaag ccgccttcat gtacgtcttc     660
tatgtcatgt acgacggctt ctccatgcag cggctggtga agtgcaacgc ctggccttgt     720
cccaacactg tggactgctt tgtgtcccgg cccacggaga agactgtctt cacagtgttc     780
atgattgcag tgtctggaat ttgcatcctg ctgaatgtca ctgaattgtg ttatttgcta     840
attagatatt gttctgggaa gtcaaaaaag ccagtttaac gcattgccca gttgttagat     900
taagaaatag acagcatgag agggatgagg caacccgtgc tcagctgtca aggctcagtc     960
gccagcattt cccaacacaa agattctgac cttaaatgca accatttgaa acccctgtag    1020
gcctcaggtg aaactccaga tgccacaatg agctctgctc ccctaaagcc tcaaaacaaa    1080
ggcctaattc tatgcctgtc ttaattttct ttcacttaag ttagttccac tgagacccca    1140
ggctgttagg ggttattggt gtaaggtact ttcatatttt aaacagagga tatcggcatt    1200
tgtttctttc tctgaggaca agagaaaaaa gccaggttcc acagaggaca cagagaaggt    1260
ttgggtgtcc tcctggggtt ctttttgcca actttcccca cgttaaaggt gaacattggt    1320
tctttcattt gctttggaag ttttaatctc taacagtgga caaagttacc agtgccttaa    1380
actctgttac actttttgga agtgaaaact ttgtagtatg ataggttatt ttgatgtaaa    1440
gatgttctgg ataccattat atgttccccc tgtttcagag gctcagattg taatatgtaa    1500
atggtatgtc attcgctact atgatttaat ttgaaatatg gtcttttggt tatgaatact    1560
ttgcagcaca gctgagagag gctgtctgtt gtattcattg tggtcatagc acctaacaac    1620
attgtagcct caatcgagtg agacagacta gaagttccta gttggcttat gatagcaaat    1680
ggcctcatgt caaatattag atgtaatttt gtgtaagaaa tacagactgg atgtaccacc    1740
aactactacc tgtaatgaca ggcctgtcca acacatctcc cttttccatg ctgtggtagc    1800
cagcatcgga aagaacgctg atttaaagag gtgagcttgg gaattttatt gacacagtac    1860
catttaatgg ggagacaaaa atgggggcca ggggagggag aagtttctgt cgttaaaaac    1920
gagtttggaa agactggact ctaaattctg ttgattaaag atgagctttg tctaccttca    1980
aaagtttgtt tggcttaccc ccttcagcct ccaatttttt aagtgaaaat ataactaata    2040
acatgtgaaa agaatagaag ctaaggttta gataaatatt gagcagatct ataggaagat    2100
tgaacctgaa tattgccatt atgcttgaca tggtttccaa aaaatggtac tccacatact    2160
tcagtgaggg taagtatttt cctgttgtca agaatagcat tgtaaaagca ttttgtaata    2220
ataaagaata gctttaatga tatgcttgta actaaaataa ttttgtaatg tatcaaatac    2280
atttaaaaca ttaaaatata atctctataa t                                   2311
```

<210> SEQ ID NO 442
<211> LENGTH: 226
<212> TYPE: PRT
<213> ORGANISM: Homo sapiens

<400> SEQUENCE: 442

```
Met Asp Trp Gly Thr Leu Gln Thr Ile Leu Gly Gly Val Asn Lys His
                5                   10                  15

Ser Thr Ser Ile Gly Lys Ile Trp Leu Thr Val Leu Phe Ile Phe Arg
            20                  25                  30

Ile Met Ile Leu Val Val Ala Ala Lys Glu Val Trp Gly Asp Glu Gln
        35                  40                  45

Ala Asp Phe Val Cys Asn Thr Leu Gln Pro Gly Cys Lys Asn Val Cys
    50                  55                  60
```

-continued

```
Tyr Asp His Tyr Phe Pro Ile Ser His Ile Arg Leu Trp Ala Leu Gln
 65                  70                  75                  80

Leu Ile Phe Val Ser Ser Pro Ala Leu Leu Val Ala Met His Val Ala
                 85                  90                  95

Tyr Arg Arg His Glu Lys Lys Arg Lys Phe Ile Lys Gly Glu Ile Lys
            100                 105                 110

Ser Glu Phe Lys Asp Ile Glu Glu Ile Lys Thr Gln Lys Val Arg Ile
        115                 120                 125

Glu Gly Ser Leu Trp Trp Thr Tyr Thr Ser Ser Ile Phe Phe Arg Val
    130                 135                 140

Ile Phe Glu Ala Ala Phe Met Tyr Val Phe Tyr Val Met Tyr Asp Gly
145                 150                 155                 160

Phe Ser Met Gln Arg Leu Val Lys Cys Asn Ala Trp Pro Cys Pro Asn
                165                 170                 175

Thr Val Asp Cys Phe Val Ser Arg Pro Thr Glu Lys Thr Val Phe Thr
            180                 185                 190

Val Phe Met Ile Ala Val Ser Gly Ile Cys Ile Leu Leu Asn Val Thr
        195                 200                 205

Glu Leu Cys Tyr Leu Leu Ile Arg Tyr Cys Ser Gly Lys Ser Lys Lys
    210                 215                 220

Pro Val
225
```

<210> SEQ ID NO 443
<211> LENGTH: 23
<212> TYPE: PRT
<213> ORGANISM: Homo sapiens

<400> SEQUENCE: 443

```
Val Lys Leu Cys Gly Ile Asp Pro Cys Pro Asn Leu Val Asp Cys Phe
                  5                  10                  15

Ile Ser Arg Pro Gly Cys Gly
             20
```

<210> SEQ ID NO 444
<211> LENGTH: 36
<212> TYPE: DNA
<213> ORGANISM: Artificial Sequence
<220> FEATURE:
<223> OTHER INFORMATION: PCR primer

<400> SEQUENCE: 444

```
caatcaggca tgcacaacaa actgtatatc ggaaac                              36
```

<210> SEQ ID NO 445
<211> LENGTH: 30
<212> TYPE: DNA
<213> ORGANISM: Artificial Sequence
<220> FEATURE:
<223> OTHER INFORMATION: PCR primer

<400> SEQUENCE: 445

```
cgtcaagatc ttcattactt ccgtcttgac                                     30
```

<210> SEQ ID NO 446
<211> LENGTH: 579
<212> TYPE: PRT
<213> ORGANISM: Homo sapiens

<400> SEQUENCE: 446

-continued

```
Met Asn Lys Leu Tyr Ile Gly Asn Leu Ser Glu Asn Ala Ala Pro Ser
                5                   10                  15

Asp Leu Glu Ser Ile Phe Lys Asp Ala Lys Ile Pro Val Ser Gly Pro
            20                  25                  30

Phe Leu Val Lys Thr Gly Tyr Ala Phe Val Asp Cys Pro Asp Glu Ser
        35                  40                  45

Trp Ala Leu Lys Ala Ile Glu Ala Leu Ser Gly Lys Ile Glu Leu His
    50                  55                  60

Gly Lys Pro Ile Glu Val Glu His Ser Val Pro Lys Arg Gln Arg Ile
65                  70                  75                  80

Arg Lys Leu Gln Ile Arg Asn Ile Pro Pro His Leu Gln Trp Glu Val
                85                  90                  95

Leu Asp Ser Leu Leu Val Gln Tyr Gly Val Val Glu Ser Cys Glu Gln
            100                 105                 110

Val Asn Thr Asp Ser Glu Thr Ala Val Val Asn Val Thr Tyr Ser Ser
        115                 120                 125

Lys Asp Gln Ala Arg Gln Ala Leu Asp Lys Leu Asn Gly Phe Gln Leu
    130                 135                 140

Glu Asn Phe Thr Leu Lys Val Ala Tyr Ile Pro Asp Glu Thr Ala Ala
145                 150                 155                 160

Gln Gln Asn Pro Leu Gln Gln Pro Arg Gly Arg Arg Gly Leu Gly Gln
                165                 170                 175

Arg Gly Ser Ser Arg Gln Gly Ser Pro Gly Ser Val Ser Lys Gln Lys
            180                 185                 190

Pro Cys Asp Leu Pro Leu Arg Leu Leu Val Pro Thr Gln Phe Val Gly
        195                 200                 205

Ala Ile Ile Gly Lys Glu Gly Ala Thr Ile Arg Asn Ile Thr Lys Gln
    210                 215                 220

Thr Gln Ser Lys Ile Asp Val His Arg Lys Glu Asn Ala Gly Ala Ala
225                 230                 235                 240

Glu Lys Ser Ile Thr Ile Leu Ser Thr Pro Glu Gly Thr Ser Ala Ala
                245                 250                 255

Cys Lys Ser Ile Leu Glu Ile Met His Lys Glu Ala Gln Asp Ile Lys
            260                 265                 270

Phe Thr Glu Glu Ile Pro Leu Lys Ile Leu Ala His Asn Asn Phe Val
        275                 280                 285

Gly Arg Leu Ile Gly Lys Glu Gly Arg Asn Leu Lys Lys Ile Glu Gln
    290                 295                 300

Asp Thr Asp Thr Lys Ile Thr Ile Ser Pro Leu Gln Glu Leu Thr Leu
305                 310                 315                 320

Tyr Asn Pro Glu Arg Thr Ile Thr Val Lys Gly Asn Val Glu Thr Cys
                325                 330                 335

Ala Lys Ala Glu Glu Glu Ile Met Lys Lys Ile Arg Glu Ser Tyr Glu
            340                 345                 350

Asn Asp Ile Ala Ser Met Asn Leu Gln Ala His Leu Ile Pro Gly Leu
        355                 360                 365

Asn Leu Asn Ala Leu Gly Leu Phe Pro Pro Thr Ser Gly Met Pro Pro
    370                 375                 380

Pro Thr Ser Gly Pro Pro Ser Ala Met Thr Pro Pro Tyr Pro Gln Phe
385                 390                 395                 400

Glu Gln Ser Glu Thr Glu Thr Val His Leu Phe Ile Pro Ala Leu Ser
                405                 410                 415

Val Gly Ala Ile Ile Gly Lys Gln Gly Gln His Ile Lys Gln Leu Ser
```

-continued

```
            420                 425                 430

Arg Phe Ala Gly Ala Ser Ile Lys Ile Ala Pro Ala Glu Ala Pro Asp
        435                 440                 445

Ala Lys Val Arg Met Val Ile Ile Thr Gly Pro Pro Glu Ala Gln Phe
    450                 455                 460

Lys Ala Gln Gly Arg Ile Tyr Gly Lys Ile Lys Glu Glu Asn Phe Val
465                 470                 475                 480

Ser Pro Lys Glu Glu Val Lys Leu Glu Ala His Ile Arg Val Pro Ser
                485                 490                 495

Phe Ala Ala Gly Arg Val Ile Gly Lys Gly Gly Lys Thr Val Asn Glu
            500                 505                 510

Leu Gln Asn Leu Ser Ser Ala Glu Val Val Val Pro Arg Asp Gln Thr
        515                 520                 525

Pro Asp Glu Asn Asp Gln Val Val Val Lys Ile Thr Gly His Phe Tyr
    530                 535                 540

Ala Cys Gln Val Ala Gln Arg Lys Ile Gln Glu Ile Leu Thr Gln Val
545                 550                 555                 560

Lys Gln His Gln Gln Gln Lys Ala Leu Gln Ser Gly Pro Pro Gln Ser
                565                 570                 575

Arg Arg Lys
```

<210> SEQ ID NO 447
<211> LENGTH: 1743
<212> TYPE: DNA
<213> ORGANISM: Homo sapiens

<400> SEQUENCE: 447

```
atgaacaaac tgtatatcgg aaacctcagc gagaacgccg ccccctcgga cctagaaagt     60

atcttcaagg acgccaagat cccggtgtcg ggacccttcc tggtgaagac tggctacgcg    120

ttcgtggact gcccggacga gagctgggcc ctcaaggcca tcgaggcgct ttcaggtaaa    180

atagaactgc acgggaaacc catagaagtt gagcactcgg tcccaaaaag gcaaaggatt    240

cggaaacttc agatacgaaa tatcccgcct catttacagt gggaggtgct ggatagttta    300

ctagtccagt atggagtggt ggagagctgt gagcaagtga acactgactc ggaaactgca    360

gttgtaaatg taacctattc cagtaaggac caagctagac aagcactaga caaactgaat    420

ggatttcagt tagagaattt caccttgaaa gtagcctata tccctgatga aacggccgcc    480

cagcaaaacc ccttgcagca gccccgaggt cgccgggggc ttgggcagag gggctcctca    540

aggcaggggt ctccaggatc cgtatccaag cagaaaccat gtgatttgcc tctgcgcctg    600

ctggttccca cccaatttgt tggagccatc ataggaaaag aaggtgccac cattcggaac    660

atcaccaaac agacccagtc taaaatcgat gtccaccgta aagaaaatgc gggggctgct    720

gagaagtcga ttactatcct ctctactcct gaaggcacct ctgcggcttg taagtctatt    780

ctggagatta tgcataagga agctcaagat ataaaattca cagaagagat ccccttgaag    840

attttagctc ataataactt tgttggacgt cttattggta aagaaggaag aaatcttaaa    900

aaaattgagc aagacacaga cactaaaatc acgatatctc cattgcagga attgacgctg    960

tataatccag aacgcactat tacagttaaa ggcaatgttg agacatgtgc caaagctgag   1020

gaggagatca tgaagaaaat cagggagtct tatgaaaatg atattgcttc tatgaatctt   1080

caagcacatt taattcctgg attaaatctg aacgccttgg gtctgttccc acccacttca   1140

gggatgccac ctcccacctc agggccccct tcagccatga ctcctcccta cccgcagttt   1200
```

-continued

```
gagcaatcag aaacggagac tgttcatctg tttatcccag ctctatcagt cggtgccatc   1260

atcggcaagc agggccagca catcaagcag ctttctcgct ttgctggagc ttcaattaag   1320

attgctccag cggaagcacc agatgctaaa gtgaggatgg tgattatcac tggaccacca   1380

gaggctcagt tcaaggctca gggaagaatt tatggaaaaa ttaaagaaga aaactttgtt   1440

agtcctaaag aagaggtgaa acttgaagct catatcagag tgccatcctt tgctgctggc   1500

agagttattg gaaaaggagg caaaacggtg aatgaacttc agaatttgtc aagtgcagaa   1560

gttgttgtcc ctcgtgacca gacacctgat gagaatgacc aagtggttgt caaaataact   1620

ggtcacttct atgcttgcca ggttgcccag agaaaaattc aggaaattct gactcaggta   1680

aagcagcacc aacaacagaa ggctctgcaa agtggaccac ctcagtcaag acggaagtaa   1740

tga                                                                 1743
```

<210> SEQ ID NO 448
<211> LENGTH: 35
<212> TYPE: DNA
<213> ORGANISM: Artificial Sequence
<220> FEATURE:
<223> OTHER INFORMATION: PCR primer

<400> SEQUENCE: 448

```
cgtactagca tatgaacaaa ctgtatatcg gaaac                                35
```

<210> SEQ ID NO 449
<211> LENGTH: 579
<212> TYPE: PRT
<213> ORGANISM: Homo sapiens

<400> SEQUENCE: 449

```
Met Asn Lys Leu Tyr Ile Gly Asn Leu Ser Glu Asn Ala Ala Pro Ser
                  5                  10                  15

Asp Leu Glu Ser Ile Phe Lys Asp Ala Lys Ile Pro Val Ser Gly Pro
             20                  25                  30

Phe Leu Val Lys Thr Gly Tyr Ala Phe Val Asp Cys Pro Asp Glu Ser
         35                  40                  45

Trp Ala Leu Lys Ala Ile Glu Ala Leu Ser Gly Lys Ile Glu Leu His
     50                  55                  60

Gly Lys Pro Ile Glu Val Glu His Ser Val Pro Lys Arg Gln Arg Ile
 65                  70                  75                  80

Arg Lys Leu Gln Ile Arg Asn Ile Pro Pro His Leu Gln Trp Glu Val
                 85                  90                  95

Leu Asp Ser Leu Leu Val Gln Tyr Gly Val Val Glu Ser Cys Glu Gln
            100                 105                 110

Val Asn Thr Asp Ser Glu Thr Ala Val Val Asn Val Thr Tyr Ser Ser
        115                 120                 125

Lys Asp Gln Ala Arg Gln Ala Leu Asp Lys Leu Asn Gly Phe Gln Leu
    130                 135                 140

Glu Asn Phe Thr Leu Lys Val Ala Tyr Ile Pro Asp Glu Thr Ala Ala
145                 150                 155                 160

Gln Gln Asn Pro Leu Gln Gln Pro Arg Gly Arg Arg Gly Leu Gly Gln
                165                 170                 175

Arg Gly Ser Ser Arg Gln Gly Ser Pro Gly Ser Val Ser Lys Gln Lys
            180                 185                 190

Pro Cys Asp Leu Pro Leu Arg Leu Leu Val Pro Thr Gln Phe Val Gly
        195                 200                 205
```

-continued

```
Ala Ile Ile Gly Lys Glu Gly Ala Thr Ile Arg Asn Ile Thr Lys Gln
    210                 215                 220

Thr Gln Ser Lys Ile Asp Val His Arg Lys Glu Asn Ala Gly Ala Ala
225                 230                 235                 240

Glu Lys Ser Ile Thr Ile Leu Ser Thr Pro Glu Gly Thr Ser Ala Ala
                245                 250                 255

Cys Lys Ser Ile Leu Glu Ile Met His Lys Glu Ala Gln Asp Ile Lys
            260                 265                 270

Phe Thr Glu Glu Ile Pro Leu Lys Ile Leu Ala His Asn Asn Phe Val
        275                 280                 285

Gly Arg Leu Ile Gly Lys Glu Gly Arg Asn Leu Lys Lys Ile Glu Gln
    290                 295                 300

Asp Thr Asp Thr Lys Ile Thr Ile Ser Pro Leu Gln Glu Leu Thr Leu
305                 310                 315                 320

Tyr Asn Pro Glu Arg Thr Ile Thr Val Lys Gly Asn Val Glu Thr Cys
                325                 330                 335

Ala Lys Ala Glu Glu Glu Ile Met Lys Lys Ile Arg Glu Ser Tyr Glu
            340                 345                 350

Asn Asp Ile Ala Ser Met Asn Leu Gln Ala His Leu Ile Pro Gly Leu
        355                 360                 365

Asn Leu Asn Ala Leu Gly Leu Phe Pro Pro Thr Ser Gly Met Pro Pro
    370                 375                 380

Pro Thr Ser Gly Pro Pro Ser Ala Met Thr Pro Pro Tyr Pro Gln Phe
385                 390                 395                 400

Glu Gln Ser Glu Thr Glu Thr Val His Leu Phe Ile Pro Ala Leu Ser
                405                 410                 415

Val Gly Ala Ile Ile Gly Lys Gln Gly Gln His Ile Lys Gln Leu Ser
            420                 425                 430

Arg Phe Ala Gly Ala Ser Ile Lys Ile Ala Pro Ala Glu Ala Pro Asp
        435                 440                 445

Ala Lys Val Arg Met Val Ile Ile Thr Gly Pro Pro Glu Ala Gln Phe
    450                 455                 460

Lys Ala Gln Gly Arg Ile Tyr Gly Lys Ile Lys Glu Glu Asn Phe Val
465                 470                 475                 480

Ser Pro Lys Glu Glu Val Lys Leu Glu Ala His Ile Arg Val Pro Ser
                485                 490                 495

Phe Ala Ala Gly Arg Val Ile Gly Lys Gly Gly Lys Thr Val Asn Glu
            500                 505                 510

Leu Gln Asn Leu Ser Ser Ala Glu Val Val Val Pro Arg Asp Gln Thr
        515                 520                 525

Pro Asp Glu Asn Asp Gln Val Val Val Lys Ile Thr Gly His Phe Tyr
    530                 535                 540

Ala Cys Gln Val Ala Gln Arg Lys Ile Gln Glu Ile Leu Thr Gln Val
545                 550                 555                 560

Lys Gln His Gln Gln Gln Lys Ala Leu Gln Ser Gly Pro Pro Gln Ser
                565                 570                 575

Arg Arg Lys
```

<210> SEQ ID NO 450
<211> LENGTH: 1743
<212> TYPE: DNA
<213> ORGANISM: Homo sapiens

<400> SEQUENCE: 450

-continued

```
atgaacaaac tgtatatcgg aaacctcagc gagaacgccg ccccctcgga cctagaaagt      60

atcttcaagg acgccaagat cccggtgtcg ggacccttcc tggtgaagac tggctacgcg     120

ttcgtggact gcccggacga gagctgggcc ctcaaggcca tcgaggcgct ttcaggtaaa     180

atagaactgc acgggaaacc catagaagtt gagcactcgg tcccaaaaag gcaaaggatt     240

cggaaacttc agatacgaaa tatcccgcct catttacagt gggaggtgct ggatagttta     300

ctagtccagt atggagtggt ggagagctgt gagcaagtga acactgactc ggaaactgca     360

gttgtaaatg taacctattc cagtaaggac caagctagac aagcactaga caaactgaat     420

ggatttcagt tagagaattt caccttgaaa gtagcctata tccctgatga aacggccgcc     480

cagcaaaacc ccttgcagca gccccgaggt cgccgggggc ttgggcagag gggctcctca     540

aggcaggggt ctccaggatc cgtatccaag cagaaaccat gtgatttgcc tctgcgcctg     600

ctggttccca cccaatttgt tggagccatc ataggaaaag aaggtgccac cattcggaac     660

atcaccaaac agacccagtc taaaatcgat gtccaccgta aagaaaatgc gggggctgct     720

gagaagtcga ttactatcct ctctactcct gaaggcacct ctgcggcttg taagtctatt     780

ctggagatta tgcataagga agctcaagat ataaaattca cagaagagat cccccttgaag    840

attttagctc ataataactt tgttggacgt cttattggta aagaaggaag aaatcttaaa     900

aaaattgagc aagacacaga cactaaaatc acgatatctc cattgcagga attgacgctg     960

tataatccag aacgcactat tacagttaaa ggcaatgttg agacatgtgc caaagctgag    1020

gaggagatca tgaagaaaat cagggagtct tatgaaaatg atattgcttc tatgaatctt    1080

caagcacatt taattcctgg attaaatctg aacgccttgg gtctgttccc acccacttca    1140

gggatgccac ctcccacctc agggccccct tcagccatga ctcctcccta cccgcagttt    1200

gagcaatcag aaacggagac tgttcatctg tttatcccag ctctatcagt cggtgccatc    1260

atcggcaagc agggccagca catcaagcag ctttctcgct ttgctggagc ttcaattaag    1320

attgctccag cggaagcacc agatgctaaa gtgaggatgg tgattatcac tggaccacca    1380

gaggctcagt tcaaggctca gggaagaatt tatggaaaaa ttaaagaaga aaactttgtt    1440

agtcctaaag aagaggtgaa acttgaagct catatcagag tgccatcctt tgctgctggc    1500

agagttattg gaaaaggagg caaaacggtg aatgaacttc agaatttgtc aagtgcagaa    1560

gttgttgtcc ctcgtgacca gacacctgat gagaatgacc aagtggttgt caaaataact    1620

ggtcacttct atgcttgcca ggttgcccag agaaaaattc aggaaattct gactcaggta    1680

aagcagcacc aacaacagaa ggctctgcaa agtggaccac ctcagtcaag acggaagtaa    1740

tga                                                                  1743
```

<210> SEQ ID NO 451
<211> LENGTH: 25
<212> TYPE: PRT
<213> ORGANISM: Homo sapiens

<400> SEQUENCE: 451

```
Leu Gly Lys Glu Val Arg Asp Ala Lys Ile Thr Pro Glu Ala Phe Glu
                5                   10                  15

Lys Leu Gly Phe Pro Ala Ala Lys Glu
            20                  25
```

<210> SEQ ID NO 452
<211> LENGTH: 25
<212> TYPE: PRT
<213> ORGANISM: Homo sapiens -continued

<400> SEQUENCE: 452

Lys Ala Ser Asp Gly Asp Tyr Tyr Thr Leu Ala Val Pro Met Gly Asp
5 10 15

Val Pro Met Asp Gly Ile Ser Val Ala
20 25

<210> SEQ ID NO 453
<211> LENGTH: 16
<212> TYPE: PRT
<213> ORGANISM: Homo sapiens

<400> SEQUENCE: 453

Pro Asp Arg Asp Val Asn Leu Thr His Gln Leu Asn Pro Lys Val Lys
5 10 15

<210> SEQ ID NO 454
<211> LENGTH: 20
<212> TYPE: PRT
<213> ORGANISM: Homo sapiens

<400> SEQUENCE: 454

Lys Ile Ala Pro Ala Glu Ala Pro Asp Ala Lys Val Arg Met Val Ile
5 10 15

Ile Thr Gly Pro
20

<210> SEQ ID NO 455
<211> LENGTH: 20
<212> TYPE: PRT
<213> ORGANISM: Homo sapiens

<400> SEQUENCE: 455

Pro Asp Glu Thr Ala Ala Gln Gln Asn Pro Leu Gln Gln Pro Arg Gly
5 10 15

Arg Arg Gly Leu
20

<210> SEQ ID NO 456
<211> LENGTH: 20
<212> TYPE: PRT
<213> ORGANISM: Homo sapiens

<400> SEQUENCE: 456

Arg Thr Ile Thr Val Lys Gly Asn Val Glu Thr Cys Ala Lys Ala Glu
5 10 15

Glu Glu Ile Met
20

<210> SEQ ID NO 457
<211> LENGTH: 20
<212> TYPE: PRT
<213> ORGANISM: Homo sapiens

<400> SEQUENCE: 457

Ala Phe Val Asp Cys Pro Asp Glu Ser Trp Ala Leu Lys Ala Ile Glu
5 10 15

Ala Leu Ser Gly
20

<210> SEQ ID NO 458
<211> LENGTH: 20

<212> TYPE: PRT
<213> ORGANISM: Homo sapiens

<400> SEQUENCE: 458

Ile Arg Lys Leu Gln Ile Arg Asn Ile Pro Pro His Leu Gln Trp Glu
5 10 15

Val Leu Asp Ser
20

<210> SEQ ID NO 459
<211> LENGTH: 20
<212> TYPE: PRT
<213> ORGANISM: Homo sapiens

<400> SEQUENCE: 459

Ala Gln Gln Asn Pro Leu Gln Gln Pro Arg Gly Arg Arg Gly Leu Gly
5 10 15

Gln Arg Gly Ser
20

<210> SEQ ID NO 460
<211> LENGTH: 20
<212> TYPE: PRT
<213> ORGANISM: Homo sapiens

<400> SEQUENCE: 460

Asp Val His Arg Lys Glu Asn Ala Gly Ala Ala Glu Lys Ser Ile Thr
5 10 15

Ile Leu Ser Thr
20

<210> SEQ ID NO 461
<211> LENGTH: 20
<212> TYPE: PRT
<213> ORGANISM: Homo sapiens

<400> SEQUENCE: 461

Leu Tyr Asn Pro Glu Arg Thr Ile Thr Val Lys Gly Asn Val Glu Thr
5 10 15

Cys Ala Lys Ala
20

<210> SEQ ID NO 462
<211> LENGTH: 20
<212> TYPE: PRT
<213> ORGANISM: Homo sapiens

<400> SEQUENCE: 462

Glu Glu Glu Ile Met Lys Lys Ile Arg Glu Ser Tyr Glu Asn Asp Ile
5 10 15

Ala Ser Met Asn
20

<210> SEQ ID NO 463
<211> LENGTH: 20
<212> TYPE: PRT
<213> ORGANISM: Homo sapiens

<400> SEQUENCE: 463

Leu Asn Ala Leu Gly Leu Phe Pro Pro Thr Ser Gly Met Pro Pro Pro
5 10 15

Thr Ser Gly Pro

-continued

20

<210> SEQ ID NO 464
<211> LENGTH: 20
<212> TYPE: PRT
<213> ORGANISM: Homo sapiens

<400> SEQUENCE: 464

Lys Ile Ala Pro Ala Glu Ala Pro Asp Ala Lys Val Arg Met Val Ile
5 10 15

Ile Thr Gly Pro
20

<210> SEQ ID NO 465
<211> LENGTH: 18
<212> TYPE: PRT
<213> ORGANISM: Homo sapiens

<400> SEQUENCE: 465

Thr Gly Tyr Ala Phe Val Asp Cys Pro Asp Glu Ser Trp Ala Leu Lys Ile
5 10 15

Glu

<210> SEQ ID NO 466
<211> LENGTH: 11
<212> TYPE: PRT
<213> ORGANISM: Homo sapiens

<400> SEQUENCE: 466

Phe Val Asp Cys Pro Asp Glu Ser Trp Ala Leu
5 10

<210> SEQ ID NO 467
<211> LENGTH: 33
<212> TYPE: DNA
<213> ORGANISM: Homo sapiens

<400> SEQUENCE: 467
ttcgtggact gcccggacga gagctgggcc ctc 33

<210> SEQ ID NO 468
<211> LENGTH: 24
<212> TYPE: PRT
<213> ORGANISM: Homo sapiens

<400> SEQUENCE: 468

Ile Pro Asp Glu Met Ala Ala Gln Gln Asn Pro Leu Gln Gln Pro Arg
5 10 15

Gly Arg Arg Gly Leu Gly Gln Arg
20

<210> SEQ ID NO 469
<211> LENGTH: 24
<212> TYPE: PRT
<213> ORGANISM: Homo sapiens

<400> SEQUENCE: 469

Ile Pro Asp Glu Thr Ala Ala Gln Gln Asn Pro Ser Pro Gln Leu Arg
5 10 15

Gly Arg Arg Gly Pro Gly Gln Arg
20